United States Patent
Emerling et al.

(10) Patent No.: US 11,655,290 B2
(45) Date of Patent: May 23, 2023

(54) ANTI-CSP ANTIBODIES

(71) Applicant: Atreca, Inc., San Carlos, CA (US)

(72) Inventors: Daniel Eric Emerling, San Carlos, CA (US); Randal R. Ketchem, Snohomish, WA (US); Shaun M. Lippow, San Carlos, CA (US); Wayne Volkmuth, San Carlos, CA (US); Katherine L. Williams, San Carlos, CA (US)

(73) Assignee: Atreca, Inc., San Carlos, CA (US)

( * ) Notice: Subject to any disclaimer, the term of this patent is extended or adjusted under 35 U.S.C. 154(b) by 0 days.

(21) Appl. No.: 17/842,351

(22) Filed: Jun. 16, 2022

(65) Prior Publication Data

US 2023/0002483 A1 Jan. 5, 2023

Related U.S. Application Data

(60) Provisional application No. 63/211,820, filed on Jun. 17, 2021.

(51) Int. Cl.
| | | |
|---|---|---|
| C07K 16/00 | (2006.01) | |
| A61K 39/395 | (2006.01) | |
| C07K 16/20 | (2006.01) | |
| A61P 33/06 | (2006.01) | |
| A61K 39/00 | (2006.01) | |

(52) U.S. Cl.
CPC ............ *C07K 16/205* (2013.01); *A61P 33/06* (2018.01); *A61K 2039/505* (2013.01); *C07K 2317/33* (2013.01); *C07K 2317/92* (2013.01)

(58) Field of Classification Search
None
See application file for complete search history.

(56) References Cited

U.S. PATENT DOCUMENTS

| 6,602,684 B1 | 8/2003 | Umaña |
| 8,088,376 B2 | 1/2012 | Chamberlain et al. |
| 11,066,464 B2 * | 7/2021 | Liang .................. C07K 16/205 |

FOREIGN PATENT DOCUMENTS

| WO | WO 1993/10152 A1 | 5/1993 |
| WO | WO 99/54342 A1 | 8/1999 |
| WO | WO 2010/054007 A1 | 5/2010 |
| WO | WO 2012/148497 A2 | 11/2012 |
| WO | WO 2017/015634 A2 | 1/2017 |
| WO | WO 2020/172220 A1 | 8/2020 |

OTHER PUBLICATIONS

Al-Lazikani et al., "Standard Conformations for the Canonical Structures of Immunoglobulins," J. Mol. Biol, 273(4), 927-948 (1997).
Altschul et al., "Gapped BLAST and PSI-BLAST: a new generation of protein database search programs," Nuc. Acids Res., 25:3389-3402 (1977).
Altschul et al., "Basic Local Alignment Search Tool," J. Mol. Biol. 215, 403-410 (1990).
Angal, et al., "A single amino acid substitution abolishes the heterogeneity of chimeric mouse/human (IgG4) antibody," Molecular Immunology, 30(1), 105-108 (1993).
Ausubel et al., "Current Protocols in Molecular Biology," John Wiley & Sons, Inc. (2003).
Beutler et al., "A novel CSP C-terminal epitope targeted by an antibody with protective activity against *Plasmodium falciparum*," PLoS Pathog 18(3): e!010409 (2022).
Bowie et al., "Deciphering the message in protein sequences: tolerance to amino acid substitutions," Science 247:1306-1310 (1990).
Chothia et al., "Canonical Structures for the Hypervariable Regions of Immunoglobulins," J. Mol. Biol., 196, 901-917 (1987).
Chothia et al., "Conformations of immunoglobulin hypervariable regions," Nature 342, 877-883 (1989).
Chothia et al., "Structural repertoire of the human $V_H$ segments," J. Mol. Biol. 227(3), 799-817 (1992).
Espinosa et al., "Robust antibody and CD8$^+$ T-cell responses induced by *P. falciparum* CSP adsorbed to cationic liposomal adjuvant CAF09 confer sterilizing immunity against experimental rodent malaria infection," NJP Vaccines, 2, 10 (2017).
Espinosa et al., "Development of a Chimeric *Plasmodium berghei* Strain Expressing the Repeat Region of the *P. vivax* Circumsporozoite Protein for In Vivo Evaluation of Vaccine Efficacy," Infect Immun., 81(8): 2882-2887 (2013).
Flores-Garcia et al., "Optimization of an in vivo model to study immunity to Plasmodium falciparum pre-erythrocytic stages," Malar J., 18(1):426, doi:10.1186/s12936-019-3055-9 (2019).
Honegger et al., "Yet Another Numbering Scheme for Immunoglobulin Variable Domains: An Automatic Modeling and Analysis Tool," J. Mol. Biol., 309:657-670 (2001).
Kabat et al., Sequences of Proteins of Immunological Interest, 5th Ed. Public Health Service, National Institute of Health, NIH Publication 91-3242, Bethesda, MD (1991).
Kester et al., "Randomized, Double-Blind, Phase 2a Trial of Falciparum Malaria Vaccines RTS,S/AS01B and RTS,S/AS02A in Malaria-Naive Adults: Safety, Efficacy, and Immunologic Associates of Protection," J Infect Dis 200: 337-346 (2009).
Lefranc, "IMGT, the international ImMunoGeneTics database," Nucleic Acids Res., 29(1): 207-209 (2001).
MacCallum et al., "Antibody-antigen interactions: Contact analysis and binding site topography," J. Mol. Biol., 262 (5), 732-745 (1996).
Martin et al., "Molecular modeling of antibody combining sites," Methods Enzymol., 203, 121-153 (1991).

(Continued)

*Primary Examiner* — Meera Natarajan

(74) *Attorney, Agent, or Firm* — Baker Botts L.L.P.

(57) ABSTRACT

The present disclosure provides anti-circumsporozoite (CSP) antibodies, compositions comprising such antibodies. Also disclosed are methods of producing the disclosed antibodies and methods of treating or preventing malaria using the same.

31 Claims, 86 Drawing Sheets

Specification includes a Sequence Listing.

(56) References Cited

OTHER PUBLICATIONS

Martin et al., "Modeling antibody hypervariable loops: a combined algorithm," Proc. Natl Acad. Sci. USA, 86, 9268-9272 (1989).
Oyen et al., "Structural basis for antibody recognition of the NANP repeats in *Plasmodium falciparum* circumsporozoite protein," Proc. Natl. Acad Sci. USA, 114(48): E10438-E10445 (2017).
Pedersen et al., "Antibody modeling: beyond homology," Immunomethods, 1, 126-136 (1992).
Pholcharee et al., "Diverse Antibody Responses to Conserved Structural Motifs in Plasmodium falciparum Circumsporozoite Protein," J. Mol. Bio., 432, 1048-1063 (2020).
"Efficacy and Safety of the RTS,S/AS01 Malaria Vaccine during 18 Months after Vaccination: A Phase 3 Randomized, Controlled Trial in Children and Young Infants at 11 African Sites," RTS,S Clinical Trials Partnership, PLoS Med. 11(7): el001685 (2014).
Ruiz et al., "IMGT, the international ImMunoGeneTics database," Nucleic Acids Res., 28, 219-221 (2000).
Sambrook & Russell, Molecular Cloning: A Laboratory Manual, Cold Spring Harbor Laboratory Press.
Sharma et al., "In silico selection of therapeutic antibodies for development: Viscosity, clearance, and chemical stability," Proc. Natl. Acad. Sci. USA, 111:18601-18606 (2014).
Singleton et al., Dictionary of Microbiology and Molecular Biology 2nd ed., J. Wiley & Sons (New York, N.Y) (1994).
Stoute et al., "A Preliminary Evaluation of a Recombinant Circumsporozoite Protein Vaccine against Plasmodium falciparum Malaria," N Engl J Med; 336:86-91(1997).
Urlaub et al., "Isolation of Chinese hamster cell mutants deficient in dihydrofolate reductase activity," Proc. Natl. Acad. Sci. USA, 77:4216-4220 (1980).
Zapata et al., "Engineering linear F(ab')$_2$ fragments for efficient production in *Escherichia coli* and enhanced antiproliferative activity," Protein Eng. 8(10): 1057-1062 (1995).
Abney et al., "Sequential Expression of Immunoglobulin on Developing Mouse B Lymphocytes: A Systematic Survey That Suggests a Model for the Generation of Immunoglobulin Isotype Diversity," The Journal of Immunology, 120(6):2041-2049 (1978).
Achidi et al., "Lack of association between levels of transplacentally acquired *Plasmodium falciparum*-specific antibodies and age of onset of clinical malaria in infants in a malaria endemic area of Nigeria," Acta Tropica 61:315-326 (1996).
Agnandji et al., "Induction of Plasmodium falciparum-Specific CD4+ T Cells and Memory B Cells in Gabonese Children Vaccinated with RTS,S/AS01E and RTS,S/AS02D," PLos ONE 6(4):e18559 (2011) 9 pgs.
Ahuja et al., "Maintenance of the plasma cell pool is independent of memory B cells," PNAS 105(12):4802-4807 (2008).
Ajua et al., "The effect of immunization schedule with the malaria vaccine candidate RTS,S/AS01E on protective efficacy and anti-circumsporozoite protein antibody avidity in African infants," Malaria Journal 14:72 (2015) 6 pgs.
Aliprandini et al., "Cytotoxic anti-circumsporozoite antibodies target malaria sporozoites in the host skin," Nature Microbiology 3:1224-1233 (2018).
Anders, "Multiple cross-reactivities amongst antigens of Plasmodium fakiparum impair the development of protective immunity against malaria," Parasite Immunology 8:529-539 (1986).
Atcheson et al., "A VLP for validation of the *Plasmodium falciparum* circumsporozoite protein junctional epitope for vaccine development," NPJ Vaccines 6:46 (2021) 9 pgs.
Aye et al., "Malaria exposure drives both cognate and bystander human B cells to adopt an atypical phenotype," Eur. J. Immunol. 50:1187-1194 (2020).
Bailly et al., "Predicting Antibody Developability Profiles Through Early Stage Discovery Screening," mAbs, 12:1, 1743053 29 pgs. (2020).
Banach et al., "Highly protective antimalarial antibodies via precision library generation and yeast display screening," J. Exp. Med. 219(8):e20220323 (2022).

Bergmann-Leitner et al., "C3d binding to the circumsporozoite protein carboxy-terminus deviates immunity against malaria," International Immunology, 17(3):245-255 (2005).
Bemasconi et al., "Maintenance of Serological Memory by Polyclonal Activation of Human Memory B Cells," Science 298:2199-2202 (2002).
Beutler et al., "A novel CSP C-terminal epitope targeted by an antibody with protective activity against *Plasmodium falciparum*," PLoS Pathog 18(3):e1010409 (2022) 21 pgs.
Calvo-Calle et al., "A Linear Peptide Containing Minimal T- and B-Cell Epitopes of *Plasmodium falciparum* Circumsporozoite Protein Elicits Protection against Transgenic Sporozoite Challenge," Infection and Immunity, 74(12):6929-6939 (Dec. 2006).
Calvo-Calle et al., "Human CD4+ T Cells Induced by Synthetic Peptide Malaria Vaccine Are Comparable to Cells Elicited by Attenuated *Plasmodium falciparum* Sporozoites," The Journal of Immunology 175:7575-7585 (2005).
Calvo-Calle et al., "Identification of a neutralizing epitope within minor repeat region of *Plasmodium falciparum* CS protein," NPJ Vaccines 6:10 (2021) 8 pgs.
Casares et al., "The RTS,S malaria vaccine," Vaccine 28:4880-4894 (2010).
Chan et al., "Affinity-based selection and the germinal center response," Immunological Reviews 247:11-23 (2012).
Chappel et al., "Molecular dissection of the human antibody response to the structural repeat epitope of Plasmodium falciparum sporozoite from a protected donor," Malaria Journal 3:28 (2004) 12 pgs.
Chatteijee et al., "Avid binding by B cells to the Plasmodium circumsporozoite protein repeat suppresses responses to protective subdominant epitopes," Cell Reports 35:108996 (2021) 30 pgs.
Chatteijee et al., "The challenges of a circumsporozoite protein-based malaria vaccine," Expert Review of Vaccines, 20(2):113-125 (2021).
Chaudhury et al., "Breadth of humoral immune responses to the C-terminus of the circumsporozoite protein is associated with protective efficacy induced by the RTS,S malaria vaccine," Vaccine 39:968-975 (2021).
Chaudhury et al., "Delayed fractional dose regimen of the RTS,S/AS01 malaria vaccine candidate enhances an IgG4 response that inhibits serum opsonophagocytosis," Scientific Reports 7:7998 (2017) 10 pgs.
Chaudhury et al., "Simulation of B Cell Affinity Maturation Explains Enhanced Antibody Cross-Reactivity Induced by the Polyvalent Malaria Vaccine AMA1," The Journal of Immunology 193:2073-2086 (2014).
Chaudhury et al., "The biological function of antibodies induced by the RTS,S/AS01 malaria vaccine candidate is determined by their fine specificity," Malar J. 15:301 (2016) 12 pgs.
Chen et al., "Systematic analysis of human antibody response to ebolavirus glycoprotein reveals high prevalence of neutralizing public clonotypes," bioRxiv preprint doi: https://doi.org/10.1101/2022.01.12.476089 (Jan. 13, 2022).
Cockbum et al., "Malaria prevention: from immunological concepts to effective vaccines and protective antibodies," Nature Immunology 19:1199-1211 (2018).
Coelho et al., "Unwanted Feedback: Malaria Antibodies Hinder Vaccine Boosting," Cell Host & Microbe 28:504-506 (2020).
Collins et al., "Ultra-low dose immunization and multi-component vaccination strategies enhance protection against malaria in mice," Scientific Reports 11:10792 (2021) 15 pgs.
Coppi et al., "The malaria circumsporozoite protein has two functional domains, each with distinct roles as sporozoites journey from mosquito to mammalian host," J. Exp. Med. 208(2):341-356 (2011).
Cox et al., "An early humoral immune response in peripheral blood following parenteral inactivated influenza vaccination," Vaccine 12(11):993-999 (1994).
Crompton et al., "A prospective analysis of the Ab response to *Plasmodium falciparum* before and after a malaria season by protein microarray," PNAS 107(15):6958-6963 (2010).
Crompton et al., "Advances and challenges in malaria vaccine development," The Journal of Clinical Investigation 120(12):4168-4178 (2010).

(56) References Cited

OTHER PUBLICATIONS

Daily, "Monoclonal Antibodies—A Different Approach to Combat Malaria," N Engl J Med 387(5):460-461 (2022).
Dame et al., "Structure of the Gene Encoding the Immunodominant Surface Antigen on the Sporozoite of the Human Malaria Parasite *Plasmodium falciparum*," Science 225:593-599 (1984).
Das et al., "Delayed fractional dosing with RTS,S/AS01 improves humoral immunity to malaria via a balance of polyfunctional NANP6- and Pf16-specific antibodies," Med 2:1269-1286 (2021).
Deal et al., "Vectored antibody gene delivery protects against Plasmodium falciparum sporozoite challenge in mice," PNAS 111(34):12528-12532 (2014).
DeKosky et al., "Large-scale sequence and structural comparisons of human naive and antigen-experienced antibody repertoires," PNAS e2636-e2645 (2016).
Dennison et al., "Qualified Biolayer Interferometry Avidity Measurements Distinguish the Heterogeneity of Antibody Interactions with *Plasmodium falciparum* Circumsporozoite Protein Antigens," J Immunol 201:1315-1326 (2018).
Dobano et al., "Concentration and avidity of antibodies to different circumsporozoite epitopes correlate with RTS,S/AS01E malaria vaccine efficacy," Nature Communications 10:2174, 13 pgs. (2019).
Dobano et al., "Differential Patterns of IgG Subclass Responses to plasmodium falciparum Antigens in Relation to Malaria Protection and RTS,S Vaccination," Frontiers in Immunology 10:439, 19 pgs. (2019).
Dobano et al., "RTS,S/AS01E immunization increases antibody responses to vaccine-unrelated *Plasmodium falciparum* antigens associated with protection against clinical malaria in African children: a case-control study," BMC Medicine 17:157, 19 pgs. (2019).
Du et al., "The Ratiometric Transcript Signature MX2/GPR183 Is Consistently Associated with RTS,S-Mediated Protection Against Controlled Human Malaria Infection," Frontiers in Immunology 11:669, 12 pgs. (2020).
Ellebedy et al., "Defining antigen-specific plasmablast and memory B cell subsets in human blood after viral infection or vaccination," Nature Immunology 17(10):1226-1234 (2016).
Elliott et al., "Affinity Maturation Drives Epitope Spreading and Generation of Proinflammatory Anti-Citrullinated Protein Antibodies in Rheumatoid Arthritis," Arthritis & Rheumatology, 70(12):1946-1958 (2018).
Enea et al., "DNA Cloning of *Plasmodium falciparum* Circumsporozoite Gene: Amino Acid Sequence of Repetitive Epitope," Science 225:628-630 (1984).
Espinosa et al., "Proteolytic Cleavage of the *Plasmodium falciparum* Circumsporozoite Protein Is a Target of Protective Antibodies," JID 212:1111-1119 (2015).
Fabra-Garcia et al., "Human antibodies against noncircumsporozoite proteins block *Plasmodium falciparum* parasite development in hepatocytes," JCI Insight 7(6):e153524 (2022) 12 pgs.
Ferguson et al., "The Repeat Region of the Circumsporozoite Protein is Critical for Sporozoite Formation and Maturation in *Plasmodium*," PLoS ONE 9(12):e113923, 25 pgs. (2014).
Fernández-Quintero et al., "Antibody CDR loops as ensembles in solution vs. canonical clusters from X-ray structures," mAbs, 12:1744328 (2020) 12 pgs.
Fink et al., "Origin and function of circulating plasmablasts during acute viral infections," Frontiers in Immunology 3:78 (2012) 5 pgs.
Fisher et al., "T-dependent B cell responses to Plasmodium induce antibodies that form a high-avidity multivalent complex with the circumsporozoite protein," PLoS Pathog 13(7):e1006469 (2017).
Flores-Garcia et al., "Optimization of an in vivo model to study immunity to *Plasmodium falciparum* pre-erythrocytic stages," Malar J. 18:426 (2019) 9 pgs.
Flores-Garcia et al., "The *P. falciparum* CSP repeat region contains three distinct epitopes required for protection by antibodies in vivo," PLoS Pathog 17(11):e1010042 (2021).
Foquet et al., "Vaccine-induced monoclonal antibodies targeting circumsporozoite protein prevent *Plasmodium falciparum* infection," J Clin Invest. 124(1):140-144 (2014).

Friedman-Klabanoff et al., "Epitope-Specific Antibody Responses to a *Plasmodium falciparum* Subunit Vaccine Target in a Malaria-Endemic Population," The Journal of Infectious Diseases XX:1-5 (2020) 5 pgs.
Gaudinski et al., "A Monoclonal Antibody for Malaria Prevention," N Engl. J Med (2021) 288 pgs.
Herrera et al., "Reversible Conformational Change in the *Plasmodium falciparum* Circumsporozoite Protein Masks Its Adhesion Domains," Infection and Immunity 83(10):3771-3780 (2015).
Hollingdale et al., "Activity of human volunteer sera to candidate Plasmodium falciparum circumsporozoite protein vaccines in the inhibition of sporozoite invasion assay of human hepatoma cells and hepatocytes," Transactions of the Royal Society of Tropical Medicine and Hygiene 84:325-329 (1990).
Höfer et al., "Adaptation of humoral memory," Immunological Reviews 211:295-302 (2006).
Imkeller et al., "Antihomotypic affinity maturation improves human B cell responses against a repetitive epitope," Science 360:1358-1362 (2018).
Jacobi et al., "Correlation Between Circulating CD27high Plasma Cells and Disease Activity in Patients With Systemic Lupus Erythematosus," Arthritis & Rheumatism 48(5):1332-1342 (2003).
Jelínková et al., "A vaccine targeting the L9 epitope of the malaria circumsporozoite protein confers protection from blood-stage infection in a mouse challenge model," 15 pgs. (year?).
Jelínková et al., "An epitope-based malaria vaccine targeting the junctional region of circumsporozoite protein," NPJ Vaccines 6:13 (2021) 10 pgs.
Julien et al., "Antibodies against Plasmodium falciparum malaria at the molecular level," Nature Reviews, Immunology 19:761-775 (2019).
Kazmin et al., "Systems analysis of protective immune responses to RTS,S malaria vaccination in humans," PNAS 114(9):2425-2430 (2017).
Keitany et al., "Blood Stage Malaria Disrupts Humoral Immunity to the Pre-erythrocytic Stage Circumsporozoite Protein," Cell Reports 17:3193-3205 (2016).
Kelley et al., "Process and operations strategies to enable global access to antibody therapies," Biotechnol Progress. 37:e3139 (2021) 15 pgs.
Kester et al., "A phase I/IIa safety, immunogenicity, and efficacy bridging randomized study of a two-dose regimen of liquid and lyophilized formulations of the candidate malaria vaccine RTS,S/AS02A in malaria-naive adults," Vaccine 25:5359-5366 (2007).
Kester et al., "Efficacy of Recombinant Circumsporozoite Protein Vaccine Regimens against Experimental Plasmodium falciparum Malaria," The Journal of Infectious Diseases 183:640-647 (2001).
Kingston et al., "Hepatitis B virus-like particles expressing Plasmodium falciparum epitopes induce complement-fixing antibodies against the circumsporozoite protein," Vaccine 37:1674-1684 (2019).
Kisalu et al., "A human monoclonal antibody prevents malaria infection and defines a new site of vulnerability on Plasmodium falciparum circumsporozoite protein," Nat Med. 24(4):408-416 (2018).
Kisalu et al., "A human monoclonal antibody prevents malaria infection by targeting a new site of vulnerability on the parasite," Nature Medicine 24(4):408-416 (2018).
Kisalu et al., "Enhancing durability of CIS43 monoclonal antibody by Fc mutation or AAV delivery for malaria prevention," JCI Insight. 6(3):e143958 (2021).
Kratochvil et al., "Vaccination in a humanized mouse model elicits highly protective PfCSP-targeting anti-malarial antibodies," Immunity 54:2859-2876 (2021).
Krishnamurty et al., "Somatically Hypermutated Plasmodium-Specific IgM+ Memory B Cells Are Rapid, Plastic, Early Responders upon Malaria Rechallenge," Immunity 45:402-414(2016).
Kucharska et al., "Structural basis of Plasmodium vivax inhibition by antibodies binding to the circumsporozoite protein repeats," eLife 11:e72908 (2022) 29 pgs.
Kucharska et al., "Structural ordering of the Plasmodium berghei circumsporozoite protein repeats by inhibitory antibody 3D11," eLife 9:e59018 (2020) 25 pgs.

(56) References Cited

OTHER PUBLICATIONS

Kurtovic et al., "Induction and decay of functional complement-fixing antibodies by the RTS,S malaria vaccine in children, and a negative impact of malaria exposure," BMC Medicine 17:45 (2019) 14 pgs.
Kurtovic et al., "Multifunctional Antibodies Are Induced by the RTS,S Malaria Vaccine and Associated With Protection in a Phase 1/2a Trial," JID (2020) 11 pgs.
Langowski et al., "Optimization of a Plasmodium falciparum circumsporozoite protein repeat vaccine using the tobacco mosaic virus platform," PNAS 117(6):3114-3122 (2020).
Langowski et al., "Restricted valency (NPNA)n repeats and junctional epitope-based circumsporozoite protein vaccines against *Plasmodium falciparum*," npj Vaccines 7:13 (2022) 11 pgs.
Laumont et al., "Noncoding regions are the main source of targetable tumor-specific antigens," Sci. Transl. Med. 10:eaau5516 (2018) 11 pgs.
Livingstone et al., "In vitro and in vivo inhibition of malaria parasite infection by monoclonal antibodies against *Plasmodium falciparum* circumsporozoite protein (CSP)," Scientific Reports 11:5318 (2021) 15 pgs.
Macia et al., "Strong off-target antibody reactivity to malarial antigens induced by RTS,S/AS01E vaccination is associated with protection," JCI Insight, 24 pgs. (2022).
Macià et al., "Strong off-target antibody reactivity to malarial antigens induced by RTS,S/AS01E vaccination is associated with protection," JCI Insight (2022) 24 pgs.
Macintyre et al., "Injectable anti-malarials revisited:discovery and development of new agents to protect against malaria," Malar J 17:402 (2018).
McNamara et al., "Antibody Feedback Limits the Expansion of B Cell Responses to Malaria Vaccination but Drives Diversification of the Humoral Response," Cell Host & Microbe 28:572-585 (2020).
McNamara et al., Splenic Dendritic Cells and Macrophages Drive B Cells to Adopt a Plasmablast Cell Fate, Frontiers in Immunology 13:825207 (2022) 15 pgs.
Mesin et al., "Germinal Center B Cell Dynamics," Immunity 45(3):471-482 (2016).
Mitchell et al., "Innate Immune Responses and P. falciparum CS Repeat-Specific Neutralizing Antibodies Following Vaccination by Skin Scarification," Frontiers in Immunology 13:801111 (2022) 14 pgs.
Moon et al., "A Phase IIa Controlled Human Malaria Infection and Immunogenicity Study of RTS,S/AS01E and RTS,S/AS01B Delayed Fractional Dose Regimens in Malaria-Naive Adults," JID 222:1681-1691 (2020).
Murugan et al., "Evolution of protective human antibodies against Plasmodium falciparum circumsporozoite protein repeat motifs," Nature Medicine 26:1135-1145 (2020).
Nadeem et al., "Mosquirix™ RTS, S/AS01 Vaccine Development, Immunogenicity, and Efficacy," Vaccines 10:713 (2022) 15 pgs.
Nardin et al., "Synthetic Malaria Peptide Vaccine Elicits High Levels of Antibodies in Vaccinees of Defined HLA Genotypes," The Journal of Infectious Diseases 182:1486-1496 (2000).
Nardin et al., "T Cell Responses to Repeat and Non-Repeat Regions of the Circumsporozoite Protein Detected in Volunteers Immunized With Plasmodium Falciparum Sporozoites," Mem. Inst. Oswald Cruz, Rio de Janeiro, 87(Suppl. III):223-227 (1992).
Neafsey et al., "Genetic Diversity and Protective Efficacy of the RTS,S/AS01 Malaria Vaccine," N Engl J Med 373(21):2025-2037 (2015).
Nielsen et al., "RTS,S malaria vaccine efficacy and immunogenicity during Plasmodium falciparum challenge is associated with HLA genotype," Vaccine 3 6:1637-1642 (2018).
Ntoumi et al., "Vaccination with fractional doses: promise or illusion?," The Lancet 22:1258-1259(2022).
Nutt et al., "The generation of antibody-secreting plasma cells," Nature Reviews Immunology 15:160-171 (2015).
O'Connor et al., "Short-lived and Long-lived Bone Marrow Plasma Cells Are Derived from a Novel Precursor Population," J. Exp. Med. 195(6):737-745 (2002).
Ochsenbein et al., "Protective long-term antibody memory by antigen-driven and T help-dependent differentiation of long-lived memory B cells to short-lived plasma cells independent of secondary lymphoid organs," PNAS 97(24):13263-13268 (2000).
Ockenhouse et al., "Ad35.CS.01—RTS,S/AS01 Heterologous Prime Boost Vaccine Efficacy against Sporozoite Challenge in Healthy Malaria-Naïve Adults," PLoS ONE 10(7):e0131571 (2015).
Olotu et al., "Avidity of Anti-Circumsporozoite Antibodies following Vaccination with RTS,S/AS01E in Young Children," PLoS ONE 9(12):e115126 (2014).
Oyen et al., "Cryo-EM structure of *P. falciparum* circumsporozoite protein with a vaccine-elicited antibody is stabilized by somatically mutated inter-Fab contacts," Sci. Adv. 4:eaau8529 (2018) 18 pgs.
Oyen et al., "Structural basis for antibody recognition of the NANP repeats in *Plasmodium falciparum* circumsporozoite protein," PNAS E10438-E10445 (2017) 19 pgs.
Oyen et al., "Structure and mechanism of monoclonal antibody binding to the junctional epitope of *Plasmodium falciparum* circumsporozoite protein," PLoS Pathog 16(3):e1008373 (2020).
Pallikkuth et al., "A delayed fractionated dose RTS,S AS01 vaccine regimen mediates protection via improved T follicular helper and B cell responses," eLife 9:e51889 (2020) 25 pgs.
Patra et al., "Force Spectroscopy of the Plasmodium falciparum Vaccine Candidate Circumsporozoite Protein Suggests a Mechanically Pliable Repeat Region," The Journal of Biological Chemistry 292(6):2110-2119 (2017).
Pholcharee et al., "Diverse Antibody Responses to Conserved Structural Motifs in Plasmodium falciparum Circumsporozoite Protein," Journal of Molecular Biology (2019).
Pholcharee et al., "Structural and biophysical correlation of anti-NANP antibodies with in vivo protection against *P. falciparum*," Nature Communications 12:1063 (2021) 31 pgs.
Pieper et al., "Public antibodies to malaria antigens generated by two LAIR1 insertion modalities," Nature 548(7669):597-601 (2017).
Radbruch et al., "Competence and competition: the challenge of becoming a long-lived plasma cell," Nature Reviews, Immunology 6:741-750 (2006).
Radin et al., "A monoclonal antibody-based immunoassay to measure the antibody response against the repeat region of the circumsporozoite protein of *Plasmodium falciparum*," Malaria J. 15:543, 11 pgs. (2016).
Raghunandan et al., "Characterization of two in vivo challenge models to measure functional activity of monoclonal antibodies to *Plasmodium falciparum* circumsporozoite protein," Malaria J. 19:113 (2020) 15 pgs.
Ralph et al., "Using B cell receptor lineage structures to predict affinity," (Apr. 25, 2020) 46 pgs.
Reeder et al., "Strategic Variants of CSP Delivered as SynDNA Vaccines Demonstrate Heterogeneity of Immunogenicity and Protection from Plasmodium Infection in a Murine Model," Infect Immun 89:e00728-20 (2021).
Regules et al., "Fractional Third and Fourth Dose of RTS,S/AS01 Malaria Candidate Vaccine: A Phase 2a Controlled Human Malaria Parasite Infection and Immunogenicity Study," JID 214:762-771 (2016).
Renia et al., "Malaria Parasites: The Great Escape," Front. Immunol. 7:463, 14 pgs. (2016).
Robinson, "Sequencing the functional antibody repertoire-diagnostic and therapeutic discovery," Nat. Rev. Rheumatol. 11:171-182 (2015).
Sánchez et al., "Antibody responses to the RTS,S/AS01E vaccine and *Plasmodium falciparum* antigens after a booster dose within the phase 3 trial in Mozambique," NPJ Vaccines 5:46 (2020) 16 pgs.
Scally et al., "Peek-Peak-Pique: Repeating Motifs of Subtle Variance Are Targets for Potent Malaria Antibodies," Immunity 48:851-854 (2018).
Scally et al., "Rare PfCSP C-terminal antibodies induced by live sporozoite vaccination are ineffective against malaria infection," J. Exp. Med., 18 pgs. (2018).

(56) References Cited

OTHER PUBLICATIONS

Schofield et al., "Lack of Ir gene control in the immune response to malaria. I. A thymus-independent antibody response to the repetitive surface protein of sporozoites," J Immunol 144:2781-2788 (1990).
Schofield, "On the Function of Repetitive Domains in Protein Antigens of Plasmodium and Other Eukaryotic Parasites," Parasitology Today, 7(5):99-105 (1991).
Schofield, "The circumsporozoite protein of Plasmodium: a mechanism of immune evasion by the malaria parasite?" Bulletin of the World Health Organization, 68:66-73 (1990).
Schwenk et al., "IgG2 Antibodies against a Clinical Grade Plasmodium falciparum CSP Vaccine Antigen Associate with Protection against Transgenic Sporozoite Challenge in Mice," PLoS One 9(10):e111020 (2014) 16 pgs.
Seaton et al., "Subclass and avidity of circumsporozoite protein specific antibodies associate with protection status against malaria infection," NPJ Vaccines 6:110 (2021) 13 pgs.
Seder et al., "Protection Against Malaria by Intravenous Immunization with a Nonreplicating Sporozoite Vaccine," Science 341:1359-1365 (2013).
Sinnis et al., "The RTS,S vaccine—a chance to regain the upper hand against malaria?" Cell 185:750-754(2022) 28 pgs.
Snapkov et al., "Progress and challenges in mass spectrometry-based analysis of antibody repertoires," Trends in Biotechnology, 40(4):463-481 (2022).
Soto et al., "High frequency of shared clonotypes in human B cell receptor repertoires," Nature, 18 pgs. (2019).
Stoute et al., "A Preliminary Evaluation of a Recombinant Circumsporozoite Protein Vaccine Against *Plasmodium falciparum* Malaria," The New England Journal of Medicine 336(2):86-91 (2022).
Suscovich et al., "Mapping functional humoral correlates of protection against malaria challenge following RTS,S/AS01 vaccination," Sci. Transl. Med. 12:eabb4757 (2020) 56 Pgs.
Tan et al., "A public antibody lineage that potently inhibits malaria infection through dual binding to the circumsporozoite protein," Nature Medicine, 24(4):401-407 (2018).
Tan et al., "Functional human IgA targets a conserved site on malaria sporozoites," Sci Transl Med., 13(599):31 pgs. (2021).
Thai et al., "A high-affinity antibody against the CSP N-terminal domain lacks Plasmodium falciparum inhibitory activity," J. Exp. Med. 217(11):e20200061 (2020) 18 Pgs.
Thompson et al., "Modelling the roles of antibody titre and avidity in protection from *Plasmodium falciparum* malaria infection following RTS,S/AS01 vaccination," Vaccine 38:7498-7507 (2020).
Triller et al., "Natural Parasite Exposure Induces Protective Human Anti-Malarial Antibodies," Immunity 47:1197-1209 (2017).
Ubillos et al., "Baseline exposure, antibody subclass, and hepatitis B response differentially affect malaria protective immunity following RTS,S/AS01E vaccination in African children," BMC Medicine 16:197 (2018) 18 pgs.
Vauquelin, "Effects of target binding kinetics on in vivo drug efficacy: koff, kon and rebinding," British Journal of Pharmacology 173:2319-2334 (2016).
Vauquelin, "Link between a high kon for drug binding and a fast clinical action: to be or not to be?" Med. Chem. Commun., 9:1426 (2018) 13 pgs.
Vijay et al., "Infection-induced plasmablasts are a nutrient sink that impairs humoral immunity to malaria," Nature Immunology 21:790-801 (2020).
Vijayan et al., "Antibody interference by a non-neutralizing antibody abrogates humoral protection against *Plasmodium yoelii* liver stage," Cell Reports 36:109489, 33 pgs. (2021).
Visweswaran et al., "Germinal center activity and B cell maturation are associated with protective antibody responses against *Plasmodium* pre-erythrocytic infection," PLoS Pathog 18(7):e1010671 (2022) 24 pgs.

Volpe et al., "SoDA: implementation of a 3D alignment algorithm for inference of antigen receptor recombinations," Bioinformatics 22(4):438-444 (2006).
Wahl et al., "Clonal evolution and TCR specificity of the human TFH cell response to *Plasmodium falciparum* CSP," Sci. Immunol. 7:eabm9644 (2022) 13 pgs.
Wahl et al., "How to induce protective humoral immunity against *Plasmodium falciparum* circumsporozoite protein," J. Exp. Med. 219(2):e20201313 (2022) 10 pgs.
Walker et al., "Passive immunotherapy of viral infections: 'super-antibodies' enter the fray," Nature Reviews, Immunology, 18:297-308 (2018).
Wang et al., "A Potent Anti-Malarial Human Monoclonal Antibody Targets Circumsporozoite Protein Minor Repeats and Neutralizes Sporozoites in the Liver," Immunity 53:733-744 (2020).
Wang et al., "Protective effects of combining monoclonal antibodies and vaccines against the *Plasmodium falciparum* circumsporozoite protein," PLoS Pathog 17(12):el010133 (2021) 26 pgs.
Wang et al., "The light chain of the L9 antibody is critical for binding circumsporozoite protein minor repeats and preventing malaria," Cell Reports 38:110367 (2022) 24 pgs.
Wardemann et al., "From human antibody structure and function towards the design of a novel Plasmodium falciparum circumsporozoite protein malaria vaccine," Current Opinion in Immunology 53:119-123 (2018).
Wee et al., "Longitudinal dynamics of the human B cell response to the yellow fever 17D vaccine," PNAS 117(12):6675-6685 (2020).
Weiss et al., "The Plasmodium falciparum-Specific Human Memory B Cell Compartment Expands Gradually with Repeated Malaria Infections," 6(5):e1000912 (2010) 13 pgs.
White et al., "A combined analysis of immunogenicity, antibody kinetics and vaccine efficacy from phase 2 trials of the RTS,S malaria vaccine," BMC Medicine 12:117 (2014) 11 Pgs.
White et al., "Immunogenicity of the RTS,S/AS01 malaria vaccine and implications for duration of vaccine efficacy: secondary analysis of data from a phase 3 randomised controlled trial," Lancet Infect Dis 15:1450-1458 (2015).
White et al., "The Relationship between RTS,S Vaccine-Induced Antibodies, CD4+ T Cell Responses and Protection against *Plasmodium falciparum* Infection," PLoS One 8(4):e61395 (2013) 10 pgs.
Woodruff et al., "B Cell Competition for Restricted T Cell Help Suppresses Rare-Epitope Responses," Cell Rep. 25(2):321-327 (2018) 19 pgs.
Wu et al., "Low-Dose Subcutaneous or Intravenous Monoclonal Antibody to Prevent Malaria," N Engl. J Med 387:397-407 (2022).
Xu et al., "Structure, heterogeneity and developability assessment of therapeutic antibodies," MABS 11(2):239-264 (2019).
Young et al., "Comprehensive Data Integration Approach to Assess Immune Responses and Correlates of RTS,S/AS01-Mediated Protection From Malaria Infection in Controlled Human Malaria Infection Trials," Frontiers in Big Data, 4:672460 (2021) 17 pgs.
Zavala et al., "Circumsporozoite Proteins of Malaria Parasites Contain a Single Immunodominant Region With Two or More Identical Epitopes," J. Exp. Med. 157:1947-1957 (1983).
Zavala et al., "Rationale for Development of a Synthetic Vaccine Against *Plasmodium falciparum* Malaria," 228:1436-1440 (1985).
Zavala, "RTS,S: the first malaria vaccine," J Clin Invest. 132(1):e156588 (2022) 3 pgs.
Zhang et al., "Monoclonal Antibodies against *Plasmodium falciparum* Circumsporozoite Protein," Antibodies 6:11 (2017) 10 pgs.
Zhao et al., "A Comprehensive Analysis of *Plasmodium* Circumsporozoite Protein Binding to Hepatocytes," PLoS ONE 11(8):e0161607 (2016).
International Search Report and Written Opinion dated Oct. 28, 2022 in International Application No. PCT/US2022/033877.
Jelínková et al., "A vaccine targeting the L9 epitope of the malaria circumsporozoite protein confers protection from blood-stage infection in a mouse challenge model," NPJ Vaccines 7(1):1-4 (2022).

\* cited by examiner

| AB-000224_LS Light Chain | | | |
|---|---|---|---|
| Residue | Linear # | Mat. Linear # | ASN # |
| M | 1 | -19 | LmdLdr:-19 |
| A | 2 | -18 | LmdLdr:-18 |
| W | 3 | -17 | LmdLdr:-17 |
| A | 4 | -16 | LmdLdr:-16 |
| L | 5 | -15 | LmdLdr:-15 |
| L | 6 | -14 | LmdLdr:-14 |
| L | 7 | -13 | LmdLdr:-13 |
| L | 8 | -12 | LmdLdr:-12 |
| T | 9 | -11 | LmdLdr:-11 |
| L | 10 | -10 | LmdLdr:-10 |
| L | 11 | -9 | LmdLdr:-9 |
| T | 12 | -8 | LmdLdr:-8 |
| Q | 13 | -7 | LmdLdr:-7 |
| G | 14 | -6 | LmdLdr:-6 |
| T | 15 | -5 | LmdLdr:-5 |
| G | 16 | -4 | LmdLdr:-4 |
| S | 17 | -3 | LmdLdr:-3 |
| W | 18 | -2 | LmdLdr:-2 |
| A | 19 | -1 | LmdLdr:-1 |
| E | 20 | 1 | LmdV:1 |
| S | 21 | 2 | LmdV:2 |
| V | 22 | 3 | LmdV:3 |
| L | 23 | 4 | LmdV:4 |
| T | 24 | 5 | LmdV:5 |
| Q | 25 | 6 | LmdV:6 |
| P | 26 | 7 | LmdV:7 |
| - | 26.1 | 7.1 | LmdV:8 |
| P | 27 | 8 | LmdV:9 |
| S | 28 | 9 | LmdV:10 |
| V | 29 | 10 | LmdV:11 |
| S | 30 | 11 | LmdV:12 |
| G | 31 | 12 | LmdV:13 |
| A | 32 | 13 | LmdV:14 |
| P | 33 | 14 | LmdV:15 |
| G | 34 | 15 | LmdV:16 |
| Q | 35 | 16 | LmdV:17 |
| R | 36 | 17 | LmdV:18 |
| V | 37 | 18 | LmdV:19 |
| T | 38 | 19 | LmdV:20 |
| I | 39 | 20 | LmdV:21 |
| S | 40 | 21 | LmdV:22 |
| C | 41 | 22 | LmdV:23 |

FIG. 6

| AB-000224_LS Light Chain | | | |
|---|---|---|---|
| Residue | Linear # | Mat. Linear # | ASN # |
| T | 42 | 23 | LmdV:24 |
| G | 43 | 24 | LmdV:25 |
| M | 44 | 25 | LmdV:26 |
| N | 45 | 26 | LmdV:27 |
| - | 45.1 | 26.1 | LmdV:28 |
| S | 46 | 27 | LmdV:29 |
| N | 47 | 28 | LmdV:30 |
| I | 48 | 29 | LmdV:31 |
| G | 49 | 30 | LmdV:32 |
| A | 50 | 31 | LmdV:33 |
| G | 51 | 32 | LmdV:34 |
| - | 51.1 | 32.1 | LmdV:35 |
| - | 51.2 | 32.2 | LmdV:36 |
| - | 51.3 | 32.3 | LmdV:37 |
| - | 51.4 | 32.4 | LmdV:38 |
| Y | 52 | 33 | LmdV:39 |
| D | 53 | 34 | LmdV:40 |
| V | 54 | 35 | LmdV:41 |
| Y | 55 | 36 | LmdV:42 |
| W | 56 | 37 | LmdV:43 |
| Y | 57 | 38 | LmdV:44 |
| Q | 58 | 39 | LmdV:45 |
| Q | 59 | 40 | LmdV:46 |
| L | 60 | 41 | LmdV:47 |
| P | 61 | 42 | LmdV:48 |
| G | 62 | 43 | LmdV:49 |
| R | 63 | 44 | LmdV:50 |
| A | 64 | 45 | LmdV:51 |
| P | 65 | 46 | LmdV:52 |
| K | 66 | 47 | LmdV:53 |
| L | 67 | 48 | LmdV:54 |
| L | 68 | 49 | LmdV:55 |
| I | 69 | 50 | LmdV:56 |
| Y | 70 | 51 | LmdV:57 |
| G | 71 | 52 | LmdV:58 |
| - | 71.1 | 52.1 | LmdV:59 |
| - | 71.2 | 52.2 | LmdV:60 |
| - | 71.3 | 52.3 | LmdV:61 |
| - | 71.4 | 52.4 | LmdV:62 |
| - | 71.5 | 52.5 | LmdV:63 |
| - | 71.6 | 52.6 | LmdV:64 |
| - | 71.7 | 52.7 | LmdV:65 |

FIG. 6 Continued

| AB-000224_LS Light Chain | | | |
|---|---|---|---|
| Residue | Linear # | Mat. Linear # | ASN # |
| - | 71.8 | 52.8 | LmdV:66 |
| N | 72 | 53 | LmdV:67 |
| S | 73 | 54 | LmdV:68 |
| N | 74 | 55 | LmdV:69 |
| R | 75 | 56 | LmdV:70 |
| P | 76 | 57 | LmdV:71 |
| S | 77 | 58 | LmdV:72 |
| G | 78 | 59 | LmdV:73 |
| V | 79 | 60 | LmdV:74 |
| P | 80 | 61 | LmdV:75 |
| D | 81 | 62 | LmdV:76 |
| R | 82 | 63 | LmdV:77 |
| F | 83 | 64 | LmdV:78 |
| S | 84 | 65 | LmdV:79 |
| G | 85 | 66 | LmdV:80 |
| S | 86 | 67 | LmdV:81 |
| R | 87 | 68 | LmdV:82 |
| S | 88 | 69 | LmdV:83 |
| G | 89 | 70 | LmdV:84 |
| - | 89.1 | 70.1 | LmdV:85 |
| - | 89.2 | 70.2 | LmdV:86 |
| T | 90 | 71 | LmdV:87 |
| S | 91 | 72 | LmdV:88 |
| A | 92 | 73 | LmdV:89 |
| S | 93 | 74 | LmdV:90 |
| L | 94 | 75 | LmdV:91 |
| A | 95 | 76 | LmdV:92 |
| I | 96 | 77 | LmdV:93 |
| T | 97 | 78 | LmdV:94 |
| G | 98 | 79 | LmdV:95 |
| L | 99 | 80 | LmdV:96 |
| Q | 100 | 81 | LmdV:97 |
| A | 101 | 82 | LmdV:98 |
| E | 102 | 83 | LmdV:99 |
| D | 103 | 84 | LmdV:100 |
| E | 104 | 85 | LmdV:101 |
| A | 105 | 86 | LmdV:102 |
| D | 106 | 87 | LmdV:103 |
| Y | 107 | 88 | LmdV:104 |
| Y | 108 | 89 | LmdV:105 |
| C | 109 | 90 | LmdV:106 |
| Q | 110 | 91 | LmdV:107 |

FIG. 6 Continued

| AB-000224_LS Light Chain | | | |
|---|---|---|---|
| Residue | Linear # | Mat. Linear # | ASN # |
| S | 111 | 92 | LmdV:108 |
| Y | 112 | 93 | LmdV:109 |
| D | 113 | 94 | LmdV:110 |
| T | 114 | 95 | LmdV:111 |
| S | 115 | 96 | LmdV:112 |
| - | 115.1 | 96.1 | LmdV:113 |
| - | 115.2 | 96.2 | LmdV:114 |
| - | 115.3 | 96.3 | LmdV:115 |
| - | 115.4 | 96.4 | LmdV:116 |
| - | 115.5 | 96.5 | LmdV:117 |
| - | 115.6 | 96.6 | LmdV:118 |
| - | 115.7 | 96.7 | LmdV:119 |
| - | 115.8 | 96.8 | LmdV:120 |
| - | 115.9 | 96.9 | LmdV:121 |
| - | 115.10 | 96.10 | LmdV:122 |
| - | 115.11 | 96.11 | LmdV:123 |
| - | 115.12 | 96.12 | LmdV:124 |
| - | 115.13 | 96.13 | LmdV:125 |
| - | 115.14 | 96.14 | LmdV:126 |
| - | 115.15 | 96.15 | LmdV:127 |
| - | 115.16 | 96.16 | LmdV:128 |
| - | 115.17 | 96.17 | LmdV:129 |
| - | 115.18 | 96.18 | LmdV:130 |
| - | 115.19 | 96.19 | LmdV:131 |
| - | 115.20 | 96.20 | LmdV:132 |
| - | 115.21 | 96.21 | LmdV:133 |
| L | 116 | 97 | LmdV:134 |
| N | 117 | 98 | LmdV:135 |
| G | 118 | 99 | LmdV:136 |
| W | 119 | 100 | LmdV:137 |
| A | 120 | 101 | LmdV:138 |
| F | 121 | 102 | LmdV:139 |
| G | 122 | 103 | LmdV:140 |
| G | 123 | 104 | LmdV:141 |
| G | 124 | 105 | LmdV:142 |
| T | 125 | 106 | LmdV:143 |
| K | 126 | 107 | LmdV:144 |
| L | 127 | 108 | LmdV:145 |
| T | 128 | 109 | LmdV:146 |
| V | 129 | 110 | LmdV:147 |
| L | 130 | 111 | LmdV:148 |
| G | 131 | 112 | LmdV:149 |

FIG. 6 Continued

| AB-000224_LS Light Chain | | | |
|---|---|---|---|
| Residue | Linear # | Mat. Linear # | ASN # |
| Q | 132 | 113 | LmdCnst-Ig:1 |
| P | 133 | 114 | LmdCnst-Ig:2 |
| K | 134 | 115 | LmdCnst-Ig:3 |
| A | 135 | 116 | LmdCnst-Ig:4 |
| A | 136 | 117 | LmdCnst-Ig:5 |
| P | 137 | 118 | LmdCnst-Ig:6 |
| S | 138 | 119 | LmdCnst-Ig:7 |
| V | 139 | 120 | LmdCnst-Ig:8 |
| T | 140 | 121 | LmdCnst-Ig:9 |
| L | 141 | 122 | LmdCnst-Ig:10 |
| F | 142 | 123 | LmdCnst-Ig:11 |
| P | 143 | 124 | LmdCnst-Ig:12 |
| P | 144 | 125 | LmdCnst-Ig:13 |
| S | 145 | 126 | LmdCnst-Ig:14 |
| S | 146 | 127 | LmdCnst-Ig:15 |
| E | 147 | 128 | LmdCnst-Ig:16 |
| - | 147.1 | 128.1 | LmdCnst-Ig:17 |
| - | 147.2 | 128.2 | LmdCnst-Ig:18 |
| E | 148 | 129 | LmdCnst-Ig:19 |
| L | 149 | 130 | LmdCnst-Ig:20 |
| - | 149.1 | 130.1 | LmdCnst-Ig:21 |
| - | 149.2 | 130.2 | LmdCnst-Ig:22 |
| Q | 150 | 131 | LmdCnst-Ig:23 |
| A | 151 | 132 | LmdCnst-Ig:24 |
| N | 152 | 133 | LmdCnst-Ig:25 |
| K | 153 | 134 | LmdCnst-Ig:26 |
| A | 154 | 135 | LmdCnst-Ig:27 |
| T | 155 | 136 | LmdCnst-Ig:28 |
| L | 156 | 137 | LmdCnst-Ig:29 |
| V | 157 | 138 | LmdCnst-Ig:30 |
| C | 158 | 139 | LmdCnst-Ig:31 |
| L | 159 | 140 | LmdCnst-Ig:32 |
| V | 160 | 141 | LmdCnst-Ig:33 |
| S | 161 | 142 | LmdCnst-Ig:34 |
| D | 162 | 143 | LmdCnst-Ig:35 |
| F | 163 | 144 | LmdCnst-Ig:36 |
| Y | 164 | 145 | LmdCnst-Ig:37 |
| P | 165 | 146 | LmdCnst-Ig:38 |
| - | 165.1 | 146.1 | LmdCnst-Ig:39 |
| - | 165.2 | 146.2 | LmdCnst-Ig:40 |
| G | 166 | 147 | LmdCnst-Ig:41 |
| A | 167 | 148 | LmdCnst-Ig:42 |

FIG. 6 Continued

| AB-000224_LS Light Chain | | | |
|---|---|---|---|
| Residue | Linear # | Mat. Linear # | ASN # |
| V | 168 | 149 | LmdCnst-Ig:43 |
| T | 169 | 150 | LmdCnst-Ig:44 |
| V | 170 | 151 | LmdCnst-Ig:45 |
| A | 171 | 152 | LmdCnst-Ig:46 |
| W | 172 | 153 | LmdCnst-Ig:47 |
| - | 172.1 | 153.1 | LmdCnst-Ig:48 |
| K | 173 | 154 | LmdCnst-Ig:49 |
| A | 174 | 155 | LmdCnst-Ig:50 |
| D | 175 | 156 | LmdCnst-Ig:51 |
| G | 176 | 157 | LmdCnst-Ig:52 |
| S | 177 | 158 | LmdCnst-Ig:53 |
| P | 178 | 159 | LmdCnst-Ig:54 |
| V | 179 | 160 | LmdCnst-Ig:55 |
| K | 180 | 161 | LmdCnst-Ig:56 |
| V | 181 | 162 | LmdCnst-Ig:57 |
| G | 182 | 163 | LmdCnst-Ig:58 |
| V | 183 | 164 | LmdCnst-Ig:59 |
| E | 184 | 165 | LmdCnst-Ig:60 |
| T | 185 | 166 | LmdCnst-Ig:61 |
| T | 186 | 167 | LmdCnst-Ig:62 |
| K | 187 | 168 | LmdCnst-Ig:63 |
| P | 188 | 169 | LmdCnst-Ig:64 |
| S | 189 | 170 | LmdCnst-Ig:65 |
| K | 190 | 171 | LmdCnst-Ig:66 |
| Q | 191 | 172 | LmdCnst-Ig:67 |
| - | 191.1 | 172.1 | LmdCnst-Ig:68 |
| - | 191.2 | 172.2 | LmdCnst-Ig:69 |
| - | 191.3 | 172.3 | LmdCnst-Ig:70 |
| - | 191.4 | 172.4 | LmdCnst-Ig:71 |
| - | 191.5 | 172.5 | LmdCnst-Ig:72 |
| S | 192 | 173 | LmdCnst-Ig:73 |
| N | 193 | 174 | LmdCnst-Ig:74 |
| N | 194 | 175 | LmdCnst-Ig:75 |
| K | 195 | 176 | LmdCnst-Ig:76 |
| Y | 196 | 177 | LmdCnst-Ig:77 |
| A | 197 | 178 | LmdCnst-Ig:78 |
| A | 198 | 179 | LmdCnst-Ig:79 |
| S | 199 | 180 | LmdCnst-Ig:80 |
| S | 200 | 181 | LmdCnst-Ig:81 |
| Y | 201 | 182 | LmdCnst-Ig:82 |
| L | 202 | 183 | LmdCnst-Ig:83 |
| S | 203 | 184 | LmdCnst-Ig:84 |

FIG. 6 Continued

| AB-000224_LS Light Chain | | | |
|---|---|---|---|
| Residue | Linear # | Mat. Linear # | ASN # |
| L | 204 | 185 | LmdCnst-Ig:85 |
| T | 205 | 186 | LmdCnst-Ig:86 |
| P | 206 | 187 | LmdCnst-Ig:87 |
| E | 207 | 188 | LmdCnst-Ig:88 |
| Q | 208 | 189 | LmdCnst-Ig:89 |
| W | 209 | 190 | LmdCnst-Ig:90 |
| - | 209.1 | 190.1 | LmdCnst-Ig:91 |
| K | 210 | 191 | LmdCnst-Ig:92 |
| S | 211 | 192 | LmdCnst-Ig:93 |
| H | 212 | 193 | LmdCnst-Ig:94 |
| R | 213 | 194 | LmdCnst-Ig:95 |
| S | 214 | 195 | LmdCnst-Ig:96 |
| - | 214.1 | 195.1 | LmdCnst-Ig:97 |
| - | 214.2 | 195.2 | LmdCnst-Ig:98 |
| Y | 215 | 196 | LmdCnst-Ig:99 |
| S | 216 | 197 | LmdCnst-Ig:100 |
| C | 217 | 198 | LmdCnst-Ig:101 |
| R | 218 | 199 | LmdCnst-Ig:102 |
| V | 219 | 200 | LmdCnst-Ig:103 |
| T | 220 | 201 | LmdCnst-Ig:104 |
| H | 221 | 202 | LmdCnst-Ig:105 |
| E | 222 | 203 | LmdCnst-Ig:106 |
| G | 223 | 204 | LmdCnst-Ig:107 |
| S | 224 | 205 | LmdCnst-Ig:108 |
| T | 225 | 206 | LmdCnst-Ig:109 |
| - | 225.1 | 206.1 | LmdCnst-Ig:110 |
| - | 225.2 | 206.2 | LmdCnst-Ig:111 |
| V | 226 | 207 | LmdCnst-Ig:112 |
| E | 227 | 208 | LmdCnst-Ig:113 |
| K | 228 | 209 | LmdCnst-Ig:114 |
| T | 229 | 210 | LmdCnst-Ig:115 |
| V | 230 | 211 | LmdCnst-Ig:116 |
| - | 230.1 | 211.1 | LmdCnst-Ig:117 |
| A | 231 | 212 | LmdCnst-Ig:118 |
| P | 232 | 213 | LmdCnst-Ig:119 |
| A | 233 | 214 | LmdCnst-Ig:120 |
| E | 234 | 215 | LmdCnst-Ig:121 |
| C | 235 | 216 | LmdCnst-Ig:122 |
| S | 236 | 217 | LmdCnst-Ig:123 |

FIG. 6 Continued

| AB-000224_LS_Heavy Chain | | | |
|---|---|---|---|
| Residue | Linear # | Mat. Linear # | ASN # |
| M | 1 | -22 | KLdr:-22 |
| D | 2 | -21 | KLdr:-21 |
| M | 3 | -20 | KLdr:-20 |
| R | 4 | -19 | KLdr:-19 |
| V | 5 | -18 | KLdr:-18 |
| P | 6 | -17 | KLdr:-17 |
| A | 7 | -16 | KLdr:-16 |
| Q | 8 | -15 | KLdr:-15 |
| L | 9 | -14 | KLdr:-14 |
| L | 10 | -13 | KLdr:-13 |
| G | 11 | -12 | KLdr:-12 |
| L | 12 | -11 | KLdr:-11 |
| L | 13 | -10 | KLdr:-10 |
| L | 14 | -9 | KLdr:-9 |
| L | 15 | -8 | KLdr:-8 |
| W | 16 | -7 | KLdr:-7 |
| L | 17 | -6 | KLdr:-6 |
| R | 18 | -5 | KLdr:-5 |
| G | 19 | -4 | KLdr:-4 |
| A | 20 | -3 | KLdr:-3 |
| R | 21 | -2 | KLdr:-2 |
| C | 22 | -1 | KLdr:-1 |
| E | 23 | 1 | HV:1 |
| V | 24 | 2 | HV:2 |
| Q | 25 | 3 | HV:3 |
| L | 26 | 4 | HV:4 |
| V | 27 | 5 | HV:5 |
| E | 28 | 6 | HV:6 |
| S | 29 | 7 | HV:7 |
| - | 29.1 | 7.1 | HV:8 |
| G | 30 | 8 | HV:9 |
| G | 31 | 9 | HV:10 |
| G | 32 | 10 | HV:11 |
| L | 33 | 11 | HV:12 |
| V | 34 | 12 | HV:13 |
| Q | 35 | 13 | HV:14 |
| P | 36 | 14 | HV:15 |
| G | 37 | 15 | HV:16 |
| R | 38 | 16 | HV:17 |
| S | 39 | 17 | HV:18 |
| L | 40 | 18 | HV:19 |

FIG. 7

| AB-000224_LS_Heavy Chain | | | |
|---|---|---|---|
| Residue | Linear # | Mat. Linear # | ASN # |
| R | 41 | 19 | HV:20 |
| L | 42 | 20 | HV:21 |
| P | 43 | 21 | HV:22 |
| C | 44 | 22 | HV:23 |
| T | 45 | 23 | HV:24 |
| A | 46 | 24 | HV:25 |
| S | 47 | 25 | HV:26 |
| G | 48 | 26 | HV:27 |
| - | 48.1 | 26.1 | HV:28 |
| F | 49 | 27 | HV:29 |
| S | 50 | 28 | HV:30 |
| F | 51 | 29 | HV:31 |
| G | 52 | 30 | HV:32 |
| D | 53 | 31 | HV:33 |
| - | 53.1 | 31.1 | HV:34 |
| - | 53.2 | 31.2 | HV:35 |
| - | 53.3 | 31.3 | HV:36 |
| - | 53.4 | 31.4 | HV:37 |
| - | 53.5 | 31.5 | HV:38 |
| H | 54 | 32 | HV:39 |
| A | 55 | 33 | HV:40 |
| M | 56 | 34 | HV:41 |
| S | 57 | 35 | HV:42 |
| W | 58 | 36 | HV:43 |
| V | 59 | 37 | HV:44 |
| R | 60 | 38 | HV:45 |
| Q | 61 | 39 | HV:46 |
| A | 62 | 40 | HV:47 |
| P | 63 | 41 | HV:48 |
| G | 64 | 42 | HV:49 |
| K | 65 | 43 | HV:50 |
| G | 66 | 44 | HV:51 |
| L | 67 | 45 | HV:52 |
| E | 68 | 46 | HV:53 |
| W | 69 | 47 | HV:54 |
| V | 70 | 48 | HV:55 |
| G | 71 | 49 | HV:56 |
| F | 72 | 50 | HV:57 |
| I | 73 | 51 | HV:58 |
| R | 74 | 52 | HV:59 |
| K | 75 | 53 | HV:60 |
| T | 76 | 54 | HV:61 |
| - | 76.1 | 54.1 | HV:62 |

FIG. 7 Continued

| AB-000224_LS_Heavy Chain | | | |
|---|---|---|---|
| Residue | Linear # | Mat. Linear # | ASN # |
| T | 77 | 55 | HV:63 |
| Y | 78 | 56 | HV:64 |
| G | 79 | 57 | HV:65 |
| A | 80 | 58 | HV:66 |
| T | 81 | 59 | HV:67 |
| T | 82 | 60 | HV:68 |
| H | 83 | 61 | HV:69 |
| Y | 84 | 62 | HV:70 |
| A | 85 | 63 | HV:71 |
| A | 86 | 64 | HV:72 |
| A | 87 | 65 | HV:73 |
| V | 88 | 66 | HV:74 |
| R | 89 | 67 | HV:75 |
| G | 90 | 68 | HV:76 |
| R | 91 | 69 | HV:77 |
| F | 92 | 70 | HV:78 |
| T | 93 | 71 | HV:79 |
| I | 94 | 72 | HV:80 |
| S | 95 | 73 | HV:81 |
| R | 96 | 74 | HV:82 |
| D | 97 | 75 | HV:83 |
| D | 98 | 76 | HV:84 |
| S | 99 | 77 | HV:85 |
| K | 100 | 78 | HV:86 |
| S | 101 | 79 | HV:87 |
| I | 102 | 80 | HV:88 |
| V | 103 | 81 | HV:89 |
| Y | 104 | 82 | HV:90 |
| L | 105 | 83 | HV:91 |
| Q | 106 | 84 | HV:92 |
| M | 107 | 85 | HV:93 |
| N | 108 | 86 | HV:94 |
| S | 109 | 87 | HV:95 |
| L | 110 | 88 | HV:96 |
| K | 111 | 89 | HV:97 |
| T | 112 | 90 | HV:98 |
| E | 113 | 91 | HV:99 |
| D | 114 | 92 | HV:100 |
| T | 115 | 93 | HV:101 |
| A | 116 | 94 | HV:102 |
| V | 117 | 95 | HV:103 |
| Y | 118 | 96 | HV:104 |
| F | 119 | 97 | HV:105 |

FIG. 7 Continued

| AB-000224_LS_Heavy Chain | | | |
|---|---|---|---|
| Residue | Linear # | Mat. Linear # | ASN # |
| C | 120 | 98 | HV:106 |
| T | 121 | 99 | HV:107 |
| R | 122 | 100 | HV:108 |
| V | 123 | 101 | HV:109 |
| Q | 124 | 102 | HV:110 |
| L | 125 | 103 | HV:111 |
| D | 126 | 104 | HV:112 |
| Y | 127 | 105 | HV:113 |
| G | 128 | 106 | HV:114 |
| P | 129 | 107 | HV:115 |
| - | 129.1 | 107.1 | HV:116 |
| - | 129.2 | 107.2 | HV:117 |
| - | 129.3 | 107.3 | HV:118 |
| - | 129.4 | 107.4 | HV:119 |
| - | 129.5 | 107.5 | HV:120 |
| - | 129.6 | 107.6 | HV:121 |
| - | 129.7 | 107.7 | HV:122 |
| - | 129.8 | 107.8 | HV:123 |
| - | 129.9 | 107.9 | HV:124 |
| - | 129.10 | 107.10 | HV:125 |
| - | 129.11 | 107.11 | HV:126 |
| - | 129.12 | 107.12 | HV:127 |
| - | 129.13 | 107.13 | HV:128 |
| - | 129.14 | 107.14 | HV:129 |
| G | 130 | 108 | HV:130 |
| Y | 131 | 109 | HV:131 |
| Q | 132 | 110 | HV:132 |
| Y | 133 | 111 | HV:133 |
| Y | 134 | 112 | HV:134 |
| G | 135 | 113 | HV:135 |
| M | 136 | 114 | HV:136 |
| D | 137 | 115 | HV:137 |
| V | 138 | 116 | HV:138 |
| W | 139 | 117 | HV:139 |
| G | 140 | 118 | HV:140 |
| Q | 141 | 119 | HV:141 |
| G | 142 | 120 | HV:142 |
| T | 143 | 121 | HV:143 |
| T | 144 | 122 | HV:144 |
| V | 145 | 123 | HV:145 |
| T | 146 | 124 | HV:146 |
| V | 147 | 125 | HV:147 |
| S | 148 | 126 | HV:148 |

FIG. 7 Continued

| AB-000224_LS_Heavy Chain | | | |
|---|---|---|---|
| Residue | Linear # | Mat. Linear # | ASN # |
| S | 149 | 127 | HV:149 |
| - | 149.1 | 127.1 | HCnst-Ig:1 |
| - | 149.2 | 127.2 | HCnst-Ig:2 |
| A | 150 | 128 | HCnst-Ig:3 |
| S | 151 | 129 | HCnst-Ig:4 |
| T | 152 | 130 | HCnst-Ig:5 |
| K | 153 | 131 | HCnst-Ig:6 |
| G | 154 | 132 | HCnst-Ig:7 |
| P | 155 | 133 | HCnst-Ig:8 |
| S | 156 | 134 | HCnst-Ig:9 |
| V | 157 | 135 | HCnst-Ig:10 |
| F | 158 | 136 | HCnst-Ig:11 |
| P | 159 | 137 | HCnst-Ig:12 |
| L | 160 | 138 | HCnst-Ig:13 |
| A | 161 | 139 | HCnst-Ig:14 |
| P | 162 | 140 | HCnst-Ig:15 |
| - | 162.1 | 140.1 | HCnst-Ig:16 |
| S | 163 | 141 | HCnst-Ig:17 |
| - | 163.1 | 141.1 | HCnst-Ig:18 |
| S | 164 | 142 | HCnst-Ig:19 |
| K | 165 | 143 | HCnst-Ig:20 |
| S | 166 | 144 | HCnst-Ig:21 |
| T | 167 | 145 | HCnst-Ig:22 |
| S | 168 | 146 | HCnst-Ig:23 |
| G | 169 | 147 | HCnst-Ig:24 |
| G | 170 | 148 | HCnst-Ig:25 |
| T | 171 | 149 | HCnst-Ig:26 |
| A | 172 | 150 | HCnst-Ig:27 |
| A | 173 | 151 | HCnst-Ig:28 |
| L | 174 | 152 | HCnst-Ig:29 |
| G | 175 | 153 | HCnst-Ig:30 |
| C | 176 | 154 | HCnst-Ig:31 |
| L | 177 | 155 | HCnst-Ig:32 |
| V | 178 | 156 | HCnst-Ig:33 |
| K | 179 | 157 | HCnst-Ig:34 |
| D | 180 | 158 | HCnst-Ig:35 |
| Y | 181 | 159 | HCnst-Ig:36 |
| F | 182 | 160 | HCnst-Ig:37 |
| P | 183 | 161 | HCnst-Ig:38 |
| - | 183.1 | 161.1 | HCnst-Ig:39 |
| - | 183.2 | 161.2 | HCnst-Ig:40 |
| E | 184 | 162 | HCnst-Ig:41 |
| P | 185 | 163 | HCnst-Ig:42 |

FIG. 7 Continued

| AB-000224_LS_Heavy Chain | | | |
|---|---|---|---|
| Residue | Linear # | Mat. Linear # | ASN # |
| V | 186 | 164 | HCnst-Ig:43 |
| T | 187 | 165 | HCnst-Ig:44 |
| V | 188 | 166 | HCnst-Ig:45 |
| S | 189 | 167 | HCnst-Ig:46 |
| W | 190 | 168 | HCnst-Ig:47 |
| - | 190.1 | 168.1 | HCnst-Ig:48 |
| N | 191 | 169 | HCnst-Ig:49 |
| S | 192 | 170 | HCnst-Ig:50 |
| G | 193 | 171 | HCnst-Ig:51 |
| A | 194 | 172 | HCnst-Ig:52 |
| L | 195 | 173 | HCnst-Ig:53 |
| T | 196 | 174 | HCnst-Ig:54 |
| S | 197 | 175 | HCnst-Ig:55 |
| G | 198 | 176 | HCnst-Ig:56 |
| V | 199 | 177 | HCnst-Ig:57 |
| H | 200 | 178 | HCnst-Ig:58 |
| T | 201 | 179 | HCnst-Ig:59 |
| - | 201.1 | 179.1 | HCnst-Ig:60 |
| - | 201.2 | 179.2 | HCnst-Ig:61 |
| - | 201.3 | 179.3 | HCnst-Ig:62 |
| F | 202 | 180 | HCnst-Ig:63 |
| P | 203 | 181 | HCnst-Ig:64 |
| A | 204 | 182 | HCnst-Ig:65 |
| V | 205 | 183 | HCnst-Ig:66 |
| L | 206 | 184 | HCnst-Ig:67 |
| Q | 207 | 185 | HCnst-Ig:68 |
| - | 207.1 | 185.1 | HCnst-Ig:69 |
| - | 207.2 | 185.2 | HCnst-Ig:70 |
| - | 207.3 | 185.3 | HCnst-Ig:71 |
| - | 207.4 | 185.4 | HCnst-Ig:72 |
| S | 208 | 186 | HCnst-Ig:73 |
| S | 209 | 187 | HCnst-Ig:74 |
| G | 210 | 188 | HCnst-Ig:75 |
| L | 211 | 189 | HCnst-Ig:76 |
| Y | 212 | 190 | HCnst-Ig:77 |
| S | 213 | 191 | HCnst-Ig:78 |
| L | 214 | 192 | HCnst-Ig:79 |
| S | 215 | 193 | HCnst-Ig:80 |
| S | 216 | 194 | HCnst-Ig:81 |
| V | 217 | 195 | HCnst-Ig:82 |
| V | 218 | 196 | HCnst-Ig:83 |
| T | 219 | 197 | HCnst-Ig:84 |
| V | 220 | 198 | HCnst-Ig:85 |

FIG. 7 Continued

| AB-000224_LS_Heavy Chain | | | |
|---|---|---|---|
| Residue | Linear # | Mat. Linear # | ASN # |
| P | 221 | 199 | HCnst-Ig:86 |
| S | 222 | 200 | HCnst-Ig:87 |
| S | 223 | 201 | HCnst-Ig:88 |
| S | 224 | 202 | HCnst-Ig:89 |
| L | 225 | 203 | HCnst-Ig:90 |
| - | 225.1 | 203.1 | HCnst-Ig:91 |
| G | 226 | 204 | HCnst-Ig:92 |
| T | 227 | 205 | HCnst-Ig:93 |
| Q | 228 | 206 | HCnst-Ig:94 |
| T | 229 | 207 | HCnst-Ig:95 |
| - | 229.1 | 207.1 | HCnst-Ig:96 |
| - | 229.2 | 207.2 | HCnst-Ig:97 |
| - | 229.3 | 207.3 | HCnst-Ig:98 |
| Y | 230 | 208 | HCnst-Ig:99 |
| I | 231 | 209 | HCnst-Ig:100 |
| C | 232 | 210 | HCnst-Ig:101 |
| N | 233 | 211 | HCnst-Ig:102 |
| V | 234 | 212 | HCnst-Ig:103 |
| N | 235 | 213 | HCnst-Ig:104 |
| H | 236 | 214 | HCnst-Ig:105 |
| K | 237 | 215 | HCnst-Ig:106 |
| P | 238 | 216 | HCnst-Ig:107 |
| S | 239 | 217 | HCnst-Ig:108 |
| N | 240 | 218 | HCnst-Ig:109 |
| - | 240.1 | 218.1 | HCnst-Ig:110 |
| - | 240.2 | 218.2 | HCnst-Ig:111 |
| T | 241 | 219 | HCnst-Ig:112 |
| K | 242 | 220 | HCnst-Ig:113 |
| V | 243 | 221 | HCnst-Ig:114 |
| D | 244 | 222 | HCnst-Ig:115 |
| K | 245 | 223 | HCnst-Ig:116 |
| - | 245.1 | 223.1 | HCnst-Ig:117 |
| K | 246 | 224 | HCnst-Ig:118 |
| V | 247 | 225 | HCnst-Ig:119 |
| - | 247.1 | 225.1 | HCnst-Ig:120 |
| - | 247.2 | 225.2 | HCnst-Ig:121 |
| - | 247.3 | 225.3 | HCnst-Ig:122 |
| - | 247.4 | 225.4 | HCnst-Ig:123 |
| - | 247.5 | 225.1 | Hinge:1 |
| - | 247.6 | 225.2 | Hinge:2 |
| - | 247.7 | 225.3 | Hinge:3 |
| - | 247.8 | 225.4 | Hinge:4 |
| - | 247.9 | 225.5 | Hinge:5 |

FIG. 7 Continued

| AB-000224_LS_Heavy Chain | | | |
|---|---|---|---|
| Residue | Linear # | Mat. Linear # | ASN # |
| - | 247.10 | 225.6 | Hinge:6 |
| - | 247.11 | 225.7 | Hinge:7 |
| - | 247.12 | 225.8 | Hinge:8 |
| - | 247.13 | 225.9 | Hinge:9 |
| - | 247.14 | 225.10 | Hinge:10 |
| - | 247.15 | 225.11 | Hinge:11 |
| - | 247.16 | 225.12 | Hinge:12 |
| - | 247.17 | 225.13 | Hinge:13 |
| - | 247.18 | 225.14 | Hinge:14 |
| - | 247.19 | 225.15 | Hinge:15 |
| - | 247.20 | 225.16 | Hinge:16 |
| - | 247.21 | 225.17 | Hinge:17 |
| - | 247.22 | 225.18 | Hinge:18 |
| - | 247.23 | 225.19 | Hinge:19 |
| - | 247.24 | 225.20 | Hinge:20 |
| - | 247.25 | 225.21 | Hinge:21 |
| - | 247.26 | 225.22 | Hinge:22 |
| - | 247.27 | 225.23 | Hinge:23 |
| - | 247.28 | 225.24 | Hinge:24 |
| - | 247.29 | 225.25 | Hinge:25 |
| - | 247.30 | 225.26 | Hinge:26 |
| - | 247.31 | 225.27 | Hinge:27 |
| - | 247.32 | 225.28 | Hinge:28 |
| - | 247.33 | 225.29 | Hinge:29 |
| - | 247.34 | 225.30 | Hinge:30 |
| - | 247.35 | 225.31 | Hinge:31 |
| - | 247.36 | 225.32 | Hinge:32 |
| - | 247.37 | 225.33 | Hinge:33 |
| - | 247.38 | 225.34 | Hinge:34 |
| - | 247.39 | 225.35 | Hinge:35 |
| - | 247.40 | 225.36 | Hinge:36 |
| - | 247.41 | 225.37 | Hinge:37 |
| - | 247.42 | 225.38 | Hinge:38 |
| - | 247.43 | 225.39 | Hinge:39 |
| - | 247.44 | 225.40 | Hinge:40 |
| - | 247.45 | 225.41 | Hinge:41 |
| - | 247.46 | 225.42 | Hinge:42 |
| - | 247.47 | 225.43 | Hinge:43 |
| - | 247.48 | 225.44 | Hinge:44 |
| - | 247.49 | 225.45 | Hinge:45 |
| - | 247.50 | 225.46 | Hinge:46 |
| - | 247.51 | 225.47 | Hinge:47 |
| - | 247.52 | 225.48 | Hinge:48 |

FIG. 7 Continued

| AB-000224_LS_Heavy Chain | | | |
|---|---|---|---|
| Residue | Linear # | Mat. Linear # | ASN # |
| - | 247.53 | 225.49 | Hinge:49 |
| - | 247.54 | 225.50 | Hinge:50 |
| - | 247.55 | 225.51 | Hinge:51 |
| - | 247.56 | 225.52 | Hinge:52 |
| - | 247.57 | 225.53 | Hinge:53 |
| - | 247.58 | 225.54 | Hinge:54 |
| - | 247.59 | 225.55 | Hinge:55 |
| - | 247.60 | 225.56 | Hinge:56 |
| - | 247.61 | 225.57 | Hinge:57 |
| - | 247.62 | 225.58 | Hinge:58 |
| - | 247.63 | 225.59 | Hinge:59 |
| - | 247.64 | 225.60 | Hinge:60 |
| - | 247.65 | 225.61 | Hinge:61 |
| - | 247.66 | 225.62 | Hinge:62 |
| - | 247.67 | 225.63 | Hinge:63 |
| - | 247.68 | 225.64 | Hinge:64 |
| - | 247.69 | 225.65 | Hinge:65 |
| - | 247.70 | 225.66 | Hinge:66 |
| - | 247.71 | 225.67 | Hinge:67 |
| - | 247.72 | 225.68 | Hinge:68 |
| - | 247.73 | 225.69 | Hinge:69 |
| - | 247.74 | 225.70 | Hinge:70 |
| - | 247.75 | 225.71 | Hinge:71 |
| - | 247.76 | 225.72 | Hinge:72 |
| - | 247.77 | 225.73 | Hinge:73 |
| - | 247.78 | 225.74 | Hinge:74 |
| - | 247.79 | 225.75 | Hinge:75 |
| - | 247.80 | 225.76 | Hinge:76 |
| - | 247.81 | 225.77 | Hinge:77 |
| - | 247.82 | 225.78 | Hinge:78 |
| - | 247.83 | 225.79 | Hinge:79 |
| - | 247.84 | 225.80 | Hinge:80 |
| - | 247.85 | 225.81 | Hinge:81 |
| - | 247.86 | 225.82 | Hinge:82 |
| - | 247.87 | 225.83 | Hinge:83 |
| - | 247.88 | 225.84 | Hinge:84 |
| - | 247.89 | 225.85 | Hinge:85 |
| - | 247.90 | 225.86 | Hinge:86 |
| - | 247.91 | 225.87 | Hinge:87 |
| - | 247.92 | 225.88 | Hinge:88 |
| - | 247.93 | 225.89 | Hinge:89 |
| - | 247.94 | 225.90 | Hinge:90 |
| - | 247.95 | 225.91 | Hinge:91 |

FIG. 7 Continued

| AB-000224_LS_Heavy Chain | | | |
|---|---|---|---|
| Residue | Linear # | Mat. Linear # | ASN # |
| - | 247.96 | 225.92 | Hinge:92 |
| - | 247.97 | 225.93 | Hinge:93 |
| - | 247.98 | 225.94 | Hinge:94 |
| - | 247.99 | 225.95 | Hinge:95 |
| E | 248 | 226 | Hinge:96 |
| P | 249 | 227 | Hinge:97 |
| K | 250 | 228 | Hinge:98 |
| S | 251 | 229 | Hinge:99 |
| - | 251.1 | 229.1 | Hinge:100 |
| - | 251.2 | 229.2 | Hinge:101 |
| - | 251.3 | 229.3 | Hinge:102 |
| - | 251.4 | 229.4 | Hinge:103 |
| - | 251.5 | 229.5 | Hinge:104 |
| - | 251.6 | 229.6 | Hinge:105 |
| - | 251.7 | 229.7 | Hinge:106 |
| C | 252 | 230 | Hinge:107 |
| D | 253 | 231 | Hinge:108 |
| K | 254 | 232 | Hinge:109 |
| T | 255 | 233 | Hinge:110 |
| H | 256 | 234 | Hinge:111 |
| T | 257 | 235 | Hinge:112 |
| C | 258 | 236 | Hinge:113 |
| P | 259 | 237 | Hinge:114 |
| P | 260 | 238 | Hinge:115 |
| C | 261 | 239 | Hinge:116 |
| P | 262 | 240 | Hinge:117 |
| A | 263 | 241 | Hinge:118 |
| P | 264 | 242 | Hinge:119 |
| E | 265 | 243 | Hinge:120 |
| L | 266 | 244 | Hinge:121 |
| L | 267 | 245 | Hinge:122 |
| G | 268 | 246 | Hinge:123 |
| - | 268.1 | 246.1 | Fc-N:1 |
| - | 268.2 | 246.2 | Fc-N:2 |
| - | 268.3 | 246.3 | Fc-N:3 |
| - | 268.4 | 246.4 | Fc-N:4 |
| G | 269 | 247 | Fc-N:5 |
| P | 270 | 248 | Fc-N:6 |
| S | 271 | 249 | Fc-N:7 |
| V | 272 | 250 | Fc-N:8 |
| F | 273 | 251 | Fc-N:9 |
| L | 274 | 252 | Fc-N:10 |
| F | 275 | 253 | Fc-N:11 |

FIG. 7 Continued

| AB-000224_LS_Heavy Chain | | | |
|---|---|---|---|
| Residue | Linear # | Mat. Linear # | ASN # |
| P | 276 | 254 | Fc-N:12 |
| P | 277 | 255 | Fc-N:13 |
| - | 277.1 | 255.1 | Fc-N:14 |
| K | 278 | 256 | Fc-N:15 |
| P | 279 | 257 | Fc-N:16 |
| K | 280 | 258 | Fc-N:17 |
| - | 280.1 | 258.1 | Fc-N:18 |
| D | 281 | 259 | Fc-N:19 |
| T | 282 | 260 | Fc-N:20 |
| L | 283 | 261 | Fc-N:21 |
| M | 284 | 262 | Fc-N:22 |
| I | 285 | 263 | Fc-N:23 |
| S | 286 | 264 | Fc-N:24 |
| R | 287 | 265 | Fc-N:25 |
| T | 288 | 266 | Fc-N:26 |
| P | 289 | 267 | Fc-N:27 |
| E | 290 | 268 | Fc-N:28 |
| V | 291 | 269 | Fc-N:29 |
| T | 292 | 270 | Fc-N:30 |
| C | 293 | 271 | Fc-N:31 |
| V | 294 | 272 | Fc-N:32 |
| V | 295 | 273 | Fc-N:33 |
| V | 296 | 274 | Fc-N:34 |
| D | 297 | 275 | Fc-N:35 |
| V | 298 | 276 | Fc-N:36 |
| S | 299 | 277 | Fc-N:37 |
| H | 300 | 278 | Fc-N:38 |
| E | 301 | 279 | Fc-N:39 |
| D | 302 | 280 | Fc-N:40 |
| P | 303 | 281 | Fc-N:41 |
| E | 304 | 282 | Fc-N:42 |
| V | 305 | 283 | Fc-N:43 |
| K | 306 | 284 | Fc-N:44 |
| F | 307 | 285 | Fc-N:45 |
| N | 308 | 286 | Fc-N:46 |
| W | 309 | 287 | Fc-N:47 |
| - | 309.1 | 287.1 | Fc-N:48 |
| Y | 310 | 288 | Fc-N:49 |
| V | 311 | 289 | Fc-N:50 |
| D | 312 | 290 | Fc-N:51 |
| G | 313 | 291 | Fc-N:52 |
| V | 314 | 292 | Fc-N:53 |
| E | 315 | 293 | Fc-N:54 |

FIG. 7 Continued

| AB-000224_LS_Heavy Chain | | | |
|---|---|---|---|
| Residue | Linear # | Mat. Linear # | ASN # |
| - | 315.1 | 293.1 | Fc-N:55 |
| - | 315.2 | 293.2 | Fc-N:56 |
| V | 316 | 294 | Fc-N:57 |
| H | 317 | 295 | Fc-N:58 |
| N | 318 | 296 | Fc-N:59 |
| A | 319 | 297 | Fc-N:60 |
| K | 320 | 298 | Fc-N:61 |
| T | 321 | 299 | Fc-N:62 |
| K | 322 | 300 | Fc-N:63 |
| P | 323 | 301 | Fc-N:64 |
| R | 324 | 302 | Fc-N:65 |
| E | 325 | 303 | Fc-N:66 |
| E | 326 | 304 | Fc-N:67 |
| Q | 327 | 305 | Fc-N:68 |
| - | 327.1 | 305.1 | Fc-N:69 |
| - | 327.2 | 305.2 | Fc-N:70 |
| - | 327.3 | 305.3 | Fc-N:71 |
| - | 327.4 | 305.4 | Fc-N:72 |
| Y | 328 | 306 | Fc-N:73 |
| N | 329 | 307 | Fc-N:74 |
| S | 330 | 308 | Fc-N:75 |
| T | 331 | 309 | Fc-N:76 |
| Y | 332 | 310 | Fc-N:77 |
| R | 333 | 311 | Fc-N:78 |
| V | 334 | 312 | Fc-N:79 |
| V | 335 | 313 | Fc-N:80 |
| S | 336 | 314 | Fc-N:81 |
| V | 337 | 315 | Fc-N:82 |
| L | 338 | 316 | Fc-N:83 |
| T | 339 | 317 | Fc-N:84 |
| V | 340 | 318 | Fc-N:85 |
| L | 341 | 319 | Fc-N:86 |
| H | 342 | 320 | Fc-N:87 |
| Q | 343 | 321 | Fc-N:88 |
| D | 344 | 322 | Fc-N:89 |
| W | 345 | 323 | Fc-N:90 |
| - | 345.1 | 323.1 | Fc-N:91 |
| L | 346 | 324 | Fc-N:92 |
| N | 347 | 325 | Fc-N:93 |
| G | 348 | 326 | Fc-N:94 |
| K | 349 | 327 | Fc-N:95 |
| E | 350 | 328 | Fc-N:96 |
| - | 350.1 | 328.1 | Fc-N:97 |

FIG. 7 Continued

| AB-000224_LS_Heavy Chain | | | |
|---|---|---|---|
| Residue | Linear # | Mat. Linear # | ASN # |
| - | 350.2 | 328.2 | Fc-N:98 |
| Y | 351 | 329 | Fc-N:99 |
| K | 352 | 330 | Fc-N:100 |
| C | 353 | 331 | Fc-N:101 |
| K | 354 | 332 | Fc-N:102 |
| V | 355 | 333 | Fc-N:103 |
| S | 356 | 334 | Fc-N:104 |
| N | 357 | 335 | Fc-N:105 |
| K | 358 | 336 | Fc-N:106 |
| A | 359 | 337 | Fc-N:107 |
| L | 360 | 338 | Fc-N:108 |
| P | 361 | 339 | Fc-N:109 |
| - | 361.1 | 339.1 | Fc-N:110 |
| - | 361.2 | 339.2 | Fc-N:111 |
| A | 362 | 340 | Fc-N:112 |
| P | 363 | 341 | Fc-N:113 |
| I | 364 | 342 | Fc-N:114 |
| E | 365 | 343 | Fc-N:115 |
| K | 366 | 344 | Fc-N:116 |
| T | 367 | 345 | Fc-N:117 |
| I | 368 | 346 | Fc-N:118 |
| S | 369 | 347 | Fc-N:119 |
| K | 370 | 348 | Fc-N:120 |
| A | 371 | 349 | Fc-N:121 |
| K | 372 | 350 | Fc-N:122 |
| G | 373 | 351 | Fc-N:123 |
| - | 373.1 | 351.1 | Fc-C:1 |
| Q | 374 | 352 | Fc-C:2 |
| P | 375 | 353 | Fc-C:3 |
| R | 376 | 354 | Fc-C:4 |
| E | 377 | 355 | Fc-C:5 |
| P | 378 | 356 | Fc-C:6 |
| Q | 379 | 357 | Fc-C:7 |
| V | 380 | 358 | Fc-C:8 |
| Y | 381 | 359 | Fc-C:9 |
| T | 382 | 360 | Fc-C:10 |
| L | 383 | 361 | Fc-C:11 |
| P | 384 | 362 | Fc-C:12 |
| P | 385 | 363 | Fc-C:13 |
| - | 385.1 | 363.1 | Fc-C:14 |
| S | 386 | 364 | Fc-C:15 |
| R | 387 | 365 | Fc-C:16 |
| D | 388 | 366 | Fc-C:17 |

FIG. 7 Continued

| AB-000224_LS_Heavy Chain | | | |
|---|---|---|---|
| Residue | Linear # | Mat. Linear # | ASN # |
| - | 388.1 | 366.1 | Fc-C:18 |
| E | 389 | 367 | Fc-C:19 |
| L | 390 | 368 | Fc-C:20 |
| - | 390.1 | 368.1 | Fc-C:21 |
| - | 390.2 | 368.2 | Fc-C:22 |
| T | 391 | 369 | Fc-C:23 |
| K | 392 | 370 | Fc-C:24 |
| N | 393 | 371 | Fc-C:25 |
| Q | 394 | 372 | Fc-C:26 |
| V | 395 | 373 | Fc-C:27 |
| S | 396 | 374 | Fc-C:28 |
| L | 397 | 375 | Fc-C:29 |
| T | 398 | 376 | Fc-C:30 |
| C | 399 | 377 | Fc-C:31 |
| L | 400 | 378 | Fc-C:32 |
| V | 401 | 379 | Fc-C:33 |
| K | 402 | 380 | Fc-C:34 |
| G | 403 | 381 | Fc-C:35 |
| F | 404 | 382 | Fc-C:36 |
| Y | 405 | 383 | Fc-C:37 |
| P | 406 | 384 | Fc-C:38 |
| - | 406.1 | 384.1 | Fc-C:39 |
| - | 406.2 | 384.2 | Fc-C:40 |
| S | 407 | 385 | Fc-C:41 |
| D | 408 | 386 | Fc-C:42 |
| I | 409 | 387 | Fc-C:43 |
| A | 410 | 388 | Fc-C:44 |
| V | 411 | 389 | Fc-C:45 |
| E | 412 | 390 | Fc-C:46 |
| W | 413 | 391 | Fc-C:47 |
| - | 413.1 | 391.1 | Fc-C:48 |
| E | 414 | 392 | Fc-C:49 |
| S | 415 | 393 | Fc-C:50 |
| N | 416 | 394 | Fc-C:51 |
| G | 417 | 395 | Fc-C:52 |
| Q | 418 | 396 | Fc-C:53 |
| P | 419 | 397 | Fc-C:54 |
| - | 419.1 | 397.1 | Fc-C:55 |
| - | 419.2 | 397.2 | Fc-C:56 |
| E | 420 | 398 | Fc-C:57 |
| N | 421 | 399 | Fc-C:58 |
| N | 422 | 400 | Fc-C:59 |
| Y | 423 | 401 | Fc-C:60 |

FIG. 7 Continued

| AB-000224_LS_Heavy Chain | | | |
|---|---|---|---|
| Residue | Linear # | Mat. Linear # | ASN # |
| K | 424 | 402 | Fc-C:61 |
| T | 425 | 403 | Fc-C:62 |
| T | 426 | 404 | Fc-C:63 |
| P | 427 | 405 | Fc-C:64 |
| P | 428 | 406 | Fc-C:65 |
| V | 429 | 407 | Fc-C:66 |
| L | 430 | 408 | Fc-C:67 |
| D | 431 | 409 | Fc-C:68 |
| - | 431.1 | 409.1 | Fc-C:69 |
| - | 431.2 | 409.2 | Fc-C:70 |
| - | 431.3 | 409.3 | Fc-C:71 |
| - | 431.4 | 409.4 | Fc-C:72 |
| S | 432 | 410 | Fc-C:73 |
| D | 433 | 411 | Fc-C:74 |
| G | 434 | 412 | Fc-C:75 |
| S | 435 | 413 | Fc-C:76 |
| F | 436 | 414 | Fc-C:77 |
| F | 437 | 415 | Fc-C:78 |
| L | 438 | 416 | Fc-C:79 |
| Y | 439 | 417 | Fc-C:80 |
| S | 440 | 418 | Fc-C:81 |
| K | 441 | 419 | Fc-C:82 |
| L | 442 | 420 | Fc-C:83 |
| T | 443 | 421 | Fc-C:84 |
| V | 444 | 422 | Fc-C:85 |
| D | 445 | 423 | Fc-C:86 |
| K | 446 | 424 | Fc-C:87 |
| S | 447 | 425 | Fc-C:88 |
| R | 448 | 426 | Fc-C:89 |
| W | 449 | 427 | Fc-C:90 |
| - | 449.1 | 427.1 | Fc-C:91 |
| Q | 450 | 428 | Fc-C:92 |
| Q | 451 | 429 | Fc-C:93 |
| G | 452 | 430 | Fc-C:94 |
| N | 453 | 431 | Fc-C:95 |
| V | 454 | 432 | Fc-C:96 |
| - | 454.1 | 432.1 | Fc-C:97 |
| - | 454.2 | 432.2 | Fc-C:98 |
| F | 455 | 433 | Fc-C:99 |
| S | 456 | 434 | Fc-C:100 |
| C | 457 | 435 | Fc-C:101 |
| S | 458 | 436 | Fc-C:102 |
| V | 459 | 437 | Fc-C:103 |

FIG. 7 Continued

| AB-000224_LS_Heavy Chain | | | |
|---|---|---|---|
| Residue | Linear # | Mat. Linear # | ASN # |
| L | 460 | 438 | Fc-C:104 |
| H | 461 | 439 | Fc-C:105 |
| E | 462 | 440 | Fc-C:106 |
| A | 463 | 441 | Fc-C:107 |
| L | 464 | 442 | Fc-C:108 |
| H | 465 | 443 | Fc-C:109 |
| - | 465.1 | 443.1 | Fc-C:110 |
| - | 465.2 | 443.2 | Fc-C:111 |
| S | 466 | 444 | Fc-C:112 |
| H | 467 | 445 | Fc-C:113 |
| Y | 468 | 446 | Fc-C:114 |
| T | 469 | 447 | Fc-C:115 |
| - | 469.1 | 447.1 | Fc-C:116 |
| Q | 470 | 448 | Fc-C:117 |
| K | 471 | 449 | Fc-C:118 |
| S | 472 | 450 | Fc-C:119 |
| L | 473 | 451 | Fc-C:120 |
| S | 474 | 452 | Fc-C:121 |
| L | 475 | 453 | Fc-C:122 |
| S | 476 | 454 | Fc-C:123 |
| P | 477 | 455 | HCnst-Po:1 |
| G | 478 | 456 | HCnst-Po:2 |
| K | 479 | 457 | HCnst-Po:3 |
| - | 479.1 | 457.1 | HCnst-Po:4 |
| - | 479.2 | 457.2 | HCnst-Po:5 |
| - | 479.3 | 457.3 | HCnst-Po:6 |
| - | 479.4 | 457.4 | HCnst-Po:7 |
| - | 479.5 | 457.5 | HCnst-Po:8 |
| - | 479.6 | 457.6 | HCnst-Po:9 |
| - | 479.7 | 457.7 | HCnst-Po:10 |
| - | 479.8 | 457.8 | HCnst-Po:11 |
| - | 479.9 | 457.9 | HCnst-Po:12 |
| - | 479.10 | 457.10 | HCnst-Po:13 |
| - | 479.11 | 457.11 | HCnst-Po:14 |
| - | 479.12 | 457.12 | HCnst-Po:15 |
| - | 479.13 | 457.13 | HCnst-Po:16 |
| - | 479.14 | 457.14 | HCnst-Po:17 |
| - | 479.15 | 457.15 | HCnst-Po:18 |
| - | 479.16 | 457.16 | HCnst-Po:19 |
| - | 479.17 | 457.17 | HCnst-Po:20 |
| - | 479.18 | 457.18 | HCnst-Po:21 |
| - | 479.19 | 457.19 | HCnst-Po:22 |
| - | 479.20 | 457.20 | HCnst-Po:23 |

FIG. 7 Continued

| AB-000224_LS_Heavy Chain | | | |
|---|---|---|---|
| Residue | Linear # | Mat. Linear # | ASN # |
| - | 479.21 | 457.21 | HCnst-Po:24 |
| - | 479.22 | 457.22 | HCnst-Po:25 |
| - | 479.23 | 457.23 | HCnst-Po:26 |
| - | 479.24 | 457.24 | HCnst-Po:27 |
| - | 479.25 | 457.25 | HCnst-Po:28 |
| - | 479.26 | 457.26 | HCnst-Po:29 |
| - | 479.27 | 457.27 | HCnst-Po:30 |
| - | 479.28 | 457.28 | HCnst-Po:31 |
| - | 479.29 | 457.29 | HCnst-Po:32 |
| - | 479.30 | 457.30 | HCnst-Po:33 |
| - | 479.31 | 457.31 | HCnst-Po:34 |
| - | 479.32 | 457.32 | HCnst-Po:35 |
| - | 479.33 | 457.33 | HCnst-Po:36 |
| - | 479.34 | 457.34 | HCnst-Po:37 |
| - | 479.35 | 457.35 | HCnst-Po:38 |
| - | 479.36 | 457.36 | HCnst-Po:39 |
| - | 479.37 | 457.37 | HCnst-Po:40 |
| - | 479.38 | 457.38 | HCnst-Po:41 |
| - | 479.39 | 457.39 | HCnst-Po:42 |
| - | 479.40 | 457.40 | HCnst-Po:43 |
| - | 479.41 | 457.41 | HCnst-Po:44 |
| - | 479.42 | 457.42 | HCnst-Po:45 |
| - | 479.43 | 457.43 | HCnst-Po:46 |
| - | 479.44 | 457.44 | HCnst-Po:47 |
| - | 479.45 | 457.45 | HCnst-Po:48 |
| - | 479.46 | 457.46 | HCnst-Po:49 |
| - | 479.47 | 457.47 | HCnst-Po:50 |
| - | 479.48 | 457.48 | HCnst-Po:51 |
| - | 479.49 | 457.49 | HCnst-Po:52 |
| - | 479.50 | 457.50 | HCnst-Po:53 |
| - | 479.51 | 457.51 | HCnst-Po:54 |
| - | 479.52 | 457.52 | HCnst-Po:55 |
| - | 479.53 | 457.53 | HCnst-Po:56 |
| - | 479.54 | 457.54 | HCnst-Po:57 |
| - | 479.55 | 457.55 | HCnst-Po:58 |
| - | 479.56 | 457.56 | HCnst-Po:59 |
| - | 479.57 | 457.57 | HCnst-Po:60 |
| - | 479.58 | 457.58 | HCnst-Po:61 |
| - | 479.59 | 457.59 | HCnst-Po:62 |
| - | 479.60 | 457.60 | HCnst-Po:63 |
| - | 479.61 | 457.61 | HCnst-Po:64 |
| - | 479.62 | 457.62 | HCnst-Po:65 |
| - | 479.63 | 457.63 | HCnst-Po:66 |

FIG. 7 Continued

| AB-000224_LS_Heavy Chain | | | |
|---|---|---|---|
| Residue | Linear # | Mat. Linear # | ASN # |
| - | 479.64 | 457.64 | HCnst-Po:67 |
| - | 479.65 | 457.65 | HCnst-Po:68 |
| - | 479.66 | 457.66 | HCnst-Po:69 |
| - | 479.67 | 457.67 | HCnst-Po:70 |
| - | 479.68 | 457.68 | HCnst-Po:71 |
| - | 479.69 | 457.69 | HCnst-Po:72 |
| - | 479.70 | 457.70 | HCnst-Po:73 |
| - | 479.71 | 457.71 | HCnst-Po:74 |
| - | 479.72 | 457.72 | HCnst-Po:75 |
| - | 479.73 | 457.73 | HCnst-Po:76 |
| - | 479.74 | 457.74 | HCnst-Po:77 |
| - | 479.75 | 457.75 | HCnst-Po:78 |
| - | 479.76 | 457.76 | HCnst-Po:79 |
| - | 479.77 | 457.77 | HCnst-Po:80 |
| - | 479.78 | 457.78 | HCnst-Po:81 |
| - | 479.79 | 457.79 | HCnst-Po:82 |
| - | 479.80 | 457.80 | HCnst-Po:83 |
| - | 479.81 | 457.81 | HCnst-Po:84 |
| - | 479.82 | 457.82 | HCnst-Po:85 |
| - | 479.83 | 457.83 | HCnst-Po:86 |
| - | 479.84 | 457.84 | HCnst-Po:87 |
| - | 479.85 | 457.85 | HCnst-Po:88 |
| - | 479.86 | 457.86 | HCnst-Po:89 |
| - | 479.87 | 457.87 | HCnst-Po:90 |
| - | 479.88 | 457.88 | HCnst-Po:91 |
| - | 479.89 | 457.89 | HCnst-Po:92 |
| - | 479.90 | 457.90 | HCnst-Po:93 |
| - | 479.91 | 457.91 | HCnst-Po:94 |
| - | 479.92 | 457.92 | HCnst-Po:95 |
| - | 479.93 | 457.93 | HCnst-Po:96 |
| - | 479.94 | 457.94 | HCnst-Po:97 |
| - | 479.95 | 457.95 | HCnst-Po:98 |
| - | 479.96 | 457.96 | HCnst-Po:99 |
| - | 479.97 | 457.97 | HCnst-Po:100 |
| - | 479.98 | 457.98 | HCnst-Po:101 |
| - | 479.99 | 457.99 | HCnst-Po:102 |
| - | 479.100 | 457.100 | HCnst-Po:103 |
| - | 479.101 | 457.101 | HCnst-Po:104 |
| - | 479.102 | 457.102 | HCnst-Po:105 |
| - | 479.103 | 457.103 | HCnst-Po:106 |
| - | 479.104 | 457.104 | HCnst-Po:107 |
| - | 479.105 | 457.105 | HCnst-Po:108 |
| - | 479.106 | 457.106 | HCnst-Po:109 |

FIG. 7 Continued

| AB-000224_LS_Heavy Chain | | | |
|---|---|---|---|
| Residue | Linear # | Mat. Linear # | ASN # |
| - | 479.107 | 457.107 | HCnst-Po:110 |
| - | 479.108 | 457.108 | HCnst-Po:111 |
| - | 479.109 | 457.109 | HCnst-Po:112 |
| - | 479.110 | 457.110 | HCnst-Po:113 |
| - | 479.111 | 457.111 | HCnst-Po:114 |
| - | 479.112 | 457.112 | HCnst-Po:115 |
| - | 479.113 | 457.113 | HCnst-Po:116 |
| - | 479.114 | 457.114 | HCnst-Po:117 |
| - | 479.115 | 457.115 | HCnst-Po:118 |
| - | 479.116 | 457.116 | HCnst-Po:119 |
| - | 479.117 | 457.117 | HCnst-Po:120 |
| - | 479.118 | 457.118 | HCnst-Po:121 |
| - | 479.119 | 457.119 | HCnst-Po:122 |
| - | 479.120 | 457.120 | HCnst-Po:123 |

FIG. 7 Continued

| AB-007088_LS_Light Chain | | | |
|---|---|---|---|
| Residue | Linear # | Mat. Linear # | ASN # |
| M | 1 | -22 | KLdr:-22 |
| D | 2 | -21 | KLdr:-21 |
| M | 3 | -20 | KLdr:-20 |
| R | 4 | -19 | KLdr:-19 |
| V | 5 | -18 | KLdr:-18 |
| P | 6 | -17 | KLdr:-17 |
| A | 7 | -16 | KLdr:-16 |
| Q | 8 | -15 | KLdr:-15 |
| L | 9 | -14 | KLdr:-14 |
| L | 10 | -13 | KLdr:-13 |
| G | 11 | -12 | KLdr:-12 |
| L | 12 | -11 | KLdr:-11 |
| L | 13 | -10 | KLdr:-10 |
| L | 14 | -9 | KLdr:-9 |
| L | 15 | -8 | KLdr:-8 |
| W | 16 | -7 | KLdr:-7 |
| L | 17 | -6 | KLdr:-6 |
| R | 18 | -5 | KLdr:-5 |
| G | 19 | -4 | KLdr:-4 |
| A | 20 | -3 | KLdr:-3 |
| R | 21 | -2 | KLdr:-2 |
| C | 22 | -1 | KLdr:-1 |
| G | 23 | 1 | KV:1 |
| V | 24 | 2 | KV:2 |
| Q | 25 | 3 | KV:3 |
| M | 26 | 4 | KV:4 |
| T | 27 | 5 | KV:5 |
| Q | 28 | 6 | KV:6 |
| S | 29 | 7 | KV:7 |
| P | 30 | 8 | KV:8 |
| S | 31 | 9 | KV:9 |
| T | 32 | 10 | KV:10 |
| L | 33 | 11 | KV:11 |
| S | 34 | 12 | KV:12 |
| A | 35 | 13 | KV:13 |
| S | 36 | 14 | KV:14 |
| V | 37 | 15 | KV:15 |
| G | 38 | 16 | KV:16 |
| D | 39 | 17 | KV:17 |
| R | 40 | 18 | KV:18 |
| V | 41 | 19 | KV:19 |
| T | 42 | 20 | KV:20 |
| L | 43 | 21 | KV:21 |

FIG. 8

| | | | |
|---|---|---|---|
| T | 44 | 22 | KV:22 |
| C | 45 | 23 | KV:23 |
| R | 46 | 24 | KV:24 |
| A | 47 | 25 | KV:25 |
| S | 48 | 26 | KV:26 |
| - | 48.1 | 26.1 | KV:27 |
| - | 48.2 | 26.2 | KV:28 |
| Q | 49 | 27 | KV:29 |
| S | 50 | 28 | KV:30 |
| I | 51 | 29 | KV:31 |
| S | 52 | 30 | KV:32 |
| S | 53 | 31 | KV:33 |
| - | 53.1 | 31.1 | KV:34 |
| - | 53.2 | 31.2 | KV:35 |
| - | 53.3 | 31.3 | KV:36 |
| - | 53.4 | 31.4 | KV:37 |
| - | 53.5 | 31.5 | KV:38 |
| - | 53.6 | 31.6 | KV:39 |
| W | 54 | 32 | KV:40 |
| L | 55 | 33 | KV:41 |
| A | 56 | 34 | KV:42 |
| W | 57 | 35 | KV:43 |
| Y | 58 | 36 | KV:44 |
| Q | 59 | 37 | KV:45 |
| Q | 60 | 38 | KV:46 |
| K | 61 | 39 | KV:47 |
| P | 62 | 40 | KV:48 |
| G | 63 | 41 | KV:49 |
| K | 64 | 42 | KV:50 |
| A | 65 | 43 | KV:51 |
| P | 66 | 44 | KV:52 |
| K | 67 | 45 | KV:53 |
| L | 68 | 46 | KV:54 |
| L | 69 | 47 | KV:55 |
| I | 70 | 48 | KV:56 |
| Y | 71 | 49 | KV:57 |
| D | 72 | 50 | KV:58 |
| - | 72.1 | 50.1 | KV:59 |
| - | 72.2 | 50.2 | KV:60 |
| - | 72.3 | 50.3 | KV:61 |
| - | 72.4 | 50.4 | KV:62 |
| - | 72.5 | 50.5 | KV:63 |
| - | 72.6 | 50.6 | KV:64 |
| - | 72.7 | 50.7 | KV:65 |
| - | 72.8 | 50.8 | KV:66 |
| A | 73 | 51 | KV:67 |

FIG. 8 Continued

| | | | |
|---|---|---|---|
| S | 74 | 52 | KV:68 |
| S | 75 | 53 | KV:69 |
| L | 76 | 54 | KV:70 |
| E | 77 | 55 | KV:71 |
| S | 78 | 56 | KV:72 |
| G | 79 | 57 | KV:73 |
| V | 80 | 58 | KV:74 |
| P | 81 | 59 | KV:75 |
| S | 82 | 60 | KV:76 |
| R | 83 | 61 | KV:77 |
| F | 84 | 62 | KV:78 |
| S | 85 | 63 | KV:79 |
| G | 86 | 64 | KV:80 |
| S | 87 | 65 | KV:81 |
| G | 88 | 66 | KV:82 |
| S | 89 | 67 | KV:83 |
| G | 90 | 68 | KV:84 |
| - | 90.1 | 68.1 | KV:85 |
| - | 90.2 | 68.2 | KV:86 |
| T | 91 | 69 | KV:87 |
| E | 92 | 70 | KV:88 |
| F | 93 | 71 | KV:89 |
| T | 94 | 72 | KV:90 |
| L | 95 | 73 | KV:91 |
| T | 96 | 74 | KV:92 |
| I | 97 | 75 | KV:93 |
| S | 98 | 76 | KV:94 |
| S | 99 | 77 | KV:95 |
| L | 100 | 78 | KV:96 |
| Q | 101 | 79 | KV:97 |
| P | 102 | 80 | KV:98 |
| D | 103 | 81 | KV:99 |
| D | 104 | 82 | KV:100 |
| F | 105 | 83 | KV:101 |
| A | 106 | 84 | KV:102 |
| T | 107 | 85 | KV:103 |
| Y | 108 | 86 | KV:104 |
| Y | 109 | 87 | KV:105 |
| C | 110 | 88 | KV:106 |
| Q | 111 | 89 | KV:107 |
| Q | 112 | 90 | KV:108 |
| Y | 113 | 91 | KV:109 |
| N | 114 | 92 | KV:110 |
| S | 115 | 93 | KV:111 |
| - | 115.1 | 93.1 | KV:112 |
| - | 115.2 | 93.2 | KV:113 |

FIG. 8 Continued

| | 115.3 | 93.3 | KV:114 |
|---|---|---|---|
| - | 115.3 | 93.3 | KV:114 |
| - | 115.4 | 93.4 | KV:115 |
| - | 115.5 | 93.5 | KV:116 |
| - | 115.6 | 93.6 | KV:117 |
| - | 115.7 | 93.7 | KV:118 |
| - | 115.8 | 93.8 | KV:119 |
| - | 115.9 | 93.9 | KV:120 |
| - | 115.10 | 93.10 | KV:121 |
| - | 115.11 | 93.11 | KV:122 |
| - | 115.12 | 93.12 | KV:123 |
| - | 115.13 | 93.13 | KV:124 |
| - | 115.14 | 93.14 | KV:125 |
| - | 115.15 | 93.15 | KV:126 |
| - | 115.16 | 93.16 | KV:127 |
| - | 115.17 | 93.17 | KV:128 |
| - | 115.18 | 93.18 | KV:129 |
| - | 115.19 | 93.19 | KV:130 |
| - | 115.20 | 93.20 | KV:131 |
| - | 115.21 | 93.21 | KV:132 |
| - | 115.22 | 93.22 | KV:133 |
| Y | 116 | 94 | KV:134 |
| S | 117 | 95 | KV:135 |
| F | 118 | 96 | KV:136 |
| W | 119 | 97 | KV:137 |
| T | 120 | 98 | KV:138 |
| F | 121 | 99 | KV:139 |
| G | 122 | 100 | KV:140 |
| Q | 123 | 101 | KV:141 |
| G | 124 | 102 | KV:142 |
| T | 125 | 103 | KV:143 |
| K | 126 | 104 | KV:144 |
| V | 127 | 105 | KV:145 |
| E | 128 | 106 | KV:146 |
| I | 129 | 107 | KV:147 |
| K | 130 | 108 | KV:148 |
| R | 131 | 109 | KV:149 |
| - | 131.1 | 109.1 | KCnst-lg:1 |
| T | 132 | 110 | KCnst-lg:2 |
| V | 133 | 111 | KCnst-lg:3 |
| A | 134 | 112 | KCnst-lg:4 |
| A | 135 | 113 | KCnst-lg:5 |
| P | 136 | 114 | KCnst-lg:6 |
| S | 137 | 115 | KCnst-lg:7 |
| V | 138 | 116 | KCnst-lg:8 |
| F | 139 | 117 | KCnst-lg:9 |
| I | 140 | 118 | KCnst-lg:10 |

FIG. 8 Continued

| | | | |
|---|---|---|---|
| F | 141 | 119 | KCnst-Ig:11 |
| P | 142 | 120 | KCnst-Ig:12 |
| P | 143 | 121 | KCnst-Ig:13 |
| S | 144 | 122 | KCnst-Ig:14 |
| D | 145 | 123 | KCnst-Ig:15 |
| E | 146 | 124 | KCnst-Ig:16 |
| - | 146.1 | 124.1 | KCnst-Ig:17 |
| - | 146.2 | 124.2 | KCnst-Ig:18 |
| Q | 147 | 125 | KCnst-Ig:19 |
| L | 148 | 126 | KCnst-Ig:20 |
| - | 148.1 | 126.1 | KCnst-Ig:21 |
| - | 148.2 | 126.2 | KCnst-Ig:22 |
| K | 149 | 127 | KCnst-Ig:23 |
| S | 150 | 128 | KCnst-Ig:24 |
| G | 151 | 129 | KCnst-Ig:25 |
| T | 152 | 130 | KCnst-Ig:26 |
| A | 153 | 131 | KCnst-Ig:27 |
| S | 154 | 132 | KCnst-Ig:28 |
| V | 155 | 133 | KCnst-Ig:29 |
| V | 156 | 134 | KCnst-Ig:30 |
| C | 157 | 135 | KCnst-Ig:31 |
| L | 158 | 136 | KCnst-Ig:32 |
| L | 159 | 137 | KCnst-Ig:33 |
| N | 160 | 138 | KCnst-Ig:34 |
| N | 161 | 139 | KCnst-Ig:35 |
| F | 162 | 140 | KCnst-Ig:36 |
| Y | 163 | 141 | KCnst-Ig:37 |
| P | 164 | 142 | KCnst-Ig:38 |
| - | 164.1 | 142.1 | KCnst-Ig:39 |
| - | 164.2 | 142.2 | KCnst-Ig:40 |
| R | 165 | 143 | KCnst-Ig:41 |
| E | 166 | 144 | KCnst-Ig:42 |
| A | 167 | 145 | KCnst-Ig:43 |
| K | 168 | 146 | KCnst-Ig:44 |
| V | 169 | 147 | KCnst-Ig:45 |
| Q | 170 | 148 | KCnst-Ig:46 |
| W | 171 | 149 | KCnst-Ig:47 |
| - | 171.1 | 149.1 | KCnst-Ig:48 |
| K | 172 | 150 | KCnst-Ig:49 |
| V | 173 | 151 | KCnst-Ig:50 |
| D | 174 | 152 | KCnst-Ig:51 |
| N | 175 | 153 | KCnst-Ig:52 |
| A | 176 | 154 | KCnst-Ig:53 |
| L | 177 | 155 | KCnst-Ig:54 |
| Q | 178 | 156 | KCnst-Ig:55 |
| S | 179 | 157 | KCnst-Ig:56 |

FIG. 8 Continued

| | | | |
|---|---|---|---|
| G | 180 | 158 | KCnst-Ig:57 |
| N | 181 | 159 | KCnst-Ig:58 |
| S | 182 | 160 | KCnst-Ig:59 |
| Q | 183 | 161 | KCnst-Ig:60 |
| E | 184 | 162 | KCnst-Ig:61 |
| S | 185 | 163 | KCnst-Ig:62 |
| V | 186 | 164 | KCnst-Ig:63 |
| T | 187 | 165 | KCnst-Ig:64 |
| E | 188 | 166 | KCnst-Ig:65 |
| Q | 189 | 167 | KCnst-Ig:66 |
| D | 190 | 168 | KCnst-Ig:67 |
| - | 190.1 | 168.1 | KCnst-Ig:68 |
| - | 190.2 | 168.2 | KCnst-Ig:69 |
| - | 190.3 | 168.3 | KCnst-Ig:70 |
| - | 190.4 | 168.4 | KCnst-Ig:71 |
| S | 191 | 169 | KCnst-Ig:72 |
| K | 192 | 170 | KCnst-Ig:73 |
| D | 193 | 171 | KCnst-Ig:74 |
| S | 194 | 172 | KCnst-Ig:75 |
| T | 195 | 173 | KCnst-Ig:76 |
| Y | 196 | 174 | KCnst-Ig:77 |
| S | 197 | 175 | KCnst-Ig:78 |
| L | 198 | 176 | KCnst-Ig:79 |
| S | 199 | 177 | KCnst-Ig:80 |
| S | 200 | 178 | KCnst-Ig:81 |
| T | 201 | 179 | KCnst-Ig:82 |
| L | 202 | 180 | KCnst-Ig:83 |
| T | 203 | 181 | KCnst-Ig:84 |
| L | 204 | 182 | KCnst-Ig:85 |
| S | 205 | 183 | KCnst-Ig:86 |
| K | 206 | 184 | KCnst-Ig:87 |
| A | 207 | 185 | KCnst-Ig:88 |
| D | 208 | 186 | KCnst-Ig:89 |
| Y | 209 | 187 | KCnst-Ig:90 |
| - | 209.1 | 187.1 | KCnst-Ig:91 |
| E | 210 | 188 | KCnst-Ig:92 |
| K | 211 | 189 | KCnst-Ig:93 |
| H | 212 | 190 | KCnst-Ig:94 |
| K | 213 | 191 | KCnst-Ig:95 |
| V | 214 | 192 | KCnst-Ig:96 |
| - | 214.1 | 192.1 | KCnst-Ig:97 |
| - | 214.2 | 192.2 | KCnst-Ig:98 |
| Y | 215 | 193 | KCnst-Ig:99 |
| A | 216 | 194 | KCnst-Ig:100 |
| C | 217 | 195 | KCnst-Ig:101 |
| E | 218 | 196 | KCnst-Ig:102 |

FIG. 8 Continued

| | | | |
|---|---|---|---|
| V | 219 | 197 | KCnst-Ig:103 |
| T | 220 | 198 | KCnst-Ig:104 |
| H | 221 | 199 | KCnst-Ig:105 |
| Q | 222 | 200 | KCnst-Ig:106 |
| G | 223 | 201 | KCnst-Ig:107 |
| L | 224 | 202 | KCnst-Ig:108 |
| S | 225 | 203 | KCnst-Ig:109 |
| - | 225.1 | 203.1 | KCnst-Ig:110 |
| S | 226 | 204 | KCnst-Ig:111 |
| P | 227 | 205 | KCnst-Ig:112 |
| V | 228 | 206 | KCnst-Ig:113 |
| T | 229 | 207 | KCnst-Ig:114 |
| K | 230 | 208 | KCnst-Ig:115 |
| S | 231 | 209 | KCnst-Ig:116 |
| F | 232 | 210 | KCnst-Ig:117 |
| N | 233 | 211 | KCnst-Ig:118 |
| R | 234 | 212 | KCnst-Ig:119 |
| G | 235 | 213 | KCnst-Ig:120 |
| E | 236 | 214 | KCnst-Ig:121 |
| C | 237 | 215 | KCnst-Ig:122 |
| - | 237.1 | 215.1 | KCnst-Ig:123 |

FIG. 8 Continued

| AB-007088_LS_Heavy Chain | | | |
|---|---|---|---|
| Residue | Linear # | Mat. Linear # | ASN # |
| M | 1 | -22 | KLdr:-22 |
| D | 2 | -21 | KLdr:-21 |
| M | 3 | -20 | KLdr:-20 |
| R | 4 | -19 | KLdr:-19 |
| V | 5 | -18 | KLdr:-18 |
| P | 6 | -17 | KLdr:-17 |
| A | 7 | -16 | KLdr:-16 |
| Q | 8 | -15 | KLdr:-15 |
| L | 9 | -14 | KLdr:-14 |
| L | 10 | -13 | KLdr:-13 |
| G | 11 | -12 | KLdr:-12 |
| L | 12 | -11 | KLdr:-11 |
| L | 13 | -10 | KLdr:-10 |
| L | 14 | -9 | KLdr:-9 |
| L | 15 | -8 | KLdr:-8 |
| W | 16 | -7 | KLdr:-7 |
| L | 17 | -6 | KLdr:-6 |
| R | 18 | -5 | KLdr:-5 |
| G | 19 | -4 | KLdr:-4 |
| A | 20 | -3 | KLdr:-3 |
| R | 21 | -2 | KLdr:-2 |
| C | 22 | -1 | KLdr:-1 |
| Q | 23 | 1 | HV:1 |
| V | 24 | 2 | HV:2 |
| Q | 25 | 3 | HV:3 |
| L | 26 | 4 | HV:4 |
| V | 27 | 5 | HV:5 |
| E | 28 | 6 | HV:6 |
| S | 29 | 7 | HV:7 |
| - | 29.1 | 7.1 | HV:8 |
| G | 30 | 8 | HV:9 |
| G | 31 | 9 | HV:10 |
| G | 32 | 10 | HV:11 |
| V | 33 | 11 | HV:12 |
| V | 34 | 12 | HV:13 |
| Q | 35 | 13 | HV:14 |
| P | 36 | 14 | HV:15 |
| G | 37 | 15 | HV:16 |
| R | 38 | 16 | HV:17 |

FIG. 9

| AB-007088_LS_Heavy Chain | | | |
|---|---|---|---|
| Residue | Linear # | Mat. Linear # | ASN # |
| S | 39 | 17 | HV:18 |
| L | 40 | 18 | HV:19 |
| R | 41 | 19 | HV:20 |
| L | 42 | 20 | HV:21 |
| S | 43 | 21 | HV:22 |
| C | 44 | 22 | HV:23 |
| A | 45 | 23 | HV:24 |
| A | 46 | 24 | HV:25 |
| S | 47 | 25 | HV:26 |
| G | 48 | 26 | HV:27 |
| - | 48.1 | 26.1 | HV:28 |
| F | 49 | 27 | HV:29 |
| A | 50 | 28 | HV:30 |
| F | 51 | 29 | HV:31 |
| N | 52 | 30 | HV:32 |
| T | 53 | 31 | HV:33 |
| - | 53.1 | 31.1 | HV:34 |
| - | 53.2 | 31.2 | HV:35 |
| - | 53.3 | 31.3 | HV:36 |
| - | 53.4 | 31.4 | HV:37 |
| - | 53.5 | 31.5 | HV:38 |
| Y | 54 | 32 | HV:39 |
| G | 55 | 33 | HV:40 |
| M | 56 | 34 | HV:41 |
| H | 57 | 35 | HV:42 |
| W | 58 | 36 | HV:43 |
| V | 59 | 37 | HV:44 |
| R | 60 | 38 | HV:45 |
| Q | 61 | 39 | HV:46 |
| T | 62 | 40 | HV:47 |
| P | 63 | 41 | HV:48 |
| G | 64 | 42 | HV:49 |
| K | 65 | 43 | HV:50 |
| G | 66 | 44 | HV:51 |
| L | 67 | 45 | HV:52 |
| E | 68 | 46 | HV:53 |
| W | 69 | 47 | HV:54 |
| V | 70 | 48 | HV:55 |
| A | 71 | 49 | HV:56 |
| I | 72 | 50 | HV:57 |
| I | 73 | 51 | HV:58 |
| W | 74 | 52 | HV:59 |
| Y | 75 | 53 | HV:60 |

FIG. 9 Continued

| AB-007088_LS_Heavy Chain | | | |
|---|---|---|---|
| Residue | Linear # | Mat. Linear # | ASN # |
| - | 75.1 | 53.1 | HV:61 |
| - | 75.2 | 53.2 | HV:62 |
| - | 75.3 | 53.3 | HV:63 |
| D | 76 | 54 | HV:64 |
| G | 77 | 55 | HV:65 |
| S | 78 | 56 | HV:66 |
| Q | 79 | 57 | HV:67 |
| K | 80 | 58 | HV:68 |
| Y | 81 | 59 | HV:69 |
| Y | 82 | 60 | HV:70 |
| A | 83 | 61 | HV:71 |
| D | 84 | 62 | HV:72 |
| S | 85 | 63 | HV:73 |
| V | 86 | 64 | HV:74 |
| Q | 87 | 65 | HV:75 |
| G | 88 | 66 | HV:76 |
| R | 89 | 67 | HV:77 |
| F | 90 | 68 | HV:78 |
| I | 91 | 69 | HV:79 |
| I | 92 | 70 | HV:80 |
| S | 93 | 71 | HV:81 |
| R | 94 | 72 | HV:82 |
| D | 95 | 73 | HV:83 |
| N | 96 | 74 | HV:84 |
| H | 97 | 75 | HV:85 |
| K | 98 | 76 | HV:86 |
| N | 99 | 77 | HV:87 |
| T | 100 | 78 | HV:88 |
| L | 101 | 79 | HV:89 |
| S | 102 | 80 | HV:90 |
| L | 103 | 81 | HV:91 |
| Q | 104 | 82 | HV:92 |
| M | 105 | 83 | HV:93 |
| N | 106 | 84 | HV:94 |
| G | 107 | 85 | HV:95 |
| L | 108 | 86 | HV:96 |
| R | 109 | 87 | HV:97 |
| A | 110 | 88 | HV:98 |
| E | 111 | 89 | HV:99 |
| D | 112 | 90 | HV:100 |
| T | 113 | 91 | HV:101 |
| A | 114 | 92 | HV:102 |
| V | 115 | 93 | HV:103 |

FIG. 9 Continued

| AB-007088_LS_Heavy Chain | | | |
|---|---|---|---|
| Residue | Linear # | Mat. Linear # | ASN # |
| Y | 116 | 94 | HV:104 |
| F | 117 | 95 | HV:105 |
| C | 118 | 96 | HV:106 |
| V | 119 | 97 | HV:107 |
| R | 120 | 98 | HV:108 |
| V | 121 | 99 | HV:109 |
| R | 122 | 100 | HV:110 |
| F | 123 | 101 | HV:111 |
| S | 124 | 102 | HV:112 |
| V | 125 | 103 | HV:113 |
| G | 126 | 104 | HV:114 |
| - | 126.1 | 104.1 | HV:115 |
| - | 126.2 | 104.2 | HV:116 |
| - | 126.3 | 104.3 | HV:117 |
| - | 126.4 | 104.4 | HV:118 |
| - | 126.5 | 104.5 | HV:119 |
| - | 126.6 | 104.6 | HV:120 |
| - | 126.7 | 104.7 | HV:121 |
| - | 126.8 | 104.8 | HV:122 |
| - | 126.9 | 104.9 | HV:123 |
| - | 126.10 | 104.10 | HV:124 |
| - | 126.11 | 104.11 | HV:125 |
| - | 126.12 | 104.12 | HV:126 |
| - | 126.13 | 104.13 | HV:127 |
| - | 126.14 | 104.14 | HV:128 |
| - | 126.15 | 104.15 | HV:129 |
| - | 126.16 | 104.16 | HV:130 |
| P | 127 | 105 | HV:131 |
| H | 128 | 106 | HV:132 |
| G | 129 | 107 | HV:133 |
| S | 130 | 108 | HV:134 |
| A | 131 | 109 | HV:135 |
| F | 132 | 110 | HV:136 |
| D | 133 | 111 | HV:137 |
| L | 134 | 112 | HV:138 |
| W | 135 | 113 | HV:139 |
| G | 136 | 114 | HV:140 |
| Q | 137 | 115 | HV:141 |
| G | 138 | 116 | HV:142 |
| T | 139 | 117 | HV:143 |
| M | 140 | 118 | HV:144 |
| V | 141 | 119 | HV:145 |
| I | 142 | 120 | HV:146 |

FIG. 9 Continued

| AB-007088_LS_Heavy Chain | | | |
|---|---|---|---|
| Residue | Linear # | Mat. Linear # | ASN # |
| V | 143 | 121 | HV:147 |
| S | 144 | 122 | HV:148 |
| S | 145 | 123 | HV:149 |
| - | 145.1 | 123.1 | HCnst-Ig:1 |
| - | 145.2 | 123.2 | HCnst-Ig:2 |
| A | 146 | 124 | HCnst-Ig:3 |
| S | 147 | 125 | HCnst-Ig:4 |
| T | 148 | 126 | HCnst-Ig:5 |
| K | 149 | 127 | HCnst-Ig:6 |
| G | 150 | 128 | HCnst-Ig:7 |
| P | 151 | 129 | HCnst-Ig:8 |
| S | 152 | 130 | HCnst-Ig:9 |
| V | 153 | 131 | HCnst-Ig:10 |
| F | 154 | 132 | HCnst-Ig:11 |
| P | 155 | 133 | HCnst-Ig:12 |
| L | 156 | 134 | HCnst-Ig:13 |
| A | 157 | 135 | HCnst-Ig:14 |
| P | 158 | 136 | HCnst-Ig:15 |
| - | 158.1 | 136.1 | HCnst-Ig:16 |
| S | 159 | 137 | HCnst-Ig:17 |
| - | 159.1 | 137.1 | HCnst-Ig:18 |
| S | 160 | 138 | HCnst-Ig:19 |
| K | 161 | 139 | HCnst-Ig:20 |
| S | 162 | 140 | HCnst-Ig:21 |
| T | 163 | 141 | HCnst-Ig:22 |
| S | 164 | 142 | HCnst-Ig:23 |
| G | 165 | 143 | HCnst-Ig:24 |
| G | 166 | 144 | HCnst-Ig:25 |
| T | 167 | 145 | HCnst-Ig:26 |
| A | 168 | 146 | HCnst-Ig:27 |
| A | 169 | 147 | HCnst-Ig:28 |
| L | 170 | 148 | HCnst-Ig:29 |
| G | 171 | 149 | HCnst-Ig:30 |
| C | 172 | 150 | HCnst-Ig:31 |
| L | 173 | 151 | HCnst-Ig:32 |
| V | 174 | 152 | HCnst-Ig:33 |
| K | 175 | 153 | HCnst-Ig:34 |
| D | 176 | 154 | HCnst-Ig:35 |
| Y | 177 | 155 | HCnst-Ig:36 |
| F | 178 | 156 | HCnst-Ig:37 |
| P | 179 | 157 | HCnst-Ig:38 |
| - | 179.1 | 157.1 | HCnst-Ig:39 |
| - | 179.2 | 157.2 | HCnst-Ig:40 |

FIG. 9 Continued

| AB-007088_LS_Heavy Chain | | | |
|---|---|---|---|
| Residue | Linear # | Mat. Linear # | ASN # |
| E | 180 | 158 | HCnst-Ig:41 |
| P | 181 | 159 | HCnst-Ig:42 |
| V | 182 | 160 | HCnst-Ig:43 |
| T | 183 | 161 | HCnst-Ig:44 |
| V | 184 | 162 | HCnst-Ig:45 |
| S | 185 | 163 | HCnst-Ig:46 |
| W | 186 | 164 | HCnst-Ig:47 |
| - | 186.1 | 164.1 | HCnst-Ig:48 |
| N | 187 | 165 | HCnst-Ig:49 |
| S | 188 | 166 | HCnst-Ig:50 |
| G | 189 | 167 | HCnst-Ig:51 |
| A | 190 | 168 | HCnst-Ig:52 |
| L | 191 | 169 | HCnst-Ig:53 |
| T | 192 | 170 | HCnst-Ig:54 |
| S | 193 | 171 | HCnst-Ig:55 |
| G | 194 | 172 | HCnst-Ig:56 |
| V | 195 | 173 | HCnst-Ig:57 |
| H | 196 | 174 | HCnst-Ig:58 |
| T | 197 | 175 | HCnst-Ig:59 |
| - | 197.1 | 175.1 | HCnst-Ig:60 |
| - | 197.2 | 175.2 | HCnst-Ig:61 |
| - | 197.3 | 175.3 | HCnst-Ig:62 |
| F | 198 | 176 | HCnst-Ig:63 |
| P | 199 | 177 | HCnst-Ig:64 |
| A | 200 | 178 | HCnst-Ig:65 |
| V | 201 | 179 | HCnst-Ig:66 |
| L | 202 | 180 | HCnst-Ig:67 |
| Q | 203 | 181 | HCnst-Ig:68 |
| - | 203.1 | 181.1 | HCnst-Ig:69 |
| - | 203.2 | 181.2 | HCnst-Ig:70 |
| - | 203.3 | 181.3 | HCnst-Ig:71 |
| - | 203.4 | 181.4 | HCnst-Ig:72 |
| S | 204 | 182 | HCnst-Ig:73 |
| S | 205 | 183 | HCnst-Ig:74 |
| G | 206 | 184 | HCnst-Ig:75 |
| L | 207 | 185 | HCnst-Ig:76 |
| Y | 208 | 186 | HCnst-Ig:77 |
| S | 209 | 187 | HCnst-Ig:78 |
| L | 210 | 188 | HCnst-Ig:79 |
| S | 211 | 189 | HCnst-Ig:80 |
| S | 212 | 190 | HCnst-Ig:81 |
| V | 213 | 191 | HCnst-Ig:82 |
| V | 214 | 192 | HCnst-Ig:83 |

FIG. 9 Continued

| AB-007088_LS_Heavy Chain | | | |
|---|---|---|---|
| Residue | Linear # | Mat. Linear # | ASN # |
| T | 215 | 193 | HCnst-Ig:84 |
| V | 216 | 194 | HCnst-Ig:85 |
| P | 217 | 195 | HCnst-Ig:86 |
| S | 218 | 196 | HCnst-Ig:87 |
| S | 219 | 197 | HCnst-Ig:88 |
| S | 220 | 198 | HCnst-Ig:89 |
| L | 221 | 199 | HCnst-Ig:90 |
| - | 221.1 | 199.1 | HCnst-Ig:91 |
| G | 222 | 200 | HCnst-Ig:92 |
| T | 223 | 201 | HCnst-Ig:93 |
| Q | 224 | 202 | HCnst-Ig:94 |
| T | 225 | 203 | HCnst-Ig:95 |
| - | 225.1 | 203.1 | HCnst-Ig:96 |
| - | 225.2 | 203.2 | HCnst-Ig:97 |
| - | 225.3 | 203.3 | HCnst-Ig:98 |
| Y | 226 | 204 | HCnst-Ig:99 |
| I | 227 | 205 | HCnst-Ig:100 |
| C | 228 | 206 | HCnst-Ig:101 |
| N | 229 | 207 | HCnst-Ig:102 |
| V | 230 | 208 | HCnst-Ig:103 |
| N | 231 | 209 | HCnst-Ig:104 |
| H | 232 | 210 | HCnst-Ig:105 |
| K | 233 | 211 | HCnst-Ig:106 |
| P | 234 | 212 | HCnst-Ig:107 |
| S | 235 | 213 | HCnst-Ig:108 |
| N | 236 | 214 | HCnst-Ig:109 |
| - | 236.1 | 214.1 | HCnst-Ig:110 |
| - | 236.2 | 214.2 | HCnst-Ig:111 |
| T | 237 | 215 | HCnst-Ig:112 |
| K | 238 | 216 | HCnst-Ig:113 |
| V | 239 | 217 | HCnst-Ig:114 |
| D | 240 | 218 | HCnst-Ig:115 |
| K | 241 | 219 | HCnst-Ig:116 |
| - | 241.1 | 219.1 | HCnst-Ig:117 |
| K | 242 | 220 | HCnst-Ig:118 |
| V | 243 | 221 | HCnst-Ig:119 |
| - | 243.1 | 221.1 | HCnst-Ig:120 |
| - | 243.2 | 221.2 | HCnst-Ig:121 |
| - | 243.3 | 221.3 | HCnst-Ig:122 |
| - | 243.4 | 221.4 | HCnst-Ig:123 |
| - | 243.5 | 221.1 | Hinge:1 |
| - | 243.6 | 221.2 | Hinge:2 |
| - | 243.7 | 221.3 | Hinge:3 |

FIG. 9 Continued

| AB-007088_LS_Heavy Chain | | | |
|---|---|---|---|
| Residue | Linear # | Mat. Linear # | ASN # |
| - | 243.8 | 221.4 | Hinge:4 |
| - | 243.9 | 221.5 | Hinge:5 |
| - | 243.10 | 221.6 | Hinge:6 |
| - | 243.11 | 221.7 | Hinge:7 |
| - | 243.12 | 221.8 | Hinge:8 |
| - | 243.13 | 221.9 | Hinge:9 |
| - | 243.14 | 221.10 | Hinge:10 |
| - | 243.15 | 221.11 | Hinge:11 |
| - | 243.16 | 221.12 | Hinge:12 |
| - | 243.17 | 221.13 | Hinge:13 |
| - | 243.18 | 221.14 | Hinge:14 |
| - | 243.19 | 221.15 | Hinge:15 |
| - | 243.20 | 221.16 | Hinge:16 |
| - | 243.21 | 221.17 | Hinge:17 |
| - | 243.22 | 221.18 | Hinge:18 |
| - | 243.23 | 221.19 | Hinge:19 |
| - | 243.24 | 221.20 | Hinge:20 |
| - | 243.25 | 221.21 | Hinge:21 |
| - | 243.26 | 221.22 | Hinge:22 |
| - | 243.27 | 221.23 | Hinge:23 |
| - | 243.28 | 221.24 | Hinge:24 |
| - | 243.29 | 221.25 | Hinge:25 |
| - | 243.30 | 221.26 | Hinge:26 |
| - | 243.31 | 221.27 | Hinge:27 |
| - | 243.32 | 221.28 | Hinge:28 |
| - | 243.33 | 221.29 | Hinge:29 |
| - | 243.34 | 221.30 | Hinge:30 |
| - | 243.35 | 221.31 | Hinge:31 |
| - | 243.36 | 221.32 | Hinge:32 |
| - | 243.37 | 221.33 | Hinge:33 |
| - | 243.38 | 221.34 | Hinge:34 |
| - | 243.39 | 221.35 | Hinge:35 |
| - | 243.40 | 221.36 | Hinge:36 |
| - | 243.41 | 221.37 | Hinge:37 |
| - | 243.42 | 221.38 | Hinge:38 |
| - | 243.43 | 221.39 | Hinge:39 |
| - | 243.44 | 221.40 | Hinge:40 |
| - | 243.45 | 221.41 | Hinge:41 |
| - | 243.46 | 221.42 | Hinge:42 |
| - | 243.47 | 221.43 | Hinge:43 |
| - | 243.48 | 221.44 | Hinge:44 |
| - | 243.49 | 221.45 | Hinge:45 |
| - | 243.50 | 221.46 | Hinge:46 |

FIG. 9 Continued

| AB-007088_LS_Heavy Chain | | | |
|---|---|---|---|
| Residue | Linear # | Mat. Linear # | ASN # |
| - | 243.51 | 221.47 | Hinge:47 |
| - | 243.52 | 221.48 | Hinge:48 |
| - | 243.53 | 221.49 | Hinge:49 |
| - | 243.54 | 221.50 | Hinge:50 |
| - | 243.55 | 221.51 | Hinge:51 |
| - | 243.56 | 221.52 | Hinge:52 |
| - | 243.57 | 221.53 | Hinge:53 |
| - | 243.58 | 221.54 | Hinge:54 |
| - | 243.59 | 221.55 | Hinge:55 |
| - | 243.60 | 221.56 | Hinge:56 |
| - | 243.61 | 221.57 | Hinge:57 |
| - | 243.62 | 221.58 | Hinge:58 |
| - | 243.63 | 221.59 | Hinge:59 |
| - | 243.64 | 221.60 | Hinge:60 |
| - | 243.65 | 221.61 | Hinge:61 |
| - | 243.66 | 221.62 | Hinge:62 |
| - | 243.67 | 221.63 | Hinge:63 |
| - | 243.68 | 221.64 | Hinge:64 |
| - | 243.69 | 221.65 | Hinge:65 |
| - | 243.70 | 221.66 | Hinge:66 |
| - | 243.71 | 221.67 | Hinge:67 |
| - | 243.72 | 221.68 | Hinge:68 |
| - | 243.73 | 221.69 | Hinge:69 |
| - | 243.74 | 221.70 | Hinge:70 |
| - | 243.75 | 221.71 | Hinge:71 |
| - | 243.76 | 221.72 | Hinge:72 |
| - | 243.77 | 221.73 | Hinge:73 |
| - | 243.78 | 221.74 | Hinge:74 |
| - | 243.79 | 221.75 | Hinge:75 |
| - | 243.80 | 221.76 | Hinge:76 |
| - | 243.81 | 221.77 | Hinge:77 |
| - | 243.82 | 221.78 | Hinge:78 |
| - | 243.83 | 221.79 | Hinge:79 |
| - | 243.84 | 221.80 | Hinge:80 |
| - | 243.85 | 221.81 | Hinge:81 |
| - | 243.86 | 221.82 | Hinge:82 |
| - | 243.87 | 221.83 | Hinge:83 |
| - | 243.88 | 221.84 | Hinge:84 |
| - | 243.89 | 221.85 | Hinge:85 |
| - | 243.90 | 221.86 | Hinge:86 |
| - | 243.91 | 221.87 | Hinge:87 |
| - | 243.92 | 221.88 | Hinge:88 |
| - | 243.93 | 221.89 | Hinge:89 |

FIG. 9 Continued

| AB-007088_LS_Heavy Chain | | | |
|---|---|---|---|
| Residue | Linear # | Mat. Linear # | ASN # |
| - | 243.94 | 221.90 | Hinge:90 |
| - | 243.95 | 221.91 | Hinge:91 |
| - | 243.96 | 221.92 | Hinge:92 |
| - | 243.97 | 221.93 | Hinge:93 |
| - | 243.98 | 221.94 | Hinge:94 |
| - | 243.99 | 221.95 | Hinge:95 |
| E | 244 | 222 | Hinge:96 |
| P | 245 | 223 | Hinge:97 |
| K | 246 | 224 | Hinge:98 |
| S | 247 | 225 | Hinge:99 |
| - | 247.1 | 225.1 | Hinge:100 |
| - | 247.2 | 225.2 | Hinge:101 |
| - | 247.3 | 225.3 | Hinge:102 |
| - | 247.4 | 225.4 | Hinge:103 |
| - | 247.5 | 225.5 | Hinge:104 |
| - | 247.6 | 225.6 | Hinge:105 |
| - | 247.7 | 225.7 | Hinge:106 |
| C | 248 | 226 | Hinge:107 |
| D | 249 | 227 | Hinge:108 |
| K | 250 | 228 | Hinge:109 |
| T | 251 | 229 | Hinge:110 |
| H | 252 | 230 | Hinge:111 |
| T | 253 | 231 | Hinge:112 |
| C | 254 | 232 | Hinge:113 |
| P | 255 | 233 | Hinge:114 |
| P | 256 | 234 | Hinge:115 |
| C | 257 | 235 | Hinge:116 |
| P | 258 | 236 | Hinge:117 |
| A | 259 | 237 | Hinge:118 |
| P | 260 | 238 | Hinge:119 |
| E | 261 | 239 | Hinge:120 |
| L | 262 | 240 | Hinge:121 |
| L | 263 | 241 | Hinge:122 |
| G | 264 | 242 | Hinge:123 |
| - | 264.1 | 242.1 | Fc-N:1 |
| - | 264.2 | 242.2 | Fc-N:2 |
| - | 264.3 | 242.3 | Fc-N:3 |
| - | 264.4 | 242.4 | Fc-N:4 |
| G | 265 | 243 | Fc-N:5 |
| P | 266 | 244 | Fc-N:6 |
| S | 267 | 245 | Fc-N:7 |
| V | 268 | 246 | Fc-N:8 |
| F | 269 | 247 | Fc-N:9 |

FIG. 9 Continued

| AB-007088_LS_Heavy Chain | | | |
|---|---|---|---|
| Residue | Linear # | Mat. Linear # | ASN # |
| L | 270 | 248 | Fc-N:10 |
| F | 271 | 249 | Fc-N:11 |
| P | 272 | 250 | Fc-N:12 |
| P | 273 | 251 | Fc-N:13 |
| - | 273.1 | 251.1 | Fc-N:14 |
| K | 274 | 252 | Fc-N:15 |
| P | 275 | 253 | Fc-N:16 |
| K | 276 | 254 | Fc-N:17 |
| - | 276.1 | 254.1 | Fc-N:18 |
| D | 277 | 255 | Fc-N:19 |
| T | 278 | 256 | Fc-N:20 |
| L | 279 | 257 | Fc-N:21 |
| M | 280 | 258 | Fc-N:22 |
| I | 281 | 259 | Fc-N:23 |
| S | 282 | 260 | Fc-N:24 |
| R | 283 | 261 | Fc-N:25 |
| T | 284 | 262 | Fc-N:26 |
| P | 285 | 263 | Fc-N:27 |
| E | 286 | 264 | Fc-N:28 |
| V | 287 | 265 | Fc-N:29 |
| T | 288 | 266 | Fc-N:30 |
| C | 289 | 267 | Fc-N:31 |
| V | 290 | 268 | Fc-N:32 |
| V | 291 | 269 | Fc-N:33 |
| V | 292 | 270 | Fc-N:34 |
| D | 293 | 271 | Fc-N:35 |
| V | 294 | 272 | Fc-N:36 |
| S | 295 | 273 | Fc-N:37 |
| H | 296 | 274 | Fc-N:38 |
| E | 297 | 275 | Fc-N:39 |
| D | 298 | 276 | Fc-N:40 |
| P | 299 | 277 | Fc-N:41 |
| E | 300 | 278 | Fc-N:42 |
| V | 301 | 279 | Fc-N:43 |
| K | 302 | 280 | Fc-N:44 |
| F | 303 | 281 | Fc-N:45 |
| N | 304 | 282 | Fc-N:46 |
| W | 305 | 283 | Fc-N:47 |
| - | 305.1 | 283.1 | Fc-N:48 |
| Y | 306 | 284 | Fc-N:49 |
| V | 307 | 285 | Fc-N:50 |
| D | 308 | 286 | Fc-N:51 |
| G | 309 | 287 | Fc-N:52 |

FIG. 9 Continued

| AB-007088_LS_Heavy Chain | | | |
|---|---|---|---|
| Residue | Linear # | Mat. Linear # | ASN # |
| V | 310 | 288 | Fc-N:53 |
| E | 311 | 289 | Fc-N:54 |
| - | 311.1 | 289.1 | Fc-N:55 |
| - | 311.2 | 289.2 | Fc-N:56 |
| V | 312 | 290 | Fc-N:57 |
| H | 313 | 291 | Fc-N:58 |
| N | 314 | 292 | Fc-N:59 |
| A | 315 | 293 | Fc-N:60 |
| K | 316 | 294 | Fc-N:61 |
| T | 317 | 295 | Fc-N:62 |
| K | 318 | 296 | Fc-N:63 |
| P | 319 | 297 | Fc-N:64 |
| R | 320 | 298 | Fc-N:65 |
| E | 321 | 299 | Fc-N:66 |
| E | 322 | 300 | Fc-N:67 |
| Q | 323 | 301 | Fc-N:68 |
| - | 323.1 | 301.1 | Fc-N:69 |
| - | 323.2 | 301.2 | Fc-N:70 |
| - | 323.3 | 301.3 | Fc-N:71 |
| - | 323.4 | 301.4 | Fc-N:72 |
| Y | 324 | 302 | Fc-N:73 |
| N | 325 | 303 | Fc-N:74 |
| S | 326 | 304 | Fc-N:75 |
| T | 327 | 305 | Fc-N:76 |
| Y | 328 | 306 | Fc-N:77 |
| R | 329 | 307 | Fc-N:78 |
| V | 330 | 308 | Fc-N:79 |
| V | 331 | 309 | Fc-N:80 |
| S | 332 | 310 | Fc-N:81 |
| V | 333 | 311 | Fc-N:82 |
| L | 334 | 312 | Fc-N:83 |
| T | 335 | 313 | Fc-N:84 |
| V | 336 | 314 | Fc-N:85 |
| L | 337 | 315 | Fc-N:86 |
| H | 338 | 316 | Fc-N:87 |
| Q | 339 | 317 | Fc-N:88 |
| D | 340 | 318 | Fc-N:89 |
| W | 341 | 319 | Fc-N:90 |
| - | 341.1 | 319.1 | Fc-N:91 |
| L | 342 | 320 | Fc-N:92 |
| N | 343 | 321 | Fc-N:93 |
| G | 344 | 322 | Fc-N:94 |
| K | 345 | 323 | Fc-N:95 |

FIG. 9 Continued

| AB-007088_LS_Heavy Chain | | | |
|---|---|---|---|
| Residue | Linear # | Mat. Linear # | ASN # |
| E | 346 | 324 | Fc-N:96 |
| - | 346.1 | 324.1 | Fc-N:97 |
| - | 346.2 | 324.2 | Fc-N:98 |
| Y | 347 | 325 | Fc-N:99 |
| K | 348 | 326 | Fc-N:100 |
| C | 349 | 327 | Fc-N:101 |
| K | 350 | 328 | Fc-N:102 |
| V | 351 | 329 | Fc-N:103 |
| S | 352 | 330 | Fc-N:104 |
| N | 353 | 331 | Fc-N:105 |
| K | 354 | 332 | Fc-N:106 |
| A | 355 | 333 | Fc-N:107 |
| L | 356 | 334 | Fc-N:108 |
| P | 357 | 335 | Fc-N:109 |
| - | 357.1 | 335.1 | Fc-N:110 |
| - | 357.2 | 335.2 | Fc-N:111 |
| A | 358 | 336 | Fc-N:112 |
| P | 359 | 337 | Fc-N:113 |
| I | 360 | 338 | Fc-N:114 |
| E | 361 | 339 | Fc-N:115 |
| K | 362 | 340 | Fc-N:116 |
| T | 363 | 341 | Fc-N:117 |
| I | 364 | 342 | Fc-N:118 |
| S | 365 | 343 | Fc-N:119 |
| K | 366 | 344 | Fc-N:120 |
| A | 367 | 345 | Fc-N:121 |
| K | 368 | 346 | Fc-N:122 |
| G | 369 | 347 | Fc-N:123 |
| - | 369.1 | 347.1 | Fc-C:1 |
| Q | 370 | 348 | Fc-C:2 |
| P | 371 | 349 | Fc-C:3 |
| R | 372 | 350 | Fc-C:4 |
| E | 373 | 351 | Fc-C:5 |
| P | 374 | 352 | Fc-C:6 |
| Q | 375 | 353 | Fc-C:7 |
| V | 376 | 354 | Fc-C:8 |
| Y | 377 | 355 | Fc-C:9 |
| T | 378 | 356 | Fc-C:10 |
| L | 379 | 357 | Fc-C:11 |
| P | 380 | 358 | Fc-C:12 |
| P | 381 | 359 | Fc-C:13 |
| - | 381.1 | 359.1 | Fc-C:14 |
| S | 382 | 360 | Fc-C:15 |

FIG. 9 Continued

| AB-007088_LS_Heavy Chain | | | |
|---|---|---|---|
| Residue | Linear # | Mat. Linear # | ASN # |
| R | 383 | 361 | Fc-C:16 |
| D | 384 | 362 | Fc-C:17 |
| - | 384.1 | 362.1 | Fc-C:18 |
| E | 385 | 363 | Fc-C:19 |
| L | 386 | 364 | Fc-C:20 |
| - | 386.1 | 364.1 | Fc-C:21 |
| - | 386.2 | 364.2 | Fc-C:22 |
| T | 387 | 365 | Fc-C:23 |
| K | 388 | 366 | Fc-C:24 |
| N | 389 | 367 | Fc-C:25 |
| Q | 390 | 368 | Fc-C:26 |
| V | 391 | 369 | Fc-C:27 |
| S | 392 | 370 | Fc-C:28 |
| L | 393 | 371 | Fc-C:29 |
| T | 394 | 372 | Fc-C:30 |
| C | 395 | 373 | Fc-C:31 |
| L | 396 | 374 | Fc-C:32 |
| V | 397 | 375 | Fc-C:33 |
| K | 398 | 376 | Fc-C:34 |
| G | 399 | 377 | Fc-C:35 |
| F | 400 | 378 | Fc-C:36 |
| Y | 401 | 379 | Fc-C:37 |
| P | 402 | 380 | Fc-C:38 |
| - | 402.1 | 380.1 | Fc-C:39 |
| - | 402.2 | 380.2 | Fc-C:40 |
| S | 403 | 381 | Fc-C:41 |
| D | 404 | 382 | Fc-C:42 |
| I | 405 | 383 | Fc-C:43 |
| A | 406 | 384 | Fc-C:44 |
| V | 407 | 385 | Fc-C:45 |
| E | 408 | 386 | Fc-C:46 |
| W | 409 | 387 | Fc-C:47 |
| - | 409.1 | 387.1 | Fc-C:48 |
| E | 410 | 388 | Fc-C:49 |
| S | 411 | 389 | Fc-C:50 |
| N | 412 | 390 | Fc-C:51 |
| G | 413 | 391 | Fc-C:52 |
| Q | 414 | 392 | Fc-C:53 |
| P | 415 | 393 | Fc-C:54 |
| - | 415.1 | 393.1 | Fc-C:55 |
| - | 415.2 | 393.2 | Fc-C:56 |
| E | 416 | 394 | Fc-C:57 |
| N | 417 | 395 | Fc-C:58 |

FIG. 9 Continued

| AB-007088_LS_Heavy Chain | | | |
|---|---|---|---|
| Residue | Linear # | Mat. Linear # | ASN # |
| N | 418 | 396 | Fc-C:59 |
| Y | 419 | 397 | Fc-C:60 |
| K | 420 | 398 | Fc-C:61 |
| T | 421 | 399 | Fc-C:62 |
| T | 422 | 400 | Fc-C:63 |
| P | 423 | 401 | Fc-C:64 |
| P | 424 | 402 | Fc-C:65 |
| V | 425 | 403 | Fc-C:66 |
| L | 426 | 404 | Fc-C:67 |
| D | 427 | 405 | Fc-C:68 |
| - | 427.1 | 405.1 | Fc-C:69 |
| - | 427.2 | 405.2 | Fc-C:70 |
| - | 427.3 | 405.3 | Fc-C:71 |
| - | 427.4 | 405.4 | Fc-C:72 |
| S | 428 | 406 | Fc-C:73 |
| D | 429 | 407 | Fc-C:74 |
| G | 430 | 408 | Fc-C:75 |
| S | 431 | 409 | Fc-C:76 |
| F | 432 | 410 | Fc-C:77 |
| F | 433 | 411 | Fc-C:78 |
| L | 434 | 412 | Fc-C:79 |
| Y | 435 | 413 | Fc-C:80 |
| S | 436 | 414 | Fc-C:81 |
| K | 437 | 415 | Fc-C:82 |
| L | 438 | 416 | Fc-C:83 |
| T | 439 | 417 | Fc-C:84 |
| V | 440 | 418 | Fc-C:85 |
| D | 441 | 419 | Fc-C:86 |
| K | 442 | 420 | Fc-C:87 |
| S | 443 | 421 | Fc-C:88 |
| R | 444 | 422 | Fc-C:89 |
| W | 445 | 423 | Fc-C:90 |
| - | 445.1 | 423.1 | Fc-C:91 |
| Q | 446 | 424 | Fc-C:92 |
| Q | 447 | 425 | Fc-C:93 |
| G | 448 | 426 | Fc-C:94 |
| N | 449 | 427 | Fc-C:95 |
| V | 450 | 428 | Fc-C:96 |
| - | 450.1 | 428.1 | Fc-C:97 |
| - | 450.2 | 428.2 | Fc-C:98 |
| F | 451 | 429 | Fc-C:99 |
| S | 452 | 430 | Fc-C:100 |
| C | 453 | 431 | Fc-C:101 |

FIG. 9 Continued

| AB-007088_LS_Heavy Chain | | | |
|---|---|---|---|
| Residue | Linear # | Mat. Linear # | ASN # |
| S | 454 | 432 | Fc-C:102 |
| V | 455 | 433 | Fc-C:103 |
| L | 456 | 434 | Fc-C:104 |
| H | 457 | 435 | Fc-C:105 |
| E | 458 | 436 | Fc-C:106 |
| A | 459 | 437 | Fc-C:107 |
| L | 460 | 438 | Fc-C:108 |
| H | 461 | 439 | Fc-C:109 |
| - | 461.1 | 439.1 | Fc-C:110 |
| - | 461.2 | 439.2 | Fc-C:111 |
| S | 462 | 440 | Fc-C:112 |
| H | 463 | 441 | Fc-C:113 |
| Y | 464 | 442 | Fc-C:114 |
| T | 465 | 443 | Fc-C:115 |
| - | 465.1 | 443.1 | Fc-C:116 |
| Q | 466 | 444 | Fc-C:117 |
| K | 467 | 445 | Fc-C:118 |
| S | 468 | 446 | Fc-C:119 |
| L | 469 | 447 | Fc-C:120 |
| S | 470 | 448 | Fc-C:121 |
| L | 471 | 449 | Fc-C:122 |
| S | 472 | 450 | Fc-C:123 |
| P | 473 | 451 | HCnst-Po:1 |
| G | 474 | 452 | HCnst-Po:2 |
| K | 475 | 453 | HCnst-Po:3 |
| - | 475.1 | 453.1 | HCnst-Po:4 |
| - | 475.2 | 453.2 | HCnst-Po:5 |
| - | 475.3 | 453.3 | HCnst-Po:6 |
| - | 475.4 | 453.4 | HCnst-Po:7 |
| - | 475.5 | 453.5 | HCnst-Po:8 |
| - | 475.6 | 453.6 | HCnst-Po:9 |
| - | 475.7 | 453.7 | HCnst-Po:10 |
| - | 475.8 | 453.8 | HCnst-Po:11 |
| - | 475.9 | 453.9 | HCnst-Po:12 |
| - | 475.10 | 453.10 | HCnst-Po:13 |
| - | 475.11 | 453.11 | HCnst-Po:14 |
| - | 475.12 | 453.12 | HCnst-Po:15 |
| - | 475.13 | 453.13 | HCnst-Po:16 |
| - | 475.14 | 453.14 | HCnst-Po:17 |
| - | 475.15 | 453.15 | HCnst-Po:18 |
| - | 475.16 | 453.16 | HCnst-Po:19 |
| - | 475.17 | 453.17 | HCnst-Po:20 |
| - | 475.18 | 453.18 | HCnst-Po:21 |

FIG. 9 Continued

| AB-007088_LS_Heavy Chain | | | |
|---|---|---|---|
| Residue | Linear # | Mat. Linear # | ASN # |
| - | 475.19 | 453.19 | HCnst-Po:22 |
| - | 475.20 | 453.20 | HCnst-Po:23 |
| - | 475.21 | 453.21 | HCnst-Po:24 |
| - | 475.22 | 453.22 | HCnst-Po:25 |
| - | 475.23 | 453.23 | HCnst-Po:26 |
| - | 475.24 | 453.24 | HCnst-Po:27 |
| - | 475.25 | 453.25 | HCnst-Po:28 |
| - | 475.26 | 453.26 | HCnst-Po:29 |
| - | 475.27 | 453.27 | HCnst-Po:30 |
| - | 475.28 | 453.28 | HCnst-Po:31 |
| - | 475.29 | 453.29 | HCnst-Po:32 |
| - | 475.30 | 453.30 | HCnst-Po:33 |
| - | 475.31 | 453.31 | HCnst-Po:34 |
| - | 475.32 | 453.32 | HCnst-Po:35 |
| - | 475.33 | 453.33 | HCnst-Po:36 |
| - | 475.34 | 453.34 | HCnst-Po:37 |
| - | 475.35 | 453.35 | HCnst-Po:38 |
| - | 475.36 | 453.36 | HCnst-Po:39 |
| - | 475.37 | 453.37 | HCnst-Po:40 |
| - | 475.38 | 453.38 | HCnst-Po:41 |
| - | 475.39 | 453.39 | HCnst-Po:42 |
| - | 475.40 | 453.40 | HCnst-Po:43 |
| - | 475.41 | 453.41 | HCnst-Po:44 |
| - | 475.42 | 453.42 | HCnst-Po:45 |
| - | 475.43 | 453.43 | HCnst-Po:46 |
| - | 475.44 | 453.44 | HCnst-Po:47 |
| - | 475.45 | 453.45 | HCnst-Po:48 |
| - | 475.46 | 453.46 | HCnst-Po:49 |
| - | 475.47 | 453.47 | HCnst-Po:50 |
| - | 475.48 | 453.48 | HCnst-Po:51 |
| - | 475.49 | 453.49 | HCnst-Po:52 |
| - | 475.50 | 453.50 | HCnst-Po:53 |
| - | 475.51 | 453.51 | HCnst-Po:54 |
| - | 475.52 | 453.52 | HCnst-Po:55 |
| - | 475.53 | 453.53 | HCnst-Po:56 |
| - | 475.54 | 453.54 | HCnst-Po:57 |
| - | 475.55 | 453.55 | HCnst-Po:58 |
| - | 475.56 | 453.56 | HCnst-Po:59 |
| - | 475.57 | 453.57 | HCnst-Po:60 |
| - | 475.58 | 453.58 | HCnst-Po:61 |
| - | 475.59 | 453.59 | HCnst-Po:62 |
| - | 475.60 | 453.60 | HCnst-Po:63 |
| - | 475.61 | 453.61 | HCnst-Po:64 |

FIG. 9 Continued

| AB-007088_LS_Heavy Chain | | | |
|---|---|---|---|
| Residue | Linear # | Mat. Linear # | ASN # |
| - | 475.62 | 453.62 | HCnst-Po:65 |
| - | 475.63 | 453.63 | HCnst-Po:66 |
| - | 475.64 | 453.64 | HCnst-Po:67 |
| - | 475.65 | 453.65 | HCnst-Po:68 |
| - | 475.66 | 453.66 | HCnst-Po:69 |
| - | 475.67 | 453.67 | HCnst-Po:70 |
| - | 475.68 | 453.68 | HCnst-Po:71 |
| - | 475.69 | 453.69 | HCnst-Po:72 |
| - | 475.70 | 453.70 | HCnst-Po:73 |
| - | 475.71 | 453.71 | HCnst-Po:74 |
| - | 475.72 | 453.72 | HCnst-Po:75 |
| - | 475.73 | 453.73 | HCnst-Po:76 |
| - | 475.74 | 453.74 | HCnst-Po:77 |
| - | 475.75 | 453.75 | HCnst-Po:78 |
| - | 475.76 | 453.76 | HCnst-Po:79 |
| - | 475.77 | 453.77 | HCnst-Po:80 |
| - | 475.78 | 453.78 | HCnst-Po:81 |
| - | 475.79 | 453.79 | HCnst-Po:82 |
| - | 475.80 | 453.80 | HCnst-Po:83 |
| - | 475.81 | 453.81 | HCnst-Po:84 |
| - | 475.82 | 453.82 | HCnst-Po:85 |
| - | 475.83 | 453.83 | HCnst-Po:86 |
| - | 475.84 | 453.84 | HCnst-Po:87 |
| - | 475.85 | 453.85 | HCnst-Po:88 |
| - | 475.86 | 453.86 | HCnst-Po:89 |
| - | 475.87 | 453.87 | HCnst-Po:90 |
| - | 475.88 | 453.88 | HCnst-Po:91 |
| - | 475.89 | 453.89 | HCnst-Po:92 |
| - | 475.90 | 453.90 | HCnst-Po:93 |
| - | 475.91 | 453.91 | HCnst-Po:94 |
| - | 475.92 | 453.92 | HCnst-Po:95 |
| - | 475.93 | 453.93 | HCnst-Po:96 |
| - | 475.94 | 453.94 | HCnst-Po:97 |
| - | 475.95 | 453.95 | HCnst-Po:98 |
| - | 475.96 | 453.96 | HCnst-Po:99 |
| - | 475.97 | 453.97 | HCnst-Po:100 |
| - | 475.98 | 453.98 | HCnst-Po:101 |
| - | 475.99 | 453.99 | HCnst-Po:102 |
| - | 475.100 | 453.100 | HCnst-Po:103 |
| - | 475.101 | 453.101 | HCnst-Po:104 |
| - | 475.102 | 453.102 | HCnst-Po:105 |
| - | 475.103 | 453.103 | HCnst-Po:106 |
| - | 475.104 | 453.104 | HCnst-Po:107 |

FIG. 9 Continued

| AB-007088_LS_Heavy Chain | | | |
|---|---|---|---|
| Residue | Linear # | Mat. Linear # | ASN # |
| - | 475.105 | 453.105 | HCnst-Po:108 |
| - | 475.106 | 453.106 | HCnst-Po:109 |
| - | 475.107 | 453.107 | HCnst-Po:110 |
| - | 475.108 | 453.108 | HCnst-Po:111 |
| - | 475.109 | 453.109 | HCnst-Po:112 |
| - | 475.110 | 453.110 | HCnst-Po:113 |
| - | 475.111 | 453.111 | HCnst-Po:114 |
| - | 475.112 | 453.112 | HCnst-Po:115 |
| - | 475.113 | 453.113 | HCnst-Po:116 |
| - | 475.114 | 453.114 | HCnst-Po:117 |
| - | 475.115 | 453.115 | HCnst-Po:118 |
| - | 475.116 | 453.116 | HCnst-Po:119 |
| - | 475.117 | 453.117 | HCnst-Po:120 |
| - | 475.118 | 453.118 | HCnst-Po:121 |
| - | 475.119 | 453.119 | HCnst-Po:122 |
| - | 475.120 | 453.120 | HCnst-Po:123 |

FIG. 9 Continued

ANTI-CSP ANTIBODIES

CROSS-REFERENCE TO RELATED APPLICATIONS

This application claims priority to U.S. Provisional Application No. 63/211,820, filed Jun. 17, 2021, the content of which is incorporated by reference in its entirety.

SEQUENCE LISTING

This application contains a Sequence Listing which has been submitted in ASCII format via EFS-Web and is hereby incorporated by reference in its entirety. Said ASCII copy, created on Jun. 16, 2022, is named 087996_0107_SL.txt and is 461,438 bytes in size.

FIELD

The present disclosure relates to compositions for treating or preventing malaria, and to antibodies conferring protection against infection by malarial parasites such as *Plasmodium falciparum* by insect vector transmission. The present disclosure also relates to methods for treating, preventing, or diagnosing *Plasmodium* infection in a mammal.

BACKGROUND

Malaria causes a large burden of morbidity and mortality, especially in the developing world. The causative agent of malaria is a protozoal parasite, which is transmitted by mosquitoes. Several infectious *Plasmodium* species cause malaria, the deadliest of which is *Plasmodium falciparum*. Others include *P. vivax*, *P. ovale*, and *P. malariae*. A first-generation vaccine (RTS,S) has been developed using portions of the malaria protein CSP, including part of the NANP repeats. CSP-based vaccines have consistently shown 30-50% efficacy in the prevention of erythrocytic-stage infection. This level of efficacy is not sufficient for eradication and new pre-erythrocytic treatments will need superior efficacy. Despite the existence of other anti-malarial products such as mefloquinine, doxycycline, and atovaquone/proguanil, there is a need for new antimalarials options for cases that are resistant to existing antimalarial drugs.

SUMMARY

The present disclosure provides to antibodies targeting *Plasmodium falciparum*. In certain non-limiting embodiments, the antibody is a recombinant anti-circumsporozoite (CSP) antibody. In certain embodiments, the recombinant antibody comprises a light chain variable region (VL) and a heavy chain variable region (VH), wherein the light chain variable region comprises a CDR1 comprising the amino acid sequence set forth in SEQ ID NO: 1, a CDR2 comprising the amino acid sequence set forth in SEQ ID NO: 2, and a CDR3 comprising the amino acid sequence set forth in SEQ ID NO: 3; and the heavy chain variable region comprises a CDR1 comprising the amino acid sequence set forth in SEQ ID NO: 4, a CDR2 comprising the amino acid sequence set forth in SEQ ID NO: 5, and a CDR3 comprising the amino acid sequence set forth in SEQ ID NO: 6.

In certain embodiments, the VL comprises the amino acid sequence set forth in SEQ ID NO: 163; the amino acid sequence set forth in SEQ ID NO: 23; the amino acid sequence set forth in SEQ ID NO: 33; the amino acid sequence set forth in SEQ ID NO: 43; the amino acid sequence set forth in SEQ ID NO: 53; the amino acid sequence set forth in SEQ ID NO: 63; the amino acid sequence set forth in SEQ ID NO: 73; the amino acid sequence set forth in SEQ ID NO: 83; the amino acid sequence set forth in SEQ ID NO: 93; the amino acid sequence set forth in SEQ ID NO: 103; the amino acid sequence set forth in SEQ ID NO: 113; the amino acid sequence set forth in SEQ ID NO: 123; the amino acid sequence set forth in SEQ ID NO: 133; the amino acid sequence set forth in SEQ ID NO: 143; the amino acid sequence set forth in SEQ ID NO: 153; or the amino acid sequence set forth in SEQ ID NO: 173. In certain embodiments, the VH comprises the amino acid sequence set forth in SEQ ID NO: 164; the amino acid sequence set forth in SEQ ID NO: 24; the amino acid sequence set forth in SEQ ID NO: 34; the amino acid sequence set forth in SEQ ID NO: 44; the amino acid sequence set forth in SEQ ID NO: 54; the amino acid sequence set forth in SEQ ID NO: 64; the amino acid sequence set forth in SEQ ID NO: 74; the amino acid sequence set forth in SEQ ID NO: 84; the amino acid sequence set forth in SEQ ID NO: 94; the amino acid sequence set forth in SEQ ID NO: 104; the amino acid sequence set forth in SEQ ID NO: 114; the amino acid sequence set forth in SEQ ID NO: 124; the amino acid sequence set forth in SEQ ID NO: 134; the amino acid sequence set forth in SEQ ID NO: 144; the amino acid sequence set forth in SEQ ID NO: 154; or the amino acid sequence set forth in SEQ ID NO: 174.

In certain embodiments, the VL comprises the amino acid sequence set forth in SEQ ID NO: 163, and the VH comprises the amino acid sequence set forth in SEQ ID NO: 164; the VL comprises the amino acid sequence set forth in SEQ ID NO: 33, and the VH comprises the amino acid sequence set forth in SEQ ID NO: 34; the VL comprises the amino acid sequence set forth in SEQ ID NO: 43, and the VH comprises the amino acid sequence set forth in SEQ ID NO: 44; the VL comprises the amino acid sequence set forth in SEQ ID NO: 53, and the VH comprises the amino acid sequence set forth in SEQ ID NO: 54; the VL comprises the amino acid sequence set forth in SEQ ID NO: 63, and the VH comprises the amino acid sequence set forth in SEQ ID NO: 64; the VL comprises the amino acid sequence set forth in SEQ ID NO: 73, and the VH comprises the amino acid sequence set forth in SEQ ID NO: 74; the VL comprises the amino acid sequence set forth in SEQ ID NO: 83, and the VH comprises the amino acid sequence set forth in SEQ ID NO: 84; the VL comprises the amino acid sequence set forth in SEQ ID NO: 93, and the VH comprises the amino acid sequence set forth in SEQ ID NO: 94; the VL comprises the amino acid sequence set forth in SEQ ID NO: 103, and the VH comprises the amino acid sequence set forth in SEQ ID NO: 104; the VL comprises the amino acid sequence set forth in SEQ ID NO: 113, and the VH comprises the amino acid sequence set forth in SEQ ID NO: 114; the VL comprises the amino acid sequence set forth in SEQ ID NO: 123, and the VH comprises the amino acid sequence set forth in SEQ ID NO: 124; the VL comprises the amino acid sequence set forth in SEQ ID NO: 133, and the VH comprises the amino acid sequence set forth in SEQ ID NO: 134; the VL comprises the amino acid sequence set forth in SEQ ID NO: 143, and the VH comprises the amino acid sequence set forth in SEQ ID NO: 144; the VL comprises the amino acid sequence set forth in SEQ ID NO: 153, and the VH comprises the amino acid sequence set forth in SEQ ID NO: 154; or the VL comprises the amino acid sequence set forth in SEQ ID NO: 173, and the VH comprises the amino acid sequence set forth in SEQ ID NO: 174.

In certain embodiments, the VL comprises the amino acid sequence set forth in SEQ ID NO: 63, and the VH comprises the amino acid sequence set forth in SEQ ID NO: 64. In certain embodiments, the VL comprises the amino acid sequence set forth in SEQ ID NO: 133, and the VH comprises the amino acid sequence set forth in SEQ ID NO: 134. In certain embodiments, the VL comprises the amino acid sequence set forth in SEQ ID NO: 163, and the VH comprises the amino acid sequence set forth in SEQ ID NO: 164.

In certain embodiments, the recombinant antibody comprises a light chain (LC) and a heavy chain (HC). In certain embodiments, the LC comprises the amino acid sequence set forth in SEQ ID NO: 27; the amino acid sequence set forth in SEQ ID NO: 37; the amino acid sequence set forth in SEQ ID NO: 47; the amino acid sequence set forth in SEQ ID NO: 57; the amino acid sequence set forth in SEQ ID NO: 67; the amino acid sequence set forth in SEQ ID NO: 77; the amino acid sequence set forth in SEQ ID NO: 87; the amino acid sequence set forth in SEQ ID NO: 97; the amino acid sequence set forth in SEQ ID NO: 107; the amino acid sequence set forth in SEQ ID NO: 117; the amino acid sequence set forth in SEQ ID NO: 127; the amino acid sequence set forth in SEQ ID NO: 137; the amino acid sequence set forth in SEQ ID NO: 147; the amino acid sequence set forth in SEQ ID NO: 157; the amino acid sequence set forth in SEQ ID NO: 167; or the amino acid sequence set forth in SEQ ID NO: 177. In certain embodiments, the HC comprises the amino acid sequence set forth in SEQ ID NO: 28 or SEQ ID NO: 29; the amino acid sequence set forth in SEQ ID NO: 38 or SEQ ID NO: 39; the amino acid sequence set forth in SEQ ID NO: 48 or SEQ ID NO: 49; the amino acid sequence set forth in SEQ ID NO: 58 or SEQ ID NO: 59; the amino acid sequence set forth in SEQ ID NO: 68 or SEQ ID NO: 69; the amino acid sequence set forth in SEQ ID NO: 78 or SEQ ID NO: 79; the amino acid sequence set forth in SEQ ID NO: 88 or SEQ ID NO: 89; the amino acid sequence set forth in SEQ ID NO: 98 or SEQ ID NO: 99; the amino acid sequence set forth in SEQ ID NO: 108 or SEQ ID NO: 109; the amino acid sequence set forth in SEQ ID NO: 118 or SEQ ID NO: 119; the amino acid sequence set forth in SEQ ID NO: 128 or SEQ ID NO: 129; the amino acid sequence set forth in SEQ ID NO: 138 or SEQ ID NO: 139; the amino acid sequence set forth in SEQ ID NO: 148 or SEQ ID NO: 149; the amino acid sequence set forth in SEQ ID NO: 158 or SEQ ID NO: 159; the amino acid sequence set forth in SEQ ID NO: 168 or SEQ ID NO: 169; or the amino acid sequence set forth in SEQ ID NO: 178 or SEQ ID NO: 179.

In certain embodiments, the LC comprises the amino acid sequence set forth in SEQ ID NO: 27, and the HC comprises the amino acid sequence set forth in SEQ ID NO: 28 or SEQ ID NO: 29; the LC comprises the amino acid sequence set forth in SEQ ID NO: 37, and the HC comprises the amino acid sequence set forth in SEQ ID NO: 38 or SEQ ID NO: 39; the LC comprises the amino acid sequence set forth in SEQ ID NO: 47, and the HC comprises the amino acid sequence set forth in SEQ ID NO: 48 or SEQ ID NO: 49; the LC comprises the amino acid sequence set forth in SEQ ID NO: 57, and the HC comprises the amino acid sequence set forth in SEQ ID NO: 58 or SEQ ID NO: 59; the LC comprises the amino acid sequence set forth in SEQ ID NO: 67, and the HC comprises the amino acid sequence set forth in SEQ ID NO: 68 or SEQ ID NO: 69; the LC comprises the amino acid sequence set forth in SEQ ID NO: 77, and the HC comprises the amino acid sequence set forth in SEQ ID NO: 78 or SEQ ID NO: 79; the LC comprises the amino acid sequence set forth in SEQ ID NO: 87, and the HC comprises the amino acid sequence set forth in SEQ ID NO: 88 or SEQ ID NO: 89; the LC comprises the amino acid sequence set forth in SEQ ID NO: 97, and the HC comprises the amino acid sequence set forth in SEQ ID NO: 98 or SEQ ID NO: 99; the LC comprises the amino acid sequence set forth in SEQ ID NO: 107, and the HC comprises the amino acid sequence set forth in SEQ ID NO: 108 or SEQ ID NO: 109; the LC comprises the amino acid sequence set forth in SEQ ID NO: 117, and the HC comprises the amino acid sequence set forth in SEQ ID NO: 118 or SEQ ID NO: 119; the LC comprises the amino acid sequence set forth in SEQ ID NO: 127, and the HC comprises the amino acid sequence set forth in SEQ ID NO: 128 or SEQ ID NO: 129; the LC comprises the amino acid sequence set forth in SEQ ID NO: 137, and the HC comprises the amino acid sequence set forth in SEQ ID NO: 138 or SEQ ID NO: 139; the LC comprises the amino acid sequence set forth in SEQ ID NO: 147, and the HC comprises the amino acid sequence set forth in SEQ ID NO: 148 or SEQ ID NO: 149; the LC comprises the amino acid sequence set forth in SEQ ID NO: 157, and the HC comprises the amino acid sequence set forth in SEQ ID NO: 158 or SEQ ID NO: 159; the LC comprises the amino acid sequence set forth in SEQ ID NO: 167, and the HC comprises the amino acid sequence set forth in SEQ ID NO: 168 or SEQ ID NO: 169; or the LC comprises the amino acid sequence set forth in SEQ ID NO: 177, and the HC comprises the amino acid sequence set forth in SEQ ID NO: 178 or SEQ ID NO: 179.

In certain embodiments, the LC comprises the amino acid sequence set forth in SEQ ID NO: 67, and the HC comprises the amino acid sequence set forth in SEQ ID NO: 69. In certain embodiments, the LC comprises the amino acid sequence set forth in SEQ ID NO: 137, and the HC comprises the amino acid sequence set forth in SEQ ID NO: 139. In certain embodiments, the LC comprises the amino acid sequence set forth in SEQ ID NO: 167, and the HC comprises the amino acid sequence set forth in SEQ ID NO: 169.

In certain embodiments, the recombinant antibody comprises a light chain variable region (VL) and a heavy chain variable region (VH), wherein the VL comprises the amino acid sequence set forth in SEQ ID NO: 13. In certain embodiments, the VL comprises at least one amino acid substitution. In certain embodiments, the at least one amino acid substitution is at position 1 and/or at position 44. In certain embodiments, the amino acid substitution at position 1 is E1Q. In certain embodiments, the amino acid substitution at position 44 is R44T. In certain embodiments, the VH comprises the amino acid sequence set forth in SEQ ID NO: 14. In certain embodiments, the VH comprises at least one amino acid substitution. In certain embodiments, the at least one amino acid substitution is at position 21, position 23, position 88, position 98, or a combination thereof. In certain embodiments, the amino acid substitution at position 1 is E1Q. In certain embodiments, the amino acid substitution at position 44 is R44T. In certain embodiments, the amino acid substitution at position 21 is P21S. In certain embodiments, the amino acid substitution at position 23 is T23A. In certain embodiments, the amino acid substitution at position 80 is I80T. In certain embodiments, the amino acid substitution at position 90 is T90A.

In certain embodiments, the recombinant antibody comprises a heavy chain (HC) comprising the amino acid sequence set forth in SEQ ID NO: 18. In certain embodiments, the HC comprises at least one amino acid substitution. In certain embodiments, the at least one amino acid substitution is at position 438 and/or or at position 444. In certain embodiments, the amino acid substitution at position 438 is M438L. In certain embodiments, the amino acid substitution at position 444 is N444S.

In certain non-limiting embodiments, the present disclosure also provides a recombinant anti-circumsporozoite (CSP) antibody comprising a light chain variable region (VL) and a heavy chain variable region (VH), wherein the VL comprises the amino acid sequence set forth in SEQ ID NO: 163 and the VH comprises the amino acid sequence set forth in SEQ ID NO: 164. In certain embodiments, the recombinant antibody comprises a light chain (LC) and a heavy chain (HC), wherein the LC comprises the amino acid sequence set forth in SEQ ID NO: 167 and the HC comprises the amino acid sequence set forth in SEQ ID NO: 169.

In certain non-limiting embodiments, the present disclosure provides a recombinant anti-circumsporozoite (CSP) antibody comprising a light chain variable region (VL) and a heavy chain variable region (VH), wherein the VL comprises the amino acid sequence set forth in SEQ ID NO: 63 and the VH comprises the amino acid sequence set forth in SEQ ID NO: 64. In certain embodiments, the recombinant antibody comprises a light chain (LC) and a heavy chain (HC), wherein the LC comprises the amino acid sequence set forth in SEQ ID NO: 67 and the HC comprises the amino acid sequence set forth in SEQ ID NO: 69.

In certain non-limiting embodiments, the present disclosure further provides a recombinant anti-circumsporozoite (CSP) antibody comprising a light chain variable region (VL) and a heavy chain variable region (VH), wherein the VL comprises the amino acid sequence set forth in SEQ ID NO: 133 and the VH comprises the amino acid sequence set forth in SEQ ID NO: 134. In certain embodiments, the recombinant antibody comprises a light chain (LC) and a heavy chain (HC), wherein the LC comprises the amino acid sequence set forth in SEQ ID NO: 137 and the HC comprises the amino acid sequence set forth in SEQ ID NO: 139.

In certain non-limiting embodiments, the present disclosure provides a recombinant anti-circumsporozoite (CSP) antibody comprising a light chain variable region (VL) and a heavy chain variable region (VH), wherein the light chain variable region comprises a CDR1 comprising the amino acid sequence set forth in SEQ ID NO: 183, a CDR2 comprising the amino acid sequence set forth in SEQ ID NO: 184, and a CDR3 comprising the amino acid sequence set forth in SEQ ID NO: 185; and the heavy chain variable region comprises a CDR1 comprising the amino acid sequence set forth in SEQ ID NO: 186, a CDR2 comprising the amino acid sequence set forth in SEQ ID NO: 187, and a CDR3 comprising the amino acid sequence set forth in SEQ ID NO: 188. In certain embodiments, the VL comprises the amino acid sequence set forth in SEQ ID NO: 195, and the VH comprises the amino acid sequence set forth in SEQ ID NO: 196. In certain embodiments, the antibody comprises comprising a LC and a HC. In certain embodiments, the LC comprises the amino acid sequence set forth in SEQ ID NO: 199, and the HC comprises the amino acid sequence set forth in SEQ ID NO: 200 or SEQ ID NO: 201.

In certain non-limiting embodiments, the present disclosure provides a recombinant anti-circumsporozoite (CSP) antibody comprising a light chain variable region (VL) and a heavy chain variable region (VH), wherein the light chain variable region comprises a CDR1 comprising the amino acid sequence set forth in SEQ ID NO: 205, a CDR2 comprising the amino acid sequence set forth in SEQ ID NO: 206, and a CDR3 comprising the amino acid sequence set forth in SEQ ID NO: 207; and the heavy chain variable region comprises a CDR1 comprising the amino acid sequence set forth in SEQ ID NO: 208, a CDR2 comprising the amino acid sequence set forth in SEQ ID NO: 209, and a CDR3 comprising the amino acid sequence set forth in SEQ ID NO: 210.

In certain embodiments, the amino acid sequence set forth in SEQ ID NO: 227; the amino acid sequence set forth in SEQ ID NO: 237; the amino acid sequence set forth in SEQ ID NO: 247; the amino acid sequence set forth in SEQ ID NO: 257; or the amino acid sequence set forth in SEQ ID NO: 267. In certain embodiments, the VH comprises the amino acid sequence set forth in SEQ ID NO: 228; the amino acid sequence set forth in SEQ ID NO: 238; the amino acid sequence set forth in SEQ ID NO: 248; the amino acid sequence set forth in SEQ ID NO: 258; or the amino acid sequence set forth in SEQ ID NO: 268.

In certain embodiments, the VL comprises the amino acid sequence set forth in SEQ ID NO: 227, and the VH comprises the amino acid sequence set forth in SEQ ID NO: 228; the VL comprises the amino acid sequence set forth in SEQ ID NO: 237, and the VH comprises the amino acid sequence set forth in SEQ ID NO: 238; the VL comprises the amino acid sequence set forth in SEQ ID NO: 247, and the VH comprises the amino acid sequence set forth in SEQ ID NO: 248; the VL comprises the amino acid sequence set forth in SEQ ID NO: 257, and the VH comprises the amino acid sequence set forth in SEQ ID NO: 258; or the VL comprises the amino acid sequence set forth in SEQ ID NO: 267, and the VH comprises the amino acid sequence set forth in SEQ ID NO: 268.

In certain embodiments, the recombinant antibody comprises a LC and a HC. In certain embodiments, the LC comprises the amino acid sequence set forth in SEQ ID NO: 231; the amino acid sequence set forth in SEQ ID NO: 241; the amino acid sequence set forth in SEQ ID NO: 251; the amino acid sequence set forth in SEQ ID NO: 261; or the amino acid sequence set forth in SEQ ID NO: 271. In certain embodiments, the HC comprises the amino acid sequence set forth in SEQ ID NO: 232 or SEQ ID NO: 233; the amino acid sequence set forth in SEQ ID NO: 242 or SEQ ID NO: 243; the amino acid sequence set forth in SEQ ID NO: 252 or SEQ ID NO: 253; the amino acid sequence set forth in SEQ ID NO: 262 or SEQ ID NO: 263; or the amino acid sequence set forth in SEQ ID NO: 272 or SEQ ID NO: 273.

In certain embodiments, the LC comprises the amino acid sequence set forth in SEQ ID NO: 231, and the HC comprises the amino acid sequence set forth in SEQ ID NO: 232 or SEQ ID NO: 233; the LC comprises the amino acid sequence set forth in SEQ ID NO: 241, and the HC comprises the amino acid sequence set forth in SEQ ID NO: 242 or SEQ ID NO: 243; the LC comprises the amino acid sequence set forth in SEQ ID NO: 251, and the HC comprises the amino acid sequence set forth in SEQ ID NO: 252 or SEQ ID NO: 253; the LC comprises the amino acid sequence set forth in SEQ ID NO: 261, and the HC comprises the amino acid sequence set forth in SEQ ID NO: 262 or SEQ ID NO: 263; or the LC comprises the amino acid sequence set forth in SEQ ID NO: 271, and the HC comprises the amino acid sequence set forth in SEQ ID NO: 272 or SEQ ID NO: 273.

In certain embodiments, the VH comprises the amino acid sequence set forth in SEQ ID NO: 218. In certain embodiments, the VH comprises at least one amino acid substitution. In certain embodiments, the at least one amino acid substitution is at position 40, position 69, position 80, position 85, position 120, or a combination thereof. In certain embodiments, the amino acid substitution at position 40 is T40A. In certain embodiments, the amino acid substitution at position 69 is I69T. In certain embodiments, the amino acid substitution at position 80 is S80Y. In certain embodiments, the amino acid substitution at position 85 is G85S. In certain embodiments, the amino acid substitution at position 120 is I120T. In certain embodiments, the HC comprises the amino acid sequence set forth in SEQ ID NO: 222. In certain embodiments, the HC comprises at least one amino acid substitution. In certain embodiments, the at least one amino acid substitution is at position 434 and/or at position 440. In certain embodiments, the amino acid substitution at position 434 is M434L. In certain embodiments, the amino acid substitution at position 440 is N440S.

In certain embodiments, the recombinant antibody exhibits at least 20% reduction in parasite liver load as compared to a reference antibody. In certain embodiments, the recombinant antibody exhibits at least 20% increase in survival rate as compared to a reference antibody. In certain embodiments, the recombinant antibody exhibits increased conformational stability as compared to a reference antibody. In certain embodiments, the recombinant antibody exhibits increased colloidal stability as compared to a reference antibody. In certain embodiments, the reference antibody is AB-000317. In certain embodiments, the reference antibody is AB-000224. In certain embodiments, the reference antibody is AB-007088.

In certain embodiments, the recombinant antibody binds to a NANP repeat region. In certain embodiments, the recombinant antibody binds to a polypeptide comprising or consisting of the amino acid sequence set forth in SEQ ID NO: 280.

In certain embodiments, the recombinant antibody comprises at least one modification relative to the native AB-000224 variable heavy chain amino acid sequence set forth in SEQ ID NO: 14. In certain embodiments, the recombinant antibody comprises at least one modification relative to the native AB-000224 variable light chain amino acid sequence set forth in SEQ ID NO: 13. In certain embodiments, the recombinant antibody comprises at least one modification relative to the native AB-000224 variable heavy chain amino acid sequence set forth in SEQ ID NO: 14 and at least one modification relative to the native AB-000224 variable light chain amino acid sequence set forth in SEQ ID NO: 13.

In certain embodiments, the recombinant antibody comprises at least one modification relative to the native AB-007088 variable heavy chain amino acid sequence set forth in SEQ ID NO: 218. In certain embodiments, the recombinant antibody comprises at least one modification relative to the native AB-007088 variable light chain amino acid sequence set forth in SEQ ID NO: 217. In certain embodiments, the recombinant antibody comprises at least one modification relative to the native AB-007088 variable heavy chain amino acid sequence set forth in SEQ ID NO: 218 and at least one modification relative to the native AB-000224 variable light chain amino acid sequence set forth in SEQ ID NO: 217.

In certain non-limiting embodiments, the present disclosure provides a polynucleotide encoding an antibody disclosed herein. In certain non-limiting embodiments, the present disclosure provides an expression vector comprising the polynucleotide disclosed herein. In certain non-limiting embodiments, the present disclosure provides a host cell comprising the expression vector or the polynucleotide disclosed herein.

In certain non-limiting embodiments, the present disclosure provides a composition comprising the antibody disclosed herein. In certain embodiments, the composition further comprises a pharmaceutically acceptable carrier.

In certain non-limiting embodiments, the present disclosure provides a method of preventing and/or treating malaria in a subject in need thereof, comprising administering an effective amount of the antibody disclosed herein or of the composition disclosed herein. In certain embodiments, the subject is a pediatric patient.

In certain non-limiting embodiments, the present disclosure provides the antibodies or compositions disclosed herein for use in the prevention and/or treatment of malaria in a subject in need thereof. Additionally, in certain non-limiting embodiments, the present disclosure provides the antibodies or compositions disclosed herein for the manufacture of a medicament for the prevention and/or treatment of malaria in a subject in need thereof. Furthermore, the present disclosure provides use of the antibodies or compositions disclosed herein for the prevention and/or treatment and/or prevention of malaria in a subject in need thereof. In certain embodiments, the subject is a pediatric patient.

BRIEF DESCRIPTION OF THE DRAWINGS

FIGS. 4A-4B illustrate sequences for the AB-000224 antibody. FIG. 4A shows the AB-000224 Lambda Light Chain sequence (SEQ ID NO: 286). FIG. 4B shows the AB-000224 IgG1 Heavy Chain sequence (SEQ ID NO: 287). Framework and CDR regions are designated using the ASN system.

FIG. 5A shows the AB-007088 Lambda Light Chain sequence (SEQ ID NO: 288). FIG. 5B shows the AB-007088 IgG1 Heavy Chain sequence (SEQ ID NO: 289). Framework and CDR regions are designated using the ASN system.

FIG. 6 shows the ASN numbering system for the light chain of AB-000224.

FIG. 7 shows the ASN numbering system for the heavy chain of AB-000224.

FIG. 8 shows the ASN numbering system for the light chain of AB-007088.

FIG. 9 shows the ASN numbering system for the heavy chain of AB-007088.

DETAILED DESCRIPTION

Figure 1A:
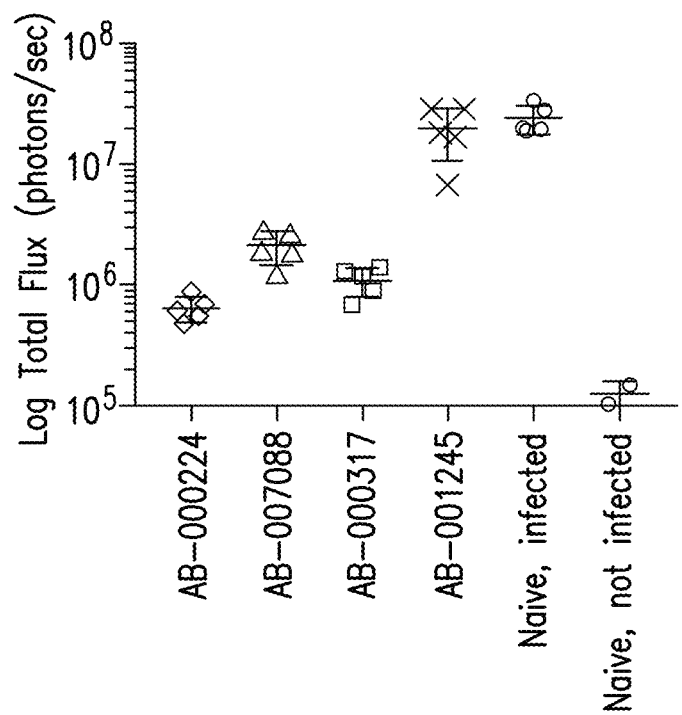
FIG. 1A illustrates parasite liver load following administration of experimental anti-CSP antibodies, AB-000224 and AB-007088. Parasite liver burden load was measured by bioluminescence (photons/sec) generated from the fluorescent sporozoites (y-axis). The individual points indicate the total amount of bioluminescence measured in a single mouse and by extension, the sporozoite liver burden. AB-001245 is a non-malaria-specific antibody that was used as a negative control. AB-000317 is a positive control.

The present disclosure is based, at least in part, on the finding of several anti-CSP antibody variants. The present disclosure surprisingly shows that the disclosed anti-CSP antibodies and variants thereof have superior properties as compared to previously disclosed antibodies.

Definitions

For purposes of interpreting this specification, the following definitions will apply and whenever appropriate, terms used in the singular will also include the plural and vice versa. In the event that any definition set forth below conflicts with any document incorporated herein by reference, the definition set forth below shall control.

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

As used in this specification and the appended claims, the singular forms "a," "an" and "the" include plural referents unless the context dictates otherwise. Thus, for example, reference to "a protein" or an "antibody" includes a plurality of proteins or antibodies, respectively; reference to "a cell" includes mixtures of cells and the like.

As used herein, the term "about" or "approximately" refers to the usual error range for the respective value readily known to the skilled person in this technical field, for example, ±20%, ±10%, or ±5%, are within the intended meaning of the recited value.

As used herein, the term "antibody" means an isolated or recombinant binding agent that comprises the necessary variable region sequences to specifically bind an antigenic epitope. Therefore, an "antibody" as used herein is any form of antibody or fragment thereof that exhibits the desired biological activity, e.g., binding the specific target antigen. Thus, it is used in the broadest sense and specifically covers a monoclonal antibody (including full-length monoclonal antibodies), human antibodies, chimeric antibodies, nanobodies, diabodies, multispecific antibodies (e.g., bispecific antibodies), and antibody fragments including but not limited to scFv, Fab, and the like so long as they exhibit the desired biological activity.

"Antibody fragments" comprise a portion of an intact antibody, for example, the antigen-binding or variable region of the intact antibody. Examples of antibody fragments include Fab, Fab', F(ab')2, and Fv fragments; diabodies; linear antibodies (e.g., Zapata et al., Protein Eng. 8(10): 1057-1062 (1995)); single-chain antibody molecules (e.g., scFv); and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')2 fragment that has two antigen combining sites and is still capable of cross-linking antigen.

As used herein, "recombinant antibody" refers to an antibody wherein the exact amino acid sequence of the antibody is not naturally found in a given organism (e.g., an antibody from a mammal). In certain embodiments, this term can refer to an antibody including one or more amino acid residues that are not found in a naturally occurring antibody. In certain embodiments, a recombinant antibody can have a CDR including an amino acid residue that is not found in a naturally occurring antibody (e.g., an antibody from a mammal). In another exemplary embodiment, a recombinant antibody can have a framework (FR) including an amino acid residue that is not found in a naturally occurring antibody (e.g., an antibody from a mammal). In certain embodiments, a recombinant antibody can have a constant region including an amino acid residue that is not found in a naturally occurring antibody (e.g., an antibody from a mammal). In certain embodiments, a recombinant antibody is variant of a naturally occurring antibody (e.g., AB-000224) including at least one modification, e.g., substitution, relative to the native variable heavy chain amino acid sequence or variable light chain amino acid sequence. For example, but without any limitation, a recombinant antibody can be an anti-CSP antibody AB-000224 disclosed herein comprising at least one modification, e.g., substitution, relative to the native AB-000224 variable heavy chain amino acid sequence (SEQ ID NO: 14) or variable light chain amino acid sequence (SEQ ID NO: 13) described herein. A recombinant antibody has improved developability, e.g., decreased heterogeneity, increased yield, increased stability, improved net charges to improve pharmacokinetics, and/or reduced immunogenicity.

As used herein, the terms, "anti-CSP antibody" and "CSP antibody" are used synonymously and refer to an antibody that binds to *Plasmodium falciparum* circumsporozoite (CSP) antigen.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more.

As used herein, "V-region" refers to an antibody variable region domain comprising the segments of Framework 1, CDR1, Framework 2, CDR2, Framework 3, CDR3, and Framework 4. The heavy chain V-region, VH, is a consequence of rearrangement of a V-gene (HV), a D-gene (HD), and a J-gene (HJ), in what is known as V(D)J recombination during B-cell differentiation. The light chain V-region, VL, is a consequence of the rearrangement of a V-gene (LV) and a J-gene. In certain embodiments, the terms "VH" and "heavy chain variable" refer to the heavy chain V-region of an antibody. In certain embodiments, the terms "VL" and "light chain variable" refer to the light chain V-region of an antibody.

As used herein, "complementarity-determining region (CDR)" refers to the three hypervariable regions (HVRs) in each chain that interrupt the four "framework" regions established by the light and heavy chain variable regions. The CDRs are the primary contributors to binding to an epitope of an antigen. The CDRs of each chain are referred to as CDR1, CDR2, and CDR3 numbered sequentially starting from the N-terminus, and are also identified by the chain in which the particular CDR is located. Thus, a VH CDR3 (HCDR3) is located in the variable domain of the heavy chain of the antibody in which it is found, whereas a VL CDR3 (LCDR3) is the CDR3 from the variable domain of the light chain of the antibody in which it is found. The term "CDR" is used interchangeably with "HVR" when referring to CDR sequences.

The amino acid sequences of the CDRs and framework regions can be determined using various definitions in the art, e.g., Kabat, Chothia, international ImMunoGeneTics database (IMGT), and AbM (see, e.g., Chothia & Lesk, 1987, Canonical structures for the hypervariable regions of immunoglobulins. J. Mol. Biol. 196, 901-917; Chothia C. et al., 1989, Conformations of immunoglobulin hypervariable regions. Nature 342, 877-883; Chothia C. et al., 1992, Structural repertoire of the human VH segments J. Mol. Biol. 227, 799-817; Al-Lazikani et al., J. Mol. Biol 1997, 273(4)). Definitions of antigen combining sites are also described in the following: Ruiz et al., IMGT, the international ImMunoGeneTics database. Nucleic Acids Res., 28, 219-221 (2000); and Lefranc, M.-P. IMGT, the international ImMunoGeneTics database. Nucleic Acids Res. January 1; 29(1):207-9 (2001); MacCallum et al, Antibody-antigen interactions: Contact analysis and binding site topography, J. Mol. Biol., 262 (5), 732-745 (1996); and Martin et al, Proc. Natl Acad. Sci. USA, 86, 9268-9272 (1989); Martin, et al, Methods Enzymol., 203, 121-153, (1991); Pedersen et al, Immunomethods, 1, 126, (1992); and Rees et al, In Sternberg M. J. E. (ed.), Protein Structure Prediction. Oxford University Press, Oxford, 141-172 1996). Reference to CDRs as determined by Kabat numbering is based, for example, on Kabat et al., Sequences of Proteins of Immunological Interest, 5th Ed. Public Health Service, National Institute of Health, Bethesda, Md. (1991)). Chothia CDRs are determined as defined by Chothia (see, e.g., Chothia and Lesk J. Mol. Biol. 196:901-917 (1987)). In certain embodiments, the amino acid sequences of the CDRs and framework regions are numbered using the Antibody Structural Numbering (ASN) system. Antibody Structural Numbering (ASN) is a numbering system developed based on the AHo numbering system (Honegger & Pluckthun, J. Mol. Biol. 309:657-670 (2001)) defined by Annemarie Honegger for the variable region, but extended to include constant domains. FIGS. 6-7 illustrates ASN numbering for AB-000224-LS light and heavy chain, respectively. FIGS. 8-9 illustrates ASN numbering for AB-007088-LS light and heavy chain, respectively.

An "Fc region" refers to the constant region of an antibody excluding the first constant region immunoglobulin domain. Thus, Fc refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, Fc comprises immunoglobulin domains Cy2 and Cy3 and the hinge between Cy1 and Cy. It is understood in the art that the boundaries of the Fc region may vary, however, the human IgG heavy chain Fc region is usually defined to comprise residues C226 or P230 to its carboxyl-terminus, using the numbering according to the EU index as in Kabat et al. (1991, NIH Publication 91-3242, National Technical Information Service, Springfield, Va.). The term "Fc region" may refer to this region in isolation or this region in the context of an antibody or antibody fragment. "Fc region" includes naturally occurring allelic variants of the Fc region as well as modifications that modulate effector function. Fc regions also include variants that don't result in alterations to biological function. For example, one or more amino acids can be deleted from the N-terminus or C-terminus of the Fc region of an immunoglobulin without substantial loss of biological function. Such variants can be selected according to general rules known in the art to have minimal effect on activity (see, e.g., Bowie, et al., Science 247:306-1310, 1990). For example, for IgG4 antibodies, a single amino acid substitution (S228P according to Kabat numbering; designated IgG4Pro) may be introduced to abolish the heterogeneity observed in recombinant IgG4 antibodies (see, e.g., Angal, et al., Mol Immunol 30:105-108, 1993). In certain embodiments, the Fc region includes substitutions that improve pharmacokinetics properties of an antibody, e.g., increased serum half-life. Non-limiting examples of substitutions of the Fc region can be found in U.S. Pat. No. 8,088,376, the content of which is incorporated by reference in its entirety.

The term "equilibrium dissociation constant" abbreviated (KD), refers to the dissociation rate constant (kd, time$^{-1}$) divided by the association rate constant (ka, time$^{-1}$ M$^{-1}$). Equilibrium dissociation constants can be measured using any method. Thus, in certain embodiments, the antibodies of the present disclosure have a KD of less than about 50 nM, typically less than about 25 nM, or less than 10 nM, e.g., less than about 5 nM, or than about 1 nM and often less than about 10 nM as determined by surface plasmon resonance analysis using a biosensor system such as a Biacore® system performed at 37° C. In certain embodiments, an antibody of the present disclosure has a KD of less than 5×10$^{-5}$ M, less than 10$^{-5}$ M, less than 5×10$^{-6}$ M, less than 10$^{-6}$ M, less than 5×10$^{-7}$ M, less than 10$^{-7}$ M, less than 5×10$^{-8}$ M, less than $10^{-8}$ M, less than $5\times10^{-9}$ M, less than $10^{-9}$ M, less than $5\times10^{-10}$ M, less than $10^{-10}$ M, less than $5\times10^{-11}$ M, less than $10^{-11}$ M, less than $5\times10^{-12}$ M, less than $10^{-12}$ M, less than $5\times10^{-13}$ M, less than $10^{-13}$ M, less than $5\times10^{-14}$ M, less than $10^{-14}$ M, less than $5\times10^{-15}$ M, or less than $10^{-15}$ M or lower as measured as a bivalent antibody. As used herein, an "improved" KD refers to a lower KD. In certain embodiments, an antibody of the present disclosure has a KD of less than $5\times10^{-5}$ M, less than $10^{-5}$ M, less than $5\times10^{-6}$ M, less than $10^{-6}$ M, less than $5\times10^{-7}$ M, less than $10^{-7}$ M, less than $5\times10^{-8}$ M, less than $10^{-8}$ M, less than $5\times10^{-9}$ M, less than $10^{-9}$ M, less than $5\times10^{-10}$ M, less than $10^{-10}$ M, less than $5\times10^{-11}$ M, less than $10^{-11}$ M, less than $5\times10^{-12}$ M, less than $10^{-12}$ M, less than $5\times10^{-13}$ M, less than $10^{-13}$ M, less than $5\times10^{-14}$ M, less than $10^{-14}$ M, less than $5\times10^{-15}$ M, or less than $10^{-15}$ M or lower as measured as a monovalent antibody, such as a monovalent Fab. In certain embodiments, an anti-CSP antibody of the present disclosure has KD less than 100 pM, e.g., or less than 75 pM, e.g., in the range of 1 to 100 pM, when measured by surface plasmon resonance analysis using a biosensor system such as a Biacore® system performed at 37° C. In certain embodiments, an anti-CSP antibody of the present disclosure has KD of greater than 100 pM, e.g., in the range of 100-1000 pM or 500-1000 pM when measured by surface plasmon resonance analysis using a biosensor system such as a Biacore® system performed at 37° C.

The term "monovalent molecule" as used herein refers to a molecule that has one antigen-binding site, e.g., a Fab or scFv.

The term "bivalent molecule" as used herein refers to a molecule that has two antigen-binding sites. In certain embodiments, a bivalent molecule of the present invention is a bivalent antibody or a bivalent fragment thereof. In certain embodiments, a bivalent molecule of the present invention is a bivalent antibody. In certain embodiments, a bivalent molecule of the present invention is an IgG. In certain embodiments, monoclonal antibodies have a bivalent basic structure. IgG and IgE have only one bivalent unit, while IgA and IgM consist of multiple bivalent units (2 and 5, respectively) and thus have higher valencies. This bivalency increases the avidity of antibodies for antigens.

The terms "monovalent binding" or "monovalently binds to" as used herein refer to the binding of one antigen-binding site to its antigen.

The terms "bivalent binding" or "bivalently binds to" as used herein refer to the binding of both antigen-binding sites of a bivalent molecule to its antigen. In certain embodiments, both antigen-binding sites of a bivalent molecule share the same antigen specificity.

The term "valency" as used herein refers to the number of different binding sites of an antibody for an antigen. A monovalent antibody includes one binding site for an antigen. A bivalent antibody (e.g., a bivalent IgG antibody) includes two binding sites for the same antigen.

The term "affinity" as used herein refers to either the single or combined strength of one or both arms of an antibody (e.g., an IgG antibody) binding to either a simple or complex antigen-expressing one or more epitopes. As defined here, the term "affinity" does not imply a specific number of valencies between the two binding partners.

The phrase "specifically (or selectively) binds" to an antigen or target or "specifically (or selectively) immunoreactive with," when referring to a protein or peptide, refers to a binding reaction whereby the antibody binds to the antigen or target of interest with an affinity that can be distinguished from non-specific interactions occurring between two proteins.

The terms "identical" or percent "identity," in the context of two or more polypeptide sequences, refer to two or more sequences or subsequences that are the same or have a specified percentage of amino acid residues that are the same (e.g., at least 70%, at least 75%, at least 80%, 85%, 90%, 91%, 92%, 93%, 94%, 95%, 96%, 97%, 98%, 99%, or higher) identity over a specified region, e.g., the length of the two sequences, when compared and aligned for maximum correspondence over a comparison window or designated region. Alignment for purposes of determining percent amino acid sequence identity can be performed in various methods, including, without any limitation, BLAST, BLAST-2, ALIGN, or Megalign (DNASTAR) software. Examples of algorithms that are suitable for determining percent sequence identity and sequence similarity the BLAST 2.0 algorithms, which are described in Altschul et al., Nuc. Acids Res. 25:3389-3402 (1977) and Altschul et al., J. Mol. Biol. 215:403-410 (1990). In certain embodiments, BLAST 2.0 can be used with the default parameters to determine percent sequence identity.

A "substitution," as used herein, denotes the replacement of one or more amino acids or nucleotides by different amino acids or nucleotides, respectively.

A "conservative" substitution as used herein refers to a substitution of an amino acid such that charge, polarity, hydropathy (hydrophobic, neutral, or hydrophilic), and/or size of the side group chain is maintained. Illustrative sets of amino acids that may be substituted for one another include (i) positively-charged amino acids Lys and Arg; and His at pH of about 6; (ii) negatively charged amino acids Glu and Asp; (iii) aromatic amino acids Phe, Tyr and Trp; (iv) nitrogen ring amino acids His and Trp; (v) aliphatic hydrophobic amino acids Ala, Val, Leu and Ile, (vi) hydrophobic sulfur-containing amino acids Met and Cys, which are not as hydrophobic as Val, Leu, and Ile, (vii) small polar uncharged amino acids Ser, Thr, Asp, and Asn (viii) small hydrophobic or neutral amino acids Gly, Ala, and Pro; (ix) amide-comprising amino acids Asn and Gln; and (xi) beta-branched amino acids Thr, Val, and Ile. Reference to the charge of an amino acid refers to the charge at pH 6-7.

As used herein, the terms "nucleic acid" and "polynucleotide" are used interchangeably and as used herein refer to both sense and anti-sense strands of RNA, cDNA, genomic DNA, and synthetic forms and mixed polymers of the above. In certain embodiments, a polynucleotide refers to a polyribonucleotide, polydeoxynucleotide or a modified form of either type of nucleotide, and combinations thereof. The terms also include, but are not limited to, single- and double-stranded forms of DNA. In addition, a polynucleotide, e.g., a cDNA or mRNA, may include either or both naturally occurring and modified nucleotides linked together by naturally occurring and/or non-naturally occurring nucleotide linkages. The nucleic acid molecules may be modified chemically or biochemically or may contain non-natural or derivatized nucleotide bases, as will be readily appreciated by those of skill in the art. Such modifications include, for example, labels, methylation, substitutions of one or more of the naturally occurring nucleotides with an analogue, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). The above term is also intended to include any topological conformation, including single-stranded, double-stranded, partially duplexed, triplex, hairpinned, circular, and padlocked conformations. A reference to a nucleic acid sequence encompasses its complement unless otherwise specified. Thus, a reference to a nucleic acid molecule having a particular sequence should be understood to encompass its complementary strand, with its complementary sequence. The term also includes codon-optimized nucleic acids that encode the same polypeptide sequence.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an antibody or fragment thereof" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. A "vector," as used herein, refers to a recombinant construct in which a nucleic acid sequence of interest is inserted into the vector. Certain vectors can direct the expression of nucleic acids to which they are operatively linked. Such vectors are referred to herein as "expression vectors".

The terms "host cell," "host cell line," and "host cell culture" are used interchangeably and refer to cells into which exogenous nucleic acid has been introduced, including the progeny of such cells. A host cell can be a recombinant host cell and includes the primary transformed cell and progeny derived therefrom without regard to the number of passages.

A polypeptide "variant," as the term is used herein, is a polypeptide that typically differs from a polypeptide specifically disclosed herein in one or more substitutions, deletions, additions, and/or insertions. In the present invention, a "variant" with reference to the sequences described in the "Anti-CSP Antibody Variants" section refers to an engineered sequence, rather than a naturally occurring sequence.

The term "comparable," in the context of describing the strength of binding of two antibodies to the same target, refers to two dissociation constant (KD) values calculated from two binding reactions that are within three (3) fold from each other. In certain embodiments, the ratio between the first KD (the KD of the binding reaction between the first antibody and the target) and the second KD (the KD of the binding reaction between the second antibody and the target) is within the range of 1:3 or 3:1, endpoints exclusive. A lower KD value denotes stronger binding. For example, without any limitation, an antibody variant that has stronger binding as compared to AB-000224 binds to the target with a KD that is at least ⅓ of the KD measured against the same target for AB-000224.

Anti-CSP Antibodies

The present disclosure provides anti-CSP antibodies AB-000224 and AB-007088 and variants thereof. AB-000224 and AB-007088 were discovered in antibody repertoires generated by Immune Repertoire Capture® (IRC®) technology from plasmablast B cells isolated from two donors enrolled in a Phase 2a study evaluating the efficacy of the RTS,S vaccine in preventing malaria infection. The IRC® technology and its use in antibody discovery is well known and disclosed in, e.g., WO 2012148497A2, the entire content of which is herein incorporated by reference. The RTS,S vaccine is a pseudo-viral particle vaccine that combines the hepatitis B surface antigen and the central repeat and C-terminal regions of the *Plasmodium falciparum* (*P. falciparum*) circumsporozoite protein (CSP). RTS,S consists of two polypeptides; RTS is a single polypeptide chain corresponding to amino acids 207 to 395 of *P. falciparum* (3D7) that is fused to HBsAg and S is a polypeptide of 226 amino acids that corresponds to HBsAg. Stoute, et. al., N Engl J Med; 336:86-91(1997); RTS,S Clinical Trials Partnership, PLoS Med. 11(7):e1001685, (2014), WO1993/10152.

CSP is composed of an N-terminal domain containing a heparan sulfate binding site for hepatocyte adhesion, a central repeat region, and a structured C-terminal α-thrombospondin repeat (αTSR) that is followed by a GPI anchor, which attaches CSP to the sporozoite membrane. The central repeat region of CSP is highly immunogenic, and in all *P. falciparum* strains with a CSP sequence available, the repeat region is composed of 1 NPDP repeat, 3-5 NVDP repeats, and 35-41 NANP repeats (e.g., a total of 1/4/38 of NPDP/NVDP/NANP motifs are present in the *P. falciparum* 3D7 strain). The repeat region begins with the junctional NPDP sequence, typically followed by three alternations of NANP and NVDP sequences, and continues with the remaining NANP repeats, with most *P. falciparum* strains having one NVDP interspersed in the middle of the long NANP repeat region. Pholcharee, T. et al., J. Mol. Bio. 432: 1048-1063 (2020).

In certain embodiments, the anti-CSP antibodies disclosed herein bind to the central repeat region of *P. falciparum* CSP. In certain embodiments, the antibodies disclosed herein bind to *P. falciparum* CSP protein in the repeat and/or junctional regions that contain NPNA, NPDP, and/or NVDP motifs. In certain embodiments, the anti-CSP antibodies disclosed herein bind to the NANP repeat region of *P. falciparum* CSP. In certain embodiments, the anti-CSP antibodies disclosed herein bind to a polypeptide comprising the amino acid sequence of (NPNA)3 (SEQ ID NO: 280).

In certain embodiments, the present disclosure provides anti-CSP antibody variants of AB-000224. In certain embodiments, the present disclosure provides anti-CSP antibody variants of AB-007088. In certain embodiments, the variants exhibit protective effects in vivo, e.g., as shown by a reduction in parasite number in a mouse model of malaria infection.

In certain embodiments, the anti-CSP variants disclosed herein maintain the binding specificity, activity and stability and/or manufacturing properties of the parental antibody. In certain embodiments, the anti-CSP variants disclosed herein generated have improved developability, e.g., as identified through various in vitro assays, such as aggregation assessment by HPLC or UPLC, hydrophobic interaction chromatography (HIC), polyspecificity assays (e.g., baculovirus particle binding), self-interaction nanoparticle spectroscopy (SINS), or mass spec analysis after incubation in an accelerated degradation condition such as high temperature, low pH, high pH, or oxidative $H_2O_2$. Mutations are successful if the activity is maintained (or enhanced) while removing or reducing the severity of the liability.

Antibody liabilities are further described in Table 1 below:

TABLE 1

Description of potential development liabilities

| | | | |
|---|---|---|---|
| Free cysteine[1] | Yield, heterogeneity, stability, activity | sequence comprises an odd number of cysteines | High |
| N-linked glycosylation | Yield, heterogeneity, activity | N(-P)(S, T)[2] | High |
| Abnormal net charge | Platform fit, PK | Sharma 2014[3] | High |
| Patches of hydrophobicity | Stability, PK | Sharma 2014 | High |
| Patches of same charge | Stability, PK | N/A (based on structure) | Medium |
| Proteolysis | Stability, PK | (K, R)(K, R)[4] | Medium |
| Proteolysis | Stability, PK | DP | Medium |
| Asparagine deamidation | Heterogeneity, stability, activity | NG; N(A, N, S, T)[5] | Medium; Low |
| Aspartate isomerization | Heterogeneity, stability, activity | DG; D(A, D, S, T)[6] | Medium; Low |
| Lysine glycation | Heterogeneity, stability, activity | K | Low |
| Methionine oxidation | Heterogeneity, stability, activity | M | Low |
| Tryptophan oxidation | Heterogeneity, stability, activity | W | Low |

[1]"Free cysteine" refers to a cysteine that does not form a disulfide bond with another cysteine and thus is left "free" as thiols. The presence of free cysteines in the antibody can be a potential development liability.
Typically, an odd net number of cysteines in the protein shows a likelihood there is a free cysteine.
[2]The N-linked glycosylation site is N-X-S/T, where X is any residue other than proline.
[3]Sharma et al., Proc. Natl. Acad. Sci. USA 111:18601-18606, 2014.
[4]This motif consists of a K or R, followed by a K or R. Stated differently, the motif can be KK, KR, RK, or RR.
[5]The dipeptide NG poses a medium risk of development liability. The dipeptides NA, NN, NS, and NT pose a low risk of development liability. N may also exhibit low risk of liability for other successor residues, e.g., D, H, or P. Stated differently, dipeptide ND, NH, or NP poses a low risk of development liability.
[6]Similarly to the above, the dipeptide DG poses a medium risk of development liability. The dipeptides DA, DD, DS, and DT pose a low risk of development liability. D may also exhibit low risk of development liability for other successor residues, e.g., N, H, or P.

Another goal for engineering variants is to reduce the risk of clinical immunogenicity. For example, reducing the generation of anti-drug antibodies against the therapeutic antibody. In certain embodiments, the anti-CSP antibody variants have reduced immunogenicity as compared to the parental antibody.

The factors that drive clinical immunogenicity can be classified into two groups. First are factors that are intrinsic to the drug, such as sequence, post-translational modifications, aggregates, degradation products, and contaminants. Second are factors related to how the drug is used, such as dose level, dose frequency, route of administration, patient immune status, and patient HLA type.

One approach to engineering a variant to be as much like self as possible is to identify a close germline sequence and mutate as many mismatched positions (also known as "germline deviations") to the germline residue type as possible. This approach applies for germline genes IGHV, IGHJ, IGKV, IGKJ, IGLV, and IGLJ, and accounts for all of the variable heavy (V11) and variable light (VL) regions except for part of H-CDR3. Germline gene IGHD codes for part of the H-CDR3 region but typically exhibits too much variation in how it is recombined with IGHV and IGHJ (e.g., forward or reverse orientation, any of three translation frames, and 5' and 3' modifications and non-templated additions) to present a "self" sequence template from a population perspective.

Each germline gene can present as different alleles in the population. The least immunogenic drug candidate, in terms of minimizing the percent of patients with an immunogenic response, would likely be one that matches an allele commonly found in the patient population. Single nucleotide polymorphism (SNP) data from the human genome can be used to approximate the frequency of alleles in the population.

Another approach to engineering a lead for reduced immunogenicity risk is to use in silico predictions of immunogenicity, such as the prediction of T cell epitopes, or use in vitro assays of immunogenicity, such as ex vivo human T cell activation. For example, services such as those offered by Lonza, United Kingdom, are available that employ platforms for prediction of HLA binding and in vitro assessment to further identify potential epitopes.

In certain embodiments, antibody variants are additionally designed to enhance the efficacy of the antibody. Design parameters for this aspect focused on CDRs, e.g., CDR3. Positions to be mutated were identified based on structural analysis of antibody-antigen co-crystals (Oyen et al., Proc. Natl. Acad Sci. USA 114:E10438-E10445, 2017) and based on sequence information of other antibodies from the same lineage as AB-000224 or AB-007088.

1. Approaches to Mutation Design

Development liabilities can be removed or reduced by one or more mutations. Mutations are designed to preserve antibody structure and function while removing or reducing development liabilities and to improve function. In certain embodiments, mutations to chemically similar residues were identified to maintain size, shape, charge, and/or polarity. Non-limiting examples of mutations are described in Table 2 below:

TABLE 2

| | | | |
|---|---|---|---|
| Free cysteine | Odd #C | High | C(A, S) |
| N-linked glycosylation | N(-P)(S, T) | High | N-*(Q, D, S, A); (S, T)-*(A, N) |
| Proteolytic cleavage | (K, R)(K, R) | Medium | K, R-*(Q, S, A) |
| Proteolytic cleavage | DP | Medium | D(E, S, A) |
| Asparagine deamidation | NG; N(A, N, S, T)* | Medium; Low | N-*(Q ,S, A); G-*(A, S) |
| Aspartate isomerization | DG; D(A, D, S, T)* | Medium; Low | D-*(E, S, A); G-*(A, S) |
| Lysine glycation | K | Low | K(R, Q, S, A) |
| Methionine oxidation | M | Low | M-*(Q, L, S, A) |
| Tryptophan oxidation | W | Low | W-*(Y, F) |
| Proteolytic cleavage | (K, R)(K, R) | Medium | K, R-*(Q, S, A) |

2. Anti-CSP Antibody Variants of AB-000224

In certain embodiments, a variant of an anti-CSP antibody AB-000224 disclosed herein comprises modifications compared to AB-000224 that provide improved pharmacokinetic properties, increased serum stability, stronger binding, and/or improved in vivo protective effects compared to AB-000224. In certain embodiments, a variant of an anti-CSP antibody AB-000224 disclosed herein exhibits reduced immunogenicity and/or increased manufacturability as compared to AB-000224. In certain embodiments, a variant of an anti-CSP antibody AB-000224 disclosed herein has at least one modification, e.g., substitution, relative to the native AB-000224 variable heavy chain amino acid sequence (SEQ ID NO: 14) or variable light chain amino acid sequence (SEQ ID NO: 13) described herein, and has improved developability, e.g., decreased heterogeneity, increased yield, increased stability, improved net charges to improve pharmacokinetics, and/or reduced immunogenicity. In certain embodiments, a VH region or a VL region of such a variant of an anti-CSP antibody AB-000224 disclosed herein has at least two, three, four, five, or six or more modifications, e.g., substitutions. In certain embodiments, a variant of the an anti-CSP antibody AB-000224 disclosed herein has a total of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 modifications, e.g. substitutions, including both variable regions, compared to AB-000224.

In certain embodiments, a variant of an anti-CSP antibody AB-000224 disclosed herein exhibits increased serum half-life as compared to AB-000224. In certain embodiments, a variant of an anti-CSP antibody AB-000224 disclosed herein has at least one modification, e.g., substitution, relative to the native AB-000224 Fc region of the heavy chain sequence described herein, and has improved pharmacokinetics properties, e.g., half-life. In certain embodiments, an Fc region of the heavy chain of such a variant of an anti-CSP antibody AB-000224 disclosed herein has at least two, three, four, five, or six, or more modifications, e.g., substitutions. In certain embodiments, a variant of an anti-CSP antibody AB-000224 disclosed herein has a total of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 modifications, e.g. substitutions, including both heavy and light chains, compared to AB-000224. In certain non-limiting embodiments, an Fc region of the heavy chain of a variant of an anti-CSP antibody AB-000224 disclosed herein can include an isoleucine at position 250, a tyrosine at position 252, an isoleucine at position 259, a glutamine at position 307, a phenylalanine at position 308, a leucine at position 319, a leucine at position 428, a histidine at position 434, a phenylalanine at position 434, an alanine at position 434, a serine at position 434, a methionine at position 434, or a combination thereof, wherein the numbering is defined by EU index as in Kabat. In certain embodiments, an Fc region of the heavy chain of a variant of an anti-CSP antibody AB-000224 disclosed herein includes a leucine at position 428 and a serine at position 434, wherein the numbering is defined by EU index as in Kabat.

The light and heavy chain CDRs of AB-000224 as defined by Kabat numbering system are shown in Table 3 below:

TABLE 3

| AB-000224 CDR sequences (Kabat) | | |
|---|---|---|
| CDR1 | CDR2 | CDR3 |
| VL region TGMNSNIGAGYDVY (SEQ ID NO: 1) | GNSNRPS (SEQ ID NO: 2) | QSYDTSLNGWA (SEQ ID NO: 3) |
| VH region DHAMS (SEQ ID NO: 4) | FIRKTTYGATTHYA AAVRG (SEQ ID NO: 5) | VQLDYGPGYQYYGM DV (SEQ ID NO: 6) |

The light and heavy chain CDRs of AB-000224 as defined by ASN numbering system are shown in Table 4 below:

TABLE 4

| AB-000224 CDR sequences (ASN) | | |
|---|---|---|
| CDR1 | CDR2 | CDR3 |
| VL region TGMNSNIGAGYDVY (SEQ ID NO: 7) | GNSNRPS (SEQ ID NO: 8) | QSYDTSLNGWA (SEQ ID NO: 9) |
| VH region DHAMS (SEQ ID NO: 10) | FI RKTTYGATTHY AAAVRG (SEQ ID NO: 11) | VQLDYGPGYQYYGM DV (SEQ ID NO: 12) |

The heavy chain variable region (VH) and light chain variable region (VL) sequences and heavy and light chain sequences of AB-000224 are shown in Table 5 below:

TABLE 5

| AB-000224 variable region and full chain sequences | |
|---|---|
| VL region | ESVLTQPPSVSGAPGQRVTISCTGMNSNIGAGYDVYWYQQLPGRAPKLLIYGNSNRP SGVPDRFSGSRSGTSASLAITGLQAEDEADYYCQSYDTSLNGWAFGGGTKLTVLG (SEQ ID NO: 13) |
| VH region | EVQLVESGGGLVQPGRSLRLPCTASGFSFGDHAMSWVRQAPGKGLEWVGFIRKTTYG ATTHYAAAVRGRFTISRDDSKSIVYLQMNSLKTEDTAVYFCTRVQLDYGPGYQYYGM DVWGQGTTVTVSS (SEQ ID NO: 14) |
| DNA for VL region | GAGTCTGTGCTGACGCAGCCGCCCTCAGTGTCTGGGGCCCCAGGGCAGAGGGTCACC ATCTCCTGCACTGGGATGAACTCCAACATCGGGGCAGGTTATGATGTATACTGGTAC CAACAACTTCCAGGAAGAGCCCCCAAACTCCTCATCTATGGTAACAGCAATCGGCCC TCAGGGGTCCCTGACCGATTCTCTGGCTCCAGGTCTGGCACCTCAGCCTCCCTGGCC ATCACTGGGCTCCAGGCTGAGGATGAGGCTGATTATTACTGCCAGTCCTATGACACC AGCCTGAATGGTTGGGCTTTCGGCGGAGGGACCAAGTTGACCGTCCTAGGC [SEQ ID NO: 15] |
| DNA for VH region | GAGGTGCAGCTGGTGGAGTCTGGGGGAGGCTTGGTACAGCCAGGGCGGTCCCTGAGA CTCCCCTGTACAGCCTCTGGGTTTAGTTTTGGTGATCATGCTATGAGCTGGGTCCGC CAGGCTCCAGGGAAGGGGCTGGAGTGGGTAGGTTTCATTAGAAAGACAACTTATGGT GCGACAACACACTACGCCGCGGCTGTGAGAGGCAGATTCACCATCTCGCGAGATGAT TCTAAAAGCATTGTCTATCTGCAAATGAACAGCCTGAAAACCGAGGACACAGCCGTG TATTTCTGTACTAGAGTGCAGCTTGACTATGGCCCGGGATACCAGTACTACGGTATG GACGTCTGGGGCCAAGGGACCACGGTCACCGTCTCCTCA [SEQ ID NO: 16] |
| Light Chain | ESVLTQPPSVSGAPGQRVTISCTGMNSNIGAGYDVYWYQQLPGRAPKLLIYGNSNRP SGVPDRFSGSRSGTSASLAITGLQAEDEADYYCQSYDTSLNGWAFGGGTKLTVLGQP KAAPSVTLFPPSSEELQANKATLVCLVSDFYPGAVTVAWKADGSPVKVGVETTKPSK QSNNKYAASSYLSLTPEQWKSHRSYSCRVTHEGSTVEKTVAPAECS [SEQ ID NO:17] |
| Heavy Chain version 1 | EVQLVESGGGLVQPGRSLRLPCTASGFSFGDHAMSWVRQAPGKGLEWVGFIRKTTYG ATTHYAAAVRGRFTISRDDSKSIVYLQMNSLKTEDTAVYFCTRVQLDYGPGYQYYGM DVWGQGTTVTVSSASTKGPSVFPLAPSSKSTSGGTAALGCLVKDYFPEPVTVSWNSG ALTSGVHTFPAVLQSSGLYSLSSWTVPSSSLGTQTYICNVNHKPSNTKVDKKVEPK |

TABLE 5-continued

AB-000224 variable region and full chain sequences

|  |  |
|---|---|
|  | SCDKTHTCPPCPAPELLGGPSVFLFPPKPKDTLMISRTPEVTCVVVDVSHEDPEVKF<br>NWYVDGVEVHNAKTKPREEQYNSTYRWSVLTVLHQDWLNGKE<br>YKCKVSNKALPAPIEKTISKAKGQPREPQVYTLPPSRDELTKNQVSLTCL<br>VKGFYPSDIAVEWESNGQPENNYKTTPPVLDSDGSFFLYSKLTVDKSRWQ<br>QGNVFSCSVMHEALHNHYTQKSLSLSPGK [SEQ ID NO: 18] |
| Heavy Chain version 2 | EVQLVESGGGLVQPGRSLRLPCTASGFSFGDHAMSWVRQAPGKGLEWVGFIRKTTYG<br>ATTHYAAAVRGRFTISRDDSKSIVYLQMNSLKTEDTAVYFCTRVQLDYGPGYQYYGM<br>DVWGQGTTVTVSSASTKGPSVFPLAPSSKSTSGGTAALGCLVKDYFPEPVTVSWNSG<br>ALTSGVHTFPAVLQSSGLYSLSSWTVPSSSLGTQTYICNVNHKPSNTKVDKKVEPK<br>SCDKTHTCPPCPAPELLGGPSVFLFPPKPKDTLMISRTPEVTCVVVDVSHEDPEVKF<br>NWYVDGVEVHNAKTKPREEQYNSTYRWSVLTVLHQDWLNGKEYKCKVSNKALPAPI<br>EKTISKAKGQPREPQVYTLPPSRDELTKNQVSLTCLVKGFYPSDIAVEWESNGQPEN<br>nyktppvldsdgsfflyskltvdksrwqqgnvfscsvlhealhshytqkslslspg<br>K [SEQ ID NO: 19] |
| DNA for Light Chain | GAGTCTGTGCTGACGCAGCCGCCCTCAGTGTCTGGGGCCCAGGGCAGAGGGTCACC<br>ATCTCCTGCACTGGGATGAACTCCAACATCGGGGCAGGTTATGATGTATACTGGTAC<br>CAACAACTTCCAGGAAGAGCCCCCAAACTCCTCATCTATGGTAACAGCAATCGGCC<br>TCAGGGGTCCCTGACCGATTCTCTGGCTCCAGGTCTGGCACCTCAGCCTCCCTGGCC<br>ATCACTGGGCTCCAGGCTGAGGATGAGGCTGATTATTACTGCCAGTCCTATGACACC<br>AGCCTGAATGGTTGGGCTTTCGGCGGAGGGACCAAGTTGACCGTCCTAGGCCAGCCC<br>AAGGCTGCCCCCTCGGTCACTCTGTTCCCACCCTCCTCTGAGGAGCTTCAAGCCAAC<br>AAGGCCACACTGGTGTGTCTCGTAAGTGACTTCTACCCGGGAGCCGTGACAGTGGCC<br>TGGAAGGCAGATGGCAGCCCCGTCAAGGTGGGAGTGGAGACCACCAAACCCTCCAAA<br>CAAAGCAACAACAAGTATGCGGCCAGCAGCTACCTGAGCCTGACGCCCGAGCAGTGG<br>AAGTCCCACAGAAGCTACAGCTGCCGGGTCACGCATGAAGGGAGCACCGTGGAGAAG<br>ACAGTGGCCCCTGCAGAATGCTCT [SEQ ID NO: 20] |
| DNA for Heavy Chain version 1 | GAGGTGCAGCTGGTGGAGTCTGGGGGAGGCTTGG<br>TACAGCCAGGGCGGTCCCTGAGACTCCCCTGTACAGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGCATTGTCTATCTGCAAATGAACAGCCTGAAAACCGAGGACACAGCCGT<br>GTATTTCTGTACTAGAGTGCAGCTTGACTATGGCCCGGGATACCAGTACT<br>ACGGTATGGACGTCTGGGGCCAAGGGACCACGGTCACCGTCTCCTCAGCC<br>TCCACCAAGGGCCCATCGGTCTTCCCCCTGGCACCCTCCTCCAAGAGCAC<br>CTCTGGGGGCACAGCAGCCCTGGGCTGCCTGGTCAAGGACTACTTCCCCG<br>AACCGGTGACGGTGTCGTGGAACTCAGGCGCCCTGACCAGCGGCGTGCAC<br>ACCTTCCCGGCTGTCCTACAGTCCTCAGGACTCTACTCCCTCAGCAGCGT<br>GGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAA<br>TCTTGTGACAAAACTCACACATGCCCACCGTGCCCAGCACCTGAACTCCT<br>GGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCA<br>TAATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG<br>GCAGCCGGAGAACAACTACAAGACCACGCCTCCCGTGCTGGACTCCGACG<br>GCTCCTTCTTCCTCTACAGCAAGCTCACCGTGGACAAGAGCAGGTGGCAG<br>CAGGGGAACGTCTTCTCATGCTCCGTGATGCATGAGGCTCTGCACAACCA<br>CTACACACAGAAGAGCCTCTCCCTGTCTCCGGGTAAA<br>[SEQ ID NO: 21] |
| DNA for Heavy Chain version 2 | GAGGTGCAGCTGGTGGAGTCTGGGGGAGGCTTGG<br>TACAGCCAGGGCGGTCCCTGAGACTCCCCTGTACAGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGCATTGTCTATCTGCAAATGAACAGCCTGAAAACCGAGGACACAGCCGT<br>GTATTTCTGTACTAGAGTGCAGCTTGACTATGGCCCGGGATACCAGTACT<br>ACGGTATGGACGTCTGGGGCCAAGGGACCACGGTCACCGTCTCCTCAGCC<br>TCCACCAAGGGCCCATCGGTCTTCCCCCTGGCACCCTCCTCCAAGAGCAC<br>CTCTGGGGGCACAGCAGCCCTGGGCTGCCTGGTCAAGGACTACTTCCCCG<br>AACCGGTGACGGTGTCGTGGAACTCAGGCGCCCTGACCAGCGGCGTGCAC<br>ACCTTCCCGGCTGTCCTACAGTCCTCAGGACTCTACTCCCTCAGCAGCGT<br>GGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAA<br>TCTTGTGACAAAACTCACACATGCCCACCGTGCCCAGCACCTGAACTCCT<br>GGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCA<br>TAATGCCAAGACAAAGCCGCGGGAGGAGCAGTACAACAGCACGTACCGTG |

TABLE 5-continued

AB-000224 variable region and full chain sequences

```
TGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAAC
CATCTCCAAAGCCAAAGGGCAGCCCCGAGAACCACAGGTGTACACCCTGC
CCCCATCCCGGGATGAGCTGACCAAGAACCAGGTCAGCCTGACCTGCCTG
GTCAAAGGCTTCTATCCCAGCGACATCGCCGTGGAGTGGGAGAGCAATGG
GCAGCCGGAGAACAACTACAAGACCACGCCTCCCGTGCTGGACTCCGACG
GCTCCTTCTTCCTCTACAGCAAGCTCACCGTGGACAAGAGCAGGTGGCAG
CAGGGGAACGTCTTCTCATGCTCCGTGCTGCATGAGGCTCTGCACTCCCA
CTACACACAGAAGAGCCTCTCCCTGTCTCCGGGTAAA [SEQ ID NO: 22]
```

In certain embodiments, a variant of an anti-CSP antibody includes one, two, or three CDRs of a VL sequence of Table 5. In certain embodiments, a variant of an anti-CSP antibody includes at least one mutation, e.g., substitution, and no more than 10, 20, 30, 40, or 50 mutations in the VL amino acid sequence set forth in SEQ ID NO: 13. In certain embodiments, the VL of the variant of an anti-CSP antibody includes at least one, at least two, or at least three mutations, e.g., substitutions, in the CDR1 amino acid sequence set forth in SEQ ID NO: 1. In certain embodiments, the VL of the variant of an anti-CSP antibody includes at least one, at least two, or at least three mutations, e.g., substitutions, in the CDR2 amino acid sequence set forth in SEQ ID NO: 2. In certain embodiments, the VL of the variant of an anti-CSP antibody includes at least one, at least two, or at least three mutations, e.g., substitutions, in the CDR3 amino acid sequence set forth in SEQ ID NO: 3. In certain embodiments, the VL of the variant of an anti-CSP antibody includes at least one, at least two, or at least three mutations, e.g., substitutions, in the CDR1 amino acid sequence set forth in SEQ ID NO: 7. In certain embodiments, the VL of the variant of an anti-CSP antibody includes at least one, at least two, or at least three mutations, e.g., substitutions, in the CDR2 amino acid sequence set forth in SEQ ID NO: 8. In certain embodiments, the VL of the variant of an anti-CSP antibody includes at least one, at least two, or at least three mutations, e.g., substitutions, in the CDR3 amino acid sequence set forth in SEQ ID NO: 9. In certain embodiments, the mutation is a conservative substitution. In certain embodiments, the VL of the variant of an anti-CSP antibody includes at least one, at least two, or at least three mutations, e.g., substitutions, in the framework of the amino acid sequence set forth in SEQ ID NO: 13. An exemplary nucleic acid sequence of SEQ ID NO: 13 is set forth in SEQ ID NO: 15. In certain embodiments, the VL of the variant of an anti-CSP antibody includes a substitution at position 1 of the SEQ ID NO: 13. In certain embodiments, the substitution is E1Q. In certain embodiments, the VL of the variant of an anti-CSP antibody includes a substitution at position 4 of the SEQ ID NO: 13. In certain embodiments, the substitution is R44T.

In certain embodiments, a variant of an anti-CSP antibody includes one, two, or three CDRs of a VH sequence of Table 5. In certain embodiments, a variant of an anti-CSP antibody includes at least one mutation, e.g., substitutions, and no more than 10, 20, 30, 40, or 50 mutations in the VH amino acid sequence set forth in SEQ ID NO: 14. In certain embodiments, the VH of the variant of an anti-CSP antibody includes at least one, at least two, or at least three mutations, e.g., substitutions, in the CDR1 amino acid sequence set forth in SEQ ID NO: 4. In certain embodiments, the VH of the variant of an anti-CSP antibody includes at least one, at least two, or at least three mutations, e.g., substitutions, in the CDR2 amino acid sequence set forth in SEQ ID NO: 5. In certain embodiments, the VH of the variant of an anti-CSP antibody includes at least one, at least two, or at least three mutations, e.g., substitutions, in the CDR3 amino acid sequence set forth in SEQ ID NO: 6. In certain embodiments, the VH of the variant of an anti-CSP antibody includes at least one, at least two, or at least three mutations, e.g., substitutions, in the CDR1 amino acid sequence set forth in SEQ ID NO: 10. In certain embodiments, the VH of the variant of an anti-CSP antibody includes at least one, at least two, or at least three mutations, e.g., substitutions, in the CDR2 amino acid sequence set forth in SEQ ID NO: 11. In certain embodiments, the VH of the variant of an anti-CSP antibody includes at least one, at least two, or at least three mutations, e.g., substitutions, in the CDR3 amino acid sequence set forth in SEQ ID NO: 12. In certain embodiments, the mutation is a conservative substitution. In certain embodiments, the VH of the variant of an anti-CSP antibody includes a CDR2 having a substitution at position 12 of the SEQ ID NO: 5. In certain embodiments, the substitution is H12K. In certain embodiments, the VH of the variant of an anti-CSP antibody includes a CDR2 having a substitution at position 18 of the SEQ ID NO: 5. In certain embodiments, the substitution is R18K. In certain embodiments, the mutation is a conservative substitution. In certain embodiments, the VH of the variant of an anti-CSP antibody includes a CDR2 having a substitution at position 12 of the SEQ ID NO: 11. In certain embodiments, the substitution is H12K. In certain embodiments, the VH of the variant of an anti-CSP antibody includes a CDR2 having a substitution at position 18 of the SEQ ID NO: 11. In certain embodiments, the substitution is R18K. In certain embodiments, the VH of the variant of an anti-CSP antibody includes at least one, at least two, at least three mutations, or at least four mutations, e.g., substitutions, in the framework of the amino acid sequence set forth in SEQ ID NO: 14. An exemplary nucleic acid sequence of SEQ ID NO: 14 is set forth in SEQ ID NO: 16. In certain embodiments, the VH of the variant of an anti-CSP antibody includes a substitution at position 21 of the SEQ ID NO: 14. In certain embodiments, the substitution is P21S. In certain embodiments, the VH of the variant of an anti-CSP antibody includes a substitution at position 23 of the SEQ ID NO: 14. In certain embodiments, the substitution is T23A. In certain embodiments, the VH of the variant of an anti-CSP antibody includes a substitution at position 80 of the SEQ ID NO: 14. In certain embodiments, the substitution is I80T. In certain embodiments, the VH of the variant of an anti-CSP antibody includes a substitution at position 90 of the SEQ ID NO: 14. In certain embodiments, the substitution is T90A. In certain embodiments, the VH of the variant of an anti-CSP antibody includes a substitution at position 99 of the SEQ ID NO: 14. In certain embodiments, the substitution is T99A.

In certain embodiments, a variant of an anti-CSP antibody includes at least one mutation, e.g., substitution, and no more than 10, 20, 30, 40, or 50 mutations in the Fc region of the heavy chain amino acid sequence set forth in SEQ ID NO: 18. In certain embodiments, the heavy chain of the variant of an anti-CSP antibody has an amino acid sequence set forth in SEQ ID NO: 18. An exemplary nucleic acid sequence of SEQ ID NO: 18 is set forth in SEQ ID NO: 21. In certain embodiments, the heavy chain of the variant of an anti-CSP antibody includes a substitution at position 438 of the SEQ ID NO: 18. In certain embodiments, the substitution is M438L. In certain embodiments, the heavy chain of the variant of an anti-CSP antibody includes a substitution at position 444 of the SEQ ID NO: 18. In certain embodiments, the substitution is N444S. In certain embodiments, the heavy chain of the variant of an anti-CSP antibody includes a substitution at position 438 of the SEQ ID NO: 18 and a substitution at position 444 of the SEQ ID NO: 18. In certain embodiments, the substitutions are M438L and N444S. In certain embodiments, the heavy chain of the variant of an anti-CSP antibody has an amino acid sequence set forth in SEQ ID NO: 19. An exemplary nucleic acid sequence of SEQ ID NO: 19 is set forth in SEQ ID NO: 22.

In certain embodiments, the light chain of the anti-CSP antibody AB-000224 and variants thereof comprises a signal peptide. In certain embodiments, the signal peptide is an IGLV2-8 signal peptide. In certain embodiments, the signal peptide has an amino acid sequence set forth in SEQ ID NO: 277. In certain embodiments, the heavy chain of the anti-CSP antibody AB-000224 and variants thereof comprises a signal peptide. In certain embodiments, the signal peptide is an IGKV1-39 signal peptide. In certain embodiments, the signal peptide has an amino acid sequence set forth in SEQ ID NO: 278. SEQ ID NO: 277 and SEQ ID NO: 278 are provided below:

[SEQ ID NO: 277]
MAWALLLLTLLTQGTGSWA

[SEQ ID NO: 278]
MDMRVPAQLLGLLLLWLRGARC

In certain embodiments, the anti-CSP antibody variant comprises a light chain variable region comprising a CDR1, a CDR2, and a CDR3 and having the amino acid sequence set forth in SEQ ID NO: 23, as shown in Table 6. In certain embodiments, the anti-CSP antibody variant comprises a heavy chain variable region comprising a CDR1, a CDR2, and a CDR3 and having the amino acid sequence set forth in SEQ ID NO: 24, as shown in Table 6. In certain embodiments, the anti-CSP antibody variant comprises a light chain having the amino acid sequence set forth in SEQ ID NO: 27, as shown in Table 6. In certain embodiments, the anti-CSP antibody variant comprises a heavy chain having the amino acid sequence set forth in SEQ ID NO: 28, as shown in Table 6. In certain embodiments, the anti-CSP antibody variant comprises a heavy chain having the amino acid sequence set forth in SEQ ID NO: 29, as shown in Table 6. Exemplary nucleic acid sequences of SEQ ID NOS: 23, 24, 27, 28, and 29 are provided in Table 6 below.

TABLE 6

| Antibody ID: AB-000224.001 | | |
|---|---|---|
| | KABAT | ASN |
| CDR1-VL | TGMNSNIGAGYDVY [SEQ ID NO: 1] | TGMNSNIGAGYDVY [SEQ ID NO: 7] |
| CDR2-VL | GNSNRPS [SEQ ID NO: 2] | GNSNRPS [SEQ ID NO: 8] |
| CDR3-VL | QSYDTSLNGWA [SEQ ID NO: 3] | QSYDTSLNGWA [SEQ ID NO: 9] |
| CDR1-VH | DHAMS [SEQ ID NO: 4] | DHAMS [SEQ ID NO: 10] |
| CDR2-VH | FIRKTTYGATTHYAAAVRG [SEQ ID NO: 5] | FIRKTTYGATTHYAAAVRG [SEQ ID NO: 11] |
| CDR3-VH | VQLDYGPGYQYYGMDV [SEQ ID NO: 6] | VQLDYGPGYQYYGMDV [SEQ ID NO: 12] |
| VL | QSVLTQPPSVSGAPGQRVTISCTGMNSNIGAGYDVYWYQQLPGTAPKLLIYGNSNRPS GVPDRFSGSRSGTSASLAITGLQAEDEADYYCQSYDTSLNGWAFGGGTKLTVLG [SEQ ID NO: 23] | |
| VH | EVQLVESGGGLVQPGRSLRLSCTASGFSFGDHAMSWVRQAPGKGLEWVGFIRKTTYGA TTHYAAAVRGRFTISRDDSKSIVYLQMNSLKTEDTAVYFCTRVQLDYGPGYQYYGMDV WGQGTTVTVSS [SEQ ID NO: 24] | |
| DNA for VL | CAGTCTGTGCTGACGCAGCCGCCCTCAGTGTCTGGGGCCCCAGGGCAGAGGGTCACCA TCTCCTGCACTGGGATGAACTCCAACATCGGGGCAGGTTATGATGTATACTGGTACCA ACAACTTCCAGGAACTGCCCCCAAACTCCTCATCTATGGTAACAGCAATCGGCCCTCA GGGGTCCCTGACCGATTCTCTGGCTCCAGGTCTGGCACCTCAGCCTCCCTGGCCATCA CTGGGCTCCAG GCTGAGGATGAGGCTGATTATTACTGCCAGTCCTATGACACCAGCCTGAATGGTTGGG CTTTCGGCGGAGGGACCAAGTTGACCGTCCTAGGC [SEQ ID NO: 25] | |
| DNA for VH | GAGGTGCAGCTGGTGGAGTCTGGGGGAGGCTTGGTACAGCCAGGGCGGTCCCTGAGAC TCAGCTGTACAGCCTCTGGGTTTAGTTTTGGTGATCATGCTATGAGCTGGGTCCGCCA GGCTCCAGGGAAGGGGCTGGAGTGGGTAGGTTTCATTAGAAAGACAACTTATGGTGCG ACAACACACTACGCCGCGGCTGTGAGAGGCAGATTCACCATCTCGCGAGATGATTCTA AAAGCATTGTCTATCTGCAAATGAACAGCCTGAAAACCGAGGACACAGCCGTGTATTT CTGTACTAGAGTGCAGCTTGACTATGGCCCGGGATACCAGTACTACGGTATGGACGTC TGGGGCCAAGGGACCACGGTCACCGTCTCCTCA [SEQ ID NO: 26] | |

TABLE 6-continued

Antibody ID: AB-000224.001

| | KABAT | ASN |
|---|---|---|

Light Chain
QSVLTQPPSVSGAPGQRVTISCTGMNSNIGA
GYDVYWYQQLPGTAPKLLIYGNSNRPSGVPDRFSGSRSGTSASLAITGLQ
AEDEADYYCQSYDTSLNGWAFGGGTKLTVLGQPKAAPSVTLFPPSSEELQ
ANKATLVCLVSDFYPGAVTVAWKADGSPVKVGVETTKPSKQSNNKYAASS
YLSLTPEQWKSHRSYSCRVTHEGSTVEKTVAPAECS [SEQ ID NO: 27]

Heavy
Chain
version 1
EVQLVESGGGLVQPGRSLRLSCTASGFSFGDHAMSWVRQAPGKGLEWVGFIRKTTYGA
TTHYAAAVRGRFTISRDDSKSIVYLQMNSLKTEDTAVYFCTRVQLDYGPGYQYYGMDV
WGQGTTVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKKVEPKSCDK
THTCPPCPAPELLGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPAPIEKTISK
AKGQPREPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPGK [SEQ
ID NO: 28]

Heavy
Chain
version 2
EVQLVESGGGLVQPGRSLRLSCTASGFSFGDHAMSWVRQAPGKGLEWVGFIRKTTYGA
TTHYAAAVRGRFTISRDDSKSIVYLQMNSLKTEDTAVYFCTRVQLDYGPGYQYYGMDV
WGQGTTVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKKVEPKSCDK
THTCPPCPAPELLGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPAPIEKTISK
AKGQPREPQVYTLPPSRDELTKNQVSLTCLVKGFYPSDIAVEWESNGQPENNYKTTPP
VLDSDGSFFLYSKLTVDKSRWQQGNVFSCSVLHEALHSHYTQKSLSLSPGK [SEQ
ID NO: 29]

DNA for
Light Chain
CAGTCTGTGCTGACGCAGCCGCCCTCAGTGTCTGGGGCCCCAGGGCAGAGGGTCACCA
TCTCCTGCACTGGGATGAACTCCAACATCGGGGCAGGTTATGATGTATACTGGTACCA
ACAACTTCCAGGAACTGCCCCCAAACTCCTCATCTATGGTAACAGCAATCGGCCCTCA
GGGGTCCCTGACCGATTCTCTGGCTCCAGGTCTGGCACCTCAGCCTCCCTGGCCATCA
CTGGGCTCCAGGCTGAGGATGAGGCTGATTATTACTGCCAGTCCTATGACACCAGCCT
GAATGGTTGGGCTTTCGGCGGAGGGACCAAGTTGACCGTCCTAGGCCAGCCCAAGGCT
GCCCCCTCGGTCACTCTGTTCCCACCCTCCTCTGAGGAGCTTCAAGCCAACAAGGCCA
CACTGGTGTGTCTCGTAAGTGACTTCTACCCGGGAGCCGTGACAGTGGCCTGGAAGGC
AGATGGCAGCCCCGTCAAGGTGGGAGTGGAGACCACCAAACCCTCCAAACAAAGCAAC
AACAAGTATGCGGCCAGCAGCTACCTGAGCCTGACGCCCGAGCAGTGGAAGTCCCACA
GAAGCTACAGCTGCCGGGTCACGCATGAAGGGAGCACCGTGGAGAAGACAGTGGCCCC
TGCAGAATGCTCT [SEQ ID NO: 30]

DNA for
Heavy
Chain
version 1
GAGGTGCAGCTGGTGGAGTCTGGGGGAGGCTTGGTACAGCCAGGGCGGTCCCTGAGAC
TCAGCTGTACAGCCTCTGGGTTTAGTTTTGGTGATCATGCTATGAGCTGGGTCCGCCA
GGCTCCAGGGAAGGGGCTGGAGTGGGTGGTTTCATTAGAAAGACAACTTATGGTGCG
ACAACACACTACGCCGCGGCTGTGAGAGGCAGATTCACCATCTCGCGAGATGATTCTA
AAAGCATTGTCTATCTGCAAATGAACAGCCTGAAAACCGAGGACACAGCCGTGTATTT
CTGTACTAGAGTGCAGCTTGACTATGGCCCGGGATACCAGTACTACGGTATGGACGTC
TGGGGCCAAGGGACCACGGTCACCGTCTCCTCAGCCTCCACCAAGGGCCCATCGGTCT
TCCCCCTGGCACCCTCCTCCAAGAGCACCTCTGGGGGCACAGCAGCCCTGGGCTGCCT
GGTCAAGGACTACTTCCCCGAACCGGTGACGGTGTCGTGGAACTCAGGCGCCCTGACC
AGCGGCGTGCACACCTTCCCGGCTGTCCTACAGTCCTCAGGACTCTACTCCCTCAGCA
GCGTGGTGACCGTGCCCTCCAGCAGCTTGGGCACCCAGACCTACATCTGCAACGTGAA
TCACAAGCCCAGCAACACCAAGGTGGACAAGAAAGTTGAGCCCAAATCTTGTGACAAA
ACTCACACATGCCCACCGTGCCCAGCACCTGAACTCCTGGGGGGACCGTCAGTCTTCC
TCTTCCCCCCAAAACCCAAGGACACCCTCATGATCTCCCGGACCCCTGAGGTCACATG
CGTGGTGGTGGACGTGAGCCACGAAGACCCTGAGGTCAAGTTCAACTGGTACGTGGAC
GGCGTGGAGGTGCATAATGCCAAGACAAAGCCGCGGGAGGAGCAGTACAACAGCACGT
ACCGTGTGGTCAGCGTCCTCACCGTCCTGCACCAGGACTGGCTGAATGGCAAGGAGTA
CAAGTGCAAGGTCTCCAACAAAGCCCTCCCAGCCCCCATCGAGAAAACCATCTCCAAA
GCCAAAGGGCAGCCCCGAGAACCACAGGTGTACACCCTGCCCCCATCCCGGGATGAGC
TGACCAAGAACCAGGTCAGCCTGACCTGCCTGGTCAAAGGCTTCTATCCCAGCGACAT
CGCCGTGGAGTGGGAGAGCAATGGGCAGCCGGAGAACAACTACAAGACCACGCCTCCC
GTGCTGGACTCCGACGGCTCCTTCTTCCTCTACAGCAAGCTCACCGTGGACAAGAGCA
GGTGGCAGCAGGGGAACGTCTTCTCATGCTCCGTGATGCATGAGGCTCTGCACAACCA
CTACACACAGAAGAGCCTCTCCCTGTCTCCGGGTAAA [SEQ ID NO: 31]

DNA for
Heavy
Chain
version 2
GAGGTGCAGCTGGTGGAGTCTGGGGGAGGCTTGGTACAGCCAGGGCGGTCCCTGAGAC
TCAGCTGTACAGCCTCTGGGTTTAGTTTTGGTGATCATGCTATGAGCTGGGTCCGCCA
GGCTCCAGGGAAGGGGCTGGAGTGGGTGGTTTCATTAGAAAGACAACTTATGGTGCG
ACAACACACTACGCCGCGGCTGTGAGAGGCAGATTCACCATCTCGCGAGATGATTCTA
AAAGCATTGTCTATCTGCAAATGAACAGCCTGAAAACCGAGGACACAGCCGTGTATTT
CTGTACTAGAGTGCAGCTTGACTATGGCCCGGGATACCAGTACTACGGTATGGACGTC
TGGGGCCAAGGGACCACGGTCACCGTCTCCTCAGCCTCCACCAAGGGCCCATCGGTCT
TCCCCCTGGCACCCTCCTCCAAGAGCACCTCTGGGGGCACAGCAGCCCTGGGCTGCCT
GGTCAAGGACTACTTCCCCGAACCGGTGACGGTGTCGTGGAACTCAGGCGCCCTGACC
AGCGGCGTGCACACCTTCCCGGCTGTCCTACAGTCCTCAGGACTCTACTCCCTCAGCA
GCGTGGTGACCGTGCCCTCCAGCAGCTTGGGCACCCAGACCTACATCTGCAACGTGAA
TCACAAGCCCAGCAACACCAAGGTGGACAAGAAAGTTGAGCCCAAATCTTGTGACAAA

TABLE 6-continued

Antibody ID: AB-000224.001

| KABAT | ASN |
|---|---|

ACTCACACATGCCCACCGTGCCCAGCACCTGAACTCCTGGGGGGACCGTCAGTCTTCC
TCTTCCCCCCAAAACCCAAGGACACCCTCATGATCTCCCGGACCCCTGAGGTCACATG
CGTGGTGGTGGACGTGAGCCACGAAGACCCTGAGGTCAAGTTCAACTGGTACGTGGAC
GGCGTGGAGGTGCATAATGCCAAGACAAAGCCGCGGGAGGAGCAGTACAACAGCACGT
ACCGTGTGGTCAGCGTCCTCACCGTCCTGCACCAGGACTGGCTGAATGGCAAGGAGTA
CAAGTGCAAGGTCTCCAACAAAGCCCTCCCAGCCCCCATCGAGAAAACCATCTCCAAA
GCCAAAGGGCAGCCCCGAGAACCACAGGTGTACACCCTGCCCCCATCCCGGGATGAGC
TGACCAAGAACCAGGTCAGCCTGACCTGCCTGGTCAAAGGCTTCTATCCCAGCGACAT
CGCCGTGGAGTGGGAGAGCAATGGGCAGCCGGAGAACAACTACAAGACCACGCCTCCC
GTGCTGGACTCCGACGGCTCCTTCTTCCTCTACAGCAAGCTCACCGTGGACAAGAGCA
GGTGGCAGCAGGGGAACGTCTTCTCATGCTCCGTGCTGCATGAGGCTCTGCACTCCCA
CTACACACAGAAGAGCCTCTCCCTGTCTCCGGGTAAA [SEQ ID NO: 32]

In certain embodiments, the anti-CSP antibody variant comprises a light chain variable region comprising a CDR1, a CDR2, and a CDR3 and having the amino acid sequence set forth in SEQ ID NO: 33, as shown in Table 7. In certain embodiments, the anti-CSP antibody variant comprises a heavy chain variable region comprising a CDR1, a CDR2, and a CDR3 and having the amino acid sequence set forth in SEQ ID NO: 34, as shown in Table 75. In certain embodiments, the anti-CSP antibody variant comprises a light chain having the amino acid sequence set forth in SEQ ID NO: 37, as shown in Table 7. In certain embodiments, the anti-CSP antibody variant comprises a heavy chain having the amino acid sequence set forth in SEQ ID NO: 38, as shown in Table 7. In certain embodiments, the anti-CSP antibody variant comprises a heavy chain having the amino acid sequence set forth in SEQ ID NO: 39, as shown in Table 7. Exemplary nucleic acid sequences of SEQ ID NOS: 33, 34, 37, 38, and 39 are provided in Table 7 below.

TABLE 7

Antibody ID: AB-000224.002

| | KABAT | ASN |
|---|---|---|
| CDR1-VL | TGMNSNIGAGYDVY [SEQ ID NO: 1] | TGMNSNIGAGYDVY [SEQ ID NO: 7] |
| CDR2-VL | GNSNRPS [SEQ ID NO: 2] | GNSNRPS [SEQ ID NO: 8] |
| CDR3-VL | QSYDTSLNGWA [SEQ ID NO: 3] | QSYDTSLNGWA [SEQ ID NO: 9] |
| CDRl-VH | DHAMS [SEQ ID NO: 4] | DHAMS [SEQ ID NO: 10] |
| CDR2-VH | FIRKTTYGATTHYAAAVRG [SEQ ID NO: 5] | FIRKTTYGATTHYAAAVRG [SEQ ID NO: 11] |
| CDR3-VH | VQLDYGPGYQYYGMDV [SEQ ID NO: 6] | VQLDYGPGYQYYGMDV [SEQ ID NO: 12] |
| VL | QSVLTQPPSVSGAPGQRVTISCTGMNSNIGAGYDVYWYQQLPGTAPKLLIYGNSNRPSGVPDRFSGSRSGTSASLAITGLQAEDEADYYCQSYDTSLNGWAFGGGTKLTVLG [SEQ ID NO: 33] | |
| VH | EVQLVESGGGLVQPGRSLRLSCAASGFSFGDHAMSWVRQAPGKGLEWVGFIRKTTYGATTHYAAAVRGRFTISRDDSKSIVYLQMNSLKTEDTAVYFCTRVQLDYGPGYQYYGMDVWGQGTTVTVSS [SEQ ID NO: 34] | |
| DNA for VL | CAGTCTGTGCTGACGCAGCCGCCCTCAGTGTCTGGGGCCCCAGGGCAGAGGGTCACCATCTCCTGCACTGGGATGAACTCCAACATCGGGGCAGGTTATGATGTATACTGGTACCAACAACTTCCAGGAACTGCCCCCAAACTCCTCATCTATGGTAACAGCAATCGGCCCTCAGGGGTCCCTGACCGATTCTCTGGCTCCAGGTCTGGCACCTCAGCCTCCCTGGCCATCACTGGGCTCCAGGCTGAGGATGAGGCTGATTATTACTGCCAGTCCTATGACACCAGCCTGAATGGTTGGGCTTTCGGCGGAGGGACCAAGTTGACCGTCCTAGGC [SEQ ID NO: 35] | |
| DNA forVH | GAGGTGCAGCTGGTGGAGTCTGGGGGAGGCTTGGTACAGCCAGGGCGGTCCCTGAGACTCAGCTGTGCGGCCTCTGGGTTTAGTTTTGGTGATCATGCTATGAGCTGGGTCCGCCAGGCTCCAGGGAAGGGGCTGGAGTGGGTAGGTTTCATTAGAAAGACAACTTATGGTGCGACAACACACTACGCCGCGGCTGTGAGAGGCAGATTCACCATCTCGCGAGATGATTCTAAAAGCATTGTCTATCTGCAAATGAACAGCCTGAAACCGAGGACACAGCCGTGTATTTCTGTACTAGAGTGCAGCTTGACTATGGCCCGGGATACCAGTACTACGGTATGGACGTCTGGGGCCAAGGGACCACGGTCACCGTCTCCTCA [SEQ ID NO: 36] | |

TABLE 7-continued

Antibody ID: AB-000224.002

| | KABAT | ASN |
|---|---|---|

Light Chain
QSVLTQPPSVSGAPGQRVTISCTGMNSNIGA
GYDVYWYQQLPGTAPKLLIYGNSNRPSGVPDRFSGSRSGTSASLAITGLQ
AEDEADYYCQSYDTSLNGWAFGGGTKLTVLGQPKAAPSVTLFPPSSEELQ
AN KAT LVC LVS D FY P GAVTVAWKADGS PVKVGVETT KPSKQSNNKYAAS S
YLSLTPEQWKSHRSYSCRVTHEGSTVEKTVAPAECS[SEQ ID NO: 37]

Heavy Chain version 1
EVQLVESGGGLVQPGRSLRLSCAASGFS
FGDHAMSWVRQAPGKGLEWVGFIRKTTYGATTHYAAAVRGRFTISRDDSK
SIVYLQMNSLKTEDTAVYFCTRVQLDYGPGYQYYGMDVWGQGTTVTVSSA
STKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKKVEPK
SCDKTHTCPPCPAPELLGGPSVFLFPPKPKDTLMISRTPEVTCVVVDVSH
EDPEVKFNWYVDGVEVHNAKTKPREEQYNSTYRWSVLTVLHQDWLNGKE
YKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQ
QGNVFSCSVMHEALHNHYTQKSLSLSPGK [SEQ ID NO: 38]

Heavy Chain version 2
EVQLVESGGGLVQPGRSLRLSCAASGFS
FGDHAMSWVRQAPGKGLEWVGFIRKTTYGATTHYAAAVRGRFTISRDDSK
SIVYLQMNSLKTEDTAVYFCTRVQLDYGPGYQYYGMDVWGQGTTVTVSSA
STKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKKVEPK
SCDKTHTCPPCPAPELLGGPSVFLFPPKPKDTLMISRTPEVTCVVVDVSH
EDPEVKFNWYVDGVEVHNAKTKPREEQYNSTYRWSVLTVLHQDWLNGKE
YKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQ
QGNVFSCSVLHEALHSHYTQKSLSLSPGK [SEQ ID NO: 39]

DNA for Light Chain
CAGTCTGTGCTGACGCAGCCGCCCTCAGTGTCTGGGGCCCCAG
GGCAGAGGGTCACCATCTCCTGCACTGGGATGAACTCCAACATCGGGGCA
GGTTATGATGTATACTGGTACCAACAACTTCCAGGAACTGCCCCCAAACT
CCTCATCTATGGTAACAGCAATCGGCCCTCAGGGGTCCCTGACCGATTCT
CTGGCTCCAGGTCTGGCACCTCAGCCTCCCTGGCCATCACTGGGCTCCAG
GCTGAGGATGAGGCTGATTATTACTGCCAGTCCTATGACACCAGCCTGAA
TGGTTGGGCTTTCGGCGGAGGGACCAAGTTGACCGTCCTAGGCCAGCCCA
AGGCTGCCCCCTCGGTCACTCTGTTCCCACCCTCCTCTGAGGAGCTTCAA
GCCAACAAGGCCACACTGGTGTGTCTCGTAAGTGACTTCTACCCGGGAGC
CGTGACAGTGGCCTGGAAGGCAGATGGCAGCCCCGTCAAGGTGGGAGTGG
AGACCACCAAACCCTCCAAACAAAGCAACAACAAGTATGCGGCCAGCAGC
TACCTGAGCCTGACGCCCGAGCAGTGGAAGTCCCACAGAAGCTACAGCTG
CCGGGTCACGCATGAAGGGAGCACCGTGGAGAAGACAGTGGCCCCTGCAG
AATGCTCT [SEQ ID NO: 40]

DNA for Heavy Chain version 1
GAGGTGCAGCTGGTGGAGTCTGGGGGAGGCTTGGTACAGCCAGGGCGGTCCCTGAGACTCA
GCTGTGCGGCCTCTGGGTTTAGTTTTGGTGATCATGCTATGAGCTGGGTCCGCCAGGCTCC
AGGGAAGGGGCTGGAGTGGGTAGGTTTCATTAGAAAGACAACTTATGGTGCGACAACACAC
TACGCCGCGGCTGTGAGAGGCAGATTCACCATCTCGCGAGATGATTCTAAAAGCATTGTCT
ATCTGCAAATGAACAGCCTGAAAACCGAGGACACAGCCGTGTATTTCTGTACTAGAGTGCA
GCTTGACTATGGCCCGGGATACCAGTACTACGGTATGGACGTCTGGGGCCAAGGGACCACG
GTCACCGTCTCCTCAGCCTCCACCAAGGGCCCATCGGTCTTCCCCCTGGCACCCTCCTCCA
AGAGCACCTCTGGGGGCACAGCAGCCCTGGGCTGCCTGGTCAAGGACTACTTCCCCGAACC
GGTGACGGTGTCGTGGAACTCAGGCGCCCTGACCAGCGGCGTGCACACCTTCCCGGCTGTC
CTACAGTCCTCAGGACTCTACTCCCTCAGCAGCGTGGTGACCGTGCCCTCCAGCAGCTTGG
GCACCCAGACCTACATCTGCAACGTGAATCACAAGCCCAGCAACACCAAGGTGGACAAGAA
AGTTGAGCCCAAATCTTGTGACAAAACTCACACATGCCCACCGTGCCCAGCACCTGAACTC
CTGGGGGGACCGTCAGTCTTCCTCTTCCCCCCAAAACCCAAGGACACCCTCATGATCTCCC
GGACCCCTGAGGTCACATGCGTGGTGGTGGACGTGAGCCACGAAGACCCTGAGGTCAAGTT
CAACTGGTACGTGGACGGCGTGGAGGTGCATAATGCCAAGACAAAGCCGCGGGAGGAGCAG
TACAACAGCACGTACCGTGTGGTCAGCGTCCTCACCGTCCTGCACCAGGACTGGCTGAATG
GCAAGGAGTACAAGTGCAAGGTCTCCAACAAAGCCCTCCCAGCCCCCATCGAGAAAACCAT
CTCCAAAGCCAAAGGGCAGCCCCGAGAACCACAGGTGTACACCCTGCCCCCATCCCGGGAT
GAGCTGACCAAGAACCAGGTCAGCCTGACCTGCCTGGTCAAAGGCTTCTATCCCAGCGACA
TCGCCGTGGAGTGGGAGAGCAATGGGCAGCCGGAGAACAACTACAAGACCACGCCTCCCGT
GCTGGACTCCGACGGCTCCTTCTTCCTCTACAGCAAGCTCACCGTGGACAAGAGCAGGTGG
CAGCAGGGGAACGTCTTCTCATGCTCCGTGATGCATGAGGCTCTGCACAACCACTACACAC
AGAAGAGCCTCTCCCTGTCTCCGGGTAAA [SEQ ID NO: 41]

DNA for Heavy Chain version 1
GAGGTGCAGCTGGTGGAGTCTGGGGGAGGCTTGGTACAGCCAGGGCGGTCCCTGAGACTCA
GCTGTGCGGCCTCTGGGTTTAGTTTTGGTGATCATGCTATGAGCTGGGTCCGCCAGGCTCC
AGGGAAGGGGCTGGAGTGGGTAGGTTTCATTAGAAAGACAACTTATGGTGCGACAACACAC
TACGCCGCGGCTGTGAGAGGCAGATTCACCATCTCGCGAGATGATTCTAAAAGCATTGTCT
ATCTGCAAATGAACAGCCTGAAAACCGAGGACACAGCCGTGTATTTCTGTACTAGAGTGCA
GCTTGACTATGGCCCGGGATACCAGTACTACGGTATGGACGTCTGGGGCCAAGGGACCACG
GTCACCGTCTCCTCAGCCTCCACCAAGGGCCCATCGGTCTTCCCCCTGGCACCCTCCTCCA
AGAGCACCTCTGGGGGCACAGCAGCCCTGGGCTGCCTGGTCAAGGACTACTTCCCCGAACC TABLE 7-continued Antibody ID: AB-000224.002

| KABAT | ASN |
|---|---|
| GGTGACGGTGTCGTGGAACTCAGGCGCCCTGACCAGCGGCGTGCACACCTTCCCGGCTGTC<br>CTACAGTCCTCAGGACTCTACTCCCTCAGCAGCGTGGTGACCGTGCCCTCCAGCAGCTTGG<br>GCACCCAGACCTACATCTGCAACGTGAATCACAAGCCCAGCAACACCAAGGTGGACAAGAA<br>AGTTGAGCCCAAATCTTGTGACAAAACTCACACATGCCCACCGTGCCCAGCACCTGAACTC<br>CTGGGGGGACCGTCAGTCTTCCTCTTCCCCCCAAAACCCAAGGACACCCTCATGATCTCCC<br>GGACCCCTGAGGTCACATGCGTGGTGGTGGACGTGAGCCACGAAGACCCTGAGGTCAAGTT<br>CAACTGGTACGTGGACGGCGTGGAGGTGCATAATGCCAAGACAAAGCCGCGGGAGGAGCAG<br>TACAACAGCACGTACCGTGTGGTCAGCGTCCTCACCGTCCTGCACCAGGACTGGCTGAATG<br>GCAAGGAGTACAAGTGCAAGGTCTCCAACAAAGCCCTCCCAGCCCCCATCGAGAAAACCAT<br>CTCCAAAGCCAAAGGGCAGCCCCGAGAACCACAGGTGTACACCCTGCCCCCATCCCGGGAT<br>GAGCTGACCAAGAACCAGGTCAGCCTGACCTGCCTGGTCAAAGGCTTCTATCCCAGCGACA<br>TCGCCGTGGAGTGGGAGAGCAATGGGCAGCCGGAGAACAACTACAAGACCACGCCTCCCGT<br>GCTGGACTCCGACGGCTCCTTCTTCCTCTACAGCAAGCTCACCGTGGACAAGAGCAGGTGG<br>CAGCAGGGGAACGTCTTCTCATGCTCCGTGCTGCATGAGGCTCTGCACTCCCACTACACAC<br>AGAAGAGCCTCTCCCTGTCTCCGGGTAAA [SEQ ID NO: 42] | |

In certain embodiments, the anti-CSP antibody variant comprises a light chain variable region comprising a CDR1, a CDR2, and a CDR3 and having the amino acid sequence set forth in SEQ ID NO: 43, as shown in Table 8. In certain embodiments, the anti-CSP antibody variant comprises a heavy chain variable region comprising a CDR1, a CDR2, and a CDR3 and having the amino acid sequence set forth in SEQ ID NO: 44, as shown in Table 8. In certain embodiments, the anti-CSP antibody variant comprises a light chain having the amino acid sequence set forth in SEQ ID NO: 47, as shown in Table 8. In certain embodiments, the anti-CSP antibody variant comprises a heavy chain having the amino acid sequence set forth in SEQ ID NO: 48, as shown in Table 8. In certain embodiments, the anti-CSP antibody variant comprises a heavy chain having the amino acid sequence set forth in SEQ ID NO: 49, as shown in Table 8. Exemplary nucleic acid sequences of SEQ ID NOS: 43, 44, 47, 48, and 49 are provided in Table 8 below.

TABLE 8

Antibody ID: AB-000224.003

| | KABAT | ASN |
|---|---|---|
| CDR1-VL | TGMNSNIGAGYDVY [SEQ ID NO: 1] | TGMNSNIGAGYDVY [SEQ ID NO: 7] |
| CDR2-VL | GNSNRPS [SEQ ID NO: 2] | GNSNRPS [SEQ ID NO: 8] |
| CDR3-VL | QSYDTSLNGWA [SEQ ID NO: 3] | QSYDTSLNGWA [SEQ ID NO: 9] |
| CDR1-VH | DHAMS [SEQ ID NO: 4] | DHAMS [SEQ ID NO: 10] |
| CDR2-VH | FIRKTTYGATTHYAAAVRG [SEQ ID NO: 5] | FIRKTTYGATTHYAAAVRG [SEQ ID NO: 11] |
| CDR3-VH | VQLDYGPGYQYYGMDV [SEQ ID NO: 6] | VQLDYGPGYQYYGMDV [SEQ ID NO: 12] |
| VL | QSVLTQPPSVSGAPGQRVTISCTGMNSNIGA GYDVYWYQQLPGTAPKLLIYGNSNRPSGVPDRFSGSRSGTSASLAITGLQ AEDEADYYCQSYDTSLNGWAFGGGTKLTVLG [SEQ ID NO: 43] | |
| VH | EVQLVESGGGLVQPGRSLRLSCTASGFS FGDHAMSWVRQAPGKGLEWVGFIRKTTYGATTHYAAAVRGRFTISRDDSK STVYLQMNSLKTEDTAVYFCTRVQLDYGPGYQYYGMDVWGQGTTVTVSS [SEQ ID NO: 44] | |
| DNA for VL | CAGTCTGTGCTGACGCAGCCGCCCTCAGTGTCTGGGGCCCCAG GGCAGAGGGTCACCATCTCCTGCACTGGGATGAACTCCAACATCGGGGCA GGTTATGATGTATACTGGTACCAACAACTTCCAGGAACTGCCCCCAAACT CCTCATCTATGGTAACAGCAATCGGCCCTCAGGGGTCCCTGACCGATTCT CTGGCTCCAGGTCTGGCACCTCAGCCTCCCTGGCCATCACTGGGCTCCAG GCTGAGGATGAGGCTGATTATTACTGCCAGTCCTATGACACCAGCCTGAA TGGTTGGGCTTTCGGCGGAGGGACCAAGTTGACCGTCCTAGGC [SEQ ID NO: 45] | |
| DNA for VH | GAGGTGCAGCTGGTGGAGTCTGGGGGAGGCTTGG TACAGCCAGGGCGGTCCCTGAGACTCAGCTGTACAGCCTCTGGGTTTAGT TTTGGTGATCATGCTATGAGCTGGGTCCGCCAGGCTCCAGGGAAGGGGCT GGAGTGGGTAGGTTTCATTAGAAAGACAACTTATGGTGCGACAACACACT ACGCCGCGGCTGTGAGAGGCAGATTCACCATCTCGCGAGATGATTCTAAA | |

TABLE 8-continued

Antibody ID: AB-000224.003

| KABAT | ASN |
|---|---|

AGCACTGTCTATCTGCAAATGAACAGCCTGAAAACCGAGGACACAGCCGT
GTATTTCTGTACTAGAGTGCAGCTTGACTATGGCCCGGGATACCAGTACT
ACGGTATGGACGTCTGGGGCCAAGGGACCACGGTCACCGTCTCCTCA [SEQ ID NO: 46]

Light Chain
QSVLTQPPSVSGAPGQRVTISCTGMNSNIGA
GYDVYWYQQLPGTAPKLLIYGNSNRPSGVPDRFSGSRSGTSASLAITGLQ
AEDEADYYCQSYDTSLNGWAFGGGTKLTVLGQPKAAPSVTLFPPSSEELQ
ANKATLVCLVSDFYPGAVTVAWKADGSPVKVGVETTKPSKQSNNKYAASS
YLSLTPEQWKSHRSYSCRVTHEGSTVEKTVAPAECS [SEQ ID NO: 47]

Heavy Chain version 1
EVQLVESGGGLVQPGRSLRLSCTASGFS
FGDHAMSWVRQAPGKGLEWVGFIRKTTYGATTHYAAAVRGRFTISRDDSK
STVYLQMNSLKTEDTAVYFCTRVQLDYGPGYQYYGMDVWGQGTTVTVSSA
STKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKKVEPK
SCDKTHTCPPCPAPELLGGPSVFLFPPKPKDTLMISRTPEVTCVVVDVSH
EDPEVKFNWYVDGVEVHNAKTKPREEQYNSTYRWSVLTVLHQDWLNGKE
YKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQ
QGNVFSCSVMHEALHNHYTQKSLSLSPGK [SEQ ID NO: 48]

Heavy Chain version 2
EVQLVESGGGLVQPGRSLRLSCTASGFS
FGDHAMSWVRQAPGKGLEWVGFIRKTTYGATTHYAAAVRGRFTISRDDSK
STVYLQMNSLKTEDTAVYFCTRVQLDYGPGYQYYGMDVWGQGTTVTVSSA
STKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKKVEPK
SCDKTHTCPPCPAPELLGGPSVFLFPPKPKDTLMISRTPEVTCVVVDVSH
EDPEVKFNWYVDGVEVHNAKTKPREEQYNSTYRWSVLTVLHQDWLNGKE
YKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQ
QGNVFSCSVLHEALHSHYTQKSLSLSPGK [SEQ ID NO: 49]

DNA for Light Chain
CAGTCTGTGCTGACGCAGCCGCCCTCAGTGTCTGGGGCCCCAG
GGCAGAGGGTCACCATCTCCTGCACTGGGATGAACTCCAACATCGGGGCA
GGTTATGATGTATACTGGTACCAACAACTTCCAGGAACTGCCCCCAAACT
CCTCATCTATGGTAACAGCAATCGGCCCTCAGGGGTCCCTGACCGATTCT
CTGGCTCCAGGTCTGGCACCTCAGCCTCCCTGGCCATCACTGGGCTCCAG
GCTGAGGATGAGGCTGATTATTACTGCCAGTCCTATGACACCAGCCTGAA
TGGTTGGGCTTTCGGCGAGGGACCAAGTTGACCGTCCTAGGCCAGCCCA
AGGCTGCCCCCTCGGTCACTCTGTTCCCACCCTCCTCTGAGGAGCTTCAA
GCCAACAAGGCCACACTGGTGTGTCTCGTAAGTGACTTCTACCCGGGAGC
CGTGACAGTGGCCTGGAAGGCAGATGGCAGCCCCGTCAAGGTGGGAGTGG
AGACCACCAAACCCTCCAAACAAAGCAACAACAAGTATGCGGCCAGCAGC
TACCTGAGCCTGACGCCCGAGCAGTGGAAGTCCCACAGAAGCTACAGCTG
CCGGGTCACGCATGAAGGGAGCACCGTGGAGAAGACAGTGGCCCCTGCAG
AATGCTCT [SEQ ID NO: 50]

DNA for Heavy Chain version 1
GAGGTGCAGCTGGTGGAGTCTGGGGGAGGCTTGGTACAGCCAGGGCGGTCCCTGAGACTCA
GCTGTACAGCCTCTGGGTTTAGTTTTGGTGATCATGCTATGAGCTGGGTCCGCCAGGCTCC
AGGGAAGGGGCTGGAGTGGGTAGGTTTCATTAGAAAGACAACTTATGGTGCGACAACACAC
TACGCCGCGGCTGTGAGAGGCAGATTCACCATCTCGCGAGATGATTCTAAAAGCACTGTCT
ATCTGCAAATGAACAGCCTGAAAACCGAGGACACAGCCGTGTATTTCTGTACTAGAGTGCA
GCTTGACTATGGCCCGGGATACCAGTACTACGGTATGGACGTCTGGGGCCAAGGGACCACG
GTCACCGTCTCCTCAGCCTCCACCAAGGGCCCATCGGTCTTCCCCCTGGCACCCTCCTCCA
AGAGCACCTCTGGGGGCACAGCAGCCCTGGGCTGCCTGGTCAAGGACTACTTCCCCGAACC
GGTGACGGTGTCGTGGAACTCAGGCGCCCTGACCAGCGGCGTGCACACCTTCCCGGCTGTC
CTACAGTCCTCAGGACTCTACTCCCTCAGCAGCGTGGTGACCGTGCCCTCCAGCAGCTTGG
GCACCCAGACCTACATCTGCAACGTGAATCACAAGCCCAGCAACACCAAGGTGGACAAGAA
AGTTGAGCCCAAATCTTGTGACAAAACTCACACATGCCCACCGTGCCCAGCACCTGAACTC
CTGGGGGGACCGTCAGTCTTCCTCTTCCCCCCAAAACCCAAGGACACCCTCATGATCTCCC
GGACCCCTGAGGTCACATGCGTGGTGGTGGACGTGAGCCACGAAGACCCTGAGGTCAAGTT
CAACTGGTACGTGGACGGCGTGGAGGTGCATAATGCCAAGACAAAGCCGCGGGAGGAGCAG
TACAACAGCACGTACCGTGTGGTCAGCGTCCTCACCGTCCTGCACCAGGACTGGCTGAATG
GCAAGGAGTACAAGTGCAAGGTCTCCAACAAAGCCCTCCCAGCCCCCATCGAGAAAACCAT
CTCCAAAGCCAAAGGGCAGCCCCGAGAACCACAGGTGTACACCCTGCCCCCATCCCGGGAT
GAGCTGACCAAGAACCAGGTCAGCCTGACCTGCCTGGTCAAAGGCTTCTATCCCAGCGACA
TCGCCGTGGAGTGGGAGAGCAATGGGCAGCCGGAGAACAACTACAAGACCACGCCTCCCGT
GCTGGACTCCGACGGCTCCTTCTTCCTCTACAGCAAGCTCACCGTGGACAAGAGCAGGTGG
CAGCAGGGGAACGTCTTCTCATGCTCCGTGATGCATGAGGCTCTGCACAACCACTACACAC
AGAAGAGCCTCTCCCTGTCTCCGGGTAAA [SEQ ID NO: 51]

TABLE 8-continued

Antibody ID: AB-000224.003

| | KABAT | ASN |
|---|---|---|
| DNA for Heavy Chain version 2 | GAGGTGCAGCTGGTGGAGTCTGGGGGAGGCTTGGTACAGCCAGGGCGGTCCCTGAGACTCA<br>GCTGTACAGCCTCTGGGTTTAGTTTTGGTGATCATGCTATGAGCTGGGTCCGCCAGGCTCC<br>AGGGAAGGGGCTGGAGTGGGTAGGTTTCATTAGAAAGACAACTTATGGTGCGACAACACAC<br>TACGCCGCGGCTGTGAGAGGCAGATTCACCATCTCGCGAGATGATTCTAAAAGCACTGTCT<br>ATCTGCAAATGAACAGCCTGAAAACCGAGGACACAGCCGTGTATTTCTGTACTAGAGTGCA<br>GCTTGACTATGGCCCGGGATACCAGTACTACGGTATGGACGTCTGGGGCCAAGGGACCACG<br>GTCACCGTCTCCTCAGCCTCCACCAAGGGCCCATCGGTCTTCCCCCTGGCACCCTCCTCCA<br>AGAGCACCTCTGGGGGCACAGCAGCCCTGGGCTGCCTGGTCAAGGACTACTTCCCCGAACC<br>GGTGACGGTGTCGTGGAACTCAGGCGCCCTGACCAGCGGCGTGCACACCTTCCCGGCTGTC<br>CTACAGTCCTCAGGACTCTACTCCCTCAGCAGCGTGGTGACCGTGCCCTCCAGCAGCTTGG<br>GCACCCAGACCTACATCTGCAACGTGAATCACAAGCCCAGCAACACCAAGGTGGACAAGAA<br>AGTTGAGCCCAAATCTTGTGACAAAACTCACACATGCCCACCGTGCCCAGCACCTGAACTC<br>CTGGGGGGACCGTCAGTCTTCCTCTTCCCCCCAAAACCCAAGGACACCCTCATGATCTCCC<br>GGACCCCTGAGGTCACATGCGTGGTGGTGGACGTGAGCCACGAAGACCCTGAGGTCAAGTT<br>CAACTGGTACGTGGACGGCGTGGAGGTGCATAATGCCAAGACAAAGCCGCGGGAGGAGCAG<br>TACAACAGCACGTACCGTGTGGTCAGCGTCCTCACCGTCCTGCACCAGGACTGGCTGAATG<br>GCAAGGAGTACAAGTGCAAGGTCTCCAACAAAGCCCTCCCAGCCCCCATCGAGAAAACCAT<br>CTCCAAAGCCAAAGGGCAGCCCCGAGAACCACAGGTGTACACCCTGCCCCCATCCCGGGAT<br>GAGCTGACCAAGAACCAGGTCAGCCTGACCTGCCTGGTCAAAGGCTTCTATCCCAGCGACA<br>TCGCCGTGGAGTGGGAGAGCAATGGGCAGCCGGAGAACAACTACAAGACCACGCCTCCCGT<br>GCTGGACTCCGACGGCTCCTTCTTCCTCTACAGCAAGCTCACCGTGGACAAGAGCAGGTGG<br>CAGCAGGGGAACGTCTTCTCATGCTCCGTGCTGCATGAGGCTCTGCACTCCCACTACACAC<br>AGAAGAGCCTCTCCCTGTCTCCGGGTAAA [SEQ ID NO: 52] | |

In certain embodiments, the anti-CSP antibody variant comprises a light chain variable region comprising a CDR1, a CDR2, and a CDR3 and having the amino acid sequence set forth in SEQ ID NO: 53, as shown in Table 9. In certain embodiments, the anti-CSP antibody variant comprises a heavy chain variable region comprising a CDR1, a CDR2, and a CDR3 and having the amino acid sequence set forth in SEQ ID NO: 55, as shown in Table 9. In certain embodiments, the anti-CSP antibody variant comprises a light chain having the amino acid sequence set forth in SEQ ID NO: 57, as shown in Table 9. In certain embodiments, the anti-CSP antibody variant comprises a heavy chain having the amino acid sequence set forth in SEQ ID NO: 58, as shown in Table 9. In certain embodiments, the anti-CSP antibody variant comprises a heavy chain having the amino acid sequence set forth in SEQ ID NO: 59, as shown in Table 9. Exemplary nucleic acid sequences of SEQ ID NOS: 53, 54, 57, 58, and 59 are provided in Table 9 below.

TABLE 9

Antibody ID: AB-000224.004

| | KABAT | ASN |
|---|---|---|
| CDR1-VL | TGMNSNIGAGYDVY [SEQ ID NO: 1] | TGMNSNIGAGYDVY [SEQ ID NO: 7] |
| CDR2-VL | GNSNRPS [SEQ ID NO: 2] | GNSNRPS [SEQ ID NO: 8] |
| CDR3-VL | QSYDTSLNGWA [SEQ ID NO: 3] | QSYDTSLNGWA [SEQ ID NO: 9] |
| CDR1-VH | DHAMS [SEQ ID NO: 4] | DHAMS [SEQ ID NO: 10] |
| CDR2-VH | FIRKTTYGATTHYAAAVRG [SEQ ID NO: 5] | FIRKTTYGATTHYAAAVRG [SEQ ID NO: 11] |
| CDR3-VH | VQLDYGPGYQYYGMDV [SEQ ID NO: 6] | VQLDYGPGYQYYGMDV [SEQ ID NO: 12] |
| VL | QSVLTQPPSVSGAPGQRVTISCTGMNSNIGAGYDVYWYQQLPGTAPKLLIYGNSNRPSGVPDRFSGSRSGTSASLAITGLQAEDEADYYCQSYDTSLNGWAFGGGTKLTVLG [SEQ ID NO: 53] | |
| VH | EVQLVESGGGLVQPGRSLRLSCTASGFSFGDHAMSWVRQAPGKGLEWVGFIRKTTYGATTHYAAAVRGRFTISRDDSKSIVYLQMNSLKAEDTAVYFCTRVQLDYGPGYQYYGMDVWGQGTTVTVSS [SEQ ID NO: 54] | |
| DNA for VL | CAGTCTGTGCTGACGCAGCCGCCCTCAGTGTCTGGGGCCCCAGGGCAGAGGGTCACCATCTCCTGCACTGGGATGAACTCCAACATCGGGGCAGGTTATGATGTATACTGGTACCAACAACTTCCAGGAACTGCCCCCAAACTCCTCATCTATGGTAACAGCAATCGGCCCTCAGGGGTCCCTGACCGATTCT | |

TABLE 9-continued

Antibody ID: AB-000224.004

| | KABAT | ASN |
|---|---|---|
| | CTGGCTCCAGGTCTGGCACCTCAGCCTCCCTGGCCATCACTGGGCTCCAG GCTGAGGATGAGGCTGATTATTACTGCCAGTCCTATGACACCAGCCTGAA TGGTTGGGCTTTCGGCGGAGGGACCAAGTTGACCGTCCTAGGC [SEQ ID NO: 55] | |
| DNA for VH | GAGGTGCAGCTGGTGGAGTCTGGGGGAGGCTTGG TACAGCCAGGGCGGTCCCTGAGACTCAGCTGTACAGCCTCTGGGTTTAGT TTTGGTGATCATGCTATGAGCTGGGTCCGCCAGGCTCCAGGGAAGGGGCT GGAGTGGGTAGGTTTCATTAGAAAGACAACTTATGGTGCGACAACACACT ACGCCGCGGCTGTGAGAGGCAGATTCACCATCTCGCGAGATGATTCTAAA AGCATTGTGTATCTGCAAATGAACAGCCTGAAAGCAGAGGACACAGCCGT GTATTTCTGTACTAGAGTGCAGCTTGACTATGGCCCGGGATACCAGTACT ACGGTATGGACGTCTGGGGCCAAGGGACCACGGTCACCGTCTCCTCA [SEQ ID NO: 56] | |
| Light Chain | QSVLTQPPSVSGAPGQRVTISCTGMNSNIGA GYDVYWYQQLPGTAPKLLIYGNSNRPSGVPDRFSGSRSGTSASLAITGLQ AEDEADYYCQSYDTSLNGWAFGGGTKLTVLGQPKAAPSVTLFPPSSEELQ ANKATLVCLVSDFYPGAVTVAWKADGSPVKVGVETTKPSKQSNNKYAASS YLSLTPEQWKSHRSYSCRVTHEGSTVEKTVAPAECS[SEQ ID NO: 57] | |
| Heavy Chain version 1 | EVQLVESGGGLVQPGRSLRLSCTASGFS FGDHAMSWVRQAPGKGLEWVGFIRKTTYGATTHYAAAVRGRFTISRDDSK SIVYLQMNSLKAEDTAVYFCTRVQLDYGPGYQYYGMDVWGQGTTVTVSSA STKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPK SCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQ QGNVFSCSVMHEALHNHYTQKSLSLSPGK[SEQ ID NO: 58] | |
| Heavy Chain version 2 | EVQLVESGGGLVQPGRSLRLSCTASGFS FGDHAMSWVRQAPGKGLEWVGFIRKTTYGATTHYAAAVRGRFTISRDDSK SIVYLQMNSLKAEDTAVYFCTRVQLDYGPGYQYYGMDVWGQGTTVTVSSA STKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPK SCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQ QGNVFSCSVLHEALHSHYTQKSLSLSPGK [SEQ ID NO: 59] | |
| DNA for Light Chain | CAGTCTGTGCTGACGCAGCCGCCCTCAGTGTCTGGGGCCCCAG GGCAGAGGGTCACCATCTCCTGCACTGGGATGAACTCCAACATCGGGGCA GGTTATGATGTATACTGGTACCAACAACTTCCAGGAACTGCCCCCAAACT CCTCATCTATGGTAACAGCAATCGGCCCTCAGGGGTCCCTGACCGATTCT CTGGCTCCAGGTCTGGCACCTCAGCCTCCCTGGCCATCACTGGGCTCCAG GCTGAGGATGAGGCTGATTATTACTGCCAGTCCTATGACACCAGCCTGAA TGGTTGGGCTTTCGGCGGAGGGACCAAGTTGACCGTCCTAGGCCAGCCCA AGGCTGCCCCCTCGGTCACTCTGTTCCCACCCTCCTCTGAGGAGCTTCAA GCCAACAAGGCCACACTGGTGTGTCTCGTAAGTGACTTCTACCCGGGAGC CGTGACAGTGGCCTGGAAGGCAGATGGCAGCCCCGTCAAGGTGGGAGTGG AGACCACCAAACCCTCCAAACAAAGCAACAACAAGTATGCGGCCAGCAGC TACCTGAGCCTGACGCCCGAGCAGTGGAAGTCCCACAGAAGCTACAGCTG CCGGGTCACGCATGAAGGGAGCACCGTGGAGAAGACAGTGGCCCCTGCAG AATGCTCT [SEQ ID NO: 60] | |
| DNA for Heavy Chain version 1 | GAGGTGCAGCTGGTGGAGTCTGGGGGAGGCTTGG TACAGCCAGGGCGGTCCCTGAGACTCAGCTGTACAGCCTCTGGGTTTAGT TTTGGTGATCATGCTATGAGCTGGGTCCGCCAGGCTCCAGGGAAGGGGCT GGAGTGGGTAGGTTTCATTAGAAAGACAACTTATGGTGCGACAACACACT ACGCCGCGGCTGTGAGAGGCAGATTCACCATCTCGCGAGATGATTCTAAA AGCATTGTGTATCTGCAAATGAACAGCCTGAAAGCAGAGGACACAGCCGT GTATTTCTGTACTAGAGTGCAGCTTGACTATGGCCCGGGATACCAGTACT ACGGTATGGACGTCTGGGGCCAAGGGACCACGGTCACCGTCTCCTCAGCC TCCACCAAGGGCCCATCGGTCTTCCCCCTGGCACCCTCCTCCAAGAGCAC CTCTGGGGGCACAGCGGCCCTGGGCTGCCTGGTCAAGGACTACTTCCCCG AACCGGTGACGGTGTCGTGGAACTCAGGCGCCCTGACCAGCGGCGTGCAC ACCTTCCCGGCTGTCCTACAGTCCTCAGGACTCTACTCCCTCAGCAGCGT GGTGACCGTGCCCTCCAGCAGCTTGGGCACCCAGACCTACATCTGCAACG TGAATCACAAGCCCAGCAACACCAAGGTGGACAAGAAAGTTGAGCCCAAA TCTTGTGACAAAACTCACACATGCCCACCGTGCCCAGCACCTGAACTCCT GGGGGGACCGTCAGTCTTCCTCTTCCCCCCAAAACCCAAGGACACCCTCA TGATCTCCCGGACCCCTGAGGTCACATGCGTGGTGGTGGACGTGAGCCAC GAAGACCCTGAGGTCAAGTTCAACTGGTACGTGGACGGCGTGGAGGTGCA TAATGCCAAGACAAAGCCGCGGGAGGAGCAGTACAACAGCACGTACCGTG | |

TABLE 9-continued

Antibody ID: AB-000224.004

| | KABAT | ASN |
|---|---|---|
| | TGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG<br>GCAGCCGGAGAACAACTACAAGACCACGCCTCCCGTGCTGGACTCCGACG<br>GCTCCTTCTTCCTCTACAGCAAGCTCACCGTGGACAAGAGCAGGTGGCAG<br>CAGGGGAACGTCTTCTCATGCTCCGTGATGCATGAGGCTCTGCACAACCA<br>CTACACACAGAAGAGCCTCTCCCTGTCTCCGGGTAAA [SEQ ID NO: 61] | |
| DNA<br>for<br>Heavy<br>Chain<br>version<br>2 | GAGGTGCAGCTGGTGGAGTCTGGGGGAGGCTTGG<br>TACAGCCAGGGCGGTCCCTGAGACTCAGCTGTACAGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGGATTGTCTATGTGCAAATGAACAGCCTGAAAGCAGAGGACACAGCCGT<br>GTATTTCTGTACTAGAGTGCAGCTTGACTATGGCCCGGGATACCAGTACT<br>ACGGTATGGACGTCTGGGGCCAAGGGACCACGGTCACCGTCTCCTCAGCC<br>TCCACCAAGGGCCCATCGGTCTTCCCCCTGGCACCCTCCTCCAAGAGCAC<br>CTCTGGGGGCACAGCAGCCCTGGGCTGCCTGGTCAAGGACTACTTCCCCG<br>AACCGGTGACGGTGTCGTGGAACTCAGGCGCCCTGACCAGCGGCGTGCAC<br>ACCTTCCCGGCTGTCCTACAGTCCTCAGGACTCTACTCCCTCAGCAGCGT<br>GGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAA<br>TCTTGTGACAAAACTCACACATGCCCACCGTGCCCAGCACCTGAACTCCT<br>GGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCA<br>TAATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG<br>GCAGCCGGAGAACAACTACAAGACCACGCCTCCCGTGCTGGACTCCGACG<br>GCTCCTTCTTCCTCTACAGCAAGCTCACCGTGGACAAGAGCAGGTGGCAG<br>CAGGGGAACGTCTTCTCATGCTCCGTGCTGCATGAGGCTCTGCACTCCCA<br>CTACACACAGAAGAGCCTCTCCCTGTCTCCGGGTAAA [SEQ ID NO: 62] | |

In certain embodiments, the anti-CSP antibody variant comprises a light chain variable region comprising a CDR1, a CDR2, and a CDR3 and having the amino acid sequence set forth in SEQ ID NO: 63, as shown in Table 10. In certain embodiments, the anti-CSP antibody variant comprises a heavy chain variable region comprising a CDR1, a CDR2, and a CDR3 and having the amino acid sequence set forth in SEQ ID NO: 64, as shown in Table 10. In certain embodiments, the anti-CSP antibody variant comprises a light chain having the amino acid sequence set forth in SEQ ID NO: 67, as shown in Table 10. In certain embodiments, the anti-CSP antibody variant comprises a heavy chain having the amino acid sequence set forth in SEQ ID NO: 68, as shown in Table 10. In certain embodiments, the anti-CSP antibody variant comprises a heavy chain having the amino acid sequence set forth in SEQ ID NO: 69, as shown in Table 10. Exemplary nucleic acid sequences of SEQ ID NOS: 63, 64, 67, 68, and 69 are provided in Table 10 below.

TABLE 10

Antibody ID: AB-000224.005

| | | KABAT | ASN |
|---|---|---|---|
| CDR1-<br>VL | | TGMNSNIGAGYDVY [SEQ ID NO: 1] | TGMNSNIGAGYDVY [SEQ ID NO: 7] |
| CDR2-<br>VL | | GNSNRPS [SEQ ID NO: 2] | GNSNRPS [SEQ ID NO: 8] |
| CDR3-<br>VL | | QSYDTSLNGWA [SEQ ID NO: 3] | QSYDTSLNGWA [SEQ ID NO: 9] |
| CDR1-<br>VH | | DHAMS [SEQ ID NO: 4] | DHAMS [SEQ ID NO: 10] |
| CDR2-<br>VH | | FIRKTTYGATTHYAAAVRG [SEQ ID NO: 5] | FIRKTTYGATTHYAAAVRG [SEQ ID NO: 11] |
| CDR3-<br>VH | | VQLDYGPGYQYYGMDV [SEQ ID NO: 6] | VQLDYGPGYQYYGMDV [SEQ ID NO: 12] |

TABLE 10-continued

| | Antibody ID: AB-000224.005 | |
|---|---|---|
| | KABAT | ASN |

| | |
|---|---|
| VL | QSVLTQPPSVSGAPGQRVTISCTGMSNIGA<br>GYDVYWYQQLPGTAPKLLIYGNSNRPSGVPDRFSGSRSGTSASLAITGLQ<br>AEDEADYYCQSYDTSLNGWAFGGGTKLTVLG<br>[SEQ ID NO: 63] |
| VH | EVQLVESGGGLVQPGRSLRLSCTASGFS<br>FGDHAMSWVRQAPGKGLEWVGFIRKTTYGATTHYAAAVRGRFTISRDDSK<br>SIVYLQMNSLKTEDTAVYFCARVQLDYGPGYQYYGMDVWGQGTTVTVSS<br>[SEQ ID NO: 64] |
| DNA for VL | CAGTCTGTGCTGACGCAGCCGCCCTCAGTGTCTGGGGCCCCAG<br>GGCAGAGGGTCACCATCTCCTGCACTGGGATGAACTCCAACATCGGGGCA<br>GGTTATGATGTATACTGGTACCAACAACTTCCAGGAACTGCCCCCAAACT<br>CCTCATCTATGGTAACAGCAATCG6CCCTCAGGGGTCCCTGACCGATTCT<br>CTGGCTCCAGGTCTGGCACCTCAGCCTCCCTGGCCATCACTGGGCTCCAG<br>GCTGAGGATGAGGCTGATTATTACTGCCAGTCCTATGACACCAGCCTGAA<br>TGGTTGGGCTTTCGGCGGAGGGACCAAGTTGACCGTCCTAGGC<br>[SEQ ID NO: 65] |
| DNA for VH | GAGGTGCAGCTGGTGGAGTCTGGGGGAGGCTTGG<br>TACAGCCAGGGCGGTCCCTGAGACTCAGCTGTACAGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGCATTGTCTATCTGCAAATGAACAGCCTGAAAACCGAGGACACAGCCGT<br>GTATTTCTGTGCTAGAGTGCAGCTTGACTATGGCCCGGGATACCAGTACT<br>ACGGTATGGACGTCTGGGGCCAAGGGACCACGGTCACCGTCTCCTCA<br>[SEQ ID NO: 66] |
| Light Chain | QSVLTQPPSVSGAPGQRVTISCTGMSNIGA<br>GYDVYWYQQLPGTAPKLLIYGNSNRPSGVPDRFSGSRSGTSASLAITGLQ<br>AEDEADYYCQSYDTSLNGWAFGGGTKLTVLGQPKAAPSVTLFPPSSEELQ<br>ANKATLVCLVSDFYPGAVTVAWKADGSPVKVGVETTKPSKQSNNKYAASS<br>YLSLTPEQWKSHRSYSCRVTHEGSTVEKTVAPAECS<br>[SEQ ID NO: 67] |
| Heavy Chain version 1 | EVQLVESGGGLVQPGRSLRLSCTASGFS<br>FGDHAMSWVRQAPGKGLEWVGFIRKTTYGATTHYAAAVRGRFTISRDDSK<br>SIVYLQMNSLKTEDTAVYFCARVQLDYGPGYQYYGMDVWGQGTTVTVSSA<br>STKGPSVFPLAPSSKSTSGGTAALGCLVKDYFPEPVTVSWNSGALTSGVH<br>TFPAVLQSSGLYSLSSVVTVPSSSLGTQTYICNVNHKPSNTKVDKKVEPK<br>SCDKTHTCPPCPAPELLGGPSVFLFPPKPKDTLMISRTPEVTCVVVDVSH<br>EDPEVKFNWYVDGVEVHNAKTKPREEQYNSTYRVVSVLTVLHQDWLNGKE<br>YKCKVSNKALPAPIEKTISKAKGQPREPQVYTLPPSRDELTKNQVSLTCL<br>VKGFYPSDIAVEWESNGQPENNYKTTPPVLDSDGSFFLYSKLTVDKSRWQ<br>QGNVFSCSVMHEALHNHYTQKSLSLSPGK<br>[SEQ ID NO: 68] |
| Heavy Chain version 2 | EVQLVESGGGLVQPGRSLRLSCTASGFS<br>FGDHAMSWVRQAPGKGLEWVGFIRKTTYGATTHYAAAVRGRFTISRDDSK<br>SIVYLQMNSLKTEDTAVYFCARVQLDYGPGYQYYGMDVWGQGTTVTVSSA<br>STKGPSVFPLAPSSKSTSGGTAALGCLVKDYFPEPVTVSWNSGALTSGVH<br>TFPAVLQSSGLYSLSSVVTVPSSSLGTQTYICNVNHKPSNTKVDKKVEPK<br>SCDKTHTCPPCPAPELLGGPSVFLFPPKPKDTLMISRTPEVTCVVVDVSH<br>EDPEVKFNWYVDGVEVHNAKTKPREEQYNSTYRVVSVLTVLHQDWLNGKE<br>YKCKVSNKALPAPIEKTISKAKGQPREPQVYTLPPSRDELTKNQVSLTCL<br>VKGFYPSDIAVEWESNGQPENNYKTTPPVLDSDGSFFLYSKLTVDKSRWQ<br>QGNVFSCSVLHEALHSHYTQKSLSLSPGK [SEQ ID NO: 69] |
| DNA for Light Chain | CAGTCTGTGCTGACGCAGCCGCCCTCAGTGTCTGGGGCCCCAG<br>GGCAGAGGGTCACCATCTCCTGCACTGGGATGAACTCCAACATCGGGGCA<br>GGTTATGATGTATACTGGTACCAACAACTTCCAGGAACTGCCCCCAAACT<br>CCTCATCTATGGTAACAGCAATCGGCCCTCAGGGGTCCCTGACCGATTCT<br>CTGGCTCCAGGTCTGGCACCTCAGCCTCCCTGGCCATCACTGGGCTCCAG<br>GCTGAGGATGAGGCTGATTATTACTGCCAGTCCTATGACACCAGCCTGAA<br>TGGTTGGGCTTTCGGCGGAGGGACCAAGTTGACCGTCCTAGGCCAGCCCA<br>AGGCTGCCCCCTCGGTCACTCTGTTCCCACCCTCCTCTGAGGAGCTTCAA<br>GCCAACAAGGCCACACTGGTGTGTCTCGTAAGTGACTTCTACCCGGGAGC<br>CGTGACAGTGGCCTGGAAGGCAGATGGCAGCCCCGTCAAGGTGGGAGTGG<br>AGACCACCAAACCCTCCAAACAAAGCAACAACAAGTATGCGGCCAGCAGC<br>TACCTGAGCCTGACGCCCGAGCAGTGGAAGTCCCACAGAAGCTACAGCTG<br>CCGGGTCACGCATGAAGGGAGCACCGTGGAGAAGACAGTGGCCCCTGCAG<br>AATGCTCT<br>[SEQ ID NO: 70] |

TABLE 10-continued

Antibody ID: AB-000224.005

| | KABAT | ASN |
|---|---|---|
| DNA for Heavy Chain version 1 | GAGGTGCAGCTGGTGGAGTCTGGGGGAGGCTTGG<br>TACAGCCAGGGCGGTCCCTGAGACTCAGCTGTACAGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGCATTGTCTATCTGCAAATGAACAGCCTGAAAACCGAGGACACAGCCGT<br>GTATTTCTGTGCTAGAGTGCAGCTTGACTATGGCCCGGGATACCAGTACT<br>ACGGTATGGACGTCTGGGGCCAAGGGACCACGGTCACCGTCTCCTCAGCC<br>TCCACCAAGGGCCCATCGGTCTTCCCCCTGGCACCCTCCTCCAAGAGCAC<br>CTCTGGGGGCACAGCAGCCCTGGGCTGCCTGGTCAAGGACTACTTCCCCG<br>AACCGGTGACGGTGTCGTGGAACTCAGGCGCCCTGACCAGCGGCGTGCAC<br>ACCTTCCCGGCTGTCCTACAGTCCTCAGGACTCTACTCCCTCAGCAGCGT<br>GGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAA<br>TCTTGTGACAAAACTCACACATGCCCACCGTGCCCAGCACCTGAACTCCT<br>GGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCA<br>TAATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG<br>GCAGCCGGAGAACAACTACAAGACCACGCCTCCCGTGCTGGACTCCGACG<br>GCTCCTTCTTCCTCTACAGCAAGCTCACCGTGGACAAGAGCAGGTGGCAG<br>CAGGGGAACGTCTTCTCATGCTCCGTGATGCATGAGGCTCTGCACAACCA<br>CTACACACAGAAGAGCCTCTCCCTGTCTCCGGGTAAA [SEQ ID NO: 71] | |
| DNA for Heavy Chain version 2 | GAGGTGCAGCTGGTGGAGTCTGGGGGAGGCTTGG<br>TACAGCCAGGGCGGTCCCTGAGACTCAGCTGTACAGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGCATTGTCTATCTGCAAATGAACAGCCTGAAAACCGAGGACACAGCCGT<br>GTATTTCTGTGCTAGAGTGCAGCTTGACTATGGCCCGGGATACCAGTACT<br>ACGGTATGGACGTCTGGGGCCAAGGGACCACGGTCACCGTCTCCTCAGCC<br>TCCACCAAGGGCCCATCGGTCTTCCCCCTGGCACCCTCCTCCAAGAGCAC<br>CTCTGGGGGCACAGCAGCCCTGGGCTGCCTGGTCAAGGACTACTTCCCCG<br>AACCGGTGACGGTGTCGTGGAACTCAGGCGCCCTGACCAGCGGCGTGCAC<br>ACCTTCCCGGCTGTCCTACAGTCCTCAGGACTCTACTCCCTCAGCAGCGT<br>GGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAA<br>TCTTGTGACAAAACTCACACATGCCCACCGTGCCCAGCACCTGAACTCCT<br>GGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCA<br>TAATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG<br>GCAGCCGGAGAACAACTACAAGACCACGCCTCCCGTGCTGGACTCCGACG<br>GCTCCTTCTTCCTCTACAGCAAGCTCACCGTGGACAAGAGCAGGTGGCAG<br>CAGGGGAACGTCTTCTCATGCTCCGTGCTGCATGAGGCTCTGCACTCCCA<br>CTACACACAGAAGAGCCTCTCCCTGTCTCCGGGTAAA [SEQ ID NO: 72] | |

In certain embodiments, the anti-CSP antibody variant comprises a light chain variable region comprising a CDR1, a CDR2, and a CDR3 and having the amino acid sequence set forth in SEQ ID NO: 73, as shown in Table 11. In certain embodiments, the anti-CSP antibody variant comprises a heavy chain variable region comprising a CDR1, a CDR2, and a CDR3 and having the amino acid sequence set forth in SEQ ID NO: 74, as shown in Table 11. In certain embodiments, the anti-CSP antibody variant comprises a light chain having the amino acid sequence set forth in SEQ ID NO: 77, as shown in Table 11. In certain embodiments, the anti-CSP antibody variant comprises a heavy chain having the amino acid sequence set forth in SEQ ID NO: 78, as shown in Table 11. In certain embodiments, the anti-CSP antibody variant comprises a heavy chain having the amino acid sequence set forth in SEQ ID NO: 79, as shown in Table 11. Exemplary nucleic acid sequences of SEQ ID NOS: 73, 74, 77, 78, and 79 are provided in Table 11 below.

TABLE 11

| | Antibody ID: AB-000224.006 | |
|---|---|---|
| | KABAT | ASN |
| CDR1-VL | TGMNSNIGAGYDVY [SEQ ID NO: 1] | TGMNSNIGAGYDVY [SEQ ID NO: 7] |
| CDR2-VL | GNSNRPS [SEQ ID NO: 2] | GNSNRPS [SEQ ID NO: 8] |
| CDR3-VL | QSYDTSLNGWA [SEQ ID NO: 3] | QSYDTSLNGWA [SEQ ID NO: 9] |
| CDR1-VH | DHAMS [SEQ ID NO: 4] | DHAMS [SEQ ID NO: 10] |
| CDR2-VH | FIRKTTYGATTHYAAAVRG [SEQ ID NO: 5] | FIRKTTYGATTHYAAAVRG [SEQ ID NO: 11] |
| CDR3-VH | VQLDYGPGYQYYGMDV [SEQ ID NO: 6] | VQLDYGPGYQYYGMDV [SEQ ID NO: 12] |
| VL | QSVLTQPPSVSGAPGQRVTISCTGMNSNIGA GYDVYWYQQLPGTAPKLLIYGNSNRPSGVPDRFSGSRSGTSASLAITGLQ AEDEADYYCQSYDTSLNGWAFGGGTKLTVLG [SEQ ID NO: 73] | |
| VH | EVQLVESGGGLVQPGRSLRLSCAASGFS FGDHAMSWVRQAPGKGLEWVGFIRKTTYGATTHYAAAVRGRFTISRDDSK STVYLQMNSLKTEDTAVYFCTRVQLDYGPGYQYYGMDVWGQGTTVTVSS [SEQ ID NO: 74] | |
| DNA for VL | CAGTCTGTGCTGACGCAGCCGCCCTCAGTGTCTGGGGCCCCAG GGCAGAGGGTCACCATCTCCTGCACTGGGATGAACTCCAACATCGGGGCA GGTTATGATGTATACTGGTACCAACAACTTCCAGGAACTGCCCCCAAACT CCTCATCTATGGTAACAGCAATCGGCCCTCAGGGGTCCCTGACCGATTCT CTGGCTCCAGGTCTGGCACCTCAGCCTCCCTGGCCATCACTGGGCTCCAG GCTGAGGATGAGGCTGATTATTACTGCCAGTCCTATGACACCAGCCTGAA TGGTTGGGCTTTCGGCGGAGGGACCAAGTTGACCGTCCTAGGC [SEQ ID NO: 75] | |
| DNA for VH | GAGGTGCAGCTGGTGGAGTCTGGGGGAGGCTTGG TACAGCCAGGGCGGTCCCTGAGACTCAGCTGTGCGGCCTCTGGGTTTAGT TTTGGTGATCATGCTATGAGCTGGGTCCGCCAGGCTCCAGGGAAGGGGCT GGAGTGGGTAGGTTTTATTAGAAAGACAACTTATGGTGCGACAACACACT ACGCCGCGGCTGTGAGAGGCAGATTCACCATCTCGCGAGATGATTCTAAA AGCACTGTCTATCTGCAAATGAACAGCCTGAAAACCGAGGACACAGCCGT GTATTTCTGTACTAGAGTGCAGCTTGACTATGGCCCGGGATACCAGTACT ACGGTATGGACGTCTGGGGCCAAGGGACCACGGTCACCGTCTCCTCA [SEQ ID NO: 76] | |
| Light Chain | QSVLTQPPSVSGAPGQRVTISCTGMNSNIGA GYDVYWYQQLPGTAPKLLIYGNSNRPSGVPDRFSGSRSGTSASLAITGLQ AEDEADYYCQSYDTSLNGWAFGGGTKLTVLGQPKAAPSVTLFPPSSEELQ ANKATLVCLVSDFYPGAVTVAWKADGSPVKVGVETTKPSKQSNNKYAASS YLSLTPEQWKSHRSYSCRVTHEGSTVEKTVAPAECS [SEQ ID NO: 77] | |
| Heavy Chain version 1 | EVQLVESGGGLVQPGRSLRLSCAASGFS FGDHAMSWVRQAPGKGLEWVGFIRKTTYGATTHYAAAVRGRFTISRDDSK STVYLQMNSLKTEDTAVYFCTRVQLDYGPGYQYYGMDVWGQGTTVTVSSA STKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPK SCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQ QGNVFSCSVMHEALHNHYTQKSLSLSPGK [SEQ ID NO: 78] | |
| Heavy Chain version 2 | EVQLVESGGGLVQPGRSLRLSCAASGFS FGDHAMSWVRQAPGKGLEWVGFIRKTTYGATTHYAAAVRGRFTISRDDSK STVYLQMNSLKTEDTAVYFCTRVQLDYGPGYQYYGMDVWGQGTTVTVSSA STKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPK SCDKTHTCPPCPAPELLGGPSVFLFPPKPKDTLMISRTPEVTCVVVDVSH | |

TABLE 11-continued

Antibody ID: AB-000224.006

| | KABAT | ASN |
|---|---|---|

EDPEVKFNWYVDGVEVHNAKTKPREEQYNSTYRVVSVLTVLHQDWLNGKE
YKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQ
QGNVFSCSVLHEALHSHYTQKSLSLSPGK
[SEQ ID NO: 79]

DNA for Light Chain
CAGTCTGTGCTGACGCAGCCGCCCTCAGTGTCTGGGGCCCCAG
GGCAGAGGGTCACCATCTCCTGCACTGGGATGAACTCCAACATCGGGGCA
GGTTATGATGTATACTGGTACCAACAACTTCCAGGAACTGCCCCCAAACT
CCTCATCTATGGTAACAGCAATCGGCCCTCAGGGGTCCCTGACCGATTCT
CTGGCTCCAGGTCTGGCACCTCAGCCTCCCTGGCCATCACTGGGCTCCAG
GCTGAGGATGAGGCTGATTATTACTGCCAGTCCTATGACACCAGCCTGAA
TGGTTGGGCTTTCGGCGGAGGGACCAAGTTGACCGTCCTAGGCCAGCCCA
AGGCTGCCCCCTCGGTCACTCTGTTCCCACCCTCCTCTGAGGAGCTTCAA
GCCAACAAGGCCACACTGGTGTGTCTCGTAAGTGACTTCTACCCGGGAGC
CGTGACAGTGGCCTGGAAGGCAGATGGCAGCCCCGTCAAGGTGGGAGTGG
AGACCACCAAACCCTCCAAACAAAGCAACAACAAGTATGCGGCCAGCAGC
TACCTGAGCCTGACGCCCGAGCAGTGGAAGTCCCACAGAAGCTACAGCTG
CCGGGTCACGCATGAAGGGAGCACCGTGGAGAAGACAGTGGCCCCTGCAG
AATGCTCT
[SEQ ID NO: 80]

DNA for Heavy Chain version 1
GAGGTGCAGCTGGTGGAGTCTGGGGGAGGCTTGG
TACAGCCAGGGCGGTCCCTGAGACTCAGCTGTGCGGCCTCTGGGTTTAGT
TTTGGTGATCATGCTATGAGCTGGGTCCGCCAGGCTCCAGGGAAGGGGCT
GGAGTGGGTAGGTTTCATTAGAAAGACAACTTATGGTGCGACAACACACT
ACGCCGCGGCTGTGAGAGGCAGATTCACCATCTCGCGAGATGATTCTAAA
AGCACTGTCTATCTGCAAATGAACAGCCTGAAAACCGAGGACACAGCCGT
GTATTTCTGTACTAGAGTGCAGCTTGACTATGGCCCGGGATACCAGTACT
ACGGTATGGACGTCTGGGGCCAAGGGACCACGGTCACCGTCTCCTCAGCC
TCCACCAAGGGCCCATCGGTCTTCCCCCTGGCACCCTCCTCCAAGAGCAC
CTCTGGGGGCACAGCAGCCCTGGGCTGCCTGGTCAAGGACTACTTCCCCG
AACCGGTGACGGTGTCGTGGAACTCAGGCGCCCTGACCAGCGGCGTGCAC
ACCTTCCCGGCTGTCCTACAGTCCTCAGGACTCTACTCCCTCAGCAGCGT
GGTGACCGTGCCCTCCAGCAGCTTGGGCACCCAGACCTACATCTGCAACG
TGAATCACAAGCCCAGCAACACCAAGGTGGACAAGAAAGTTGAGCCCAAA
TCTTGTGACAAAACTCACACATGCCCACCGTGCCCAGCACCTGAACTCCT
GGGGGGACCGTCAGTCTTCCTCTTCCCCCCAAAACCCAAGGACACCCTCA
TGATCTCCCGGACCCCTGAGGTCACATGCGTGGTGGTGGACGTGAGCCAC
GAAGACCCTGAGGTCAAGTTCAACTGGTACGTGGACGGCGTGGAGGTGCA
TAATGCCAAGACAAAGCCGCGGGAGGAGCAGTACAACAGCACGTACCGTG
TGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAAC
CATCTCCAAAGCCAAAGGGCAGCCCCGAGAACCACAGGTGTACACCCTGC
CCCCATCCCGGGATGAGCTGACCAAGAACCAGGTCAGCCTGACCTGCCTG
GTCAAAGGCTTCTATCCCAGCGACATCGCCGTGGAGTGGGAGAGCAATGG
GCAGCCGGAGAACAACTACAAGACCACGCCTCCCGTGCTGGACTCCGACG
GCTCCTTCTTCCTCTACAGCAAGCTCACCGTGGACAAGAGCAGGTGGCAG
CAGGGGAACGTCTTCTCATGCTCCGTGATGCATGAGGCTCTGCACAACCA
CTACACACAGAAGAGCCTCTCCCTGTCTCCGGGTAAA [SEQ ID NO: 81]

DNA for Heavy Chain version 2
GAGGTGCAGCTGGTGGAGTCTGGGGGAGGCTTGG
TACAGCCAGGGCGGTCCCTGAGACTCAGCTGTGCGGCCTCTGGGTTTAGT
TTTGGTGATCATGCTATGAGCTGGGTCCGCCAGGCTCCAGGGAAGGGGCT
GGAGTGGGTAGGTTTCATTAGAAAGACAACTTATGGTGCGACAACACACT
ACGCCGCGGCTGTGAGAGGCAGATTCACCATCTCGCGAGATGATTCTAAA
AGCACTGTCTATCTGCAAATGAACAGCCTGAAAACCGAGGACACAGCCGT
GTATTTCTGTACTAGAGTGCAGCTTGACTATGGCCCGGGATACCAGTACT
ACGGTATGGACGTCTGGGGCCAAGGGACCACGGTCACCGTCTCCTCAGCC
TCCACCAAGGGCCCATCGGTCTTCCCCCTGGCACCCTCCTCCAAGAGCAC
CTCTGGGGGCACAGCAGCCCTGGGCTGCCTGGTCAAGGACTACTTCCCCG
AACCGGTGACGGTGTCGTGGAACTCAGGCGCCCTGACCAGCGGCGTGCAC
ACCTTCCCGGCTGTCCTACAGTCCTCAGGACTCTACTCCCTCAGCAGCGT
GGTGACCGTGCCCTCCAGCAGCTTGGGCACCCAGACCTACATCTGCAACG
TGAATCACAAGCCCAGCAACACCAAGGTGGACAAGAAAGTTGAGCCCAAA
TCTTGTGACAAAACTCACACATGCCCACCGTGCCCAGCACCTGAACTCCT
GGGGGGACCGTCAGTCTTCCTCTTCCCCCCAAAACCCAAGGACACCCTCA
TGATCTCCCGGACCCCTGAGGTCACATGCGTGGTGGTGGACGTGAGCCAC
GAAGACCCTGAGGTCAAGTTCAACTGGTACGTGGACGGCGTGGAGGTGCA
TAATGCCAAGACAAAGCCGCGGGAGGAGCAGTACAACAGCACGTACCGTG
TGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAAC
CATCTCCAAAGCCAAAGGGCAGCCCCGAGAACCACAGGTGTACACCCTGC
CCCCATCCCGGGATGAGCTGACCAAGAACCAGGTCAGCCTGACCTGCCTG
GTCAAAGGCTTCTATCCCAGCGACATCGCCGTGGAGTGGGAGAGCAATGG
GCAGCCGGAGAACAACTACAAGACCACGCCTCCCGTGCTGGACTCCGACG

TABLE 11-continued

Antibody ID: AB-000224.006

| KABAT | ASN |
|---|---|
| GCTCCTTCTTCCTCTACAGCAAGCTCACCGTGGACAAGAGCAGGTGGCAG CAGGGGAACGTCTTCTCATGCTCCGTGCTGCATGAGGCTCTGCACTCCCA CTACACACAGAAGAGCCTCTCCCTGTCTCCGGGTAAA [SEQ ID NO: 82] | |

In certain embodiments, the anti-CSP antibody variant comprises a light chain variable region comprising a CDR1, a CDR2, and a CDR3 and having the amino acid sequence set forth in SEQ ID NO: 83, as shown in Table 12. In certain embodiments, the anti-CSP antibody variant comprises a heavy chain variable region comprising a CDR1, a CDR2, and a CDR3 and having the amino acid sequence set forth in SEQ ID NO: 84, as shown in Table 12. In certain embodiments, the anti-CSP antibody variant comprises a light chain having the amino acid sequence set forth in SEQ ID NO: 87, as shown in Table 12. In certain embodiments, the anti-CSP antibody variant comprises a heavy chain having the amino acid sequence set forth in SEQ ID NO: 88, as shown in Table 12. In certain embodiments, the anti-CSP antibody variant comprises a heavy chain having the amino acid sequence set forth in SEQ ID NO: 89, as shown in Table 12. Exemplary nucleic acid sequences of SEQ ID NOS: 83, 84, 87, 88, and 89 are provided in Table 12 below.

TABLE 12

Antibody ID: AB-000224.007

| | KABAT | ASN |
|---|---|---|
| CDR1-VL | TGMNSNIGAGYDVY [SEQ ID NO: 1] | TGMNSNIGAGYDVY [SEQ ID NO: 7] |
| CDR2-VL | GNSNRPS [SEQ ID NO: 2] | GNSNRPS [SEQ ID NO: 8] |
| CDR3-VL | QSYDTSLNGWA [SEQ ID NO: 3] | QSYDTSLNGWA [SEQ ID NO: 9] |
| CDR1-VH | DHAMS [SEQ ID NO: 4] | DHAMS [SEQ ID NO: 10] |
| CDR2-VH | FIRKTTYGATTHYAAAVRG [SEQ ID NO: 5] | FIRKTTYGATTHYAAAVRG [SEQ ID NO: 11] |
| CDR3-VH | VQLDYGPGYQYYGMDV [SEQ ID NO: 6] | VQLDYGPGYQYYGMDV [SEQ ID NO: 12] |
| VL | QSVLTQPPSVSGAPGQRVTISCTGMNSNIGA GYDVYWYQQLPGTAPKLLIYGNSNRPSGVPDRFSGSRSGTSASLAITGLQ AEDEADYYCQSYDTSLNGWAFGGGTKLTVLG [SEQ ID NO: 83] | |
| VH | EVQLVESGGGLVQPGRSLRLSCAASGFS FGDHAMSWVRQAPGKGLEWVGFIRKTTYGATTHYAAAVRGRFTISRDDSK SIVYLQMNSLKAEDTAVYFCTRVQLDYGPGYQYYGMDVWGQGTTVTVSS [SEQ ID NO: 84] | |
| DNA for VL | CAGTCTGTGCTGACGCAGCCGCCCTCAGTGTCTGGGGCCCCAG GGCAGAGGGTCACCATCTCCTGCACTGGGATGAACTCCAACATCGGGGCA GGTTATGATGTATACTGGTACCAACAACTTCCAGGAACTGCCCCCAAACT CCTCATCTATGGTAACAGCAATCGGCCCTCAGGGGTCCCTGACCGATTCT CTGGCTCCAGGTCTGGCACCTCAGCCTCCCTGGCCATCACTGGGCTCCAG GCTGAGGATGAGGCTGATTATTACTGCCAGTCCTATGACACCAGCCTGAA TGGTTGGGCTTTCGGCGGAGGGACCAAGTTGACCGTCCTAGGC [SEQ ID NO: 85] | |
| DNA for VH | GAGGTGCAGCTGGTGGAGTCTGGGGGAGGCTTGG TACAGCCAGGGCGGTCCCTGAGACTCAGCTGTGCGGCCTCTGGGTTTAGT TTTGGTGATCATGCTATGAGCTGGGTCCGCCAGGCTCCAGGGAAGGGGCT GGAGTGGGTAGGTTTCATTAGAAAGACAACTTATGGTGCGACAACACACT ACGCCGCGGCTGTGAGAGGCAGATTCACCATCTCGCGAGATGATTCTAAA AGOATTGTGTATCTGCAAATGAACAGCCTGAAAGCAGAGGACACAGCCGT GTATTTCTGTACTAGAGTGCAGCTTGACTATGGCCCGGGATACCAGTACT ACGGTATGGACGTCTGGGGCCAAGGGACCACGGTCACCGTCTCCTCA [SEQ ID NO: 86] | |

TABLE 12-continued

Antibody ID: AB-000224.007

| | KABAT | ASN |
|---|---|---|

Light
Chain
QSVLTQPPSVSGAPGQRVTISCTGMNSNIGA
GYDVYWYQQLPGTAPKLLIYGNSNRPSGVPDRFSGSRSGTSASLAITGLQ
AEDEADYYCQSYDTSLNGWAFGGGTKLTVLGQPKAAPSVTLFPPSSEELQ
ANKATLVCLVSDFYPGAVTVAWKADGSPVKVGVETTKPSKQSNNKYAASS
YLSLTPEQWKSHRSYSCRVTHEGSTVEKTVAPAECS
[SEQ ID NO: 87]

Heavy
Chain
version
1
EVQLVESGGGLVQPGRSLRLSCAASGFS
FGDHAMSWVRQAPGKGLEWVGFIRKTTYGATTHYAAAVRGRFTISRDDSK
SIVYLQMNSLKAEDTAVYFCTRVQLDYGPGYQYYGMDVWGQGTTVTVSSA
STKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKKVEPK
SCDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKE
YKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQ
QGNVFSCSVMHEALHNHYTQKSLSLSPGK
[SEQ ID NO: 88]

Heavy
Chain
version
2
EVQLVESGGGLVQPGRSLRLSCAASGFS
FGDHAMSWVRQAPGKGLEWVGFIRKTTYGATTHYAAAVRGRFTISRDDSK
SIVYLQMNSLKAEDTAVYFCTRVQLDYGPGYQYYGMDVWGQGTTVTVSSA
STKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKKVEPK
SCDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKE
YKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQ
QGNVFSCSVLHEALHSHYTQKSLSLSPGK [SEQ ID NO: 89]

DNA
for
Light
Chain
CAGTCTGTGCTGACGCAGCCGCCCTCAGTGTCTGGGGCCCCAG
GGCAGAGGGTCACCATCTCCTGCACTGGGATGAACTCCAACATCGGGGCA
GGTTATGATGTATACTGGTACCAACAACTTCCAGGAACTGCCCCCAAACT
CCTCATCTATGGTAACAGCAATCGGCCCTCAGGGGTCCCTGACCGATTCT
CTGGCTCCAGGTCTGGCACCTCAGCCTCCCTGGCCATCACTGGGCTCCAG
GCTGAGGATGAGGCTGATTATTACTGCCAGTCCTATGACACCAGCCTGAA
TGGTTGGGCTTTCGGCGGAGGGACCAAGTTGACCGTCCTAGGCCAGCCCA
AGGCTGCCCCCTCGGTCACTCTGTTCCCACCCTCCTCTGAGGAGCTTCAA
GCCAACAAGGCCACACTGGTGTGTCTCGTAAGTGACTTCTACCCGGGAGC
CGTGACAGTGGCCTGGAAGGCAGATGGCAGCCCCGTCAAGGTGGGAGTGG
AGACCACCAAACCCTCCAAACAAAGCAACAACAAGTATGCGGCCAGCAGC
TACCTGAGCCTGACGCCCGAGCAGTGGAAGTCCACAGAAGCTACAGCTG
CCGGGTCACGCATGAAGGGAGCACCGTGGAGAAGACAGTGGCCCCTGCAG
AATGCTCT
[SEQ ID NO: 90]

DNA
for
Heavy
Chain
version
1
GAGGTGCAGCTGGTGGAGTCTGGGGGAGGCTTGG
TACAGCCAGGGCGGTCCCTGAGACTCAGCTGTGCGGCCTCTGGGTTTAGT
TTTGGTGATCATGCTATGAGCTGGGTCCGCCAGGCTCCAGGGAAGGGGCT
GGAGTGGGTAGGTTTCATTAGAAAGACAACTTATGGTGCGACAACACACT
ACGCCGCGGCTGTGAGAGGCAGATTCACCATCTCGCGAGATGATTCTAAA
AGGATTGTCTATGTGCAAATGAACAGCCTGAAAGCAGAGGACACAGCCGT
GTATTTCTGTACTAGAGTGCAGCTTGACTATGGCCCGGGATACCAGTAT
ACGGTATGGACGTCTGGGGCCAAGGGACCACGGTCACCGTCTCCTCAGCC
TCCACCAAGGGCCCATCGGTCTTCCCCCTGGCACCCTCCTCCAAGAGCAC
CTCTGGGGGCACAGCAGCCCTGGGCTGCCTGGTCAAGGACTACTTCCCCG
AACCGGTGACGGTGTCGTGGAACTCAGGCGCCCTGACCAGCGGCGTGCAC
ACCTTCCCGGCTGTCCTACAGTCCTCAGGACTCTACTCCCTCAGCAGCGT
GGTGACCGTGCCCTCCAGCAGCTTGGGCACCCAGACCTACATCTGCAACG
TGAATCACAAGCCCAGCAACACCAAGGTGGACAAGAAAGTTGAGCCCAAA
TCTTGTGACAAAACTCACACATGCCCACCGTGCCCAGCACCTGAACTCCT
GGGGGGACCGTCAGTCTTCCTCTTCCCCCCAAAACCCAAGGACACCCTCA
TGATCTCCCGGACCCCTGAGGTCACATGCGTGGTGGTGGACGTGAGCCAC
GAAGACCCTGAGGTCAAGTTCAACTGGTACGTGGACGGCGTGGAGGTGCA
TAATGCCAAGACAAAGCCGCGGGAGGAGCAGTACAACAGCACGTACCGTG
TGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAAC
CATCTCCAAAGCCAAAGGGCAGCCCCGAGAACCACAGGTGTACACCCTGC
CCCCATCCCGGGATGAGCTGACCAAGAACCAGGTCAGCCTGACCTGCCTG
GTCAAAGGCTTCTATCCCAGCGACATCGCCGTGGAGTGGGAGAGCAATGG
GCAGCCGGAGAACAACTACAAGACCACGCCTCCCGTGCTGGACTCCGACG
GCTCCTTCTTCCTCTACAGCAAGCTCACCGTGGACAAGAGCAGGTGGCAG
CAGGGGAACGTCTTCTCATGCTCCGTGATGCATGAGGCTCTGCACAACCA
CTACACACAGAAGAGCCTCTCCCTGTCTCCGGGTAAA [SEQ ID NO: 91]

TABLE 12-continued

Antibody ID: AB-000224.007

| | KABAT | ASN |
|---|---|---|
| DNA for Heavy Chain version 2 | GAGGTGCAGCTGGTGGAGTCTGGGGGAGGCTTGG<br>TACAGCCAGGGCGGTCCCTGAGACTCAGCTGTGCGGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGCATTGTCTATCTGCAAATGAACAGCCTGAAAGCAGAGGACACAGCCGT<br>GTATTTCTGTACTAGAGTGCAGCTTGACTATGGCCCGGGATACCAGTACT<br>ACGGTATGGACGTCTGGGGCCAAGGGACCACGGTCACCGTCTCCTCAGCC<br>TCCACCAAGGGCCCATCGGTCTTCCCCCTGGCACCCTCCTCCAAGAGCAC<br>CTCTGGGGGCACAGCAGCCCTGGGCTGCCTGGTCAAGGACTACTTCCCCG<br>AACCGGTGACGGTGTCGTGGAACTCAGGCGCCCTGACCAGCGGCGTGCAC<br>ACCTTCCCGGCTGTCCTACAGTCCTCAGGACTCTACTCCCTCAGCAGCGT<br>GGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAA<br>TCTTGTGACAAAACTCACACATGCCCACCGTGCCCAGCACCTGAACTCCT<br>GGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCA<br>TAATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG<br>GCAGCCGGAGAACAACTACAAGACCACGCCTCCCGTGCTGGACTCCGACG<br>GCTCCTTCTTCCTCTACAGCAAGCTCACCGTGGACAAGAGCAGGTGGCAG<br>CAGGGGAACGTCTTCTCATGCTCCGTGCTGCATGAGGCTCTGCACTCCCA<br>CTACACACAGAAGAGCCTCTCCCTGTCTCCGGGTAAA [SEQ ID NO: 92] | |

In certain embodiments, the anti-CSP antibody variant comprises a light chain variable region comprising a CDR1, a CDR2, and a CDR3 and having the amino acid sequence set forth in SEQ ID NO: 93, as shown in Table 13. In certain embodiments, the anti-CSP antibody variant comprises a heavy chain variable region comprising a CDR1, a CDR2, and a CDR3 and having the amino acid sequence set forth in SEQ ID NO: 94, as shown in Table 13. In certain embodiments, the anti-CSP antibody variant comprises a light chain having the amino acid sequence set forth in SEQ ID NO: 97, as shown in Table 13. In certain embodiments, the anti-CSP antibody variant comprises a heavy chain having the amino acid sequence set forth in SEQ ID NO: 98, as shown in Table 13. In certain embodiments, the anti-CSP antibody variant comprises a heavy chain having the amino acid sequence set forth in SEQ ID NO: 99, as shown in Table 13. Exemplary nucleic acid sequences of SEQ ID NOS: 93, 94, 97, 98, and 99 are provided in Table 13 below.

TABLE 13

Antibody ID: AB-000224.008

| | KABAT | ASN |
|---|---|---|
| CDR1-VL | TGMNSNIGAGYDVY [SEQ ID NO: 1] | TGMNSNIGAGYDVY [SEQ ID NO: 7] |
| CDR2-VL | GNSNRPS [SEQ ID NO: 2] | GNSNRPS [SEQ ID NO: 8] |
| CDR3-VL | QSYDTSLNGWA [SEQ ID NO: 3] | QSYDTSLNGWA [SEQ ID NO: 9] |
| CDR1-VH | DHAMS [SEQ ID NO: 4] | DHAMS [SEQ ID NO: 10] |
| CDR2-VH | FIRKTTYGATTHYAAAVRG [SEQ ID NO: 5] | FIRKTTYGATTHYAAAVRG [SEQ ID NO: 11] |
| CDR3-VH | VQLDYGPGYQYYGMDV [SEQ ID NO: 6] | VQLDYGPGYQYYGMDV [SEQ ID NO: 12] |
| VL | QSVLTQPPSVSGAPGQRVTISCTGMNSNIGA<br>GYDVYWYQQLPGTAPKLLIYGNSNRPSGVPDRFSGSRSGTSASLAITGLQ<br>AEDEADYYCQSYDTSLNGWAFGGGTKLTVLG<br>[SEQ ID NO: 93] | |
| VH | EVQLVESGGGLVQPGRSLRLSCAASGFS<br>FGDHAMSWVRQAPGKGLEWVGFIRKTTYGATTHYAAAVRGRFTISRDDSK<br>SIVYLQMNSLKTEDTAVYFCARVQLDYGPGYQYYGMDVWGQGTTVTVSS<br>[SEQ ID NO: 94] | |

TABLE 13-continued

Antibody ID: AB-000224.008

| | KABAT | ASN |
|---|---|---|

DNA for VL
CAGTCTGTGCTGACGCAGCCGCCCTCAGTGTCTGGGGCCCAG
GGCAGAGGGTCACCATCTCCTGCACTGGGATGAACTCCAACATCGGGGCA
GGTTATGATGTATACTGGTACCAACAACTTCCAGGAACTGCCCCCAAACT
CCTCATCTATGGTAACAGCAATCGGCCCTCAGGGGTCCCTGACCGATTCT
CTGGCTCCAGGTCTGGCACCTCAGCCTCCCTGGCCATCACTGGGCTCCAG
GCTGAGGATGAGGCTGATTATTACTGCCAGTCCTATGACACCAGCCTGAA
TGGTTGGGCTTTCGGCGGAGGGACCAAGTTGACCGTCCTAGGC
[SEQ ID NO: 95]

DNA for VH
GAGGTGCAGCTGGTGGAGTCTGGGGGAGGCTTGG
TACAGCCAGGGCGGTCCCTGAGACTCAGCTGTGCGGCCTCTGGGTTTAGT
TTTGGTGATCATGCTATGAGCTGGGTCCGCCAGGCTCCAGGGAAGGGGCT
GGAGTGGGTAGGTTTCATTAGAAAGACAACTTATGGTGCGACAACACACT
ACGCCGCGGCTGTGAGAGGCAGATTCACCATCTCGCGAGATGATTCTAAA
AGCATTGTCTATCTGCAAATGAACAGCCTGAAAACCGAGGACACAGCCGT
GTATTTCTGTGCTAGAGTGCAGCTTGACTATGGCCGGGATACCAGTACT
ACGGTATGGACGTCTGGGGCCAAGGGACCACGGTCACCGTCTCCTCA
[SEQ ID NO: 96]

Light Chain
QSVLTQPPSVSGAPGQRVTISCTGMNSNIGA
GYDVYWYQQLPGTAPKLLIYGNSNRPSGVPDRFSGSRSGTSASLAITGLQ
AEDEADYYCQSYDTSLNGWAFGGGTKLTVLGQPKAAPSVTLFPPSSEELQ
ANKATLVCLVSDFYPGAVTVAWKADGSPVKVGVETTKPSKQSNNKYAASS
YLSLTPEQWKSHRSYSCRVTHEGSTVEKTVAPAECS
[SEQ ID NO: 97]

Heavy Chain version 1
EVQLVESGGGLVQPGRSLRLSCAASGFS
FGDHAMSWVRQAPGKGLEWVGFIRKTTYGATTHYAAAVRGRFTISRDDSK
SIVYLQMNSLKTEDTAVYFCARVQLDYGPGYQYYGMDVWGQGTTVTSSA
STKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKKVEPK
SCDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKE
YKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQ
QGNVFSCSVMHEALHNHYTQKSLSLSPGK
[SEQ ID NO: 98]

Heavy Chain version 2
EVQLVESGGGLVQPGRSLRLSCAASGFS
FGDHAMSWVRQAPGKGLEWVGFIRKTTYGATTHYAAAVRGRFTISRDDSK
SIVYLQMNSLKTEDTAVYFCARVQLDYGPGYQYYGMDVWGQGTTVTSSA
STKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKKVEPK
SCDKTHTCPPCPAPELLGGPSVFLFPPKPKDTLMISRTPEVTCVVVDVSH
EDPEVKFNWYVDGVEVHNAKTKPREEQYNSTYRWSVLTVLHQDWLNGKE
YKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQ
QGNVFSCSVLHEALHSHYTQKSLSLSPGK [SEQ ID NO: 99]

DNA for Light Chain
CAGTCTGTGCTGACGCAGCCGCCCTCAGTGTCTGGGGCCCAG
GGCAGAGGGTCACCATCTCCTGCACTGGGATGAACTCCAACATCGGGGCA
GGTTATGATGTATACTGGTACCAACAACTTCCAGGAACTGCCCCCAAACT
CCTCATCTATGGTAACAGCAATCGGCCCTCAGGGGTCCCTGACCGATTCT
CTGGCTCCAGGTCTGGCACCTCAGCCTCCCTGGCCATCACTGGGCTCCAG
GCTGAGGATGAGGCTGATTATTACTGCCAGTCCTATGACACCAGCCTGAA
TGGTTGGGCTTTCGGCGGAGGGACCAAGTTGACCGTCCTAGGCCAGCCCA
AGGCTGCCCCCTCGGTCACTCTGTTCCCACCCTCCTCTGAGGAGCTTCAA
GCCAACAAGGCCACACTGGTGTGTCTCGTAAGTGACTTCTACCCGGGAGC
CGTGACAGTGGCCTGGAAGGCAGATGGCAGCCCCGTCAAGGTGGGAGTGG
AGACCACCAAACCCTCCAAACAAAGCAACAACAAGTATGCGGCCAGCAGC
TACCTGAGCCTGACGCCCGAGCAGTGGAAGTCCACAGAAGCTACAGCTG
CCGGGTCACGCATGAAGGGAGCACCGTGGAGAAGACAGTGGCCCCTGCAG
AATGCTCT
[SEQ ID NO: 100]

DNA for Heavy Chain version 1
GAGGTGCAGCTGGTGGAGTCTGGGGGAGGCTTGG
TACAGCCAGGGCGGTCCCTGAGACTCAGCTGTGCGGCCTCTGGGTTTAGT
TTTGGTGATCATGCTATGAGCTGGGTCCGCCAGGCTCCAGGGAAGGGGCT
GGAGTGGGTAGGTTTCATTAGAAAGACAACTTATGGTGCGACAACACACT
ACGCCGCGGCTGTGAGAGGCAGATTCACCATCTCGCGAGATGATTCTAAA
AGCATTGTCTATCTGCAAATGAACAGCCTGAAAACCGAGGACACAGCCGT
GTATTTCTGTGCTAGAGTGCAGCTTGACTATGGCCGGGATACCAGTACT
ACGGTATGGACGTCTGGGGCCAAGGGACCACGGTCACCGTCTCCTCAGCC
TCCACCAAGGGCCCATCGGTCTTCCCCCTGGCACCCTCCTCCAAGAGCAC
CTCTGGGGGCACAGCAGCCCTGGGCTGCCTGGTCAAGGACTACTTCCCCG TABLE 13-continued Antibody ID: AB-000224.008

| | KABAT | ASN |
|---|---|---|
| | AACCGGTGACGGTGTCGTGGAACTCAGGCGCCCTGACCAGCGGCGTGCAC<br>ACCTTCCCGGCTGTCCTACAGTCCTCAGGACTCTACTCCCTCAGCAGCGT<br>GGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAA<br>TCTTGTGACAAAACTCACACATGCCCACCGTGCCCAGCACCTGAACTCCT<br>GGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCA<br>TAATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG<br>GCAGCCGGAGAACAACTACAAGACCACGCCTCCCGTGCTGGACTCCGACG<br>GCTCCTTCTTCCTCTACAGCAAGCTCACCGTGGACAAGAGCAGGTGGCAG<br>CAGGGGAACGTCTTCTCATGCTCCGTGATGCATGAGGCTCTGCACAACCA<br>CTACACACAGAAGAGCCTCTCCCTGTCTCCGGGTAAA [SEQ ID NO: 101] | |
| DNA<br>for<br>Heavy<br>Chain<br>version<br>2 | GAGGTGCAGCTGGTGGAGTCTGGGGGAGGCTTGG<br>TACAGCCAGGGCGGTCCCTGAGACTCAGCTGTGCGGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGCATTGTCTATCTGCAAATGAACAGCCTGAAAACCGAGGACACAGCCGT<br>GTATTTCTGTGCTAGAGTGCAGCTTGACTATGGCCCGGGATACCAGTACT<br>ACGGTATGGACGTCTGGGGCCAAGGGACCACGGTCACCGTCTCCTCAGCC<br>TCCACCAAGGGCCCATCGGTCTTCCCCCTGGCACCCTCCTCCAAGAGCAC<br>CTCTGGGGGCACAGCAGCCCTGGGCTGCCTGGTCAAGGACTACTTCCCCG<br>AACCGGTGACGGTGTCGTGGAACTCAGGCGCCCTGACCAGCGGCGTGCAC<br>ACCTTCCCGGCTGTCCTACAGTCCTCAGGACTCTACTCCCTCAGCAGCGT<br>GGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAA<br>TCTTGTGACAAAACTCACACATGCCCACCGTGCCCAGCACCTGAACTCCT<br>GGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCA<br>TAATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG<br>GCAGCCGGAGAACAACTACAAGACCACGCCTCCCGTGCTGGACTCCGACG<br>GCTCCTTCTTCCTCTACAGCAAGCTCACCGTGGACAAGAGCAGGTGGCAG<br>CAGGGGAACGTCTTCTCATGCTCCGTGCTGCATGAGGCTCTGCACTCCCA<br>CTACACACAGAAGAGCCTCTCCCTGTCTCCGGGTAAA [SEQ ID NO: 102] | |

In certain embodiments, the anti-CSP antibody variant comprises a light chain variable region comprising a CDR1, a CDR2, and a CDR3 and having the amino acid sequence set forth in SEQ ID NO: 103, as shown in Table 14. In certain embodiments, the anti-CSP antibody variant comprises a heavy chain variable region comprising a CDR1, a CDR2, and a CDR3 and having the amino acid sequence set forth in SEQ ID NO: 104, as shown in Table 14. In certain embodiments, the anti-CSP antibody variant comprises a light chain having the amino acid sequence set forth in SEQ ID NO: 107, as shown in Table 14. In certain embodiments, the anti-CSP antibody variant comprises a heavy chain having the amino acid sequence set forth in SEQ ID NO: 108, as shown in Table 14. In certain embodiments, the anti-CSP antibody variant comprises a heavy chain having the amino acid sequence set forth in SEQ ID NO: 109, as shown in Table 14. Exemplary nucleic acid sequences of SEQ ID NOS: 103, 104, 107, 108, and 109 are provided in Table 14 below.

TABLE 14

Antibody ID: AB-000224.009

| | KABAT | ASN |
|---|---|---|
| CDR1-<br>VL | TGMNSNIGAGYDVY [SEQ ID NO: 1] | TGMNSNIGAGYDVY [SEQ ID NO: 7] |
| CDR2-<br>VL | GNSNRPS [SEQ ID NO: 2] | GNSNRPS [SEQ ID NO: 8] |

TABLE 14-continued

Antibody ID: AB-000224.009

| | KABAT | ASN |
|---|---|---|
| CDR3-VL | QSYDTSLNGWA [SEQ ID NO: 3] | QSYDTSLNGWA [SEQ ID NO: 9] |
| CDR1-VH | DHAMS [SEQ ID NO: 4] | DHAMS [SEQ ID NO: 10] |
| CDR2-VH | FIRKTTYGATTHYAAAVRG [SEQ ID NO: 5] | FIRKTTYGATTHYAAAVRG [SEQ ID NO: 11] |
| CDR3-VH | VQLDYGPGYQYYGMDV [SEQ ID NO: 6] | VQLDYGPGYQYYGMDV [SEQ ID NO: 12] |
| VL | QSVLTQPPSVSGAPGQRVTISCTGMNSNIGA GYDVYWYQQLPGTAPKLLIYGNSNRPSGVPDRFSGSRSGTSASLAITGLQ AEDEADYYCQSYDTSLNGWAFGGGTKLTVLG [SEQ ID NO: 103] | |
| VH | EVQLVESGGGLVQPGRSLRLSCTASGFS FGDHAMSWVRQAPGKGLEWVGFIRKTTYGATTHYAAAVRGRFTISRDDSK STVYLQMNSLKAEDTAVYFCTRVQLDYGPGYQYYGMDVWGQGTTVTVSS [SEQ ID NO: 104] | |
| DNA for VL | CAGTCTGTGCTGACGCAGCCGCCCTCAGTGTCTGGGGCCCCAG GGCAGAGGGTCACCATCTCCTGCACTGGGATGAACTCCAACATCGGGGCA GGTTATGATGTATACTGGTACCAACAACTTCCAGGAACTGCCCCCAAACT CCTCATCTATGGTAACAGCAATCGGCCCTCAGGGGTCCCTGACCGATTCT CTGGCTCCAGGTCTGGCACCTCAGCCTCCCTGGCCATCACTGGGCTCCAG GCTGAGGATGAGGCTGATTATTACTGCCAGTCCTATGACACCAGCCTGAA TGGTTGGGCTTTCGGCGGAGGGACCAAGTTGACCGTCCTAGGC [SEQ ID NO: 105] | |
| DNA for VH | GAGGTGCAGCTGGTGGAGTCTGGGGGAGGCTTGG TACAGCCAGGGCGGTCCCTGAGACTCAGCTGTACAGCCTCTGGGTTTAGT TTTGGTGATCATGCTATGAGCTGGGTCCGCCAGGCTCCAGGGAAGGGGCT GGAGTGGGTAGGTTTCATTAGAAAGACAACTTATGGTGCGACAACACACT ACGCCGCGGCTGTGAGAGGCAGATTCACCATCTCGCGAGATGATTCTAAA AGCAACTGTGTATCTGCAAATGAACAGCCTGAAAGCAGAGGACACAGCCGT GTATTTCTGTACTAGAGTGCAGCTTGACTATGGCCCGGGATACCAGTACT ACGGTATGGACGTCTGGGGCCAAGGGACCACGGTCACCGTCTCCTCA [SEQ ID NO: 106] | |
| Light Chain | QSVLTQPPSVSGAPGQRVTISCTGMNSNIGA GYDVYWYQQLPGTAPKLLIYGNSNRPSGVPDRFSGSRSGTSASLAITGLQ AEDEADYYCQSYDTSLNGWAFGGGTKLTVLGQPKAAPSVTLFPPSSEELQ ANKATLVCLVSDFYPGAVTVAWKADGSPVKVGVETTKPSKQSNNKYAASS YLSLTPEQWKSHRSYSCRVTHEGSTVEKTVAPAECS [SEQ ID NO: 107] | |
| Heavy Chain version 1 | EVQLVESGGGLVQPGRSLRLSCTASGFS FGDHAMSWVRQAPGKGLEWVGFIRKTTYGATTHYAAAVRGRFTISRDDSK STVYLQMNSLKAEDTAVYFCTRVQLDYGPGYQYYGMDVWGQGTTVTVSSA STKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPK SCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQ QGNVFSCSVMHEALHNHYTQKSLSLSPGK [SEQ ID NO: 108] | |
| Heavy Chain version 2 | EVQLVESGGGLVQPGRSLRLSCTASGFS FGDHAMSWVRQAPGKGLEWVGFIRKTTYGATTHYAAAVRGRFTISRDDSK STVYLQMNSLKAEDTAVYFCTRVQLDYGPGYQYYGMDVWGQGTTVTVSSA STKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPK SCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQ QGNVFSCSVLHEALHSHYTQKSLSLSPGK [SEQ ID NO: 109] | |

TABLE 14-continued

Antibody ID: AB-000224.009

| | KABAT | ASN |
|---|---|---|

DNA for Light Chain

CAGTCTGTGCTGACGCAGCCGCCCTCAGTGTCTGGGGCCCCAG
GGCAGAGGGTCACCATCTCCTGCACTGGGATGAACTCCAACATCGGGGCA
GGTTATGATGTATACTGGTACCAACAACTTCCAGGAACTGCCCCCAAACT
CCTCATCTATGGTAACAGCAATCGGCCCTCAGGGGTCCCTGACCGATTCT
CTGGCTCCAGGTCTGGCACCTCAGCCTCCCTGGCCATCACTGGGCTCCAG
GCTGAGGATGAGGCTGATTATTACTGCCAGTCCTATGACACCAGCCTGAA
TGGTTGGGCTTTCGGCGGAGGGACCAAGTTGACCGTCCTAGGCCAGCCCA
AGGCTGCCCCCTCGGTCACTCTGTTCCCACCCTCCTCTGAGGAGCTTCAA
GCCAACAAGGCCACACTGGTGTGTCTCGTAAGTGACTTCTACCCGGGAGC
CGTGACAGTGGCCTGGAAGGCAGATGGCAGCCCCGTCAAGGTGGGAGTGG
AGACCACCAAACCCTCCAAACAAAGCAACAACAAGTATGCGGCCAGCAGC
TACCTGAGCCTGACGCCCGAGCAGTGGAAGTCCCACAGAAGCTACAGCTG
CCGGGTCACGCATGAAGGGAGCACCGTGGAGAAGACAGTGGCCCCTGCAG
AATGCTCT
[SEQ ID NO: 110]

DNA for Heavy Chain version 1

GAGGTGCAGCTGGTGGAGTCTGGGGGAGGCTTGG
TACAGCCAGGGCGGTCCCTGAGACTCAGCTGTACAGCCTCTGGGTTTAGT
TTTGGTGATCATGCTATGAGCTGGGTCCGCCAGGCTCCAGGGAAGGGGCT
GGAGTGGGTAGGTTTCATTAGAAAGACAACTTATGGTGCGACAACACACT
ACGCCGCGGCTGTGAGAGGCAGATTCACCATCTCGCGAGATGATTCTAAA
AGCACTGTCTATCTGCAAATGAACAGCCTGAAAGCAGAGGACACAGCCGT
GTATTTCTGTACTAGAGTGCAGCTTGACTATGGCCCGGGATACCAGTACT
ACGGTATGGACGTCTGGGGCCAAGGGACCACGGTCACCGTCTCCTCAGCC
TCCACCAAGGGCCCATCGGTCTTCCCCCTGGCACCCTCCTCCAAGAGCAC
CTCTGGGGGCACAGCAGCCCTGGGCTGCCTGGTCAAGGACTACTTCCCCG
AACCGGTGACGGTGTCGTGGAACTCAGGCGCCCTGACCAGCGGCGTGCAC
ACCTTCCCGGCTGTCCTACAGTCCTCAGGACTCTACTCCCTCAGCAGCGT
GGTGACCGTGCCCTCCAGCAGCTTGGGCACCCAGACCTACATCTGCAACG
TGAATCACAAGCCCAGCAACACCAAGGTGGACAAGAAAGTTGAGCCCAAA
TCTTGTGACAAAACTCACACATGCCCACCGTGCCCAGCACCTGAACTCCT
GGGGGGACCGTCAGTCTTCCTCTTCCCCCCAAAACCCAAGGACACCCTCA
TGATCTCCCGGACCCCTGAGGTCACATGCGTGGTGGTGGACGTGAGCCAC
GAAGACCCTGAGGTCAAGTTCAACTGGTACGTGGACGGCGTGGAGGTGCA
TAATGCCAAGACAAAGCCGCGGGAGGAGCAGTACAACAGCACGTACCGTG
TGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAAC
CATCTCCAAAGCCAAAGGGCAGCCCCGAGAACCACAGGTGTACACCCTGC
CCCCATCCCGGGATGAGCTGACCAAGAACCAGGTCAGCCTGACCTGCCTG
GTCAAAGGCTTCTATCCCAGCGACATCGCCGTGGAGTGGGAGAGCAATGG
GCAGCCGGAGAACAACTACAAGACCACGCCTCCCGTGCTGGACTCCGACG
GCTCCTTCTTCCTCTACAGCAAGCTCACCGTGGACAAGAGCAGGTGGCAG
CAGGGGAACGTCTTCTCATGCTCCGTGATGCATGAGGCTCTGCACAACCA
CTACACACAGAAGAGCCTCTCCCTGTCTCCGGGTAAA [SEQ ID NO: 111]

DNA for Heavy Chain version 2

GAGGTGCAGCTGGTGGAGTCTGGGGGAGGCTTGG
TACAGCCAGGGCGGTCCCTGAGACTCAGCTGTACAGCCTCTGGGTTTAGT
TTTGGTGATCATGCTATGAGCTGGGTCCGCCAGGCTCCAGGGAAGGGGCT
GGAGTGGGTAGGTTTCATTAGAAAGACAACTTATGGTGCGACAACACACT
ACGCCGCGGCTGTGAGAGGCAGATTCACCATCTCGCGAGATGATTCTAAA
AGCACTGTCTATCTGCAAATGAACAGCCTGAAAGCAGAGGACACAGCCGT
GTATTTCTGTACTAGAGTGCAGCTTGACTATGGCCCGGGATACCAGTACT
ACGGTATGGACGTCTGGGGCCAAGGGACCACGGTCACCGTCTCCTCAGCC
TCCACCAAGGGCCCATCGGTCTTCCCCCTGGCACCCTCCTCCAAGAGCAC
CTCTGGGGGCACAGCAGCCCTGGGCTGCCTGGTCAAGGACTACTTCCCCG
AACCGGTGACGGTGTCGTGGAACTCAGGCGCCCTGACCAGCGGCGTGCAC
ACCTTCCCGGCTGTCCTACAGTCCTCAGGACTCTACTCCCTCAGCAGCGT
GGTGACCGTGCCCTCCAGCAGCTTGGGCACCCAGACCTACATCTGCAACG
TGAATCACAAGCCCAGCAACACCAAGGTGGACAAGAAAGTTGAGCCCAAA
TCTTGTGACAAAACTCACACATGCCCACCGTGCCCAGCACCTGAACTCCT
GGGGGGACCGTCAGTCTTCCTCTTCCCCCCAAAACCCAAGGACACCCTCA
TGATCTCCCGGACCCCTGAGGTCACATGCGTGGTGGTGGACGTGAGCCAC
GAAGACCCTGAGGTCAAGTTCAACTGGTACGTGGACGGCGTGGAGGTGCA
TAATGCCAAGACAAAGCCGCGGGAGGAGCAGTACAACAGCACGTACCGTG
TGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAAC
CATCTCCAAAGCCAAAGGGCAGCCCCGAGAACCACAGGTGTACACCCTGC
CCCCATCCCGGGATGAGCTGACCAAGAACCAGGTCAGCCTGACCTGCCTG
GTCAAAGGCTTCTATCCCAGCGACATCGCCGTGGAGTGGGAGAGCAATGG
GCAGCCGGAGAACAACTACAAGACCACGCCTCCCGTGCTGGACTCCGACG
GCTCCTTCTTCCTCTACAGCAAGCTCACCGTGGACAAGAGCAGGTGGCAG
CAGGGGAACGTCTTCTCATGCTCCGTGCTGCATGAGGCTCTGCACTCCCA
CTACACACAGAAGAGCCTCTCCCTGTCTCCGGGTAAA [SEQ ID NO: 112]

In certain embodiments, the anti-CSP antibody variant comprises a light chain variable region comprising a CDR1, a CDR2, and a CDR3 and having the amino acid sequence set forth in SEQ ID NO: 113, as shown in Table 15. In certain embodiments, the anti-CSP antibody variant comprises a heavy chain variable region comprising a CDR1, a CDR2, and a CDR3 and having the amino acid sequence set forth in SEQ ID NO: 114, as shown in Table 15. In certain embodiments, the anti-CSP antibody variant comprises a light chain having the amino acid sequence set forth in SEQ ID NO: 117, as shown in Table 15. In certain embodiments, the anti-CSP antibody variant comprises a heavy chain having the amino acid sequence set forth in SEQ ID NO: 118, as shown in Table 15. In certain embodiments, the anti-CSP antibody variant comprises a heavy chain having the amino acid sequence set forth in SEQ ID NO: 119, as shown in Table 15. Exemplary nucleic acid sequences of SEQ ID NOS: 113, 114, 117, 118, and 119 are provided in Table 15 below.

TABLE 15

| Antibody ID: AB-000224.010 | | |
|---|---|---|
| | KABAT | ASN |
| CDR1-VL | TGMNSNIGAGYDVY [SEQ ID NO: 1] | TGMNSNIGAGYDVY [SEQ ID NO: 7] |
| CDR2-VL | GNSNRPS [SEQ ID NO: 2] | GNSNRPS [SEQ ID NO: 8] |
| CDR3-VL | QSYDTSLNGWA [SEQ ID NO: 3] | QSYDTSLNGWA [SEQ ID NO: 9] |
| CDR1-VH | DHAMS [SEQ ID NO: 4] | DHAMS [SEQ ID NO: 10] |
| CDR2-VH | FIRKTTYGATTHYAAAVRG [SEQ ID NO: 5] | FIRKTTYGATTHYAAAVRG [SEQ ID NO: 11] |
| CDR3-VH | VQLDYGPGYQYYGMDV [SEQ ID NO: 6] | VQLDYGPGYQYYGMDV [SEQ ID NO: 12] |
| VL | QSVLTQPPSVSGAPGQRVTISCTGMNSNIGA GYDVYWYQQLPGTAPKLLIYGNSNRPSGVPDRFSGSRSGTSASLAITGLQ AEDEADYYCQSYDTSLNGWAFGGGTKLTVLG [SEQ ID NO: 113] | |
| VH | EVQLVESGGGLVQPGRSLRLSCTASGFS FGDHAMSWVRQAPGKGLEWVGFIRKTTYGATTHYAAAVRGRFTISRDDSK STVYLQMNSLKTEDTAVYFCARVQLDYGPGYQYYGMDVWGQGTTVTVSS [SEQ ID NO: 114] | |
| DNA for VL | CAGTCTGTGCTGACGCAGCCGCCCTCAGTGTCTGGGGCCCCAG GGCAGAGGGTCACCATCTCCTGCACTGGGATGAACTCCAACATCGGGGCA GGTTATGATGTATACTGGTACCAACAACTTCCAGGAACTGCCCCCAAACT CCTCATCTATGGTAACAGCAATCGGCCCTCAGGGGTCCCTGACCGATTCT CTGGCTCCAGGTCTGGCACCTCAGCCTCCCTGGCCATCACTGGGCTCCAG GCTGAGGATGAGGCTGATTATTACTGCCAGTCCTATGACACCAGCCTGAA TGGTTGGGCTTTCGGCGGAGGGACCAAGTTGACCGTCCTAGGC [SEQ ID NO: 115] | |
| DNA for VH | GAGGTGCAGCTGGTGGAGTCTGGGGGAGGCTTGG TACAGCCAGGGCGGTCCCTGAGACTCAGCTGTACAGCCTCTGGGTTTAGT TTTGGTGATCATGCTATGAGCTGGGTCCGCCAGGCTCCAGGGAAGGGGCT GGAGTGGGTAGGTTTCATTAGAAAGACAACTTATGGTGCGACAACACACT ACGCCGCGGCTGTGAGAGGCAGATTCACCATCTCGCGAGATGATTCTAAA AGCACTGTCTATCTGCAAATGAACAGCCTGAAAACCGAGGACACAGCCGT GTATTTCTGTGCTAGAGTGCAGCTTGACTATGGCCCGGGATACCAGTACT ACGGTATGGACGTCTGGGGCCAAGGGACCACGGTCACCGTCTCCTCA [SEQ ID NO: 116] | |
| Light Chain | QSVLTQPPSVSGAPGQRVTISCTGMNSNIGA GYDVYWYQQLPGTAPKLLIYGNSNRPSGVPDRFSGSRSGTSASLAITGLQ AEDEADYYCQSYDTSLNGWAFGGGTKLTVLGQPKAAPSVTLFPPSSEELQ ANKATLVCLVSDFYPGAVTVAWKADGSPVKVGVETTKPSKQSNNKYAASS YLSLTPEQWKSHRSYSCRVTHEGSTVEKTVAPAECS [SEQ ID NO: 117] | |
| Heavy Chain version 1 | EVQLVESGGGLVQPGRSLRLSCTASGFS FGDHAMSWVRQAPGKGLEWVGFIRKTTYGATTHYAAAVRGRFTISRDDSK STVYLQMNSLKTEDTAVYFCARVQLDYGPGYQYYGMDVWGQGTTVTVSSA STKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPK SCDKTHTCPPCPAPELLGGPSVFLFPPKPKDTLMISRTPEVTCVVVDVSH | |

TABLE 15-continued

Antibody ID: AB-000224.010

| | KABAT | ASN |
|---|---|---|
| | | EDPEVKFNWYVDGVEVHNAKTKPREEQYNSTYRWSVLTVLHQDWLNGKE YKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQ QGNVFSCSVMHEALHNHYTQKSLSLSPGK [SEQ ID NO: 118] |
| Heavy Chain version 2 | | EVQLVESGGGLVQPGRSLRLSCTASGFS FGDHAMSWVRQAPGKGLEWVGFIRKTTYGATTHYAAAVRGRFTISRDDSK STVYLQMNSLKTEDTAVYFCARVQLDYGPGYQYYGMDVWGQGTTVTVSSA STKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPK SCDKTHTCPPCPAPELLGGPSVFLFPPKPKDTLMISRTPEVTCVVVDVSH EDPEVKFNWYVDGVEVHNAKTKPREEQYNSTYRWSVLTVLHQDWLNGKE YKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQ QGNVFSCSVLHEALHSHYTQKSLSLSPGK [SEQ ID NO: 119] |
| DNA for Light Chain | | CAGTCTGTGCTGACGCAGCCGCCCTCAGTGTCTGGGGCCCCAG GGCAGAGGGTCACCATCTCCTGCACTGGGATGAACTCCAACATCGGGGCA GGTTATGATGTATACTGGTACCAACAACTTCCAGGAACTGCCCCCAAACT CCTCATCTATGGTAACAGCAATCGGCCCTCAGGGGTCCCTGACCGATTCT CTGGCTCCAGGTCTGGCACCTCAGCCTCCCTGGCCATCACTGGGCTCCAG GCTGAGGATGAGGCTGATTATTACTGCCAGTCCTATGACACCAGCCTGAA TGGTTGGGCTTTCGGCGGAGGGACCAAGTTGACCGTCCTAGGCCAGCCCA AGGCTGCCCCCTCGGTCACTCTGTTCCCACCCTCCTCTGAGGAGCTTCAA GCCAACAAGGCCACACTGGTGTGTCTCGTAAGTGACTTCTACCCGGGAGC CGTGACAGTGGCCTGGAAGGCAGATGGCAGCCCCGTCAAGGTGGGAGTGG AGACCACCAAACCCTCCAAACAAAGCAACAACAAGTATGCGGCCAGCAGC TACCTGAGCCTGACGCCCGAGCAGTGGAAGTCCCACAGAAGCTACAGCTG CCGGGTCACGCATGAAGGGAGCACCGTGGAGAAGACAGTGGCCCCTGCAG AATGCTCT [SEQ ID NO: 120] |
| DNA for Heavy Chain version 1 | | GAGGTGCAGCTGGTGGAGTCTGGGGGAGGCTTGG TACAGCCAGGGCGGTCCCTGAGACTCAGCTGTACAGCCTCTGGGTTTAGT TTTGGTGATCATGCTATGAGCTGGGTCCGCCAGGCTCCAGGGAAGGGGCT GGAGTGGGTAGGTTTCATTAGAAAGACAACTTATGGTGCGACAACACACT ACGCCGCGGCTGTGAGAGGCAGATTCACCATCTCGCGAGATGATTCTAAA AGCACTGTCTATCTGCAAATGAACAGCCTGAAAACCGAGGACACAGCCGT GTATTTCTGTGCTAGAGTGCAGCTTGACTATGGCCCGGGATACCAGTACT ACGGTATGGACGTCTGGGGCCAAGGGACCACGGTCACCGTCTCCTCAGCC TCCACCAAGGGCCCATCGGTCTTCCCCCTGGCACCCTCCTCCAAGAGCAC CTCTGGGGGCACAGCGGCCCTGGGCTGCCTGGTCAAGGACTACTTCCCCG AACCGGTGACGGTGTCGTGGAACTCAGGCGCCCTGACCAGCGGCGTGCAC ACCTTCCCGGCTGTCCTACAGTCCTCAGGACTCTACTCCCTCAGCAGCGT GGTGACCGTGCCCTCCAGCAGCTTGGGCACCCAGACCTACATCTGCAACG TGAATCACAAGCCCAGCAACACCAAGGTGGACAAGAAAGTTGAGCCCAAA TCTTGTGACAAAACTCACACATGCCCACCGTGCCCAGCACCTGAACTCCT GGGGGGACCGTCAGTCTTCCTCTTCCCCCCAAAACCCAAGGACACCCTCA TGATCTCCCGGACCCCTGAGGTCACATGCGTGGTGGTGGACGTGAGCCAC GAAGACCCTGAGGTCAAGTTCAACTGGTACGTGGACGGCGTGGAGGTGCA TAATGCCAAGACAAAGCCGCGGGAGGAGCAGTACAACAGCACGTACCGTG TGGTCAGCGTCCTCACCGTCCTGCACCAGGACTGGCTGAATGGCAAGGAG TACAAGTGCAAGGTCTCCAACAAAGCCCTCCCAGCCCCCATCGAGAAAAC CATCTCCAAAGCCAAAGGGCAGCCCCGAGAACCACAGGTGTACACCCTGC CCCCATCCCGGGATGAGCTGACCAAGAACCAGGTCAGCCTGACCTGCCTG GTCAAAGGCTTCTATCCCAGCGACATCGCCGTGGAGTGGGAGAGCAATGG GCAGCCGGAGAACAACTACAAGACCACGCCTCCCGTGCTGGACTCCGACG GCTCCTTCTTCCTCTACAGCAAGCTCACCGTGGACAAGAGCAGGTGGCAG CAGGGGAACGTCTTCTCATGCTCCGTGATGCATGAGGCTCTGCACAACCA CTACACACAGAAGAGCCTCTCCCTGTCTCCGGGTAAA [SEQ ID NO: 121] |
| DNA for Heavy Chain version 2 | | GAGGTGCAGCTGGTGGAGTCTGGGGGAGGCTTGG TACAGCCAGGGCGGTCCCTGAGACTCAGCTGTACAGCCTCTGGGTTTAGT TTTGGTGATCATGCTATGAGCTGGGTCCGCCAGGCTCCAGGGAAGGGGCT GGAGTGGGTAGGTTTCATTAGAAAGACAACTTATGGTGCGACAACACACT ACGCCGCGGCTGTGAGAGGCAGATTCACCATCTCGCGAGATGATTCTAAA AGCACTGTCTATCTGCAAATGAACAGCCTGAAAACCGAGGACACAGCCGT GTATTTCTGTGCTAGAGTGCAGCTTGACTATGGCCCGGGATACCAGTACT ACGGTATGGACGTCTGGGGCCAAGGGACCACGGTCACCGTCTCCTCAGCC TCCACCAAGGGCCCATCGGTCTTCCCCCTGGCACCCTCCTCCAAGAGCAC CTCTGGGGGCACAGCGGCCCTGGGCTGCCTGGTCAAGGACTACTTCCCCG AACCGGTGACGGTGTCGTGGAACTCAGGCGCCCTGACCAGCGGCGTGCAC ACCTTCCCGGCTGTCCTACAGTCCTCAGGACTCTACTCCCTCAGCAGCGT GGTGACCGTGCCCTCCAGCAGCTTGGGCACCCAGACCTACATCTGCAACG TGAATCACAAGCCCAGCAACACCAAGGTGGACAAGAAAGTTGAGCCCAAA TCTTGTGACAAAACTCACACATGCCCACCGTGCCCAGCACCTGAACTCCT |

TABLE 15-continued

Antibody ID: AB-000224.010

| KABAT | ASN |
|---|---|
| GGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCA<br>TAATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG<br>GCAGCCGGAGAACAACTACAAGACCACGCCTCCCGTGCTGGACTCCGACG<br>GCTCCTTCTTCCTCTACAGCAAGCTCACCGTGGACAAGAGCAGGTGGCAG<br>CAGGGGAACGTCTTCTCATGCTCCGTGCTGCATGAGGCTCTGCACTCCCA<br>CTACACACAGAAGAGCCTCTCCCTGTCTCCGGGTAAA [SEQ ID NO: 122] | |

In certain embodiments, the anti-CSP antibody variant comprises a light chain variable region comprising a CDR1, a CDR2, and a CDR3 and having the amino acid sequence set forth in SEQ ID NO: 123, as shown in Table 16. In certain embodiments, the anti-CSP antibody variant comprises a heavy chain variable region comprising a CDR1, a CDR2, and a CDR3 and having the amino acid sequence set forth in SEQ ID NO: 124, as shown in Table 16. In certain embodiments, the anti-CSP antibody variant comprises a light chain having the amino acid sequence set forth in SEQ ID NO: 127, as shown in Table 16. In certain embodiments, the anti-CSP antibody variant comprises a heavy chain having the amino acid sequence set forth in SEQ ID NO: 128, as shown in Table 16. In certain embodiments, the anti-CSP antibody variant comprises a heavy chain having the amino acid sequence set forth in SEQ ID NO: 129, as shown in Table 16. Exemplary nucleic acid sequences of SEQ ID NOS: 123, 124, 127, 128, and 129 are provided in Table 16 below.

TABLE 16

Antibody ID: AB-000224.011

| | KABAT | ASN |
|---|---|---|
| CDR1-VL | TGMNSNIGAGYDVY [SEQ ID NO: 1] | TGMNSNIGAGYDVY [SEQ ID NO: 7] |
| CDR2-VL | GNSNRPS [SEQ ID NO: 2] | GNSNRPS [SEQ ID NO: 8] |
| CDR3-VL | QSYDTSLNGWA [SEQ ID NO: 3] | QSYDTSLNGWA [SEQ ID NO: 9] |
| CDR1-VH | DHAMS [SEQ ID NO: 4] | DHAMS [SEQ ID NO: 10] |
| CDR2-VH | FIRKTTYGATTHYAAAVRG [SEQ ID NO: 5] | FIRKTTYGATTHYAAAVRG [SEQ ID NO: 11] |
| CDR3-VH | VQLDYGPGYQYYGMDV [SEQ ID NO: 6] | VQLDYGPGYQYYGMDV [SEQ ID NO: 12] |
| VL | QSVLTQPPSVSGAPGQRVTISCTGMNSNIGA<br>GYDVYWYQQLPGTAPKLLIYGNSNRPSGVPDRFSGSRSGTSASLAITGLQ<br>AEDEADYYCQSYDTSLNGWAFGGGTKLTVLG<br>[SEQ ID NO: 123] | |
| VH | EVQLVESGGGLVQPGRSLRLSCTASGFS<br>FGDHAMSWVRQAPGKGLEWVGFIRKTTYGATTHYAAAVRGRFTISRDDSK<br>SIVYLQMNSLKAEDTAVYFCARVQLDYGPGYQYYGMDVWGQGTTVTVSS<br>[SEQ ID NO: 124] | |
| DNA for VL | CAGTCTGTGCTGACGCAGCCGCCCTCAGTGTCTGGGGCCCCAG<br>GGCAGAGGGTCACCATCTCCTGCACTGGGATGAACTCCAACATCGGGGCA<br>GGTTATGATGTATACTGGTACCAACAACTTCCAGGAACTGCCCCCAAACT<br>CCTCATCTATGGTAACAGCAATCGGCCCTCAGGGGTCCCTGACCGATTCT<br>CTGGCTCCAGGTCTGGCACCTCAGCCTCCCTGGCCATCACTGGGCTCCAG<br>GCTGAGGATGAGGCTGATTATTACTGCCAGTCCTATGACACCAGCCTGAA<br>TGGTTGGGCTTTCGGCGGAGGGACCAAGTTGACCGTCCTAGGC<br>[SEQ ID NO: 125] | |
| DNA forVH | GAGGTGCAGCTGGTGGAGTCTGGGGGAGGCTTGG<br>TACAGCCAGGGCGGTCCCTGAGACTCAGCTGTACAGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT | |

TABLE 16-continued

Antibody ID: AB-000224.011

| | KABAT | ASN |
|---|---|---|
| | ACGCCGCGGCTGTGAGAGGCAGATTCACCATCTCGCGAGATGATTCTAAA<br>AGCATTGTGTATCTGCAAATGAACAGCCTGAAAGCAGAGGACACAGCCGT<br>GTATTTCTGTGCTAGAGTGCAGCTTGACTATGGCCCGGGATACCAGTACT<br>ACGGTATGGACGTCTGGGGCCAAGGGACCACGGTCACCGTCTCCTCA<br>[SEQ ID NO: 126] | |
| Light<br>Chain | QSVLTQPPSVSGAPGQRVTISCTGMNSNIGA<br>GYDVYWYQQLPGTAPKLLIYGNSNRPSGVPDRFSGSRSGTSASLAITGLQ<br>AEDEADYYCQSYDTSLNGWAFGGGTKLTVLGQPKAAPSVTLFPPSSEELQ<br>ANKATLVCLVSDFYPGAVTVAWKADGSPVKVGVETTKPSKQSNNKYAASS<br>YLSLTPEQWKSHRSYSCRVTHEGSTVEKTVAPAECS<br>[SEQ ID NO: 127] | |
| Heavy<br>Chain<br>version<br>1 | EVQLVESGGGLVQPGRSLRLSCTASGFS<br>FGDHAMSWVRQAPGKGLEWVGFIRKTTYGATTHYAAAVRGRFTISRDDSK<br>SIVYLQMNSLKAEDTAVYFCARVQLDYGPGYQYYGMDVWGQGTTVTVSSA<br>STKGPSVFPLAPSSKSTSGGTAALGCLVKDYFPEPVTVSWNSGALTSGVH<br>TFPAVLQSSGLYSLSSVVTVPSSSLGTQTYICNVNHKPSNTKVDKKVEPK<br>SCDKTHTCPPCPAPELLGGPSVFLFPPKPKDTLMISRTPEVTCVVVDVSH<br>EDPEVKFNWYVDGVEVHNAKTKPREEQYNSTYRWSVLTVLHQDWLNGKE<br>YKCKVSNKALPAPIEKTISKAKGQPREPQVYTLPPSRDELTKNQVSLTCL<br>VKGFYPSDIAVEWESNGQPENNYKTTPPVLDSDGSFFLYSKLTVDKSRWQ<br>QGNVFSCSVMHEALHNHYTQKSLSLSPGK<br>[SEQ ID NO: 128] | |
| Heavy<br>Chain<br>version<br>2 | EVQLVESGGGLVQPGRSLRLSCTASGFS<br>FGDHAMSWVRQAPGKGLEWVGFIRKTTYGATTHYAAAVRGRFTISRDDSK<br>SIVYLQMNSLKAEDTAVYFCARVQLDYGPGYQYYGMDVWGQGTTVTVSSA<br>STKGPSVFPLAPSSKSTSGGTAALGCLVKDYFPEPVTVSWNSGALTSGVH<br>TFPAVLQSSGLYSLSSVVTVPSSSLGTQTYICNVNHKPSNTKVDKKVEPK<br>SCDKTHTCPPCPAPELLGGPSVFLFPPKPKDTLMISRTPEVTCVVVDVSH<br>EDPEVKFNWYVDGVEVHNAKTKPREEQYNSTYRWSVLTVLHQDWLNGKE<br>YKCKVSNKALPAPIEKTISKAKGQPREPQVYTLPPSRDELTKNQVSLTCL<br>VKGFYPSDIAVEWESNGQPENNYKTTPPVLDSDGSFFLYSKLTVDKSRWQ<br>QGNVFSCSVLHEALHSHYTQKSLSLSPGK<br>[SEQ ID NO: 129] | |
| DNA<br>for<br>Light<br>Chain | CAGTCTGTGCTGACGCAGCCGCCCTCAGTGTCTGGGGCCCCAG<br>GGCAGAGGGTCACCATCTCCTGCACTGGGATGAACTCCAACATCGGGGCA<br>GGTTATGATGTATACTGGTACCAACAACTTCCAGGAACTGCCCCCAAACT<br>CCTCATCTATGGTAACAGCAATCGGCCCTCAGGGGTCCCTGACCGATTCT<br>CTGGCTCCAGGTCTGGCACCTCAGCCTCCCTGGCCATCACTGGGCTCCAG<br>GCTGAGGATGAGGCTGATTATTACTGCCAGTCCTATGACACCAGCCTGAA<br>TGGTTGGGCTTTCGGCGGAGGGACCAAGTTGACCGTCCTAGGCCAGCCCA<br>AGGCTGCCCCCTCGGTCACTCTGTTCCCACCCTCCTCTGAGGAGCTTCAA<br>GCCAACAAGGCCACACTGGTGTGTCTCGTAAGTGACTTCTACCCGGGAGC<br>CGTGACAGTGGCCTGGAAGGCAGATGGCAGCCCCGTCAAGGTGGGAGTGG<br>AGACCACCAAACCCTCCAAACAAAGCAACAACAAGTATGCGGCCAGCAGC<br>TACCTGAGCCTGACGCCCGAGCAGTGGAAGTCCCACAGAAGCTACAGCTG<br>CCGGGTCACGCATGAAGGGAGCACCGTGGAGAAGACAGTGGCCCCTGCAG<br>AATGCTCT [SEQ ID NO: 130] | |
| DNA<br>for<br>Heavy<br>Chain<br>version<br>1 | GAGGTGCAGCTGGTGGAGTCTGGGGGAGGCTTGG<br>TACAGCCAGGGCGGTCCCTGAGACTCAGCTGTACAGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGCATTGTCTATCTGCAAATGAACAGCCTGAAAGCAGAGGACACAGCCGT<br>GTATTTCTGTGCTAGAGTGCAGCTTGACTATGGCCCGGGATACCAGTACT<br>ACGGTATGGACGTCTGGGGCCAAGGGACCACGGTCACCGTCTCCTCAGCC<br>TCCACCAAGGGCCCATCGGTCTTCCCCCTGGCACCCTCCTCCAAGAGCAC<br>CTCTGGGGGCACAGCAGCCCTGGGCTGCCTGGTCAAGGACTACTTCCCCG<br>AACCGGTGACGGTGTCGTGGAACTCAGGCGCCCTGACCAGCGGCGTGCAC<br>ACCTTCCCGGCTGTCCTACAGTCCTCAGGACTCTACTCCCTCAGCAGCGT<br>GGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAA<br>TCTTGTGACAAAACTCACACATGCCCACCGTGCCCAGCACCTGAACTCCT<br>GGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCA<br>TAATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG | |

TABLE 16-continued

Antibody ID: AB-000224.011

| | KABAT | ASN |
|---|---|---|
| | GCAGCCGGAGAACAACTACAAGACCACGCCTCCCGTGCTGGACTCCGACG<br>GCTCCTTCTTCCTCTACAGCAAGCTCACCGTGGACAAGAGCAGGTGGCAG<br>CAGGGGAACGTCTTCTCATGCTCCGTGATGCATGAGGCTCTGCACAACCA<br>CTACACACAGAAGAGCCTCTCCCTGTCTCCGGGTAAA [SEQ ID NO: 131] | |
| DNA<br>for<br>Heavy<br>Chain<br>version<br>2 | GAGGTGCAGCTGGTGGAGTCTGGGGGAGGCTTGG<br>TACAGCCAGGGCGGTCCCTGAGACTCAGCTGTACAGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGCATTGTCTATCTGCAAATGAACAGCCTGAAAGCAGAGGACACAGCCGT<br>GTATTTCTGTGCTAGAGTGCAGCTTGACTATGGCCCGGGATACCAGTACT<br>ACGGTATGGACGTCTGGGGCCAAGGGACCACGGTCACCGTCTCCTCAGCC<br>TCCACCAAGGGCCCATCGGTCTTCCCCCTGGCACCCTCCTCCAAGAGCAC<br>CTCTGGGGGCACAGCAGCCCTGGGCTGCCTGGTCAAGGACTACTTCCCCG<br>AACCGGTGACGGTGTCGTGGAACTCAGGCGCCCTGACCAGCGGCGTGCAC<br>ACCTTCCCGGCTGTCCTACAGTCCTCAGGACTCTACTCCCTCAGCAGCGT<br>GGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAA<br>TCTTGTGACAAAACTCACACATGCCCACCGTGCCCAGCACCTGAACTCCT<br>GGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCA<br>TAATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG<br>GCAGCCGGAGAACAACTACAAGACCACGCCTCCCGTGCTGGACTCCGACG<br>GCTCCTTCTTCCTCTACAGCAAGCTCACCGTGGACAAGAGCAGGTGGCAG<br>CAGGGGAACGTCTTCTCATGCTCCGTGCTGCATGAGGCTCTGCACTCCCA<br>CTACACACAGAAGAGCCTCTCCCTGTCTCCGGGTAAA<br>[SEQ ID NO: 132] | |

In certain embodiments, the anti-CSP antibody variant comprises a light chain variable region comprising a CDR1, a CDR2, and a CDR3 and having the amino acid sequence set forth in SEQ ID NO: 133, as shown in Table 17. In certain embodiments, the anti-CSP antibody variant comprises a heavy chain variable region comprising a CDR1, a CDR2, and a CDR3 and having the amino acid sequence set forth in SEQ ID NO: 134, as shown in Table 17. In certain embodiments, the anti-CSP antibody variant comprises a light chain having the amino acid sequence set forth in SEQ ID NO: 137, as shown in Table 17. In certain embodiments, the anti-CSP antibody variant comprises a heavy chain having the amino acid sequence set forth in SEQ ID NO: 138, as shown in Table 17. In certain embodiments, the anti-CSP antibody variant comprises a heavy chain having the amino acid sequence set forth in SEQ ID NO: 139, as shown in Table 17. Exemplary nucleic acid sequences of SEQ ID NOS: 133, 134, 137, 138, and 139 are provided in Table 17 below.

TABLE 17

Antibody ID: AB-000224.012

| | KABAT | ASN |
|---|---|---|
| CDR1-VL | TGMNSNIGAGYDVY [SEQ ID NO: 1] | TGMNSNIGAGYDVY [SEQ ID NO: 7] |
| CDR2-VL | GNSNRPS [SEQ ID NO: 2] | GNSNRPS [SEQ ID NO: 8] |
| CDR3-VL | QSYDTSLNGWA [SEQ ID NO: 3] | QSYDTSLNGWA [SEQ ID NO: 9] |
| CDR1-VH | DHAMS [SEQ ID NO: 4] | DHAMS [SEQ ID NO: 10] |
| CDR2-VH | FIRKTTYGATTHYAAAVRG [SEQ ID NO: 5] | FIRKTTYGATTHYAAAVRG [SEQ ID NO: 11] |
| CDR3-VH | VQLDYGPGYQYYGMDV [SEQ ID NO: 6] | VQLDYGPGYQYYGMDV [SEQ ID NO: 12] |

TABLE 17-continued

Antibody ID: AB-000224.012

| | KABAT | ASN |
|---|---|---|
| VL | QSVLTQPPSVSGAPGQRVTISCTGMNSNIGA
GYDVYWYQQLPGTAPKLLIYGNSNRPSGVPDRFSGSRSGTSASLAITGLQ
AEDEADYYCQSYDTSLNGWAFGGGTKLTVLG
[SEQ ID NO: 133] | |
| VH | EVQLVESGGGLVQPGRSLRLSCAASGFS
FGDHAMSWVRQAPGKGLEWVGFIRKTTYGATTHYAAAVRGRFTISRDDSK
STVYLQMNSLKAEDTAVYFCTRVQLDYGPGYQYYGMDVWGQGTTVTSS
[SEQ ID NO: 134] | |
| DNA
for VL | CAGTCTGTGCTGACGCAGCCGCCCTCAGTGTCTGGGGCCCCAG
GGCAGAGGGTCACCATCTCCTGCACTGGGATGAACTCCAACATCGGGGCA
GGTTATGATGTATACTGGTACCAACAACTTCCAGGAACTGCCCCCAAAACT
CCTCATCTATGGTAACAGCAATCGGCCCTCAGGGGTCCCTGACCGATTCT
CTGGCTCCAGGTCTGGCACCTCAGCCTCCCTGGCCATCACTGGGCTCCAG
GCTGAGGATGAGGCTGATTATTACTGCCAGTCCTATGACACCAGCCTGAA
TGGTTGGGCTTTCGGCGGAGGGACCAAGTTGACCGTCCTAGGC
[SEQ ID NO: 135] | |
| DNA
forVH | GAGGTGCAGCTGGTGGAGTCTGGGGGAGGCTTGG
TACAGCCAGGGCGGTCCCTGAGACTCAGCTGTGCGGCCTCTGGGTTTAGT
TTTGGTGATCATGCTATGAGCTGGGTCCGCCAGGCTCCAGGGAAGGGGCT
GGAGTGGGTAGGTTTCATTAGAAAGACAACTTATGGTGCGACAACACACT
ACGCCGCGGCTGTGAGAGGCAGATTCACCATCTCGCGAGATGATTCTAAA
AGGACTGTCTATCTGCAAATGAACAGCCTGAAAGCAGAGGACACAGCCGT
GTATTTCTGTACTAGAGTGCAGCTTGACTATGGCCCGGGATACCAGTACT
ACGGTATGGACGTCTGGGGCCAAGGGACCACGGTCACCGTCTCCTCA
[SEQ ID NO: 136] | |
| Light
Chain | QSVLTQPPSVSGAPGQRVTISCTGMNSNIGA
GYDVYWYQQLPGTAPKLLIYGNSNRPSGVPDRFSGSRSGTSASLAITGLQ
AEDEADYYCQSYDTSLNGWAFGGGTKLTVLGQPKAAPSVTLFPPSSEELQ
ANKATLVCLVSDFYPGAVTVAWKADGSPVKVGVETTKPSKQSNNKYAASS
YLSLTPEQWKSHRSYSCRVTHEGSTVEKTVAPAECS
[SEQ ID NO: 137] | |
| Heavy
Chain
version
1 | EVQLVESGGGLVQPGRSLRLSCAASGFS
FGDHAMSWVRQAPGKGLEWVGFIRKTTYGATTHYAAAVRGRFTISRDDSK
STVYLQMNSLKAEDTAVYFCTRVQLDYGPGYQYYGMDVWGQGTTVTVSSA
STKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKKVEPK
SCDKTHTCPPCPAPELLGGPSVFLFPPKPKDTLMISRTPEVTCVVVDVSH
EDPEVKFNWYVDGVEVHNAKTKPREEQYNSTYRWSVLTVLHQDWLNGKE
YKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQ
QGNVFSCSVMHEALHNHYTQKSLSLSPGK
[SEQ ID NO: 138] | |
| Heavy
Chain
version
2 | EVQLVESGGGLVQPGRSLRLSCAASGFS
FGDHAMSWVRQAPGKGLEWVGFIRKTTYGATTHYAAAVRGRFTISRDDSK
STVYLQMNSLKAEDTAVYFCTRVQLDYGPGYQYYGMDVWGQGTTVTVSSA
STKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKKVEPK
SCDKTHTCPPCPAPELLGGPSVFLFPPKPKDTLMISRTPEVTCVVVDVSH
EDPEVKFNWYVDGVEVHNAKTKPREEQYNSTYRWSVLTVLHQDWLNGKE
YKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQ
QGNVFSCSVLHEALHSHYTQKSLSLSPGK
[SEQ ID NO: 139] | |
| DNA
for
Light
Chain | CAGTCTGTGCTGACGCAGCCGCCCTCAGTGTCTGGGGCCCCAG
GGCAGAGGGTCACCATCTCCTGCACTGGGATGAACTCCAACATCGGGGCA
GGTTATGATGTATACTGGTACCAACAACTTCCAGGAACTGCCCCCAAAACT
CCTCATCTATGGTAACAGCAATCGGCCCTCAGGGGTCCCTGACCGATTCT
CTGGCTCCAGGTCTGGCACCTCAGCCTCCCTGGCCATCACTGGGCTCCAG
GCTGAGGATGAGGCTGATTATTACTGCCAGTCCTATGACACCAGCCTGAA
TGGTTGGGCTTTCGGCGGAGGGACCAAGTTGACCGTCCTAGGCCAGCCCA
AGGCTGCCCCCTCGGTCACTCTGTTCCCACCCTCCTCTGAGGAGCTTCAA
GCCAACAAGGCCACACTGGTGTGTCTCGTAAGTGACTTCTACCCGGGAGC
CGTGACAGTGGCCTGGAAGGCAGATGGCAGCCCCGTCAAGGTGGGAGTGG
AGACCACCAAACCCTCCAAACAAAGCAACAACAAGTATGCGGCCAGCAGC
TACCTGAGCCTGACGCCCGAGCAGTGGAAGTCCCACAGAAGCTACAGCTG
CCGGGTCACGCATGAAGGGAGCACCGTGGAGAAGACAGTGGCCCCTGCAG
AATGCTCT[SEQ ID NO: 140] | |

TABLE 17-continued

Antibody ID: AB-000224.012

| | KABAT | ASN |
|---|---|---|
| DNA for Heavy Chain version 1 | GAGGTGCAGCTGGTGGAGTCTGGGGGAGGCTTGG
TACAGCCAGGGCGGTCCCTGAGACTCAGCTGTGCGGCCTCTGGGTTTAGT
TTTGGTGATCATGCTATGAGCTGGGTCCGCCAGGCTCCAGGGAAGGGGCT
GGAGTGGGTAGGTTTCATTAGAAAGACAACTTATGGTGCGACAACACACT
ACGCCGCGGCTGTGAGAGGCAGATTCACCATCTCGCGAGATGATTCTAAA
AGCACTGTCTATCTGCAAATGAACAGCCTGAAAGCAGAGGACACAGCCGT
GTATTTCTGTACTAGAGTGCAGCTTGACTATGGCCCGGGATACCAGTACT
ACGGTATGGACGTCTGGGGCCAAGGGACCACGGTCACCGTCTCCTCAGCC
TCCACCAAGGGCCCATCGGTCTTCCCCCTGGCACCCTCCTCCAAGAGCAC
CTCTGGGGGCACAGCAGCCCTGGGCTGCCTGGTCAAGGACTACTTCCCCG
AACCGGTGACGGTGTCGTGGAACTCAGGCGCCCTGACCAGCGGCGTGCAC
ACCTTCCCGGCTGTCCTACAGTCCTCAGGACTCTACTCCCTCAGCAGCGT
GGTGACCGTGCCCTCCAGCAGCTTGGGCACCCAGACCTACATCTGCAACG
TGAATCACAAGCCCAGCAACACCAAGGTGGACAAGAAAGTTGAGCCCAAA
TCTTGTGACAAAACTCACACATGCCCACCGTGCCCAGCACCTGAACTCCT
GGGGGGACCGTCAGTCTTCCTCTTCCCCCCAAAACCCAAGGACACCCTCA
TGATCTCCCGGACCCCTGAGGTCACATGCGTGGTGGTGGACGTGAGCCAC
GAAGACCCTGAGGTCAAGTTCAACTGGTACGTGGACGGCGTGGAGGTGCA
TAATGCCAAGACAAAGCCGCGGGAGGAGCAGTACAACAGCACGTACCGTG
TGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAAC
CATCTCCAAAGCCAAAGGGCAGCCCCGAGAACCACAGGTGTACACCCTGC
CCCCATCCCGGGATGAGCTGACCAAGAACCAGGTCAGCCTGACCTGCCTG
GTCAAAGGCTTCTATCCCAGCGACATCGCCGTGGAGTGGGAGAGCAATGG
GCAGCCGGAGAACAACTACAAGACCACGCCTCCCGTGCTGGACTCCGACG
GCTCCTTCTTCCTCTACAGCAAGCTCACCGTGGACAAGAGCAGGTGGCAG
CAGGGGAACGTCTTCTCATGCTCCGTGATGCATGAGGCTCTGCACAACCA
CTACACACAGAAGAGCCTCTCCCTGTCTCCGGGTAAA [SEQ ID NO: 141] | |
| DNA for Heavy Chain version 2 | GAGGTGCAGCTGGTGGAGTCTGGGGGAGGCTTGG
TACAGCCAGGGCGGTCCCTGAGACTCAGCTGTGCGGCCTCTGGGTTTAGT
TTTGGTGATCATGCTATGAGCTGGGTCCGCCAGGCTCCAGGGAAGGGGCT
GGAGTGGGTAGGTTTCATTAGAAAGACAACTTATGGTGCGACAACACACT
ACGCCGCGGCTGTGAGAGGCAGATTCACCATCTCGCGAGATGATTCTAAA
AGGACTGTCTATCTGCAAATGAACAGCCTGAAAGCAGAGGACACAGCCGT
GTATTTCTGTACTAGAGTGCAGCTTGACTATGGCCCGGGATACCAGTACT
ACGGTATGGACGTCTGGGGCCAAGGGACCACGGTCACCGTCTCCTCAGCC
TCCACCAAGGGCCCATCGGTCTTCCCCCTGGCACCCTCCTCCAAGAGCAC
CTCTGGGGGCACAGCAGCCCTGGGCTGCCTGGTCAAGGACTACTTCCCCG
AACCGGTGACGGTGTCGTGGAACTCAGGCGCCCTGACCAGCGGCGTGCAC
ACCTTCCCGGCTGTCCTACAGTCCTCAGGACTCTACTCCCTCAGCAGCGT
GGTGACCGTGCCCTCCAGCAGCTTGGGCACCCAGACCTACATCTGCAACG
TGAATCACAAGCCCAGCAACACCAAGGTGGACAAGAAAGTTGAGCCCAAA
TCTTGTGACAAAACTCACACATGCCCACCGTGCCCAGCACCTGAACTCCT
GGGGGGACCGTCAGTCTTCCTCTTCCCCCCAAAACCCAAGGACACCCTCA
TGATCTCCCGGACCCCTGAGGTCACATGCGTGGTGGTGGACGTGAGCCAC
GAAGACCCTGAGGTCAAGTTCAACTGGTACGTGGACGGCGTGGAGGTGCA
TAATGCCAAGACAAAGCCGCGGGAGGAGCAGTACAACAGCACGTACCGTG
TGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAAC
CATCTCCAAAGCCAAAGGGCAGCCCCGAGAACCACAGGTGTACACCCTGC
CCCCATCCCGGGATGAGCTGACCAAGAACCAGGTCAGCCTGACCTGCCTG
GTCAAAGGCTTCTATCCCAGCGACATCGCCGTGGAGTGGGAGAGCAATGG
GCAGCCGGAGAACAACTACAAGACCACGCCTCCCGTGCTGGACTCCGACG
GCTCCTTCTTCCTCTACAGCAAGCTCACCGTGGACAAGAGCAGGTGGCAG
CAGGGGAACGTCTTCTCATGCTCCGTGCTGCATGAGGCTCTGCACTCCCA
CTACACACAGAAGAGCCTCTCCCTGTCTCCGGGTAAA [SEQ ID NO: 142] | |

In certain embodiments, the anti-CSP antibody variant comprises a light chain variable region comprising a CDR1, a CDR2, and a CDR3 and having the amino acid sequence set forth in SEQ ID NO: 143, as shown in Table 18. In certain embodiments, the anti-CSP antibody variant comprises a heavy chain variable region comprising a CDR1, a CDR2, and a CDR3 and having the amino acid sequence set forth in SEQ ID NO: 144, as shown in Table 18. In certain embodiments, the anti-CSP antibody variant comprises a light chain having the amino acid sequence set forth in SEQ ID NO: 147, as shown in Table 18. In certain embodiments, the anti-CSP antibody variant comprises a heavy chain having the amino acid sequence set forth in SEQ ID NO: 148, as shown in Table 18. In certain embodiments, the anti-CSP antibody variant comprises a heavy chain having the amino acid sequence set forth in SEQ ID NO: 149, as shown in Table 18. Exemplary nucleic acid sequences of SEQ ID NOS: 143, 144, 147, 148, and 149 are provided in Table 18 below.

TABLE 18

| | Antibody ID: AB-000224.013 | |
|---|---|---|
| | KABAT | ASN |
| CDR1-VL | TGMNSNIGAGYDVY [SEQ ID NO: 1] | TGMNSNIGAGYDVY [SEQ ID NO: 7] |
| CDR2-VL | GNSNRPS [SEQ ID NO: 2] | GNSNRPS [SEQ ID NO: 8] |
| CDR3-VL | QSYDTSLNGWA [SEQ ID NO: 3] | QSYDTSLNGWA [SEQ ID NO: 9] |
| CDR1-VH | DHAMS [SEQ ID NO: 4] | DHAMS [SEQ ID NO: 10] |
| CDR2-VH | FIRKTTYGATTHYAAAVRG [SEQ ID NO: 5] | FIRKTTYGATTHYAAAVRG [SEQ ID NO: 11] |
| CDR3-VH | VQLDYGPGYQYYGMDV [SEQ ID NO: 6] | VQLDYGPGYQYYGMDV [SEQ ID NO: 12] |
| VL | QSVLTQPPSVSGAPGQRVTISCTGMNSNIGA GYDVYWYQQLPGTAPKLLIYGNSNRPSGVPDRFSGSRSGTSASLAITGLQ AEDEADYYCQSYDTSLNGWAFGGGTKLTVLG [SEQ ID NO: 143] | |
| VH | EVQLVESGGGLVQPGRSLRLSCAASGFS FGDHAMSWVRQAPGKGLEWVGFIRKTTYGATTHYAAAVRGRFTISRDDSK STVYLQMNSLKTEDTAVYFCARVQLDYGPGYQYYGMDVWGQGTTVTVSS [SEQ ID NO: 144] | |
| DNA for VL | CAGTCTGTGCTGACGCAGCCGCCCTCAGTGTCTGGGGCCCAG GGCAGAGGGTCACCATCTCCTGCACTGGGATGAACTCCAACATCGGGGCA GGTTATGATGTATACTGGTACCAACAACTTCCAGGAACTGCCCCCAAACT CCTCATCTATGGTAACAGCAATCGGCCCTCAGGGGTCCCTGACCGATTCT CTGGCTCCAGGTCTGGCACCTCAGCCTCCCTGGCCATCACTGGGCTCCAG GCTGAGGATGAGGCTGATTATTACTGCCAGTCCTATGACACCAGCCTGAA TGGTTGGGCTTTCGGCGGAGGGACCAAGTTGACCGTCCTAGGC [SEQ ID NO: 145] | |
| DNA for VH | GAGGTGCAGCTGGTGGAGTCTGGGGGAGGCTTGG TACAGCCAGGGCGGTCCCTGAGACTCAGCTGTGCGGCCTCTGGGTTTAGT TTTGGTGATCATGCTATGAGCTGGGTCCGCCAGGCTCCAGGGAAGGGGCT GGAGTGGGTAGGTTTCATTAGAAAGACAACTTATGGTGCGACAACACACT ACGCCGCGGCTGTGAGAGGCAGATTCACCATCTCGCGAGATGATTCTAAA AGCACTGTCTATCTGCAAATGAACAGCCTGAAAACCGAGGACACAGCCGT GTATTTCTGTGCTAGAGTGCAGCTTGACTATGGCCCGGGATACCAGTACT ACGGTATGGACGTCTGGGGCCAAGGGACCACGGTCACCGTCTCCTCA [SEQ ID NO: 146] | |
| Light Chain | QSVLTQPPSVSGAPGQRVTISCTGMNSNIGA GYDVYWYQQLPGTAPKLLIYGNSNRPSGVPDRFSGSRSGTSASLAITGLQ AEDEADYYCQSYDTSLNGWAFGGGTKLTVLGQPKAAPSVTLFPPSSEELQ ANKATLVCLVSDFYPGAVTVAWKADSPVKVGVETTKPSKQSNNKYAASS YLSLTPEQWKSHRSYSCRVTHEGSTVEKTVAPAECS [SEQ ID NO: 147] | |
| Heavy Chain version 1 | EVQLVESGGGLVQPGRSLRLSCAASGFS FGDHAMSWVRQAPGKGLEWVGFIRKTTYGATTHYAAAVRGRFTISRDDSK STVYLQMNSLKTEDTAVYFCARVQLDYGPGYQYYGMDVWGQGTTVTVSSA STKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPK SCDKTHTCPPCPAPELLGGPSVFLFPPKPKDTLMISRTPEVTCVVVDVSH EDPEVKFNWYVDGVEVHNAKTKPREEQYNSTYRWSVLTVLHQDWLNGKE YKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQ QGNVFSCSVMHEALHNHYTQKSLSLSPGK [SEQ ID NO: 148] | |
| Heavy Chain version 2 | EVQLVESGGGLVQPGRSLRLSCAASGFS FGDHAMSWVRQAPGKGLEWVGFIRKTTYGATTHYAAAVRGRFTISRDDSK STVYLQMNSLKTEDTAVYFCARVQLDYGPGYQYYGMDVWGQGTTVTVSSA STKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPK SCDKTHTCPPCPAPELLGGPSVFLFPPKPKDTLMISRTPEVTCVVVDVSH EDPEVKFNWYVDGVEVHNAKTKPREEQYNSTYRWSVLTVLHQDWLNGKE YKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQ QGNVFSCSVLHEALHSHYTQKSLSLSPGK [SEQ ID NO: 149] | |

TABLE 18-continued

Antibody ID: AB-000224.013

| | KABAT | ASN |
|---|---|---|
| DNA for Light Chain | CAGTCTGTGCTGACGCAGCCGCCCTCAGTGTCTGGGGCCCAG<br>GGCAGAGGGTCACCATCTCCTGCACTGGGATGAACTCCAACATCGGGGCA<br>GGTTATGATGTATACTGGTACCAACAACTTCCAGGAACTGCCCCCAAACT<br>CCTCATCTATGGTAACAGCAATCGGCCCTCAGGGGTCCCTGACCGATTCT<br>CTGGCTCCAGGTCTGGCACCTCAGCCTCCCTGGCCATCACTGGGCTCCAG<br>GCTGAGGATGAGGCTGATTATTACTGCCAGTCCTATGACACCAGCCTGAA<br>TGGTTGGGCTTTCGGCGGAGGGACCAAGTTGACCGTCCTAGGCCAGCCCA<br>AGGCTGCCCCCTCGGTCACTCTGTTCCCACCCTCCTCTGAGGAGCTTCAA<br>GCCAACAAGGCCACACTGGTGTGTCTCGTAAGTGACTTCTACCCGGGAGC<br>CGTGACAGTGGCCTGGAAGGCAGATGGCAGCCCGTCAAGGTGGGAGTGG<br>AGACCACCAAACCCTCCAAACAAAGCAACAACAAGTATGCGGCCAGCAGC<br>TACCTGAGCCTGACGCCCGAGCAGTGGAAGTCCCACAGAAGCTACAGCTG<br>CCGGGTCACGCATGAAGGGAGCACCGTGGAGAAGACAGTGGCCCCTGCAG<br>AATGCTCT<br>[SEQ ID NO: 150] | |
| DNA for Heavy Chain version 1 | GAGGTGCAGCTGGTGGAGTCTGGGGGAGGCTTGG<br>TACAGCCAGGGCGGTCCCTGAGACTCAGCTGTGCGGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGCACTGTCTATCTGCAAATGAACAGCCTGAAAACCGAGGACACAGCCGT<br>GTATTTCTGTGCTAGAGTGCAGCTTGACTATGGCCCGGGATACCAGTACT<br>ACGGTATGGACGTCTGGGGCCAAGGGACCACGGTCACCGTCTCCTCAGCC<br>TCCACCAAGGGCCCATCGGTCTTCCCCCTGGCACCCTCCTCCAAGAGCAC<br>CTCTGGGGGCACAGCAGCCCTGGGCTGCCTGGTCAAGGACTACTTCCCCG<br>AACCGGTGACGGTGTCGTGGAACTCAGGCGCCCTGACCAGCGGCGTGCAC<br>ACCTTCCCGGCTGTCCTACAGTCCTCAGGACTCTACTCCCTCAGCAGCGT<br>GGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAA<br>TCTTGTGACAAAACTCACACATGCCCACCGTGCCCAGCACCTGAACTCCT<br>GGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCA<br>TAATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG<br>GCAGCCGGAGAACAACTACAAGACCACGCCTCCCGTGCTGGACTCCGACG<br>GCTCCTTCTTCCTCTACAGCAAGCTCACCGTGGACAAGAGCAGGTGGCAG<br>CAGGGGAACGTCTTCTCATGCTCCGTGATGCATGAGGCTCTGCACAACCA<br>CTACACACAGAAGAGCCTCTCCCTGTCTCCGGGTAAA<br>[SEQ ID NO: 151] | |
| DNA for Heavy Chain version 2 | GAGGTGCAGCTGGTGGAGTCTGGGGGAGGCTTGG<br>TACAGCCAGGGCGGTCCCTGAGACTCAGCTGTGCGGCCTCTGGGTTTAGT<br>TTTGGTGATCATGCTATGAGCTGGGTCCGCCAGGCTCCAGGGAAGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGCACTGTCTATCTGCAAATGAACAGCCTGAAAACCGAGGACACAGCCGT<br>GTATTTCTGTGCTAGAGTGCAGCTTGACTATGGCCCGGGATACCAGTACT<br>ACGGTATGGACGTCTGGGGCCAAGGGACCACGGTCACCGTCTCCTCAGCC<br>TCCACCAAGGGCCCATCGGTCTTCCCCCTGGCACCCTCCTCCAAGAGCAC<br>CTCTGGGGGCACAGCAGCCCTGGGCTGCCTGGTCAAGGACTACTTCCCCG<br>AACCGGTGACGGTGTCGTGGAACTCAGGCGCCCTGACCAGCGGCGTGCAC<br>ACCTTCCCGGCTGTCCTACAGTCCTCAGGACTCTACTCCCTCAGCAGCGT<br>GGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAA<br>TCTTGTGACAAAACTCACACATGCCCACCGTGCCCAGCACCTGAACTCCT<br>GGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCA<br>TAATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG<br>GCAGCCGGAGAACAACTACAAGACCACGCCTCCCGTGCTGGACTCCGACG<br>GCTCCTTCTTCCTCTACAGCAAGCTCACCGTGGACAAGAGCAGGTGGCAG<br>CAGGGGAACGTCTTCTCATGCTCCGTGCTGCATGAGGCTCTGCACTCCCA<br>CTACACACAGAAGAGCCTCTCCCTGTCTCCGGGTAAA [SEQ ID NO: 152] | |

In certain embodiments, the anti-CSP antibody variant comprises a light chain variable region comprising a CDR1, a CDR2, and a CDR3 and having the amino acid sequence set forth in SEQ ID NO: 153, as shown in Table 19. In certain embodiments, the anti-CSP antibody variant comprises a heavy chain variable region comprising a CDR1, a CDR2, and a CDR3 and having the amino acid sequence set forth in SEQ ID NO: 154, as shown in Table 19. In certain embodiments, the anti-CSP antibody variant comprises a light chain having the amino acid sequence set forth in SEQ ID NO: 157, as shown in Table 19. In certain embodiments, the anti-CSP antibody variant comprises a heavy chain having the amino acid sequence set forth in SEQ ID NO: 158, as shown in Table 19. In certain embodiments, the anti-CSP antibody variant comprises a heavy chain having the amino acid sequence set forth in SEQ ID NO: 159, as shown in Table 19. Exemplary nucleic acid sequences of SEQ ID NOS: 153, 154, 157, 158, and 159 are provided in Table 19 below.

TABLE 19

| Antibody ID: AB-000224.014 | | |
|---|---|---|
| | KABAT | ASN |
| CDR1-VL | TGMNSNIGAGYDVY [SEQ ID NO: 1] | TGMNSNIGAGYDVY [SEQ ID NO: 7] |
| CDR2-VL | GNSNRPS [SEQ ID NO: 2] | GNSNRPS [SEQ ID NO: 8] |
| CDR3-VL | QSYDTSLNGWA [SEQ ID NO: 3] | QSYDTSLNGWA [SEQ ID NO: 9] |
| CDR1-VH | DHAMS [SEQ ID NO: 4] | DHAMS [SEQ ID NO: 10] |
| CDR2-VH | FIRKTTYGATTHYAAAVRG [SEQ ID NO: 5] | FIRKTTYGATTHYAAAVRG [SEQ ID NO: 11] |
| CDR3-VH | VQLDYGPGYQYYGMDV [SEQ ID NO: 6] | VQLDYGPGYQYYGMDV [SEQ ID NO: 12] |
| VL | QSVLTQPPSVSGAPGQRVTISCTGMNSNIGA GYDVYWYQQLPGTAPKLLIYGNSNRPSGVPDRFSGSRSGTSASLAITGLQ AEDEADYYCQSYDTSLNGWAFGGGTKLTVLG [SEQ ID NO: 153] | |
| VH | EVQLVESGGGLVQPGRSLRLSCAASGFS FGDHAMSWVRQAPGKGLEWVGFIRKTTYGATTHYAAAVRGRFTISRDDSK SIVYLQMNSLKAEDTAVYFCARVQLDYGPGYQYYGMDVWGQGTTVTVSS [SEQ ID NO: 154] | |
| DNA for VL | CAGTCTGTGCTGACGCAGCCGCCCTCAGTGTCTGGGGCCCCAG GGCAGAGGGTCACCATCTCCTGCACTGGGATGAACTCCAACATCGGGGCA GGTTATGATGTATACTGGTACCAACAACTTCCAGGAACTGCCCCCAAACT CCTCATCTATGGTAACAGCAATCGGCCCTCAGGGGTCCCTGACCGATTCT CTGGCTCCAGGTCTGGCACCTCAGCCTCCCTGGCCATCACTGGGCTCCAG GCTGAGGATGAGGCTGATTATTACTGCCAGTCCTATGACACCAGCCTGAA TGGTTGGGCTTTCGGCGGAGGGACCAAGTTGACCGTCCTAGGC [SEQ ID NO: 155] | |
| DNA for VH | GAGGTGCAGCTGGTGGAGTCTGGGGGAGGCTTGG TACAGCCAGGGCGGTCCCTGAGACTCAGCTGTGCGGCCTCTGGGTTTAGT TTTGGTGATCATGCTATGAGCTGGGTCCGCCAGGCTCCAGGGAAGGGGCT GGAGTGGGTAGGTTTCATTAGAAAGACAACTTATGGTGCGACAACACACT ACGCCGCGGCTGTGAGAGGCAGATTCACCATCTCGCGAGATGATTCTAAA AGOATTGTGTATCTGCAAATGAACAGCCTGAAAGCAGAGGACACAGCCGT GTATTTCTGTGCTAGAGTGCAGCTTGACTATGGCCCGGGATACCAGTACT ACGGTATGGACGTCTGGGGCCAAGGGACCACGGTCACCGTCTCCTCA [SEQ ID NO: 156] | |
| Light Chain | QSVLTQPPSVSGAPGQRVTISCTGMNSNIGA GYDVYWYQQLPGTAPKLLIYGNSNRPSGVPDRFSGSRSGTSASLAITGLQ AEDEADYYCQSYDTSLNGWAFGGGTKLTVLGQPKAAPSVTLFPPSSEELQ ANKATLVCLVSDFYPGAVTVAWKADGSPVKVGVETTKPSKQSNNKYAASS YLSLTPEQWKSHRSYSCRVTHEGSTVEKTVAPAECS [SEQ ID NO: 157] | |
| Heavy Chain version 1 | EVQLVESGGGLVQPGRSLRLSCAASGFS FGDHAMSWVRQAPGKGLEWVGFIRKTTYGATTHYAAAVRGRFTISRDDSK SIVYLQMNSLKAEDTAVYFCARVQLDYGPGYQYYGMDVWGQGTTVTVSSA STKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPK SCDKTHTCPPCPAPELLGGPSVFLFPPKPKDTLMISRTPEVTCVVVDVSH | |

TABLE 19-continued

Antibody ID: AB-000224.014

| | KABAT | ASN |
|---|---|---|

EDPEVKFNWYVDGVEVHNAKTKPREEQYNSTYRWSVLTVLHQDWLNGKE
YKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQ
QGNVFSCSVMHEALHNHYTQKSLSLSPGK
[SEQ ID NO: 158]

Heavy Chain version 2
EVQLVESGGGLVQPGRSLRLSCAASGFS
FGDHAMSWVRQAPGKGLEWVGFIRKTTYGATTHYAAAVRGRFTISRDDSK
SIVYLQMNSLKAEDTAVYFCARVQLDYGPGYQYYGMDVWGQGTTVTVSSA
STKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKKVEPK
SCDKTHTCPPCPAPELLGGPSVFLFPPKPKDTLMISRTPEVTCVVVDVSH
EDPEVKFNWYVDGVEVHNAKTKPREEQYNSTYRWSVLTVLHQDWLNGKE
YKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQ
QGNVFSCSVLHEALHSHYTQKSLSLSPGK [SEQ ID NO: 159]

DNA for Light Chain
CAGTCTGTGCTGACGCAGCCGCCCTCAGTGTCTGGGGCCCAG
GGCAGAGGGTCACCATCTCCTGCACTGGGATGAACTCCAACATCGGGGCA
GGTTATGATGTATACTGGTACCAACAACTTCCAGGAACTGCCCCCAAACT
CCTCATCTATGGTAACAGCAATCGGCCCTCAGGGGTCCCTGACCGATTCT
CTGGCTCCAGGTCTGGCACCTCAGCCTCCCTGGCCATCACTGGGCTCCAG
GCTGAGGATGAGGCTGATTATTACTGCCAGTCCTATGACACCAGCCTGAA
TGGTTGGGCTTTCGGCGGAGGGACCAAGTTGACCGTCCTAGGCCAGCCCA
AGGCTGCCCCCTCGGTCACTCTGTTTCCACCCTCCTCTGAGGAGCTTCAA
GCCAACAAGGCCACACTGGTGTGTCTCGTAAGTGACTTCTACCCGGGAGC
CGTGACAGTGGCCTGGAAGGCAGATGGCAGCCCCGTCAAGGTGGGAGTGG
AGACCACCAAACCCTCCAAACAAAGCAACAACAAGTATGCGGCCAGCAGC
TACCTGAGCCTGACGCCCGAGCAGTGGAAGTCCCACAGAAGCTACAGCTG
CCGGGTCACGCATGAAGGGAGCACCGTGGAGAAGACAGTGGCCCCTGCAG
AATGCTCT [SEQ ID NO: 160]

DNA for Heavy Chain version 1
GAGGTGCAGCTGGTGGAGTCTGGGGGAGGCTTGG
TACAGCCAGGGCGGTCCCTGAGACTCAGCTGTGCGGCCTCTGGGTTTAGT
TTTGGTGATCATGCTATGAGCTGGGTCCGCCAGGCTCCAGGGAAGGGGCT
GGAGTGGGTAGGTTTCATTAGAAAGACAACTTATGGTGCGACAACACACT
ACGCCGCGGCTGTGAGAGGCAGATTCACCATCTCGCGAGATGATTCTAAA
AGCATTGTCTATCTGCAAATGAACAGCCTGAAAGCAGAGGACACAGCCGT
GTATTTCTGTGCTAGAGTGCAGCTTGACTATGGCCCGGGATACCAGTACT
ACGGTATGGACGTCTGGGGCCAAGGGACCACGGTCACCGTCTCCTCAGCC
TCCACCAAGGGCCCATCGGTCTTCCCCCTGGCACCCTCCTCCAAGAGCAC
CTCTGGGGGCACAGCAGCCCTGGGCTGCCTGGTCAAGGACTACTTCCCCG
AACCGGTGACGGTGTCGTGGAACTCAGGCGCCCTGACCAGCGGCGTGCAC
ACCTTCCCGGCTGTCCTACAGTCCTCAGGACTCTACTCCCTCAGCAGCGT
GGTGACCGTGCCCTCCAGCAGCTTGGGCACCCAGACCTACATCTGCAACG
TGAATCACAAGCCCAGCAACACCAAGGTGGACAAGAAAGTTGAGCCCAAA
TCTTGTGACAAAACTCACACATGCCCACCGTGCCCAGCACCTGAACTCCT
GGGGGGACCGTCAGTCTTCCTCTTCCCCCCAAAACCCAAGGACACCCTCA
TGATCTCCCGGACCCCTGAGGTCACATGCGTGGTGGTGGACGTGAGCCAC
GAAGACCCTGAGGTCAAGTTCAACTGGTACGTGGACGGCGTGGAGGTGCA
TAATGCCAAGACAAAGCCGCGGGAGGAGCAGTACAACAGCACGTACCGTG
TGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAAC
CATCTCTCCAAAGCCAAAGGGCAGCCCCGAGAACCACAGGTGTACACCCTGC
CCCCATCCCGGGATGAGCTGACCAAGAACCAGGTCAGCCTGACCTGCCTG
GTCAAAGGCTTCTATCCCAGCGACATCGCCGTGGAGTGGGAGAGCAATGG
GCAGCCGGAGAACAACTACAAGACCACGCCTCCCGTGCTGGACTCCGACG
GCTCCTTCTTCCTCTACAGCAAGCTCACCGTGGACAAGAGCAGGTGGCAG
CAGGGGAACGTCTTCTCATGCTCCGTGATGCATGAGGCTCTGCACAACCA
CTACACACAGAAGAGCCTCTCCCTGTCTCCGGGTAAA [SEQ ID NO: 161]

DNA for Heavy Chain version 2
GAGGTGCAGCTGGTGGAGTCTGGGGGAGGCTTGG
TACAGCCAGGGCGGTCCCTGAGACTCAGCTGTGCGGCCTCTGGGTTTAGT
TTTGGTGATCATGCTATGAGCTGGGTCCGCCAGGCTCCAGGGAAGGGGCT
GGAGTGGGTAGGTTTCATTAGAAAGACAACTTATGGTGCGACAACACACT
ACGCCGCGGCTGTGAGAGGCAGATTCACCATCTCGCGAGATGATTCTAAA
AGGATTGTCTATGTGCAAATGAACAGCCTGAAAGCAGAGGACACAGCCGT
GTATTTCTGTGCTAGAGTGCAGCTTGACTATGGCCCGGGATACCAGTACT
ACGGTATGGACGTCTGGGGCCAAGGGACCACGGTCACCGTCTCCTCAGCC
TCCACCAAGGGCCCATCGGTCTTCCCCCTGGCACCCTCCTCCAAGAGCAC
CTCTGGGGGCACAGCAGCCCTGGGCTGCCTGGTCAAGGACTACTTCCCCG
AACCGGTGACGGTGTCGTGGAACTCAGGCGCCCTGACCAGCGGCGTGCAC
ACCTTCCCGGCTGTCCTACAGTCCTCAGGACTCTACTCCCTCAGCAGCGT
GGTGACCGTGCCCTCCAGCAGCTTGGGCACCCAGACCTACATCTGCAACG
TGAATCACAAGCCCAGCAACACCAAGGTGGACAAGAAAGTTGAGCCCAAA
TCTTGTGACAAAACTCACACATGCCCACCGTGCCCAGCACCTGAACTCCT

TABLE 19-continued

Antibody ID: AB-000224.014

| KABAT | ASN |
|---|---|
| GGGGGGACCGTCAGTCTTCCTCTTCCCCCCAAAACCCAAGGACACCCTCA | |
| TGATCTCCCGGACCCCTGAGGTCACATGCGTGGTGGTGGACGTGAGCCAC | |
| GAAGACCCTGAGGTCAAGTTCAACTGGTACGTGGACGGCGTGGAGGTGCA | |
| TAATGCCAAGACAAAGCCGCGGGAGGAGCAGTACAACAGCACGTACCGTG | |
| TGGTCAGCGTCCTCACCGTCCTGCACCAGGACTGGCTGAATGGCAAGGAG | |
| TACAAGTGCAAGGTCTCCAACAAAGCCCTCCCAGCCCCCATCGAGAAAAC | |
| CATCTCCAAAGCCAAAGGGCAGCCCCGAGAACCACAGGTGTACACCCTGC | |
| CCCCATCCCGGGATGAGCTGACCAAGAACCAGGTCAGCCTGACCTGCCTG | |
| GTCAAAGGCTTCTATCCCAGCGACATCGCCGTGGAGTGGGAGAGCAATGG | |
| GCAGCCGGAGAACAACTACAAGACCACGCCTCCCGTGCTGGACTCCGACG | |
| GCTCCTTCTTCCTCTACAGCAAGCTCACCGTGGACAAGAGCAGGTGGCAG | |
| CAGGGGAACGTCTTCTCATGCTCCGTGCTGCATGAGGCTCTGCACTCCCA | |
| CTACACACAGAAGAGCCTCTCCCTGTCTCCGGGTAAA [SEQ ID NO: 162] | |

In certain embodiments, the anti-CSP antibody variant comprises a light chain variable region comprising a CDR1, a CDR2, and a CDR3 and having the amino acid sequence set forth in SEQ ID NO: 163, as shown in Table 20. In certain embodiments, the anti-CSP antibody variant comprises a heavy chain variable region comprising a CDR1, a CDR2, and a CDR3 and having the amino acid sequence set forth in SEQ ID NO: 164, as shown in Table 20. In certain embodiments, the anti-CSP antibody variant comprises a light chain having the amino acid sequence set forth in SEQ ID NO: 167, as shown in Table 20. In certain embodiments, the anti-CSP antibody variant comprises a heavy chain having the amino acid sequence set forth in SEQ ID NO: 168, as shown in Table 20. In certain embodiments, the anti-CSP antibody variant comprises a heavy chain having the amino acid sequence set forth in SEQ ID NO: 169, as shown in Table 20. Exemplary nucleic acid sequences of SEQ ID NOS: 163, 164, 167, 168, and 169 are provided in Table 20 below.

TABLE 20

Antibody ID: AB-000224.015

| | KABAT | ASN |
|---|---|---|
| CDR1-VL | TGMNSNIGAGYDVY [SEQ ID NO: 1] | TGMNSNIGAGYDVY [SEQ ID NO: 7] |
| CDR2-VL | GNSNRPS [SEQ ID NO: 2] | GNSNRPS [SEQ ID NO: 8] |
| CDR3-VL | QSYDTSLNGWA [SEQ ID NO: 3] | QSYDTSLNGWA [SEQ ID NO: 9] |
| CDR1-VH | DHAMS [SEQ ID NO: 4] | DHAMS [SEQ ID NO: 10] |
| CDR2-VH | FIRKTTYGATTHYAAAVRG [SEQ ID NO: 5] | FIRKTTYGATTHYAAAVRG [SEQ ID NO: 11] |
| CDR3-VH | VQLDYGPGYQYYGMDV [SEQ ID NO: 6] | VQLDYGPGYQYYGMDV [SEQ ID NO: 12] |
| VL | QSVLTQPPSVSGAPGQRVTISCTGMNSNIGA GYDVYWYQQLPGTAPKLLIYGNSNRPSGVPDRFSGSRSGTSASLAITGLQ AEDEADYYCQSYDTSLNGWAFGGGTKLTVLG [SEQ ID NO: 163] | |
| VH | EVQLVESGGGLVQPGRSLRLSCTASGFS FGDHAMSWVRQAPGKGLEWVGFIRKTTYGATTHYAAAVRGRFTISRDDSK STVYLQMNSLKAEDTAVYFCARVQLDYGPGYQYYGMDVWGQGTTVTVSS [SEQ ID NO: 164] | |
| DNA for VL | CAGTCTGTGCTGACGCAGCCGCCCTCAGTGTCTGGGGCCCCAG GGCAGAGGGTCACCATCTCCTGCACTGGGATGAACTCCAACATCGGGGCA GGTTATGATGTATACTGGTACCAACAACTTCCAGGAACTGCCCCCAAACT CCTCATCTATGGTAACAGCAATCGGCCCTCAGGGGTCCCTGACCGATTCT CTGGCTCCAGGTCTGGCACCTCAGCCTCCCTGGCCATCACTGGGCTCCAG GCTGAGGATGAGGCTGATTATTACTGCCAGTCCTATGACACCAGCCTGAA TGGTTGGGCTTTCGGCGGAGGGACCAAGTTGACCGTCCTAGGC [SEQ ID NO: 165] | |
| DNA forVH | GAGGTGCAGCTGGTGGAGTCTGGGGGAGGCTTGG TACAGCCAGGGCGGTCCCTGAGACTCAGCTGTACAGCCTCTGGGTTTAGT TTTGGTGATCATGCTATGAGCTGGGTCCGCCAGGCTCCAGGGAAGGGGCT GGAGTGGGTAGGTTTCATTAGAAAGACAACTTATGGTGCGACAACACACT | |

TABLE 20-continued

Antibody ID: AB-000224.015

| | KABAT | ASN |
|---|---|---|

ACGCCGCGGCTGTGAGAGGCAGATTCACCATCTCGCGAGATGATTCTAAA
AGOACTGTOTATCTGCAAATGAACAGCCTGAAAGCAGAGGACACAGCCGT
GTATTTCTGTGCTAGAGTGCAGCTTGACTATGGCCCGGGATACCAGTACT
ACGGTATGGACGTCTGGGGCCAAGGGACCACGGTCACCGTCTCCTCA
[SEQ ID NO: 166]

Light
Chain
QSVLTQPPSVSGAPGQRVTISCTGMNSNIGA
GYDVYWYQQLPGTAPKLLIYGNSNRPSGVPDRFSGSRSGTSASLAITGLQ
AEDEADYYCQSYDTSLNGWAFGGGTKLTVLGQPKAAPSVTLFPPSSEELQ
ANKATLVCLVSDFYPGAVTVAWKADGSPVKVGVETTKPSKQSNNKYAASS
YLSLTPEQWKSHRSYSCRVTHEGSTVEKTVAPAECS
[SEQ ID NO: 167]

Heavy
Chain
version
1
EVQLVESGGGLVQPGRSLRLSCTASGFS
FGDHAMSWVRQAPGKGLEWVGFIRKTTYGATTHYAAAVRGRFTISRDDSK
STVYLQMNSLKAEDTAVYFCARVQLDYGPGYQYYGMDVWGQGTTVTVSSA
STKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKKVEPK
SCDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKE
YKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQ
QGNVFSCSVMHEALHNHYTQKSLSLSPGK
[SEQ ID NO: 168]

Heavy
Chain
version
2
EVQLVESGGGLVQPGRSLRLSCTASGFS
FGDHAMSWVRQAPGKGLEWVGFIRKTTYGATTHYAAAVRGRFTISRDDSK
STVYLQMNSLKAEDTAVYFCARVQLDYGPGYQYYGMDVWGQGTTVTVSSA
STKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKKVEPK
SCDKTHTCPPCPAPELLGGPSVFLFPPKPKDTLMISRTPEVTCVVVDVSH
EDPEVKFNWYVDGVEVHNAKTKPREEQYNSTYRWSVLTVLHQDWLNGKE
YKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQ
QGNVFSCSVLHEALHSHYTQKSLSLSPGK [SEQ ID NO: 169]

DNA
for
Light
Chain
CAGTCTGTGCTGACGCAGCCGCCCTCAGTGTCTGGGGCCCCAG
GGCAGAGGGTCACCATCTCCTGCACTGGGATGAACTCCAACATCGGGGCA
GGTTATGATGTATACTGGTACCAACAACTTCCAGGAACTGCCCCCAAACT
CCTCATCTATGGTAACAGCAATCGGCCCTCAGGGGTCCCTGACCGATTCT
CTGGCTCCAGGTCTGGCACCTCAGCCTCCCTGGCCATCACTGGGCTCCAG
GCTGAGGATGAGGCTGATTATTACTGCCAGTCCTATGACACCAGCCTGAA
TGGTTGGGCTTTCGGCGGAGGGACCAAGTTGACCGTCCTAGGCCAGCCCA
AGGCTGCCCCCTCGGTCACTCTGTTCCCACCCTCCTCTGAGGAGCTTCAA
GCCAACAAGGCCACACTGGTGTGTCTCGTAAGTGACTTCTACCCGGGAGC
CGTGACAGTGGCCTGGAAGGCAGATGGCAGCCCCGTCAAGGTGGGAGTGG
AGACCACCAAACCCTCCAAACAAAGCAACAACAAGTATGCGGCCAGCAGC
TACCTGAGCCTGACGCCCGAGCAGTGGAAGTCCACAGAAGCTACAGCTG
CCGGGTCACGCATGAAGGGAGCACCGTGGAGAAGACAGTGGCCCCTGCAG
AATGCTCT [SEQ ID NO: 170]

DNA
for
Heavy
Chain
version
1
GAGGTGCAGCTGGTGGAGTCTGGGGGAGGCTTGG
TACAGCCAGGGCGGTCCCTGAGACTCAGCTGTACAGCCTCTGGGTTTAGT
TTTGGTGATCATGCTATGAGCTGGGTCCGCCAGGCTCCAGGGAAGGGGCT
GGAGTGGGTAGGTTTCATTAGAAAAGACAACTTATGGTGCGACAACACACT
ACGCCGCGGCTGTGAGAGGCAGATTCACCATCTCGCGAGATGATTCTAAA
AGOACTGTOTATCTGCAAATGAACAGCCTGAAAGCAGAGGACACAGCCGT
GTATTTCTGTGCTAGAGTGCAGCTTGACTATGGCCCGGGATACCAGTACT
ACGGTATGGACGTCTGGGGCCAAGGGACCACGGTCACCGTCTCCTCAGCC
TCCACCAAGGGCCCATCGGTCTTCCCCCTGGCACCCTCCTCCAAGAGCAC
CTCTGGGGGCACAGCAGCCCTGGGCTGCCTGGTCAAGGACTACTTCCCCG
AACCGGTGACGGTGTCGTGGAACTCAGGCGCCCTGACCAGCGGCGTGCAC
ACCTTCCCGGCTGTCCTACAGTCCTCAGGACTCTACTCCCTCAGCAGCGT
GGTGACCGTGCCCTCCAGCAGCTTGGGCACCCAGACCTACATCTGCAACG
TGAATCACAAGCCCAGCAACACCAAGGTGGACAAGAAAGTTGAGCCCAAA
TCTTGTGACAAAACTCACACATGCCCACCGTGCCCAGCACCTGAACTCCT
GGGGGGACCGTCAGTCTTCCTCTTCCCCCCAAAACCCAAGGACACCCTCA
TGATCTCCCGGACCCCTGAGGTCACATGCGTGGTGGTGGACGTGAGCCAC
GAAGACCCTGAGGTCAAGTTCAACTGGTACGTGGACGGCGTGGAGGTGCA
TAATGCCAAGACAAAGCCGCGGGAGGAGCAGTACAACAGCACGTACCGTG
TGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAAC
CATCTCCAAAGCCAAAGGGCAGCCCCGAGAACCACAGGTGTACACCCTGC
CCCCATCCCGGGATGAGCTGACCAAGAACCAGGTCAGCCTGACCTGCCTG
GTCAAAGGCTTCTATCCCAGCGACATCGCCGTGGAGTGGGAGAGCAATGG
GCAGCCGGAGAACAACTACAAGACCACGCCTCCCGTGCTGGACTCCGACG

TABLE 20-continued

Antibody ID: AB-000224.015

| | KABAT | ASN |
|---|---|---|
| | GCTCCTTCTTCCTCTACAGCAAGCTCACCGTGGACAAGAGCAGGTGGCAG<br>CAGGGGAACGTCTTCTCATGCTCCGTGATGCATGAGGCTCTGCACAACCA<br>CTACACACAGAAGAGCCTCTCCCTGTCTCCGGGTAAA [SEQ ID NO: 171] | |
| DNA<br>for<br>Heavy<br>Chain<br>version<br>2 | GAGGTGCAGCTGGTGGAGTCTGGGGGAGGCTTGG<br>TACAGCCAGGGCGGTCCCTGAGACTCAGCTGTACAGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGGACTGTCTATCTGCAAATGAACAGCCTGAAAGCAGAGGACACAGCCGT<br>GTATTTCTGTGCTAGAGTGCAGCTTGACTATGGCCCGGGATACCAGTACT<br>ACGGTATGGACGTCTGGGGCCAAGGGACCACGGTCACCGTCTCCTCAGCC<br>TCCACCAAGGGCCCATCGGTCTTCCCCCTGGCACCCTCCTCCAAGAGCAC<br>CTCTGGGGGCACAGCAGCCCTGGGCTGCCTGGTCAAGGACTACTTCCCCG<br>AACCGGTGACGGTGTCGTGGAACTCAGGCGCCCTGACCAGCGGCGTGCAC<br>ACCTTCCCGGCTGTCCTACAGTCCTCAGGACTCTACTCCCTCAGCAGCGT<br>GGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAA<br>TCTTGTGACAAAACTCACACATGCCCACCGTGCCCAGCACCTGAACTCCT<br>GGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCA<br>TAATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG<br>GCAGCCGGAGAACAACTACAAGACCACGCCTCCCGTGCTGGACTCCGACG<br>GCTCCTTCTTCCTCTACAGCAAGCTCACCGTGGACAAGAGCAGGTGGCAG<br>CAGGGGAACGTCTTCTCATGCTCCGTGCTGCATGAGGCTCTGCACTCCCA<br>CTACACACAGAAGAGCCTCTCCCTGTCTCCGGGTAAA [SEQ ID NO: 172] | |

In certain embodiments, the anti-CSP antibody variant comprises a light chain variable region comprising a CDR1, a CDR2, and a CDR3 and having the amino acid sequence set forth in SEQ ID NO: 173, as shown in Table 21. In certain embodiments, the anti-CSP antibody variant comprises a heavy chain variable region comprising a CDR1, a CDR2, and a CDR3 and having the amino acid sequence set forth in SEQ ID NO: 174, as shown in Table 21. In certain embodiments, the anti-CSP antibody variant comprises a light chain having the amino acid sequence set forth in SEQ ID NO: 177, as shown in Table 21. In certain embodiments, the anti-CSP antibody variant comprises a heavy chain having the amino acid sequence set forth in SEQ ID NO: 178, as shown in Table 21. In certain embodiments, the anti-CSP antibody variant comprises a heavy chain having the amino acid sequence set forth in SEQ ID NO: 179, as shown in Table 21. Exemplary nucleic acid sequences of SEQ ID NOS: 173, 174, 177, 178, and 179 are provided in Table 21 below.

TABLE 21

Antibody ID: AB-000224.016

| | KABAT | ASN |
|---|---|---|
| CDR1-<br>VL | TGMNSNIGAGYDVY [SEQ ID NO: 1] | TGMNSNIGAGYDVY [SEQ ID NO: 7] |
| CDR2-<br>VL | GNSNRPS [SEQ ID NO: 2] | GNSNRPS [SEQ ID NO: 8] |
| CDR3-<br>VL | QSYDTSLNGWA [SEQ ID NO: 3] | QSYDTSLNGWA [SEQ ID NO: 9] |
| CDR1-<br>VH | DHAMS [SEQ ID NO: 4] | DHAMS [SEQ ID NO: 10] |
| CDR2-<br>VH | FIRKTTYGATTHYAAAVRG [SEQ ID NO: 5] | FIRKTTYGATTHYAAAVRG [SEQ ID NO: 11] |
| CDR3-<br>VH | VQLDYGPGYQYYGMDV [SEQ ID NO: 6] | VQLDYGPGYQYYGMDV [SEQ ID NO: 12] |
| VL | QSVLTQPPSVSGAPGQRVTISCTGMNSNIGA<br>GYDVYWYQQLPGTAPKLLIYGNSNRPSGVPDRFSGSRSGTSASLAITGLQ<br>AEDEADYYCQSYDTSLNGWAFGGGTKLTVLG<br>[SEQ ID NO: 173] | |

TABLE 21-continued

Antibody ID: AB-000224.016

| | KABAT | ASN |
|---|---|---|

VH
EVQLVESGGGLVQPGRSLRLSCAASGFS
FGDHAMSWVRQAPGKGLEWVGFIRKTTYGATTHYAAAVRGRFTISRDDSK
STVYLQMNSLKAEDTAVYFCARVQLDYGPGYQYYGMDVWGQGTTVTVSS
[SEQ ID NO: 174]

DNA
for VL
CAGTCTGTGCTGACGCAGCCGCCCTCAGTGTCTGGGGCCCAG
GGCAGAGGGTCACCATCTCCTGCACTGGGATGAACTCCAACATCGGGGCA
GGTTATGATGTATACTGGTACCAACAACTTCCAGGAACTGCCCCCAAACT
CCTCATCTATGGTAACAGCAATCGGCCCTCAGGGGTCCCTGACCGATTCT
CTGGCTCCAGGTCTGGCACCTCAGCCTCCCTGGCCATCACTGGGCTCCAG
GCTGAGGATGAGGCTGATTATTACTGCCAGTCCTATGACACCAGCCTGAA
TGGTTGGGCTTTCGGCGGAGGGACCAAGTTGACCGTCCTAGGC
[SEQ ID NO: 175]

DNA
forVH
GAGGTGCAGCTGGTGGAGTCTGGGGGAGGCTTGG
TACAGCCAGGGCGGTCCCTGAGACTCAGCTGTGCGGCCTCTGGGTTTAGT
TTTGGTGATCATGCTATGAGCTGGGTCCGCCAGGCTCCAGGGAAGGGGCT
GGAGTGGGTAGGTTTCATTAGAAAGACAACTTATGGTGCGACAACACACT
ACGCCGCGGCTGTGAGAGGCAGATTCACCATCTCGCGAGATGATTCTAAA
AGCACTGTGTATCTGCAAATGAACAGCCTGAAAGCAGAGGACACAGCCGT
GTATTTCTGTGCTAGAGTGCAGCTTGACTATGGCCCGGGATACCAGTACT
ACGGTATGGACGTCTGGGGCCAAGGGACCACGGTCACCGTCTCCTCA
[SEQ ID NO: 176]

Light
Chain
QSVLTQPPSVSGAPGQRVTISCTGMNSNIGA
GYDVYWYQQLPGTAPKLLIYGNSNRPSGVPDRFSGSRSGTSASLAITGLQ
AEDEADYYCQSYDTSLNGWAFGGGTKLTVLGQPKAAPSVTLFPPSSEELQ
ANKATLVCLVSDFYPGAVTVAWKADGSPVKVGVETTKPSKQSNNKYAASS
YLSLTPEQWKSHRSYSCRVTHEGSTVEKTVAPAECS
[SEQ ID NO: 177]

Heavy
Chain
version
1
EVQLVESGGGLVQPGRSLRLSCAASGFS
FGDHAMSWVRQAPGKGLEWVGFIRKTTYGATTHYAAAVRGRFTISRDDSK
STVYLQMNSLKAEDTAVYFCARVQLDYGPGYQYYGMDVWGQGTTVTVSSA
STKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKKVEPK
SCDKTHTCPPCPAPELLGGPSVFLFPPKPKDTLMISRTPEVTCVVVDVSH
EDPEVKFNWYVDGVEVHNAKTKPREEQYNSTYRWSVLTVLHQDWLNGKE
YKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQ
QGNVFSCSVMHEALHNHYTQKSLSLSPGK
[SEQ ID NO: 178]

Heavy
Chain
version
2
EVQLVESGGGLVQPGRSLRLSCAASGFS
FGDHAMSWVRQAPGKGLEWVGFIRKTTYGATTHYAAAVRGRFTISRDDSK
STVYLQMNSLKAEDTAVYFCARVQLDYGPGYQYYGMDVWGQGTTVTVSSA
STKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKKVEPK
SCDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKE
YKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQ
QGNVFSCSVLHEALHSHYTQKSLSLSPGK [SEQ ID NO: 179]

DNA
for
Light
Chain
CAGTCTGTGCTGACGCAGCCGCCCTCAGTGTCTGGGGCCCAG
GGCAGAGGGTCACCATCTCCTGCACTGGGATGAACTCCAACATCGGGGCA
GGTTATGATGTATACTGGTACCAACAACTTCCAGGAACTGCCCCCAAACT
CCTCATCTATGGTAACAGCAATCGGCCCTCAGGGGTCCCTGACCGATTCT
CTGGCTCCAGGTCTGGCACCTCAGCCTCCCTGGCCATCACTGGGCTCCAG
GCTGAGGATGAGGCTGATTATTACTGCCAGTCCTATGACACCAGCCTGAA
TGGTTGGGCTTTCGGCGGAGGGACCAAGTTGACCGTCCTAGGCCAGCCCA
AGGCTGCCCCCTCGGTCACTCTGTTCCCACCCTCCTCTGAGGAGCTTCAA
GCCAACAAGGCCACACTGGTGTGTCTCGTAAGTGACTTCTACCCGGGAGC
CGTGACAGTGGCCTGGAAGGCAGATGGCAGCCCCGTCAAGGTGGGAGTGG
AGACCACCAAACCCTCCAAACAAAGCAACAACAAGTATGCGGCCAGCAGC
TACCTGAGCCTGACGCCCGAGCAGTGGAAGTCCCACAGAAGCTACAGCTG
CCGGGTCACGCATGAAGGGAGCACCGTGGAGAAGACAGTGGCCCCTGCAG
AATGCTCT [SEQ ID NO: 180]

TABLE 21-continued

Antibody ID: AB-000224.016

| | KABAT | ASN |
|---|---|---|

| | |
|---|---|
| DNA for Heavy Chain version 1 | GAGGTGCAGCTGGTGGAGTCTGGGGGAGGCTTGG<br>TACAGCCAGGGCGGTCCCTGAGACTCAGCTGTGCGGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGOACTGTOTATCTGCAAATGAACAGCCTGAAAGCAGAGGACACAGCCGT<br>GTATTTCTGTGCTAGAGTGCAGCTTGACTATGGCCCGGGATACCAGTACT<br>ACGGTATGGACGTCTGGGGCCAAGGGACCACGGTCACCGTCTCCTCAGCC<br>TCCACCAAGGGCCCATCGGTCTTCCCCCTGGCACCCTCCTCCAAGAGCAC<br>CTCTGGGGGCACAGCAGCCCTGGGCTGCCTGGTCAAGGACTACTTCCCCG<br>AACCGGTGACGGTGTCGTGGAACTCAGGCGCCCTGACCAGCGGCGTGCAC<br>ACCTTCCCGGCTGTCCTACAGTCCTCAGGACTCTACTCCCTCAGCAGCGT<br>GGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAA<br>TCTTGTGACAAAACTCACACATGCCCACCGTGCCCAGCACCTGAACTCCT<br>GGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCA<br>TAATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG<br>GCAGCCGGAGAACAACTACAAGACCACGCCTCCCGTGCTGGACTCCGACG<br>GCTCCTTCTTCCTCTACAGCAAGCTCACCGTGGACAAGAGCAGGTGGCAG<br>CAGGGGAACGTCTTCTCATGCTCCGTGATGCATGAGGCTCTGCACAACCA<br>CTACACACAGAAGAGCCTCTCCCTGTCTCCGGGTAAA [SEQ ID NO: 181] |
| DNA for Heavy Chain version 2 | GAGGTGCAGCTGGTGGAGTCTGGGGGAGGCTTGG<br>TACAGCCAGGGCGGTCCCTGAGACTCAGCTGTGCGGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGCACTGTCTATCTGCAAATGAACAGCCTGAAAGCAGAGGACACAGCCGT<br>GTATTTCTGTGCTAGAGTGCAGCTTGACTATGGCCCGGGATACCAGTACT<br>ACGGTATGGACGTCTGGGGCCAAGGGACCACGGTCACCGTCTCCTCAGCC<br>TCCACCAAGGGCCCATCGGTCTTCCCCCTGGCACCCTCCTCCAAGAGCAC<br>CTCTGGGGGCACAGCAGCCCTGGGCTGCCTGGTCAAGGACTACTTCCCCG<br>AACCGGTGACGGTGTCGTGGAACTCAGGCGCCCTGACCAGCGGCGTGCAC<br>ACCTTCCCGGCTGTCCTACAGTCCTCAGGACTCTACTCCCTCAGCAGCGT<br>GGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAA<br>TCTTGTGACAAAACTCACACATGCCCACCGTGCCCAGCACCTGAACTCCT<br>GGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCA<br>TAATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG<br>GCAGCCGGAGAACAACTACAAGACCACGCCTCCCGTGCTGGACTCCGACG<br>GCTCCTTCTTCCTCTACAGCAAGCTCACCGTGGACAAGAGCAGGTGGCAG<br>CAGGGGAACGTCTTCTCATGCTCCGTGCTGCATGAGGCTCTGCACTCCCA<br>CTACACACAGAAGAGCCTCTCCCTGTCTCCGGGTAAA [SEQ ID NO: 182] |

In certain embodiments, the VL of the variant of an anti-CSP antibody includes at least one, at least two, or at least three mutations, e.g., substitutions, in the CDR1 amino acid sequence set forth in SEQ ID NO: 183. In certain embodiments, the VL of the variant of an anti-CSP antibody includes at least one, at least two, or at least three mutations, e.g., substitutions, in the CDR2 amino acid sequence set forth in SEQ ID NO: 184. In certain embodiments, the VL of the variant of an anti-CSP antibody includes at least one, at least two, or at least three mutations, e.g., substitutions, in the CDR3 amino acid sequence set forth in SEQ ID NO: 185. In certain embodiments, the VH of the variant of an anti-CSP antibody includes at least one, at least two, or at least three mutations, e.g., substitutions, in the CDR1 amino acid sequence set forth in SEQ ID NO: 186. In certain embodiments, the VL of the variant of an anti-CSP antibody includes at least one, at least two, or at least three mutations, e.g., substitutions, in the CDR2 amino acid sequence set forth in SEQ ID NO: 187. In certain embodiments, the VL of the variant of an anti-CSP antibody includes at least one, at least two, or at least three mutations, e.g., substitutions, in the CDR3 amino acid sequence set forth in SEQ ID NO: 188.

In certain embodiments, the VL of the variant of an anti-CSP antibody includes at least one, at least two, or at least three mutations, e.g., substitutions, in the CDR1 amino acid sequence set forth in SEQ ID NO: 189. In certain embodiments, the VL of the variant of an anti-CSP antibody includes at least one, at least two, or at least three mutations, e.g., substitutions, in the CDR2 amino acid sequence set forth in SEQ ID NO: 190. In certain embodiments, the VL of the variant of an anti-CSP antibody includes at least one, at least two, or at least three mutations, e.g., substitutions, in the CDR3 amino acid sequence set forth in SEQ ID NO: 191. In certain embodiments, the VH of the variant of an anti-CSP antibody includes at least one, at least two, or at least three mutations, e.g., substitutions, in the CDR1 amino acid sequence set forth in SEQ ID NO: 192. In certain embodiments, the VL of the variant of an anti-CSP antibody includes at least one, at least two, or at least three mutations, e.g., substitutions, in the CDR2 amino acid sequence set forth in SEQ ID NO: 193. In certain embodiments, the VL of the variant of an anti-CSP antibody includes at least one, at least two, or at least three mutations, e.g., substitutions, in the CDR3 amino acid sequence set forth in SEQ ID NO: 194.

In certain embodiments, the anti-CSP antibody variant comprises a light chain variable region comprising a CDR1, a CDR2, and a CDR3 and having the amino acid sequence set forth in SEQ ID NO: 195, as shown in Table 22. In certain embodiments, the anti-CSP antibody variant comprises a heavy chain variable region comprising a CDR1, a CDR2, and a CDR3 and having the amino acid sequence set forth in SEQ ID NO: 196, as shown in Table 22. In certain embodiments, the anti-CSP antibody variant comprises a light chain having the amino acid sequence set forth in SEQ ID NO: 199, as shown in Table 22. In certain embodiments, the anti-CSP antibody variant comprises a heavy chain having the amino acid sequence set forth in SEQ ID NO: 200, as shown in Table 22. In certain embodiments, the anti-CSP antibody variant comprises a heavy chain having the amino acid sequence set forth in SEQ ID NO: 201, as shown in Table 22. Exemplary nucleic acid sequences of SEQ ID NOS: 195, 196, 199, 200, and 201 are provided in Table 22 below.

TABLE 22

| Antibody ID: AB-000224.017 | | |
|---|---|---|
| | KABAT | ASN |
| CDR1-VL | TGMNSNIGAGYDVY [SEQ ID NO: 183] | TGMNSNIGAGYDVY [SEQ ID NO: 189] |
| CDR2-VL | GNSNRPS [SEQ ID NO: 184] | GNSNRPS [SEQ ID NO: 190] |
| CDR3-VL | QSYDTSLDGWA [SEQ ID NO: 185] | QSYDTSLDGWA [SEQ ID NO: 191] |
| CDR1-VH | DHAMS [SEQ ID NO: 186] | DHAMS [SEQ ID NO: 192] |
| CDR2-VH | FIRKTTYGATTKYAAAVKG [SEQ ID NO: 187] | FIRKTTYGATTKYAAAVKG [SEQ ID NO: 193] |
| CDR3-VH | VQLDYGPGYQYYGMDV [SEQ ID NO: 188] | VQLDYGPGYQYYGMDV [SEQ ID NO: 194] |
| VL | ESVLTQPPSVSGAPGQRVTISCTGMNSNIGA GYDVYWYQQLPGRAPKLLIYGNSNRPSGVPDRFSGSRSGTSASLAITGLQ AEDEADYYCQSYDTSLDGWAFGGGTKLTVLG [SEQ ID NO: 195] | |
| VH | EVQLVESGGGLVQPGRSLRLPCTASGFS FGDHAMSWVRQAPGKGLEWVGFIRKTTYGATTKYAAAVKGRFTISRDDSK SIVYLQMNSLKTEDTAVYFCTRVQLDYGPGYQYYGMDVWGQGTTVTVSS [SEQ ID NO: 196] | |
| DNA for VL | GAGTCTGTGCTGACGCAGCCGCCCTCAGTGTCTGGGGCCCCAG GGCAGAGGGTCACCATCTCCTGCACTGGGATGAACTCCAACATCGGGGCA GGTTATGATGTATACTGGTACCAACAACTTCCAGGAAGAGCCCCCAAACT CCTCATCTATGGTAACAGCAATCGGCCCTCAGGGGTCCCTGACCGATTCT CTGGCTCCAGGTCTGGCACCTCAGCCTCCCTGGCCATCACTGGGCTCCAG GCTGAGGATGAGGCTGATTATTACTGCCAGTCCTATGACACCAGCCTGGA CGGTTGGGCTTTCGGCGGAGGGACCAAGTTGACCGTCCTAGGC [SEQ ID NO: 197] | |
| DNA fo rVH | GAGGTGCAGCTGGTGGAGTCTGGGGGAGGCTTGG TACAGCCAGGGCGGTCCCTGAGACTCCCCTGTACAGCCTCTGGGTTTAGT TTTGGTGATCATGCTATGAGCTGGGTCCGCCAGGCTCCAGGGAAGGGGCT GGAGTGGGTAGGTTTCATTAGAAAGACAACTTATGGTGCGACAACAAAGT ACGCCGCGGCTGTGAAGGGCAGATTCACCATCTCGCGAGATGATTCTAAA AGCATTGTCTATCTGCAAATGAACAGCCTGAAAACCGAGGACACAGCCGT GTATTTCTGTACTAGAGTGCAGCTTGACTATGGCCCGGGATACCAGTACT ACGGTATGGACGTCTGGGGCCAAGGGACCACGGTCACCGTCTCCTCA [SEQ ID NO: 198] | |
| Light Chain | ESVLTQPPSVSGAPGQRVTISCTGMNSNIGA GYDVYWYQQLPGRAPKLLIYGNSNRPSGVPDRFSGSRSGTSASLAITGLQ AEDEADYYCQSYDTSLDGWAFGGGTKLTVLGQPKAAPSVTLFPPSSEELQ | |

TABLE 22-continued

Antibody ID: AB-000224.017

| | KABAT | ASN |
|---|---|---|
| | | ANKATLVCLVSDFYPGAVTVAWKADGSPVKVGVETTKPSKQSNNKYAASS<br>YLSLTPEQWKSHRSYSCRVTHEGSTVEKTVAPAECS<br>[SEQ ID NO: 199] |
| Heavy<br>Chain<br>version<br>1 | | EVQLVESGGGLVQPGRSLRLPCTASGFS<br>FGDHAMSWVRQAPGKGLEWVGFIRKTTYGATTKYAAAVKGRFTISRDDSK<br>SIVYLQMNSLKTEDTAVYFCTRVQLDYGPGYQYYGMDVWGQGTTVTVSSA<br>STKGPSVFPLAPSSKSTSGGTAALGCLVKDYFPEPVTVSWNSGALTSGVH<br>TFPAVLQSSGLYSLSSVVTVPSSSLGTQTYICNVNHKPSNTKVDKKVEPK<br>SCDKTHTCPPCPAPELLGGPSVFLFPPKPKDTLMISRTPEVTCVVVDVSH<br>EDPEVKFNWYVDGVEVHNAKTKPREEQYNSTYRWSVLTVLHQDWLNGKE<br>YKCKVSNKALPAPIEKTISKAKGQPREPQVYTLPPSRDELTKNQVSLTCL<br>VKGFYPSDIAVEWESNGQPENNYKTTPPVLDSDGSFFLYSKLTVDKSRWQ<br>QGNVFSCSVMHEALHNHYTQKSLSLSPGK<br>[SEQ ID NO: 200] |
| Heavy<br>Chain<br>version<br>2 | | EVQLVESGGGLVQPGRSLRLPCTASGFS<br>FGDHAMSWVRQAPGKGLEWVGFIRKTTYGATTKYAAAVKGRFTISRDDSK<br>SIVYLQMNSLKTEDTAVYFCTRVQLDYGPGYQYYGMDVWGQGTTVTVSSA<br>STKGPSVFPLAPSSKSTSGGTAALGCLVKDYFPEPVTVSWNSGALTSGVH<br>TFPAVLQSSGLYSLSSVVTVPSSSLGTQTYICNVNHKPSNTKVDKKVEPK<br>SCDKTHTCPPCPAPELLGGPSVFLFPPKPKDTLMISRTPEVTCVVVDVSH<br>EDPEVKFNWYVDGVEVHNAKTKPREEQYNSTYRWSVLTVLHQDWLNGKE<br>YKCKVSNKALPAPIEKTISKAKGQPREPQVYTLPPSRDELTKNQVSLTCL<br>VKGFYPSDIAVEWESNGQPENNYKTTPPVLDSDGSFFLYSKLTVDKSRWQ<br>QGNVFSCSVLHEALHSHYTQKSLSLSPGK [SEQ ID NO: 201] |
| DNA<br>for<br>Light<br>Chain | | GAGTCTGTGCTGACGCAGCCGCCCTCAGTGTCTGGGGCCCCAG<br>GGCAGAGGGTCACCATCTCCTGCACTGGGATGAACTCCAACATCGGGGCA<br>GGTTATGATGTATACTGGTACCAACAACTTCCAGGAAGAGCCCCCAAACT<br>CCTCATCTATGGTAACAGCAATCGGCCCTCAGGGGTCCCTGACCGATTCT<br>CTGGCTCCAGGTCTGGCACCTCAGCCTCCCTGGCCATCACTGGGCTCCAG<br>GCTGAGGATGAGGCTGATTATTACTGCCAGTCCTATGACACCAGCCTGGA<br>CGGTTGGGCTTTCGGCGGAGGGACCAAGTTGACCGTCCTAGGCCAGCCCA<br>AGGCTGCCCCCTCGGTCACTCTGTTCCCACCCTCCTCTGAGGAGCTTCAA<br>GCCAACAAGGCCACACTGGTGTGTCTCGTAAGTGACTTCTACCCGGGAGC<br>CGTGACAGTGGCCTGGAAGGCAGATGGCAGCCCCGTCAAGGTGGGAGTGG<br>AGACCACCAAACCCTCCAAACAAAGCAACAACAAGTATGCGGCCAGCAGC<br>TACCTGAGCCTGACGCCCGAGCAGTGGAAGTCCCACAGAAGCTACAGCTG<br>CCGGGTCACGCATGAAGGGAGCACCGTGGAGAAGACAGTGGCCCCTGCAG<br>AATGCTCT [SEQ ID NO: 202] |
| DNA<br>for<br>Heavy<br>Chain<br>version<br>1 | | GAGGTGCAGCTGGTGGAGTCTGGGGGAGGCTTGG<br>TACAGCCAGGGCGGTCCCTGAGACTCCCCTGTACAGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACAAAGT<br>ACGCCGCGGCTGTGAAGGGCAGATTCACCATCTCGCGAGATGATTCTAAA<br>AGCATTGTCTATCTGCAAATGAACAGCCTGAAAACCGAGGACACAGCCGT<br>GTATTTCTGTACTAGAGTGCAGCTTGACTATGGCCCGGGATACCAGTACT<br>ACGGTATGGACGTCTGGGGCCAAGGGACCACGGTCACCGTCTCCTCAGCC<br>TCCACCAAGGGCCCATCGGTCTTCCCCCTGGCACCCTCCTCCAAGAGCAC<br>CTCTGGGGGCACAGCAGCCCTGGGCTGCCTGGTCAAGGACTACTTCCCCG<br>AACCGGTGACGGTGTCGTGGAACTCAGGCGCCCTGACCAGCGGCGTGCAC<br>ACCTTCCCGGCTGTCCTACAGTCCTCAGGACTCTACTCCCTCAGCAGCGT<br>GGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAA<br>TCTTGTGACAAAACTCACACATGCCCACCGTGCCCAGCACCTGAACTCCT<br>GGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCA<br>TAATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG<br>GCAGCCGGAGAACAACTACAAGACCACGCCTCCCGTGCTGGACTCCGACG<br>GCTCCTTCTTCCTCTACAGCAAGCTCACCGTGGACAAGAGCAGGTGGCAG<br>CAGGGGAACGTCTTCTCATGCTCCGTGATGCATGAGGCTCTGCACAACCA<br>CTACACACAGAAGAGCCTCTCCCTGTCTCCGGGTAAA [SEQ ID NO: 203] |

TABLE 22-continued

Antibody ID: AB-000224.017

| KABAT | ASN |
|---|---|

DNA for Heavy Chain version 2
GAGGTGCAGCTGGTGGAGTCTGGGGGAGGCTTGG
TACAGCCAGGGCGGTCCCTGAGACTCCCCTGTACAGCCTCTGGGTTTAGT
TTTGGTGATCATGCTATGAGCTGGGTCCGCCAGGCTCCAGGGAAGGGGCT
GGAGTGGGTAGGTTTCATTAGAAAGACAACTTATGGTGCGACAACAAAGT
ACGCCGCGGCTGTGAAGGGCAGATTCACCATCTCGCGAGATGATTCTAAA
AGCATTGTCTATCTGCAAATGAACAGCCTGAAAACCGAGGACACAGCCGT
GTATTTCTGTACTAGAGTGCAGCTTGACTATGGCCCGGGATACCAGTACT
ACGGTATGGACGTCTGGGGCCAAGGGACCACGGTCACCGTCTCCTCAGCC
TCCACCAAGGGCCCATCGGTCTTCCCCCTGGCACCCTCCTCCAAGAGCAC
CTCTGGGGGCACAGCAGCCCTGGGCTGCCTGGTCAAGGACTACTTCCCCG
AACCGGTGACGGTGTCGTGGAACTCAGGCGCCCTGACCAGCGGCGTGCAC
ACCTTCCCGGCTGTCCTACAGTCCTCAGGACTCTACTCCCTCAGCAGCGT
GGTGACCGTGCCCTCCAGCAGCTTGGGCACCCAGACCTACATCTGCAACG
TGAATCACAAGCCCAGCAACACCAAGGTGGACAAGAAAGTTGAGCCCAAA
TCTTGTGACAAAACTCACACATGCCCACCGTGCCCAGCACCTGAACTCCT
GGGGGGACCGTCAGTCTTCCTCTTCCCCCCAAAACCCAAGGACACCCTCA
TGATCTCCCGGACCCCTGAGGTCACATGCGTGGTGGTGGACGTGAGCCAC
GAAGACCCTGAGGTCAAGTTCAACTGGTACGTGGACGGCGTGGAGGTGCA
TAATGCCAAGACAAAGCCGCGGGAGGAGCAGTACAACAGCACGTACCGTG
TGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAAC
CATCTCCAAAGCCAAAGGGCAGCCCCGAGAACCACAGGTGTACACCCTGC
CCCCATCCCGGGATGAGCTGACCAAGAACCAGGTCAGCCTGACCTGCCTG
GTCAAAGGCTTCTATCCCAGCGACATCGCCGTGGAGTGGGAGAGCAATGG
GCAGCCGGAGAACAACTACAAGACCACGCCTCCCGTGCTGGACTCCGACG
GCTCCTTCTTCCTCTACAGCAAGCTCACCGTGGACAAGAGCAGGTGGCAG
CAGGGGAACGTCTTCTCATGCTCCGTGCTGCATGAGGCTCTGCACTCCCA
CTACACACAGAAGAGCCTCTCCCTGTCTCCGGGTAAA [SEQ ID NO: 204]

3. Anti-CSP Antibody Variants of AB-007088

In certain embodiments, a variant of an anti-CSP antibody AB-007088 disclosed herein comprises modifications compared to AB-007088 that provide improved pharmacokinetic properties, increased serum stability, stronger binding, and/or improved in vivo protective effects compared to AB-007088. In certain embodiments, a variant of an anti-CSP antibody AB-007088 disclosed herein exhibits reduced immunogenicity and/or increased manufacturability as compared to AB-007088. In certain embodiments, a variant of an anti-CSP antibody AB-007088 disclosed herein has at least one modification, e.g., substitution, relative to the native AB-007088 variable heavy chain amino acid sequence (SEQ ID NO: 196) or variable light chain amino acid sequence (SEQ ID NO: 195), and has improved developability, e.g., decreased heterogeneity, increased yield, increased stability, improved net charges to improve pharmacokinetics, and/or reduced immunogenicity. In certain embodiments, a VH region or a VL region of such a variant of an anti-CSP antibody AB-007088 disclosed herein has at least two, three, four, five, or six, or more modifications, e.g., substitutions. In certain embodiments, a variant of the an anti-CSP antibody AB-007088 disclosed herein has a total of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 modifications, e.g. substitutions, including both variable regions, compared to AB-007088.

In certain embodiments, a variant of an anti-CSP antibody AB-007088 disclosed herein exhibits increased serum half-life as compared to AB-007088. In certain embodiments, a variant of an anti-CSP antibody AB-007088 disclosed herein has at least one modification, e.g., substitution, relative to the native AB-007088 Fc region of the heavy chain herein, and has improved pharmacokinetics properties, e.g., half-life. In certain embodiments, an Fc region of the heavy chain of such a variant of an anti-CSP antibody AB-007088 disclosed herein has at least two, three, four, five, or six, or more modifications, e.g., substitutions. In certain embodiments, a variant of the an anti-CSP antibody AB-007088 disclosed herein has a total of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 modifications, e.g. substitutions, including both heavy and light chains, compared to AB-007088. In certain non-limiting embodiments, an Fc region of the heavy chain of a variant of an anti-CSP antibody AB-007088 disclosed herein can include an isoleucine at position 250, a tyrosine at position 252, an isoleucine at position 259, a glutamine at position 307, a phenylalanine at position 308, a leucine at position 319, a leucine at position 428, a histidine at position 434, a phenylalanine at position 434, an alanine at position 434, a serine at position 434, a methionine at position 434, or a combination thereof, wherein the numbering is defined by EU index as in Kabat. In certain embodiments, an Fc region of the heavy chain of a variant of an anti-CSP antibody AB-007088 disclosed herein includes a leucine at position 428 and a serine at position 434, wherein the numbering is defined by EU index as in Kabat.

The light and heavy chain CDRs of AB-007088 as defined by Kabat numbering system are shown in Table 23 below:

TABLE 23

AB-007088 CDR sequences (Kabat)

|  | CDR1 | CDR2 | CDR3 |
|---|---|---|---|
| VL region | RASQSISSWLA (SEQ ID NO: 205) | DASSLES (SEQ ID NO: 206) | QQYNSYSFWT (SEQ ID NO: 207) |
| VH region | TYGMH (SEQ ID NO: 208) | IIWYDGSQKYYADSVQG (SEQ ID NO: 209) | VRFSVGPHGSAFDL (SEQ ID NO: 210) |

The light and heavy chain CDRs of AB-007088 as defined by ASN are shown in Table 24 below:

TABLE 24

AB-007088 CDR sequences (ASN)

|  | CDR1 | CDR2 | CDR3 |
|---|---|---|---|
| VL region | RASQSISSWLA (SEQ ID NO: 211) | DASSLES (SEQ ID NO: 212) | QQYNSYWT (SEQ ID NO: 213) |
| VH region | TYGMH (SEQ ID NO: 214) | IIWYDGSQKYYADSVQG (SEQ ID NO: 215) | SAFDL (SEQ ID NO: 216) |

The heavy chain variable region (VH) and light chain variable region (VL) sequences and heavy and light chain sequences of AB-007088 are shown in Table 25 below:

TABLE 25

AB-007088 variable region and full-length sequences

| | |
|---|---|
| VL region | GVQMTQSPSTLSASVGDRVTLTCRASQSISSWLAWYQQKPGKAPKLLIYDASSLESG VPSRFSGSGSGTEFTLTISSLQPDDFATYYCQQYNSYSFWTFGQGTKVEIKR (SEQ ID NO: 217) |
| VH region | QVQLVESGGGWQPGRSLRLSCAASGFAFNTYGMHWVRQTPGKGLEWVAIIWYDGSQ KYYADSVQGRFIISRDNHKNTLSLQMNGLRAEDTAVYFCVRVRFSVGPHGSAFDLWG QGTMVIVSS (SEQ ID NO: 218) |
| DNA for VL region | GGCGTCCAGATGACCCAGTCTCCTTCCACCCTGT CTGCATCTGTGGGAGACAGAGTCACCCTCACTTGCCGGGCCAGTCAGAGT ATTAGTAGTTGGTTGGCCTGGTATCAGCAGAAACCAGGGAAAGCCCCTAA ACTCCTGATCTATGATGCCTCCAGTTTGGAAAGTGGGGTCCCATCAAGGT TCAGCGGCAGTGGATCTGGGACAGAATTCACTCTCACCATCAGCAGCCTG CAACCTGATGATTTTGCAACTTATTACTGCCAACAGTATAATAGTTATTC TTTTTGGACGTTCGGCCAAGGGACCAAGGTGGAAATCAAACGC [SEQ ID NO: 219] |
| DNA for VH region | CAGGTGCAACTGGTGGAGTCTGGGGGAGGCGTGG TCCAGCCTGGGAGGTCCCTGAGACTCTCCTGTGCAGCGTCTGGGTTCGCT TTCAATACCTATGGCATGCACTGGGTCCGCCAGACTCCAGGCAAGGGGCT GGAGTGGGTGGCAATTATCTGGTATGATGGGAGCCAGAAATACTATGCAG ACTCCGTGCAGGGCCGATTCATCATCTCCAGAGACAATCACAAGAACACG TTGTCTCTGCAAATGAACGGCCTGAGAGCCGAGGACACGGCTGTGTATTT CTGTGTGAGAGTCCGCTTTAGCGTTGGCCCCCACGGGAGTGCTTTTGATC TCTGGGGCCAGGGGACAATGGTCATCGTCTCTTCA [SEQ ID NO: 220] |
| Light Chain | GVQMTQSPSTLSASVGDRVTLTCRASQS ISSWLAWYQQKPGKAPKLLIYDASSLESGVPSRFSGSGSGTEFTLTISSL QPDDFATYYCQQYNSYSFWTFGQGTKVEIKRTVAAPSVFIFPPSDEQLKS GTASVVCLLNNFYPREAKVQWKVDNALQSGNSQESVTEQDSKDSTYSLSS TLTLSKADYEKHKVYACEVTHQGLSSPVTKSFNRGEC [SEQ ID NO: 221] |
| Heavy Chain version 1 | QVQLVESGGGVVQPGRSLRLSCAASGFA FNTYGMHWVRQTPGKGLEWVAIIWYDGSQKYYADSVQGRFIISRDNHKNT LSLQMNGLRAEDTAVYFCVRVRFSVGPHGSAFDLWGQGTMVIVSSASTKG PSVFPLAPSSKSTSGGTAALGCLVKDYFPEPVTVSWNSGALTSGVHTFPA VLQSSGLYSLSSVVTVPSSSLGTQTYICNVNHKPSNTKVDKKVEPKSCDK |

TABLE 25-continued

AB-007088 variable region and full-length sequences

|  |  |
|---|---|
|  | THTCPPCPAPELLGGPSVFLFPPKPKDTLMISRTPEVTCVVVDVSHEDPE<br>VKFNWYVDGVEVHNAKTKPREEQYNSTYRWSVLTVLHQDWLNGKEYKCK<br>VSNKALPAPIEKTISKAKGQPREPQVYTLPPSRDELTKNQVSLTCLVKGF<br>YPSDIAVEWESNGQPENNYKTTPPVLDSDGSFFLYSKLTVDKSRWQQGNV<br>FSCSVMHEALHNHYTQKSLSLSPGK [SEQ ID NO: 222] |
| Heavy Chain version 2 | QVQLVESGGGVVQPGRSLRLSCAASGFA<br>FNTYGMHWVRQTPGKGLEWVAIIWYDGSQKYYADSVQGRFIISRDNHKNT<br>LSLQMNGLRAEDTAVYFCVRVRFSVGPHGSAFDLWGQGTMVIVSSASTKG<br>PSVFPLAPSSKSTSGGTAALGCLVKDYFPEPVTVSWNSGALTSGVHTFPA<br>VLQSSGLYSLSSVVTVPSSSLGTQTYICNVNHKPSNTKVDKKVEPKSCDK<br>THTCPPCPAPELLGGPSVFLFPPKPKDTLMISRTPEVTCVVVDVSHEDPE<br>VKFNWYVDGVEVHNAKTKPREEQYNSTYRWSVLTVLHQDWLNGKEYKCK<br>VSNKALPAPIEKTISKAKGQPREPQVYTLPPSRDELTKNQVSLTCLVKGF<br>YPSDIAVEWESNGQPENNYKTTPPVLDSDGSFFLYSKLTVDKSRWQQGNV<br>FSCSVLHEALHSHYTQKSLSLSPGK [SEQ ID NO: 223] |
| DNA for Light Chain | GGCGTCCAGATGACCCAGTCTCCTTCCACCCTGT<br>CTGCATCTGTGGGAGACAGAGTCACCCTCACTTGCCGGGCCAGTCAGAGT<br>ATTAGTAGTTGGTTGGCCTGGTATCAGCAGAAACCAGGGAAAGCCCCTAA<br>ACTCCTGATCTATGATGCCTCCAGTTTGGAAAGTGGGGTCCCATCAAGGT<br>TCAGCGGCAGTGGATCTGGGACAGAATTCACTCTCACCATCAGCAGCCTG<br>CAACCTGATGATTTTGCAACTTATTACTGCCAACAGTATAATAGTTATTC<br>TTTTTGGACGTTCGGCCAAGGGACCAAGGTGGAAATCAAACGCACTGTGG<br>CTGCACCATCTGTCTTCATCTTCCCGCCATCTGATGAGCAGTTGAAATCT<br>GGAACTGCCTCTGTTGTGTGCCTGCTGAATAACTTCTATCCCAGAGAGGC<br>CAAAGTACAGTGGAAGGTGGATAACGCCCTCCAATCGGGTAACTCCCAGG<br>AGAGTGTCACAGAGCAGGACAGCAAGGACAGCACCTACAGCCTCAGCAGC<br>ACCCTGACGCTGAGCAAAGCAGACTACGAGAAACACAAAGTCTACGCCTG<br>CGAAGTCACCCATCAGGGCCTGAGCTCGCCCGTCACAAAGAGCTTCAACA<br>GGGGAGAGTGT<br>[SEQ ID NO: 224] |
| DNA for Heavy Chain version 1 | CAGGTGCAACTGGTGGAGTCTGGGGGAGGCGTGG<br>TCCAGCCTGGGAGGTCCCTGAGACTCTCCTGTGCAGCGTCTGGGTTCGCT<br>TTCAATACCTATGGCATGCACTGGGTCCGCCAGACTCCAGGCAAGGGGCT<br>GGAGTGGGTGGCAATTATCTGGTATGATGGGAGCCAGAAATACTATGCAG<br>ACTCCGTGCAGGGCCGATTCATCATCTCCAGAGACAATCACAAGAACACG<br>TTGTCTCTGCAAATGAACGGCCTGAGAGCCGAGGACACGGCTGTGTATTT<br>CTGTGTGAGAGTCCGCTTTAGCGTTGGCCCCCACGGGAGTGCTTTTGATC<br>TCTGGGGCCAGGGGACAATGGTCATCGTCTCTTCAGCCTCCACCAAGGGC<br>CCATCGGTCTTCCCCCTGGCACCCTCCTCCAAGAGCACCTCTGGGGGCAC<br>AGCAGCCCTGGGCTGCCTGGTCAAGGACTACTTCCCCGAACCGGTGACGG<br>TGTCGTGGAACTCAGGCGCCCTGACCAGCGGCGTGCACACCTTCCCGGCT<br>GTCCTACAGTCCTCAGGACTCTACTCCCTCAGCAGCGTGGTGACCGTGCC<br>CTCCAGCAGCTTGGGCACCCAGACCTACATCTGCAACGTGAATCACAAGC<br>CCAGCAACACCAAGGTGGACAAGAAAGTTGAGCCCAAATCTTGTGACAAA<br>ACTCACACATGCCCACCGTGCCCAGCACCTGAACTCCTGGGGGGACCGTC<br>AGTCTTCCTCTTCCCCCCAAAACCCAAGGACACCCTCATGATCTCCCGGA<br>CCCCTGAGGTCACATGCGTGGTGGTGGACGTGAGCCACGAAGACCCTGAG<br>GTCAAGTTCAACTGGTACGTGGACGGCGTGGAGGTGCATAATGCCAAGAC<br>AAAGCCGCGGGAGGAGCAGTACAACAGCACGTACCGTGTGGTCAGCGTCC<br>TCACCGTCCTGCACCAGGACTGGCTGAATGGCAAGGAGTACAAGTGCAAG<br>GTCTCCAACAAAGCCCTCCCAGCCCCCATCGAGAAAACCATCTCCAAAGC<br>CAAAGGGCAGCCCCGAGAACCACAGGTGTACACCCTGCCCCCATCCCGGG<br>ATGAGCTGACCAAGAACCAGGTCAGCCTGACCTGCCTGGTCAAAGGCTTC<br>TATCCCAGCGACATCGCCGTGGAGTGGGAGAGCAATGGGCAGCCGGAGAA<br>CAACTACAAGACCACGCCTCCCGTGCTGGACTCCGACGGCTCCTTCTTCC<br>TCTACAGCAAGCTCACCGTGGACAAGAGCAGGTGGCAGCAGGGGAACGTC<br>TTCTCATGCTCCGTGATGCATGAGGCTCTGCACAACCACTACACACAGAA<br>GAGCCTCTCCCTGTCTCCGGGTAAA [SEQ ID NO: 225] |
| DNA for Heavy Chain version 2 | CAGGTGCAACTGGTGGAGTCTGGGGGAGGCGTGG<br>TCCAGCCTGGGAGGTCCCTGAGACTCTCCTGTGCAGCGTCTGGGTTCGCT<br>TTCAATACCTATGGCATGCACTGGGTCCGCCAGACTCCAGGCAAGGGGCT<br>GGAGTGGGTGGCAATTATCTGGTATGATGGGAGCCAGAAATACTATGCAG<br>ACTCCGTGCAGGGCCGATTCATCATCTCCAGAGACAATCACAAGAACACG<br>TTGTCTCTGCAAATGAACGGCCTGAGAGCCGAGGACACGGCTGTGTATTT<br>CTGTGTGAGAGTCCGCTTTAGCGTTGGCCCCCACGGGAGTGCTTTTGATC<br>TCTGGGGCCAGGGGACAATGGTCATCGTCTCTTCAGCCTCCACCAAGGGC<br>CCATCGGTCTTCCCCCTGGCACCCTCCTCCAAGAGCACCTCTGGGGGCAC<br>AGCAGCCCTGGGCTGCCTGGTCAAGGACTACTTCCCCGAACCGGTGACGG<br>TGTCGTGGAACTCAGGCGCCCTGACCAGCGGCGTGCACACCTTCCCGGCT<br>GTCCTACAGTCCTCAGGACTCTACTCCCTCAGCAGCGTGGTGACCGTGCC<br>CTCCAGCAGCTTGGGCACCCAGACCTACATCTGCAACGTGAATCACAAGC<br>CCAGCAACACCAAGGTGGACAAGAAAGTTGAGCCCAAATCTTGTGACAAA<br>ACTCACACATGCCCACCGTGCCCAGCACCTGAACTCCTGGGGGGACCGTC<br>AGTCTTCCTCTTCCCCCCAAAACCCAAGGACACCCTCATGATCTCCCGGA |

TABLE 25-continued

AB-007088 variable region and full-length sequences

```
CCCCTGAGGTCACATGCGTGGTGGTGGACGTGAGCCACGAAGACCCTGAG
GTCAAGTTCAACTGGTACGTGGACGGCGTGGAGGTGCATAATGCCAAGAC
AAAGCCGCGGGAGGAGCAGTACAACAGCACGTACCGTGTGGTCAGCGTCC
TCACCGTCCTGCACCAGGACTGGCTGAATGGCAAGGAGTACAAGTGCAAG
GTCTCCAACAAAGCCCTCCCAGCCCCCATCGAGAAAACCATCTCCAAAGC
CAAAGGGCAGCCCCGAGAACCACAGGTGTACACCCTGCCCCCATCCCGGG
ATGAGCTGACCAAGAACCAGGTCAGCCTGACCTGCCTGGTCAAAGGCTTC
TATCCCAGCGACATCGCCGTGGAGTGGGAGAGCAATGGGCAGCCGGAGAA
CAACTACAAGACCACGCCTCCCGTGCTGGACTCCGACGGCTCCTTCTTCC
TCTACAGCAAGCTCACCGTGGACAAGAGCAGGTGGCAGCAGGGGAACGTC
TTCTCATGCTCCGTGCTGCATGAGGCTCTGCACTCCCACTACACACAGAA
GAGCCTCTCCCTGTCTCCGGGTAAA [SEQ ID NO: 226]
```

In certain embodiments, a variant of an anti-CSP antibody includes one, two, or three CDRs of a VL sequence of Table 25. In certain embodiments, a variant of an anti-CSP antibody includes at least one mutation, e.g., a substitution, and no more than 10, 20, 30, 40, or 50 mutations in the VL amino acid sequence set forth in SEQ ID NO: 217. In certain embodiments, the VL of the variant of an anti-CSP antibody includes at least one, at least two, or at least three mutations, e.g., substitutions, in the CDR1 amino acid sequence set forth in SEQ ID NO: 205. In certain embodiments, the VL of the variant of an anti-CSP antibody includes at least one, at least two, or at least three mutations, e.g., substitutions, in the CDR2 amino acid sequence set forth in SEQ ID NO: 206. In certain embodiments, the VL of the variant of an anti-CSP antibody includes at least one, at least two, or at least three mutations, e.g., substitutions, in the CDR3 amino acid sequence set forth in SEQ ID NO: 207. In certain embodiments, the VL of the variant of an anti-CSP antibody includes at least one, at least two, or at least three mutations, e.g., substitutions, in the CDR1 amino acid sequence set forth in SEQ ID NO: 211. In certain embodiments, the VL of the variant of an anti-CSP antibody includes at least one, at least two, or at least three mutations, e.g., substitutions, in the CDR2 amino acid sequence set forth in SEQ ID NO: 212. In certain embodiments, the VL of the variant of an anti-CSP antibody includes at least one, at least two, or at least three mutations, e.g., substitutions, in the CDR3 amino acid sequence set forth in SEQ ID NO: 213. In certain embodiments, the mutation is a conservative substitution. In certain embodiments, the VL of the variant of an anti-CSP antibody includes at least one, at least two, or at least three mutations, e.g., substitutions, in the framework of the amino acid sequence set forth in SEQ ID NO: 217. An exemplary nucleic acid sequence of SEQ ID NO: 217 is set forth in SEQ ID NO: 219.

In certain embodiments, a variant of an anti-CSP antibody includes one, two, or three CDRs of a VH sequence of Table 25. In certain embodiments, a variant of an anti-CSP antibody includes at least one mutation, e.g., a substitution, and no more than 10, 20, 30, 40, or 50 mutations in the VH amino acid sequence set forth in SEQ ID NO: 218. In certain embodiments, the VH of the variant of an anti-CSP antibody includes at least one, at least two, or at least three mutations, e.g., substitutions, in the CDR1 amino acid sequence set forth in SEQ ID NO: 208. In certain embodiments, the VH of the variant of an anti-CSP antibody includes at least one, at least two, or at least three mutations, e.g., substitutions, in the CDR2 amino acid sequence set forth in SEQ ID NO: 209. In certain embodiments, the VH of the variant of an anti-CSP antibody includes at least one, at least two, or at least three mutations, e.g., substitutions, in the CDR3 amino acid sequence set forth in SEQ ID NO: 210. In certain embodiments, the VH of the variant of an anti-CSP antibody includes at least one, at least two, or at least three mutations, e.g., substitutions, in the CDR1 amino acid sequence set forth in SEQ ID NO: 214. In certain embodiments, the VH of the variant of an anti-CSP antibody includes at least one, at least two, or at least three mutations, e.g., substitutions, in the CDR2 amino acid sequence set forth in SEQ ID NO: 215. In certain embodiments, the VH of the variant of an anti-CSP antibody includes at least one, at least two, or at least three mutations, e.g., substitutions, in the CDR3 amino acid sequence set forth in SEQ ID NO: 216. In certain embodiments, the mutation is a conservative substitution. In certain embodiments, the VH of the variant of an anti-CSP antibody includes at least one, at least two, at least three mutations, at least four mutations, at least five mutations, or at least six mutations, e.g., substitutions, in the framework of the amino acid sequence set forth in SEQ ID NO: 218. An exemplary nucleic acid sequence of SEQ ID NO: 218 is set forth in SEQ ID NO: 220. In certain embodiments, the VH of the variant of an anti-CSP antibody includes a substitution at position 28 of the SEQ ID NO: 218. In certain embodiments, the substitution is A28T. In certain embodiments, the VH of the variant of an anti-CSP antibody includes a substitution at position 40 of the SEQ ID NO: 218. In certain embodiments, the substitution is T40A. In certain embodiments, the VH of the variant of an anti-CSP antibody includes a substitution at position 69 of the SEQ ID NO: 218. In certain embodiments, the substitution is I69T. In certain embodiments, the VH of the variant of an anti-CSP antibody includes a substitution at position 80 of the SEQ ID NO: 218. In certain embodiments, the substitution is S80Y. In certain embodiments, the VH of the variant of an anti-CSP antibody includes a substitution at position 85 of the SEQ ID NO: 218. In certain embodiments, the substitution is G85S. In certain embodiments, the VH of the variant of an anti-CSP antibody includes a substitution at position 120 of the SEQ ID NO: 218. In certain embodiments, the substitution is I120T.

In certain embodiments, the light chain of the variant of an anti-CSP antibody has an amino acid sequence set forth in SEQ ID NO: 221. An exemplary nucleic acid sequence of SEQ ID NO: 221 is set forth in SEQ ID NO: 224. In certain embodiments, a variant of an anti-CSP antibody includes at least one mutation, e.g., substitution, and no more than 10, 20, 30, 40, or 50 mutations in the Fc region of the heavy chain amino acid sequence set forth in SEQ ID NO: 222. In certain embodiments, the heavy chain of the variant of an anti-CSP antibody has an amino acid sequence set forth in SEQ ID NO: 222. An exemplary nucleic acid sequence of SEQ ID NO: 222 is set forth in SEQ ID NO: 225. In certain embodiments, the heavy chain of the variant of an anti-CSP antibody includes a substitution at position 434 of the SEQ ID NO: 222. In certain embodiments, the substitution is M434L. In certain embodiments, the heavy chain of the variant of an anti-CSP antibody includes a substitution at position 440 of the SEQ ID NO: 222. In certain embodiments, the substitution is L440S. In certain embodiments, the heavy chain of the variant of an anti-CSP antibody includes a substitution at position 434 of the SEQ ID NO: 222 and a substitution at position 440 of the SEQ ID NO: 222. In certain embodiments, the substitutions are M434L and N440S. In certain embodiments, the heavy chain of the variant of an anti-CSP antibody has an amino acid sequence set forth in SEQ ID NO: 223. An exemplary nucleic acid sequence of SEQ ID NO: 223 is set forth in SEQ ID NO: 226.

In certain embodiments, the light chain of the anti-CSP antibody AB-007088 and variants thereof comprises a signal peptide. In certain embodiments, the signal peptide is an IGLV2-8 signal peptide. In certain embodiments, the signal peptide has an amino acid sequence set forth in SEQ ID NO: 277. In certain embodiments, the heavy chain of the anti-CSP antibody AB-007088 and variants thereof comprises a signal peptide. In certain embodiments, the signal peptide is an IGKV1-39 signal peptide. In certain embodiments, the signal peptide has an amino acid sequence set forth in SEQ ID NO: 278.

In certain embodiments, the anti-CSP antibody variant comprises a light chain variable region comprising a CDR1, a CDR2, and a CDR3 and having the amino acid sequence set forth in SEQ ID NO: 227, as shown in Table 26. In certain embodiments, the anti-CSP antibody variant comprises a heavy chain variable region comprising a CDR1, a CDR2, and a CDR3 and having the amino acid sequence set forth in SEQ ID NO: 228, as shown in Table 26. In certain embodiments, the anti-CSP antibody variant comprises a light chain having the amino acid sequence set forth in SEQ ID NO: 231, as shown in Table 26. In certain embodiments, the anti-CSP antibody variant comprises a heavy chain having the amino acid sequence set forth in SEQ ID NO: 232, as shown in Table 26. In certain embodiments, the anti-CSP antibody variant comprises a heavy chain having the amino acid sequence set forth in SEQ ID NO: 233, as shown in Table 26. Exemplary nucleic acid sequences of SEQ ID NOS: 227, 228, 231, 232, and 233 are provided in Table 26 below.

TABLE 26

Antibody ID: AB-007088.001

| | KABAT | ASN |
|---|---|---|
| CDR1-VL | RASQSISSWLA [SEQ ID NO: 205] | RASQSISSWLA [SEQ ID NO: 211] |
| CDR2-VL | DASSLES [SEQ ID NO: 206] | DASSLES [SEQ ID NO: 212] |
| CDR3-VL | QQYNSYSFWT [SEQ ID NO: 207] | QQYNSYSFWTF [SEQ ID NO: 213] |
| CDR1-VH | TYGMH [SEQ ID NO: 208] | TYGMH [SEQ ID NO: 214] |
| CDR2-VH | IIWYDGSQKYYADSVQG [SEQ ID NO: 209] | IIWYDGSQKYYADSVQG [SEQ ID NO: 215] |
| CDR3-VH | VRFSVGPHGSAFDL [SEQ ID NO: 210] | SAFDL [SEQ ID NO: 216] |
| VL | GVQMTQSPSTLSASVGDRVTLTCRASQSISSWLAWYQQKPGKAPKLLIYDASSLESGVPSRFSGSGSGTEFTLTISSLQPDDFATYYCQQYNSYSFWTFGQGTKVEIKR [SEQ ID NO: 227] | |
| VH | QVQLVESGGGVVQPGRSLRLSCAASGFAFNTYGMHWVRQAPGKGLEWVAIIWYDGSQKYYADSVQGRFIISRDNHKNTLSLQMNSLRAEDTAVYFCVRVRFSVGPHGSAFDLWGQGTMVTVSS [SEQ ID NO: 228] | |
| DNA for VL | GGCGTCCAGATGACCCAGTCTCCTTCCACCCTGTCTGCATCTGTGGGAGACAGAGTCACCCTCACTTGCCGGGCCAGTCAGAGTATTAGTAGTTGGTTGGCCTGGTATCAGCAGAAACCAGGGAAAGCCCCTAAACTCCTGATCTATGATGCCTCCAGTTTGGAAAGTGGGGTCCCATCAAGGTTCAGCGGCAGTGGATCTGGGACAGAATTCACTCTCACCATCAGCAGCCTGCAACCTGATGATTTTGCAACTTATTACTGCCAACAGTATAATAGTTATTCTTTTTGGACGTTCGGCCAAGGGACCAAGGTGGAAATCAAACGC [SEQ ID NO: 229] | |
| DNA for VH | CAGGTGCAACTGGTGGAGTCTGGGGGAGGCGTGGTCCAGCCTGGGAGGTCCCTGAGACTCTCCTGTGCAGCGTCTGGGTTCGCTTTCAATACCTATGGCATGCACTGGGTCCGCCAGGCACCAGGCAAGGGGCTGGAGTGGGTGGCAATTATCTGGTATGATGGGAGCCAGAAATACTATGCAGACTCCGTGCAGGGCCGATTCATCATCTCCAGAGACAATCACAAGAACACGTTGTCTCTGCAAATGAACTCCCTGAGAGCCGAGGACACGGCTGTGTATTTCTGTGTGAGAGTCCGCTTTAGCGTTGGCCCCACGGGAGTGCTTTTGATCTCTGGGGCCAGGGGACAATGGTCACAGTCTCTTCA [SEQ ID NO: 230] | |

TABLE 26-continued

Antibody ID: AB-007088.001

| | KABAT | ASN |
|---|---|---|

Light Chain
GVQMTQSPSTLSASVGDRVTLTCRASQS
ISSWLAWYQQKPGKAPKLLIYDASSLESGVPSRFSGSGSGTEFTLTISSL
QPDDFATYYCQQYNSYSFWTFGQGTKVEIKRTVAAPSVFIFPPSDEQLKS
GTASVVCLLNNFYPREAKVQWKVDNALQSGNSQESVTEQDSKDSTYSLSS
TLTLSKADYEKHKVYACEVTHQGLSSPVTKSFNRGEC
[SEQ ID NO: 231]

Heavy Chain version 1
QVQLVESGGGVVQPGRSLRLSCAASGFA
FNTYGMHWVRQAPGKGLEWVAIIWYDGSQKYYADSVQGRFIISRDNHKNT
LSLQMNSLRAEDTAVYFCVRVRFSVGPHGSAFDLWGQGTMVTVSSASTKG
PSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDK
THTCPPCPAPELLGGPSVFLFPPKPKDTLMISRTPEVTCVVVDVSHEDPE
VKFNWYVDGVEVHNAKTKPREEQYNSTYRWSVLTVLHQDWLNGKEYKCK
VSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNV
FSCSVMHEALHNHYTQKSLSLSPGK
[SEQ ID NO: 232]

Heavy Chain version 2
QVQLVESGGGVVQPGRSLRLSCAASGFA
FNTYGMHWVRQAPGKGLEWVAIIWYDGSQKYYADSVQGRFIISRDNHKNT
LSLQMNSLRAEDTAVYFCVRVRFSVGPHGSAFDLWGQGTMVTVSSASTKG
PSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDK
THTCPPCPAPELLGGPSVFLFPPKPKDTLMISRTPEVTCVVVDVSHEDPE
VKFNWYVDGVEVHNAKTKPREEQYNSTYRWSVLTVLHQDWLNGKEYKCK
VSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNV
FSCSVLHEALHSHYTQKSLSLSPGK [SEQ ID NO: 233]

DNA for Light Chain
GGCGTCCAGATGACCCAGTCTCCTTCCACCCTGT
CTGCATCTGTGGGAGACAGAGTCACCCTCACTTGCCGGGCCAGTCAGAGT
ATTAGTAGTTGGTTGGCCTGGTATCAGCAGAAACCAGGGAAAGCCCCTAA
ACTCCTGATCTATGATGCCTCCAGTTTGGAAAGTGGGGTCCCATCAAGGT
TCAGCGGCAGTGGATCTGGGACAGAATTCACTCTCACCATCAGCAGCCTG
CAACCTGATGATTTTGCAACTTATTACTGCCAACAGTATAATAGTTATTC
TTTTTTGGACGTTCGGCCAAGGGACCAAGGTGGAAATCAAACGCACTGTGG
CTGCACCATCTGTCTTCATCTTCCCGCCATCTGATGAGCAGTTGAAATCT
GGAACTGCCTCTGTTGTGTGCCTGCTGAATAACTTCTATCCCAGAGAGGC
CAAAGTACAGTGGAAGGTGGATAACGCCCTCCAATCGGGTAACTCCCAGG
AGAGTGTCACAGAGCAGGACAGCAAGGACAGCACCTACAGCCTCAGCAGC
ACCCTGACGCTGAGCAAAGCAGACTACGAGAAACACAAAGTCTACGCCTG
CGAAGTCACCCATCAGGGCCTGAGCTCGCCCGTCACAAAGAGCTTCAACA
GGGGAGAGTGT
[SEQ ID NO: 234]

DNA for Heavy Chain version 1
CAGGTGCAACTGGTGGAGTCTGGGGGAGGCGTGG
TCCAGCCTGGGAGGTCCCTGAGACTCTCCTGTGCAGCGTCTGGGTTCGCT
TTCAATACCTATGGCATGCACTGGGTCCGCCAGGCACCAGGCAAGGGGCT
GGAGTGGGTGGCAATTATCTGGTATGATGGGAGCCAGAAATACTATGCAG
ACTCCGTGCAGGGCCGATTCATCATCTCCAGAGACAATCACAAGAACACG
TTGTCTCTGCAAATGAACTCCCTGAGAGCCGAGGACACGGCTGTGTATTT
CTGTGTGAGAGTCCGCTTTAGCGTTGGCCCCCACGGGAGTGCTTTTGATC
TCTGGGGCCAGGGGACAATGGTCACAGTCTCTTCAGCCTCCACCAAGGGC
CCATCGGTCTTCCCCCTGGCACCCTCCTCCAAGAGCACCTCTGGGGGCAC
AGCAGCCCTGGGCTGCCTGGTCAAGGACTACTTCCCCGAACCGGTGACGG
TGTCGTGGAACTCAGGCGCCCTGACCAGCGGCGTGCACACCTTCCCGGCT
GTCCTACAGTCCTCAGGACTCTACTCCCTCAGCAGCGTGGTGACCGTGCC
CTCCAGCAGCTTGGGCACCCAGACCTACATCTGCAACGTGAATCACAAGC
CCAGCAACACCAAGGTGGACAAGAAAGTTGAGCCCAAATCTTGTGACAAA
ACTCACACATGCCCACCGTGCCCAGCACCTGAACTCCTGGGGGGACCGTC
AGTCTTCCTCTTCCCCCCAAAACCCAAGGACACCCTCATGATCTCCCGGA
CCCCTGAGGTCACATGCGTGGTGGTGGACGTGAGCCACGAAGACCCTGAG
GTCAAGTTCAACTGGTACGTGGACGGCGTGGAGGTGCATAATGCCAAGAC
AAAGCCGCGGGAGGAGCAGTACAACAGCACGTACCGTGTGGTCAGCGTCC
TCACCGTCCTGCACCAGGACTGGCTGAATGGCAAGGAGTACAAGTGCAAG
GTCTCCAACAAAGCCCTCCCAGCCCCCATCGAGAAAACCATCTCCAAAGC
CAAAGGGCAGCCCCGAGAACCACAGGTGTACACCCTGCCCCCATCCCGGG
ATGAGCTGACCAAGAACCAGGTCAGCCTGACCTGCCTGGTCAAAGGCTTC
TATCCCAGCGACATCGCCGTGGAGTGGGAGAGCAATGGGCAGCCGGAGAA
CAACTACAAGACCACGCCTCCCGTGCTGGACTCCGACGGCTCCTTCTTCC
TCTACAGCAAGCTCACCGTGGACAAGAGCAGGTGGCAGCAGGGGAACGTC
TTCTCATGCTCCGTGATGCATGAGGCTCTGCACAACCACTACACACAGAA
GAGCCTCTCCCTGTCTCCGGGTAAA [SEQ ID NO: 235]

TABLE 26-continued

Antibody ID: AB-007088.001

| | KABAT | ASN |
|---|---|---|
| DNA for Heavy Chain version 2 | CAGGTGCAACTGGTGGAGTCTGGGGGAGGCGTGG<br>TCCAGCCTGGGAGGTCCCTGAGACTCTCCTGTGCAGCGTCTGGGTTCGCT<br>TTCAATACCTATGGCATGCACTGGGTCCGCCAGGCACCAGGCAAGGGGCT<br>GGAGTGGGTGGCAATTATCTGGTATGATGGGAGCCAGAAATACTATGCAG<br>ACTCCGTGCAGGGCCGATTCATCATCTCCAGAGACAATCACAAGAACACG<br>TTGTCTCTGCAAATGAACTCCCTGAGAGCCGAGGACACGGCTGTGTATTT<br>CTGTGTGAGAGTCCGCTTTAGCGTTGGCCCCCACGGGAGTGCTTTTGATC<br>TCTGGGGCCAGGGGACAATGGTCACAGTCTCTTCAGCCTCCACCAAGGGC<br>CCATCGGTCTTCCCCCTGGCACCCTCCTCCAAGAGCACCTCTGGGGGCAC<br>AGCAGCCCTGGGCTGCCTGGTCAAGGACTACTTCCCCGAACCGGTGACGG<br>TGTCGTGGAACTCAGGCGCCCTGACCAGCGGCGTGCACACCTTCCCGGCT<br>GTCCTACAGTCCTCAGGACTCTACTCCCTCAGCAGCGTGGTGACCGTGCC<br>CTCCAGCAGCTTGGGCACCCAGACCTACATCTGCAACGTGAATCACAAGC<br>CCAGCAACACCAAGGTGGACAAGAAAGTTGAGCCCAAATCTTGTGACAAA<br>ACTCACACATGCCCACCGTGCCCAGCACCTGAACTCCTGGGGGGACCGTC<br>AGTCTTCCTCTTCCCCCCAAAACCCAAGGACACCCTCATGATCTCCCGGA<br>CCCCTGAGGTCACATGCGTGGTGGTGGACGTGAGCCACGAAGACCCTGAG<br>GTCAAGTTCAACTGGTACGTGGACGGCGTGGAGGTGCATAATGCCAAGAC<br>AAAGCCGCGGGAGGAGCAGTACAACAGCACGTACCGTGTGGTCAGCGTCC<br>TCACCGTCCTGCACCAGGACTGGCTGAATGGCAAGGAGTACAAGTGCAAG<br>GTCTCCAACAAAGCCCTCCCAGCCCCCATCGAGAAAACCATCTCCAAAGC<br>CAAAGGGCAGCCCCGAGAACCACAGGTGTACACCCTGCCCCCATCCCGGG<br>ATGAGCTGACCAAGAACCAGGTCAGCCTGACCTGCCTGGTCAAAGGCTTC<br>TATCCCAGCGACATCGCCGTGGAGTGGGAGAGCAATGGGCAGCCGGAGAA<br>CAACTACAAGACCACGCCTCCCGTGCTGGACTCCGACGGCTCCTTCTTCC<br>TCTACAGCAAGCTCACCGTGGACAAGAGCAGGTGGCAGCAGGGGAACGTC<br>TTCTCATGCTCCGTGCTGCATGAGGCTCTGCACTCCCACTACACACAGAA<br>GAGCCTCTCCCTGTCTCCGGGTAAA [SEQ ID NO: 236] | |

In certain embodiments, the anti-CSP antibody variant comprises a light chain variable region comprising a CDR1, a CDR2, and a CDR3 and having the amino acid sequence set forth in SEQ ID NO: 237, as shown in Table 27. In certain embodiments, the anti-CSP antibody variant comprises a heavy chain variable region comprising a CDR1, a CDR2, and a CDR3 and having the amino acid sequence set forth in SEQ ID NO: 238, as shown in Table 27. In certain embodiments, the anti-CSP antibody variant comprises a light chain having the amino acid sequence set forth in SEQ ID NO: 241, as shown in Table 27. In certain embodiments, the anti-CSP antibody variant comprises a heavy chain having the amino acid sequence set forth in SEQ ID NO: 242, as shown in Table 27. In certain embodiments, the anti-CSP antibody variant comprises a heavy chain having the amino acid sequence set forth in SEQ ID NO: 243, as shown in Table 27. Exemplary nucleic acid sequences of SEQ ID NOS: 237, 238, 241, 242, and 243 are provided in Table 27 below.

TABLE 27

Antibody ID: AB-007088.002

| | KABAT | ASN |
|---|---|---|
| CDR1-VL | RASQSISSWLA [SEQ ID NO: 205] | RASQSISSWLA [SEQ ID NO: 211] |
| CDR2-VL | DASSLES [SEQ ID NO: 206] | DASSLES [SEQ ID NO: 212] |
| CDR3-VL | QQYNSYSFWT [SEQ ID NO: 207] | QQYNSYSFWTF [SEQ ID NO: 213] |
| CDR1-VH | TYGMH [SEQ ID NO: 208] | TYGMH [SEQ ID NO: 214] |
| CDR2-VH | IIWYDGSQKYYADSVQG [SEQ ID NO: 209] | IIWYDGSQKYYADSVQG [SEQ ID NO: 215] |
| CDR3-VH | VRFSVGPHGSAFDL [SEQ ID NO: 210] | SAFDL [SEQ ID NO: 216] |
| VL | GVQMTQSPSTLSASVGDRVTLTCRASQS<br>ISSWLAWYQQKPGKAPKLLIYDASSLESGVPSRFSGSGSGTEFTLTISSL<br>QPDDFATYYCQQYNSYSFWTFGQGTKVEIKR<br>[SEQ ID NO: 237] | |

TABLE 27-continued

Antibody ID: AB-007088.002

| | KABAT | ASN |
|---|---|---|

VH
QVQLVESGGGVVQPGRSLRLSCAASGFT
FNTYGMHWVRQAPGKGLEWVAIIWYDGSQKYYADSVQGRFIISRDNHKNT
LSLQMNSLRAEDTAVYFCVRVRFSVGPHGSAFDLWGQGTMVTVSS
[SEQ ID NO: 238]

DNA for VL
GGCGTCCAGATGACCCAGTCTCCTTCCACCCTGT
CTGCATCTGTGGGAGACAGAGTCACCCTCACTTGCCGGGCCAGTCAGAGT
ATTAGTAGTTGGTTGGCCTGGTATCAGCAGAAACCAGGGAAAGCCCCTAA
ACTCCTGATCTATGATGCCTCCAGTTTGGAAAGTGGGGTCCCATCAAGGT
TCAGCGGCAGTGGATCTGGGACAGAATTCACTCTCACCATCAGCAGCCTG
CAACCTGATGATTTTGCAACTTATTACTGCCAACAGTATAATAGTTATTC
TTTTTGGACGTTCGGCCAAGGGACCAAGGTGGAAATCAAACGC
[SEQ ID NO: 239]

DNA forVH
CAGGTGCAACTGGTGGAGTCTGGGGGAGGCGTGG
TCCAGCCTGGGAGGTCCCTGAGACTCTCCTGTGCAGCGTCTGGGTTCACT
TTCAATACCTATGGCATGCACTGGGTCCGCCAGGCACCAGGCAAGGGGCT
GGAGTGGGTGGCAATTATCTGGTATGATGGGAGCCAGAAATACTATGCAG
ACTCCGTGCAGGGCCGATTCATCATCTCCAGAGACAATCACAAGAACACG
TTGTCTCTGCAAATGAACTCCCTGAGAGCCGAGGACACGGCTGTGTATTT
CTGTGTGAGAGTCCGCTTTAGCGTTGGCCCCCACGGGAGTGCTTTTGATC
TCTGGGGCCAGGGGACAATGGTCACAGTCTCTTCA
[SEQ ID NO: 240]

Light Chain
GVQMTQSPSTLSASVGDRVTLTCRASQS
ISSWLAWYQQKPGKAPKLLIYDASSLESGVPSRFSGSGSGTEFTLTISSL
QPDDFATYYCQQYNSYSFWTFGQGTKVEIKRTVAAPSVFIFPPSDEQLKS
GTASVVCLLNNFYPREAKVQWKVDNALQSGNSQESVTEQDSKDSTYSLSS
TLTLSKADYEKHKVYACEVTHQGLSSPVTKSFNRGEC
[SEQ ID NO: 241]

Heavy Chain version 1
QVQLVESGGGVVQPGRSLRLSCAASGFT
FNTYGMHWVRQAPGKGLEWVAIIWYDGSQKYYADSVQGRFIISRDNHKNT
LSLQMNSLRAEDTAVYFCVRVRFSVGPHGSAFDLWGQGTMVTVSSASTKG
PSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDK
THTCPPCPAPELLGGPSVFLFPPKPKDTLMISRTPEVTCVVVDVSHEDPE
VKFNWYVDGVEVHNAKTKPREEQYNSTYRWSVLTVLHQDWLNGKEYKCK
VSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNV
FSCSVMHEALHNHYTQKSLSLSPGK
[SEQ ID NO: 242]

Heavy Chain version 2
QVQLVESGGGVVQPGRSLRLSCAASGFT
FNTYGMHWVRQAPGKGLEWVAIIWYDGSQKYYADSVQGRFIISRDNHKNT
LSLQMNSLRAEDTAVYFCVRVRFSVGPHGSAFDLWGQGTMVTVSSASTKG
PSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDK
THTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKCK
VSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNV
FSCSVLHEALHSHYTQKSLSLSPGK [SEQ ID NO: 243]

DNA for Light Chain
GGCGTCCAGATGACCCAGTCTCCTTCCACCCTGT
CTGCATCTGTGGGAGACAGAGTCACCCTCACTTGCCGGGCCAGTCAGAGT
ATTAGTAGTTGGTTGGCCTGGTATCAGCAGAAACCAGGGAAAGCCCCTAA
ACTCCTGATCTATGATGCCTCCAGTTTGGAAAGTGGGGTCCCATCAAGGT
TCAGCGGCAGTGGATCTGGGACAGAATTCACTCTCACCATCAGCAGCCTG
CAACCTGATGATTTTGCAACTTATTACTGCCAACAGTATAATAGTTATTC
TTTTTGGACGTTCGGCCAAGGGACCAAGGTGGAAATCAAACGCACTGTGG
CTGCACCATCTGTCTTCATCTTCCCGCCATCTGATGAGCAGTTGAAATCT
GGAACTGCCTCTGTTGTGTGCCTGCTGAATAACTTCTATCCCAGAGAGGC
CAAAGTACAGTGGAAGGTGGATAACGCCCTCCAATCGGGTAACTCCCAGG
AGAGTGTCACAGAGCAGGACAGCAAGGACAGCACCTACAGCCTCAGCAGC
ACCCTGACGCTGAGCAAAGCAGACTACGAGAAACACAAAGTCTACGCCTG
CGAAGTCACCCATCAGGGCCTGAGCTCGCCCGTCACAAAGAGCTTCAACA
GGGGAGAGTGT
[SEQ ID NO: 244]

TABLE 27-continued

Antibody ID: AB-007088.002

| | KABAT | ASN |
|---|---|---|

| DNA for Heavy Chain version 1 | CAGGTGCAACTGGTGGAGTCTGGGGGAGGCGTGG<br>TCCAGCCTGGGAGGTCCCTGAGACTCTCCTGTGCAGCGTCTGGGTTCACT<br>TTCAATACCTATGGCATGCACTGGGTCCGCCAGGCACCAGGCAAGGGGCT<br>GGAGTGGGTGGCAATTATCTGGTATGATGGGAGCCAGAAATACTATGCAG<br>ACTCCGTGCAGGGCCGATTCATCATCTCCAGAGACAATCACAAGAACACG<br>TTGTCTCTGCAAATGAACTCCCTGAGAGCCGAGGACACGGCTGTGTATTT<br>CTGTGTGAGAGTCCGCTTTAGCGTTGGCCCCCACGGGAGTGCTTTTGATC<br>TCTGGGGCCAGGGGACAATGGTCACAGTCTCTTCAGCCTCCACCAAGGGC<br>CCATCGGTCTTCCCCCTGGCACCCTCCTCCAAGAGCACCTCTGGGGGCAC<br>AGCAGCCTGGGCTGCCTGGTCAAGGACTACTTCCCCGAACCGGTGACGG<br>TGTCGTGGAACTCAGGCGCCCTGACCAGCGGCGTGCACACCTTCCCGGCT<br>GTCCTACAGTCCTCAGGACTCTACTCCCTCAGCAGCGTGGTGACCGTGCC<br>CTCCAGCAGCTTGGGCACCCAGACCTACATCTGCAACGTGAATCACAAGC<br>CCAGCAACACCAAGGTGGACAAGAAAGTTGAGCCCAAATCTTGTGACAAA<br>ACTCACACATGCCCACCGTGCCCAGCACCTGAACTCCTGGGGGACCGTC<br>AGTCTTCCTCTTCCCCCCAAAACCCAAGGACACCCTCATGATCTCCCGGA<br>CCCCTGAGGTCACATGCGTGGTGGTGGACGTGAGCCACGAAGACCCTGAG<br>GTCAAGTTCAACTGGTACGTGGACGGCGTGGAGGTGCATAATGCCAAGAC<br>AAAGCCGCGGGAGGAGCAGTACAACAGCACGTACCGTGTGGTCAGCGTCC<br>TCACCGTCCTGCACCAGGACTGGCTGAATGGCAAGGAGTACAAGTGCAAG<br>GTCTCCAACAAAGCCCTCCCAGCCCCCATCGAGAAAACCATCTCCAAAGC<br>CAAAGGGCAGCCCCGAGAACCACAGGTGTACACCCTGCCCCCATCCCGGG<br>ATGAGCTGACCAAGAACCAGGTCAGCCTGACCTGCCTGGTCAAAGGCTTC<br>TATCCCAGCGACATCGCCGTGGAGTGGGAGAGCAATGGGCAGCCGGAGAA<br>CAACTACAAGACCACGCCTCCCGTGCTGGACTCCGACGGCTCCTTCTTCC<br>TCTACAGCAAGCTCACCGTGGACAAGAGCAGGTGGCAGCAGGGGAACGTC<br>TTCTCATGCTCCGTGATGCATGAGGCTCTGCACAACCACTACACACAGAA<br>GAGCCTCTCCCTGTCTCCGGGTAAA [SEQ ID NO: 245] | |

| DNA for Heavy Chain version 2 | CAGGTGCAACTGGTGGAGTCTGGGGGAGGCGTGG<br>TCCAGCCTGGGAGGTCCCTGAGACTCTCCTGTGCAGCGTCTGGGTTCACT<br>TTCAATACCTATGGCATGCACTGGGTCCGCCAGGCACCAGGCAAGGGGCT<br>GGAGTGGGTGGCAATTATCTGGTATGATGGGAGCCAGAAATACTATGCAG<br>ACTCCGTGCAGGGCCGATTCATCATCTCCAGAGACAATCACAAGAACACG<br>TTGTCTCTGCAAATGAACTCCCTGAGAGCCGAGGACACGGCTGTGTATTT<br>CTGTGTGAGAGTCCGCTTTAGCGTTGGCCCCCACGGGAGTGCTTTTGATC<br>TCTGGGGCCAGGGGACAATGGTCACAGTCTCTTCAGCCTCCACCAAGGGC<br>CCATCGGTCTTCCCCCTGGCACCCTCCTCCAAGAGCACCTCTGGGGGCAC<br>AGCAGCCTGGGCTGCCTGGTCAAGGACTACTTCCCCGAACCGGTGACGG<br>TGTCGTGGAACTCAGGCGCCCTGACCAGCGGCGTGCACACCTTCCCGGCT<br>GTCCTACAGTCCTCAGGACTCTACTCCCTCAGCAGCGTGGTGACCGTGCC<br>CTCCAGCAGCTTGGGCACCCAGACCTACATCTGCAACGTGAATCACAAGC<br>CCAGCAACACCAAGGTGGACAAGAAAGTTGAGCCCAAATCTTGTGACAAA<br>ACTCACACATGCCCACCGTGCCCAGCACCTGAACTCCTGGGGGACCGTC<br>AGTCTTCCTCTTCCCCCCAAAACCCAAGGACACCCTCATGATCTCCCGGA<br>CCCCTGAGGTCACATGCGTGGTGGTGGACGTGAGCCACGAAGACCCTGAG<br>GTCAAGTTCAACTGGTACGTGGACGGCGTGGAGGTGCATAATGCCAAGAC<br>AAAGCCGCGGGAGGAGCAGTACAACAGCACGTACCGTGTGGTCAGCGTCC<br>TCACCGTCCTGCACCAGGACTGGCTGAATGGCAAGGAGTACAAGTGCAAG<br>GTCTCCAACAAAGCCCTCCCAGCCCCCATCGAGAAAACCATCTCCAAAGC<br>CAAAGGGCAGCCCCGAGAACCACAGGTGTACACCCTGCCCCCATCCCGGG<br>ATGAGCTGACCAAGAACCAGGTCAGCCTGACCTGCCTGGTCAAAGGCTTC<br>TATCCCAGCGACATCGCCGTGGAGTGGGAGAGCAATGGGCAGCCGGAGAA<br>CAACTACAAGACCACGCCTCCCGTGCTGGACTCCGACGGCTCCTTCTTCC<br>TCTACAGCAAGCTCACCGTGGACAAGAGCAGGTGGCAGCAGGGGAACGTC<br>TTCTCATGCTCCGTGCTGCATGAGGCTCTGCACTCCCACTACACACAGAA<br>GAGCCTCTCCCTGTCTCCGGGTAAA [SEQ ID NO: 246] | |

In certain embodiments, the anti-CSP antibody variant comprises a light chain variable region comprising a CDR1, a CDR2, and a CDR3 and having the amino acid sequence set forth in SEQ ID NO: 247, as shown in Table 28. In certain embodiments, the anti-CSP antibody variant comprises a heavy chain variable region comprising a CDR1, a CDR2, and a CDR3 and having the amino acid sequence set forth in SEQ ID NO: 248, as shown in Table 28. In certain embodiments, the anti-CSP antibody variant comprises a light chain having the amino acid sequence set forth in SEQ ID NO: 251, as shown in Table 28. In certain embodiments, the anti-CSP antibody variant comprises a heavy chain having the amino acid sequence set forth in SEQ ID NO: 252, as shown in Table 28. In certain embodiments, the anti-CSP antibody variant comprises a heavy chain having the amino acid sequence set forth in SEQ ID NO: 253, as shown in Table 28. Exemplary nucleic acid sequences of SEQ ID NOS: 247, 248, 251, 252, and 253 are provided in Table 28 below.

TABLE 28

| | Antibody ID: AB-007088.003 | |
|---|---|---|
| | KABAT | ASN |
| CDR1-VL | RASQSISSWLA [SEQ ID NO: 205] | RASQSISSWLA [SEQ ID NO: 211] |
| CDR2-VL | DASSLES [SEQ ID NO: 206] | DASSLES [SEQ ID NO: 212] |
| CDR3-VL | QQYNSYSFWT [SEQ ID NO: 207] | QQYNSYSFWTF [SEQ ID NO: 213] |
| CDR1-VH | TYGMH [SEQ ID NO: 208] | TYGMH [SEQ ID NO: 214] |
| CDR2-VH | IIWYDGSQKYYADSVQG [SEQ ID NO: 209] | IIWYDGSQKYYADSVQG [SEQ ID NO: 215] |
| CDR3-VH | VRFSVGPHGSAFDL [SEQ ID NO: 210] | SAFDL [SEQ ID NO: 216] |
| VL | GVQMTQSPSTLSASVGDRVTLTCRASQS ISSWLAWYQQKPGKAPKLLIYDASSLESGVPSRFSGSGSGTEFTLTISSL QPDDFATYYCQQYNSYSFWTFGQGTKVEIKR [SEQ ID NO: 247] | |
| VH | QVQLVESGGGVVQPGRSLRLSCAASGFA FNTYGMHWVRQAPGKGLEWVAIIWYDGSQKYYADSVQGRFTISRDNHKNT LSLQMNSLRAEDTAVYFCVRVRFSVGPHGSAFDLWGQGTMVTVSS [SEQ ID NO: 248] | |
| DNA for VL | GGCGTCCAGATGACCCAGTCTCCTTCCACCCTGT CTGCATCTGTGGGAGACAGAGTCACCCTCACTTGCCGGGCCAGTCAGAGT ATTAGTAGTTGGTTGGCCTGGTATCAGCAGAAACCAGGGAAAGCCCCTAA ACTCCTGATCTATGATGCCTCCAGTTTGGAAAGTGGGGTCCCATCAAGGT TCAGCGGCAGTGGATCTGGGACAGAATTCACTCTCACCATCAGCAGCCTG CAACCTGATGATTTTGCAACTTATTACTGCCAACAGTATAATAGTTATTC TTTTTGGACGTTCGGCCAAGGGACCAAGGTGGAAATCAAACGC [SEQ ID NO: 249] | |
| DNA forVH | CAGGTGCAACTGGTGGAGTCTGGGGGAGGCGTGG TCCAGCCTGGGAGGTCCCTGAGACTCTCCTGTGCAGCGTCTGGGTTCGCT TTCAATACCTATGGCATGCACTGGGTCCGCCAGGCACCAGGCAAGGGGCT GGAGTGGGTGGCAATTATCTGGTATGATGGGAGCCAGAAATACTATGCAG ACTCCGTGCAGGGCCGATTCACTATCTCCAGAGACAATCACAAGAACACG TTGTCTCTGCAAATGAACTCCCTGAGAGCCGAGGACACGGCTGTGTATTT CTGTGTGAGAGTCCGCTTTAGCGTTGGCCCCCACGGGAGTGCTTTTGATC TCTGGGGCCAGGGGACAATGGTCACAGTCTCTTCA [SEQ ID NO: 250] | |
| Light Chain | GVQMTQSPSTLSASVGDRVTLTCRASQS ISSWLAWYQQKPGKAPKLLIYDASSLESGVPSRFSGSGSGTEFTLTISSL QPDDFATYYCQQYNSYSFWTFGQGTKVEIKRTVAAPSVFIFPPSDEQLKS GTASVVCLLNNFYPREAKVQWKVDNALQSGNSQESVTEQDSKDSTYSLSS TLTLSKADYEKHKVYACEVTHQGLSSPVTKSFNRGEC [SEQ ID NO: 251] | |
| Heavy Chain version 1 | QVQLVESGGGVVQPGRSLRLSCAASGFA FNTYGMHWVRQAPGKGLEWVAIIWYDGSQKYYADSVQGRFTISRDNHKNT LSLQMNSLRAEDTAVYFCVRVRFSVGPHGSAFDLWGQGTMVTVSSASTKG PSVFPLAPSSKSTSGGTAALGCLVKDYFPEPVTVSWNSGALTSGVHTFPA VLQSSGLYSLSSVVTVPSSSLGTQTYICNVNHKPSNTKVDKKVEPKSCDK THTCPPCPAPELLGGPSVFLFPPKPKDTLMISRTPEVTCVVVDVSHEDPE VKFNWYVDGVEVHNAKTKPREEQYNSTYRWSVLTVLHQDWLNGKEYKCK VSNKALPAPIEKTISKAKGQPREPQVYTLPPSRDELTKNQVSLTCLVKGF YPSDIAVEWESNGQPENNYKTTPPVLDSDGSFFLYSKLTVDKSRWQQGNV FSCSVMHEALHNHYTQKSLSLSPGK [SEQ ID NO: 252] | |
| Heavy Chain version 2 | QVQLVESGGGVVQPGRSLRLSCAASGFA FNTYGMHWVRQAPGKGLEWVAIIWYDGSQKYYADSVQGRFTISRDNHKNT LSLQMNSLRAEDTAVYFCVRVRFSVGPHGSAFDLWGQGTMVTVSSASTKG PSVFPLAPSSKSTSGGTAALGCLVKDYFPEPVTVSWNSGALTSGVHTFPA VLQSSGLYSLSSVVTVPSSSLGTQTYICNVNHKPSNTKVDKKVEPKSCDK THTCPPCPAPELLGGPSVFLFPPKPKDTLMISRTPEVTCVVVDVSHEDPE VKFNWYVDGVEVHNAKTKPREEQYNSTYRWSVLTVLHQDWLNGKEYKCK VSNKALPAPIEKTISKAKGQPREPQVYTLPPSRDELTKNQVSLTCLVKGF YPSDIAVEWESNGQPENNYKTTPPVLDSDGSFFLYSKLTVDKSRWQQGNV FSCSVLHEALHSHYTQKSLSLSPGK [SEQ ID NO: 253] | |

TABLE 28-continued

Antibody ID: AB-007088.003

| | KABAT | ASN |
|---|---|---|

| DNA for Light Chain | GGCGTCCAGATGACCCAGTCTCCTTCCACCCTGT<br>CTGCATCTGTGGGAGACAGAGTCACCCTCACTTGCCGGGCCAGTCAGAGT<br>ATTAGTAGTTGGTTGGCCTGGTATCAGCAGAAACCAGGGAAAGCCCCTAA<br>ACTCCTGATCTATGATGCCTCCAGTTTGGAAAGTGGGGTCCCATCAAGGT<br>TCAGCGGCAGTGGATCTGGGACAGAATTCACTCTCACCATCAGCAGCCTG<br>CAACCTGATGATTTTGCAACTTATTACTGCCAACAGTATAATAGTTATTC<br>TTTTTGGACGTTCGGCCAAGGGACCAAGGTGGAAATCAAACGCACTGTGG<br>CTGCACCATCTGTCTTCATCTTCCCGCCATCTGATGAGCAGTTGAAATCT<br>GGAACTGCCTCTGTTGTGTGCCTGCTGAATAACTTCTATCCCAGAGAGGC<br>CAAAGTACAGTGGAAGGTGGATAACGCCCTCCAATCGGGTAACTCCCAGG<br>AGAGTGTCACAGAGCAGGACAGCAAGGACAGCACCTACAGCCTCAGCAGC<br>ACCCTGACGCTGAGCAAAGCAGACTACGAGAAACACAAAGTCTACGCCTG<br>CGAAGTCACCCATCAGGGCCTGAGCTCGCCCGTCACAAAGAGCTTCAACA<br>GGGGAGAGTGT<br>[SEQ ID NO: 254] | |
| DNA for Heavy Chain version 1 | CAGGTGCAACTGGTGGAGTCTGGGGGAGGCGTGG<br>TCCAGCCTGGGAGGTCCCTGAGACTCTCCTGTGCAGCGTCTGGGTTCGCT<br>TTCAATACCTATGGCATGCACTGGGTCCGCCAGGCACCAGGCAAGGGGCT<br>GGAGTGGGTGGCAATTATCTGGTATGATGGGAGCCAGAAATACTATGCAG<br>ACTCCGTGCAGGGCCGATTCACTATCTCCAGAGACAATCACAAGAACACG<br>TTGTCTCTGCAAATGAACTCCCTGAGAGCCGAGGACACGGCTGTGTATTT<br>CTGTGTGAGAGTCCGCTTTAGCGTTGGCCCCACGGGAGTGCTTTTGATC<br>TCTGGGGCCAGGGGACAATGGTCACAGTCTCTTCAGCCTCCACCAAGGGC<br>CCATCGGTCTTCCCCCTGGCACCCTCCTCCAAGAGCACCTCTGGGGGCAC<br>AGCAGCCCTGGGCTGCCTGGTCAAGGACTACTTCCCCGAACCGGTGACGG<br>TGTCGTGGAACTCAGGCGCCCTGACCAGCGGCGTGCACACCTTCCCGGCT<br>GTCCTACAGTCCTCAGGACTCTACTCCCTCAGCAGCGTGGTGACCGTGCC<br>CTCCAGCAGCTTGGGCACCCAGACCTACATCTGCAACGTGAATCACAAGC<br>CCAGCAACACCAAGGTGGACAAGAAAGTTGAGCCCAAATCTTGTGACAAA<br>ACTCACACATGCCCACCGTGCCCAGCACCTGAACTCCTGGGGGGACCGTC<br>AGTCTTCCTCTTCCCCCCAAAACCCAAGGACACCCTCATGATCTCCCGGA<br>CCCCTGAGGTCACATGCGTGGTGGTGGACGTGAGCCACGAAGACCCTGAG<br>GTCAAGTTCAACTGGTACGTGGACGGCGTGGAGGTGCATAATGCCAAGAC<br>AAAGCCGCGGGAGGAGCAGTACAACAGCACGTACCGTGTGGTCAGCGTCC<br>TCACCGTCCTGCACCAGGACTGGCTGAATGGCAAGGAGTACAAGTGCAAG<br>GTCTCCAACAAAGCCCTCCCAGCCCCCATCGAGAAAACCATCTCCAAAGC<br>CAAAGGGCAGCCCCGAGAACCACAGGTGTACACCCTGCCCCCATCCCGGG<br>ATGAGCTGACCAAGAACCAGGTCAGCCTGACCTGCCTGGTCAAAGGCTTC<br>TATCCCAGCGACATCGCCGTGGAGTGGGAGAGCAATGGGCAGCCGGAGAA<br>CAACTACAAGACCACGCCTCCCGTGCTGGACTCCGACGGCTCCTTCTTCC<br>TCTACAGCAAGCTCACCGTGGACAAGAGCAGGTGGCAGCAGGGGAACGTC<br>TTCTCATGCTCCGTGATGCATGAGGCTCTGCACAACCACTACACACAGAA<br>GAGCCTCTCCCTGTCTCCGGGTAAA [SEQ ID NO: 255] | |
| DNA for Heavy Chain version 2 | CAGGTGCAACTGGTGGAGTCTGGGGGAGGCGTGG<br>TCCAGCCTGGGAGGTCCCTGAGACTCTCCTGTGCAGCGTCTGGGTTCGCT<br>TTCAATACCTATGGCATGCACTGGGTCCGCCAGGCACCAGGCAAGGGGCT<br>GGAGTGGGTGGCAATTATCTGGTATGATGGGAGCCAGAAATACTATGCAG<br>ACTCCGTGCAGGGCCGATTCACTATCTCCAGAGACAATCACAAGAACACG<br>TTGTCTCTGCAAATGAACTCCCTGAGAGCCGAGGACACGGCTGTGTATTT<br>CTGTGTGAGAGTCCGCTTTAGCGTTGGCCCCCACGGGAGTGCTTTTGATC<br>TCTGGGGCCAGGGGACAATGGTCACAGTCTCTTCAGCCTCCACCAAGGGC<br>CCATCGGTCTTCCCCCTGGCACCCTCCTCCAAGAGCACCTCTGGGGGCAC<br>AGCAGCCCTGGGCTGCCTGGTCAAGGACTACTTCCCCGAACCGGTGACGG<br>TGTCGTGGAACTCAGGCGCCCTGACCAGCGGCGTGCACACCTTCCCGGCT<br>GTCCTACAGTCCTCAGGACTCTACTCCCTCAGCAGCGTGGTGACCGTGCC<br>CTCCAGCAGCTTGGGCACCCAGACCTACATCTGCAACGTGAATCACAAGC<br>CCAGCAACACCAAGGTGGACAAGAAAGTTGAGCCCAAATCTTGTGACAAA<br>ACTCACACATGCCCACCGTGCCCAGCACCTGAACTCCTGGGGGGACCGTC<br>AGTCTTCCTCTTCCCCCCAAAACCCAAGGACACCCTCATGATCTCCCGGA<br>CCCCTGAGGTCACATGCGTGGTGGTGGACGTGAGCCACGAAGACCCTGAG<br>GTCAAGTTCAACTGGTACGTGGACGGCGTGGAGGTGCATAATGCCAAGAC<br>AAAGCCGCGGGAGGAGCAGTACAACAGCACGTACCGTGTGGTCAGCGTCC<br>TCACCGTCCTGCACCAGGACTGGCTGAATGGCAAGGAGTACAAGTGCAAG<br>GTCTCCAACAAAGCCCTCCCAGCCCCCATCGAGAAAACCATCTCCAAAGC<br>CAAAGGGCAGCCCCGAGAACCACAGGTGTACACCCTGCCCCCATCCCGGG<br>ATGAGCTGACCAAGAACCAGGTCAGCCTGACCTGCCTGGTCAAAGGCTTC<br>TATCCCAGCGACATCGCCGTGGAGTGGGAGAGCAATGGGCAGCCGGAGAA<br>CAACTACAAGACCACGCCTCCCGTGCTGGACTCCGACGGCTCCTTCTTCC<br>TCTACAGCAAGCTCACCGTGGACAAGAGCAGGTGGCAGCAGGGGAACGTC<br>TTCTCATGCTCCGTGCTGCATGAGGCTCTGCACTCCCACTACACACAGAA<br>GAGCCTCTCCCTGTCTCCGGGTAAA [SEQ ID NO: 256] | |

In certain embodiments, the anti-CSP antibody variant comprises a light chain variable region comprising a CDR1, a CDR2, and a CDR3 and having the amino acid sequence set forth in SEQ ID NO: 257, as shown in Table 29. In certain embodiments, the anti-CSP antibody variant comprises a heavy chain variable region comprising a CDR1, a CDR2, and a CDR3 and having the amino acid sequence set forth in SEQ ID NO: 258, as shown in Table 29. In certain embodiments, the anti-CSP antibody variant comprises a light chain having the amino acid sequence set forth in SEQ ID NO: 261, as shown in Table 29. In certain embodiments, the anti-CSP antibody variant comprises a heavy chain having the amino acid sequence set forth in SEQ ID NO: 262, as shown in Table 29. In certain embodiments, the anti-CSP antibody variant comprises a heavy chain having the amino acid sequence set forth in SEQ ID NO: 263, as shown in Table 29. Exemplary nucleic acid sequences of SEQ ID NOS: 257, 258, 261, 262, and 263 are provided in Table 29 below.

TABLE 29

| Antibody ID: AB-007088.004 | | |
|---|---|---|
| | KABAT | ASN |
| CDR1-VL | RASQSISSWLA [SEQ ID NO: 205] | RASQSISSWLA [SEQ ID NO: 211] |
| CDR2-VL | DASSLES [SEQ ID NO: 206] | DASSLES [SEQ ID NO: 212] |
| CDR3-VL | QQYNSYSFWT [SEQ ID NO: 207] | QQYNSYSFWTF [SEQ ID NO: 213] |
| CDR1-VH | TYGMH [SEQ ID NO: 208] | TYGMH [SEQ ID NO: 214] |
| CDR2-VH | IIWYDGSQKYYADSVQG [SEQ ID NO: 209] | IIWYDGSQKYYADSVQG [SEQ ID NO: 215] |
| CDR3-VH | VRFSVGPHGSAFDL [SEQ ID NO: 210] | SAFDL [SEQ ID NO: 216] |
| VL | GVQMTQSPSTLSASVGDRVTLTCRASQS ISSWLAWYQQKPGKAPKLLIYDASSLESGVPSRFSGSGSGTEFTLTISSL QPDDFATYYCQQYNSYSFWTFGQGTKVEIKR [SEQ ID NO: 257] | |
| VH | QVQLVESGGGVVQPGRSLRLSCAASGFT FNTYGMHWVRQAPGKGLEWVAIIWYDGSQKYYADSVQGRFTISRDNHKNT LSLQMNSLRAEDTAVYFCVRVRFSVGPHGSAFDLWGQGTMVTVSS [SEQ ID NO: 258] | |
| DNA for VL | GGCGTCCAGATGACCCAGTCTCCTTCCACCCTGT CTGCATCTGTGGGAGACAGAGTCACCCTCACTTGCCGGGCCAGTCAGAGT ATTAGTAGTTGGTTGGCCTGGTATCAGCAGAAACCAGGGAAAGCCCCTAA ACTCCTGATCTATGATGCCTCCAGTTTGGAAAGTGGGGTCCCATCAAGGT TCAGCGGCAGTGGATCTGGGACAGAATTCACTCTCACCATCAGCAGCCTG CAACCTGATGATTTTGCAACTTATTACTGCCAACAGTATAATAGTTATTC TTTTTGGACGTTCGGCCAAGGGACCAAGGTGGAAATCAAACGC [SEQ ID NO: 259] | |
| DNA forVH | CAGGTGCAACTGGTGGAGTCTGGGGGAGGCGTGG TCCAGCCTGGGAGGTCCCTGAGACTCTCCTGTGCAGCGTCTGGGTTCACT TTCAATACCTATGGCATGCACTGGGTCCGCCAGGCACCAGGCAAGGGGCT GGAGTGGGTGGCAATTATCTGGTATGATGGGAGCCAGAAATACTATGCAG ACTCCGTGCAGGGCCGATTCACTATCTCCAGAGACAATCACAAGAACACG TTGTCTCTGCAAATGAACTCCCTGAGAGCCGAGGACACGGCTGTGTATTT CTGTGTGAGAGTCCGCTTTAGCGTTGGCCCCCACGGGAGTGCTTTTGATC TCTGGGGCCAGGGGACAATGGTCACAGTCTCTTCA [SEQ ID NO: 260] | |
| Light Chain | GVQMTQSPSTLSASVGDRVTLTCRASQS ISSWLAWYQQKPGKAPKLLIYDASSLESGVPSRFSGSGSGTEFTLTISSL QPDDFATYYCQQYNSYSFWTFGQGTKVEIKRTVAAPSVFIFPPSDEQLKS GTASVVCLLNNFYPREAKVQWKVDNALQSGNSQESVTEQDSKDSTYSLSS TLTLSKADYEKHKVYACEVTHQGLSSPVTKSFNRGEC [SEQ ID NO: 261] | |
| Heavy Chain version 1 | QVQLVESGGGVVQPGRSLRLSCAASGFT FNTYGMHWVRQAPGKGLEWVAIIWYDGSQKYYADSVQGRFTISRDNHKNT LSLQMNSLRAEDTAVYFCVRVRFSVGPHGSAFDLWGQGTMVTVSSASTKG PSVFPLAPSSKSTSGGTAALGCLVKDYFPEPVTVSWNSGALTSGVHTFPA VLQSSGLYSLSSVVTVPSSSLGTQTYICNVNHKPSNTKVDKKVEPKSCDK THTCPPCPAPELLGGPSVFLFPPKPKDTLMISRTPEVTCVVVDVSHEDPE | |

TABLE 29-continued

Antibody ID: AB-007088.004

| KABAT | ASN |
|---|---|

VKFNWYVDGVEVHNAKTKPREEQYNSTYRWSVLTVLHQDWLNGKEYKCK
VSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNV
FSCSVMHEALHNHYTQKSLSLSPGK
[SEQ ID NO: 262]

Heavy Chain version 2
QVQLVESGGGVVQPGRSLRLSCAASGFT
FNTYGMHWVRQAPGKGLEWVAIIWYDGSQKYYADSVQGRFTISRDNHKNT
LSLQMNSLRAEDTAVYFCVRVRFSVGPHGSAFDLWGQGTMVTVSSASTKG
PSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDK
THTCPPCPAPELLGGPSVFLFPPKPKDTLMISRTPEVTCVVVDVSHEDPE
VKFNWYVDGVEVHNAKTKPREEQYNSTYRWSVLTVLHQDWLNGKEYKCK
VSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNV
FSCSVLHEALHSHYTQKSLSLSPGK [SEQ ID NO: 263]

DNA for Light Chain
GGCGTCCAGATGACCCAGTCTCCTTCCACCCTGT
CTGCATCTGTGGGAGACAGAGTCACCCTCACTTGCCGGGCCAGTCAGAGT
ATTAGTAGTTGGTTGGCCTGGTATCAGCAGAAACCAGGGAAAGCCCCTAA
ACTCCTGATCTATGATGCCTCCAGTTTGGAAAGTGGGGTCCCATCAAGGT
TCAGCGGCAGTGGATCTGGGACAGAATTCACTCTCACCATCAGCAGCCTG
CAACCTGATGATTTTGCAACTTATTACTGCCAACAGTATAATAGTTATTC
TTTTTGGACGTTCGGCCAAGGGACCAAGGTGGAAATCAAACGCACTGTGG
CTGCACCATCTGTCTTCATCTTCCCGCCATCTGATGAGCAGTTGAAATCT
GGAACTGCCTCTGTTGTGTGCCTGCTGAATAACTTCTATCCCAGAGAGGC
CAAAGTACAGTGGAAGGTGGATAACGCCCTCCAATCGGGTAACTCCCAGG
AGAGTGTCACAGAGCAGGACAGCAAGGACAGCACCTACAGCCTCAGCAGC
ACCCTGACGCTGAGCAAAGCAGACTACGAGAAACACAAAGTCTACGCCTG
CGAAGTCACCCATCAGGGCCTGAGCTCGCCCGTCACAAAGAGCTTCAACA
GGGGAGAGTGT
[SEQ ID NO: 264]

DNA for Heavy Chain version 1
CAGGTGCAACTGGTGGAGTCTGGGGGAGGCGTGG
TCCAGCCTGGGAGGTCCCTGAGACTCTCCTGTGCAGCGTCTGGGTTCACT
TTCAATACCTATGGCATGCACTGGGTCCGCCAGGCACCAGGCAAGGGGCT
GGAGTGGGTGGCAATTATCTGGTATGATGGGAGCCAGAAATACTATGCAG
ACTCCGTGCAGGGCCGATTCACTATCTCCAGAGACAATCACAAGAACACG
TTGTCTCTGCAAATGAACTCCCTGAGAGCCGAGGACACGGCTGTGTATTT
CTGTGTGAGAGTCCGCTTTAGCGTTGGCCCCACGGGAGTGCTTTTGATC
TCTGGGGCCAGGGGACAATGGTCACAGTCTCTTCAGCCTCCACCAAGGGC
CCATCGGTCTTCCCCCTGGCACCCTCCTCCAAGAGCACCTCTGGGGGCAC
AGCAGCCCTGGGCTGCCTGGTCAAGGACTACTTCCCCGAACCGGTGACGG
TGTCGTGGAACTCAGGCGCCCTGACCAGCGGCGTGCACACCTTCCCGGCT
GTCCTACAGTCCTCAGGACTCTACTCCCTCAGCAGCGTGGTGACCGTGCC
CTCCAGCAGCTTGGGCACCCAGACCTACATCTGCAACGTGAATCACAAGC
CCAGCAACACCAAGGTGGACAAGAAAGTTGAGCCCAAATCTTGTGACAAA
ACTCACACATGCCCACCGTGCCCAGCACCTGAACTCCTGGGGGGACCGTC
AGTCTTCCTCTTCCCCCCAAAACCCAAGGACACCCTCATGATCTCCCGGA
CCCCTGAGGTCACATGCGTGGTGGTGGACGTGAGCCACGAAGACCCTGAG
GTCAAGTTCAACTGGTACGTGGACGGCGTGGAGGTGCATAATGCCAAGAC
AAAGCCGCGGGAGGAGCAGTACAACAGCACGTACCGTGTGGTCAGCGTCC
TCACCGTCCTGCACCAGGACTGGCTGAATGGCAAGGAGTACAAGTGCAAG
GTCTCCAACAAAGCCCTCCCAGCCCCCATCGAGAAAACCATCTCCAAAGC
CAAAGGGCAGCCCCGAGAACCACAGGTGTACACCCTGCCCCCATCCCGGG
ATGAGCTGACCAAGAACCAGGTCAGCCTGACCTGCCTGGTCAAAGGCTTC
TATCCCAGCGACATCGCCGTGGAGTGGGAGAGCAATGGGCAGCCGGAGAA
CAACTACAAGACCACGCCTCCCGTGCTGGACTCCGACGGCTCCTTCTTCC
TCTACAGCAAGCTCACCGTGGACAAGAGCAGGTGGCAGCAGGGGAACGTC
TTCTCATGCTCCGTGATGCATGAGGCTCTGCACAACCACTACACACAGAA
GAGCCTCTCCCTGTCTCCGGGTAAA [SEQ ID NO: 265]

DNA for Heavy Chain version 2
CAGGTGCAACTGGTGGAGTCTGGGGGAGGCGTGG
TCCAGCCTGGGAGGTCCCTGAGACTCTCCTGTGCAGCGTCTGGGTTCACT
TTCAATACCTATGGCATGCACTGGGTCCGCCAGGCACCAGGCAAGGGGCT
GGAGTGGGTGGCAATTATCTGGTATGATGGGAGCCAGAAATACTATGCAG
ACTCCGTGCAGGGCCGATTCACTATCTCCAGAGACAATCACAAGAACACG
TTGTCTCTGCAAATGAACTCCCTGAGAGCCGAGGACACGGCTGTGTATTT
CTGTGTGAGAGTCCGCTTTAGCGTTGGCCCCACGGGAGTGCTTTTGATC
TCTGGGGCCAGGGGACAATGGTCACAGTCTCTTCAGCCTCCACCAAGGGC
CCATCGGTCTTCCCCCTGGCACCCTCCTCCAAGAGCACCTCTGGGGGCAC
AGCAGCCCTGGGCTGCCTGGTCAAGGACTACTTCCCCGAACCGGTGACGG
TGTCGTGGAACTCAGGCGCCCTGACCAGCGGCGTGCACACCTTCCCGGCT
GTCCTACAGTCCTCAGGACTCTACTCCCTCAGCAGCGTGGTGACCGTGCC
CTCCAGCAGCTTGGGCACCCAGACCTACATCTGCAACGTGAATCACAAGC
CCAGCAACACCAAGGTGGACAAGAAAGTTGAGCCCAAATCTTGTGACAAA
ACTCACACATGCCCACCGTGCCCAGCACCTGAACTCCTGGGGGGACCGTC

TABLE 29-continued

Antibody ID: AB-007088.004

| KABAT | ASN |
|---|---|
| AGTCTTCCTCTTCCCCCCAAAACCCAAGGACACCCTCATGATCTCCCGGA | |
| CCCCTGAGGTCACATGCGTGGTGGTGGACGTGAGCCACGAAGACCCTGAG | |
| GTCAAGTTCAACTGGTACGTGGACGGCGTGGAGGTGCATAATGCCAAGAC | |
| AAAGCCGCGGGAGGAGCAGTACAACAGCACGTACCGTGTGGTCAGCGTCC | |
| TCACCGTCCTGCACCAGGACTGGCTGAATGGCAAGGAGTACAAGTGCAAG | |
| GTCTCCAACAAAGCCCTCCCAGCCCCCATCGAGAAAACCATCTCCAAAGC | |
| CAAAGGGCAGCCCCGAGAACCACAGGTGTACACCCTGCCCCCATCCCGGG | |
| ATGAGCTGACCAAGAACCAGGTCAGCCTGACCTGCCTGGTCAAAGGCTTC | |
| TATCCCAGCGACATCGCCGTGGAGTGGGAGAGCAATGGGCAGCCGGAGAA | |
| CAACTACAAGACCACGCCTCCCGTGCTGGACTCCGACGGCTCCTTCTTCC | |
| TCTACAGCAAGCTCACCGTGGACAAGAGCAGGTGGCAGCAGGGGAACGTC | |
| TTCTCATGCTCCGTGCTGCATGAGGCTCTGCACTCCCACTACACACAGAA | |
| GAGCCTCTCCCTGTCTCCGGGTAAA [SEQ ID NO: 266] | |

In certain embodiments, the anti-CSP antibody variant comprises a light chain variable region comprising a CDR1, a CDR2, and a CDR3 and having the amino acid sequence set forth in SEQ ID NO: 267, as shown in Table 30. In certain embodiments, the anti-CSP antibody variant comprises a heavy chain variable region comprising a CDR1, a CDR2, and a CDR3 and having the amino acid sequence set forth in SEQ ID NO: 268, as shown in Table 30. In certain embodiments, the anti-CSP antibody variant comprises a light chain having the amino acid sequence set forth in SEQ ID NO: 271, as shown in Table 30. In certain embodiments, the anti-CSP antibody variant comprises a heavy chain having the amino acid sequence set forth in SEQ ID NO: 272, as shown in Table 30. In certain embodiments, the anti-CSP antibody variant comprises a heavy chain having the amino acid sequence set forth in SEQ ID NO: 273, as shown in Table 30. Exemplary nucleic acid sequences of SEQ ID NOS: 267, 268, 271, 272, and 273 are provided in Table 30 below.

TABLE 30

Antibody ID: AB-007088.005

| | KABAT | ASN |
|---|---|---|
| CDR1-VL | RASQSISSWLA [SEQ ID NO: 205] | RASQSISSWLA [SEQ ID NO: 211] |
| CDR2-VL | DASSLES [SEQ ID NO: 206] | DASSLES [SEQ ID NO: 212] |
| CDR3-VL | QQYNSYSFWT [SEQ ID NO: 207] | QQYNSYSFWTF [SEQ ID NO: 213] |
| CDR1-VH | TYGMH [SEQ ID NO: 208] | TYGMH [SEQ ID NO: 214] |
| CDR2-VH | IIWYDGSQKYYADSVQG [SEQ ID NO: 209] | IIWYDGSQKYYADSVQG [SEQ ID NO: 215] |
| CDR3-VH | VRFSVGPHGSAFDL [SEQ ID NO: 210] | SAFDL [SEQ ID NO: 216] |
| VL | GVQMTQSPSTLSASVGDRVTLTCRASQSISSWLAWYQQKPGKAPKLLIYDASSLESGVPSRFSGSGSGTEFTLTISSLQPDDFATYYCQQYNSYSFWTFGQGTKVEIKR [SEQ ID NO: 267] | |
| VH | QVQLVESGGGVVQPGRSLRLSCAASGFTFNTYGMHWVRQAPGKGLEWVAIIWYDGSQKYYADSVQGRFTISRDNHKNTLYLQMNSLRAEDTAVYFCVRVRFSVGPHGSAFDLWGQGTMVTVSS [SEQ ID NO: 268] | |
| DNA for VL | GGCGTCCAGATGACCCAGTCTCCTTCCACCCTGTCTGCATCTGTGGGAGACAGAGTCACCCTCACTTGCCGGGCCAGTCAGAGTATTAGTAGTTGGTTGGCCTGGTATCAGCAGAAACCAGGGAAAGCCCCTAAACTCCTGATCTATGATGCCTCCAGTTTGGAAAGTGGGGTCCCATCAAGGTTCAGCGGCAGTGGATCTGGGACAGAATTCACTCTCACCATCAGCAGCCTGCAACCTGATGATTTTGCAACTTATTACTGCCAACAGTATAATAGTTATTCTTTTTGGACGTTCGGCCAAGGGACCAAGGTGGAAATCAAACGC [SEQ ID NO: 269] | |
| DNA forVH | CAGGTGCAACTGGTGGAGTCTGGGGGAGGCGTGGTCCAGCCTGGGAGGTCCCTGAGACTCTCCTGTGCAGCGTCTGGGTTCACTTTCAATACCTATGGCATGCACTGGGTCCGCCAGGCACCAGGCAAGGGGCTGGAGTGGGTGGCAATTATCTGGTATGATGGGAGCCAGAAATACTATGCAG | |

TABLE 30-continued

Antibody ID: AB-007088.005

| | KABAT | ASN |
|---|---|---|
| | ACTCCGTGCAGGGCCGATTCACTATCTCCAGAGACAATCACAAGAACACG<br>TTGTACCTGCAAATGAACTCCCTGAGAGCCGAGGACACGGCTGTGTATTT<br>CTGTGTGAGAGTCCGCTTTAGCGTTGGCCCCCACGGGAGTGCTTTTGATC<br>TCTGGGGCCAGGGGACAATGGTCACAGTCTCTTCA<br>[SEQ ID NO: 270] | |
| Light<br>Chain | GVQMTQSPSTLSASVGDRVTLTCRASQS<br>ISSWLAWYQQKPGKAPKLLIYDASSLESGVPSRFSGSGSGTEFTLTISSL<br>QPDDFATYYCQQYNSYSFWTFGQGTKVEIKRTVAAPSVFIFPPSDEQLKS<br>GTASVVCLLNNFYPREAKVQWKVDNALQSGNSQESVTEQDSKDSTYSLSS<br>TLTLSKADYEKHKVYACEVTHQGLSSPVTKSFNRGEC<br>[SEQ ID NO: 271] | |
| Heavy<br>Chain<br>version<br>1 | QVQLVESGGGVVQPGRSLRLSCAASGFT<br>FNTYGMHWVRQAPGKGLEWVAIIWYDGSQKYYADSVQGRFTISRDNHKNT<br>LYLQMNSLRAEDTAVYFCVRVRFSVGPHGSAFDLWGQGTMVTVSSASTKG<br>PSVFPLAPSSKSTSGGTAALGCLVKDYFPEPVTVSWNSGALTSGVHTFPA<br>VLQSSGLYSLSSVVTVPSSSLGTQTYICNVNHKPSNTKVDKKVEPKSCDK<br>THTCPPCPAPELLGGPSVFLFPPKPKDTLMISRTPEVTCVVVDVSHEDPE<br>VKFNWYVDGVEVHNAKTKPREEQYNSTYRWSVLTVLHQDWLNGKEYKCK<br>VSNKALPAPIEKTISKAKGQPREPQVYTLPPSRDELTKNQVSLTCLVKGF<br>YPSDIAVEWESNGQPENNYKTTPPVLDSDGSFFLYSKLTVDKSRWQQGNV<br>FSCSVMHEALHNHYTQKSLSLSPGK<br>[SEQ ID NO: 272] | |
| Heavy<br>Chain<br>version<br>2 | QVQLVESGGGVVQPGRSLRLSCAASGFT<br>FNTYGMHWVRQAPGKGLEWVAIIWYDGSQKYYADSVQGRFTISRDNHKNT<br>LYLQMNSLRAEDTAVYFCVRVRFSVGPHGSAFDLWGQGTMVTVSSASTKG<br>PSVFPLAPSSKSTSGGTAALGCLVKDYFPEPVTVSWNSGALTSGVHTFPA<br>VLQSSGLYSLSSVVTVPSSSLGTQTYICNVNHKPSNTKVDKKVEPKSCDK<br>THTCPPCPAPELLGGPSVFLFPPKPKDTLMISRTPEVTCVVVDVSHEDPE<br>VKFNWYVDGVEVHNAKTKPREEQYNSTYRWSVLTVLHQDWLNGKEYKCK<br>VSNKALPAPIEKTISKAKGQPREPQVYTLPPSRDELTKNQVSLTCLVKGF<br>YPSDIAVEWESNGQPENNYKTTPPVLDSDGSFFLYSKLTVDKSRWQQGNV<br>FSCSVLHEALHSHYTQKSLSLSPGK [SEQ ID NO: 273] | |
| DNA<br>for<br>Light<br>Chain | GGCGTCCAGATGACCCAGTCTCCTTCCACCCTGT<br>CTGCATCTGTGGGAGACAGAGTCACCCTCACTTGCCGGGCCAGTCAGAGT<br>ATTAGTAGTTGGTTGGCCTGGTATCAGCAGAAACCAGGGAAAGCCCCTAA<br>ACTCCTGATCTATGATGCCTCCAGTTTGGAAAGTGGGGTCCCATCAAGGT<br>TCAGCGGCAGTGGATCTGGGACAGAATTCACTCTCACCATCAGCAGCCTG<br>CAACCTGATGATTTTGCAACTTATTACTGCCAACAGTATAATAGTTATTC<br>TTTTTTGGACGTTCGGCCAAGGGACCAAGGTGGAAATCAAACGCACTGTGG<br>CTGCACCATCTGTCTTCATCTTCCCGCCATCTGATGAGCAGTTGAAATCT<br>GGAACTGCCTCTGTTGTGTGCCTGCTGAATAACTTCTATCCCAGAGAGGC<br>CAAAGTACAGTGGAAGGTGGATAACGCCCTCCAATCGGGTAACTCCCAGG<br>AGAGTGTCACAGAGCAGGACAGCAAGGACAGCACCTACAGCCTCAGCAGC<br>ACCCTGACGCTGAGCAAAGCAGACTACGAGAAACACAAAGTCTACGCCTG<br>CGAAGTCACCCATCAGGGCCTGAGCTCGCCCGTCACAAAGAGCTTCAACA<br>GGGGAGAGTGT<br>[SEQ ID NO: 274] | |
| DNA<br>for<br>Heavy<br>Chain<br>version<br>1 | CAGGTGCAACTGGTGGAGTCTGGGGGAGGCGTGG<br>TCCAGCCTGGGAGGTCCCTGAGACTCTCCTGTGCAGCGTCTGGGTTCACT<br>TTCAATACCTATGGCATGCACTGGGTCCGCCAGGCACCAGGCAAGGGGCT<br>GGAGTGGGTGGCAATTATCTGGTATGATGGGAGCCAGAAATACTATGCAG<br>ACTCCGTGCAGGGCCGATTCACTATCTCCAGAGACAATCACAAGAACACG<br>TTGTACCTGCAAATGAACTCCCTGAGAGCCGAGGACACGGCTGTGTATTT<br>CTGTGTGAGAGTCCGCTTTAGCGTTGGCCCCCACGGGAGTGCTTTTGATC<br>TCTGGGGCCAGGGGACAATGGTCACAGTCTCTTCAGCCTCCACCAAGGGC<br>CCATCGGTCTTCCCCCTGGCACCCTCCTCCAAGAGCACCTCTGGGGGCAC<br>AGCAGCCCTGGGCTGCCTGGTCAAGGACTACTTCCCCGAACCGGTGACGG<br>TGTCGTGGAACTCAGGCGCCCTGACCAGCGGCGTGCACACCTTCCCGGCT<br>GTCCTACAGTCCTCAGGACTCTACTCCCTCAGCAGCGTGGTGACCGTGCC<br>CTCCAGCAGCTTGGGCACCCAGACCTACATCTGCAACGTGAATCACAAGC<br>CCAGCAACACCAAGGTGGACAAGAAAGTTGAGCCCAAATCTTGTGACAAA<br>ACTCACACATGCCCACCGTGCCCAGCACCTGAACTCCTGGGGGGACCGTC<br>AGTCTTCCTCTTCCCCCCAAAACCCAAGGACACCCTCATGATCTCCCGGA<br>CCCCTGAGGTCACATGCGTGGTGGTGGACGTGAGCCACGAAGACCCTGAG<br>GTCAAGTTCAACTGGTACGTGGACGGCGTGGAGGTGCATAATGCCAAGAC<br>AAAGCCGCGGGAGGAGCAGTACAACAGCACGTACCGTGTGGTCAGCGTCC<br>TCACCGTCCTGCACCAGGACTGGCTGAATGGCAAGGAGTACAAGTGCAAG<br>GTCTCCAACAAAGCCCTCCCAGCCCCCATCGAGAAAACCATCTCCAAAGC<br>CAAAGGGCAGCCCCGAGAACCACAGGTGTACACCCTGCCCCCATCCCGGG<br>ATGAGCTGACCAAGAACCAGGTCAGCCTGACCTGCCTGGTCAAAGGCTTC<br>TATCCCAGCGACATCGCCGTGGAGTGGGAGAGCAATGGGCAGCCGGAGAA | |

TABLE 30-continued

Antibody ID: AB-007088.005

| KABAT | ASN |
|---|---|
| | CAACTACAAGACCACGCCTCCCGTGCTGGACTCCGACGGCTCCTTCTTCC<br>TCTACAGCAAGCTCACCGTGGACAAGAGCAGGTGGCAGCAGGGGAACGTC<br>TTCTCATGCTCCGTGATGCATGAGGCTCTGCACAACCACTACACACAGAA<br>GAGCCTCTCCCTGTCTCCGGGTAAA [SEQ ID NO: 275] |
| DNA<br>for<br>Heavy<br>Chain<br>version<br>2 | CAGGTGCAACTGGTGGAGTCTGGGGGAGGCGTGG<br>TCCAGCCTGGGAGGTCCCTGAGACTCTCCTGTGCAGCGTCTGGGTTCACT<br>TTCAATACCTATGGCATGCACTGGGTCCGCCAGGCACCAGGCAAGGGGCT<br>GGAGTGGGTGGCAATTATCTGGTATGATGGGAGCCAGAAATACTATGCAG<br>ACTCCGTGCAGGGCCGATTCACTATCTCCAGAGACAATCACAAGAACACG<br>TTGTACCTGCAAATGAACTCCCTGAGAGCCGAGGACACGGCTGTGTATTT<br>CTGTGTGAGAGTCCGCTTTAGCGTTGGCCCCCACGGGAGTGCTTTTGATC<br>TCTGGGGCCAGGGGACAATGGTCACAGTCTCTTCAGCCTCCACCAAGGGC<br>CCATCGGTCTTCCCCCTGGCACCCTCCTCCAAGAGCACCTCTGGGGGCAC<br>AGCAGCCCTGGGCTGCCTGGTCAAGGACTACTTCCCCGAACCGGTGACGG<br>TGTCGTGGAACTCAGGCGCCCTGACCAGCGGCGTGCACACCTTCCCGGCT<br>GTCCTACAGTCCTCAGGACTCTACTCCCTCAGCAGCGTGGTGACCGTGCC<br>CTCCAGCAGCTTGGGCACCCAGACCTACATCTGCAACGTGAATCACAAGC<br>CCAGCAACACCAAGGTGGACAAGAAAGTTGAGCCCAAATCTTGTGACAAA<br>ACTCACACATGCCCACCGTGCCCAGCACCTGAACTCCTGGGGGACCGTC<br>AGTCTTCCTCTTCCCCCCAAAACCCAAGGACACCCTCATGATCTCCCGGA<br>CCCCTGAGGTCACATGCGTGGTGGTGGACGTGAGCCACGAAGACCCTGAG<br>GTCAAGTTCAACTGGTACGTGGACGGCGTGGAGGTGCATAATGCCAAGAC<br>AAAGCCGCGGGAGGAGCAGTACAACAGCACGTACCGTGTGGTCAGCGTCC<br>TCACCGTCCTGCACCAGGACTGGCTGAATGGCAAGGAGTACAAGTGCAAG<br>GTCTCCAACAAAGCCCTCCCAGCCCCCATCGAGAAAACCATCTCCAAAGC<br>CAAAGGGCAGCCCCGAGAACCACAGGTGTACACCCTGCCCCCATCCCGGG<br>ATGAGCTGACCAAGAACCAGGTCAGCCTGACCTGCCTGGTCAAAGGCTTC<br>TATCCCAGCGACATCGCCGTGGAGTGGGAGAGCAATGGGCAGCCGGAGAA<br>CAACTACAAGACCACGCCTCCCGTGCTGGACTCCGACGGCTCCTTCTTCC<br>TCTACAGCAAGCTCACCGTGGACAAGAGCAGGTGGCAGCAGGGGAACGTC<br>TTCTCATGCTCCGTGCTGCATGAGGCTCTGCACTCCCACTACACACAGAA<br>GAGCCTCTCCCTGTCTCCGGGTAAA [SEQ ID NO: 276] |

4. Glycosylation of Anti-CSP Antibodies and Variants Thereof

Glycosylation of antibodies and engineered antibodies has been previously disclosed (see, e.g., U.S. Pat. No. 6,602,684, the content of which is incorporated in its entirety). Antibody Fc regions are generally post-translationally modified via the addition of N-glycans at specific asparagine residues on the antibody heavy chain. IgG molecules bear a N-linked glycosylation asparagine of each heavy chain. It has been shown that a modified glycosylation profile can regulate the antibody functions. For example, without any limitation, altered glycosylation can improve the binding affinity or the half-life of the antibody as compared to the non-modified form.

In certain embodiments, the present disclosure provides anti-CSP antibodies and variants thereof with modified glycosylation. In certain embodiments, the antibodies disclosed herein include an Fc region with increased glycosylation. In certain non-limiting embodiments, the Fc region with increased glycosylation includes increased amounts of bisected oligosaccharides. In certain embodiments, the Fc region with increased glycosylation includes increased amounts of nonfucosylated oligosaccharides. In certain embodiments, the Fc region with increased glycosylation includes increased amounts of fucose-containing oligosaccharides.

In certain embodiments, the antibodies disclosed herein include an Fc region with decreased glycosylation. In certain non-limiting embodiments, the Fc region with decreased glycosylation includes reduced amounts of bisected oligosaccharides. In certain embodiments, the Fc region with decreased glycosylation includes reduced amounts of nonfucosylated oligosaccharides. In certain embodiments, the Fc region with increased glycosylation includes reduced amounts of fucose-containing oligosaccharides.

In certain embodiments, the antibodies disclosed herein include a V region with increased glycosylation. In certain non-limiting embodiments, the V region with increased glycosylation includes increased amounts of bisected oligosaccharides. In certain embodiments, the V region with increased glycosylation includes increased amounts of nonfucosylated oligosaccharides. In certain embodiments, the V region with increased glycosylation includes increased amounts of fucose-containing oligosaccharides.

In certain embodiments, the antibodies disclosed herein include a V region with decreased glycosylation. In certain non-limiting embodiments, the V region with decreased glycosylation includes reduced amounts of bisected oligosaccharides. In certain embodiments, the V region with decreased glycosylation includes reduced amounts of nonfucosylated oligosaccharides. In certain embodiments, the V region with increased glycosylation includes reduced amounts of fucose-containing oligosaccharides.

In certain embodiments, the modified glycosylation can be obtained by expressing any of the antibodies disclosed herein in a host cell with altered glycosylation machinery. For example, without any limitation, a host cell can include a functional disruption of the fucosyltransferase gene and antibodies expressed in this host cell with show reduced glycosylation, e.g., reduced fucosylation (see PCT Patent Publication No. WO 99/54342).

In certain embodiments, the present disclosure provides anti-CSP antibody variants disclosed herein including one or more amino acid substitution resulting in the alteration of a glycosylation acceptor site. In certain embodiments, the alteration includes the elimination of the glycosylation acceptor site. In certain embodiments, the alteration includes modification of a glycosylation acceptor site. In certain embodiments, the alteration includes insertion of a glycosylation acceptor site.

As used herein, "glycosylation acceptor site" refers to an amino acid residue of the light chain or heavy chain of the antibody which can be N- or O-glycosylated. In certain embodiments, the N-linked glycosylation acceptor site can be an asparagine residue. In certain embodiments, the O-linked glycosylation acceptor site can be a serine residue, a threonine residue, a tyrosine residue, a hydroxylysine residue, or a hydroxyproline residue.

In certain embodiments, the Fc region of the antibodies disclosed herein includes one or more glycosylation acceptor site. In certain embodiments, the V region of any of the antibodies disclosed herein includes one or more glycosylation acceptor site. In certain embodiments, the light chain of any of the antibodies disclosed herein includes one or more glycosylation acceptor site. In certain embodiments, the heavy chain of any one of the antibodies disclosed herein includes one or more glycosylation acceptor site. In certain embodiments, the light chain variable region of any of the antibodies disclosed herein includes one or more glycosylation acceptor site. In certain embodiments, the heavy chain variable region of any of the antibodies disclosed herein includes one or more glycosylation acceptor site.

5. PEGylation and Other Chemical Modifications of Anti-CSP Antibodies and Variants Thereof The present disclosure provides anti-CSP antibodies and variants thereof including additional modifications. In certain embodiments, the modifications can improve pharmacological properties of the antibodies, e.g., half-life. In certain non-limiting embodiments, the modification includes PEGylation, deamination, derivatization with polymers, lipidation, removal and/or introduction of disulfide bonds, oxidation, and removal of C-terminal lysine In certain embodiments, the modification is a PEGylation. PEGylation of antibodies and engineered antibodies includes attachment of one or more polyethylene glycol (PEG) to the antibody. In certain non-limitation embodiments, for example, the PEGylation can be carried out by an acylation reaction or an alkylation reaction with a reactive PEG molecule (or an analogous reactive water-soluble polymer). As used herein, the term "polyethylene glycol" refers to any of the forms of PEG that have been used to derivatize other proteins, such as mono (C1-C10) alkoxy- or aryloxy-polyethylene glycol or polyethylene glycol-maleimide.

In certain embodiments, the modification is the derivatization with a hydrophilic polymer. In certain non-limiting embodiments, for example, the hydrophilic polymer can be carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof.

In certain embodiments, the modification is a lipidation. Lipidation is the conjugation of a protein with a lipid. Lipidation of peptides improves metabolic stability, membrane permeability, bioavailability, and changes the pharmacokinetic and pharmacodynamic properties of the peptides. For example, a lipidated peptide has a high affinity with serum albumin resulting in increased half-life and stability. In certain non-limiting embodiments, for example, the lipid can be myristic acid, palmitic acid, stearic acid, lauric acid, cholesterol, and mixtures thereof.

In certain embodiments, the modification is a substitution of an amino acid residue to form a disulfide bond. In certain embodiments, the amino acid substitution introduces a cysteine. Under certain redox conditions, two cysteines can form a non-natural disulfide bond. In certain non-limiting embodiments, the disulfide bond improves the stability of the antibody, e.g., corrected pairing of the antibody chains. In certain embodiments, the cysteine is introduced in the V region. In certain embodiments, the cysteine is introduced in the Fc region. In certain embodiments, the modification is a substitution of an amino acid residue to remove a disulfide bond. In certain embodiments, the amino acid substitution removes a cysteine. In certain embodiments, the cysteine is substituted with a serine. In certain non-limiting embodiments, removing a cysteine improves the stability of the antibody, e.g., improved long-term stability. In certain embodiments, the cysteine is removed in the V region. In certain embodiments, the cysteine is removed in the Fc region.

6. Anti-CSP Antibody and Anti-CSP Antibody Variants Conjugates

In certain embodiments, the present disclosure provides an anti-CSP antibody or variant thereof conjugated or linked to therapeutic and/or imaging/detectable moieties. For example, without any limitation, the anti-CSP antibody or variant thereof can be conjugated to a detectable marker, a toxin, or a therapeutic agent. The moiety may be linked to the antibody covalently or by non-covalent linkages.

In certain embodiments, the antibody or variant thereof is conjugated to cytotoxic moiety or other moiety that inhibits cell proliferation. In certain embodiments, the antibody or variant thereof is conjugated to a cytotoxic agent including, but not limited to, a ricin A chain, doxorubicin, daunorubicin, a maytansinoid, taxol, ethidium bromide, mitomycin, etoposide, tenoposide, vincristine, vinblastine, colchicine, dihydroxy anthracin dione, actinomycin, a diphtheria toxin, extotoxin A from *Pseudomonas*, *Pseudomonas* exotoxin (PE) A, PE40, abrin, abrin A chain, modeccin A chain, alpha sarcin, gelonin, mitogellin, restrictocin, cobran venom factor, a ribonuclease, phenomycin, enomycin, curicin, crotin, calicheamicin, *Saponaria officinalis* inhibitor, glucocorticoid, auristatin, auromycin, yttrium, bismuth, combrestatin, duocarmycins, dolastatin, cc1065, or a cisplatin. In certain embodiments, the antibody or variant thereof can be linked to an agent such as an enzyme inhibitor, a proliferation inhibitor, a lytic agent, a DNA or RNA synthesis inhibitors, a membrane permeability modifier, a DNA metabolites, a dichloroethyl sulfide derivative, a protein production inhibitor, a ribosome inhibitor, or an inducer of apoptosis.

In certain embodiments, the antibody or variant thereof can be linked to a radionuclide, an iron-related compound, a dye, a fluorescent agent, or an imaging agent. In certain embodiments, an antibody may be linked to agents, such as, but not limited to, metals; metal chelators; lanthanides; lanthanide chelators; radiometals; radiometal chelators; positron-emitting nuclei; microbubbles (for ultrasound); liposomes; molecules microencapsulated in liposomes or nanosphere; monocrystalline iron oxide nano-compounds; magnetic resonance imaging contrast agents; light absorbing, reflecting and/or scattering agents; colloidal particles; fluorophores, such as near-infrared fluorophores.

In certain embodiments, the present disclosure provides bispecific molecules comprising an anti-CSP antibody, a variant thereof, or a fragment thereof, disclosed herein. The anti-CSP antibody, anti-CSP antibody variant or antigen-binding portions thereof can be derivatized or linked to another functional molecule, e.g., another peptide or protein (e.g., another antibody or ligand for a receptor) to generate a bispecific molecule that binds to at least two different binding sites or target molecules. The anti-CSP antibody or variant thereof disclosed herein can be derivatized or linked to more than one other functional molecule to generate multispecific molecules that bind to more than two different binding sites (e.g., two different epitopes on the CSP protein) and/or target molecules; such multispecific molecules are also intended to be encompassed by the term "bispecific molecule" as used herein. To create a bispecific molecule of the invention, an antibody of the invention can be functionally linked (e.g., by chemical coupling, genetic fusion, noncovalent association, or otherwise) to one or more other binding molecules, such as another antibody, antibody fragment, peptide or binding mimetic, such that a bispecific molecule results. In certain non-limiting embodiments, for example and without any limitation, the bispecific antibody can be created using the knobs-into-holes strategy. This strategy typically involves creation of a first half of a first antibody that recognizes a first antigen, e.g., CSP, and a second half of the antibody that recognizes a second antigen or binding site, and then joining the two halves to create the bispecific antibody. In certain embodiments, the first antigen and the second antigen are different epitopes of the CSP protein.

7. Activity

The activity of any of the anti-CSP antibodies disclosed herein can be assessed by using different endpoints. In certain embodiments, the activity is assessed for binding to CSP, either binding to a series of linear peptides with varying lengths representing the immunodominant regions of the CSP protein or to the entire CSP protein. In certain embodiments, the activity is assessed for the ability to protect against challenge with Plasmodium that comprises P. falciparum CSP, e.g., in in vivo animal models of malaria. In certain embodiments, effector function, e.g., ADCC, is also evaluated.

In certain embodiments, the binding activity of an anti-CSP antibody disclosed herein to P. falciparum CSP protein can be assessed by surface plasmon resonance (SPR) using a biosensor system. Systems suitable for use in SPR are, for example, and without any limitation, LSA™ (Carterra, Dublin, Calif.), Biacore™ (General Electric, Boston, Mass.), and OpenSPR (Nicoya, East Kitchener, ON, Canada). In an exemplary SPR assay, each antibody can be either directly immobilized to a Carterra CMD200M Chip or captured to the CMD200M Carterra Chip with a goat anti-human IgG Fc antibody. The uncoupled antibodies can be washed off and various concentration gradients of the targets can be flowed over the antibodies. In certain experimental conditions, the highest concentration of each target can be in the range of 0.5-8 μg/mL. For better accuracy, each antibody can be immobilized in different locations (e.g., at least 2) on the chip, and the affinity for each antibody-target combination can be determined using multiple (e.g., 4-5) target concentrations according to standard methods. If the variation between the two duplicates is >3-fold, the antibody-target measurement is repeated.

In certain embodiments, the binding activity of an anti-CSP antibody disclosed herein to P. falciparum CSP protein can be assessed by bio-layer interferometry (BLI). For BLI, each of the antigens (e.g., those disclosed in Table 35) can be immobilized on sensors according to the manufacturer's instructions. Systems suitable for use in BLI include, but are not limited to, Octet™ (ForteBio, Fremont, Calif.) and Gator™ (Probelife, Palo Alto, Calif.). In certain embodiments, for example and without any limitation, the antigen can be biotinylated and immobilized to streptavidin sensors. For better accuracy, each antibody can be evaluated in replicates at a suitable concentration (e.g., 5 μg/mL). If the variation between the two duplicates is >3-fold, the antibody-target measurement is repeated. The assays are typically performed under conditions according to the manufacturer's instructions. The assays can be performed under a temperature in the range of 20° C. to 37° C., for example, 20° C.-25° C. In certain embodiments, the assay is performed at 25° C. In certain embodiments, the assay is performed at 37° C.

In certain embodiments, binding to CSP protein is assessed in a competitive assay format with a reference antibody AB-000224 or a reference antibody having the variable regions of AB-000224. In certain embodiments, binding to CSP protein is assessed in a competitive assay format with a reference antibody AB-007088 or a reference antibody having the variable regions of AB-007088. In certain embodiments, a variant anti-CSP antibody disclosed herein can block binding of the reference antibody in a competition assay by about 50% or more.

Anti-CSP antibodies and anti-CSP antibody variants of the present disclosure may also be evaluated in various assays for their ability to mediate FcR-dependent activity. In certain embodiments, an antibody of the present disclosure has enhanced ADCC and/or serum stability compared to antibody AB-000224 when the antibodies are assayed in a human IgG1 isotype format. In certain embodiments, an antibody of the present disclosure has enhanced ADCC and/or serum stability compared to antibody AB-007088 when the antibodies are assayed in a human IgG1 isotype format.

In certain embodiments, the activity of an anti-CSP antibody can be evaluated in vivo in an animal model, e.g., as described in the Examples section. In certain non-limiting embodiments, for example, the mouse malaria liver burden assay can be used, as disclosed in, for example, Flores-Garcia Y, et al. Malar J. 2019; 18(1):426, doi:10.1186/s12936-019-3055-9, the content of which is herein incorporated by reference. Mice are administered antibody and infected with chimeric P. berghei expressing GFP-luciferase and P. falciparum CSP protein. Parasite liver load can be evaluated, e.g., by RT-qPCR or by measuring bioluminescence with an IVIS Spectrum imager. A reduction in parasite liver load reflects the prophylactic activity of an antibody.

In certain embodiments, the activity of an anti-CSP antibody can be determined by evaluating the in vivo protection and survival of animal models, e.g., mice. For example, but without any limitation, mice are administered antibody and challenged with chimeric P. berghei expressing P. falciparum CSP protein as disclosed in, for example, Espinosa, D., et al. npj Vaccines 2017; 2, 10 (2017); Espinosa, D., et al. Infect Immun. 2013 August; 81(8): 2882-2887. The in vivo protection can be determined by detecting blood-stage parasitaemia in microscopy. The survival rate can be determined using the absence of parasitaemia during an observation period, e.g., two weeks, immediately following the challenge. An increased survival rate reflects the prophylactic and/or therapeutic activity of an antibody.

In certain embodiments, an anti-CSP antibody, e.g., AB-000224 or AB-007088, disclosed herein has at least 20%, or at least 30%, or at least 40%, or at least 50%, or at least 60%, or 70%, or greater, of the activity of antibody AB-000317 when evaluated under the same assay conditions. In certain embodiments, an anti-CSP antibody exhibits improved activity, i.e., greater than 100%, activity compared to antibody AB-000317. In certain non-limiting embodiments, an anti-CSP antibody disclosed herein exhibits at least 20%, or at least 30%, or at least 40%, or at least 50%, or at least 60%, or 70%, or greater reduction in parasite liver load as compared to antibody AB-000317. In certain non-limiting embodiments, an anti-CSP antibody disclosed herein exhibits at least 20%, or at least 30%, or at least 40%, or at least 50%, or at least 60%, or 70%, or greater increase in survival rate as compared to antibody AB-000317.

In certain embodiments, an anti-CSP antibody variant disclosed herein has at least 50%, or at least 60%, or 70%, or greater, of the activity of AB-000224 when evaluated under the same assay conditions. In certain embodiments, an anti-CSP antibody exhibits improved activity, i.e., greater than 100%, activity compared to AB-000224. In certain embodiments, the anti-CSP antibody variants disclosed herein have similar activity against malaria infection as compared to AB-000224. In certain embodiment, an anti-CSP antibody variant disclosed herein has at least 50%, or at least 60%, or 70%, or greater, of the activity of AB-007088 when evaluated under the same assay conditions. In certain embodiments, an anti-CSP antibody exhibits improved activity, i.e., greater than 100%, activity compared to AB-007088. In certain embodiments, the anti-CSP antibody variants disclosed herein have similar activity against malaria infection as compared to AB-007088. The term "similar activity," when used to compare in vivo activity of antibodies, refers to that two measurements of the activity is no more than 30%, no more than 25%, no more than 20%, no more than 15% different, no more than 10%, no more than 8%, or no more than 5% different from each other.

In certain embodiments, the native anti-CSP antibody, AB-000224, is modified to have improved developability (i.e., reduced development liabilities), including but not limited to, decreased heterogeneity, increased yield, increased stability, improved net charges to improve pharmacokinetics, and or/reduced immunogenicity. In certain embodiments, antibodies having improved developability can be obtained by introducing mutations to reduce or eliminate potential development liabilities, as described in Table 1. In certain embodiments, antibodies having improved developability possess modifications as compared to AB-000224 in their amino acid sequence, as disclosed in Table 2.

In certain embodiments, the native anti-CSP antibody, AB-007088, is modified to have improved developability (i.e., reduced development liabilities), including but not limited to, decreased heterogeneity, increased yield, increased stability, improved net charges to improve pharmacokinetics, and or/reduced immunogenicity. In certain embodiments, antibodies having improved developability can be obtained by introducing mutations to reduce or eliminate potential development liabilities, as described in Table 1. In certain embodiments, antibodies having improved developability possess modifications as compared to AB-007088 in their amino acid sequence, as disclosed in Table 2.

In certain embodiments, the anti-CSP antibody variants disclosed herein have improved developability while maintaining comparable or improved binding affinity to the target as compared to AB-000224. Non-limiting examples of such anti-CSP antibody variants are disclosed herein. In certain embodiments, the anti-CSP antibody variants disclosed herein have improved developability while maintaining activities that are similar to AB-000224.

In certain embodiments, the anti-CSP antibody variants disclosed herein have improved developability while maintaining comparable or improved binding affinity to the target as compared to AB-007088. Non-limiting examples of such anti-CSP antibody variants are disclosed herein. In certain embodiments, the anti-CSP antibody variants disclosed herein have improved developability while maintaining activities that are similar to AB-007088.

8. Generation of Antibodies

CSP antibodies and variants thereof disclosed herein can be produced using vectors and recombinant methodology (see, e.g., Sambrook & Russell, Molecular Cloning: A Laboratory Manual, Cold Spring Harbor Laboratory Press; Ausubel, Current Protocols in Molecular Biology). Reagents, cloning vectors, and kits for genetic manipulation are available from commercial vendors.

The present disclosure provides isolated nucleic acids encoding a VH and/or VL region, or fragment thereof, of any of the anti-CSP antibodies and anti-CSP antibody variants disclosed herein. In certain embodiments, the present disclosure provides vectors comprising said nucleic acids and host cells into which the nucleic acids are introduced that are used to replicate the antibody-encoding nucleic acids and/or to express the antibodies. These nucleic acids can encode an amino acid sequence containing the VL, and/or an amino acid sequence containing the VH of the anti-CSP antibody or variant thereof (e.g., the light and/or heavy chains of the antibody). In certain embodiments, the host cell contains (1) a vector containing a polynucleotide that encodes the VL amino acid sequence and a polynucleotide that encodes the VH amino acid sequence, or (2) a first vector containing a polynucleotide that encodes the VL amino acid sequence and a second vector containing a polynucleotide that encodes the VH amino acid sequence.

In certain embodiments, the present disclosure provides a method of making an anti-CSP antibody disclosed herein. In certain embodiments, the method includes culturing a host cell previously described under conditions suitable for expression of the antibody. In certain embodiments, the antibody is subsequently recovered from the host cell (or host cell culture medium).

Suitable vectors containing polynucleotides encoding antibodies of the present disclosure, or fragments thereof, include cloning vectors and expression vectors. While the cloning vector selected can vary according to the host cell intended to be used, useful cloning vectors generally can self-replicate, can possess a single target for a particular restriction endonuclease, and/or may carry genes for a marker that can be used in selecting clones containing the vector. Non-limiting examples include plasmids and bacterial viruses, e.g., pUC18, pUC19, Bluescript (e.g., pBS SK+) and its derivatives, mp18, mp19, pBR322, pMB9, ColE1 plasmids, pCR1, RP4, phage DNAs, and shuttle vectors.

Expression vectors generally are replicable polynucleotide constructs that contain a nucleic acid of the present disclosure. The expression vector can replicate in the host cells either as episomes or as an integral part of the chromosomal DNA. Suitable expression vectors include, but are not limited to, plasmids and viral vectors, including adenoviruses, adeno-associated viruses, retroviruses, and any other vector.

Suitable host cells for expressing an anti-CSP antibody or anti-CSP antibody variant disclosed herein include both prokaryotic or eukaryotic cells. For example, but without any limitation, anti-CSP antibodies can be produced in bacteria, in particular when glycosylation and Fc effector function are not needed. After expression, the antibody can be isolated from the bacterial cell lysate in a soluble fraction and can be further purified. Alternatively, the host cell can be a eukaryotic host cell, including, without limitation, eukaryotic microorganisms, such as filamentous fungi or yeast, fungi and yeast strains whose glycosylation pathways have been "humanized," resulting in the production of an antibody with a partially or fully human glycosylation pattern, vertebrate, invertebrate, and plant cells. Non-limiting examples of invertebrate cells include insect cells. Numerous baculoviral strains have been identified which may be used in conjunction with insect cells. Plant cell cultures can also be utilized as host cells.

In certain embodiments, vertebrate host cells are used for producing anti-CSP antibodies of the present disclosure. For example, without any limitation, mammalian cell lines that can be used to express anti-CSP antibodies include monkey kidney CV1 line transformed by SV40 (COS-7); human embryonic kidney line (293 or 293 cells); baby hamster kidney cells (BHK); mouse Sertoli cells (TM4 cells); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells; MRC 5 cells; and FS4 cells. In certain embodiments, the mammalian cell line used to express anti-CSP antibodies can be Chinese hamster ovary (CHO) cell line; DHFR-CHO cell line (Urlaub et al., Proc. Natl. Acad. Sci. USA 77:4216, 1980); and myeloma cell lines such as YO, NSO, and Sp2/0. Host cells of the present disclosure also include, without limitation, isolated cells, in vitro cultured cells, and ex vivo cultured cells.

A host cell transfected with an expression vector encoding an anti-CSP antibody of the present disclosure, or fragment thereof, can be cultured under appropriate conditions to allow expression of the polypeptide to occur. The polypeptides can be secreted and isolated from a mixture of cells and medium containing the polypeptides. Alternatively, the polypeptide can be retained in the cytoplasm or a membrane fraction and the cells harvested, lysed, and the polypeptide isolated using a desired method.

In certain embodiments, the present disclosure provides a method of generating variants of an anti-CSP antibody disclosed herein. In certain non-limiting embodiments, for example and without any limitation, a construct encoding a variant of VH CDR2 as described in the "anti-CSP Antibody Variant" section can be additionally modified and the VH region encoded by the additionally modified construct can be tested for binding activity to CSP and/or in vivo protective efficacy in the context of a VH region comprising the native AB-000224 CDR1 and CDR3, or a variant CDR1 or CDR3 as described herein, that is paired with a native AB-000224 VL region or variant region as described herein. Similarly, a construct encoding a variant VL CDR3 as described in the "anti-CSP Antibody Variant" section can be additionally modified and the VL region encoded by the additionally modified construct can be tested for binding activity to CSP and/or protective efficacy. Such an analysis can also be performed with other CDRs or framework regions and an antibody having the desired activity can then be selected.

Pharmaceutical Compositions and Methods of Treatment

In certain embodiments, the present disclosure provides pharmaceutical compositions for the administration of an anti-CSP antibody and variants thereof. In certain embodiments, the pharmaceutical compositions can be administered to a mammalian subject, e.g., a human, who has malaria or is at risk for malaria, in a therapeutically effective amount and according to a schedule sufficient to prevent *Plasmodium* infection, e.g., infection with *Plasmodium falciparum* or a *Plasmodium* sp. having a cross-reactive CSP protein, or to reduce a symptom of malaria in the subject. In certain embodiments, the pharmaceutical compositions can include any of the anti-CSP antibodies and variants thereof disclosed herein, or a polynucleotide encoding the same, and a pharmaceutically acceptable diluent or carrier. In certain embodiments, a polynucleotide encoding the antibody can be contained in a plasmid vector for delivery, or a viral vector. In certain embodiments, the pharmaceutical composition comprises a therapeutically effective amount of the antibody. As used herein, a "therapeutically effective dose" or a "therapeutically effective amount" refers to an amount sufficient to prevent, cure, or at least partially arrest malaria or symptoms of malaria. A therapeutically effective dose can be determined by monitoring a patient's response to therapy. Typical benchmarks indicative of a therapeutically effective dose include amelioration or prevention of symptoms of malaria in the patient, including, for example, and without limitation, reduction in the number of parasites. Amounts effective for this use will depend upon the severity of the disease and the general state of the patient's health, including other factors such as age, weight, gender, administration route, etc. Single or multiple administrations of the antibody will be dependent on the dosage and frequency as required and tolerated by the patient.

In certain embodiments, the antibody is administered at a pre-erythrocyte stage of infection, i.e., the antibody is administered in a time frame to prevent or reduce hepatocyte infection.

Various pharmaceutically acceptable diluents, carriers, and excipients, and techniques for the preparation and use of pharmaceutical compositions are also disclosed herein. Illustrative pharmaceutical compositions and pharmaceutically acceptable diluents, carriers, and excipients are also described in Remington: The Science and Practice of Pharmacy 20th Ed. (Lippincott, Williams & Wilkins 2012). In certain embodiments, each carrier, diluent, or excipient is "acceptable" in the sense of being compatible with the other ingredients of the pharmaceutical composition and not injurious to the subject. Often, the pharmaceutically acceptable carrier is an aqueous pH-buffered solution. In certain non-limiting embodiments, for example, pharmaceutically-acceptable carriers, diluents or excipients include water; buffers, e.g., phosphate-buffered saline; sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

In certain embodiments, the pharmaceutical composition can be formulated for any suitable route of administration, including for example, parenteral, intrapulmonary, intranasal, or local administration. Parenteral administration can include intramuscular, intravenous, intraarterial, intraperitoneal, oral, or subcutaneous administration. In certain embodiments, the pharmaceutical composition is formulated for intravenous administration and has a concentration of antibody of 10-100 mg/ml, 10-50 mg/ml, 20 to 40 mg/ml, or about 30 mg/ml. In certain embodiments, the pharmaceutical composition is formulated for subcutaneous injection and has a concentration of antibody of 50-500 mg/ml, 50-250 mg/ml, or 100 to 150 mg/ml, and a viscosity less than 50 cP, less than 30 cP, less than 20 cP, or about 10 cP. In certain embodiments, the pharmaceutical compositions are liquids or solids. In certain embodiments, the pharmaceutical compositions are formulated for parenteral, e.g., intravenous, subcutaneous, intraperitoneal, or intramuscular administration.

In certain embodiments, the formulation of and delivery methods of pharmaceutical compositions are adapted according to the site and the disease to be treated. For example, without any limitation, formulations include those in which the antibody is encapsulated in micelles, liposomes, or drug-release capsules (active agents incorporated within a biocompatible coating designed for slow-release); ingestible formulations; formulations for topical use, such as creams, ointments, and gels; and other formulations such as inhalants, aerosols, and sprays.

In certain non-limiting embodiments, for example for parenteral administration, the antibodies or antigen-binding fragments thereof are formulated in a unit dosage injectable form (solution, suspension, emulsion) in association with a pharmaceutically acceptable, parenteral vehicle. Non-limiting examples of vehicles include water, saline, Ringer's solution, dextrose solution, and 5% human serum albumin. Nonaqueous vehicles such as fixed oils and ethyl oleate may also be used.

The dose and dosage regimen depend upon a variety of factors readily determined by a physician, such as the nature of the infection, the characteristics of the subject, and the subject's history. In certain embodiments, the amount of antibody or antigen-binding fragment thereof administered or provided to the subject is in the range of about 0.1 mg/kg to about 50 mg/kg of the subject's body weight. Depending on the type and severity of the infection, in certain embodiments, about 0.1 mg/kg to about 50 mg/kg body weight (e.g., about 0.1-15 mg/kg/dose) of antibody or antigen-binding fragment thereof may be provided as an initial candidate dosage to the patient, whether, for example, by one or more separate administrations, or by continuous infusion. The progress of the therapy is readily monitored by conventional methods and assays and based on criteria known to the physician or other persons of skill in the art.

An antibody or variant thereof of the present disclosure can be administered to a subject using any route of administration, e.g., systemic, parenterally, locally, in accordance with known methods. Such routes include, but are not limited to, intravenous administration, e.g., as a bolus or by continuous infusion over a period of time, by intramuscular, intraperitoneal, intracerobrospinal, subcutaneous, intraarticular, intrasynovial, intrathecal, oral, topical, or inhalation routes. A subject can be administered an antibody of the present invention one or more times; and can be administered before, after, or concurrently with another therapeutic agent as further described below.

In certain embodiments, the antibodies or variants thereof of the present disclosure can be administered to prevent malaria. In certain embodiments, the antibodies disclosed herein can inhibit or reduce the risk of *Plasmodium* infection. In certain embodiments, the antibodies disclosed herein can inhibit or reduce the pre-erythrocytic or sporozoite stage of infection. In certain embodiments, the antibodies disclosed herein can prevent malaria by targeting the *Plasmodium* at an early stage of entry to the vertebrate of a subject, to thereby arrest the infection from taking place.

In certain embodiments, antibody or variant thereof of the present disclosure can be administered to treat malaria. In certain embodiments, the antibodies disclosed herein can inhibit or reduce the progression of *Plasmodium* infection in the blood stream. In certain embodiments, the antibodies disclosed herein can inhibit or reduce the risk of transmission of *Plasmodium* from a subject to another via insect feeding, e.g., mosquito bite or via contact with infected blood.

In certain embodiments, the pharmaceutical compositions disclosed herein can be administered to a pediatric patient. As used herein, the term "pediatric patient" refers to a patient up to the age of 18 years old. In certain embodiments, the pediatric patient is a patient from age 3 months to less than 12 years old. In certain non-limiting embodiments, the pediatric patient can be a patient between from about 1 year old to about 2 years old, from about 2 years old to about 3 years old, from about 3 years old to about 4 years old, from about 4 years old to about 5 years old, from about 5 years old to about 6 years old, from about 6 years old to about 7 years old, from about 7 years old to about 8 years old, from about 8 years old to about 9 years old, from about 9 years old to about 10 years old, or from about 11 years old to about 12 years old. In certain embodiments, the pediatric patient is not responsive or poorly responsive to another treatment to malaria. In certain embodiments, the pediatric patient is human.

In certain embodiments, the dose of the pharmaceutical compositions disclosed herein is administered based on the weight of the pediatric patient. In certain non-limiting embodiments, the dose of the pharmaceutical compositions is about 5 mg/kg, about 10 mg/kg, about 15 mg/kg, about 20 mg/kg about 25 mg/kg, about 50 mg/kg, about 75 mg/kg, about 100 mg/kg, about 150 mg/kg, about 200 mg/kg, about 250 mg/kg, about 300 mg/kg, or about 350 mg/kg. In certain embodiments, the pediatric patient has a weight of from about 2.5 kg to about 5 kg, from about 5 kg to about 10 kg, from about 10 kg to about 15 kg, from about 15 kg to about 20 kg, from about 20 kg to about 30 kg, or from about 30 kg to about 40 kg.

In certain embodiments, the antibody is provided to the subject in combination with one or more additional therapeutic agents used to treat or prevent malaria or a related disease or disorder. In certain embodiments, a method for treating or preventing malaria is provided, comprising administering to the human a therapeutically effective amount of an antibody as disclosed herein, or a pharmaceutically acceptable salt thereof, in combination with a therapeutically effective amount of one or more additional therapeutic agents. In certain embodiments, a method for treating malaria in a human having or at risk of having the infection is provided, comprising administering to the human a therapeutically effective amount of an antibody as disclosed herein, or a pharmaceutically acceptable salt thereof, in combination with a therapeutically effective amount of one or more additional therapeutic agents.

In certain embodiments, when an antibody of the present disclosure as described herein is combined with one or more additional therapeutic agents as described above, the components of the composition are administered as a simultaneous or sequential regimen. When administered sequentially, the combination may be administered in two or more administrations.

In certain embodiments, an antibody as disclosed herein is combined with one or more additional therapeutic agents in a unitary dosage form for simultaneous administration to a patient.

A "patient" refers to any subject receiving the antibody regardless of whether they have malaria. In certain embodiments, a "patient" is a non-human subject, e.g., an animal that is used as a model for evaluating the effects of antibody administration.

"Co-administration" of an antibody disclosed herein with one or more additional therapeutic agents generally refers to simultaneous or sequential administration of an antibody or fragment thereof disclosed herein and one or more additional therapeutic agents, such that therapeutically effective amounts of the antibody or fragment thereof disclosed herein and one or more additional therapeutic agents are both present in the body of the patient. Co-administration includes administration of unit dosages of the antibody disclosed herein before or after administration of unit dosages of one or more additional therapeutic agents, for example, and without limitation, administration of the antibody within seconds, minutes, or hours of the administration of one or more additional therapeutic agents. In certain non-limiting embodiments, for example, a unit dose of an antibody disclosed herein is administered first, followed within seconds or minutes by administration of a unit dose of one or more additional therapeutic agents. In certain non-limiting embodiments, a unit dose of one or more additional therapeutic agents is administered first, followed by administration of a unit dose of an antibody within seconds or minutes. In certain embodiments, a unit dose of an antibody disclosed herein is administered first, followed, after a period of hours (e.g., 1-12 hours), by administration of a unit dose of one or more additional therapeutic agents. In certain embodiments, a unit dose of one or more additional therapeutic agents is administered first, followed, after a period of hours (e.g., 1-12 hours), by administration of a unit dose of the antibody.

The combined administration may be co-administration, using separate pharmaceutical compositions or a single pharmaceutical composition, or consecutive administration in either order, wherein there is optionally a time period while both (or all) therapeutic agents simultaneously exert their biological activities. Such combined therapy may result in a synergistic therapeutic effect. In certain embodiments, it is desirable to combine administration of an antibody of the invention with another antibody directed against another *Plasmodium falciparum* antigen, or against a different CSP target epitope.

CSP has multiple domains and regions that include the N-terminal domain, the immunogenic central NANP repeat region, and the C-terminal (ctCSP) domain or α-thrombospondin repeat (αTSR) domain. Between the N-terminal domain and the central repeat region is the junctional region that contains an NPDP sequence and a minor repeat region that contains three NVDP motifs that are both related to the dominant NANP motif (Pholcharee, T. et al., J. Mol. Bio. 432: 1048-1063 (2020). In certain embodiments, an antibody disclosed herein is co-administered with an antibody that binds to ctCSP. In certain embodiments, an antibody disclosed herein is co-administered with an antibody that binds to the alpha epitope (α-ctCSP) domain of ctCSP. The α-ctCSP consists of an α-helix that includes the T-cell epitope Th2R (region III), and the CS flap, which contains another T-cell epitope Th3R (Beutler N, PLoS Pathog 18(3): e1010409 (2022), FIG. 2, incorporated by reference herein). In certain embodiments, an antibody disclosed herein is co-administered with an antibody that binds to the beta epitope (β-ctCSP) domain of ctCSP (Beutler N, PLoS Pathog 18(3):e1010409 (2022), FIG. 2).

In certain embodiments, the antibody can be administered by gene therapy via a nucleic acid comprising one or more polynucleotides encoding the antibody. In certain embodiments, the polynucleotide encodes an scFv. In certain embodiments, the polynucleotide comprises DNA, cDNA or RNA. In certain embodiments, the polynucleotide is present in a vector, e.g., a viral vector.

Exemplary Embodiments of the Presently Disclosed Subject Matter

The present disclosure provides to antibodies targeting *Plasmodium falciparum*. In certain non-limiting embodiments, the antibody is a recombinant anti-circumsporozoite (CSP) antibody. In certain embodiments, the recombinant antibody comprises a light chain variable region (VL) and a heavy chain variable region (VH), wherein the light chain variable region comprises a CDR1 comprising the amino acid sequence set forth in SEQ ID NO: 1, a CDR2 comprising the amino acid sequence set forth in SEQ ID NO: 2, and a CDR3 comprising the amino acid sequence set forth in SEQ ID NO: 3; and the heavy chain variable region comprises a CDR1 comprising the amino acid sequence set forth in SEQ ID NO: 4, a CDR2 comprising the amino acid sequence set forth in SEQ ID NO: 5, and a CDR3 comprising the amino acid sequence set forth in SEQ ID NO: 6.

In certain embodiments, the VL of the recombinant antibodies disclosed herein comprises the amino acid sequence set forth in SEQ ID NO: 163; the amino acid sequence set forth in SEQ ID NO: 23; the amino acid sequence set forth in SEQ ID NO: 33; the amino acid sequence set forth in SEQ ID NO: 43; the amino acid sequence set forth in SEQ ID NO: 53; the amino acid sequence set forth in SEQ ID NO: 63; the amino acid sequence set forth in SEQ ID NO: 73; the amino acid sequence set forth in SEQ ID NO: 83; the amino acid sequence set forth in SEQ ID NO: 93; the amino acid sequence set forth in SEQ ID NO: 103; the amino acid sequence set forth in SEQ ID NO: 113; the amino acid sequence set forth in SEQ ID NO: 123; the amino acid sequence set forth in SEQ ID NO: 133; the amino acid sequence set forth in SEQ ID NO: 143; the amino acid sequence set forth in SEQ ID NO: 153; or the amino acid sequence set forth in SEQ ID NO: 173. In certain embodiments, the VH of the recombinant antibodies disclosed herein comprises the amino acid sequence set forth in SEQ ID NO: 164; the amino acid sequence set forth in SEQ ID NO: 24; the amino acid sequence set forth in SEQ ID NO: 34; the amino acid sequence set forth in SEQ ID NO: 44; the amino acid sequence set forth in SEQ ID NO: 54; the amino acid sequence set forth in SEQ ID NO: 64; the amino acid sequence set forth in SEQ ID NO: 74; the amino acid sequence set forth in SEQ ID NO: 84; the amino acid sequence set forth in SEQ ID NO: 94; the amino acid sequence set forth in SEQ ID NO: 104; the amino acid sequence set forth in SEQ ID NO: 114; the amino acid sequence set forth in SEQ ID NO: 124; the amino acid sequence set forth in SEQ ID NO: 134; the amino acid sequence set forth in SEQ ID NO: 144; the amino acid sequence set forth in SEQ ID NO: 154; or the amino acid sequence set forth in SEQ ID NO: 174.

In certain embodiments of the recombinant antibodies disclosed herein, the VL comprises the amino acid sequence set forth in SEQ ID NO: 163, and the VH comprises the amino acid sequence set forth in SEQ ID NO: 164; the VL comprises the amino acid sequence set forth in SEQ ID NO: 33, and the VH comprises the amino acid sequence set forth in SEQ ID NO: 34; the VL comprises the amino acid sequence set forth in SEQ ID NO: 43, and the VH comprises the amino acid sequence set forth in SEQ ID NO: 44; the VL comprises the amino acid sequence set forth in SEQ ID NO: 53, and the VH comprises the amino acid sequence set forth in SEQ ID NO: 54; the VL comprises the amino acid sequence set forth in SEQ ID NO: 63, and the VH comprises the amino acid sequence set forth in SEQ ID NO: 64; the VL comprises the amino acid sequence set forth in SEQ ID NO: 73, and the VH comprises the amino acid sequence set forth in SEQ ID NO: 74; the VL comprises the amino acid sequence set forth in SEQ ID NO: 83, and the VH comprises the amino acid sequence set forth in SEQ ID NO: 84; the VL comprises the amino acid sequence set forth in SEQ ID NO: 93, and the VH comprises the amino acid sequence set forth in SEQ ID NO: 94; the VL comprises the amino acid sequence set forth in SEQ ID NO: 103, and the VH comprises the amino acid sequence set forth in SEQ ID NO: 104; the VL comprises the amino acid sequence set forth in SEQ ID NO: 113, and the VH comprises the amino acid sequence set forth in SEQ ID NO: 114; the VL comprises the amino acid sequence set forth in SEQ ID NO: 123, and the VH comprises the amino acid sequence set forth in SEQ ID NO: 124; the VL comprises the amino acid sequence set forth in SEQ ID NO: 133, and the VH comprises the amino acid sequence set forth in SEQ ID NO: 134; the VL comprises the amino acid sequence set forth in SEQ ID NO: 143, and the VH comprises the amino acid sequence set forth in SEQ ID NO: 144; the VL comprises the amino acid sequence set forth in SEQ ID NO: 153, and the VH comprises the amino acid sequence set forth in SEQ ID NO: 154; or the VL comprises the amino acid sequence set forth in SEQ ID NO: 173, and the VH comprises the amino acid sequence set forth in SEQ ID NO: 174. In certain embodiments of the recombinant antibodies disclosed herein, the VL comprises the amino acid sequence set forth in SEQ ID NO: 63, and the VH comprises the amino acid sequence set forth in SEQ ID NO: 64. In certain embodiments of the recombinant antibodies disclosed herein, the VL comprises the amino acid sequence set forth in SEQ ID NO: 133, and the VH comprises the amino acid sequence set forth in SEQ ID NO: 134. In certain embodiments of the recombinant antibodies disclosed herein, the VL comprises the amino acid sequence set forth in SEQ ID NO: 163, and the VH comprises the amino acid sequence set forth in SEQ ID NO: 164.

In certain embodiments, the recombinant antibodies disclosed herein comprise a light chain (LC) and a heavy chain (HC). In certain embodiments, the LC of the recombinant antibodies disclosed herein comprises the amino acid sequence set forth in SEQ ID NO: 27; the amino acid sequence set forth in SEQ ID NO: 37; the amino acid sequence set forth in SEQ ID NO: 47; the amino acid sequence set forth in SEQ ID NO: 57; the amino acid sequence set forth in SEQ ID NO: 67; the amino acid sequence set forth in SEQ ID NO: 77; the amino acid sequence set forth in SEQ ID NO: 87; the amino acid sequence set forth in SEQ ID NO: 97; the amino acid sequence set forth in SEQ ID NO: 107; the amino acid sequence set forth in SEQ ID NO: 117; the amino acid sequence set forth in SEQ ID NO: 127; the amino acid sequence set forth in SEQ ID NO: 137; the amino acid sequence set forth in SEQ ID NO: 147; the amino acid sequence set forth in SEQ ID NO: 157; the amino acid sequence set forth in SEQ ID NO: 167; or the amino acid sequence set forth in SEQ ID NO: 177. In certain embodiments, the HC of the recombinant antibodies disclosed herein comprises the amino acid sequence set forth in SEQ ID NO: 28 or SEQ ID NO: 29; the amino acid sequence set forth in SEQ ID NO: 38 or SEQ ID NO: 39; the amino acid sequence set forth in SEQ ID NO: 48 or SEQ ID NO: 49; the amino acid sequence set forth in SEQ ID NO: 58 or SEQ ID NO: 59; the amino acid sequence set forth in SEQ ID NO: 68 or SEQ ID NO: 69; the amino acid sequence set forth in SEQ ID NO: 78 or SEQ ID NO: 79; the amino acid sequence set forth in SEQ ID NO: 88 or SEQ ID NO: 89; the amino acid sequence set forth in SEQ ID NO: 98 or SEQ ID NO: 99; the amino acid sequence set forth in SEQ ID NO: 108 or SEQ ID NO: 109; the amino acid sequence set forth in SEQ ID NO: 118 or SEQ ID NO: 119; the amino acid sequence set forth in SEQ ID NO: 128 or SEQ ID NO: 129; the amino acid sequence set forth in SEQ ID NO: 138 or SEQ ID NO: 139; the amino acid sequence set forth in SEQ ID NO: 148 or SEQ ID NO: 149; the amino acid sequence set forth in SEQ ID NO: 158 or SEQ ID NO: 159; the amino acid sequence set forth in SEQ ID NO: 168 or SEQ ID NO: 169; or the amino acid sequence set forth in SEQ ID NO: 178 or SEQ ID NO: 179.

In certain embodiments of the recombinant antibodies disclosed herein, the LC comprises the amino acid sequence set forth in SEQ ID NO: 27, and the HC comprises the amino acid sequence set forth in SEQ ID NO: 28 or SEQ ID NO: 29; the LC comprises the amino acid sequence set forth in SEQ ID NO: 37, and the HC comprises the amino acid sequence set forth in SEQ ID NO: 38 or SEQ ID NO: 39; the LC comprises the amino acid sequence set forth in SEQ ID NO: 47, and the HC comprises the amino acid sequence set forth in SEQ ID NO: 48 or SEQ ID NO: 49; the LC comprises the amino acid sequence set forth in SEQ ID NO: 57, and the HC comprises the amino acid sequence set forth in SEQ ID NO: 58 or SEQ ID NO: 59; the LC comprises the amino acid sequence set forth in SEQ ID NO: 67, and the HC comprises the amino acid sequence set forth in SEQ ID NO: 68 or SEQ ID NO: 69; the LC comprises the amino acid sequence set forth in SEQ ID NO: 77, and the HC comprises the amino acid sequence set forth in SEQ ID NO: 78 or SEQ ID NO: 79; the LC comprises the amino acid sequence set forth in SEQ ID NO: 87, and the HC comprises the amino acid sequence set forth in SEQ ID NO: 88 or SEQ ID NO: 89; the LC comprises the amino acid sequence set forth in SEQ ID NO: 97, and the HC comprises the amino acid sequence set forth in SEQ ID NO: 98 or SEQ ID NO: 99; the LC comprises the amino acid sequence set forth in SEQ ID NO: 107, and the HC comprises the amino acid sequence set forth in SEQ ID NO: 108 or SEQ ID NO: 109; the LC comprises the amino acid sequence set forth in SEQ ID NO: 117, and the HC comprises the amino acid sequence set forth in SEQ ID NO: 118 or SEQ ID NO: 119; the LC comprises the amino acid sequence set forth in SEQ ID NO: 127, and the HC comprises the amino acid sequence set forth in SEQ ID NO: 128 or SEQ ID NO: 129; the LC comprises the amino acid sequence set forth in SEQ ID NO: 137, and the HC comprises the amino acid sequence set forth in SEQ ID NO: 138 or SEQ ID NO: 139; the LC comprises the amino acid sequence set forth in SEQ ID NO: 147, and the HC comprises the amino acid sequence set forth in SEQ ID NO:

148 or SEQ ID NO: 149; the LC comprises the amino acid sequence set forth in SEQ ID NO: 157, and the HC comprises the amino acid sequence set forth in SEQ ID NO: 158 or SEQ ID NO: 159; the LC comprises the amino acid sequence set forth in SEQ ID NO: 167, and the HC comprises the amino acid sequence set forth in SEQ ID NO: 168 or SEQ ID NO: 169; or the LC comprises the amino acid sequence set forth in SEQ ID NO: 177, and the HC comprises the amino acid sequence set forth in SEQ ID NO: 178 or SEQ ID NO: 179. In certain embodiments of the recombinant antibodies disclosed herein, the LC comprises the amino acid sequence set forth in SEQ ID NO: 67, and the HC comprises the amino acid sequence set forth in SEQ ID NO: 69. In certain embodiments, the LC comprises the amino acid sequence set forth in SEQ ID NO: 137, and the HC comprises the amino acid sequence set forth in SEQ ID NO: 139. In certain embodiments, the LC comprises the amino acid sequence set forth in SEQ ID NO: 167, and the HC comprises the amino acid sequence set forth in SEQ ID NO: 169.

In certain embodiments, the VL of the recombinant antibodies disclosed herein comprises the amino acid sequence set forth in SEQ ID NO: 13. In certain embodiments of the recombinant antibodies disclosed herein, the VL comprises at least one amino acid substitution. In certain embodiments of the recombinant antibodies disclosed herein, the at least one amino acid substitution is at position 1 and/or at position 44. In certain embodiments of the recombinant antibodies disclosed herein, the amino acid substitution at position 1 is E1Q. In certain embodiments of the recombinant antibodies disclosed herein, the amino acid substitution at position 44 is R44T.

In certain embodiments, the VH of the recombinant antibodies disclosed herein comprises the amino acid sequence set forth in SEQ ID NO: 14. In certain embodiments of the recombinant antibodies disclosed herein, the VH comprises at least one amino acid substitution. In certain embodiments of the recombinant antibodies disclosed herein, the at least one amino acid substitution is at position 21, position 23, position 88, position 98, or a combination thereof. In certain embodiments of the recombinant antibodies disclosed herein, the amino acid substitution at position 1 is E1Q. In certain embodiments of the recombinant antibodies disclosed herein, the amino acid substitution at position 44 is R44T. In certain embodiments of the recombinant antibodies disclosed herein, the amino acid substitution at position 21 is P21S. In certain embodiments of the recombinant antibodies disclosed herein, the amino acid substitution at position 23 is T23A. In certain embodiments of the recombinant antibodies disclosed herein, the amino acid substitution at position 80 is I80T. In certain embodiments, the amino acid substitution at position 90 is T90A.

In certain embodiments, the HC of the recombinant antibodies disclosed herein comprises the amino acid sequence set forth in SEQ ID NO: 18. In certain embodiments of the recombinant antibodies disclosed herein, the HC comprises at least one amino acid substitution. In certain embodiments of the recombinant antibodies disclosed herein, the at least one amino acid substitution is at position 438 and/or or at position 444. In certain embodiments, the amino acid substitution at position 438 is M438L. In certain embodiments of the recombinant antibodies disclosed herein, the amino acid substitution at position 444 is N444S.

In certain non-limiting embodiments, the present disclosure provides a recombinant anti-circumsporozoite (CSP) antibody comprising a light chain variable region (VL) and a heavy chain variable region (VH), wherein the VL comprises the amino acid sequence set forth in SEQ ID NO: 63 and the VH comprises the amino acid sequence set forth in SEQ ID NO: 64. In certain embodiments, the recombinant antibody comprises a light chain (LC) and a heavy chain (HC), wherein the LC comprises the amino acid sequence set forth in SEQ ID NO: 67 and the HC comprises the amino acid sequence set forth in SEQ ID NO: 69.

In certain non-limiting embodiments, the present disclosure further provides a recombinant anti-circumsporozoite (CSP) antibody comprising a light chain variable region (VL) and a heavy chain variable region (VH), wherein the VL comprises the amino acid sequence set forth in SEQ ID NO: 133 and the VH comprises the amino acid sequence set forth in SEQ ID NO: 134. In certain embodiments, the recombinant antibody comprises a light chain (LC) and a heavy chain (HC), wherein the LC comprises the amino acid sequence set forth in SEQ ID NO: 137 and the HC comprises the amino acid sequence set forth in SEQ ID NO: 139.

In certain non-limiting embodiments, the present disclosure also provides a recombinant anti-circumsporozoite (CSP) antibody comprising a light chain variable region (VL) and a heavy chain variable region (VH), wherein the VL comprises the amino acid sequence set forth in SEQ ID NO: 163 and the VH comprises the amino acid sequence set forth in SEQ ID NO: 164. In certain embodiments, the recombinant antibody comprises a light chain (LC) and a heavy chain (HC), wherein the LC comprises the amino acid sequence set forth in SEQ ID NO: 167 and the HC comprises the amino acid sequence set forth in SEQ ID NO: 169.

In certain non-limiting embodiments, the present disclosure provides a recombinant anti-circumsporozoite (CSP) antibody comprising a light chain variable region (VL) and a heavy chain variable region (VH), wherein the light chain variable region comprises a CDR1 comprising the amino acid sequence set forth in SEQ ID NO: 183, a CDR2 comprising the amino acid sequence set forth in SEQ ID NO: 184, and a CDR3 comprising the amino acid sequence set forth in SEQ ID NO: 185; and the heavy chain variable region comprises a CDR1 comprising the amino acid sequence set forth in SEQ ID NO: 186, a CDR2 comprising the amino acid sequence set forth in SEQ ID NO: 187, and a CDR3 comprising the amino acid sequence set forth in SEQ ID NO: 188. In certain embodiments, the VL comprises the amino acid sequence set forth in SEQ ID NO: 195, and the VH comprises the amino acid sequence set forth in SEQ ID NO: 196. In certain embodiments, the recombinant antibody comprises comprising a LC and a HC. In certain embodiments of the recombinant antibodies disclosed herein, the LC comprises the amino acid sequence set forth in SEQ ID NO: 199, and the HC comprises the amino acid sequence set forth in SEQ ID NO: 200 or SEQ ID NO: 201.

In certain non-limiting embodiments, the present disclosure provides a recombinant anti-circumsporozoite (CSP) antibody comprising a light chain variable region (VL) and a heavy chain variable region (VH), wherein the light chain variable region comprises a CDR1 comprising the amino acid sequence set forth in SEQ ID NO: 205, a CDR2 comprising the amino acid sequence set forth in SEQ ID NO: 206, and a CDR3 comprising the amino acid sequence set forth in SEQ ID NO: 207; and the heavy chain variable region comprises a CDR1 comprising the amino acid sequence set forth in SEQ ID NO: 208, a CDR2 comprising the amino acid sequence set forth in SEQ ID NO: 209, and a CDR3 comprising the amino acid sequence set forth in SEQ ID NO: 210.

In certain embodiments, the VL of the recombinant antibodies disclosed herein comprises the amino acid sequence set forth in SEQ ID NO: 227; the amino acid sequence set forth in SEQ ID NO: 237; the amino acid sequence set forth in SEQ ID NO: 247; the amino acid sequence set forth in SEQ ID NO: 257; or the amino acid sequence set forth in SEQ ID NO: 267. In certain embodiments, the VH of the recombinant antibodies disclosed herein comprises the amino acid sequence set forth in SEQ ID NO: 228; the amino acid sequence set forth in SEQ ID NO: 238; the amino acid sequence set forth in SEQ ID NO: 248; the amino acid sequence set forth in SEQ ID NO: 258; or the amino acid sequence set forth in SEQ ID NO: 268. In certain embodiments of the recombinant antibodies disclosed herein, the VL comprises the amino acid sequence set forth in SEQ ID NO: 227, and the VH comprises the amino acid sequence set forth in SEQ ID NO: 228; the VL comprises the amino acid sequence set forth in SEQ ID NO: 237, and the VH comprises the amino acid sequence set forth in SEQ ID NO: 238; the VL comprises the amino acid sequence set forth in SEQ ID NO: 247, and the VH comprises the amino acid sequence set forth in SEQ ID NO: 248; the VL comprises the amino acid sequence set forth in SEQ ID NO: 257, and the VH comprises the amino acid sequence set forth in SEQ ID NO: 258; or the VL comprises the amino acid sequence set forth in SEQ ID NO: 267, and the VH comprises the amino acid sequence set forth in SEQ ID NO: 268.

In certain embodiments, the recombinant antibodies disclosed herein comprise a LC and a HC. In certain embodiments, the LC of the recombinant antibodies disclosed herein comprises the amino acid sequence set forth in SEQ ID NO: 231; the amino acid sequence set forth in SEQ ID NO: 241; the amino acid sequence set forth in SEQ ID NO: 251; the amino acid sequence set forth in SEQ ID NO: 261; or the amino acid sequence set forth in SEQ ID NO: 271. In certain embodiments, the HC of the recombinant antibodies disclosed herein comprises the amino acid sequence set forth in SEQ ID NO: 232 or SEQ ID NO: 233; the amino acid sequence set forth in SEQ ID NO: 242 or SEQ ID NO: 243; the amino acid sequence set forth in SEQ ID NO: 252 or SEQ ID NO: 253; the amino acid sequence set forth in SEQ ID NO: 262 or SEQ ID NO: 263; or the amino acid sequence set forth in SEQ ID NO: 272 or SEQ ID NO: 273. In certain embodiments of the recombinant antibodies disclosed herein, the LC comprises the amino acid sequence set forth in SEQ ID NO: 231, and the HC comprises the amino acid sequence set forth in SEQ ID NO: 232 or SEQ ID NO: 233; the LC comprises the amino acid sequence set forth in SEQ ID NO: 241, and the HC comprises the amino acid sequence set forth in SEQ ID NO: 242 or SEQ ID NO: 243; the LC comprises the amino acid sequence set forth in SEQ ID NO: 251, and the HC comprises the amino acid sequence set forth in SEQ ID NO: 252 or SEQ ID NO: 253; the LC comprises the amino acid sequence set forth in SEQ ID NO: 261, and the HC comprises the amino acid sequence set forth in SEQ ID NO: 262 or SEQ ID NO: 263; or the LC comprises the amino acid sequence set forth in SEQ ID NO: 271, and the HC comprises the amino acid sequence set forth in SEQ ID NO: 272 or SEQ ID NO: 273.

In certain embodiments, the VH of the recombinant antibodies disclosed herein comprises the amino acid sequence set forth in SEQ ID NO: 218. In certain embodiments of the recombinant antibodies disclosed herein, the VH comprises at least one amino acid substitution. In certain embodiments of the recombinant antibodies disclosed herein, the at least one amino acid substitution is at position 40, position 69, position 80, position 85, position 120, or a combination thereof. In certain embodiments of the recombinant antibodies disclosed herein, the amino acid substitution at position 40 is T40A. In certain embodiments of the recombinant antibodies disclosed herein, the amino acid substitution at position 69 is I69T. In certain embodiments of the recombinant antibodies disclosed herein, the amino acid substitution at position 80 is S80Y. In certain embodiments of the recombinant antibodies disclosed herein, the amino acid substitution at position 85 is G85S. In certain embodiments of the recombinant antibodies disclosed herein, the amino acid substitution at position 120 is I120T. In certain embodiment of the recombinant antibodies disclosed herein s, the HC comprises the amino acid sequence set forth in SEQ ID NO: 222. In certain embodiments of the recombinant antibodies disclosed herein, the HC comprises at least one amino acid substitution. In certain embodiments of the recombinant antibodies disclosed herein, the at least one amino acid substitution is at position 434 and/or at position 440. In certain embodiments of the recombinant antibodies disclosed herein, the amino acid substitution at position 434 is M434L. In certain embodiments of the recombinant antibodies disclosed herein, the amino acid substitution at position 440 is N440S.

In certain embodiments, the recombinant antibodies disclosed herein exhibit at least 20% reduction in parasite liver load as compared to a reference antibody. In certain embodiments, the recombinant antibodies disclosed herein exhibit at least 20% increase in survival rate as compared to a reference antibody. In certain embodiments, the recombinant antibodies disclosed herein exhibit increased conformational stability as compared to a reference antibody. In certain embodiments, the recombinant antibodies disclosed herein exhibit increased colloidal stability as compared to a reference antibody. In certain embodiments, the reference antibody is AB-000317. In certain embodiments, the reference antibody is AB-000224. In certain embodiments, the reference antibody is AB-007088.

In certain embodiments, the recombinant antibodies disclosed herein binds to a NANP repeat region. In certain embodiments, the recombinant antibodies disclosed herein binds to a polypeptide comprising or consisting of the amino acid sequence set forth in SEQ ID NO: 280.

In certain embodiments, the recombinant antibodies disclosed herein comprise at least one modification relative to the native AB-000224 variable heavy chain amino acid sequence set forth in SEQ ID NO: 14. In certain embodiments, the recombinant antibodies disclosed herein comprise at least one modification relative to the native AB-000224 variable light chain amino acid sequence set forth in SEQ ID NO: 13. In certain embodiments, the recombinant antibodies disclosed herein comprise at least one modification relative to the native AB-000224 variable heavy chain amino acid sequence set forth in SEQ ID NO: 14 and at least one modification relative to the native AB-000224 variable light chain amino acid sequence set forth in SEQ ID NO: 13.

In certain embodiments, the recombinant antibodies disclosed herein comprise at least one modification relative to the native AB-007088 variable heavy chain amino acid sequence set forth in SEQ ID NO: 218. In certain embodiments, the recombinant antibodies disclosed herein comprise at least one modification relative to the native AB-007088 variable light chain amino acid sequence set forth in SEQ ID NO: 217. In certain embodiments, the recombinant antibodies disclosed herein comprise at least one modification relative to the native AB-007088 variable heavy chain amino acid sequence set forth in SEQ ID NO:

218 and at least one modification relative to the native AB-000224 variable light chain amino acid sequence set forth in SEQ ID NO: 217. In certain non-limiting embodiments, the present disclosure provides a polynucleotide encoding a recombinant antibody disclosed herein. In certain non-limiting embodiments, the present disclosure provides an expression vector comprising the polynucleotide disclosed herein. In certain non-limiting embodiments, the present disclosure provides a host cell comprising the expression vector or the polynucleotide disclosed herein.

In certain non-limiting embodiments, the present disclosure provides a composition comprising the recombinant antibody disclosed herein. In certain embodiments, the composition further comprises a pharmaceutically acceptable carrier.

In certain non-limiting embodiments, the present disclosure provides a method of preventing and/or treating malaria in a subject in need thereof, comprising administering an effective amount of the recombinant antibody disclosed herein or of the composition disclosed herein. In certain embodiments, the subject is a pediatric patient.

In certain non-limiting embodiments, the present disclosure provides the recombinant antibodies or compositions disclosed herein for use in the prevention and/or treatment and/or prevention of malaria in a subject in need thereof. Additionally, in certain non-limiting embodiments, the present disclosure provides the recombinant antibodies or compositions disclosed herein for the manufacture of a medicament for the prevention and/or treatment and/or prevention of malaria in a subject in need thereof. Furthermore, the present disclosure provides use of the recombinant antibodies or compositions disclosed herein for the prevention and/or treatment and/or prevention of malaria in a subject in need thereof. In certain embodiments, the subject is a pediatric patient.

From the foregoing description, it will be apparent that variations and modifications may be made to the presently disclosed subject matter to adopt it to various usages and conditions. Such embodiments are also within the scope of the following claims.

The recitation of a listing of elements in any definition of a variable herein includes definitions of that variable as any single element or combination (or sub-combination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

The foregoing written description is considered to be sufficient to enable one skilled in the art to practice the methods and/or obtain the compositions described herein.

The following examples and detailed description are offered by way of illustration and not by way of limitation.

EXAMPLES

The Examples are offered for illustrative purposes only, and are not intended to limit the scope of the present invention in any way. Indeed, various modifications in addition to those shown and described herein will become apparent to those skilled in the art from the foregoing description and fall within the scope of the appended claims.

It is understood that various other embodiments may be practiced, given the general description provided above.

Example 1. Identification of Functionally Active Anti-CSP Antibodies

AB-000224 and AB-007088 were discovered in antibody repertoires generated by Immune Repertoire Capture® (IRC®) technology from plasmablast B cells isolated from two donors enrolled in a Phase 2a study evaluating the efficacy of the RTS,S vaccine in preventing malaria infection. The IRC® technology and its use in antibody discovery is well known and disclosed in, e.g., WO 2012148497A2, the entire content of which is herein incorporated by reference. The RTS,S vaccine is a pseudo-viral particle vaccine that combines the hepatitis B surface antigen and the central repeat and C-terminal regions of the CSP protein. RTS,S consists of two polypeptides; RTS is a single polypeptide chain corresponding to amino acids 207 to 395 of *P. falciparum* (3D7) that is fused to HBsAg and S is a polypeptide of 226 amino acids that corresponds to HBsAg. Stoute, et. al., N Engl J Med; 336:86-91(1997); RTS,S Clinical Trials Partnership, PLoS Med. 11(7):e1001685, (2014), WO1993/10152. The RTS,S vaccine was administered with the adjuvant AS01B to increase efficacy. AS01B is a liposome-based formulation that contains the immunostimulants monophosphoryl lipid A (MPL) and QS21 and was shown to be more immunogenic than another adjuvant, AS02A, used in initial studies. Kester, et al., J Infect Dis 200: 337-346 (2009). All study participants were vaccinated with one of two vaccine schedules (standard full-dose: 0, 1, 2 M or fractional-third dose: 0, 1, 7 M), or placebo and subsequently challenged with a controlled human malaria parasite infection. The donors from whom AB-000224 and AB-007088 were identified and protected following challenge. Heavy and light chain AB-000224 sequences were expressed as a human IgG1 monoclonal antibody. Heavy and light chain AB-007088 sequences were expressed as a human IgG1 monoclonal antibody. Compared to other antibodies obtained from the same or different donors, AB-000224 and AB-007088 demonstrated strong binding and affinity to CSP protein in vitro, no binding to Hepatitis B protein, and exceptional functional activity when tested in vivo.

The present example provides the design of improved variants of AB-000224 or AB-007088. In certain embodiments, the variants generated have improved developability, e.g., as identified through various in vitro assays, such as aggregation assessment by HPLC or UPLC, hydrophobic interaction chromatography (HIC), polyspecificity assays (e.g., baculovirus particle binding), self-interaction nanoparticle spectroscopy (SINS), or mass spec analysis after incubation in an accelerated degradation condition such as high temperature, low pH, high pH, or oxidative $H_2O_2$. Mutations are successful if the activity is maintained (or enhanced) while removing or reducing the severity of the liability.

Example 2. Generation of Anti-CSP Antibody Variants

Assessment of AB-000224

Figure 4A:
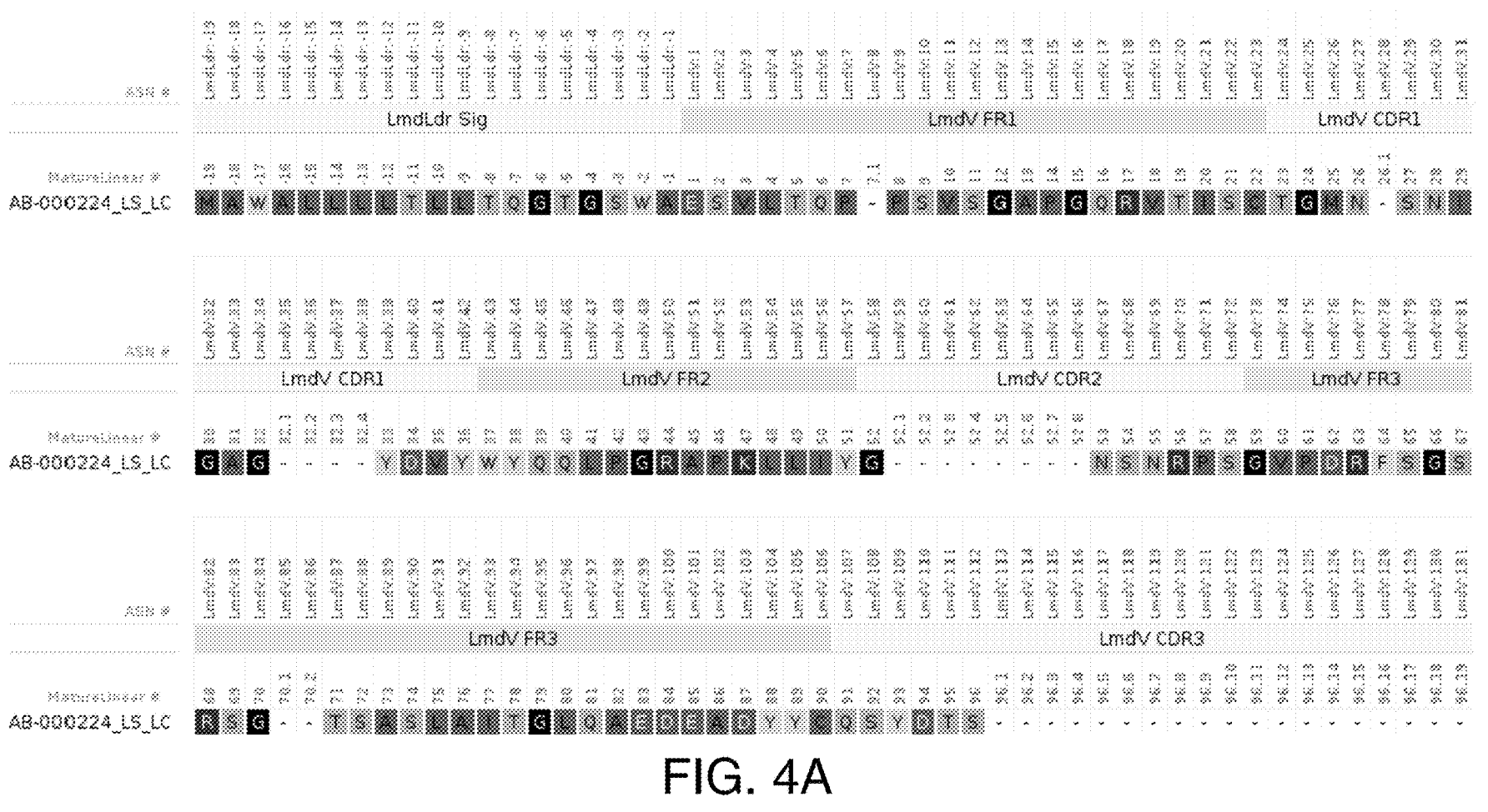
Figure 4A:
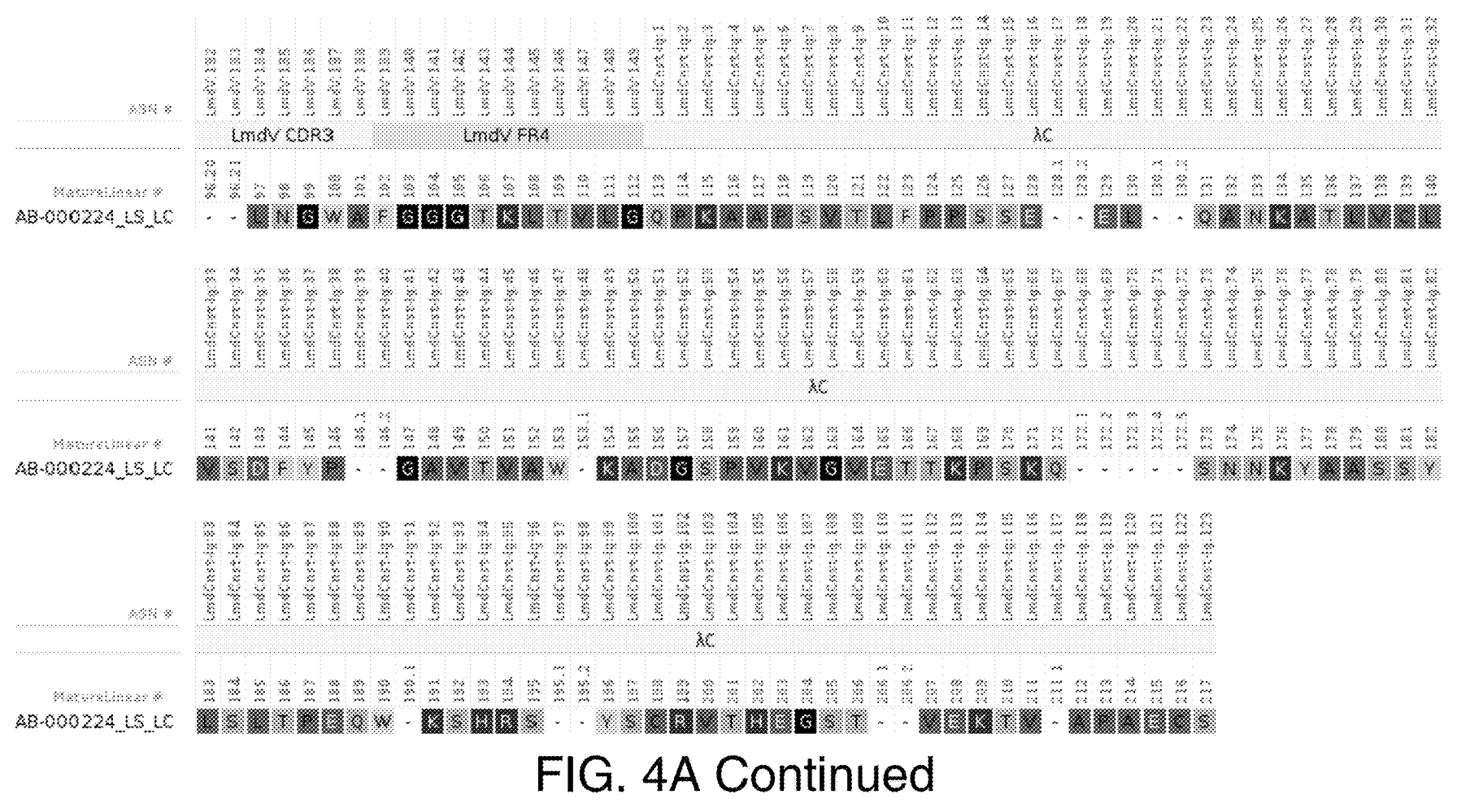
Figure 4B:
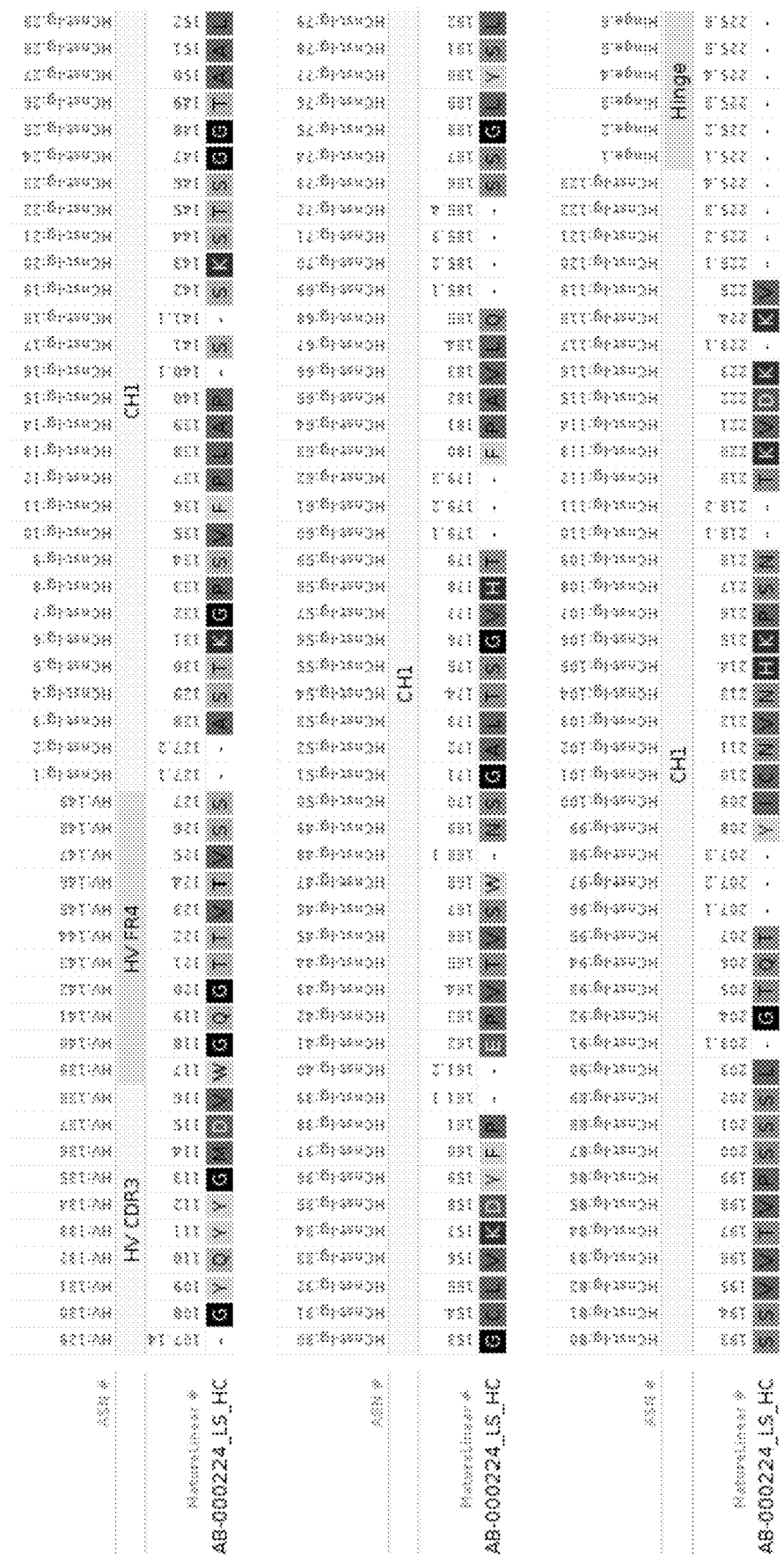
Figure 4B:
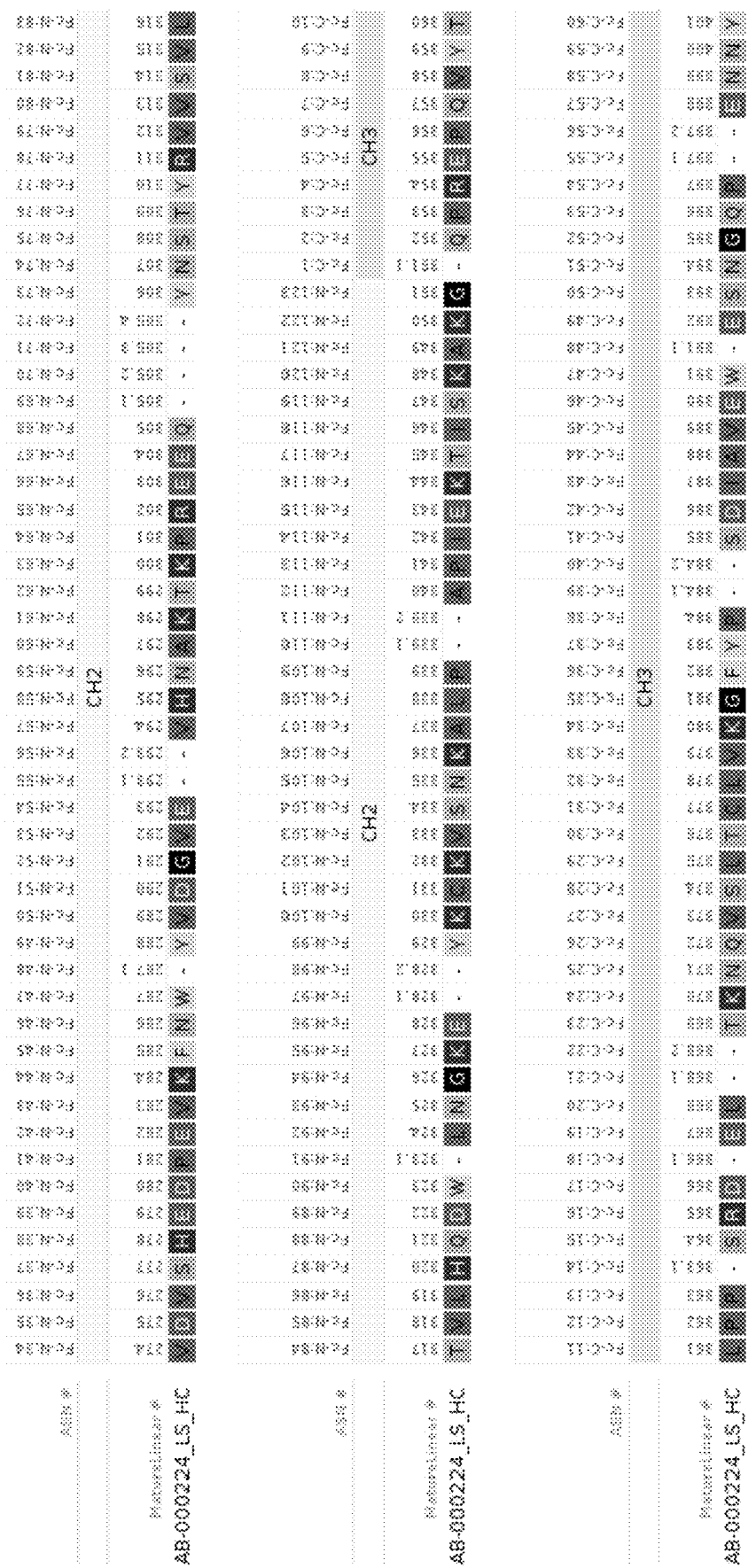
Figure 4B:
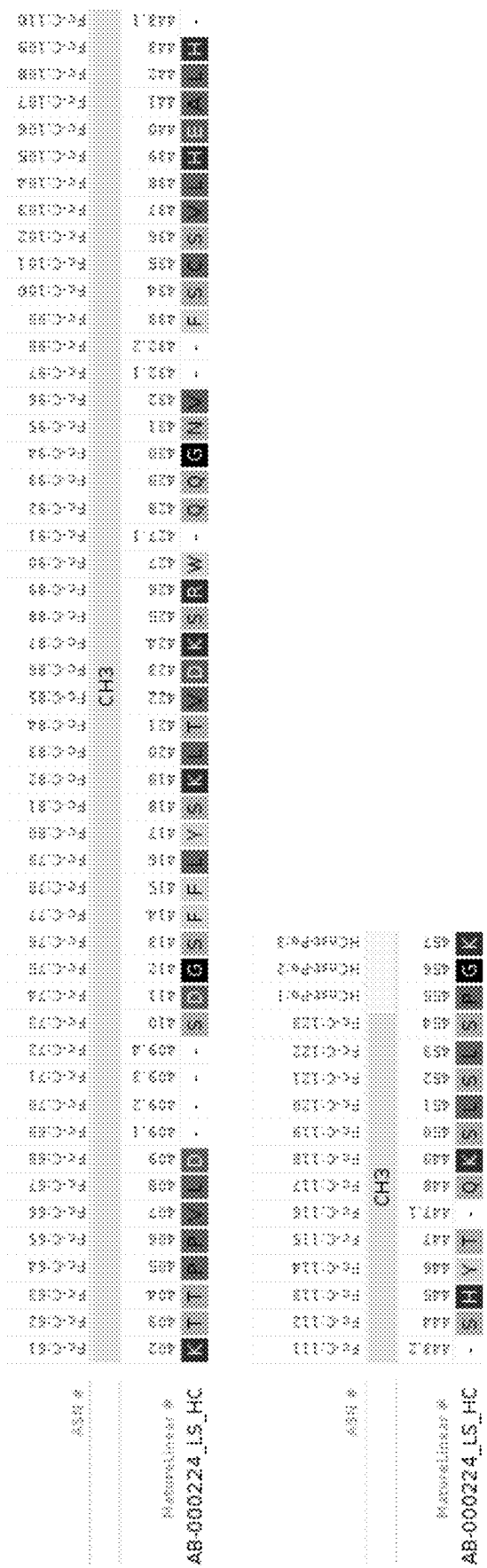

In vivo generated antibodies undergo genomic recombination followed by somatic hypermutation. Germline information was obtained from the AB-000224 antibody and used for the optimization of variant design. FIGS. 4A and 4B show the alignment of the AB-0002224 to the putative V and J germlines genes. CDRs, germline deviations, and potential liabilities were identified. N-linked glycosylation sites, non-typical cysteine residues, and other potential liability motifs were identified across the VH and VL.

The close siblings to AB-000224 are AB-007110, AB-007111, and AB-007112. These were evaluated at the sequence and structure level to find any possible beneficial modifications to AB-000224. AB-007110 in particular has been shown in biophysical characterization to have improved thermal stability over AB-000224. The positions evaluated below differ from AB-000224 and are either consistent amongst the siblings or of structural interest.

Design of Variants of AB-000224

Framework and complementary-determining region (CDR) germline deviations in AB-000224 were analyzed for their potential to be mutated, individually or in combination, to germline sequence, without negatively impacting binding to the (NANP)3 region of the CSP protein or potency. For each of the candidate mutations from AB-000224 sequence to germline sequence, the risk of making the mutation was assessed based on: (1) the change in charge, if any, since change in charge is intrinsically risky, and a change to more positive charge is particularly risky given the already net positive charge of AB-000224 Fv; (2) conservation of the native AB-000224 residue in the lineage versus the presence of the germline residue or other mutations at that position in the lineage and (3) the structural location of the position with respect to the NANP motif. Some mutations were noted to be coupled to at least one other mutation, meaning that the risk prediction is based on making the mutation in conjunction with the other mutation(s). Proposed AB-000224 Residue Modifications according to the ASN numbering system are shown in Table 31 below:

TABLE 31

| Site | Mutation | Design Group |
|---|---|---|
| LmdV:E1 | Q | Standard |
| LmdV:R50 | T | Standard |
| LmdV:N135 | NS | Siblings |
| HV:P22 | S | Standard |
| HV:T24 | TA | Standard |
| HV:H69 | HK | Siblings |
| HV:R75 | RK | Siblings |
| HV:D84 | DN | Do not repair |
| HV:I88 | IT | Standard |
| HV:T98 | TA | Standard |
| HV:F105 | FY | Do not repair |
| HV:T107 | TA | Standard |

Mutations were built by grouping the "Standard" Design Group in all combinations. This results in 16 variants. Add a single variant using the "Sibling" Design Group with all three sites together. This totals 17 variants. Adding the parent results in 18 antibodies required for production. Mutation site positions in the AB-000224 variants according to the ASN numbering system are specified in the table below:

TABLE 32

| Variant | LC-LmdV: E1 | LC-LmdV: R50 | LC-LmdV: N135 | HV: P22 | HV: T24 | HV: H69 | HV: R75 | HV: I88 | HV: T98 | HV: T107 |
|---|---|---|---|---|---|---|---|---|---|---|
| AB-000224_LS | | | | | | | | | | |
| AB-000224.001 | Q | T | | S | | | | | | |
| AB-000224.002 | Q | T | | S | A | | | | | |
| AB-000224.003 | Q | T | | S | | | | T | | |
| AB-000224.004 | Q | T | | S | | | | | A | |
| AB-000224.005 | Q | T | | S | | | | | | A |
| AB-000224.006 | Q | T | | S | A | | | T | | |
| AB-000224.007 | Q | T | | S | A | | | | A | |
| AB-000224.008 | Q | T | | S | A | | | | | A |
| AB-000224.009 | Q | T | | S | | | | T | A | |
| AB-000224.010 | Q | T | | S | | | | T | | A |
| AB-000224.011 | Q | T | | S | | | | | A | A |
| AB-000224.012 | Q | T | | S | A | | | T | A | |
| AB-000224.013 | Q | T | | S | A | | | T | | A |
| AB-000224.014 | Q | T | | S | A | | | | A | A |
| AB-000224.015 | Q | T | | S | | | | T | A | A |
| AB-000224.016 | Q | T | | S | A | | | T | A | A |
| AB-000224.017 | | | D | | | K | K | | | |

Assessment of AB-007088

Figure 5A:
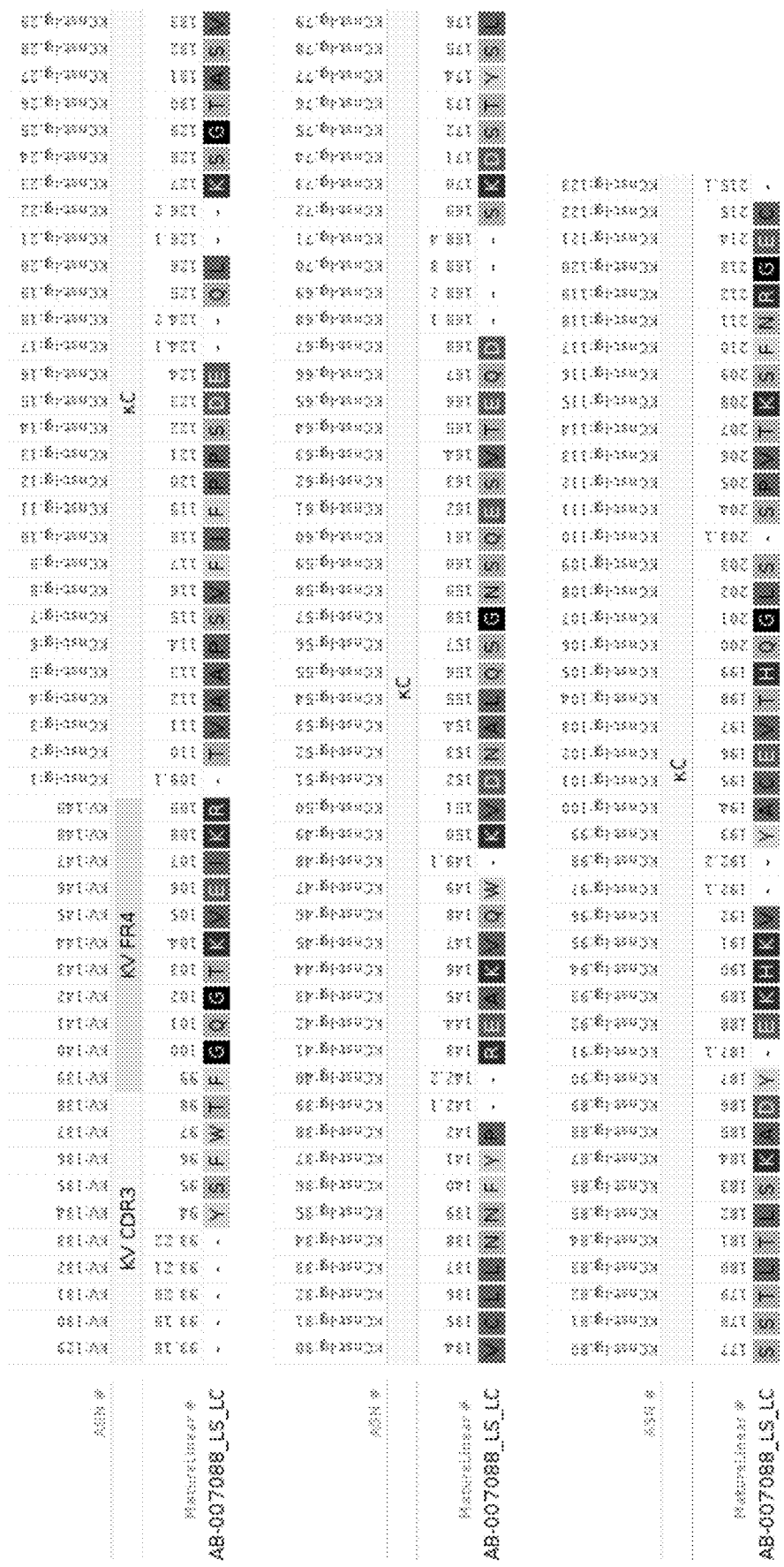
FIGS. 5A-5B illustrate sequences for the AB-007088 antibody.
Figure 5B:
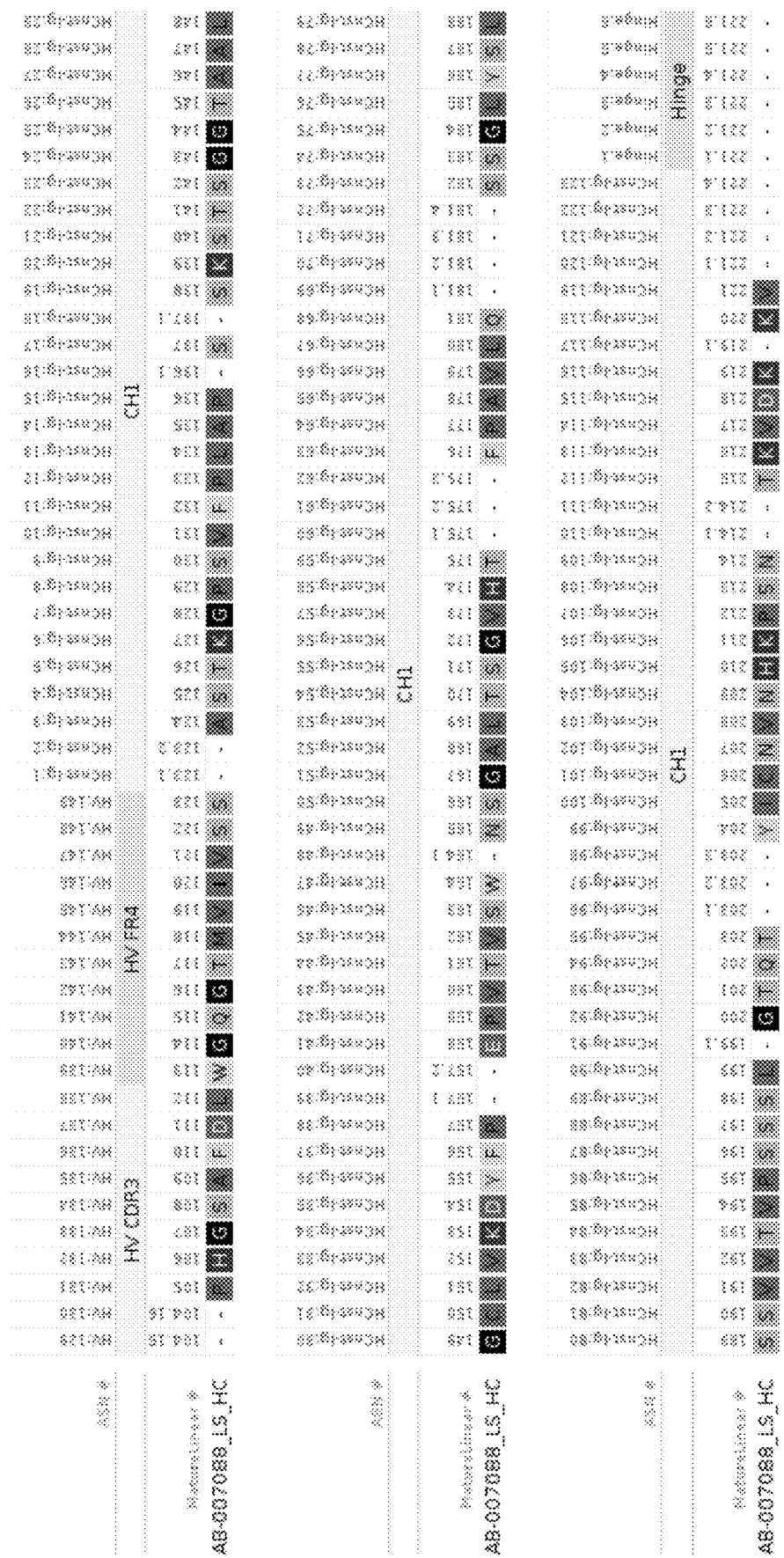
Figure 5B:

Germline information was obtained from the AB-007088 antibody and used for the optimization of variant design. FIGS. 5A and 5B show the alignment of the AB-0070884 to the putative V and J germlines genes. CDRs, germline deviations, and potential liabilities were identified. N-linked glycosylation sites, non-typical cysteine residues, and other potential liability motifs were identified across the VH and VL.

Design of Variants of AB-007088

Framework and complementary-determining region (CDR) germline deviations in AB-007088 were analyzed for their potential to be mutated, individually or in combination, to germline sequence, without negatively impacting binding to the (NANP)3 region of the CSP protein or potency. For each of the candidate mutations from AB-007088 sequence to germline sequence, the risk of making the mutation was assessed based on: (1) the change in charge, if any, since change in charge is intrinsically risky, and a change to more positive charge is particularly risky given the already net positive charge of AB-007088 Fv; (2) conservation of the native AB-007088 residue in the lineage versus the presence of the germline residue or other mutations at that position in the lineage and (3) the structural location of the position with respect to the NANP motif. Some mutations were noted to be coupled to at least one other mutation, meaning that the risk prediction is based on making the mutation in conjunction with the other mutation(s). Proposed AB-007088 Residue Modifications according to the ASN numbering system are shown in Table 33 below:

TABLE 33

| Site | Mutation | Design Group |
| --- | --- | --- |
| HV:A30 | AT | Group 1 |
| HV:T47 | A | Group 1 |
| HV:I79 | IT | Group 1 |
| HV:S90 | SY | Group 2 |
| HV:G95 | S | Group 1 |
| HV:I146 | T | Group 1 |

Mutations were built by grouping the "Group 1" Design Group in all combinations. This resulted in 4 variants. By adding a single variant using HV:S90Y to the design with all mutations, a total of five designs were obtained. Mutation site positions in the AB-007088 variants according to the ASN numbering system are specified in the table below:

TABLE 34

| Variant | HV:A30 | HV:T47 | HV:I79 | HV:S90 | HV:G95 | HV:I146 |
| --- | --- | --- | --- | --- | --- | --- |
| AB-007088_LS | | | | | | |
| AB-007088.001 | | A | | | S | T |
| AB-007088.002 | T | A | | | S | T |
| AB-007088.003 | | A | T | | S | T |
| AB-007088.004 | T | A | T | | S | T |
| AB-007088.005 | T | A | T | Y | S | T |

Example 3. Binding Assays

AB-000224 and AB-007088 were evaluated for binding to the complete CSP protein and a series of linear peptides representing the immunodominant NANP repeat region. Two assay platforms, bio-layer interferometry (BLI) and surface plasmon resonance (SPR), were used to quantify antibody-target binding strength. Five binding targets were evaluated in the SPR assay and six targets were evaluated in the BLI platform and described in Table 35 below:

TABLE 35

| Target Name | Peptide Sequence | Used in BLI, SPR, or both assays |
| --- | --- | --- |
| (NANP)6 | NANPNANPNANPNANPNANPNANP (SEQ ID NO: 279) | Both |
| (NPNA)3 | NPNANPNANPNA (SEQ ID NO: 280) | Both |
| (NVDP)3 (NANP)2 | NVDPNANPNVDPNANPNVDP (SEQ ID NO: 281) | Both |
| NANPNV DPNANP | NPDPNANPNVDPNANP (SEQ ID NO: 282) | Both |
| NANPNV DP | DPNANPNVDPNA (SEQ ID NO: 283) | BLI only |
| N-Interface | KQPADGNPDPNANPN (SEQ ID NO: 284) | BLI only |
| CSP Protein | MMRKLAILSVSSFLFVEALFQEYQCYGSSSNTRVLNELNYDNAGINLYNELEMNYYG KQENWYSLKKNSRSLGENDDGNNNNGDNGREGKDEDKRDGNNEDNEKLRKPKHKKLK QPGDGNPDPNANPNVDPNANPNVDPNANPNVDPNANPNANPNANPNANPNANPNANP NANPNANPNANPNANPNANPNANPNANPNANPNANPNANPNANPNANPNANPNANPN ANPNANPNANPNANPNANPNANPNANPNANPNANPNANPNANPNANPNANPNANPNA NPNANPNANPNANPNKNNQGNGQGHNMPNDPNRNVDENANANNAVKNNNNEEPSDKH IEQYLKKIQNSLSTEWSPCSVTCGNGIQVRIKPGSANKPKDELDYENDIEKKICKME KCSSVFNVVNSSIGLIMVLSFLFLN (SEQ ID NO: 285) | SPR only |

For BLI, each of the targets specified in Table 35 was biotinylated and immobilized to streptavidin sensors. Each antibody was evaluated in duplicate at 5 μg/mL. If the variation between the two duplicates was >3-fold, the antibody-target measurement was repeated.

For SPR, each antibody was either directly coupled to a Carterra Chip or coupled using a goat anti-human Fc antibody. The uncoupled antibodies were washed off and various concentration gradients of the targets were flowed over the antibodies, where the highest concentration of each target was in the range 0.5-8 μg/mL. Each antibody was immobilized in two different locations on the chip to allow for duplicate measurements. The affinity for each antibody-target combination was determined using 4-5 target concentrations in Mathematica software. If the variation between the two duplicates was >3-fold, the antibody-target measurement was repeated.

While the data generated by the BLI and SPR assays are similar, the assays were designed with opposite orientations of the target and antibody. Specifically, the target was immobilized while the antibody flowed over it in the BLI assay, while the SPR assay was designed so that the antibody was immobilized and the target flowed over it. Given these orientations, an antibody, when evaluated in the BLI assay, would be more likely to engage in binding interactions that involve multiple target molecules. As such, the binding of antibodies to targets in the BLI assay may exhibit more similarities to binding the complete CSP protein, which coats the surface of the malaria sporozoite. In contrast, the activity measured in the SPR assay would more accurately represent an interaction between an antibody F(ab) and a single target molecule. The data generated for the antibodies AB-000224 and AB-007088 are summarized in Table 36 below:

TABLE 36

| Antibody ID | AB-000224 | AB-007088 |
| --- | --- | --- |
| NANP6 $K_{ON}$ BLI | 5.44 | 5.22 |
| NANP6 $K_{OFF}$ BLI | −4.75 | −4.32 |
| NANP6 $K_D$ BLI | −10.19 | −9.55 |
| NANP6 $K_{ON}$ SPR | 5.01 | 5.52 |
| NANP6 $K_{OFF}$ SPR | −5.00 | −4.14 |
| NANP6 $K_D$ SPR | −10.00 | −9.63 |
| NPNA3 $K_{ON}$ BLI | 5.35 | 5.23 |
| NPNA3 $K_{OFF}$ BLI | −4.32 | −6.00 |
| NPNA3 $K_D$ BLI | −9.67 | −11.23 |
| NPNA3 $K_{ON}$ SPR | 4.87 | 5.08 |
| NPNA3 $K_{OFF}$ SPR | −3.47 | −3.25 |
| NPNA3 $K_D$ SPR | −8.34 | −8.33 |
| NVDP3NANP2 $K_{ON}$ BLI | 5.53 | 4.94 |
| NVDP3NANP2 $K_{OFF}$ BLI | −5.12 | −6.00 |
| NVDP3NANP2 $K_D$ BLI | −10.65 | −10.94 |
| NVDP3NANP2 $K_{ON}$ SPR | 4.81 | 4.29 |
| NVDP3NANP2 $K_{OFF}$ SPR | −4.02 | −4.40 |
| NVDP3NANP2 $K_D$ SPR | −8.77 | −8.71 |
| NANPNVDPNANP $K_{ON}$ BLI | 5.59 | 5.03 |
| NANPNVDPNANP $K_{OFF}$ BLI | −2.68 | −6.00 |
| NANPNVDPNANP $K_D$ BLI | −8.27 | −11.03 |
| NANPNVDPNANP $K_{ON}$ SPR | 4.08 | <LLOQ |
| NANPNVDPNANP $K_{OFF}$ SPR | −1.77 | <LLOQ |
| NANPNVDPNANP $K_D$ SPR | −5.85 | <LLOQ |
| NANPNVDP $K_{ON}$ BLI | <LLOQ | 4.89 |
| NANPNVDP $K_{OFF}$ BLI | <LLOQ | −6.00 |
| NANPNVDP $K_D$ BLI | <LLOQ | −10.89 |
| NVDPNANP $K_{ON}$ BLI | 5.35 | 5.02 |
| NVDPNANP $K_{OFF}$ BLI | −4.50 | −6.00 |
| NVDPNANP $K_D$ BLI | −9.85 | −11.02 |
| N-Interface $K_{ON}$ BLI | 6.42 | 5.13 |
| N-Interface $K_{OFF}$ BLI | −1.92 | −6.00 |
| N-Interface $K_D$ BLI | −8.34 | −11.13 |
| N-Interface $K_{ON}$ SPR | <LLOQ | 4.17 |
| N-Interface $K_{OFF}$ SPR | <LLOQ | −2.42 |
| N-Interface $K_D$ SPR | <LLOQ | −6.60 |
| CSP $K_{ON}$ SPR | 5.47 | 5.08 |
| CSP $K_{OFF}$ SPR | −5.00 | −4.59 |
| CSP $K_D$ SPR | −10.44 | −9.67 |

Summary of AB-000224 Antibody Variants

Seventeen (17) variants (AB-000224.001, AB-000224.002, AB-000224.003, AB-000224.004, AB-000224.005, AB-000224.006, AB-000224.007, AB-000224.008, AB-000224.009, AB-000224.010, AB-000224.011, AB-000224.012, AB-000224.013, AB-000224.014, AB-000224.015, AB-000224.016, AB-000224.017)) were designed to germline antibodies by mutating residues in either the framework regions or CDRs to reduce the risk of antibody-directed immunogenicity.

Summary of AB-007088 Antibody Variants

Five (5) variants (AB-007088.001, AB-007088.002, AB-007088.003, AB-007088.004, AB-007088.005) were designed to germline antibodies by mutating residues in either the framework regions or CDRs to reduce the risk of antibody-directed immunogenicity.

Example 4. In Vivo Performance of the Antibodies

Liver Burden Assay

AB-000224 and AB-007088 and variants thereof (with those in format comprising Heavy Chain version 2 indicated with the "LS") were evaluated for in vivo activity in a mouse malaria liver burden assay, as described in Flores-Garcia Y, et al. Malar J. 2019; 18(1):426, doi:10.1186/s12936-019-3055-9. Experimental antibodies were compared to both positive (AB-000317) and negative (AB-001245) antibody controls. AB-000317 is an anti-CSP antibody described in WO2020/172220. AB-001245 is non-CSP isotype control.

For each antibody, five C57B1/6 mice per experimental or control arm were administered 100 of antibody 16 hours prior to intravenous infection with fluorescent chimeric *P. berghei* sporozoites expressing *P. falciparum* CSP protein. Forty-two (42) hours following parasite challenge, the sporozoite liver load was quantified by bioluminescence. For each experimental mouse, the percent liver burden was calculated by subtracting the average background luminescence measured from two untreated, naive mice and calculating the percent reduction as compared to the average luminescence measured in five untreated, infected mice. The average percent reduction was reported for each of the experimental antibody groups.

Figure 1B:
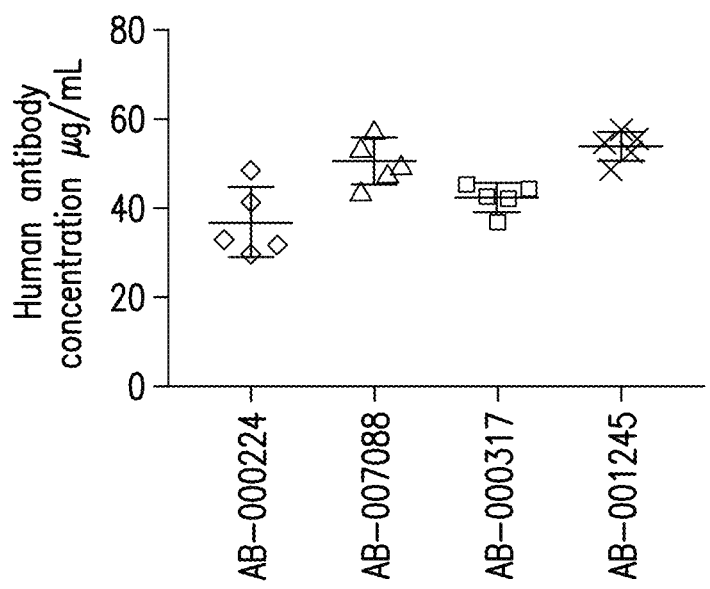
FIG. 1B illustrates the associated human IgG serum concentrations determined by ELISA obtained 15 hours following antibody administration. The individual points indicate the total amount of human IgG in a single mouse. AB-001245 is a non-malaria-specific antibody that was used as a negative control. AB-000317 is a positive control.

Mice administered AB-000224, AB-007088 or positive control antibody AB-000317 all exhibited a similar reduction in liver burden load as compared to naïve infected mice and mice treated with the negative control, AB-001245 (FIG. 1A). The level of experimental and control human antibodies circulating in the mice at the time of infection was quantified via an ELISA assay (FIG. 1B) and was similar between the experimental and control antibodies.

Figure 10A:
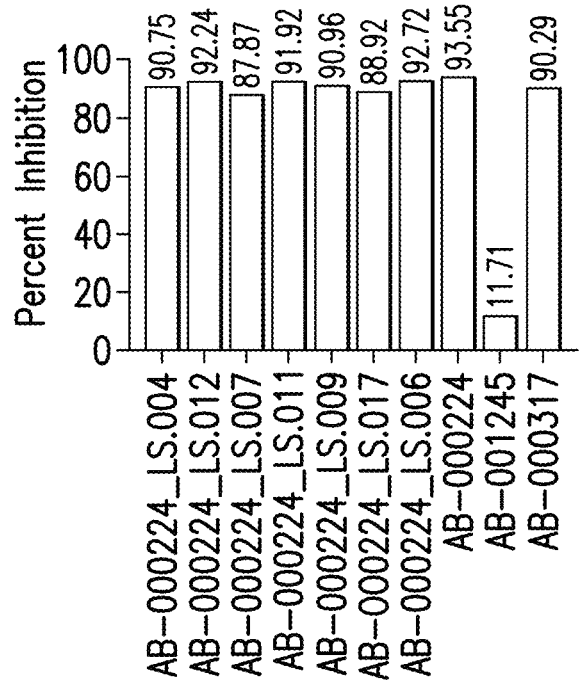
FIGS. 10A-10F illustrate parasite liver load following administration of experimental anti-CSP antibodies variants disclosed herein. Results are expressed as percentage inhibition, where naïve infected were considered as 100%.
Figure 10B:
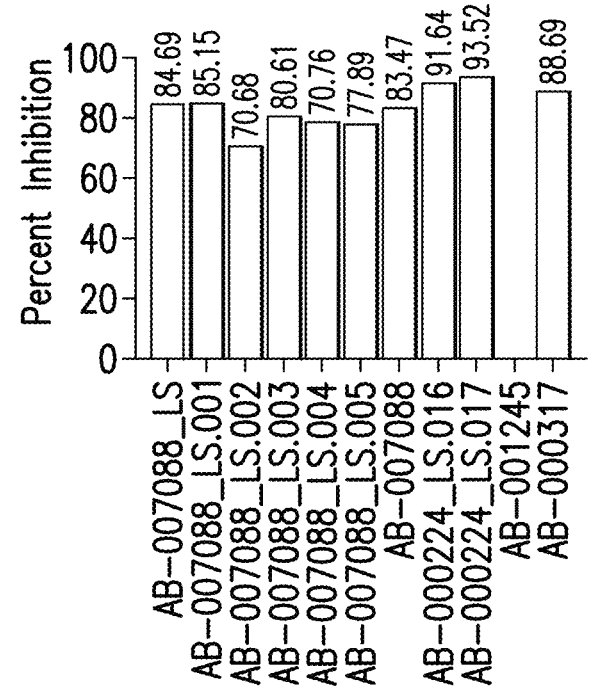
Figure 10C:
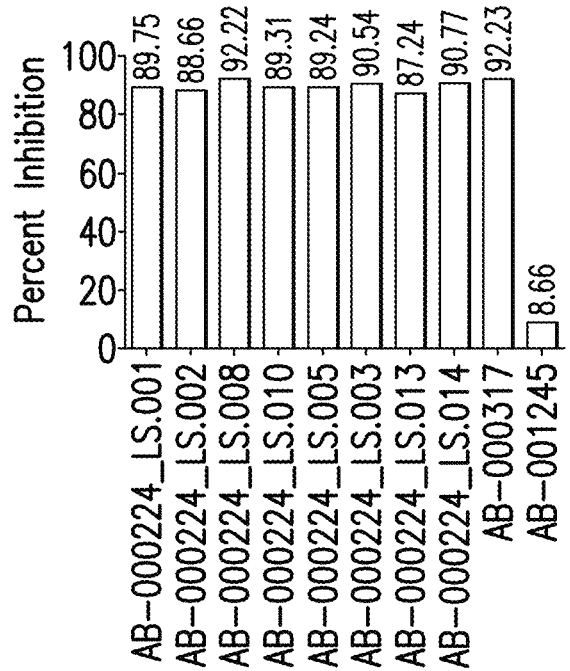
Figure 10D:
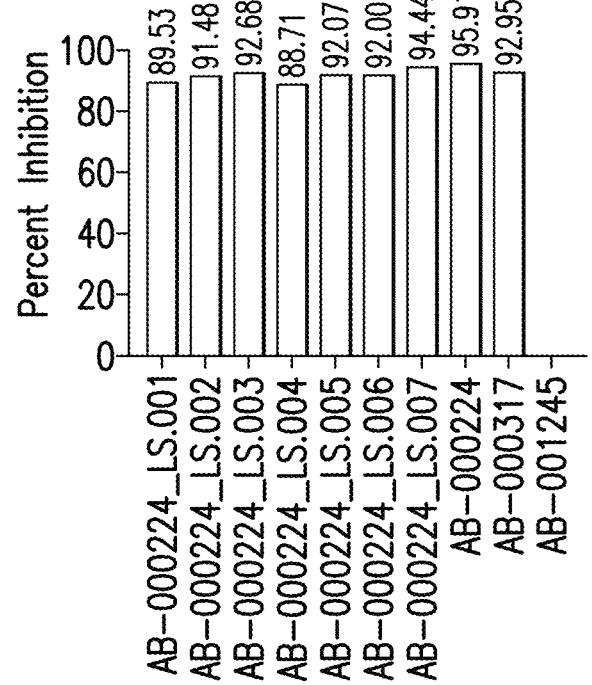
Figure 10E:
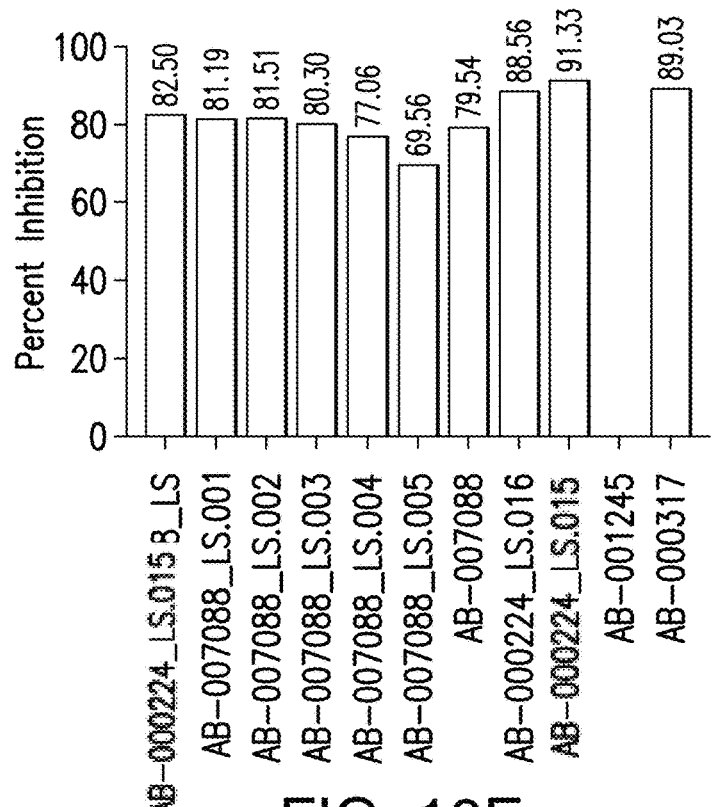
Figure 10F:
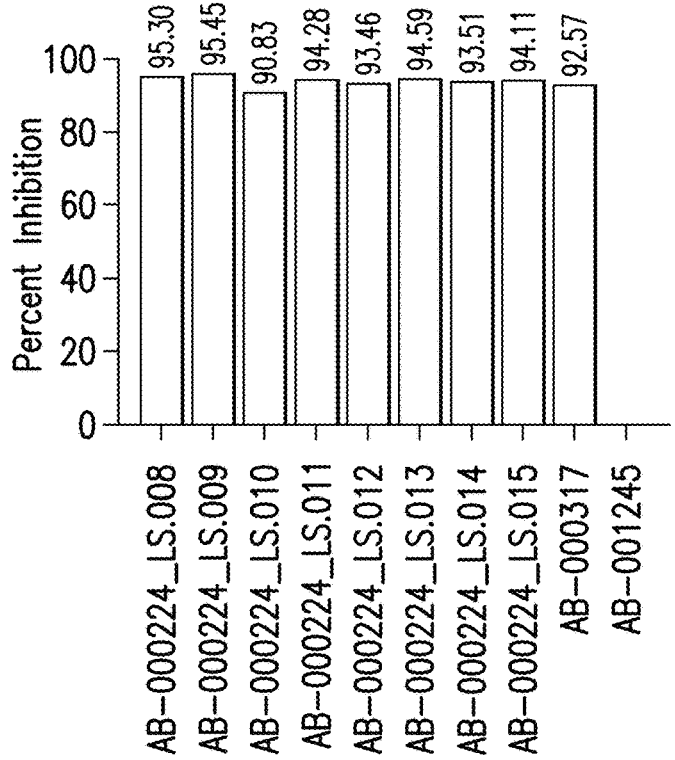
Figure 10G:
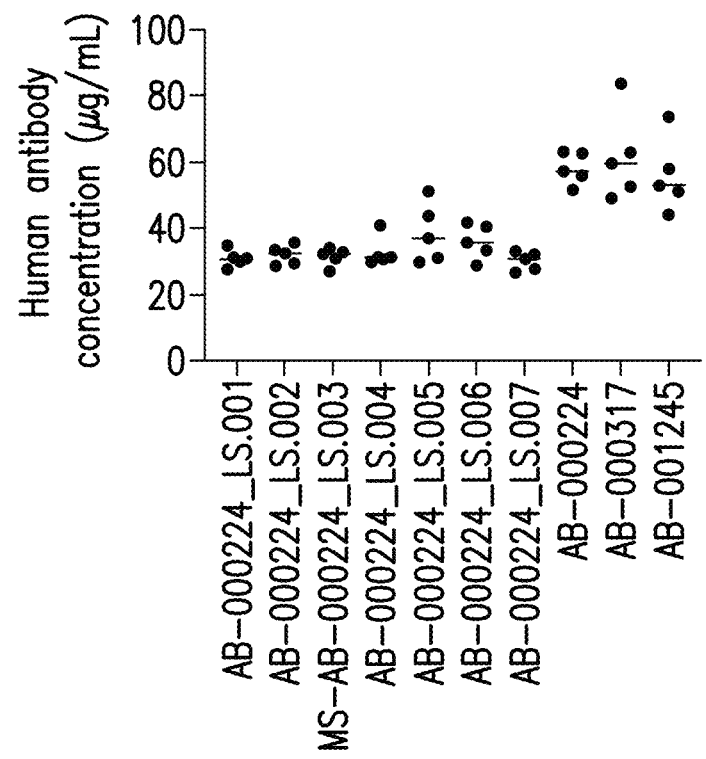
FIGS. 10G-10I show concentration of human antibodies that were circulating in the mice at the time of infection as determined by ELISA for the assays shown in FIGS. 10D-F, respectively. AB-001245 is a non-malaria-specific antibody that was used as a negative control. AB-000317 is a positive control.
Figure 10H:
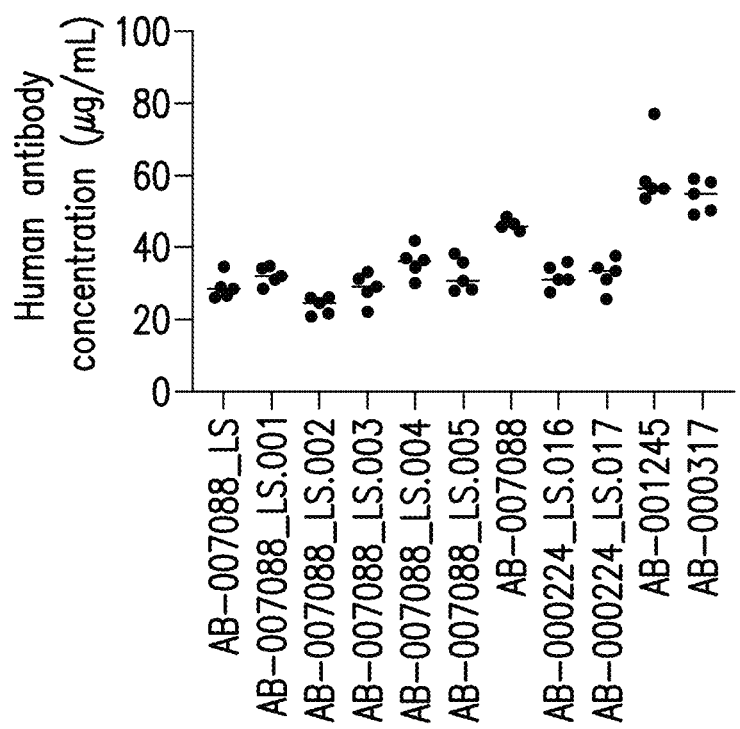
Figure 10I:
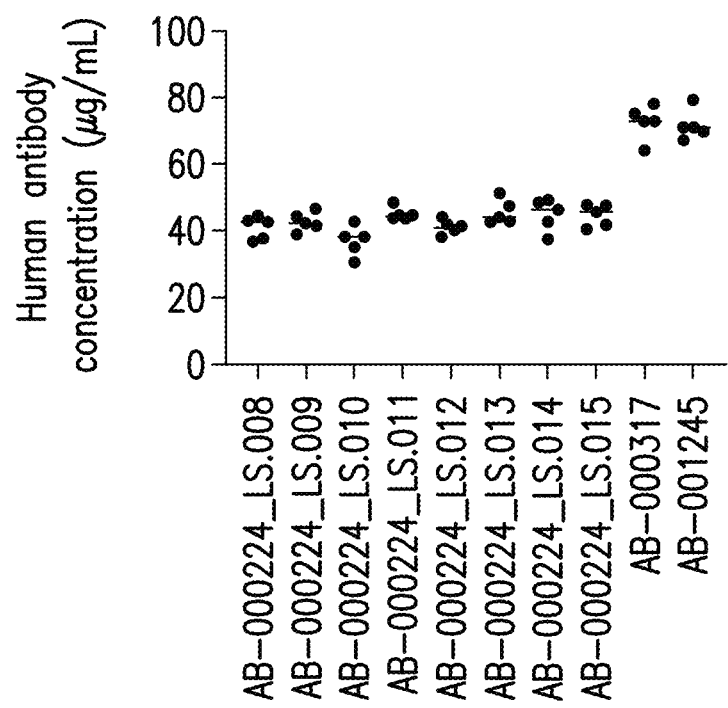

Variants of AB-000224 and AB-007088 drove reduction in liver burden load in treated mice that was comparable to the respective parent antibody AB-000224 or AB-007088 and the positive control antibody AB-000317. Liver burden levels measured in animals administered either the variants, the parent molecules or positive control antibody AB-000317 was significantly lower than liver burden levels in either the naïve infected mice or mice treated with the negative control, AB-001245 (FIGS. 10A-10F). Biological replicates of each antibody variant are shown in FIGS. 10A-10F. The concentration of human antibodies that were circulating in the mice at the time of infection was determined by ELISA and is shown in FIGS. 10G-10I.

Bite Parasitemia Assay

AB-000224 and AB-007088 and variants thereof were also evaluated for their ability to protect against infection (with those in format comprising Heavy Chain version 2 indicated with the "LS"). In this experiment, animals were exposed to mosquitoes infected with chimeric *P. berghei* expressing *P. falciparum* CSP protein, as described in Espinosa, D., et al. npj Vaccines 2017; 2, 10 (2017); Espinosa, D., et al. Infect Immun. 2013 August; 81(8): 2882-2887.

C57Bl/6 Mice were administered 150 μg of antibody and 16 hours later were exposed to six or seven chimeric *P. berghei*-infected mosquitoes. At least 70%-80% of the mosquito population are infected with chimeric *P. berghei* expressing *P. falciparum* CSP protein, resulting in exposure to at least one infectious event. Each mouse was subsequently evaluated for blood stage parasitemia from days 4-10 following infection by microscopy. Parasitemia data were recorded as positive or negative and the data used to generate a survival curve. Experimental antibodies were compared to both the positive (AB-000317) and negative (AB-001245) controls.

Figure 2A:
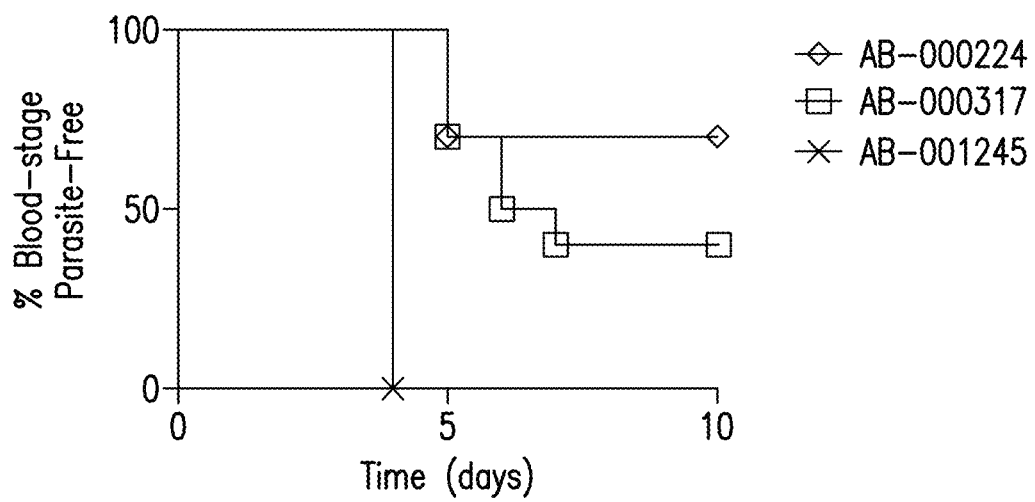
FIGS. 2A and 2C illustrate the survival rate of mice following administration of anti-CSP antibody AB-000224 and exposure to mosquitoes infected with chimeric *P. berghei* expressing *P. falciparum* CSP protein in two experiments.
Figure 2B:
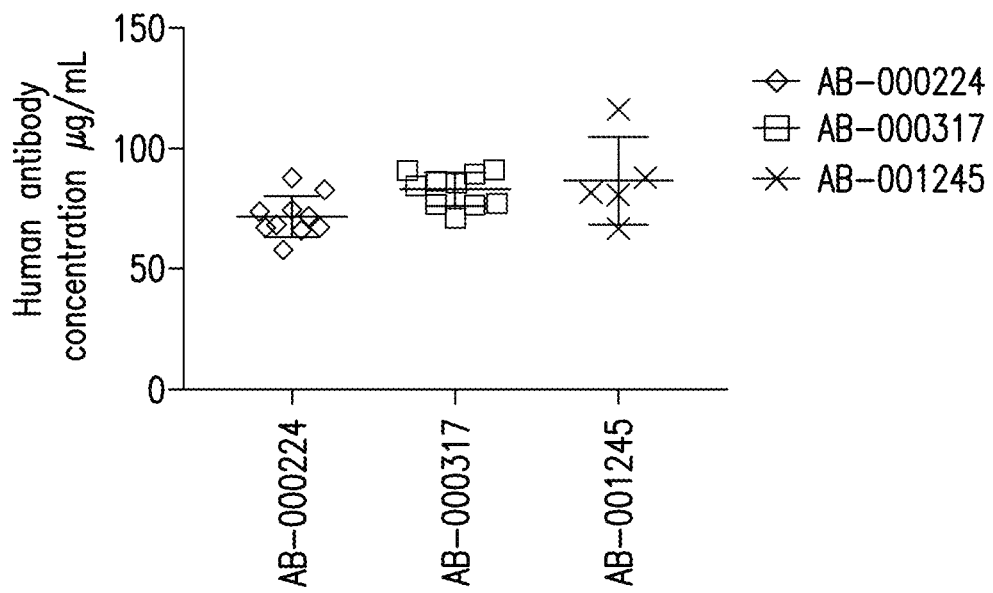
FIG. 2B shows the associated human IgG serum concentrations determined by ELISA obtained 15 hours following antibody administration in the experiment shown in FIG. 2A. AB-001245 is a non-malaria-specific antibody that was used as a negative control. AB-000317 is a positive control.
Figure 2C:
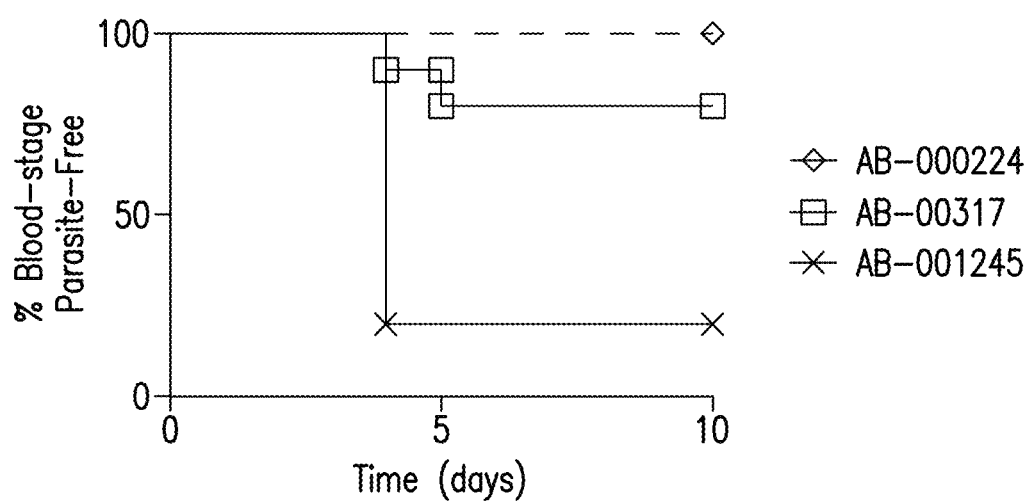
Figure 3A:
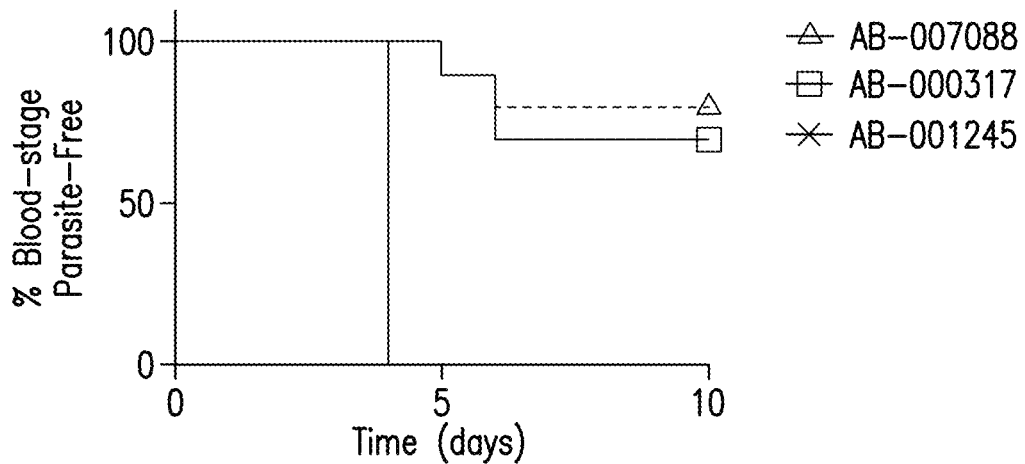
FIGS. 3A and 3C illustrate the survival rate of mice following administration of anti-CSP antibody AB-007088 and exposure to mosquitoes infected with chimeric *P. berghei* expressing *P. falciparum* CSP protein in two experiments.
Figure 3B:
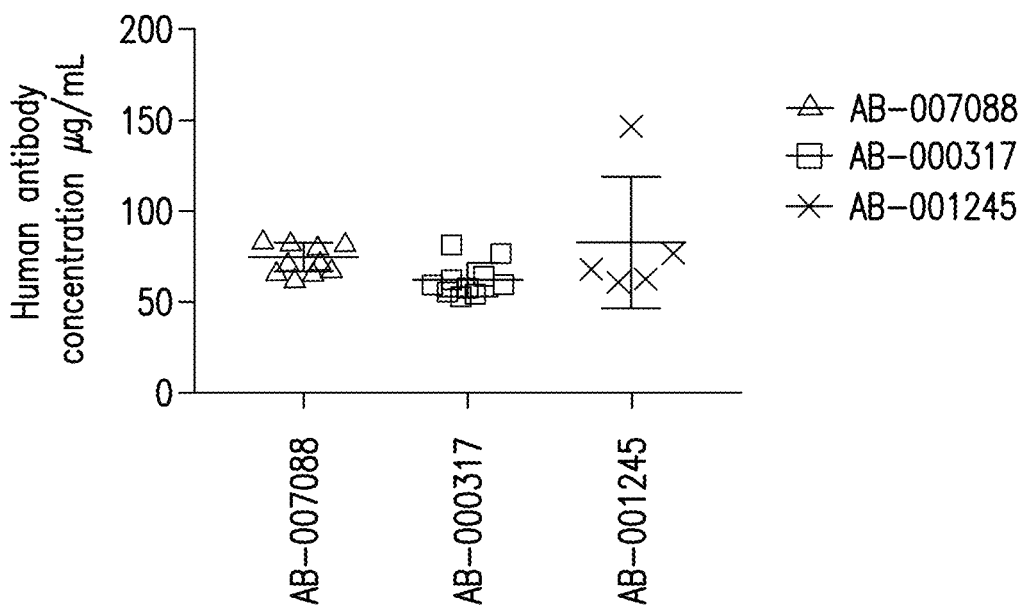
FIG. 3B shows the associated human IgG serum concentrations determined by ELISA obtained 15 hours following antibody administration in the experiment shown in FIG. 3A. AB-001245 is a non-malaria-specific antibody that was used as a negative control. AB-000317 is a positive control.
Figure 3C:
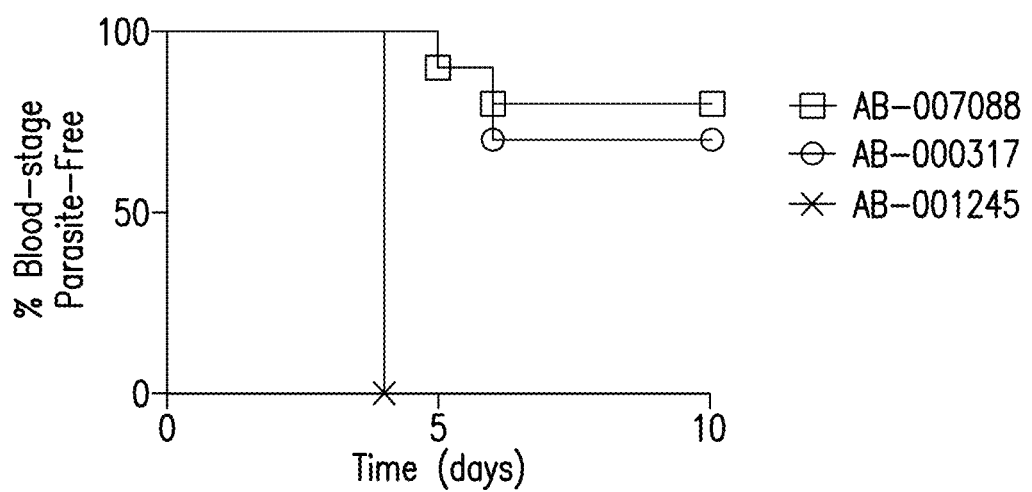

Mice treated with AB-000224, AB-007088 or the positive control AB-000317 were less likely to develop parasitemia as compared to mice treated with the negative control AB-001245. (FIGS. 2A and 2C show AB-000224 experimental data and FIGS. 3A and 3C show AB-007088 experimental data). The level of human antibodies circulating in the mice at the time of infection was quantified via an ELISA assay (FIGS. 2B and 3B) and was similar between the experimental and control antibodies.

Figure 11A:
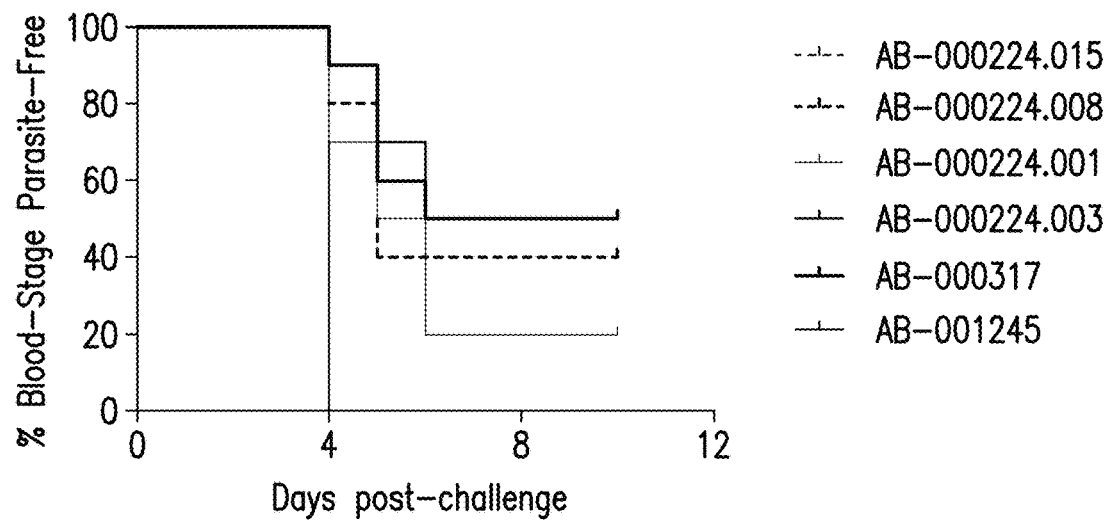
FIGS. 11A-11C illustrate the survival rate of mice following administration of anti-CSP antibody variants disclosed herein and exposure to mosquitoes infected with chimeric P. berghei expressing P. falciparum CSP protein.
Figure 11B:
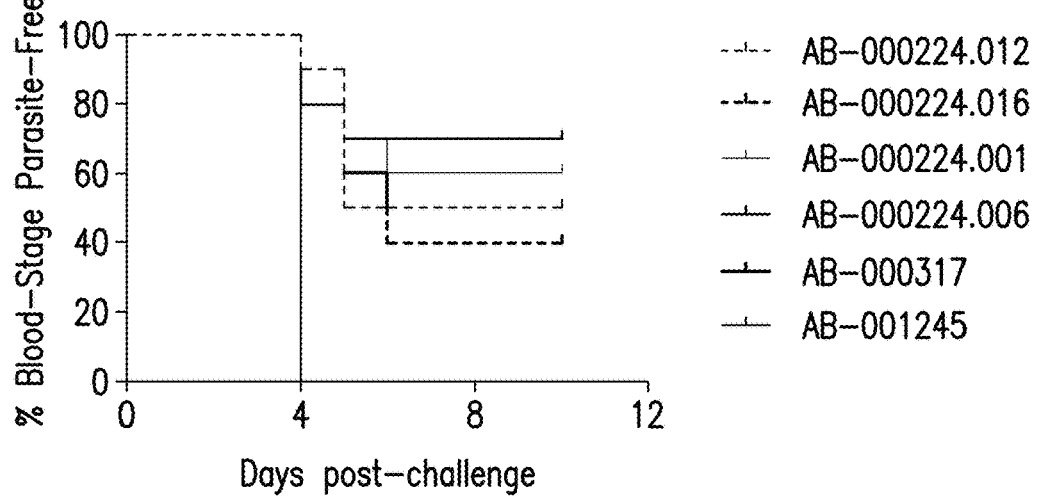
Figure 11C:
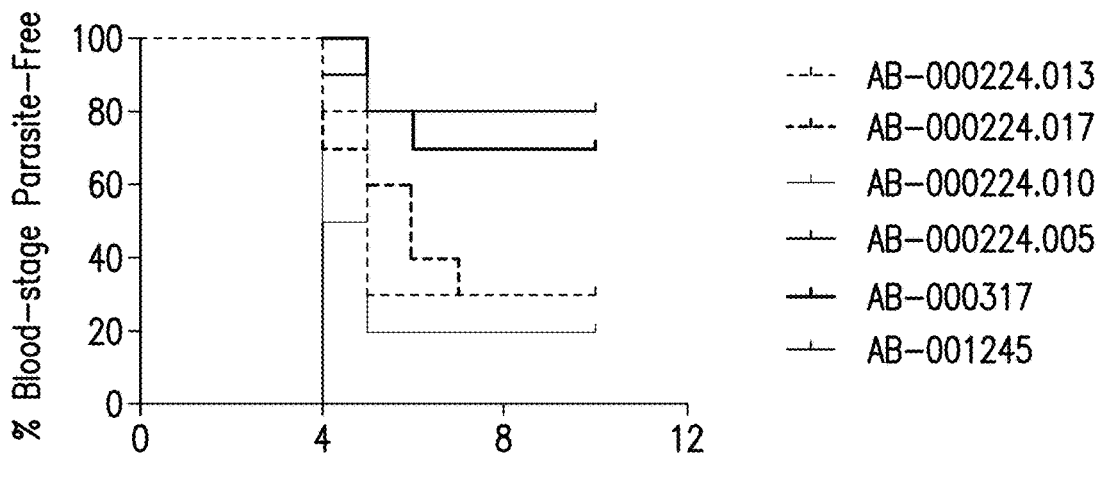
Figure 11F:
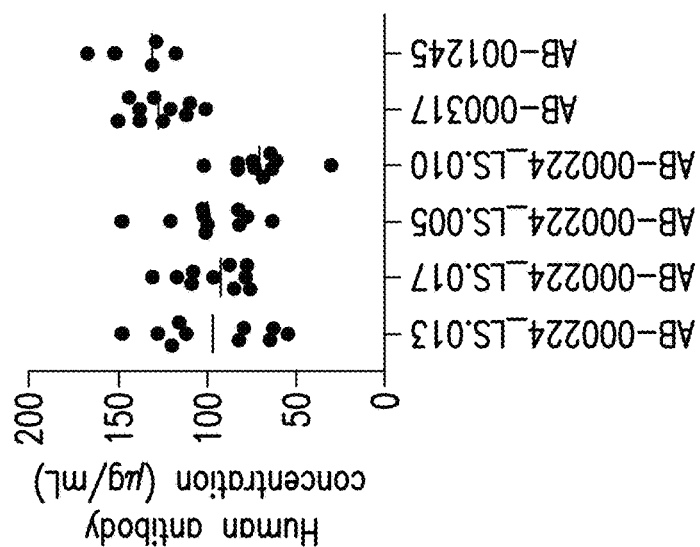
FIGS. 11D-F show concentration of human antibodies that were circulating in the mice at the time of infection as determined by ELISA for the assays shown in FIGS. 11A-C, respectively. AB-001245 is a non-malaria-specific antibody that was used as a negative control. AB-000317 is a positive control.
Figure 11E:
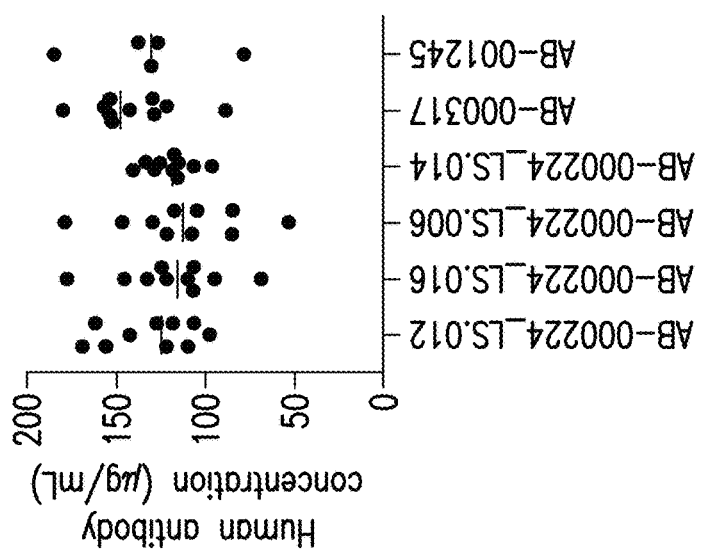
Figure 11D:
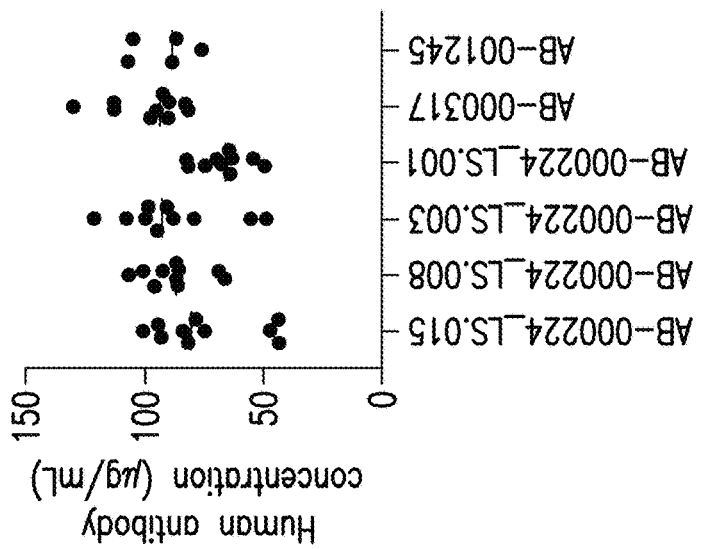

Finally, mice administered variants of AB-000224 or AB-007088 were comparably likely to remain parasite-free as mice treated with either of the parent antibodies, or the positive control antibody AB-000317 (FIGS. 11A-11C). The concentration of human antibodies that were circulating in the mice at the time of infection was determined by ELISA and is shown in FIGS. 11D-11F.

Example 5. Biophysical Characterization

The present example describes the biophysical hallmarks of the anti-CSP antibody variants. AB-000224 and AB-007088 and variants thereof (all in the format comprising Heavy Chain version 2) were evaluated for their conformational stability and colloidal stability. Several methods were used to analyze these endpoints and are summarized in the Tables 37 and 38 below:

TABLE 37

Conformational Stability Methods

| Method Name | Attribute Measured | Characterization | Desired Outcome | Values that indicate instability |
| --- | --- | --- | --- | --- |
| Differential scanning fluorimetry (DSF) | Melting temperature | Lower Tm(app) is indicative of decreased conformational stability | Increase in Tm or formation of additional Tm's indicating increased domain stability | Weighted Shoulder Score (WSS) Below 20 |
| Thermal hold | Temperature induced aggregation | Define conditions for precipitation relating to potential destabilization during room temperature incubation | Increase in thermal stability indicated by the absence of precipitation | Absorbance at 350 nm is above 0.5 |
| Low pH Aggregation | Low pH stability by high molecular weight | Molecules with an increase in high molecule weight following neutralization after low pH exposure may show increased aggregation during low pH viral inactivation | No significant increase in high molecular weight species following low pH exposure and neutralization | More than 10% aggregation after low pH exposure |
| Chemical Unfolding | Conformational stability | Molecules with an increased inflection point may show lower rates of aggregation during storage and are more conformationally stable | Increased inflection point compared to the parent molecule | Less than 2.1M inflection point |

TABLE 38

Colloidal Stability Methods

| Method Name | Attribute Measured | Characterization | Desired Outcome | Values that indicate instability |
| --- | --- | --- | --- | --- |
| Self-interaction nanoparticle spectroscopy (SINS) | Protein-protein interaction | Define relative protein self-association to help identify potential for higher viscosity during concentration and problems with filterability | Decrease in parameters indicating self-association of the molecule | Wavelength Maximum Above 550 nm |

TABLE 38-continued

Colloidal Stability Methods

| Method Name | Attribute Measured | Characterization | Desired Outcome | Values that indicate instability |
|---|---|---|---|---|
| Standup Monolayer Affinity Chromatography (Zenix Column) | Colloidal stability | Molecules with reduced retention times may show increase solubility and lower rates of aggregation during storage | Decreased main peak retention time compared to parent molecule | Longer retention times, there is no established values correlating to instability at this time |
| Relative Solubility Analysis (RSA) | Polyethylene glycol based solubility analysis | Molecules with higher relative solubility may show lower rates of aggregation during storage | Increased solubility compared to parent molecule | 50% Loss of protein occurring less than 7% PEG |
| Polyreactivity | Non-specific binding | Molecules that have the potential to non-specifically bind to an array of different antigens can potentially have a higher clearance rate. | Decreased non-specific binding compared to the parent molecule | Absorbance at 405 nm is above 1.5-2.0 |

AB-000224 Variants Showed Improved Stability

AB-000224 and variants thereof showed comparable harvest yield and titer results. Thus, additional end-points were assessed. AB-000224 and variants thereof were evaluated for their thermal stability by differential scanning fluorimetry (DSF). Thermal unfolding was monitored by measuring the intensity of an extrinsic dye (sypro orange) as the sample was heated from 20° C. to 90° C. The data was reported as Tm1 and Tm2 with the first transition correlating with the CH2 domain and the 2nd transition correlating with the unfolding of the Fab and CH3 domain regions. Higher unfolding temperatures are desirable and have been linked with an increase in a product's conformational stability. Lack of a Tm2 is indicative of the Fab unfolding at the same or similar temperature to the CH2 domain, reported as Tm1. Additional information is also obtained from a proprietary parameter termed the weighted shoulder score which accounts for multiple pieces of information from the unfolding curve. Again, higher values are indicative of greater conformational stability. The DSF analysis was conducted in PBS buffer, with all samples being diluted down to a final antibody concentration of 0.15 mg/mL.

The propensity to aggregate at elevated temperatures was assessed using the thermal aggregation method. Samples were place in a 96 well Biorad PCR plate and heated to various temperatures for 5 minutes using a Biorad Thermal Cycler. After heating, protein precipitation was determined by reading the absorbance at 350 nm (A350) using a Spectrostar nano plate reader. Almost all AB-000224 variants showed higher WSS as compared to the parent antibody AB-000224, a T2 that approached 80° C., and no precipitation during thermal hold assays. However, AB-000224.017 did not have a T2 and showed precipitation during thermal hold assay.

Further, AB-000224 and variants thereof were also evaluated for their chemical stability. Sensitivity to low pH was assessed by titrating the samples to pH 3.3 using acetic acid, holding the samples for 30 minutes, neutralizing the samples to pH 5 with tris base, and measuring aggregation by size exclusion HPLC. Samples that were diluted with PBS using the same volume of acetic acid and tris base as used in the test samples were used as a control. AB-000224 and all variants thereof did not show low pH instability.

AB-000224 and variants thereof were tested for stability against chemical unfolding as assayed by denaturation with guanidine. Chemical unfolding curves were produced by exposing the antibodies to increasing concentrations of guanidine hydrochloride. After 24 hours, the intrinsic fluorescence of the samples is measured using a SUPR-UV plate reader. The collected raw data was then processed and the chemical unfolding curve and its inflection point calculated from the processed data as a function of denaturant condition. Antibodies with denaturation inflection points higher than 2.1 M guanidine are considered to be conformationally stable by this method. AB-000224 and all variants showed inflection points above 2 M guanidine (Gdn). Notably, AB-000224.005, AB-000224.008, AB-000224.010, AB-000224.011, AB-000224.013, and AB-000224.015 showed improved stability against chemical unfolding as compared to AB-000224, each having an inflection point above 2.3 M guanidine.

AB-000224 and variants thereof were also evaluated for their colloidal stability by self-interaction nanoparticle spectroscopy (SINS) which monitors protein-protein interactions by capture on the surface of a gold colloid and measuring shifts of the wavelength of maximum absorption. Maximum absorption values of wavelengths higher than 550 nm are consider interacting and could manifest in increase viscosity and filterability issues. All variants had maximum absorption values less than 550 nm and showed a slight improvement in the SINS values as compared to AB-000224.

AB-000224 and variants thereof were tested for potential hydrophobic interactions that might results in manufacturability challenges by monitoring retention time on a Zenix HPLC column. Undiluted samples were loaded onto the Zenix column and eluted isocratically with a 100 mM sodium phosphate, pH 7.0 running buffer and monitored at 220 nm. Longer retention times indicates hydrophobic interactions. Most antibodies have a retention time of 8.5-9.0 minutes under conditions tested. AB-00224 and all variants thereof showed comparable retention times of approximately 10 minutes.

Solubility of AB-000224 and variants thereof was assayed by precipitating the antibody samples with increasing amounts of PEG 10,000, filtering the samples, and measuring the soluble protein concentration. For each parent molecule, an initial experiment was performed to determine the ideal PEG concentration to precipitate the parent by approximately 50%, subsequent experiments used this PEG concentration on all variants to assess if a variant is more or less soluble than the parent molecule. Antibodies that precipitate above 8-10% PEG are considered highly soluble while poorly soluble antibodies precipitate at 4-5% PEG. AB-000224 and all variants thereof showed high solubility.

Polyreactivity of AB-000224 and variants thereof was determined by testing the antibodies for binding to KLH, insulin and dsDNA by Elisa. Samples were diluted to 1 μg/mL and a secondary anti-human antibody was used to detect the amount of protein that has bound to the different antigens. After substrate addition, absorbance was measured at 405 nm. A polyreactive antibody was used as a positive control. Non-specific binding to such common physiological components can cause an increase clearance rate, negatively impacting pK. Absorbance values above 1.5 for KLH and Insulin and 2.0 for dsDNA could indicate non-specific binding issues for a molecule. While most of the AB-000224 variants did not show any polyreactivity, some variants showed polyreactive signal against insulin (AB-000224.006, AB-000224.007, AB-000224.008, AB-000224.009, AB-000224.010).

Figure 12A:
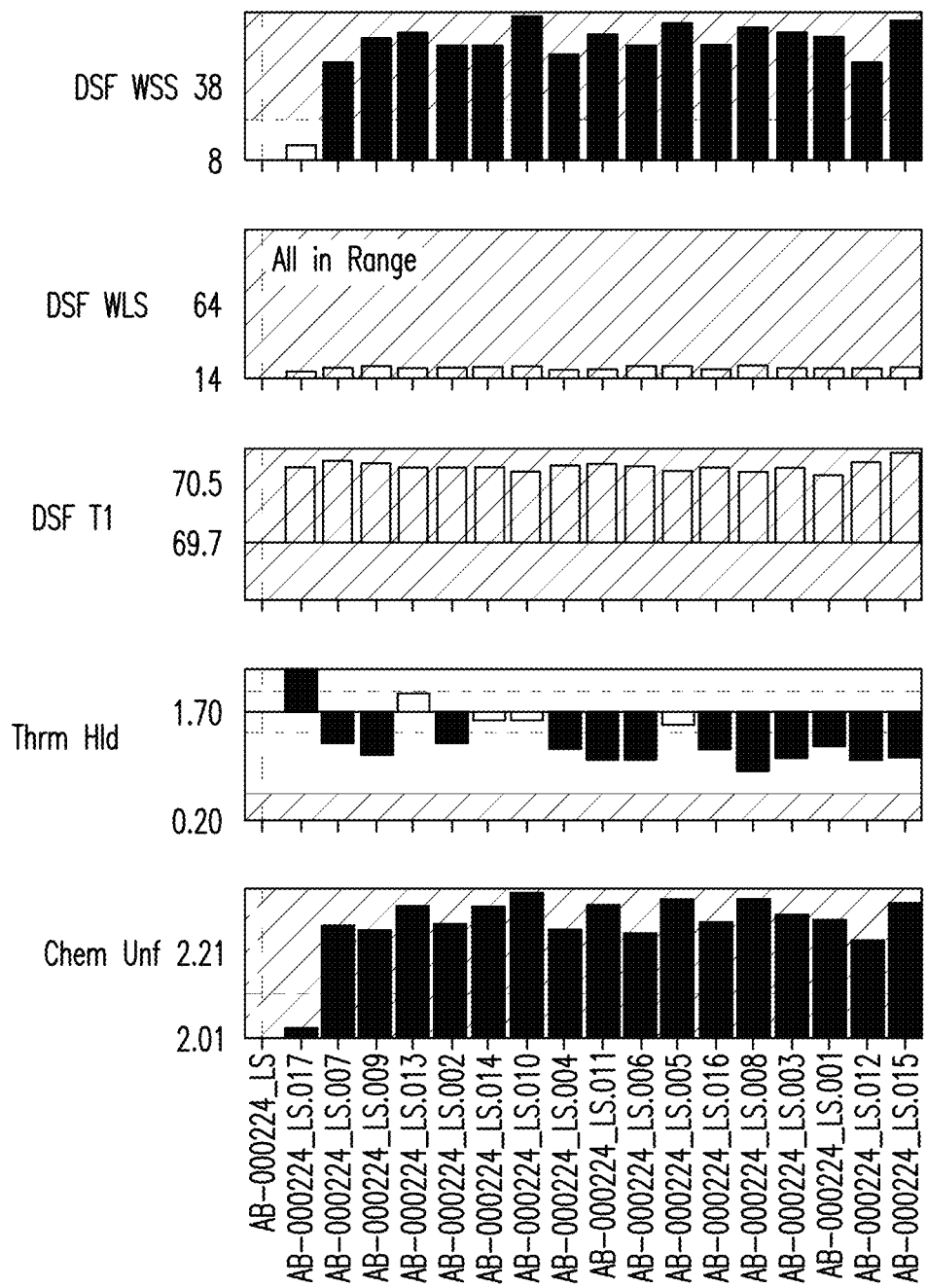
FIG. 12A illustrates the biophysical characterization of AB-000224 and variants thereof.
Figure 12A:
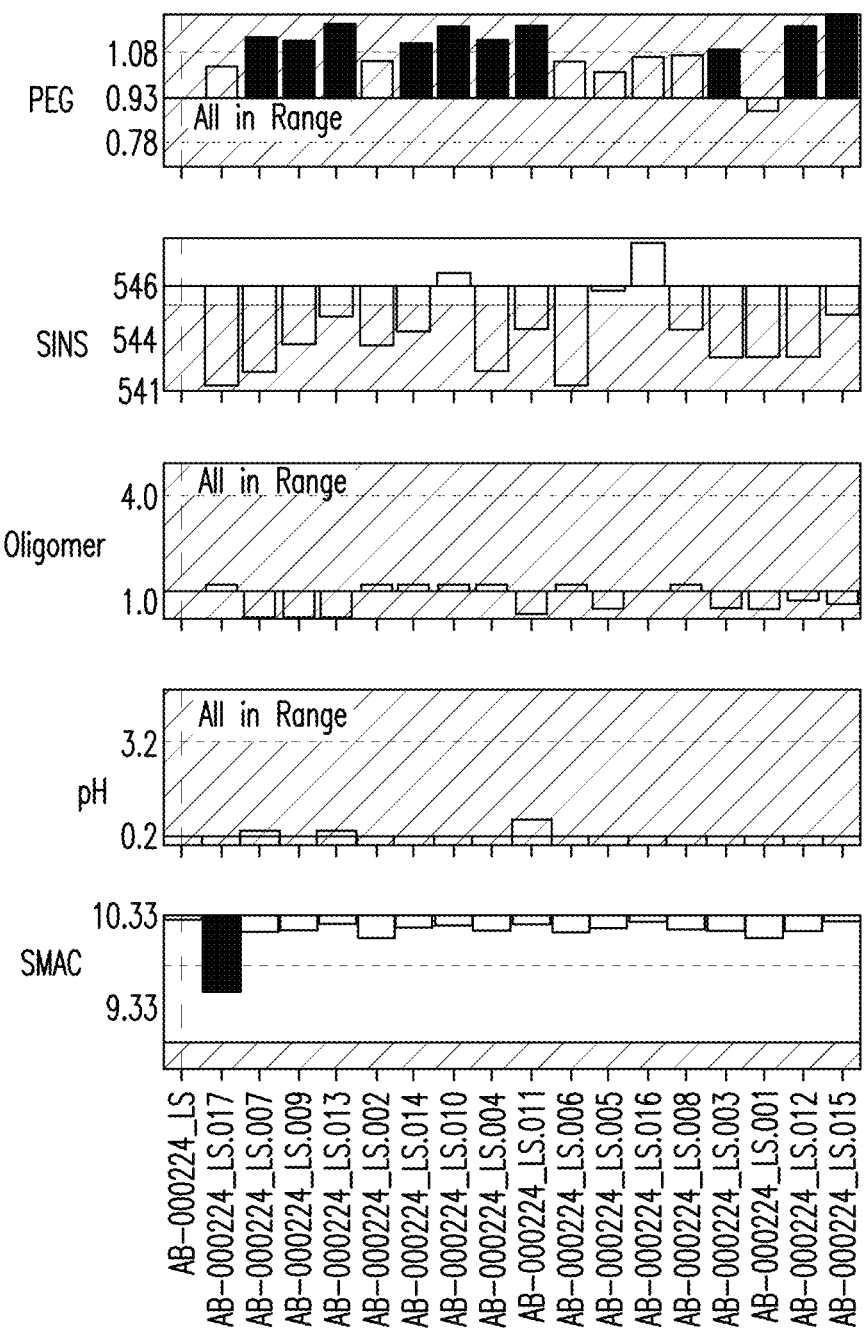
Figure 12A:
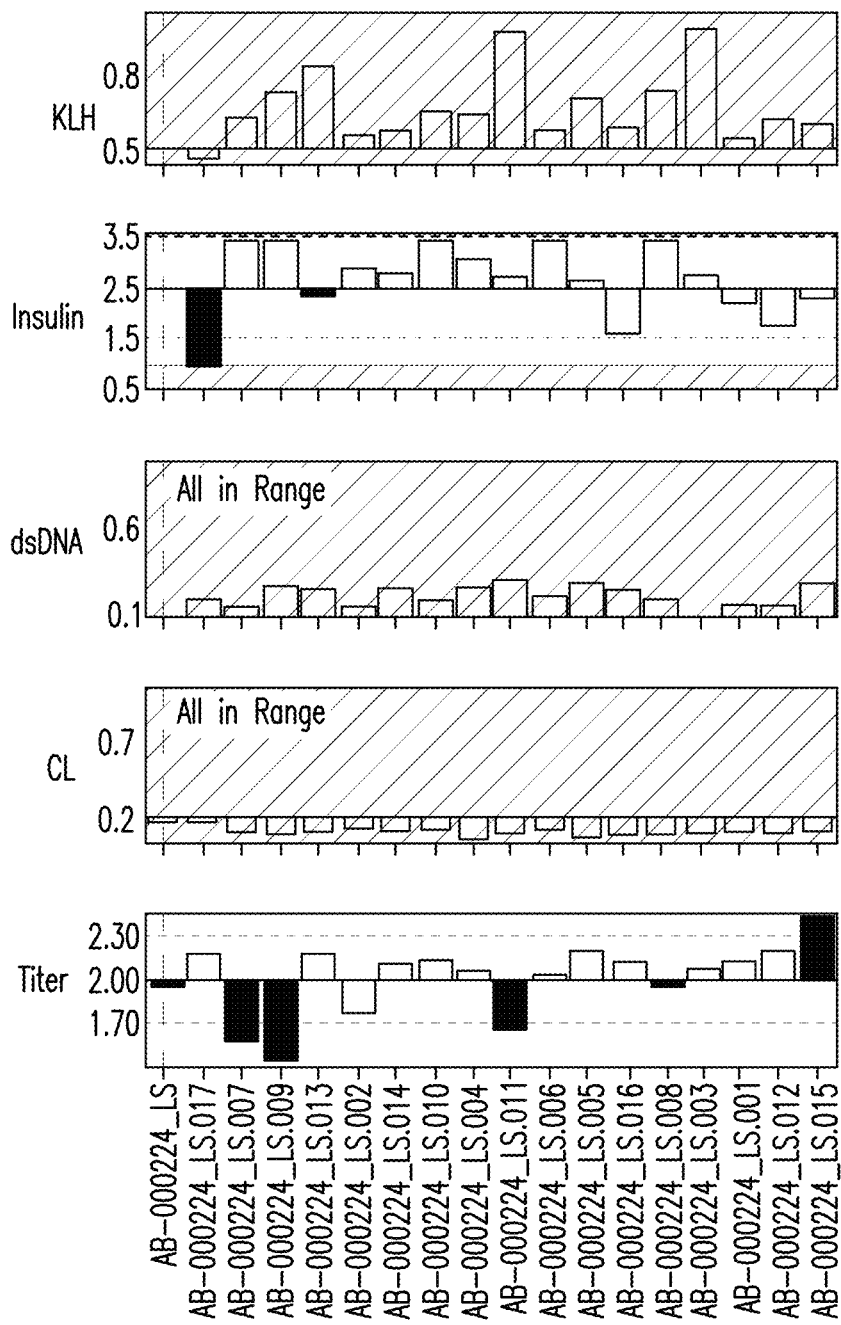
Figure 12B:
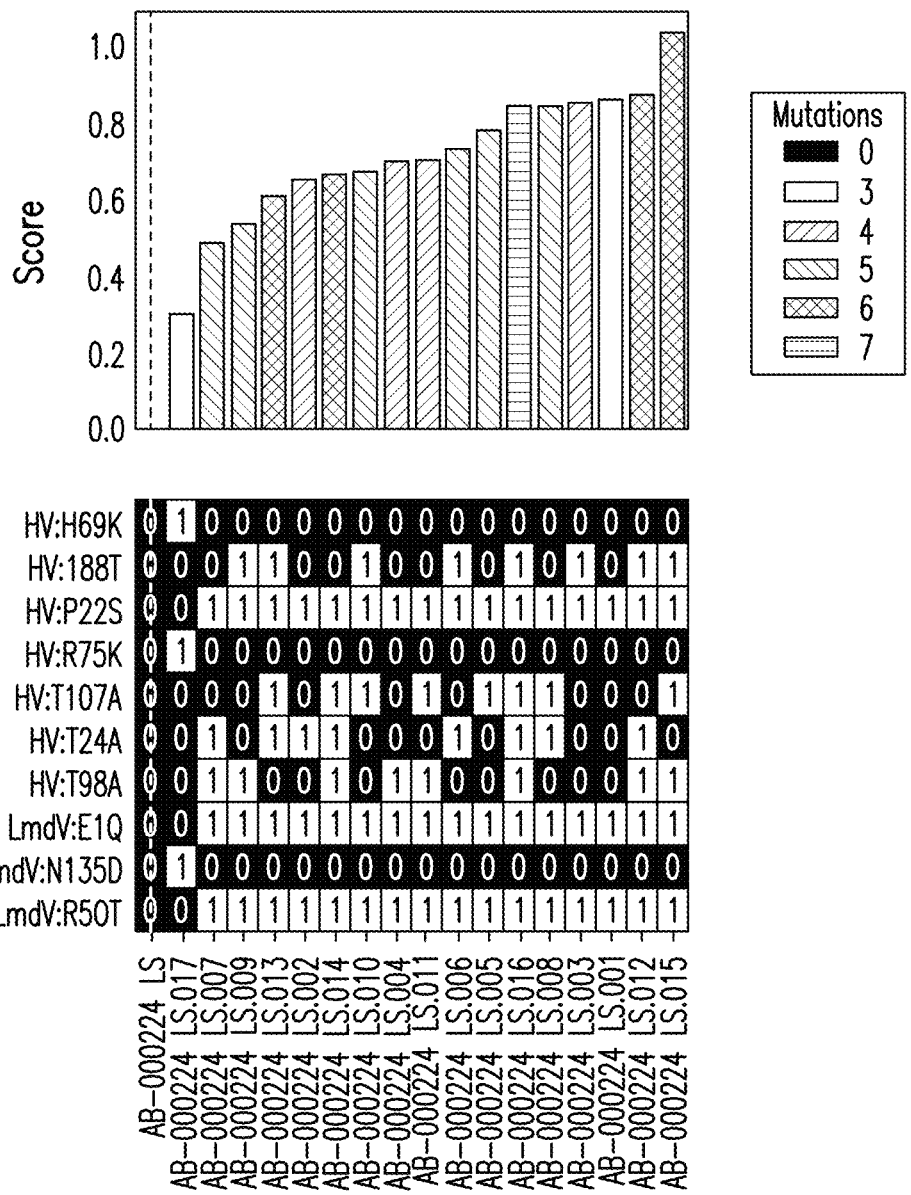
FIG. 12B shows the ranking of the AB-000224 and variants thereof based on all data obtained during biophysical characterization.
Figure 12C:
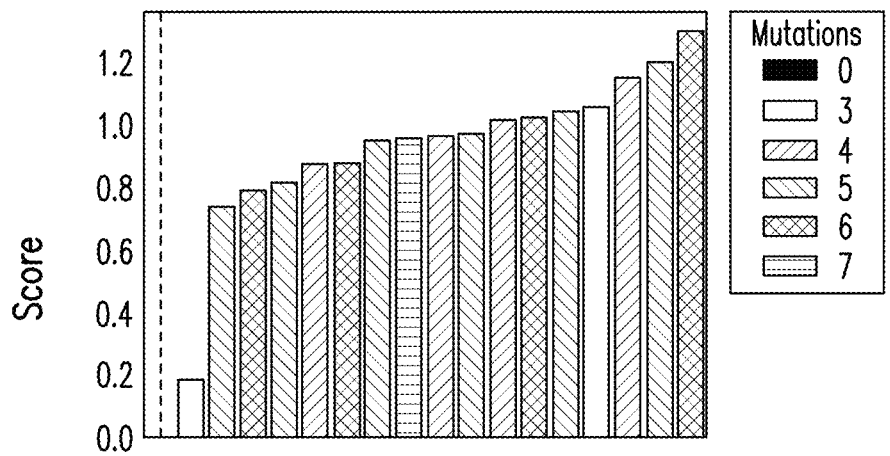
FIG. 12C shows the ranking of the AB-000224 and variants thereof excluding polyreactivity and including titer.

The AB-000224 and variants thereof were ranked based on the different assays and titer results and ranked as described in FIGS. 12B and 12C.

AB-007088 Variants Showed Improved Stability

The harvest yield and titer of the AB-007088 and variants thereof were initially evaluated. The AB-007088 variants showed comparable harvest yield and titer results. AB-007088 and variants thereof were evaluated to determine conformational and colloidal stability as described above for AB-000224 and variants thereof.

The AB-007088.005 variant showed improved thermal stability by the DFS method and a T2 that approached 75° C., while the other variants were similar to the parent AB-007088 with T1 values of approximately 70° C. and no measurable T2. In addition, AB-007088.005 showed a slightly reduced precipitation as compared to the parent AB-007088 and the other variants. When chemical stability was evaluated, AB-007088 and all variants thereof did not show low pH instability (at pH 3.3). Further, AB-007088 and all variants thereof showed stability against chemical unfolding with an inflection point above 2 M guanidine (Gdn). Notably, AB-007088.001 showed improved stability as compared to AB-007088 with an inflection point above 2.3 M guanidine.

AB-007088 and variants thereof were also evaluated for their colloidal stability. When protein-protein interactions were monitored (SINS), all variants showed very low SINS values, indicating absence of protein-protein interactions. In addition, AB-007088 and variants thereof showed comparable retention times on Zenix column. Notably, when PEG solubility was determined, AB-007088 and all variants thereof showed high solubility. Further, while most of the AB-007088 variants did not show any polyreactivity, some variants showed polyreactive signal against insulin (AB-007088.001, AB-007088.003, AB-007088.004).

Figure 13A:
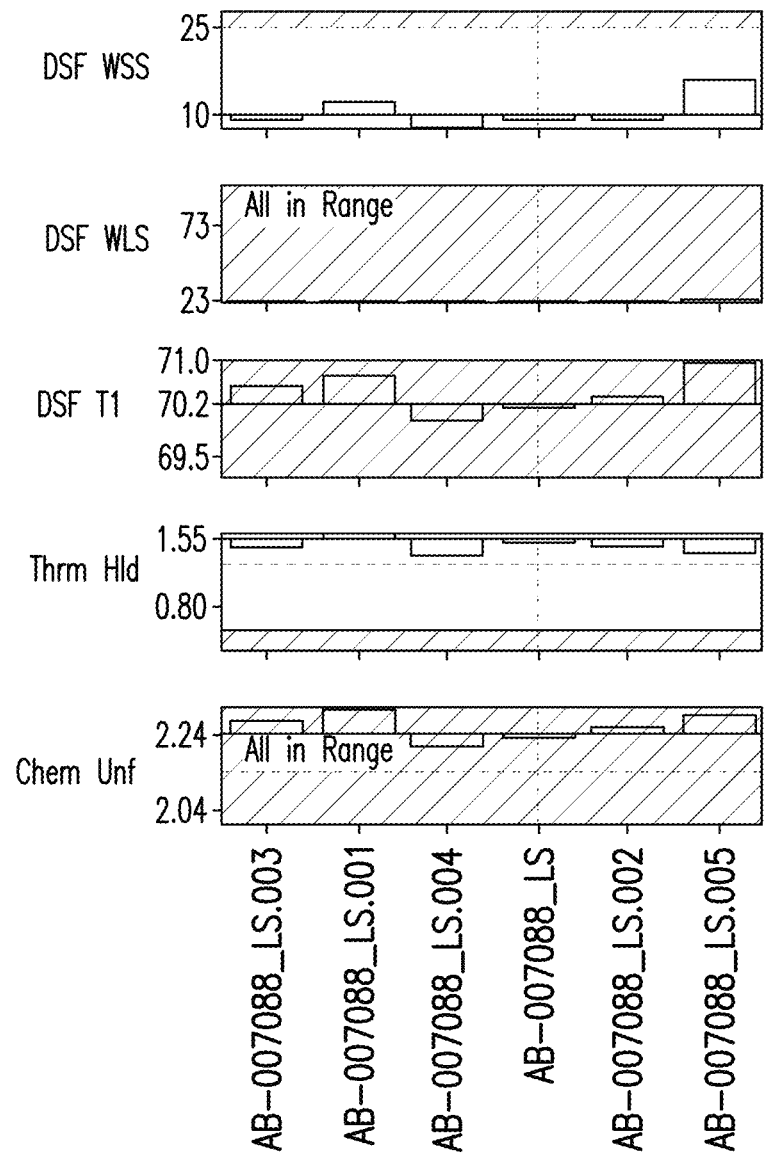
FIG. 13A illustrates the biophysical characterization of AB-007088 and variants thereof.
Figure 13A:
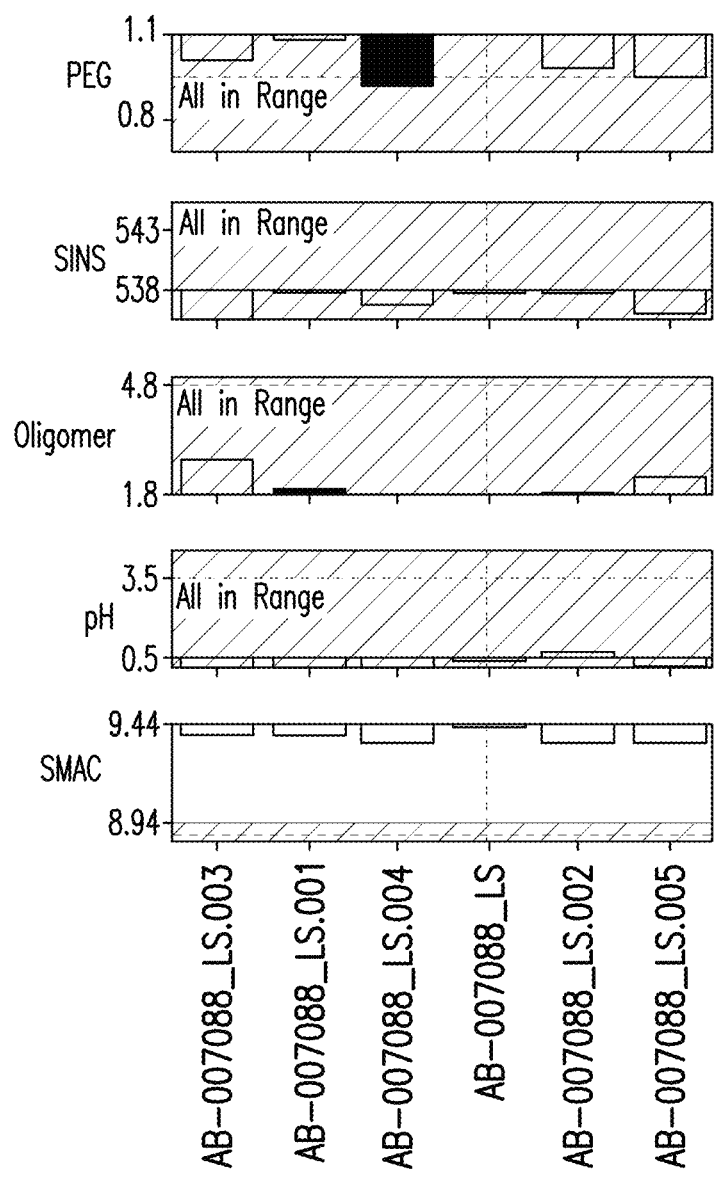
Figure 13A:
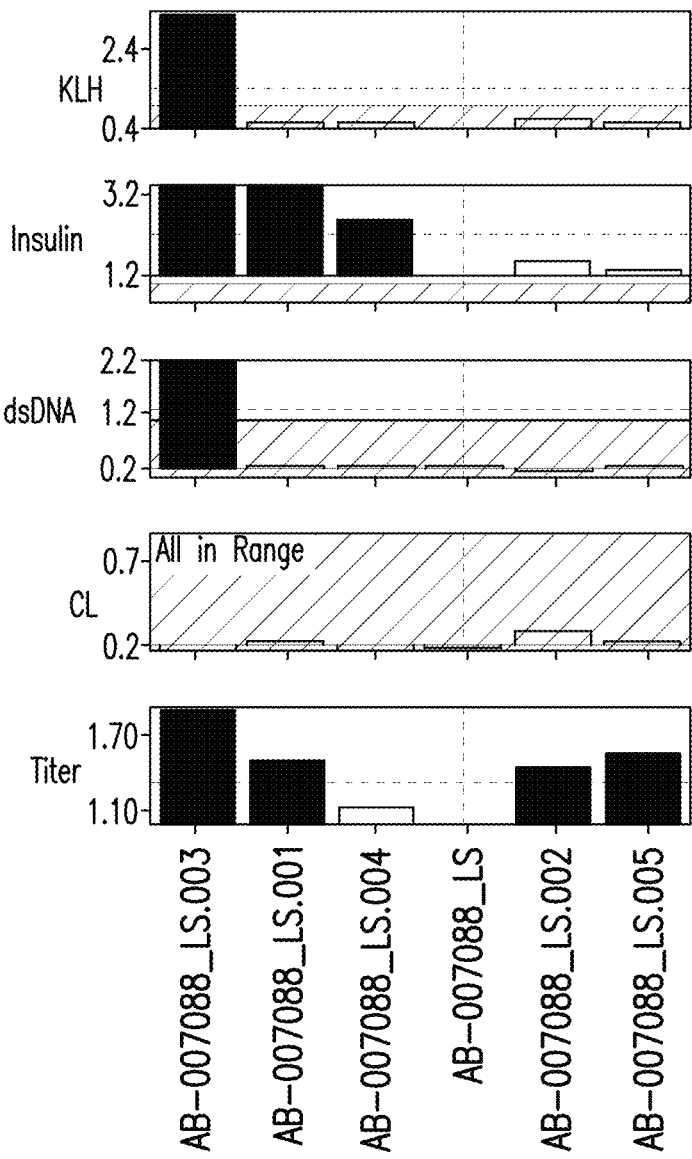
Figure 13B:
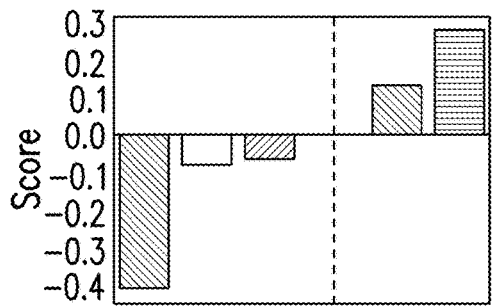
FIG. 13B shows the ranking of the AB-007088 and variants thereof based on all data obtained during biophysical characterization.
Figure 13C:
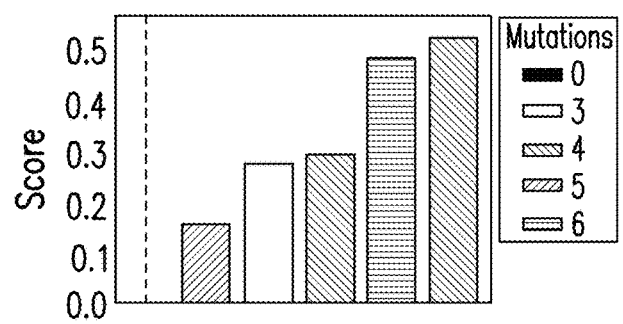
FIG. 13C shows the ranking of the AB-007088 and variants thereof excluding polyreactivity and including titer.

The AB-007088 and variants thereof were ranked based on the different assays and titer results, and ranked as described in FIGS. 13B and 13C.

What is claimed is:

1. A recombinant anti-circumsporozoite (CSP) antibody comprising a light chain variable region (VL) and a heavy chain variable region (VH), wherein:
   a) the light chain variable region comprises a CDR1 comprising the amino acid sequence set forth in SEQ ID NO: 1, a CDR2 comprising the amino acid sequence set forth in SEQ ID NO: 2, and a CDR3 comprising the amino acid sequence set forth in SEQ ID NO: 3; and the heavy chain variable region comprises a CDR1 comprising the amino acid sequence set forth in SEQ ID NO: 4, a CDR2 comprising the amino acid sequence set forth in SEQ ID NO: 5, and a CDR3 comprising the amino acid sequence set forth in SEQ ID NO: 6;
   b) the light chain variable region comprises a CDR1 comprising the amino acid sequence set forth in SEQ ID NO: 183, a CDR2 comprising the amino acid sequence set forth in SEQ ID NO: 184, and a CDR3 comprising the amino acid sequence set forth in SEQ ID NO: 185; and the heavy chain variable region comprises a CDR1 comprising the amino acid sequence set forth in SEQ ID NO: 186, a CDR2 comprising the amino acid sequence set forth in SEQ ID NO: 187, and a CDR3 comprising the amino acid sequence set forth in SEQ ID NO: 188;
   c) the light chain variable region comprises a CDR1 comprising the amino acid sequence set forth in SEQ ID NO: 205, a CDR2 comprising the amino acid sequence set forth in SEQ ID NO: 206, and a CDR3 comprising the amino acid sequence set forth in SEQ ID NO: 207; and the heavy chain variable region comprises a CDR1 comprising the amino acid sequence set forth in SEQ ID NO: 208, a CDR2 comprising the amino acid sequence set forth in SEQ ID NO: 209, and a CDR3 comprising the amino acid sequence set forth in SEQ ID NO: 210.

2. The recombinant antibody of claim 1, wherein the light chain variable region (VL) comprises:
   a) the amino acid sequence set forth in SEQ ID NO: 23;
   b) the amino acid sequence set forth in SEQ ID NO: 33;
   c) the amino acid sequence set forth in SEQ ID NO: 43;
   d) the amino acid sequence set forth in SEQ ID NO: 53;
   e) the amino acid sequence set forth in SEQ ID NO: 63;
   f) the amino acid sequence set forth in SEQ ID NO: 73;
   g) the amino acid sequence set forth in SEQ ID NO: 83;
   h) the amino acid sequence set forth in SEQ ID NO: 93;
   i) the amino acid sequence set forth in SEQ ID NO: 103;
   j) the amino acid sequence set forth in SEQ ID NO: 113;
   k) the amino acid sequence set forth in SEQ ID NO: 123;
   l) The amino acid sequence set forth in SEQ ID NO: 133;
   m) the amino acid sequence set forth in SEQ ID NO: 143;
   n) the amino acid sequence set forth in SEQ ID NO: 153;
   o) the amino acid sequence set forth in SEQ ID NO: 163;
   p) the amino acid sequence set forth in SEQ ID NO: 173;
   q) the amino acid sequence set forth in SEQ ID NO: 195;
   r) the amino acid sequence set forth in SEQ ID NO: 227;
   s) the amino acid sequence set forth in SEQ ID NO: 237;
   t) the amino acid sequence set forth in SEQ ID NO: 247;
   u) the amino acid sequence set forth in SEQ ID NO: 257; or
   v) the amino acid sequence set forth in SEQ ID NO: 267.

3. The recombinant antibody of claim 1, wherein the heavy chain variable region (VH) comprises:
   a) the amino acid sequence set forth in SEQ ID NO: 24;
   b) the amino acid sequence set forth in SEQ ID NO: 34;
   c) the amino acid sequence set forth in SEQ ID NO: 44;
   d) the amino acid sequence set forth in SEQ ID NO: 54;
   e) the amino acid sequence set forth in SEQ ID NO: 64;
   f) the amino acid sequence set forth in SEQ ID NO: 74;
   g) the amino acid sequence set forth in SEQ ID NO: 84;
   h) the amino acid sequence set forth in SEQ ID NO: 94;

i) the amino acid sequence set forth in SEQ ID NO: 104;
j) the amino acid sequence set forth in SEQ ID NO: 114;
k) the amino acid sequence set forth in SEQ ID NO: 124;
l) The amino acid sequence set forth in SEQ ID NO: 134;
m) the amino acid sequence set forth in SEQ ID NO: 144;
n) the amino acid sequence set forth in SEQ ID NO: 154;
o) the amino acid sequence set forth in SEQ ID NO: 164;
p) the amino acid sequence set forth in SEQ ID NO: 174;
q) the amino acid sequence set forth in SEQ ID NO: 196;
r) the amino acid sequence set forth in SEQ ID NO: 228;
s) the amino acid sequence set forth in SEQ ID NO: 238;
t) the amino acid sequence set forth in SEQ ID NO: 248;
u) the amino acid sequence set forth in SEQ ID NO: 258; or
v) the amino acid sequence set forth in SEQ ID NO: 268.

4. The recombinant antibody of claim 1, wherein:
a) the VL comprises the amino acid sequence set forth in SEQ ID NO: 23, and the VH comprises the amino acid sequence set forth in SEQ ID NO: 24;
b) the VL comprises the amino acid sequence set forth in SEQ ID NO: 33, and the VH comprises the amino acid sequence set forth in SEQ ID NO: 34;
c) the VL comprises the amino acid sequence set forth in SEQ ID NO: 43, and the VH comprises the amino acid sequence set forth in SEQ ID NO: 44;
d) the VL comprises the amino acid sequence set forth in SEQ ID NO: 53, and the VH comprises the amino acid sequence set forth in SEQ ID NO: 54;
e) the VL comprises the amino acid sequence set forth in SEQ ID NO: 63, and the VH comprises the amino acid sequence set forth in SEQ ID NO: 64;
f) the VL comprises the amino acid sequence set forth in SEQ ID NO: 73, and the VH comprises the amino acid sequence set forth in SEQ ID NO: 74;
g) the VL comprises the amino acid sequence set forth in SEQ ID NO: 83, and the VH comprises the amino acid sequence set forth in SEQ ID NO: 84;
h) the VL comprises the amino acid sequence set forth in SEQ ID NO: 93, and the VH comprises the amino acid sequence set forth in SEQ ID NO: 94;
i) the VL comprises the amino acid sequence set forth in SEQ ID NO: 103, and the VH comprises the amino acid sequence set forth in SEQ ID NO: 104;
j) the VL comprises the amino acid sequence set forth in SEQ ID NO: 113, and the VH comprises the amino acid sequence set forth in SEQ ID NO: 114;
k) the VL comprises the amino acid sequence set forth in SEQ ID NO: 123, and the VH comprises the amino acid sequence set forth in SEQ ID NO: 124;
l) the VL comprises the amino acid sequence set forth in SEQ ID NO: 133, and the VH comprises the amino acid sequence set forth in SEQ ID NO: 134;
m) the VL comprises the amino acid sequence set forth in SEQ ID NO: 143, and the VH comprises the amino acid sequence set forth in SEQ ID NO: 144;
n) the VL comprises the amino acid sequence set forth in SEQ ID NO: 153, and the VH comprises the amino acid sequence set forth in SEQ ID NO: 154;
o) the VL comprises the amino acid sequence set forth in SEQ ID NO: 163, and the VH comprises the amino acid sequence set forth in SEQ ID NO: 164;
p) the VL comprises the amino acid sequence set forth in SEQ ID NO: 173, and the VH comprises the amino acid sequence set forth in SEQ ID NO: 174;
q) the VL comprises the amino acid sequence set forth in SEQ ID NO: 195, and the VH comprises the amino acid sequence set forth in SEQ ID NO: 196;
r) the VL comprises the amino acid sequence set forth in SEQ ID NO: 227, and the VH comprises the amino acid sequence set forth in SEQ ID NO: 228;
s) the VL comprises the amino acid sequence set forth in SEQ ID NO: 237, and the VH comprises the amino acid sequence set forth in SEQ ID NO: 238;
t) the VL comprises the amino acid sequence set forth in SEQ ID NO: 247, and the VH comprises the amino acid sequence set forth in SEQ ID NO: 248;
u) the VL comprises the amino acid sequence set forth in SEQ ID NO: 257, and the VH comprises the amino acid sequence set forth in SEQ ID NO: 258; or
v) the VL comprises the amino acid sequence set forth in SEQ ID NO: 267, and the VH comprises the amino acid sequence set forth in SEQ ID NO: 268.

5. The recombinant antibody of claim 1 comprising a light chain (LC) and a heavy chain (HC), wherein the LC comprises:
a) the amino acid sequence set forth in SEQ ID NO: 27;
b) the amino acid sequence set forth in SEQ ID NO: 37;
c) the amino acid sequence set forth in SEQ ID NO: 47;
d) the amino acid sequence set forth in SEQ ID NO: 57;
e) the amino acid sequence set forth in SEQ ID NO: 67;
f) the amino acid sequence set forth in SEQ ID NO: 77;
g) the amino acid sequence set forth in SEQ ID NO: 87;
h) the amino acid sequence set forth in SEQ ID NO: 97;
i) the amino acid sequence set forth in SEQ ID NO: 107;
j) the amino acid sequence set forth in SEQ ID NO: 117;
k) the amino acid sequence set forth in SEQ ID NO: 127;
l) The amino acid sequence set forth in SEQ ID NO: 137;
m) the amino acid sequence set forth in SEQ ID NO: 147;
n) the amino acid sequence set forth in SEQ ID NO: 157;
o) the amino acid sequence set forth in SEQ ID NO: 167;
p) the amino acid sequence set forth in SEQ ID NO: 177;
q) the amino acid sequence set forth in SEQ ID NO: 199;
r) the amino acid sequence set forth in SEQ ID NO: 231;
s) the amino acid sequence set forth in SEQ ID NO: 241;
t) the amino acid sequence set forth in SEQ ID NO: 251;
u) the amino acid sequence set forth in SEQ ID NO: 261; or
v) the amino acid sequence set forth in SEQ ID NO: 271.

6. The recombinant antibody of claim 1 comprising a light chain (LC) and a heavy chain (HC), wherein the HC comprises:
a) the amino acid sequence set forth in SEQ ID NO: 28 or SEQ ID NO: 29;
b) the amino acid sequence set forth in SEQ ID NO: 38 or SEQ ID NO: 39;
c) the amino acid sequence set forth in SEQ ID NO: 48 or SEQ ID NO: 49;
d) the amino acid sequence set forth in SEQ ID NO: 58 or SEQ ID NO: 59;
e) the amino acid sequence set forth in SEQ ID NO: 68 or SEQ ID NO: 69;
f) the amino acid sequence set forth in SEQ ID NO: 78 or SEQ ID NO: 79;
g) the amino acid sequence set forth in SEQ ID NO: 88 or SEQ ID NO: 89;
h) the amino acid sequence set forth in SEQ ID NO: 98 or SEQ ID NO: 99;
i) the amino acid sequence set forth in SEQ ID NO: 108 or SEQ ID NO: 109;
j) the amino acid sequence set forth in SEQ ID NO: 118 or SEQ ID NO: 119;
k) the amino acid sequence set forth in SEQ ID NO: 128 or SEQ ID NO: 129;

l) The amino acid sequence set forth in SEQ ID NO: 138 or SEQ ID NO: 139;
m) the amino acid sequence set forth in SEQ ID NO: 148 or SEQ ID NO: 149;
n) the amino acid sequence set forth in SEQ ID NO: 158 or SEQ ID NO: 159;
o) the amino acid sequence set forth in SEQ ID NO: 168 or SEQ ID NO: 169;
p) the amino acid sequence set forth in SEQ ID NO: 178 or SEQ ID NO: 179;
q) the amino acid sequence set forth in SEQ ID NO: 200 or SEQ ID NO: 201;
r) the amino acid sequence set forth in SEQ ID NO: 232 or SEQ ID NO: 233;
s) the amino acid sequence set forth in SEQ ID NO: 242 or SEQ ID NO: 243;
t) the amino acid sequence set forth in SEQ ID NO: 252 or SEQ ID NO: 253;
u) the amino acid sequence set forth in SEQ ID NO: 262 or SEQ ID NO: 263; or
v) the amino acid sequence set forth in SEQ ID NO: 272 or SEQ ID NO: 273.

7. The recombinant antibody of claim 1 comprising a light chain (LC) and a heavy chain (HC), wherein:
a) the LC comprises the amino acid sequence set forth in SEQ ID NO: 27, and the HC comprises the amino acid sequence set forth in SEQ ID NO: 28 or SEQ ID NO: 29;
b) the LC comprises the amino acid sequence set forth in SEQ ID NO: 37, and the HC comprises the amino acid sequence set forth in SEQ ID NO: 38 or SEQ ID NO: 39;
c) the LC comprises the amino acid sequence set forth in SEQ ID NO: 47, and the HC comprises the amino acid sequence set forth in SEQ ID NO: 48 or SEQ ID NO: 49;
d) the LC comprises the amino acid sequence set forth in SEQ ID NO: 57, and the HC comprises the amino acid sequence set forth in SEQ ID NO: 58 or SEQ ID NO: 59;
e) the LC comprises the amino acid sequence set forth in SEQ ID NO: 67, and the HC comprises the amino acid sequence set forth in SEQ ID NO: 68 or SEQ ID NO: 69;
f) the LC comprises the amino acid sequence set forth in SEQ ID NO: 77, and the HC comprises the amino acid sequence set forth in SEQ ID NO: 78 or SEQ ID NO: 79;
g) the LC comprises the amino acid sequence set forth in SEQ ID NO: 87, and the HC comprises the amino acid sequence set forth in SEQ ID NO: 88 or SEQ ID NO: 89;
h) the LC comprises the amino acid sequence set forth in SEQ ID NO: 97, and the HC comprises the amino acid sequence set forth in SEQ ID NO: 98 or SEQ ID NO: 99;
i) the LC comprises the amino acid sequence set forth in SEQ ID NO: 107, and the HC comprises the amino acid sequence set forth in SEQ ID NO: 108 or SEQ ID NO: 109;
j) the LC comprises the amino acid sequence set forth in SEQ ID NO: 117, and the HC comprises the amino acid sequence set forth in SEQ ID NO: 118 or SEQ ID NO: 119;
k) the LC comprises the amino acid sequence set forth in SEQ ID NO: 127, and the HC comprises the amino acid sequence set forth in SEQ ID NO: 128 or SEQ ID NO: 129;
l) The LC comprises the amino acid sequence set forth in SEQ ID NO: 137, and the HC comprises the amino acid sequence set forth in SEQ ID NO: 138 or SEQ ID NO: 139;
m) the LC comprises the amino acid sequence set forth in SEQ ID NO: 147, and the HC comprises the amino acid sequence set forth in SEQ ID NO: 148 or SEQ ID NO: 149;
n) the LC comprises the amino acid sequence set forth in SEQ ID NO: 157, and the HC comprises the amino acid sequence set forth in SEQ ID NO: 158 or SEQ ID NO: 159;
o) the LC comprises the amino acid sequence set forth in SEQ ID NO: 167, and the HC comprises the amino acid sequence set forth in SEQ ID NO: 168 or SEQ ID NO: 169;
p) the LC comprises the amino acid sequence set forth in SEQ ID NO: 177, and the HC comprises the amino acid sequence set forth in SEQ ID NO: 178 or SEQ ID NO: 179;
q) the LC comprises the amino acid sequence set forth in SEQ ID NO: 199, and the HC comprises the amino acid sequence set forth in SEQ ID NO: 200 or SEQ ID NO: 201;
r) the LC comprises the amino acid sequence set forth in SEQ ID NO: 231, and the HC comprises the amino acid sequence set forth in SEQ ID NO: 232 or SEQ ID NO: 233;
s) the LC comprises the amino acid sequence set forth in SEQ ID NO: 241, and the HC comprises the amino acid sequence set forth in SEQ ID NO: 242 or SEQ ID NO: 243;
t) the LC comprises the amino acid sequence set forth in SEQ ID NO: 251, and the HC comprises the amino acid sequence set forth in SEQ ID NO: 252 or SEQ ID NO: 253;
u) the LC comprises the amino acid sequence set forth in SEQ ID NO: 261, and the HC comprises the amino acid sequence set forth in SEQ ID NO: 262 or SEQ ID NO: 263; or
v) the LC comprises the amino acid sequence set forth in SEQ ID NO: 271, and the HC comprises the amino acid sequence set forth in SEQ ID NO: 272 or SEQ ID NO: 273.

8. The recombinant antibody of claim 1, wherein the VL comprises the amino acid sequence set forth in SEQ ID NO: 13 and at least one amino acid substitution at position 1 and/or at position 44.

9. The recombinant antibody of claim 8, wherein the amino acid substitution at position 1 is E1Q and the amino acid substitution at position 44 is R44T.

10. The recombinant antibody of claim 1, wherein the VH comprises the amino acid sequence set forth in SEQ ID NO: 14 and at least one amino acid substitution at position 21, position 23, position 88, position 98, or a combination thereof.

11. The recombinant antibody of claim 10, wherein
a) the amino acid substitution at position 21 is P21S;
b) the amino acid substitution at position 23 is T23A;
c) the amino acid substitution at position 80 is I80T; and
d) the amino acid substitution at position 90 is T90A.

12. The recombinant antibody of claim 1, wherein the antibody comprises a heavy chain (HC) comprising the amino acid sequence set forth in SEQ ID NO: 18 and at least one amino acid substitution at position 438 and/or or at position 444.

13. The recombinant antibody of claim 12, wherein the amino acid substitution at position 438 is M438L and the amino acid substitution at position 444 is N444S.

14. The recombinant antibody of claim 1, wherein the VH comprises the amino acid sequence set forth in SEQ ID NO: 218 and at least one amino acid substitution at position 40, position 69, position 80, position 85, position 120, or a combination thereof.

15. The recombinant antibody of claim 14, wherein
a) the amino acid substitution at position 40 is T40A;
b) the amino acid substitution at position 69 is I69T;
c) the amino acid substitution at position 80 is S80Y;
d) the amino acid substitution at position 85 is G85S; and
e) the amino acid substitution at position 120 is I120T.

16. The recombinant antibody of claim 1, wherein the HC comprises the amino acid sequence set forth in SEQ ID NO: 222 and at least one amino acid substitution at position 434 and/or at position 440.

17. The recombinant antibody of claim 16, wherein the amino acid substitution at position 434 is M434L and the amino acid substitution at position 440 is N440S.

18. The recombinant antibody of claim 1, wherein the antibody exhibits at
a) least 20% reduction in parasite liver load as compared to a reference antibody;
b) at least 20% increase in survival rate as compared to a reference antibody;
c) increased conformational stability as compared to a reference antibody;
d) increased colloidal stability as compared to a reference antibody;
wherein the reference antibody is selected from the group consisting of AB-000317, AB-000224, and AB-007088.

19. An anti-circumsporozoite (CSP) recombinant antibody comprising a light chain variable region (VL) and a heavy chain variable region (VH), wherein
a) the VL comprises the amino acid sequence set forth in SEQ ID NO: 63 and the VH comprises the amino acid sequence set forth in SEQ ID NO: 64;
b) the VL comprises the amino acid sequence set forth in SEQ ID NO: 133 and the VH comprises the amino acid sequence set forth in SEQ ID NO: 134;
c) the VL comprises the amino acid sequence set forth in SEQ ID NO: 163 and the VH comprises the amino acid sequence set forth in SEQ ID NO: 164.

20. The recombinant antibody of claim 19 comprising a light chain (LC) and a heavy chain (HC), wherein
a) the LC comprises the amino acid sequence set forth in SEQ ID NO: 67 and the HC comprises the amino acid sequence set forth in SEQ ID NO: 69;
b) the LC comprises the amino acid sequence set forth in SEQ ID NO: 137 and the HC comprises the amino acid sequence set forth in SEQ ID NO: 139; or
c) the LC comprises the amino acid sequence set forth in SEQ ID NO: 167 and the HC comprises the amino acid sequence set forth in SEQ ID NO: 169.

21. A recombinant anti-circumsporozoite (CSP) antibody comprising a light chain variable region (VL) and a heavy chain variable region (VH), wherein the VL comprises a CDR1 comprising the amino acid sequence set forth in SEQ ID NO: 1, a CDR2 comprising the amino acid sequence set forth in SEQ ID NO: 2, and a CDR3 comprising the amino acid sequence set forth in SEQ ID NO: 3; and the VH comprises a CDR1 comprising the amino acid sequence set forth in SEQ ID NO: 4, a CDR2 comprising the amino acid sequence set forth in SEQ ID NO: 5, and a CDR3 comprising the amino acid sequence set forth in SEQ ID NO: 6.

22. A recombinant anti-circumsporozoite (CSP) antibody comprising a light chain variable region (VL) comprising the amino acid sequence set forth in SEQ ID NO: 163 and a heavy chain variable region (VH) comprising the amino acid sequence set forth in SEQ ID NO: 164.

23. A recombinant anti-circumsporozoite (CSP) antibody comprising a light chain (LC) comprising the amino acid sequence set forth in SEQ ID NO: 167 and a heavy chain (HC) comprising the amino acid sequence set forth in SEQ ID NO: 168 or SEQ ID NO: 169.

24. A polynucleotide encoding the antibody of any one of claims 1, 4, 7, 19, 20, 21, 22, and 23.

25. A host cell comprising the polynucleotide of claim 24.

26. A composition comprising the antibody of any one of claims 1, 4, 7, 19, 20, 21, 22, and 23.

27. The composition of claim 26, further comprising a pharmaceutically acceptable carrier.

28. A method of preventing and/or treating malaria in a subject in need thereof, comprising administering an effective amount of the antibody of any one of claims 1, 4, 7, 19, 20, 21, 22, and 23.

29. The method of claim 28, wherein the subject is a pediatric patient.

30. A method of preventing and/or treating malaria in a subject in need thereof, comprising administering an effective amount of the composition of any one of claim 26 or 27.

31. The method of claim 30, wherein the subject is a pediatric patient.

* * * * *

UNITED STATES PATENT AND TRADEMARK OFFICE
CERTIFICATE OF CORRECTION

| | | |
|---|---|---|
| PATENT NO. | : 11,655,290 B2 | Page 1 of 1 |
| APPLICATION NO. | : 17/842351 | |
| DATED | : May 23, 2023 | |
| INVENTOR(S) | : Daniel Eric Emerling et al. | |

It is certified that error appears in the above-identified patent and that said Letters Patent is hereby corrected as shown below:

In the Specification

In Column 89, Table 20, SEQ ID No. 169, Line 7:
"RWSVLT" should read -- RVVSVLT --.

Signed and Sealed this
Tenth Day of October, 2023

Katherine Kelly Vidal
*Director of the United States Patent and Trademark Office*

SEQUENCE LISTING

```
<160> NUMBER OF SEQ ID NOS: 289

<210> SEQ ID NO 1
<211> LENGTH: 14
<212> TYPE: PRT
<213> ORGANISM: Artificial Sequence
<220> FEATURE:
<223> OTHER INFORMATION: Synthetic

<400> SEQUENCE: 1

Thr Gly Met Asn Ser Asn Ile Gly Ala Gly Tyr Asp Val Tyr
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Synthetic

<400> SEQUENCE: 2

Gly Asn Ser Asn Arg Pro Ser
1               5

<210> SEQ ID NO 3
<211> LENGTH: 11
<212> TYPE: PRT
<213> ORGANISM: Artificial Sequence
<220> FEATURE:
<223> OTHER INFORMATION: Synthetic
```

```
<400> SEQUENCE: 3

Gln Ser Tyr Asp Thr Ser Leu Asn Gly Trp Ala
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Synthetic

<400> SEQUENCE: 4

Asp His Ala Met Ser
1               5

<210> SEQ ID NO 5
<211> LENGTH: 19
<212> TYPE: PRT
<213> ORGANISM: Artificial Sequence
<220> FEATURE:
<223> OTHER INFORMATION: Synthetic

<400> SEQUENCE: 5

Phe Ile Arg Lys Thr Thr Tyr Gly Ala Thr Thr His Tyr Ala Ala Ala
1               5                   10                  15

Val Arg Gly

<210> SEQ ID NO 6
<211> LENGTH: 16
<212> TYPE: PRT
<213> ORGANISM: Artificial Sequence
<220> FEATURE:
<223> OTHER INFORMATION: Synthetic

<400> SEQUENCE: 6

Val Gln Leu Asp Tyr Gly Pro Gly Tyr Gln Tyr Tyr Gly Met Asp Val
1               5                   10                  15

<210> SEQ ID NO 7
<211> LENGTH: 14
<212> TYPE: PRT
<213> ORGANISM: Artificial Sequence
<220> FEATURE:
<223> OTHER INFORMATION: Synthetic

<400> SEQUENCE: 7

Thr Gly Met Asn Ser Asn Ile Gly Ala Gly Tyr Asp Val Tyr
1               5                   10

<210> SEQ ID NO 8
<211> LENGTH: 7
<212> TYPE: PRT
<213> ORGANISM: Artificial Sequence
<220> FEATURE:
<223> OTHER INFORMATION: Synthetic

<400> SEQUENCE: 8

Gly Asn Ser Asn Arg Pro Ser
1               5

<210> SEQ ID NO 9
<211> LENGTH: 11
<212> TYPE: PRT
<213> ORGANISM: Artificial Sequence
<220> FEATURE:
<223> OTHER INFORMATION: Synthetic
```

-continued

<400> SEQUENCE: 9

Gln Ser Tyr Asp Thr Ser Leu Asn Gly Trp Ala
1               5                   10

<210> SEQ ID NO 10
<211> LENGTH: 5
<212> TYPE: PRT
<213> ORGANISM: Artificial Sequence
<220> FEATURE:
<223> OTHER INFORMATION: Synthetic

<400> SEQUENCE: 10

Asp His Ala Met Ser
1               5

<210> SEQ ID NO 11
<211> LENGTH: 19
<212> TYPE: PRT
<213> ORGANISM: Artificial Sequence
<220> FEATURE:
<223> OTHER INFORMATION: Synthetic

<400> SEQUENCE: 11

Phe Ile Arg Lys Thr Thr Tyr Gly Ala Thr Thr His Tyr Ala Ala Ala
1               5                   10                  15

Val Arg Gly

<210> SEQ ID NO 12
<211> LENGTH: 16
<212> TYPE: PRT
<213> ORGANISM: Artificial Sequence
<220> FEATURE:
<223> OTHER INFORMATION: Synthetic

<400> SEQUENCE: 12

Val Gln Leu Asp Tyr Gly Pro Gly Tyr Gln Tyr Tyr Gly Met Asp Val
1               5                   10                  15

<210> SEQ ID NO 13
<211> LENGTH: 112
<212> TYPE: PRT
<213> ORGANISM: Artificial Sequence
<220> FEATURE:
<223> OTHER INFORMATION: Synthetic

<400> SEQUENCE: 13

Glu Ser Val Leu Thr Gln Pro Pro Ser Val Ser Gly Ala Pro Gly Gln
1               5                   10                  15

Arg Val Thr Ile Ser Cys Thr Gly Met Asn Ser Asn Ile Gly Ala Gly
                20                  25                  30

Tyr Asp Val Tyr Trp Tyr Gln Gln Leu Pro Gly Arg Ala Pro Lys Leu
            35                  40                  45

Leu Ile Tyr Gly Asn Ser Asn Arg Pro Ser Gly Val Pro Asp Arg Phe
        50                  55                  60

Ser Gly Ser Arg Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Ser
                85                  90                  95

Leu Asn Gly Trp Ala Phe Gly Gly Gly Thr Lys Leu Thr Val Leu Gly
            100                 105                 110

```
<210> SEQ ID NO 14
<211> LENGTH: 127
<212> TYPE: PRT
<213> ORGANISM: Artificial Sequence
<220> FEATURE:
<223> OTHER INFORMATION: Synthetic

<400> SEQUENCE: 14
```

Glu Val Gln Leu Val Glu Ser Gly Gly Leu Val Gln Pro Gly Arg
1               5                   10                  15

Ser Leu Arg Leu Pro Cys Thr Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr Thr His Tyr Ala Ala
    50                  55                  60

Ala Val Arg Gly Arg Phe Thr Ile Ser Arg Asp Asp Ser Lys Ser Ile
65                  70                  75                  80

Val Tyr Leu Gln Met Asn Ser Leu Lys Thr Glu Asp Thr Ala Val Tyr
                85                  90                  95

Phe Cys Thr Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser
        115                 120                 125

```
<210> SEQ ID NO 15
<211> LENGTH: 336
<212> TYPE: DNA
<213> ORGANISM: Artificial Sequence
<220> FEATURE:
<223> OTHER INFORMATION: Synthetic
<400> SEQUENCE: 15
gagtctgtgc tgacgcagcc gcccctcagtg tctggggccc cagggcagag ggtcaccatc        60
tcctgcactg ggatgaactc caacatcggg gcaggttatg atgtatactg gtaccaacaa       120
cttccaggaa gagcccccaa actcctcatc tatggtaaca gcaatcggcc ctcagggggtc      180 cctgaccgat tctctggctc caggtctggc acctcagcct ccctggccat cactgggctc      240
caggctgagg atgaggctga ttattactgc cagtcctatg acaccagcct gaatggttgg      300
gctttcggcg gagggaccaa gttgaccgtc ctaggc                                336

<210> SEQ ID NO 16
<211> LENGTH: 381
<212> TYPE: DNA
<213> ORGANISM: Artificial Sequence
<220> FEATURE:
<223> OTHER INFORMATION: Synthetic
<400> SEQUENCE: 16
gaggtgcagc tggtggagtc tgggggaggc ttggtacagc cagggcggtc cctgagactc        60
ccctgtacag cctctgggtt tagttttggt gatcatgcta tgagctgggt ccgccaggct       120
ccagggaagg ggctggagtg gtaggtttc attagaaaga caacttatgg tgcgacaaca        180
cactacgccg cggctgtgag aggcagattc accatctcgc gagatgattc taaaagcatt       240
gtctatctgc aaatgaacag cctgaaaacc gaggacacag ccgtgtattt ctgtactaga       300
gtgcagcttg actatggccc gggataccag tactacggta tggacgtctg gggccaaggg       360
accacggtca ccgtctcctc a                                                 381
```

```
<210> SEQ ID NO 17
<211> LENGTH: 217
<212> TYPE: PRT
<213> ORGANISM: Artificial Sequence
<220> FEATURE:
<223> OTHER INFORMATION: Synthetic

<400> SEQUENCE: 17

Glu Ser Val Leu Thr Gln Pro Pro Ser Val Ser Gly Ala Pro Gly Gln
1               5                   10                  15

Arg Val Thr Ile Ser Cys Thr Gly Met Asn Ser Asn Ile Gly Ala Gly
            20                  25                  30

Tyr Asp Val Tyr Trp Tyr Gln Gln Leu Pro Gly Arg Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Arg Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Ser
                85                  90                  95

Leu Asn Gly Trp Ala Phe Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Val Ser Asp Phe
    130                 135                 140

Tyr Pro Gly Ala Val Thr Val Ala Trp Lys Ala Asp Gly Ser Pro Val
145                 150                 155                 160

Lys Val Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Arg Val Thr His Glu Gly Ser Thr Val Glu
        195                 200                 205

Lys Thr Val Ala Pro Ala Glu Cys Ser
    210                 215

<210> SEQ ID NO 18
<211> LENGTH: 457
<212> TYPE: PRT
<213> ORGANISM: Artificial Sequence
<220> FEATURE:
<223> OTHER INFORMATION: Synthetic

<400> SEQUENCE: 18

Glu Val Gln Leu Val Glu Ser Gly Gly Gly Leu Val Gln Pro Gly Arg
1               5                   10                  15

Ser Leu Arg Leu Pro Cys Thr Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr Thr His Tyr Ala Ala
    50                  55                  60

Ala Val Arg Gly Arg Phe Thr Ile Ser Arg Asp Asp Ser Lys Ser Ile
65                  70                  75                  80

Val Tyr Leu Gln Met Asn Ser Leu Lys Thr Glu Asp Thr Ala Val Tyr
                85                  90                  95
```

Phe Cys Thr Arg Val Gln Leu Asp Tyr Gly Pro Gly Tyr Gln Tyr Tyr
            100                 105                 110

Gly Met Asp Val Trp Gly Gln Gly Thr Val Thr Val Ser Ser Ala
            115                 120                 125

Ser Thr Lys Gly Pro Ser Val Phe Pro Leu Ala Pro Ser Ser Lys Ser
130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
            195                 200                 205

Ile Cys Asn Val Asn His Lys Pro Ser Asn Thr Lys Val Asp Lys Lys
210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
            275                 280                 285

Val Asp Gly Val Glu Val His Asn Ala Lys Thr Lys Pro Arg Glu Glu
290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
            355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
            435                 440                 445

Lys Ser Leu Ser Leu Ser Pro Gly Lys
450                 455

<210> SEQ ID NO 19
<211> LENGTH: 457
<212> TYPE: PRT
<213> ORGANISM: Artificial Sequence
<220> FEATURE:
<223> OTHER INFORMATION: Synthetic

<400> SEQUENCE: 19

```
Glu Val Gln Leu Val Glu Ser Gly Gly Leu Val Gln Pro Gly Arg
1               5                   10                  15

Ser Leu Arg Leu Pro Cys Thr Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr His Tyr Ala Ala
50                  55                  60

Ala Val Arg Gly Arg Phe Thr Ile Ser Arg Asp Asp Ser Lys Ser Ile
65                  70                  75                  80

Val Tyr Leu Gln Met Asn Ser Leu Lys Thr Glu Asp Thr Ala Val Tyr
                85                  90                  95

Phe Cys Thr Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415
```

```
Tyr Ser Lys Leu Thr Val Asp Lys Ser Arg Trp Gln Gln Gly Asn Val
            420                 425                 430

Phe Ser Cys Ser Val Leu His Glu Ala Leu His Ser His Tyr Thr Gln
        435                 440                 445

Lys Ser Leu Ser Leu Ser Pro Gly Lys
    450                 455

<210> SEQ ID NO 20
<211> LENGTH: 651
<212> TYPE: DNA
<213> ORGANISM: Artificial Sequence
<220> FEATURE:
<223> OTHER INFORMATION: Synthetic

<400> SEQUENCE: 20
gagtctgtgc tgacgcagcc gccctcagtg tctggggccc cagggcagag ggtcaccatc    60
tcctgcactg ggatgaactc caacatcggg caggttatg atgtatactg gtaccaacaa   120
cttccaggaa gagcccccaa actcctcatc tatggtaaca gcaatcggcc ctcaggggtc   180
cctgaccgat tctctggctc caggtctggc acctcagcct ccctggccat cactgggctc   240
caggctgagg atgaggctga ttattactgc cagtcctatg acaccagcct gaatggttgg   300
gctttcggcg agggaccaa gttgaccgtc ctaggccagc ccaaggctgc cccctcggtc   360
actctgttcc caccctcctc tgaggagctt caagccaaca ggccacact ggtgtgtctc   420 gtaagtgact tctacccggg agccgtgaca gtggcctgga aggcagatgg cagccccgtc   480
aaggtgggag tggagaccac caaaccctcc aaacaaagca acaacaagta tgcggccagc   540
agctacctga gcctgacgcc cgagcagtgg aagtcccaca aagctacag ctgccgggtc   600 acgcatgaag ggagcaccgt ggagaagaca gtggcccctg cagaatgctc t            651

<210> SEQ ID NO 21
<211> LENGTH: 1371
<212> TYPE: DNA
<213> ORGANISM: Artificial Sequence
<220> FEATURE:
<223> OTHER INFORMATION: Synthetic

<400> SEQUENCE: 21
gaggtgcagc tggtggagtc tgggggaggc ttggtacagc cagggcggtc cctgagactc    60
ccctgtacag cctctgggtt tagttttggt gatcatgcta tgagctgggt ccgccaggct   120
ccagggaagg ggctggagtg ggtaggtttc attagaaaga caacttatgg tgcgacaaca   180
cactacgccg cggctgtgag aggcagattc accatctcgc gagatgattc aaaagcatt   240 gtctatctgc aaatgaacag cctgaaaacc gaggacacag ccgtgtattt ctgtactaga   300
gtgcagcttg actatggccc gggataccag tactacggta tggacgtctg ggccaaggg   360 accacggtca ccgtctcctc agcctccacc aagggcccat cggtcttccc cctggcaccc   420
tcctccaaga gcacctctgg gggcacagca gccctgggct gcctggtcaa ggactacttc   480
cccgaaccgg tgacggtgtc gtggaactca ggcgccctga ccagcggcgt gcacaccttc   540
ccggctgtcc tacagtcctc aggactctac tccctcagca gcgtggtgac cgtgccctcc   600
agcagcttgg gcacccagac ctacatctgc aacgtgaatc acaagcccag caacaccaag   660
gtggacaaga agttgagcc caaatcttgt gacaaaactc acacatgccc accgtgccca   720
gcacctgaac tcctggggg accgtcagtc ttcctcttcc cccaaaaacc caaggacacc   780
ctcatgatct cccggacccc tgaggtcaca tgcgtggtgg tggacgtgag ccacgaagac   840
```

| | |
|---|---|
| cctgaggtca agttcaactg gtacgtggac ggcgtggagg tgcataatgc aagacaaag | 900 |
| ccgcgggagg agcagtacaa cagcacgtac cgtgtggtca gcgtcctcac cgtcctgcac | 960 |
| caggactggc tgaatggcaa ggagtacaag tgcaaggtct ccaacaaagc cctcccagcc | 1020 |
| cccatcgaga aaaccatctc caaagccaaa gggcagcccc gagaaccaca ggtgtacacc | 1080 |
| ctgcccccat cccgggatga gctgaccaag aaccaggtca gcctgacctg cctggtcaaa | 1140 |
| ggcttctatc ccagcgacat cgccgtggag tgggagagca atgggcagcc ggagaacaac | 1200 |
| tacaagacca cgcctcccgt gctggactcc gacggctcct tcttcctcta cagcaagctc | 1260 |
| accgtggaca agagcaggtg gcagcagggg aacgtcttct catgctccgt gatgcatgag | 1320 |
| gctctgcaca accactacac acagaagagc ctctccctgt ctccgggtaa a | 1371 |

<210> SEQ ID NO 22
<211> LENGTH: 1371
<212> TYPE: DNA
<213> ORGANISM: Artificial Sequence
<220> FEATURE:
<223> OTHER INFORMATION: Synthetic

<400> SEQUENCE: 22

| | |
|---|---|
| gaggtgcagc tggtggagtc tgggggaggc ttggtacagc cagggcggtc cctgagactc | 60 |
| ccctgtacag cctctgggtt tagttttggt gatcatgcta tgagctgggt ccgccaggct | 120 |
| ccagggaagg ggctggagtg ggtaggtttc attagaaaga caacttatgg tgcgacaaca | 180 |
| cactacgccg cggctgtgag aggcagattc accatctcgc gagatgattc aaaagcatt | 240 |
| gtctatctgc aaatgaacag cctgaaaacc gaggacacag ccgtgtattt ctgtactaga | 300 |
| gtgcagcttg actatggccc gggataccag tactacggta tggacgtctg gggccaaggg | 360 |
| accacggtca ccgtctcctc agcctccacc aagggcccat cggtcttccc cctggcaccc | 420 |
| tcctccaaga gcacctctgg gggcacagca gccctgggct gcctggtcaa ggactacttc | 480 |
| cccgaaccgg tgacggtgtc gtggaactca ggcgccctga ccagcggcgt gcacaccttc | 540 |
| ccggctgtcc tacagtcctc aggactctac tccctcagca gcgtggtgac cgtgccctcc | 600 |
| agcagcttgg gcacccagac ctacatctgc aacgtgaatc acaagcccag caacaccaag | 660 |
| gtggacaaga agttgagcc caaatcttgt gacaaaactc acacatgccc accgtgccca | 720 |
| gcacctgaac tcctgggggg accgtcagtc ttcctcttcc ccccaaaacc caaggacacc | 780 |
| ctcatgatct cccggacccc tgaggtcaca tgcgtggtgg tggacgtgag ccacgaagac | 840 |
| cctgaggtca agttcaactg gtacgtggac ggcgtggagg tgcataatgc caagacaaag | 900 |
| ccgcgggagg agcagtacaa cagcacgtac cgtgtggtca gcgtcctcac cgtcctgcac | 960 |
| caggactggc tgaatggcaa ggagtacaag tgcaaggtct ccaacaaagc cctcccagcc | 1020 |
| cccatcgaga aaaccatctc caaagccaaa gggcagcccc gagaaccaca ggtgtacacc | 1080 |
| ctgcccccat cccgggatga gctgaccaag aaccaggtca gcctgacctg cctggtcaaa | 1140 |
| ggcttctatc ccagcgacat cgccgtggag tgggagagca atgggcagcc ggagaacaac | 1200 |
| tacaagacca cgcctcccgt gctggactcc gacggctcct tcttcctcta cagcaagctc | 1260 |
| accgtggaca agagcaggtg gcagcagggg aacgtcttct catgctccgt gctgcatgag | 1320 |
| gctctgcact cccactacac acagaagagc ctctccctgt ctccgggtaa a | 1371 |

<210> SEQ ID NO 23
<211> LENGTH: 112
<212> TYPE: PRT
<213> ORGANISM: Artificial Sequence
<220> FEATURE:
<223> OTHER INFORMATION: Synthetic

<400> SEQUENCE: 23

Gln Ser Val Leu Thr Gln Pro Pro Ser Val Ser Gly Ala Pro Gly Gln
1               5                   10                  15

Arg Val Thr Ile Ser Cys Thr Gly Met Asn Ser Asn Ile Gly Ala Gly
            20                  25                  30

Tyr Asp Val Tyr Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Arg Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Ser
                85                  90                  95

Leu Asn Gly Trp Ala Phe Gly Gly Gly Thr Lys Leu Thr Val Leu Gly
            100                 105                 110

<210> SEQ ID NO 24
<211> LENGTH: 127
<212> TYPE: PRT
<213> ORGANISM: Artificial Sequence
<220> FEATURE:
<223> OTHER INFORMATION: Synthetic

<400> SEQUENCE: 24

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr His Tyr Ala Ala
    50                  55                  60

Ala Val Arg Gly Arg Phe Thr Ile Ser Arg Asp Asp Ser Lys Ser Ile
65                  70                  75                  80

Val Tyr Leu Gln Met Asn Ser Leu Lys Thr Glu Asp Thr Ala Val Tyr
                85                  90                  95

Phe Cys Thr Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser
        115                 120                 125

<210> SEQ ID NO 25
<211> LENGTH: 336
<212> TYPE: DNA
<213> ORGANISM: Artificial Sequence
<220> FEATURE:
<223> OTHER INFORMATION: Synthetic

<400> SEQUENCE: 25
cagtctgtgc tgacgcagcc gcccctcagtg tctggggccc cagggcagag ggtcaccatc      60
tcctgcactg ggatgaactc aaacatcggg gcaggttatg atgtatactg gtaccaacaa     120
cttccaggaa ctgcccccaa actcctcatc tatggtaaca gcaatcggcc ctcaggggtc     180
cctgaccgat tctctggctc caggtctggc acctcagcct ccctggccat cactgggctc     240
caggctgagg atgaggctga ttattactgc cagtcctatg acaccagcct gaatggttgg     300

```
gctttcggcg agggaccaa gttgaccgtc ctaggc                                   336
```

<210> SEQ ID NO 26
<211> LENGTH: 381
<212> TYPE: DNA
<213> ORGANISM: Artificial Sequence
<220> FEATURE:
<223> OTHER INFORMATION: Synthetic

<400> SEQUENCE: 26

```
gaggtgcagc tggtggagtc tgggggaggc ttggtacagc cagggcggtc cctgagactc         60
agctgtacag cctctgggtt tagttttggt gatcatgcta tgagctgggt ccgccaggct        120
ccagggaagg ggctggagtg ggtaggtttc attagaaaga caacttatgg tgcgacaaca        180
cactacgccg cggctgtgag aggcagattc accatctcgc gagatgattc aaaagcatt         240
gtctatctgc aaatgaacag cctgaaaacc gaggacacag ccgtgtattt ctgtactaga        300
gtgcagcttg actatggccc gggataccag tactacggta tggacgtctg gggccaaggg        360
accacggtca ccgtctcctc a                                                  381
```

<210> SEQ ID NO 27
<211> LENGTH: 217
<212> TYPE: PRT
<213> ORGANISM: Artificial Sequence
<220> FEATURE:
<223> OTHER INFORMATION: Synthetic

<400> SEQUENCE: 27

Gln Ser Val Leu Thr Gln Pro Pro Ser Val Ser Gly Ala Pro Gly Gln
1               5                   10                  15

Arg Val Thr Ile Ser Cys Thr Gly Met Asn Ser Asn Ile Gly Ala Gly
            20                  25                  30

Tyr Asp Val Tyr Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Arg Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Ser
                85                  90                  95

Leu Asn Gly Trp Ala Phe Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Val Ser Asp Phe
    130                 135                 140

Tyr Pro Gly Ala Val Thr Val Ala Trp Lys Ala Asp Gly Ser Pro Val
145                 150                 155                 160

Lys Val Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Arg Val Thr His Glu Gly Ser Thr Val Glu
        195                 200                 205

Lys Thr Val Ala Pro Ala Glu Cys Ser
    210                 215

```
<210> SEQ ID NO 28
<211> LENGTH: 457
<212> TYPE: PRT
<213> ORGANISM: Artificial Sequence
<220> FEATURE:
<223> OTHER INFORMATION: Synthetic

<400> SEQUENCE: 28

Glu Val Gln Leu Val Glu Ser Gly Gly Gly Leu Val Gln Pro Gly Arg
 1               5                  10                  15

Ser Leu Arg Leu Ser Cys Thr Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr Thr His Tyr Ala Ala
    50                  55                  60

Ala Val Arg Gly Arg Phe Thr Ile Ser Arg Asp Asp Ser Lys Ser Ile
65                  70                  75                  80

Val Tyr Leu Gln Met Asn Ser Leu Lys Thr Glu Asp Thr Ala Val Tyr
                85                  90                  95

Phe Cys Thr Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365
```

```
Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
                420                 425                 430

Phe Ser Cys Ser Val Met His Glu Ala Leu His Asn His Tyr Thr Gln
                435                 440                 445

Lys Ser Leu Ser Leu Ser Pro Gly Lys
    450                 455

<210> SEQ ID NO 29
<211> LENGTH: 457
<212> TYPE: PRT
<213> ORGANISM: Artificial Sequence
<220> FEATURE:
<223> OTHER INFORMATION: Synthetic

<400> SEQUENCE: 29

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Ser Phe Gly Asp His
                20                  25                  30

Ala Met Ser Trp Val Arg Gln Ala Pro Gly Lys Gly Leu Glu Trp Val
            35                  40                  45

Gly Phe Ile Arg Lys Thr Thr Tyr Gly Ala Thr His Tyr Ala Ala
    50                  55                  60

Ala Val Arg Gly Arg Phe Thr Ile Ser Arg Asp Asp Ser Lys Ser Ile
65                  70                  75                  80

Val Tyr Leu Gln Met Asn Ser Leu Lys Thr Glu Asp Thr Ala Val Tyr
                85                  90                  95

Phe Cys Thr Arg Val Gln Leu Asp Tyr Gly Pro Gly Tyr Gln Tyr Tyr
                100                 105                 110

Gly Met Asp Val Trp Gly Gln Gly Thr Thr Val Thr Val Ser Ser Ala
            115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
    195                 200                 205

Ile Cys Asn Val Asn His Lys Pro Ser Asn Thr Lys Val Asp Lys Lys
210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270
```

Val Val Asp Val Ser His Glu Asp Pro Glu Val Lys Phe Asn Trp Tyr
            275                 280                 285

Val Asp Gly Val Glu Val His Asn Ala Lys Thr Lys Pro Arg Glu Glu
        290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Leu His Glu Ala Leu His Ser His Tyr Thr Gln
        435                 440                 445

Lys Ser Leu Ser Leu Ser Pro Gly Lys
    450                 455

<210> SEQ ID NO 30
<211> LENGTH: 651
<212> TYPE: DNA
<213> ORGANISM: Artificial Sequence
<220> FEATURE:
<223> OTHER INFORMATION: Synthetic

<400> SEQUENCE: 30
cagtctgtgc tgacgcagcc gccctcagtg tctggggccc cagggcagag ggtcaccatc      60
tcctgcactg ggatgaactc caacatcggg gcaggttatg atgtatactg gtaccaacaa     120
cttccaggaa ctgcccccaa actcctcatc tatggtaaca gcaatcggcc ctcaggggtc     180
cctgaccgat tctctggctc caggtctggc acctcagcct ccctggccat cactgggctc     240
caggctgagg atgaggctga ttattactgc cagtcctatg acaccagcct gaatggttgg     300
gctttcggcg agggaccaa gttgaccgtc ctaggccagc ccaaggctgc ccctcggtc       360 actctgttcc caccctcctc tgaggagctt caagccaaca ggccacact ggtgtgtctc      420 gtaagtgact tctacccggg agccgtgaca gtggcctgga aggcagatgg cagccccgtc     480
aaggtgggag tggagaccac caaaccctcc aaacaaagca caacaagta tgcggccagc     540 agctacctga gcctgacgcc cgagcagtgg aagtcccaca gaagctacag ctgccgggtc    600
acgcatgaag ggagcaccgt ggagaagaca gtggcccctg cagaatgctc t             651

<210> SEQ ID NO 31
<211> LENGTH: 1371
<212> TYPE: DNA
<213> ORGANISM: Artificial Sequence
<220> FEATURE:
<223> OTHER INFORMATION: Synthetic

<400> SEQUENCE: 31
gaggtgcagc tggtggagtc tgggggaggc ttggtacagc cagggcggtc cctgagactc      60

```
agctgtacag cctctgggtt tagttttggt gatcatgcta tgagctgggt ccgccaggct    120
ccagggaagg ggctggagtg ggtaggtttc attagaaaga caacttatgg tgcgacaaca    180
cactacgccg cggctgtgag aggcagattc accatctcgc gagatgattc taaaagcatt    240
gtctatctgc aaatgaacag cctgaaaacc gaggacacag ccgtgtattt ctgtactaga    300
gtgcagcttg actatggccc gggataccag tactacggta tggacgtctg gggccaaggg    360
accacggtca ccgtctcctc agcctccacc aagggcccat cggtcttccc cctggcaccc    420
tcctccaaga gcacctctgg gggcacagca gccctgggct gcctggtcaa ggactacttc    480
cccgaaccgg tgacggtgtc gtggaactca ggcgccctga ccagcggcgt gcacaccttc    540
ccggctgtcc tacagtcctc aggactctac tccctcagca gcgtggtgac cgtgccctcc    600
agcagcttgg gcacccagac ctacatctgc aacgtgaatc acaagcccag caacaccaag    660
gtggacaaga agttgagccc aaatcttgtg acaaaactca cacatgccca ccgtgccca    720
gcacctgaac tcctgggggg accgtcagtc ttcctcttcc ccccaaaacc caaggacacc    780
ctcatgatct cccggacccc tgaggtcaca tgcgtggtgg tggacgtgag ccacgaagac    840
cctgaggtca agttcaactg gtacgtggac ggcgtggagg tgcataatgc caagacaaag    900
ccgcgggagg agcagtacaa cagcacgtac cgtgtggtca gcgtcctcac cgtcctgcac    960
caggactggc tgaatggcaa ggagtacaag tgcaaggtct ccaacaaagc cctcccagcc   1020
cccatcgaga aaaccatctc caaagccaaa gggcagcccc gagaaccaca ggtgtacacc   1080
ctgcccccat cccgggatga gctgaccaag aaccaggtca gcctgacctg cctggtcaaa   1140
ggcttctatc ccagcgacat cgccgtggag tgggagagca atgggcagcc ggagaacaac   1200
tacaagacca cgcctcccgt gctggactcc gacggctcct tcttcctcta cagcaagctc   1260
accgtggaca agagcaggtg gcagcagggg aacgtcttct catgctccgt gatgcatgag   1320
gctctgcaca accactacac acagaagagc ctctccctgt ctccgggtaa a            1371
```

<210> SEQ ID NO 32
<211> LENGTH: 1371
<212> TYPE: DNA
<213> ORGANISM: Artificial Sequence
<220> FEATURE:
<223> OTHER INFORMATION: Synthetic

<400> SEQUENCE: 32

```
gaggtgcagc tggtggagtc tgggggaggc ttggtacagc cagggcggtc cctgagactc     60
agctgtacag cctctgggtt tagttttggt gatcatgcta tgagctgggt ccgccaggct    120
ccagggaagg ggctggagtg ggtaggtttc attagaaaga caacttatgg tgcgacaaca    180
cactacgccg cggctgtgag aggcagattc accatctcgc gagatgattc taaaagcatt    240
gtctatctgc aaatgaacag cctgaaaacc gaggacacag ccgtgtattt ctgtactaga    300
gtgcagcttg actatggccc gggataccag tactacggta tggacgtctg gggccaaggg    360
accacggtca ccgtctcctc agcctccacc aagggcccat cggtcttccc cctggcaccc    420
tcctccaaga gcacctctgg gggcacagca gccctgggct gcctggtcaa ggactacttc    480
cccgaaccgg tgacggtgtc gtggaactca ggcgccctga ccagcggcgt gcacaccttc    540
ccggctgtcc tacagtcctc aggactctac tccctcagca gcgtggtgac cgtgccctcc    600
agcagcttgg gcacccagac ctacatctgc aacgtgaatc acaagcccag caacaccaag    660
gtggacaaga agttgagccc aaatcttgtg acaaaactca cacatgccca ccgtgccca    720
```

```
gcacctgaac tcctgggggg accgtcagtc ttcctcttcc ccccaaaacc caaggacacc    780
ctcatgatct cccggacccc tgaggtcaca tgcgtggtgg tggacgtgag ccacgaagac    840
cctgaggtca agttcaactg gtacgtggac ggcgtggagg tgcataatgc caagacaaag    900
ccgcgggagg agcagtacaa cagcacgtac cgtgtggtca gcgtcctcac cgtcctgcac    960
caggactggc tgaatggcaa ggagtacaag tgcaaggtct ccaacaaagc cctcccagcc   1020
cccatcgaga aaaccatctc caaagccaaa gggcagcccc gagaaccaca ggtgtacacc   1080
ctgcccccat cccgggatga gctgaccaag aaccaggtca gcctgacctg cctggtcaaa   1140
ggcttctatc ccagcgacat cgccgtggag tgggagagca atgggcagcc ggagaacaac   1200
tacaagacca cgcctcccgt gctggactcc gacggctcct tcttcctcta cagcaagctc   1260
accgtggaca agagcaggtg gcagcagggg aacgtcttct catgctccgt gctgcatgag   1320
gctctgcact cccactacac acagaagagc ctctccctgt ctccgggtaa a           1371
```

<210> SEQ ID NO 33
<211> LENGTH: 112
<212> TYPE: PRT
<213> ORGANISM: Artificial Sequence
<220> FEATURE:
<223> OTHER INFORMATION: Synthetic

<400> SEQUENCE: 33

Gln Ser Val Leu Thr Gln Pro Pro Ser Val Ser Gly Ala Pro Gly Gln
1               5                   10                  15

Arg Val Thr Ile Ser Cys Thr Gly Met Asn Ser Asn Ile Gly Ala Gly
            20                  25                  30

Tyr Asp Val Tyr Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Arg Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Ser
                85                  90                  95

Leu Asn Gly Trp Ala Phe Gly Gly Gly Thr Lys Leu Thr Val Leu Gly
            100                 105                 110

<210> SEQ ID NO 34
<211> LENGTH: 127
<212> TYPE: PRT
<213> ORGANISM: Artificial Sequence
<220> FEATURE:
<223> OTHER INFORMATION: Synthetic

<400> SEQUENCE: 34

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr His Tyr Ala Ala
    50                  55                  60

Ala Val Arg Gly Arg Phe Thr Ile Ser Arg Asp Asp Ser Lys Ser Ile
65                  70                  75                  80

Val Tyr Leu Gln Met Asn Ser Leu Lys Thr Glu Asp Thr Ala Val Tyr

```
                    85                  90                  95
Phe Cys Thr Arg Val Gln Leu Asp Tyr Gly Pro Gly Tyr Gln Tyr Tyr
                100                 105                 110

Gly Met Asp Val Trp Gly Gln Gly Thr Thr Val Thr Val Ser Ser
                115                 120                 125

<210> SEQ ID NO 35
<211> LENGTH: 336
<212> TYPE: DNA
<213> ORGANISM: Artificial Sequence
<220> FEATURE:
<223> OTHER INFORMATION: Synthetic

<400> SEQUENCE: 35
cagtctgtgc tgacgcagcc gcccctcagtg tctggggccc cagggcagag ggtcaccatc      60
tcctgcactg ggatgaactc caacatcggg gcaggttatg atgtatactg gtaccaacaa     120
cttccaggaa ctgcccccaa actcctcatc tatggtaaca gcaatcggcc ctcaggggtc     180
cctgaccgat tctctggctc caggtctggc acctcagcct ccctggccat cactgggctc     240
caggctgagg atgaggctga ttattactgc cagtcctatg acaccagcct gaatggttgg     300
gctttcggcg agggaccaa gttgaccgtc ctaggc                                336

<210> SEQ ID NO 36
<211> LENGTH: 381
<212> TYPE: DNA
<213> ORGANISM: Artificial Sequence
<220> FEATURE:
<223> OTHER INFORMATION: Synthetic

<400> SEQUENCE: 36
gaggtgcagc tggtggagtc tgggggaggc ttggtacagc cagggcggtc cctgagactc      60
agctgtgcgg cctctgggtt tagttttggt gatcatgcta tgagctgggt ccgccaggct     120
ccagggaagg ggctggagtg ggtaggtttc attagaaaga caacttatgg tgcgacaaca     180
cactacgccg cggctgtgag aggcagattc accatctcgc gagatgattc aaaagcatt      240 gtctatctgc aaatgaacag cctgaaaacc gaggacacag ccgtgtattt ctgtactaga     300
gtgcagcttg actatggccc gggataccag tactacggta tggacgtctg gggccaaggg     360
accacggtca ccgtctcctc a                                                381

<210> SEQ ID NO 37
<211> LENGTH: 217
<212> TYPE: PRT
<213> ORGANISM: Artificial Sequence
<220> FEATURE:
<223> OTHER INFORMATION: Synthetic

<400> SEQUENCE: 37

Gln Ser Val Leu Thr Gln Pro Pro Ser Val Ser Gly Ala Pro Gly Gln
1               5                   10                  15

Arg Val Thr Ile Ser Cys Thr Gly Met Asn Ser Asn Ile Gly Ala Gly
                20                  25                  30

Tyr Asp Val Tyr Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
        50                  55                  60

Ser Gly Ser Arg Ser Gly Thr Ser Ala Ser Leu Ala Ile Thr Gly Leu
65                  70                  75                  80
```

```
Gln Ala Glu Asp Glu Ala Asp Tyr Tyr Cys Gln Ser Tyr Asp Thr Ser
                85                  90                  95

Leu Asn Gly Trp Ala Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Val Ser Asp Phe
    130                 135                 140

Tyr Pro Gly Ala Val Thr Val Ala Trp Lys Ala Asp Gly Ser Pro Val
145                 150                 155                 160

Lys Val Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Arg Val Thr His Glu Gly Ser Thr Val Glu
        195                 200                 205

Lys Thr Val Ala Pro Ala Glu Cys Ser
    210                 215
```

<210> SEQ ID NO 38
<211> LENGTH: 457
<212> TYPE: PRT
<213> ORGANISM: Artificial Sequence
<220> FEATURE:
<223> OTHER INFORMATION: Synthetic

<400> SEQUENCE: 38

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ser Phe Gly Asp His
                20                  25                  30

Ala Met Ser Trp Val Arg Gln Ala Pro Gly Lys Gly Leu Glu Trp Val
            35                  40                  45

Gly Phe Ile Arg Lys Thr Thr Tyr Gly Ala Thr Thr His Tyr Ala Ala
        50                  55                  60

Ala Val Arg Gly Arg Phe Thr Ile Ser Arg Asp Asp Ser Lys Ser Ile
65                  70                  75                  80

Val Tyr Leu Gln Met Asn Ser Leu Lys Thr Glu Asp Thr Ala Val Tyr
                85                  90                  95

Phe Cys Thr Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220
```

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
            245                 250                 255

Pro Lys Asp Thr Leu Met Ile Ser Arg Thr Pro Glu Val Thr Cys Val
        260                 265                 270

Val Val Asp Val Ser His Glu Asp Pro Glu Val Lys Phe Asn Trp Tyr
    275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
            325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
        370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
            405                 410                 415

Tyr Ser Lys Leu Thr Val Asp Lys Ser Arg Trp Gln Gln Gly Asn Val
        420                 425                 430

Phe Ser Cys Ser Val Met His Glu Ala Leu His Asn His Tyr Thr Gln
        435                 440                 445

Lys Ser Leu Ser Leu Ser Pro Gly Lys
450                 455

<210> SEQ ID NO 39
<211> LENGTH: 457
<212> TYPE: PRT
<213> ORGANISM: Artificial Sequence
<220> FEATURE:
<223> OTHER INFORMATION: Synthetic

<400> SEQUENCE: 39

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr His Tyr Ala Ala
    50                  55                  60

Ala Val Arg Gly Arg Phe Thr Ile Ser Arg Asp Asp Ser Lys Ser Ile
65                  70                  75                  80

Val Tyr Leu Gln Met Asn Ser Leu Lys Thr Glu Asp Thr Ala Val Tyr
            85                  90                  95

Phe Cys Thr Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
                180                 185                 190

Ser Ser Val Val Thr Val Pro Ser Ser Ser Leu Gly Thr Gln Thr Tyr
            195                 200                 205

Ile Cys Asn Val Asn His Lys Pro Ser Asn Thr Lys Val Asp Lys Lys
210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
                260                 265                 270

Val Val Asp Val Ser His Glu Asp Pro Glu Val Lys Phe Asn Trp Tyr
            275                 280                 285

Val Asp Gly Val Glu Val His Asn Ala Lys Thr Lys Pro Arg Glu Glu
290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
                340                 345                 350

Pro Arg Glu Pro Gln Val Tyr Thr Leu Pro Pro Ser Arg Asp Glu Leu
            355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
                420                 425                 430

Phe Ser Cys Ser Val Leu His Glu Ala Leu His Ser His Tyr Thr Gln
            435                 440                 445

Lys Ser Leu Ser Leu Ser Pro Gly Lys
    450                 455

<210> SEQ ID NO 40
<211> LENGTH: 651
<212> TYPE: DNA
<213> ORGANISM: Artificial Sequence
<220> FEATURE:
<223> OTHER INFORMATION: Synthetic

<400> SEQUENCE: 40
cagtctgtgc tgacgcagcc gccctcagtg tctggggccc cagggcagag ggtcaccatc    60
tcctgcactg ggatgaactc caacatcggg gcaggttatg atgtatactg gtaccaacaa   120
cttccaggaa ctgcccccaa actcctcatc tatggtaaca gcaatcggcc ctcaggggtc   180

| | |
|---|---|
| cctgaccgat tctctggctc caggtctggc acctcagcct ccctggccat cactgggctc | 240 |
| caggctgagg atgaggctga ttattactgc cagtcctatg acaccagcct gaatggttgg | 300 |
| gctttcggcg agggaccaa gttgaccgtc ctaggccagc ccaaggctgc ccctcggtc | 360 |
| actctgttcc caccctcctc tgaggagctt caagccaaca aggccacact ggtgtgtctc | 420 |
| gtaagtgact tctacccggg agccgtgaca gtggcctgga aggcagatgg cagccccgtc | 480 |
| aaggtgggag tggagaccac caaaccctcc aaacaaagca caacaagta tgcggccagc | 540 |
| agctacctga gcctgacgcc cgagcagtgg aagtcccaca gaagctacag ctgccgggtc | 600 |
| acgcatgaag ggagcaccgt ggagaagaca gtggcccctg cagaatgctc t | 651 |

<210> SEQ ID NO 41
<211> LENGTH: 1371
<212> TYPE: DNA
<213> ORGANISM: Artificial Sequence
<220> FEATURE:
<223> OTHER INFORMATION: Synthetic

<400> SEQUENCE: 41

| | |
|---|---|
| gaggtgcagc tggtggagtc tgggggaggc ttggtacagc cagggcggtc cctgagactc | 60 |
| agctgtgcgg cctctgggtt tagttttggt gatcatgcta tgagctgggt ccgccaggct | 120 |
| ccagggaagg ggctggagtg ggtaggtttc attagaaaga caacttatgg tgcgacaaca | 180 |
| cactacgccg cggctgtgag aggcagattc accatctcgc gagatgattc aaaagcatt | 240 |
| gtctatctgc aaatgaacag cctgaaaacc gaggacacag ccgtgtattt ctgtactaga | 300 |
| gtgcagcttg actatggccc gggataccag tactacggta tggacgtctg ggggcaaggg | 360 |
| accacggtca ccgtctcctc agcctccacc aagggcccat cggtcttccc cctggcaccc | 420 |
| tcctccaaga gcacctctgg gggcacagca gccctgggct gcctggtcaa ggactacttc | 480 |
| cccgaaccgg tgacggtgtc gtggaactca ggcgccctga ccagcggcgt gcacaccttc | 540 |
| ccggctgtcc tacagtcctc aggactctac tccctcagca gcgtggtgac cgtgccctcc | 600 |
| agcagcttgg gcacccagac ctacatctgc aacgtgaatc acaagcccag caacaccaag | 660 |
| gtggacaaga agttgagcc caaatcttgt gacaaaactc acacatgccc accgtgccca | 720 |
| gcacctgaac tcctgggggg accgtcagtc ttcctcttcc ccccaaaacc caaggacacc | 780 |
| ctcatgatct cccggacccc tgaggtcaca tgcgtggtgg tggacgtgag ccacgaagac | 840 |
| cctgaggtca agttcaactg gtacgtggac ggcgtggagg tgcataatgc caagacaaag | 900 |
| ccgcgggagg agcagtacaa cagcacgtac cgtgtggtca gcgtcctcac cgtcctgcac | 960 |
| caggactggc tgaatggcaa ggagtacaag tgcaaggtct ccaacaaagc cctcccagcc | 1020 |
| cccatcgaga aaaccatctc caaagccaaa gggcagcccc gagaaccaca ggtgtacacc | 1080 |
| ctgcccccat cccgggatga gctgaccaag aaccaggtca gcctgacctg cctggtcaaa | 1140 |
| ggcttctatc ccagcgacat cgccgtggag tgggagagca atgggcagcc ggagaacaac | 1200 |
| tacaagacca cgcctcccgt gctggactcc gacggctcct tcttcctcta cagcaagctc | 1260 |
| accgtggaca agagcaggtg gcagcagggg aacgtcttct catgctccgt gatgcatgag | 1320 |
| gctctgcaca accactacac acagaagagc ctctccctgt ctccgggtaa a | 1371 |

<210> SEQ ID NO 42
<211> LENGTH: 1371
<212> TYPE: DNA
<213> ORGANISM: Artificial Sequence
<220> FEATURE:
<223> OTHER INFORMATION: Synthetic

<400> SEQUENCE: 42

```
gaggtgcagc tggtggagtc tgggggaggc ttggtacagc cagggcggtc cctgagactc    60
agctgtgcgg cctctgggtt tagttttggt gatcatgcta tgagctgggt ccgccaggct   120
ccagggaagg ggctggagtg ggtaggtttc attagaaaga caacttatgg tgcgacaaca   180
cactacgccg cggctgtgag aggcagattc accatctcgc gagatgattc aaaagcatt   240
gtctatctgc aaatgaacag cctgaaaacc gaggacacag ccgtgtattt ctgtactaga   300
gtgcagcttg actatggccc gggataccag tactacggta tggacgtctg gggccaaggg   360
accacggtca ccgtctcctc agcctccacc aagggcccat cggtcttccc cctggcaccc   420
tcctccaaga gcacctctgg gggcacagca gccctgggct gcctggtcaa ggactacttc   480
cccgaaccgg tgacggtgtc gtggaactca ggcgccctga ccagcggcgt gcacaccttc   540
ccggctgtcc tacagtcctc aggactctac tccctcagca gcgtggtgac cgtgccctcc   600
agcagcttgg gcacccagac ctacatctgc aacgtgaatc acaagcccag caacaccaag   660
gtggacaaga agttgagccc aaatcttgt gacaaaactc acacatgccc accgtgccca   720
gcacctgaac tcctgggggg accgtcagtc ttcctcttcc ccccaaaacc caaggacacc   780
ctcatgatct cccggacccc tgaggtcaca tgcgtggtgg tggacgtgag ccacgaagac   840
cctgaggtca agttcaactg gtacgtggac ggcgtggagg tgcataatgc caagacaaag   900
ccgcgggagg agcagtacaa cagcacgtac cgtgtggtca gcgtcctcac cgtcctgcac   960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgcccccat cccgggatga gctgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
accgtggaca agagcaggtg gcagcagggg aacgtcttct catgctccgt gctgcatgag  1320
gctctgcact cccactacac acagaagagc ctctccctgt ctccgggtaa a            1371
```

<210> SEQ ID NO 43
<211> LENGTH: 112
<212> TYPE: PRT
<213> ORGANISM: Artificial Sequence
<220> FEATURE:
<223> OTHER INFORMATION: Synthetic

<400> SEQUENCE: 43

```
Gln Ser Val Leu Thr Gln Pro Pro Ser Val Ser Gly Ala Pro Gly Gln
1               5                   10                  15
Arg Val Thr Ile Ser Cys Thr Gly Met Asn Ser Asn Ile Gly Ala Gly
                20                  25                  30
Tyr Asp Val Tyr Trp Tyr Gln Gln Leu Pro Gly Thr Ala Pro Lys Leu
            35                  40                  45
Leu Ile Tyr Gly Asn Ser Asn Arg Pro Ser Gly Val Pro Asp Arg Phe
        50                  55                  60
Ser Gly Ser Arg Ser Gly Thr Ser Ala Ser Leu Ala Ile Thr Gly Leu
65                  70                  75                  80
Gln Ala Glu Asp Glu Ala Asp Tyr Tyr Cys Gln Ser Tyr Asp Thr Ser
                85                  90                  95
Leu Asn Gly Trp Ala Phe Gly Gly Gly Thr Lys Leu Thr Val Leu Gly
            100                 105                 110
```

<210> SEQ ID NO 44
<211> LENGTH: 127
<212> TYPE: PRT
<213> ORGANISM: Artificial Sequence
<220> FEATURE:
<223> OTHER INFORMATION: Synthetic

<400> SEQUENCE: 44

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr His Tyr Ala Ala
    50                  55                  60

Ala Val Arg Gly Arg Phe Thr Ile Ser Arg Asp Asp Ser Lys Ser Thr
65                  70                  75                  80

Val Tyr Leu Gln Met Asn Ser Leu Lys Thr Glu Asp Thr Ala Val Tyr
                85                  90                  95

Phe Cys Thr Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser
        115                 120                 125

<210> SEQ ID NO 45
<211> LENGTH: 336
<212> TYPE: DNA
<213> ORGANISM: Artificial Sequence
<220> FEATURE:
<223> OTHER INFORMATION: Synthetic

<400> SEQUENCE: 45
cagtctgtgc tgacgcagcc gccctcagtg tctggggccc cagggcagag ggtcaccatc      60
tcctgcactg ggatgaactc caacatcggg gcaggttatg atgtatactg gtaccaacaa     120
cttccaggaa ctgcccccaa actcctcatc tatggtaaca gcaatcggcc ctcagggtc      180 cctgaccgat tctctggctc caggtctggc acctcagcct ccctggccat cactgggctc     240
caggctgagg atgaggctga ttattactgc cagtcctatg acaccagcct gaatggttgg     300
gctttcggcg gagggaccaa gttgaccgtc ctaggc                               336

<210> SEQ ID NO 46
<211> LENGTH: 381
<212> TYPE: DNA
<213> ORGANISM: Artificial Sequence
<220> FEATURE:
<223> OTHER INFORMATION: Synthetic

<400> SEQUENCE: 46
gaggtgcagc tggtggagtc tgggggaggc ttggtacagc cagggcggtc cctgagactc      60
agctgtacag cctctgggtt tagttttggt gatcatgcta tgagctgggt ccgccaggct     120
ccagggaagg ggctggagtg ggtaggtttc attagaaaga caacttatgg tgcgacaaca     180
cactacgccg cggctgtgag aggcagattc accatctcgc gagatgattc taaaagcact     240
gtctatctgc aaatgaacag cctgaaaacc gaggacacag ccgtgtattt ctgtactaga     300
gtgcagcttg actatggccc gggataccag tactacggta tggacgtctg gggccaaggg     360
accacggtca ccgtctcctc a                                             381

<210> SEQ ID NO 47
<211> LENGTH: 217
<212> TYPE: PRT
<213> ORGANISM: Artificial Sequence
<220> FEATURE:
<223> OTHER INFORMATION: Synthetic

<400> SEQUENCE: 47

Gln Ser Val Leu Thr Gln Pro Pro Ser Val Ser Gly Ala Pro Gly Gln
1               5                   10                  15

Arg Val Thr Ile Ser Cys Thr Gly Met Asn Ser Asn Ile Gly Ala Gly
            20                  25                  30

Tyr Asp Val Tyr Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
50                  55                  60

Ser Gly Ser Arg Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Ser
                85                  90                  95

Leu Asn Gly Trp Ala Phe Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Val Ser Asp Phe
130                 135                 140

Tyr Pro Gly Ala Val Thr Val Ala Trp Lys Ala Asp Gly Ser Pro Val
145                 150                 155                 160

Lys Val Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Arg Val Thr His Glu Gly Ser Thr Val Glu
        195                 200                 205

Lys Thr Val Ala Pro Ala Glu Cys Ser
    210                 215

<210> SEQ ID NO 48
<211> LENGTH: 457
<212> TYPE: PRT
<213> ORGANISM: Artificial Sequence
<220> FEATURE:
<223> OTHER INFORMATION: Synthetic

<400> SEQUENCE: 48

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr Thr His Tyr Ala Ala
50                  55                  60

Ala Val Arg Gly Arg Phe Thr Ile Ser Arg Asp Asp Ser Lys Ser Thr
65                  70                  75                  80

Val Tyr Leu Gln Met Asn Ser Leu Lys Thr Glu Asp Thr Ala Val Tyr
            85                  90                  95

Phe Cys Thr Arg Val Gln Leu Asp Tyr Gly Pro Gly Tyr Gln Tyr Tyr
        100                 105                 110

Gly Met Asp Val Trp Gly Gln Gly Thr Thr Val Thr Val Ser Ser Ala
    115                 120                 125

Ser Thr Lys Gly Pro Ser Val Phe Pro Leu Ala Pro Ser Ser Lys Ser
130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 49
<211> LENGTH: 457
<212> TYPE: PRT
<213> ORGANISM: Artificial Sequence
<220> FEATURE:
<223> OTHER INFORMATION: Synthetic

<400> SEQUENCE: 49

```
Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr His Tyr Ala Ala
    50                  55                  60

Ala Val Arg Gly Arg Phe Thr Ile Ser Arg Asp Asp Ser Lys Ser Thr
65                  70                  75                  80

Val Tyr Leu Gln Met Asn Ser Leu Lys Thr Glu Asp Thr Ala Val Tyr
                85                  90                  95

Phe Cys Thr Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser Ala
            115                 120                 125

Ser Thr Lys Gly Pro Ser Val Phe Pro Leu Ala Pro Ser Ser Lys Ser
        130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
```

405                 410                 415
Tyr Ser Lys Leu Thr Val Asp Lys Ser Arg Trp Gln Gln Gly Asn Val
            420                 425                 430

Phe Ser Cys Ser Val Leu His Glu Ala Leu His Ser His Tyr Thr Gln
            435                 440                 445

Lys Ser Leu Ser Leu Ser Pro Gly Lys
            450                 455

<210> SEQ ID NO 50
<211> LENGTH: 651
<212> TYPE: DNA
<213> ORGANISM: Artificial Sequence
<220> FEATURE:
<223> OTHER INFORMATION: Synthetic

<400> SEQUENCE: 50

| | | | | |
|---|---|---|---|---|
| cagtctgtgc tgacgcagcc gccctcagtg tctggggccc cagggcagag ggtcaccatc | 60 |
| tcctgcactg ggatgaactc caacatcggg gcaggttatg atgtatactg gtaccaacaa | 120 |
| cttccaggaa ctgcccccaa actcctcatc tatggtaaca gcaatcggcc ctcagggagc | 180 |
| cctgaccgat tctctggctc caggtctggc acctcagcct ccctggccat cactgggctc | 240 |
| caggctgagg atgaggctga ttattactgc cagtcctatg acaccagcct gaatggttgg | 300 |
| gctttcggcg gagggaccaa gttgaccgtc ctaggccagc ccaaggctgc cccctcggtc | 360 |
| actctgttcc caccctcctc tgaggagctt caagccaaca aggccacact ggtgtgtctc | 420 |
| gtaagtgact tctacccggg agccgtgaca gtggcctgga aggcagatgg cagccccgtc | 480 |
| aaggtgggag tggagaccac caaaccctcc aaacaaagca acaacaagta tgcggccagc | 540 |
| agctacctga gcctgacgcc cgagcagtgg aagtcccaca gaagctacag ctgccgggtc | 600 |
| acgcatgaag ggagcaccgt ggagaagaca gtggcccctg cagaatgctc t | 651 |

<210> SEQ ID NO 51
<211> LENGTH: 1371
<212> TYPE: DNA
<213> ORGANISM: Artificial Sequence
<220> FEATURE:
<223> OTHER INFORMATION: Synthetic

<400> SEQUENCE: 51

| | | | | |
|---|---|---|---|---|
| gaggtgcagc tggtggagtc tgggggaggc ttggtacagc cagggcggtc cctgagactc | 60 |
| agctgtacag cctctgggtt tagttttggt gatcatgcta tgagctgggt ccgccaggct | 120 |
| ccagggaagg ggctggagtg ggtaggtttc attagaaaga aacttatgg tgcgacaaca | 180 |
| cactacgccg cggctgtgag aggcagattc accatctcgc gagatgattc aaaagcact | 240 |
| gtctatctgc aaatgaacag cctgaaaacc gaggacacag ccgtgtattt ctgtactaga | 300 |
| gtgcagcttg actatggccc gggataccag tactacggta tggacgtctg gggccaaggg | 360 |
| accacggtca ccgtctcctc agcctccacc aagggcccat cggtcttccc cctggcaccc | 420 |
| tcctccaaga gcacctctgg gggcacagca gccctgggct gcctggtcaa ggactacttc | 480 |
| cccgaaccgg tgacggtgtc gtggaactca ggcgccctga ccagcggcgt gcacaccttc | 540 |
| ccggctgtcc tacagtcctc aggactctac tccctcagca gcgtggtgac cgtgccctcc | 600 |
| agcagcttgg gcacccagac ctacatctgc aacgtgaatc acaagcccag caacaccaag | 660 |
| gtggacaaga aagttgagcc caaatcttgt gacaaaactc acacatgccc accgtgccca | 720 |
| gcacctgaac tcctgggggg accgtcagtc ttcctcttcc ccccaaaacc caaggacacc | 780 |

| | |
|---|---|
| ctcatgatct cccggacccc tgaggtcaca tgcgtggtgg tggacgtgag ccacgaagac | 840 |
| cctgaggtca agttcaactg gtacgtggac ggcgtggagg tgcataatgc aagacaaag | 900 |
| ccgcgggagg agcagtacaa cagcacgtac cgtgtggtca gcgtcctcac cgtcctgcac | 960 |
| caggactggc tgaatggcaa ggagtacaag tgcaaggtct ccaacaaagc cctcccagcc | 1020 |
| cccatcgaga aaaccatctc caaagccaaa gggcagcccc gagaaccaca ggtgtacacc | 1080 |
| ctgcccccat cccgggatga gctgaccaag aaccaggtca gcctgacctg cctggtcaaa | 1140 |
| ggcttctatc ccagcgacat cgccgtggag tgggagagca atgggcagcc ggagaacaac | 1200 |
| tacaagacca cgcctcccgt gctggactcc gacggctcct tcttcctcta cagcaagctc | 1260 |
| accgtggaca agagcaggtg gcagcagggg aacgtcttct catgctccgt gatgcatgag | 1320 |
| gctctgcaca accactacac acagaagagc ctctccctgt ctccgggtaa a | 1371 |

<210> SEQ ID NO 52
<211> LENGTH: 1371
<212> TYPE: DNA
<213> ORGANISM: Artificial Sequence
<220> FEATURE:
<223> OTHER INFORMATION: Synthetic

<400> SEQUENCE: 52

| | |
|---|---|
| gaggtgcagc tggtggagtc tgggggaggc ttggtacagc cagggcggtc cctgagactc | 60 |
| agctgtacag cctctgggtt tagttttggt gatcatgcta tgagctgggt ccgccaggct | 120 |
| ccagggaagg ggctggagtg ggtaggtttc attagaaaga caacttatgg tgcgacaaca | 180 |
| cactacgccg cggctgtgag aggcagattc accatctcgc gagatgattc aaaaagcact | 240 |
| gtctatctgc aaatgaacag cctgaaaacc gaggacacag ccgtgtattt ctgtactaga | 300 |
| gtgcagcttg actatggccc gggataccag tactacggta tggacgtctg gggccaaggg | 360 |
| accacggtca ccgtctcctc agcctccacc aagggcccat cggtcttccc cctggcaccc | 420 |
| tcctccaaga gcacctctgg gggcacagca gccctgggct gcctggtcaa ggactacttc | 480 |
| cccgaaccgg tgacggtgtc gtggaactca ggcgccctga ccagcggcgt gcacaccttc | 540 |
| ccggctgtcc tacagtcctc aggactctac tccctcagca gcgtggtgac cgtgccctcc | 600 |
| agcagcttgg gcacccagac ctacatctgc aacgtgaatc acaagcccag caacaccaag | 660 |
| gtggacaaga agttgagcc caaatcttgt gacaaaactc acacatgccc accgtgccca | 720 |
| gcacctgaac tcctgggggg accgtcagtc ttcctcttcc ccccaaaacc caaggacacc | 780 |
| ctcatgatct cccggacccc tgaggtcaca tgcgtggtgg tggacgtgag ccacgaagac | 840 |
| cctgaggtca agttcaactg gtacgtggac ggcgtggagg tgcataatgc aagacaaag | 900 |
| ccgcgggagg agcagtacaa cagcacgtac cgtgtggtca gcgtcctcac cgtcctgcac | 960 |
| caggactggc tgaatggcaa ggagtacaag tgcaaggtct ccaacaaagc cctcccagcc | 1020 |
| cccatcgaga aaaccatctc caaagccaaa gggcagcccc gagaaccaca ggtgtacacc | 1080 |
| ctgcccccat cccgggatga gctgaccaag aaccaggtca gcctgacctg cctggtcaaa | 1140 |
| ggcttctatc ccagcgacat cgccgtggag tgggagagca atgggcagcc ggagaacaac | 1200 |
| tacaagacca cgcctcccgt gctggactcc gacggctcct tcttcctcta cagcaagctc | 1260 |
| accgtggaca agagcaggtg gcagcagggg aacgtcttct catgctccgt gctgcatgag | 1320 |
| gctctgcact cccactacac acagaagagc ctctccctgt ctccgggtaa a | 1371 |

<210> SEQ ID NO 53
<211> LENGTH: 112

<212> TYPE: PRT
<213> ORGANISM: Artificial Sequence
<220> FEATURE:
<223> OTHER INFORMATION: Synthetic

<400> SEQUENCE: 53

Gln Ser Val Leu Thr Gln Pro Pro Ser Val Ser Gly Ala Pro Gly Gln
1               5                   10                  15

Arg Val Thr Ile Ser Cys Thr Gly Met Asn Ser Asn Ile Gly Ala Gly
            20                  25                  30

Tyr Asp Val Tyr Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Arg Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Ser
                85                  90                  95

Leu Asn Gly Trp Ala Phe Gly Gly Gly Thr Lys Leu Thr Val Leu Gly
            100                 105                 110

<210> SEQ ID NO 54
<211> LENGTH: 127
<212> TYPE: PRT
<213> ORGANISM: Artificial Sequence
<220> FEATURE:
<223> OTHER INFORMATION: Synthetic

<400> SEQUENCE: 54

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr Thr His Tyr Ala Ala
    50                  55                  60

Ala Val Arg Gly Arg Phe Thr Ile Ser Arg Asp Asp Ser Lys Ser Ile
65                  70                  75                  80

Val Tyr Leu Gln Met Asn Ser Leu Lys Ala Glu Asp Thr Ala Val Tyr
                85                  90                  95

Phe Cys Thr Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser
        115                 120                 125

<210> SEQ ID NO 55
<211> LENGTH: 336
<212> TYPE: DNA
<213> ORGANISM: Artificial Sequence
<220> FEATURE:
<223> OTHER INFORMATION: Synthetic

<400> SEQUENCE: 55
cagtctgtgc tgacgcagcc gccctcagtg tctggggccc cagggcagag ggtcaccatc     60
tcctgcactg ggatgaactc caacatcggg gcaggttatg atgtatactg gtaccaacaa    120
cttccaggaa ctgcccccaa actcctcatc tatggtaaca gcaatcggcc ctcagggttc    180
cctgaccgat tctctggctc caggtctggc acctcagcct ccctggccat cactgggctc    240
caggctgagg atgaggctga ttattactgc cagtcctatg acaccagcct gaatggttgg    300
gctttcggcg agggaccaa gttgaccgtc ctaggc    336

<210> SEQ ID NO 56
<211> LENGTH: 381
<212> TYPE: DNA
<213> ORGANISM: Artificial Sequence
<220> FEATURE:
<223> OTHER INFORMATION: Synthetic

<400> SEQUENCE: 56
gaggtgcagc tggtggagtc tgggggaggc ttggtacagc cagggcggtc cctgagactc    60
agctgtacag cctctgggtt tagttttggt gatcatgcta tgagctgggt ccgccaggct    120
ccagggaagg ggctggagtg gtaggtttc attagaaaga caacttatgg tgcgacaaca    180
cactacgccg cggctgtgag aggcagattc accatctcgc gagatgattc taaaagcatt    240
gtctatctgc aaatgaacag cctgaaagca gaggacacag ccgtgtattt ctgtactaga    300
gtgcagcttg actatggccc gggataccag tactacggta tggacgtctg gggccaaggg    360
accacggtca ccgtctcctc a    381

<210> SEQ ID NO 57
<211> LENGTH: 217
<212> TYPE: PRT
<213> ORGANISM: Artificial Sequence
<220> FEATURE:
<223> OTHER INFORMATION: Synthetic

<400> SEQUENCE: 57

Gln Ser Val Leu Thr Gln Pro Pro Ser Val Gly Ala Pro Gly Gln
1               5                   10                  15

Arg Val Thr Ile Ser Cys Thr Gly Met Asn Ser Asn Ile Gly Ala Gly
            20                  25                  30

Tyr Asp Val Tyr Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
50                  55                  60

Ser Gly Ser Arg Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Ser
                85                  90                  95

Leu Asn Gly Trp Ala Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Val Ser Asp Phe
130                 135                 140

Tyr Pro Gly Ala Val Thr Val Ala Trp Lys Ala Asp Gly Ser Pro Val
145                 150                 155                 160

Lys Val Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Arg Val Thr His Glu Gly Ser Thr Val Glu
        195                 200                 205

Lys Thr Val Ala Pro Ala Glu Cys Ser

<210> SEQ ID NO 58
<211> LENGTH: 457
<212> TYPE: PRT
<213> ORGANISM: Artificial Sequence
<220> FEATURE:
<223> OTHER INFORMATION: Synthetic

<400> SEQUENCE: 58

```
Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr Thr His Tyr Ala Ala
    50                  55                  60

Ala Val Arg Gly Arg Phe Thr Ile Ser Arg Asp Asp Ser Lys Ser Ile
65                  70                  75                  80

Val Tyr Leu Gln Met Asn Ser Leu Lys Ala Glu Asp Thr Ala Val Tyr
                85                  90                  95

Phe Cys Thr Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
```

```
            355                 360                 365
Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 59
<211> LENGTH: 457
<212> TYPE: PRT
<213> ORGANISM: Artificial Sequence
<220> FEATURE:
<223> OTHER INFORMATION: Synthetic

<400> SEQUENCE: 59

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr His Tyr Ala Ala
    50                  55                  60

Ala Val Arg Gly Arg Phe Thr Ile Ser Arg Asp Asp Ser Lys Ser Ile
65                  70                  75                  80

Val Tyr Leu Gln Met Asn Ser Leu Lys Ala Glu Asp Thr Ala Val Tyr
                85                  90                  95

Phe Cys Thr Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
```

```
                260                 265                 270
Val Val Asp Val Ser His Glu Asp Pro Glu Val Lys Phe Asn Trp Tyr
            275                 280                 285
Val Asp Gly Val Glu Val His Asn Ala Lys Thr Lys Pro Arg Glu Glu
        290                 295                 300
Gln Tyr Asn Ser Thr Tyr Arg Val Val Ser Val Leu Thr Val Leu His
305                 310                 315                 320
Gln Asp Trp Leu Asn Gly Lys Glu Tyr Lys Cys Lys Val Ser Asn Lys
                325                 330                 335
Ala Leu Pro Ala Pro Ile Glu Lys Thr Ile Ser Lys Ala Lys Gly Gln
            340                 345                 350
Pro Arg Glu Pro Gln Val Tyr Thr Leu Pro Pro Ser Arg Asp Glu Leu
        355                 360                 365
Thr Lys Asn Gln Val Ser Leu Thr Cys Leu Val Lys Gly Phe Tyr Pro
    370                 375                 380
Ser Asp Ile Ala Val Glu Trp Glu Ser Asn Gly Gln Pro Glu Asn Asn
385                 390                 395                 400
Tyr Lys Thr Thr Pro Pro Val Leu Asp Ser Asp Gly Ser Phe Phe Leu
                405                 410                 415
Tyr Ser Lys Leu Thr Val Asp Lys Ser Arg Trp Gln Gln Gly Asn Val
            420                 425                 430
Phe Ser Cys Ser Val Leu His Glu Ala Leu His Ser His Tyr Thr Gln
        435                 440                 445
Lys Ser Leu Ser Leu Ser Pro Gly Lys
    450                 455
```

<210> SEQ ID NO 60
<211> LENGTH: 651
<212> TYPE: DNA
<213> ORGANISM: Artificial Sequence
<220> FEATURE:
<223> OTHER INFORMATION: Synthetic

<400> SEQUENCE: 60

```
cagtctgtgc tgacgcagcc gccctcagtg tctggggccc cagggcagag ggtcaccatc    60
tcctgcactg ggatgaactc caacatcggg gcaggttatg atgtatactg gtaccaacaa   120
cttccaggaa ctgcccccaa actcctcatc tatggtaaca gcaatcggcc ctcaggggtc   180
cctgaccgat tctctggctc caggtctggc acctcagcct cctggccat cactgggctc    240
caggctgagg atgaggctga ttattactgc cagtcctatg acaccagcct gaatggttgg   300
gctttcggcg gagggaccaa gttgaccgtc ctaggccagc ccaaggctgc cccctcggtc   360
actctgttcc cacccctcctc tgaggagctt caagccaaca ggccacact ggtgtgtctc   420
gtaagtgact tctacccggg agccgtgaca gtggcctgga aggcagatgg cagccccgtc   480
aaggtgggag tggagaccac caaaccctcc aaacaaagca acaacaagta tgcggccagc   540
agctacctga gcctgacgcc cgagcagtgg aagtcccaca gaagctacag ctgccgggtc   600
acgcatgaag ggagcaccgt ggagaagaca gtggcccctg cagaatgctc t            651
```

<210> SEQ ID NO 61
<211> LENGTH: 1371
<212> TYPE: DNA
<213> ORGANISM: Artificial Sequence
<220> FEATURE:
<223> OTHER INFORMATION: Synthetic

<400> SEQUENCE: 61

```
gaggtgcagc tggtggagtc tgggggaggc ttggtacagc cagggcggtc cctgagactc    60
agctgtacag cctctgggtt tagttttggt gatcatgcta tgagctgggt ccgccaggct   120
ccagggaagg ggctggagtg ggtaggtttc attagaaaga caacttatgg tgcgacaaca   180
cactacgccg cggctgtgag aggcagattc accatctcgc gagatgattc taaaagcatt   240
gtctatctgc aaatgaacag cctgaaagca gaggacacag ccgtgtattt ctgtactaga   300
gtgcagcttg actatggccc gggataccag tactacggta tggacgtctg gggccaaggg   360
accacggtca ccgtctcctc agcctccacc aagggcccat cggtcttccc cctggcaccc   420
tcctccaaga gcacctctgg gggcacagcg gccctgggct gcctggtcaa ggactacttc   480
cccgaaccgg tgacggtgtc gtggaactca ggcgccctga ccagcggcgt gcacaccttc   540
ccggctgtcc tacagtcctc aggactctac tccctcagca gcgtggtgac cgtgccctcc   600
agcagcttgg gcacccagac ctacatctgc aacgtgaatc acaagcccag caacaccaag   660
gtggacaaga agttgagccc aaatcttgtg acaaaactca cacatgccca ccgtgccca   720 gcacctgaac tcctgggggg accgtcagtc ttcctcttcc ccccaaaacc caaggacacc   780
ctcatgatct cccggacccc tgaggtcaca tgcgtggtgg tggacgtgag ccacgaagac   840
cctgaggtca agttcaactg gtacgtggac ggcgtggagg tgcataatgc caagacaaag   900
ccgcgggagg agcagtacaa cagcacgtac cgtgtggtca gcgtcctcac cgtcctgcac   960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgcccccat cccgggatga gctgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
accgtggaca gagcaggtg gcagcagggg aacgtcttct catgctccgt gatgcatgag  1320
gctctgcaca accactacac acagaagagc ctctccctgt ctccgggtaa a            1371
```

<210> SEQ ID NO 62
<211> LENGTH: 1371
<212> TYPE: DNA
<213> ORGANISM: Artificial Sequence
<220> FEATURE:
<223> OTHER INFORMATION: Synthetic

<400> SEQUENCE: 62

```
gaggtgcagc tggtggagtc tgggggaggc ttggtacagc cagggcggtc cctgagactc    60
agctgtacag cctctgggtt tagttttggt gatcatgcta tgagctgggt ccgccaggct   120
ccagggaagg ggctggagtg ggtaggtttc attagaaaga caacttatgg tgcgacaaca   180
cactacgccg cggctgtgag aggcagattc accatctcgc gagatgattc taaaagcatt   240
gtctatctgc aaatgaacag cctgaaagca gaggacacag ccgtgtattt ctgtactaga   300
gtgcagcttg actatggccc gggataccag tactacggta tggacgtctg gggccaaggg   360
accacggtca ccgtctcctc agcctccacc aagggcccat cggtcttccc cctggcaccc   420
tcctccaaga gcacctctgg gggcacagcg gccctgggct gcctggtcaa ggactacttc   480
cccgaaccgg tgacggtgtc gtggaactca ggcgccctga ccagcggcgt gcacaccttc   540
ccggctgtcc tacagtcctc aggactctac tccctcagca gcgtggtgac cgtgccctcc   600
agcagcttgg gcacccagac ctacatctgc aacgtgaatc acaagcccag caacaccaag   660
```

```
gtggacaaga aagttgagcc caaatcttgt gacaaaactc acacatgccc accgtgccca    720
gcacctgaac tcctgggggg accgtcagtc ttcctcttcc ccccaaaacc caaggacacc    780
ctcatgatct cccggacccc tgaggtcaca tgcgtggtgg tggacgtgag ccacgaagac    840
cctgaggtca agttcaactg gtacgtggac ggcgtggagg tgcataatgc caagacaaag    900
ccgcgggagg agcagtacaa cagcacgtac cgtgtggtca gcgtcctcac cgtcctgcac    960
caggactggc tgaatggcaa ggagtacaag tgcaaggtct ccaacaaagc cctcccagcc    1020
cccatcgaga aaaccatctc caaagccaaa gggcagcccc gagaaccaca ggtgtacacc    1080
ctgcccccat cccgggatga gctgaccaag aaccaggtca gcctgacctg cctggtcaaa    1140
ggcttctatc ccagcgacat cgccgtggag tgggagagca atgggcagcc ggagaacaac    1200
tacaagacca cgcctcccgt gctggactcc gacggctcct tcttcctcta cagcaagctc    1260
accgtggaca agagcaggtg gcagcagggg aacgtcttct catgctccgt gctgcatgag    1320
gctctgcact cccactacac acagaagagc ctctccctgt ctccgggtaa a             1371
```

<210> SEQ ID NO 63
<211> LENGTH: 112
<212> TYPE: PRT
<213> ORGANISM: Artificial Sequence
<220> FEATURE:
<223> OTHER INFORMATION: Synthetic

<400> SEQUENCE: 63

Gln Ser Val Leu Thr Gln Pro Pro Ser Val Ser Gly Ala Pro Gly Gln
1               5                   10                  15

Arg Val Thr Ile Ser Cys Thr Gly Met Asn Ser Asn Ile Gly Ala Gly
            20                  25                  30

Tyr Asp Val Tyr Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Arg Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Ser
                85                  90                  95

Leu Asn Gly Trp Ala Phe Gly Gly Gly Thr Lys Leu Thr Val Leu Gly
            100                 105                 110

<210> SEQ ID NO 64
<211> LENGTH: 127
<212> TYPE: PRT
<213> ORGANISM: Artificial Sequence
<220> FEATURE:
<223> OTHER INFORMATION: Synthetic

<400> SEQUENCE: 64

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr Thr His Tyr Ala Ala
    50                  55                  60

Ala Val Arg Gly Arg Phe Thr Ile Ser Arg Asp Asp Ser Lys Ser Ile
65                  70                  75                  80

```
Val Tyr Leu Gln Met Asn Ser Leu Lys Thr Glu Asp Thr Ala Val Tyr
                85                  90                  95

Phe Cys Ala Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser
        115                 120                 125
```

<210> SEQ ID NO 65
<211> LENGTH: 336
<212> TYPE: DNA
<213> ORGANISM: Artificial Sequence
<220> FEATURE:
<223> OTHER INFORMATION: Synthetic

<400> SEQUENCE: 65

```
cagtctgtgc tgacgcagcc gccctcagtg tctggggccc cagggcagag ggtcaccatc      60
tcctgcactg ggatgaactc caacatcggg gcaggttatg atgtatactg gtaccaacaa     120
cttccaggaa ctgcccccaa actcctcatc tatggtaaca gcaatcggcc ctcagggatc     180
cctgaccgat tctctggctc caggtctggc acctcagcct ccctggccat cactgggctc     240
caggctgagg atgaggctga ttattactgc cagtcctatg acaccagcct gaatggttgg     300
gctttcggcg gagggaccaa gttgaccgtc ctaggc                               336
```

<210> SEQ ID NO 66
<211> LENGTH: 381
<212> TYPE: DNA
<213> ORGANISM: Artificial Sequence
<220> FEATURE:
<223> OTHER INFORMATION: Synthetic

<400> SEQUENCE: 66

```
gaggtgcagc tggtggagtc tgggggaggc ttggtacagc cagggcggtc cctgagactc      60
agctgtacag cctctgggtt tagttttggt gatcatgcta tgagctgggt ccgccaggct     120
ccagggaagg gctggagtg gtaggtttc attagaaaga caacttatgg tgcgacaaca      180
cactacgccg cggctgtgag aggcagattc accatctcgc gagatgattc aaaaagcatt     240
gtctatctgc aaatgaacag cctgaaaacc gaggacacag ccgtgtattt ctgtgctaga     300
gtgcagcttg actatggccc gggataccag tactacggta tggacgtctg gggccaaggg     360
accacggtca ccgtctcctc a                                                381
```

<210> SEQ ID NO 67
<211> LENGTH: 217
<212> TYPE: PRT
<213> ORGANISM: Artificial Sequence
<220> FEATURE:
<223> OTHER INFORMATION: Synthetic

<400> SEQUENCE: 67

```
Gln Ser Val Leu Thr Gln Pro Pro Ser Val Ser Gly Ala Pro Gly Gln
1               5                   10                  15

Arg Val Thr Ile Ser Cys Thr Gly Met Asn Ser Asn Ile Gly Ala Gly
            20                  25                  30

Tyr Asp Val Tyr Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Arg Ser Gly Thr Ser Ala Ser Leu Ala Ile Thr Gly Leu
```

```
             65                  70                  75                  80
        Gln Ala Glu Asp Glu Ala Asp Tyr Tyr Cys Gln Ser Tyr Asp Thr Ser
                         85                  90                  95

Leu Asn Gly Trp Ala Phe Gly Gly Thr Lys Leu Thr Val Leu Gly
                        100                 105                 110

Gln Pro Lys Ala Ala Pro Ser Val Thr Leu Phe Pro Pro Ser Ser Glu
                        115                 120                 125

Glu Leu Gln Ala Asn Lys Ala Thr Leu Val Cys Leu Val Ser Asp Phe
                    130                 135                 140

Tyr Pro Gly Ala Val Thr Val Ala Trp Lys Ala Asp Gly Ser Pro Val
        145                 150                 155                 160

Lys Val Gly Val Glu Thr Thr Lys Pro Ser Lys Gln Ser Asn Asn Lys
                        165                 170                 175

Tyr Ala Ala Ser Ser Tyr Leu Ser Leu Thr Pro Glu Gln Trp Lys Ser
                        180                 185                 190

His Arg Ser Tyr Ser Cys Arg Val Thr His Glu Gly Ser Thr Val Glu
                        195                 200                 205

Lys Thr Val Ala Pro Ala Glu Cys Ser
                    210                 215

<210> SEQ ID NO 68
<211> LENGTH: 457
<212> TYPE: PRT
<213> ORGANISM: Artificial Sequence
<220> FEATURE:
<223> OTHER INFORMATION: Synthetic

<400> SEQUENCE: 68

Glu Val Gln Leu Val Glu Ser Gly Gly Gly Leu Val Gln Pro Gly Arg
        1               5                   10                  15

Ser Leu Arg Leu Ser Cys Thr Ala Ser Gly Phe Ser Phe Gly Asp His
                        20                  25                  30

Ala Met Ser Trp Val Arg Gln Ala Pro Gly Lys Gly Leu Glu Trp Val
                    35                  40                  45

Gly Phe Ile Arg Lys Thr Thr Tyr Gly Ala Thr Thr His Tyr Ala Ala
        50                  55                  60

Ala Val Arg Gly Arg Phe Thr Ile Ser Arg Asp Asp Ser Lys Ser Ile
        65                  70                  75                  80

Val Tyr Leu Gln Met Asn Ser Leu Lys Thr Glu Asp Thr Ala Val Tyr
                        85                  90                  95

Phe Cys Ala Arg Val Gln Leu Asp Tyr Gly Pro Gly Tyr Gln Tyr Tyr
                        100                 105                 110

Gly Met Asp Val Trp Gly Gln Gly Thr Thr Val Thr Val Ser Ser Ala
                    115                 120                 125

Ser Thr Lys Gly Pro Ser Val Phe Pro Leu Ala Pro Ser Ser Lys Ser
                130                 135                 140

Thr Ser Gly Gly Thr Ala Ala Leu Gly Cys Leu Val Lys Asp Tyr Phe
        145                 150                 155                 160

Pro Glu Pro Val Thr Val Ser Trp Asn Ser Gly Ala Leu Thr Ser Gly
                        165                 170                 175

Val His Thr Phe Pro Ala Val Leu Gln Ser Ser Gly Leu Tyr Ser Leu
                        180                 185                 190

Ser Ser Val Val Thr Val Pro Ser Ser Ser Leu Gly Thr Gln Thr Tyr
                        195                 200                 205

Ile Cys Asn Val Asn His Lys Pro Ser Asn Thr Lys Val Asp Lys Lys
```

```
              210                 215                 220
Val Glu Pro Lys Ser Cys Asp Lys Thr His Thr Cys Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 69
<211> LENGTH: 457
<212> TYPE: PRT
<213> ORGANISM: Artificial Sequence
<220> FEATURE:
<223> OTHER INFORMATION: Synthetic

<400> SEQUENCE: 69

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Ser Phe Gly Asp His
                20                  25                  30

Ala Met Ser Trp Val Arg Gln Ala Pro Gly Lys Gly Leu Glu Trp Val
            35                  40                  45

Gly Phe Ile Arg Lys Thr Thr Tyr Gly Ala Thr Thr His Tyr Ala Ala
        50                  55                  60

Ala Val Arg Gly Arg Phe Thr Ile Ser Arg Asp Asp Ser Lys Ser Ile
65                  70                  75                  80

Val Tyr Leu Gln Met Asn Ser Leu Lys Thr Glu Asp Thr Ala Val Tyr
                85                  90                  95

Phe Cys Ala Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser Ala
```

```
            115                 120                 125
Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Leu His Glu Ala Leu His Ser His Tyr Thr Gln
        435                 440                 445

Lys Ser Leu Ser Leu Ser Pro Gly Lys
    450                 455

<210> SEQ ID NO 70
<211> LENGTH: 651
<212> TYPE: DNA
<213> ORGANISM: Artificial Sequence
<220> FEATURE:
<223> OTHER INFORMATION: Synthetic

<400> SEQUENCE: 70
cagtctgtgc tgacgcagcc gccctcagtg tctggggccc cagggcagag ggtcaccatc      60
tcctgcactg ggatgaactc caacatcggg gcaggttatg atgtatactg gtaccaacaa     120
```

| | |
|---|---|
| cttccaggaa ctgcccccaa actcctcatc tatggtaaca gcaatcggcc ctcaggggtc | 180 |
| cctgaccgat tctctggctc caggtctggc acctcagcct ccctggccat cactgggctc | 240 |
| caggctgagg atgaggctga ttattactgc cagtcctatg acaccagcct gaatggttgg | 300 |
| gctttcggcg agggaccaa gttgaccgtc ctaggccagc ccaaggctgc ccctcggtc | 360 |
| actctgttcc caccctcctc tgaggagctt caagccaaca aggccacact ggtgtgtctc | 420 |
| gtaagtgact ctacccgggg agccgtgaca gtggcctgga aggcagatgg cagcccgtc | 480 |
| aaggtgggag tggagaccac caaaccctcc aaacaaagca caacaagta tgcggccagc | 540 |
| agctacctga gcctgacgcc cgagcagtgg aagtcccaca aagctacag ctgccgggtc | 600 |
| acgcatgaag ggagcaccgt ggagaagaca gtggcccctg cagaatgctc t | 651 |

<210> SEQ ID NO 71
<211> LENGTH: 1371
<212> TYPE: DNA
<213> ORGANISM: Artificial Sequence
<220> FEATURE:
<223> OTHER INFORMATION: Synthetic

<400> SEQUENCE: 71

| | |
|---|---|
| gaggtgcagc tggtggagtc tgggggaggc ttggtacagc cagggcggtc cctgagactc | 60 |
| agctgtacag cctctgggtt tagttttggt gatcatgcta tgagctgggt ccgccaggct | 120 |
| ccagggaagg ggctggagtg ggtaggtttc attagaaaga caacttatgg tgcgacaaca | 180 |
| cactacgccg cggctgtgag aggcagattc accatctcgc gagatgattc taaaagcatt | 240 |
| gtctatctgc aaatgaacag cctgaaaacc gaggacacag ccgtgtattt ctgtgctaga | 300 |
| gtgcagcttg actatggccc gggataccag tactacggta tggacgtctg gggccaaggg | 360 |
| accacggtca ccgtctcctc agcctccacc aagggcccat cggtcttccc cctggcaccc | 420 |
| tcctccaaga gcacctctgg gggcacagca gccctgggct gcctggtcaa ggactacttc | 480 |
| cccgaaccgg tgacggtgtc gtggaactca ggcgccctga ccagcggcgt gcacaccttc | 540 |
| ccggctgtcc tacagtcctc aggactctac tccctcagca gcgtggtgac cgtgccctcc | 600 |
| agcagcttgg gcacccagac ctacatctgc aacgtgaatc acaagcccag caacaccaag | 660 |
| gtggacaaga agttgagcc caaatcttgt gacaaaactc acacatgccc accgtgccca | 720 |
| gcacctgaac tcctgggggg accgtcagtc ttcctcttcc ccccaaaacc caaggacacc | 780 |
| ctcatgatct cccggacccc tgaggtcaca tgcgtggtgg tggacgtgag ccacgaagac | 840 |
| cctgaggtca agttcaactg gtacgtggac ggcgtggagg tgcataatgc caagacaaag | 900 |
| ccgcgggagg agcagtacaa cagcacgtac cgtgtggtca gcgtcctcac cgtcctgcac | 960 |
| caggactggc tgaatggcaa ggagtacaag tgcaaggtct ccaacaaagc cctcccagcc | 1020 |
| cccatcgaga aaaccatctc caaagccaaa gggcagcccc gagaaccaca ggtgtacacc | 1080 |
| ctgcccccat cccgggatga gctgaccaag aaccaggtca gcctgacctg cctggtcaaa | 1140 |
| ggcttctatc ccagcgacat cgccgtggag tgggagagca atgggcagcc ggagaacaac | 1200 |
| tacaagacca cgcctcccgt gctggactcc gacggctcct tcttcctcta cagcaagctc | 1260 |
| accgtggaca gagcaggtg gcagcagggg aacgtcttct catgctccgt gatgcatgag | 1320 |
| gctctgcaca accactacac acagaagagc ctctccctgt ctccgggtaa a | 1371 |

<210> SEQ ID NO 72
<211> LENGTH: 1371
<212> TYPE: DNA
<213> ORGANISM: Artificial Sequence
<220> FEATURE:
<223> OTHER INFORMATION: Synthetic

<400> SEQUENCE: 72

```
gaggtgcagc tggtggagtc tgggggaggc ttggtacagc cagggcggtc cctgagactc     60
agctgtacag cctctgggtt tagttttggt gatcatgcta tgagctgggt ccgccaggct    120
ccagggaagg ggctggagtg ggtaggtttc attagaaaga caacttatgg tgcgacaaca    180
cactacgccg cggctgtgag aggcagattc accatctcgc gagatgattc aaaagcatt     240
gtctatctgc aaatgaacag cctgaaaacc gaggacacag ccgtgtattt ctgtgctaga    300
gtgcagcttg actatggccc gggataccag tactacggta tggacgtctg ggggccaaggg   360
accacggtca ccgtctcctc agcctccacc aagggcccat cggtcttccc cctggcaccc    420
tcctccaaga gcacctctgg gggcacagca gccctgggct gcctggtcaa ggactacttc    480
cccgaaccgg tgacggtgtc gtggaactca ggcgccctga ccagcggcgt gcacaccttc    540
ccggctgtcc tacagtcctc aggactctac tccctcagca gcgtggtgac cgtgccctcc    600
agcagcttgg gcacccagac ctacatctgc aacgtgaatc acaagcccag caacaccaag    660
gtggacaaga agttgagcc caaatcttgt gacaaaactc acacatgccc accgtgccca    720
gcacctgaac tcctgggggg accgtcagtc ttcctcttcc ccccaaaacc caaggacacc    780
ctcatgatct cccggacccc tgaggtcaca tgcgtggtgg tggacgtgag ccacgaagac    840
cctgaggtca agttcaactg gtacgtggac ggcgtggagg tgcataatgc caagacaaag    900
ccgcgggagg agcagtacaa cagcacgtac cgtgtggtca gcgtcctcac cgtcctgcac    960
caggactggc tgaatggcaa ggagtacaag tgcaaggtct ccaacaaagc cctcccagcc   1020
cccatcgaga aaaccatctc caaagccaaa gggcagcccc gagaaccaca ggtgtacacc   1080
ctgcccccat cccgggatga gctgaccaag aaccaggtca gcctgacctg cctggtcaaa   1140
ggcttctatc ccagcgacat cgccgtggag tgggagagca atgggcagcc ggagaacaac   1200
tacaagacca cgcctcccgt gctggactcc gacggctcct tcttcctcta cagcaagctc   1260
accgtggaca agagcaggtg gcagcagggg aacgtcttct catgctccgt gctgcatgag   1320
gctctgcact cccactacac acagaagagc ctctccctgt ctccgggtaa a            1371
```

<210> SEQ ID NO 73
<211> LENGTH: 112
<212> TYPE: PRT
<213> ORGANISM: Artificial Sequence
<220> FEATURE:
<223> OTHER INFORMATION: Synthetic

<400> SEQUENCE: 73

```
Gln Ser Val Leu Thr Gln Pro Pro Ser Val Ser Gly Ala Pro Gly Gln
1               5                   10                  15

Arg Val Thr Ile Ser Cys Thr Gly Met Asn Ser Asn Ile Gly Ala Gly
            20                  25                  30

Tyr Asp Val Tyr Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Arg Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Ser
                85                  90                  95
```

Leu Asn Gly Trp Ala Phe Gly Gly Gly Thr Lys Leu Thr Val Leu Gly
            100                 105                 110

<210> SEQ ID NO 74
<211> LENGTH: 127
<212> TYPE: PRT
<213> ORGANISM: Artificial Sequence
<220> FEATURE:
<223> OTHER INFORMATION: Synthetic

<400> SEQUENCE: 74

Glu Val Gln Leu Val Glu Ser Gly Gly Leu Val Gln Pro Gly Arg
1               5                   10                  15

Ser Leu Arg Leu Ser Cys Ala Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr Thr His Tyr Ala Ala
    50                  55                  60

Ala Val Arg Gly Arg Phe Thr Ile Ser Arg Asp Asp Ser Lys Ser Thr
65                  70                  75                  80

Val Tyr Leu Gln Met Asn Ser Leu Lys Thr Glu Asp Thr Ala Val Tyr
                85                  90                  95

Phe Cys Thr Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser
        115                 120                 125

<210> SEQ ID NO 75
<211> LENGTH: 336
<212> TYPE: DNA
<213> ORGANISM: Artificial Sequence
<220> FEATURE:
<223> OTHER INFORMATION: Synthetic

<400> SEQUENCE: 75
cagtctgtgc tgacgcagcc gccctcagtg tctggggccc cagggcagag ggtcaccatc    60
tcctgcactg ggatgaactc caacatcggg gcaggttatg atgtatactg gtaccaacaa   120
cttccaggaa ctgcccccaa actcctcatc tatggtaaca gcaatcggcc ctcaggggtc   180
cctgaccgat tctctggctc caggtctggc acctcagcct ccctggccat cactgggctc   240
caggctgagg atgaggctga ttattactgc cagtcctatg acaccagcct gaatggttgg   300
gctttcggcg agggaccaa gttgaccgtc ctaggc                              336

<210> SEQ ID NO 76
<211> LENGTH: 381
<212> TYPE: DNA
<213> ORGANISM: Artificial Sequence
<220> FEATURE:
<223> OTHER INFORMATION: Synthetic

<400> SEQUENCE: 76
gaggtgcagc tggtggagtc tgggggaggc ttggtacagc cagggcggtc cctgagactc    60
agctgtgcgg cctctgggtt tagttttggt gatcatgcta tgagctgggt ccgccaggct   120
ccagggaagg ggctggagtg ggtaggtttc attagaaaga caacttatgg tgcgacaaca   180
cactacgccg cggctgtgag aggcagattc accatctcgc gagatgattc aaaaagcact   240
gtctatctgc aaatgaacag cctgaaaacc gaggacacag ccgtgtattt ctgtactaga   300

```
gtgcagcttg actatggccc gggataccag tactacggta tggacgtctg gggccaaggg      360
accacggtca ccgtctcctc a                                                 381
```

<210> SEQ ID NO 77
<211> LENGTH: 217
<212> TYPE: PRT
<213> ORGANISM: Artificial Sequence
<220> FEATURE:
<223> OTHER INFORMATION: Synthetic

<400> SEQUENCE: 77

Gln Ser Val Leu Thr Gln Pro Pro Ser Val Gly Ala Pro Gly Gln
1               5                   10                  15

Arg Val Thr Ile Ser Cys Thr Gly Met Asn Ser Asn Ile Gly Ala Gly
                20                  25                  30

Tyr Asp Val Tyr Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
    50                  55                  60

Ser Gly Ser Arg Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Ser
                85                  90                  95

Leu Asn Gly Trp Ala Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
    115                 120                 125

Glu Leu Gln Ala Asn Lys Ala Thr Leu Val Cys Leu Val Ser Asp Phe
130                 135                 140

Tyr Pro Gly Ala Val Thr Val Ala Trp Lys Ala Asp Gly Ser Pro Val
145                 150                 155                 160

Lys Val Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Arg Val Thr His Glu Gly Ser Thr Val Glu
        195                 200                 205

Lys Thr Val Ala Pro Ala Glu Cys Ser
    210                 215

<210> SEQ ID NO 78
<211> LENGTH: 457
<212> TYPE: PRT
<213> ORGANISM: Artificial Sequence
<220> FEATURE:
<223> OTHER INFORMATION: Synthetic

<400> SEQUENCE: 78

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ser Phe Gly Asp His
                20                  25                  30

Ala Met Ser Trp Val Arg Gln Ala Pro Gly Lys Gly Leu Glu Trp Val
            35                  40                  45

Gly Phe Ile Arg Lys Thr Thr Tyr Gly Ala Thr Thr His Tyr Ala Ala
    50                  55                  60

Ala Val Arg Gly Arg Phe Thr Ile Ser Arg Asp Asp Ser Lys Ser Thr

```
            65                  70                  75                  80
        Val Tyr Leu Gln Met Asn Ser Leu Lys Thr Glu Asp Thr Ala Val Tyr
                            85                  90                  95

Phe Cys Thr Arg Val Gln Leu Asp Tyr Gly Pro Gly Tyr Gln Tyr Tyr
                            100                 105                 110

Gly Met Asp Val Trp Gly Gln Gly Thr Thr Val Thr Val Ser Ser Ala
                            115                 120                 125

Ser Thr Lys Gly Pro Ser Val Phe Pro Leu Ala Pro Ser Ser Lys Ser
            130                 135                 140

Thr Ser Gly Gly Thr Ala Ala Leu Gly Cys Leu Val Lys Asp Tyr Phe
        145                 150                 155                 160

Pro Glu Pro Val Thr Val Ser Trp Asn Ser Gly Ala Leu Thr Ser Gly
                            165                 170                 175

Val His Thr Phe Pro Ala Val Leu Gln Ser Ser Gly Leu Tyr Ser Leu
                            180                 185                 190

Ser Ser Val Val Thr Val Pro Ser Ser Ser Leu Gly Thr Gln Thr Tyr
                            195                 200                 205

Ile Cys Asn Val Asn His Lys Pro Ser Asn Thr Lys Val Asp Lys Lys
            210                 215                 220

Val Glu Pro Lys Ser Cys Asp Lys Thr His Thr Cys Pro Pro Cys Pro
        225                 230                 235                 240

Ala Pro Glu Leu Leu Gly Gly Pro Ser Val Phe Leu Phe Pro Pro Lys
                            245                 250                 255

Pro Lys Asp Thr Leu Met Ile Ser Arg Thr Pro Glu Val Thr Cys Val
                            260                 265                 270

Val Val Asp Val Ser His Glu Asp Pro Glu Val Lys Phe Asn Trp Tyr
                            275                 280                 285

Val Asp Gly Val Glu Val His Asn Ala Lys Thr Lys Pro Arg Glu Glu
            290                 295                 300

Gln Tyr Asn Ser Thr Tyr Arg Val Val Ser Val Leu Thr Val Leu His
        305                 310                 315                 320

Gln Asp Trp Leu Asn Gly Lys Glu Tyr Lys Cys Lys Val Ser Asn Lys
                            325                 330                 335

Ala Leu Pro Ala Pro Ile Glu Lys Thr Ile Ser Lys Ala Lys Gly Gln
                            340                 345                 350

Pro Arg Glu Pro Gln Val Tyr Thr Leu Pro Pro Ser Arg Asp Glu Leu
                            355                 360                 365

Thr Lys Asn Gln Val Ser Leu Thr Cys Leu Val Lys Gly Phe Tyr Pro
            370                 375                 380

Ser Asp Ile Ala Val Glu Trp Glu Ser Asn Gly Gln Pro Glu Asn Asn
        385                 390                 395                 400

Tyr Lys Thr Thr Pro Pro Val Leu Asp Ser Asp Gly Ser Phe Phe Leu
                            405                 410                 415

Tyr Ser Lys Leu Thr Val Asp Lys Ser Arg Trp Gln Gln Gly Asn Val
                            420                 425                 430

Phe Ser Cys Ser Val Met His Glu Ala Leu His Asn His Tyr Thr Gln
                            435                 440                 445

Lys Ser Leu Ser Leu Ser Pro Gly Lys
            450                 455

<210> SEQ ID NO 79
<211> LENGTH: 457
<212> TYPE: PRT
<213> ORGANISM: Artificial Sequence
```

<220> FEATURE:
<223> OTHER INFORMATION: Synthetic

<400> SEQUENCE: 79

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr Thr His Tyr Ala Ala
    50                  55                  60

Ala Val Arg Gly Arg Phe Thr Ile Ser Arg Asp Asp Ser Lys Ser Thr
65                  70                  75                  80

Val Tyr Leu Gln Met Asn Ser Leu Lys Thr Glu Asp Thr Ala Val Tyr
                85                  90                  95

Phe Cys Thr Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
        195                 200                 205

Ile Cys Asn Val Asn His Lys Pro Ser Asn Thr Lys Val Asp Lys Lys
210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
            405                 410                 415

Tyr Ser Lys Leu Thr Val Asp Lys Ser Arg Trp Gln Gln Gly Asn Val
        420                 425                 430

Phe Ser Cys Ser Val Leu His Glu Ala Leu His Ser His Tyr Thr Gln
    435                 440                 445

Lys Ser Leu Ser Leu Ser Pro Gly Lys
    450                 455

<210> SEQ ID NO 80
<211> LENGTH: 651
<212> TYPE: DNA
<213> ORGANISM: Artificial Sequence
<220> FEATURE:
<223> OTHER INFORMATION: Synthetic

<400> SEQUENCE: 80
cagtctgtgc tgacgcagcc gccctcagtg tctggggccc cagggcagag ggtcaccatc      60
tcctgcactg ggatgaactc caacatcggg gcaggttatg atgtatactg gtaccaacaa     120
cttccaggaa ctgcccccaa actcctcatc tatggtaaca gcaatcggcc ctcaggggtc     180
cctgaccgat tctctggctc caggtctggc acctcagcct ccctggccat cactgggctc     240
caggctgagg atgaggctga ttattactgc cagtcctatg acaccagcct gaatggttgg     300
gctttcggcg agggaccaa gttgaccgtc ctaggccagc ccaaggctgc ccctcggtc       360 actctgttcc caccctcctc tgaggagctt caagccaaca ggccacact ggtgtgtctc      420 gtaagtgact tctacccggg agccgtgaca gtggcctgga aggcagatgg cagccccgtc     480
aaggtgggag tggagaccac caaaccctcc aaacaaagca caacaagta tgcggccagc     540 agctacctga gcctgacgcc cgagcagtgg aagtcccaca aagctacag ctgccgggtc      600 acgcatgaag ggagcaccgt ggagaagaca gtggcccctg cagaatgctc t              651

<210> SEQ ID NO 81
<211> LENGTH: 1371
<212> TYPE: DNA
<213> ORGANISM: Artificial Sequence
<220> FEATURE:
<223> OTHER INFORMATION: Synthetic

<400> SEQUENCE: 81
gaggtgcagc tggtggagtc tgggggaggc ttggtacagc cagggcggtc cctgagactc      60
agctgtgcgg cctctgggtt tagttttggt gatcatgcta tgagctgggt ccgccaggct     120
ccagggaagg ggctggagtg ggtaggtttc attagaaaga caacttatgg tgcgacaaca     180
cactacgccg cggctgtgag aggcagattc accatctcgc gagatgattc taaaagcact     240
gtctatctgc aaatgaacag cctgaaaacc gaggacacag ccgtgtattt ctgtactaga     300
gtgcagcttg actatggccc gggataccag tactacggta tggacgtctg gggccaaggg     360
accacggtca ccgtctcctc agcctccacc aagggcccat cggtcttccc cctggcaccc     420
tcctccaaga gcacctctgg gggcacagca gccctgggct gcctggtcaa ggactacttc     480
cccgaaccgg tgacggtgtc gtggaactca ggcgccctga ccagcggcgt gcacaccttc     540
ccggctgtcc tacagtcctc aggactctac tccctcagca gcgtggtgac cgtgccctcc     600
agcagcttgg gcacccagac ctacatctgc aacgtgaatc acaagcccag caacaccaag     660
gtggacaaga aagttgagcc caaatcttgt gacaaaactc acacatgccc accgtgccca     720

| | |
|---|---|
| gcacctgaac tcctgggggg accgtcagtc ttcctcttcc ccccaaaacc caaggacacc | 780 |
| ctcatgatct cccggacccc tgaggtcaca tgcgtggtgg tggacgtgag ccacgaagac | 840 |
| cctgaggtca agttcaactg gtacgtggac ggcgtggagg tgcataatgc caagacaaag | 900 |
| ccgcgggagg agcagtacaa cagcacgtac cgtgtggtca gcgtcctcac cgtcctgcac | 960 |
| caggactggc tgaatggcaa ggagtacaag tgcaaggtct ccaacaaagc cctcccagcc | 1020 |
| cccatcgaga aaaccatctc caaagccaaa gggcagcccc gagaaccaca ggtgtacacc | 1080 |
| ctgcccccat cccgggatga gctgaccaag aaccaggtca gcctgacctg cctggtcaaa | 1140 |
| ggcttctatc ccagcgacat cgccgtggag tgggagagca atgggcagcc ggagaacaac | 1200 |
| tacaagacca cgcctcccgt gctggactcc gacggctcct tcttcctcta cagcaagctc | 1260 |
| accgtggaca agagcaggtg gcagcagggg aacgtcttct catgctccgt gatgcatgag | 1320 |
| gctctgcaca accactacac acagaagagc ctctccctgt ctccgggtaa a | 1371 |

<210> SEQ ID NO 82
<211> LENGTH: 1371
<212> TYPE: DNA
<213> ORGANISM: Artificial Sequence
<220> FEATURE:
<223> OTHER INFORMATION: Synthetic

<400> SEQUENCE: 82

| | |
|---|---|
| gaggtgcagc tggtggagtc tgggggaggc ttggtacagc cagggcggtc cctgagactc | 60 |
| agctgtgcgg cctctgggtt tagttttggt gatcatgcta tgagctgggt ccgccaggct | 120 |
| ccagggaagg ggctggagtg ggtaggtttc attagaaaga caacttatgg tgcgacaaca | 180 |
| cactacgccg cggctgtgag aggcagattc accatctcgc gagatgattc aaaaagcact | 240 |
| gtctatctgc aaatgaacag cctgaaaacc gaggacacag ccgtgtattt ctgtactaga | 300 |
| gtgcagcttg actatggccc gggataccag tactacggta tggacgtctg gggccaaggg | 360 |
| accacggtca ccgtctcctc agcctccacc aagggcccat cggtcttccc cctggcaccc | 420 |
| tcctccaaga gcacctctgg gggcacagca gccctgggct gcctggtcaa ggactacttc | 480 |
| cccgaaccgg tgacggtgtc gtggaactca ggcgccctga ccagcggcgt gcacaccttc | 540 |
| ccggctgtcc tacagtcctc aggactctac tccctcagca gcgtggtgac cgtgccctcc | 600 |
| agcagcttgg gcacccagac ctacatctgc aacgtgaatc acaagcccag caacaccaag | 660 |
| gtggacaaga agttgagccc aaatcttgtg acaaaactca cacatgccca ccgtgccca | 720 |
| gcacctgaac tcctgggggg accgtcagtc ttcctcttcc ccccaaaacc caaggacacc | 780 |
| ctcatgatct cccggacccc tgaggtcaca tgcgtggtgg tggacgtgag ccacgaagac | 840 |
| cctgaggtca agttcaactg gtacgtggac ggcgtggagg tgcataatgc caagacaaag | 900 |
| ccgcgggagg agcagtacaa cagcacgtac cgtgtggtca gcgtcctcac cgtcctgcac | 960 |
| caggactggc tgaatggcaa ggagtacaag tgcaaggtct ccaacaaagc cctcccagcc | 1020 |
| cccatcgaga aaaccatctc caaagccaaa gggcagcccc gagaaccaca ggtgtacacc | 1080 |
| ctgcccccat cccgggatga gctgaccaag aaccaggtca gcctgacctg cctggtcaaa | 1140 |
| ggcttctatc ccagcgacat cgccgtggag tgggagagca atgggcagcc ggagaacaac | 1200 |
| tacaagacca cgcctcccgt gctggactcc gacggctcct tcttcctcta cagcaagctc | 1260 |
| accgtggaca agagcaggtg gcagcagggg aacgtcttct catgctccgt gctgcatgag | 1320 |
| gctctgcact cccactacac acagaagagc ctctccctgt ctccgggtaa a | 1371 |

```
<210> SEQ ID NO 83
<211> LENGTH: 112
<212> TYPE: PRT
<213> ORGANISM: Artificial Sequence
<220> FEATURE:
<223> OTHER INFORMATION: Synthetic

<400> SEQUENCE: 83

Gln Ser Val Leu Thr Gln Pro Pro Ser Val Ser Gly Ala Pro Gly Gln
1               5                   10                  15

Arg Val Thr Ile Ser Cys Thr Gly Met Asn Ser Asn Ile Gly Ala Gly
            20                  25                  30

Tyr Asp Val Tyr Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Arg Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Ser
                85                  90                  95

Leu Asn Gly Trp Ala Phe Gly Gly Gly Thr Lys Leu Thr Val Leu Gly
            100                 105                 110

<210> SEQ ID NO 84
<211> LENGTH: 127
<212> TYPE: PRT
<213> ORGANISM: Artificial Sequence
<220> FEATURE:
<223> OTHER INFORMATION: Synthetic

<400> SEQUENCE: 84

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr Thr His Tyr Ala Ala
    50                  55                  60

Ala Val Arg Gly Arg Phe Thr Ile Ser Arg Asp Asp Ser Lys Ser Ile
65                  70                  75                  80

Val Tyr Leu Gln Met Asn Ser Leu Lys Ala Glu Asp Thr Ala Val Tyr
                85                  90                  95

Phe Cys Thr Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser
        115                 120                 125

<210> SEQ ID NO 85
<211> LENGTH: 336
<212> TYPE: DNA
<213> ORGANISM: Artificial Sequence
<220> FEATURE:
<223> OTHER INFORMATION: Synthetic

<400> SEQUENCE: 85
cagtctgtgc tgacgcagcc gccctcagtg tctggggccc cagggcagag ggtcaccatc        60
tcctgcactg ggatgaactc caacatcggg gcaggttatg atgtatactg gtaccaacaa       120
cttccaggaa ctgccccaa actcctcatc tatggtaaca gcaatcggcc ctcaggggtc       180
```

```
cctgaccgat tctctggctc caggtctggc acctcagcct ccctggccat cactgggctc    240
caggctgagg atgaggctga ttattactgc cagtcctatg acaccagcct gaatggttgg    300
gctttcggcg gagggaccaa gttgaccgtc ctaggc                              336
```

<210> SEQ ID NO 86
<211> LENGTH: 381
<212> TYPE: DNA
<213> ORGANISM: Artificial Sequence
<220> FEATURE:
<223> OTHER INFORMATION: Synthetic

<400> SEQUENCE: 86

```
gaggtgcagc tggtggagtc tgggggaggc ttggtacagc cagggcggtc cctgagactc     60
agctgtgcgg cctctgggtt tagttttggt gatcatgcta tgagctgggt ccgccaggct    120
ccagggaagg ggctggagtg ggtaggtttc attagaaaga caacttatgg tgcgacaaca    180
cactacgccg cggctgtgag aggcagattc accatctcgc gagatgattc aaaagcatt     240 gtctatctgc aaatgaacag cctgaaagca gaggacacag ccgtgtattt ctgtactaga    300
gtgcagcttg actatggccc gggataccag tactacggta tggacgtctg gggccaaggg    360
accacggtca ccgtctcctc a                                              381
```

<210> SEQ ID NO 87
<211> LENGTH: 217
<212> TYPE: PRT
<213> ORGANISM: Artificial Sequence
<220> FEATURE:
<223> OTHER INFORMATION: Synthetic

<400> SEQUENCE: 87

```
Gln Ser Val Leu Thr Gln Pro Pro Ser Val Ser Gly Ala Pro Gly Gln
 1               5                  10                  15

Arg Val Thr Ile Ser Cys Thr Gly Met Asn Ser Asn Ile Gly Ala Gly
            20                  25                  30

Tyr Asp Val Tyr Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Arg Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Ser
                85                  90                  95

Leu Asn Gly Trp Ala Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Val Ser Asp Phe
    130                 135                 140

Tyr Pro Gly Ala Val Thr Val Ala Trp Lys Ala Asp Gly Ser Pro Val
145                 150                 155                 160

Lys Val Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Arg Val Thr His Glu Gly Ser Thr Val Glu
        195                 200                 205
```

```
Lys Thr Val Ala Pro Ala Glu Cys Ser
    210                 215

<210> SEQ ID NO 88
<211> LENGTH: 457
<212> TYPE: PRT
<213> ORGANISM: Artificial Sequence
<220> FEATURE:
<223> OTHER INFORMATION: Synthetic

<400> SEQUENCE: 88

Glu Val Gln Leu Val Glu Ser Gly Gly Leu Val Gln Pro Gly Arg
1               5                   10                  15

Ser Leu Arg Leu Ser Cys Ala Ala Ser Gly Phe Ser Phe Gly Asp His
                20                  25                  30

Ala Met Ser Trp Val Arg Gln Ala Pro Gly Lys Gly Leu Glu Trp Val
            35                  40                  45

Gly Phe Ile Arg Lys Thr Thr Tyr Gly Ala Thr Thr His Tyr Ala Ala
    50                  55                  60

Ala Val Arg Gly Arg Phe Thr Ile Ser Arg Asp Asp Ser Lys Ser Ile
65                  70                  75                  80

Val Tyr Leu Gln Met Asn Ser Leu Lys Ala Glu Asp Thr Ala Val Tyr
                85                  90                  95

Phe Cys Thr Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350
```

```
Pro Arg Glu Pro Gln Val Tyr Thr Leu Pro Pro Ser Arg Asp Glu Leu
            355                 360                 365

Thr Lys Asn Gln Val Ser Leu Thr Cys Leu Val Lys Gly Phe Tyr Pro
        370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
            435                 440                 445

Lys Ser Leu Ser Leu Ser Pro Gly Lys
        450                 455

<210> SEQ ID NO 89
<211> LENGTH: 457
<212> TYPE: PRT
<213> ORGANISM: Artificial Sequence
<220> FEATURE:
<223> OTHER INFORMATION: Synthetic

<400> SEQUENCE: 89

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr His Tyr Ala Ala
    50                  55                  60

Ala Val Arg Gly Arg Phe Thr Ile Ser Arg Asp Asp Ser Lys Ser Ile
65                  70                  75                  80

Val Tyr Leu Gln Met Asn Ser Leu Lys Ala Glu Asp Thr Ala Val Tyr
                85                  90                  95

Phe Cys Thr Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255
```

```
Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Leu His Glu Ala Leu His Ser His Tyr Thr Gln
        435                 440                 445

Lys Ser Leu Ser Leu Ser Pro Gly Lys
    450                 455
```

<210> SEQ ID NO 90
<211> LENGTH: 651
<212> TYPE: DNA
<213> ORGANISM: Artificial Sequence
<220> FEATURE:
<223> OTHER INFORMATION: Synthetic

<400> SEQUENCE: 90

```
cagtctgtgc tgacgcagcc gccctcagtg tctggggccc cagggcagag ggtcaccatc      60
tcctgcactg ggatgaactc caacatcggg gcaggttatg atgtatactg gtaccaacaa     120
cttccaggaa ctgcccccaa actcctcatc tatggtaaca gcaatcggcc ctcaggggtc     180
cctgaccgat tctctggctc caggtctggc acctcagcct ccctggccat cactgggctc     240
caggctgagg atgaggctga ttattactgc agtcctatg acaccagcct gaatggttgg     300
gctttcggcg agggaccaa gttgaccgtc ctaggccagc ccaaggctgc ccctcggtc      360 actctgttcc caccctcctc tgaggagctt caagccaaca ggccacact ggtgtgtctc      420 gtaagtgact tctacccggg agccgtgaca gtggcctgga aggcagatgg cagcccgtc      480 aaggtgggag tggagaccac caaaccctcc aaacaaagca caacaagta tgcggccagc     540 agctacctga gcctgacgcc cgagcagtgg aagtcccaca aagctacag ctgccgggtc      600 acgcatgaag ggagcaccgt ggagaagaca gtggcccctg cagaatgctc t              651
```

<210> SEQ ID NO 91
<211> LENGTH: 1371
<212> TYPE: DNA
<213> ORGANISM: Artificial Sequence
<220> FEATURE:
<223> OTHER INFORMATION: Synthetic

<400> SEQUENCE: 91

```
gaggtgcagc tggtggagtc tgggggaggc ttggtacagc cagggcggtc cctgagactc      60
agctgtgcgg cctctgggtt tagttttggt gatcatgcta tgagctgggt ccgccaggct     120
ccagggaagg ggctggagtg ggtaggtttc attagaaaga caacttatgg tgcgacaaca     180
cactacgccg cggctgtgag aggcagattc accatctcgc gagatgattc taaaagcatt     240
gtctatctgc aaatgaacag cctgaaagca gaggacacag ccgtgtattt ctgtactaga     300
gtgcagcttg actatggccc gggataccag tactacggta tggacgtctg gggccaaggg     360
accacggtca ccgtctcctc agcctccacc aagggcccat cggtcttccc cctggcaccc     420
tcctccaaga gcacctctgg gggcacagca gccctgggct gcctggtcaa ggactacttc     480
cccgaaccgg tgacggtgtc gtggaactca ggcgccctga ccagcggcgt gcacaccttc     540
ccggctgtcc tacagtcctc aggactctac tccctcagca gcgtggtgac cgtgccctcc     600
agcagcttgg gcacccagac ctacatctgc aacgtgaatc acaagcccag caacaccaag     660
gtggacaaga agttgagccc aaatcttgt gacaaaactc acacatgccc accgtgccca     720
gcacctgaac tcctgggggg accgtcagtc ttcctcttcc ccccaaaacc caaggacacc     780
ctcatgatct cccggacccc tgaggtcaca tgcgtggtgg tggacgtgag ccacgaagac     840
cctgaggtca agttcaactg gtacgtggac ggcgtggagg tgcataatgc caagacaaag     900
ccgcgggagg agcagtacaa cagcacgtac cgtgtggtca gcgtcctcac cgtcctgcac     960
caggactggc tgaatggcaa ggagtacaag tgcaaggtct ccaacaaagc cctcccagcc    1020
cccatcgaga aaaccatctc caaagccaaa gggcagcccc gagaaccaca ggtgtacacc    1080
ctgcccccat cccgggatga gctgaccaag aaccaggtca gcctgacctg cctggtcaaa    1140
ggcttctatc ccagcgacat cgccgtggag tgggagagca atgggcagcc ggagaacaac    1200
tacaagacca cgcctcccgt gctggactcc gacggctcct tcttcctcta cagcaagctc    1260
accgtggaca agagcaggtg gcagcagggg aacgtcttct catgctccgt gatgcatgag    1320
gctctgcaca accactacac acagaagagc ctctccctgt ctccgggtaa a             1371
```

<210> SEQ ID NO 92
<211> LENGTH: 1371
<212> TYPE: DNA
<213> ORGANISM: Artificial Sequence
<220> FEATURE:
<223> OTHER INFORMATION: Synthetic

<400> SEQUENCE: 92

```
gaggtgcagc tggtggagtc tgggggaggc ttggtacagc cagggcggtc cctgagactc      60
agctgtgcgg cctctgggtt tagttttggt gatcatgcta tgagctgggt ccgccaggct     120
ccagggaagg ggctggagtg ggtaggtttc attagaaaga caacttatgg tgcgacaaca     180
cactacgccg cggctgtgag aggcagattc accatctcgc gagatgattc taaaagcatt     240
gtctatctgc aaatgaacag cctgaaagca gaggacacag ccgtgtattt ctgtactaga     300
gtgcagcttg actatggccc gggataccag tactacggta tggacgtctg gggccaaggg     360
accacggtca ccgtctcctc agcctccacc aagggcccat cggtcttccc cctggcaccc     420
tcctccaaga gcacctctgg gggcacagca gccctgggct gcctggtcaa ggactacttc     480
cccgaaccgg tgacggtgtc gtggaactca ggcgccctga ccagcggcgt gcacaccttc     540
ccggctgtcc tacagtcctc aggactctac tccctcagca gcgtggtgac cgtgccctcc     600
```

```
agcagcttgg gcacccagac ctacatctgc aacgtgaatc acaagcccag caacaccaag      660
gtggacaaga aagttgagcc caaatcttgt gacaaaactc acacatgccc accgtgccca      720
gcacctgaac tcctgggggg accgtcagtc ttcctcttcc ccccaaaacc caaggacacc      780
ctcatgatct cccggacccc tgaggtcaca tgcgtggtgg tggacgtgag ccacgaagac      840
cctgaggtca agttcaactg gtacgtggac ggcgtggagg tgcataatgc caagacaaag      900
ccgcgggagg agcagtacaa cagcacgtac cgtgtggtca gcgtcctcac cgtcctgcac      960
caggactggc tgaatggcaa ggagtacaag tgcaaggtct ccaacaaagc cctcccagcc     1020
cccatcgaga aaaccatctc caaagccaaa gggcagcccc gagaaccaca ggtgtacacc     1080
ctgcccccat cccgggatga gctgaccaag aaccaggtca gcctgacctg cctggtcaaa     1140
ggcttctatc ccagcgacat cgccgtggag tgggagagca atgggcagcc ggagaacaac     1200
tacaagacca cgcctcccgt gctggactcc gacggctcct tcttcctcta cagcaagctc     1260
accgtggaca gagcaggtg gcagcagggg aacgtcttct catgctccgt gctgcatgag     1320
gctctgcact cccactacac acagaagagc ctctccctgt ctccgggtaa a              1371
```

<210> SEQ ID NO 93
<211> LENGTH: 112
<212> TYPE: PRT
<213> ORGANISM: Artificial Sequence
<220> FEATURE:
<223> OTHER INFORMATION: Synthetic

<400> SEQUENCE: 93

```
Gln Ser Val Leu Thr Gln Pro Pro Ser Val Ser Gly Ala Pro Gly Gln
1               5                  10                  15

Arg Val Thr Ile Ser Cys Thr Gly Met Asn Ser Asn Ile Gly Ala Gly
            20                  25                  30

Tyr Asp Val Tyr Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Arg Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Ser
                85                  90                  95

Leu Asn Gly Trp Ala Phe Gly Gly Gly Thr Lys Leu Thr Val Leu Gly
            100                 105                 110
```

<210> SEQ ID NO 94
<211> LENGTH: 127
<212> TYPE: PRT
<213> ORGANISM: Artificial Sequence
<220> FEATURE:
<223> OTHER INFORMATION: Synthetic

<400> SEQUENCE: 94

```
Glu Val Gln Leu Val Glu Ser Gly Gly Gly Leu Val Gln Pro Gly Arg
1               5                  10                  15

Ser Leu Arg Leu Ser Cys Ala Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr His Tyr Ala Ala
    50                  55                  60
```

```
Ala Val Arg Gly Arg Phe Thr Ile Ser Arg Asp Asp Ser Lys Ser Ile
 65                  70                  75                  80

Val Tyr Leu Gln Met Asn Ser Leu Lys Thr Glu Asp Thr Ala Val Tyr
                 85                  90                  95

Phe Cys Ala Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser
            115                 120                 125
```

<210> SEQ ID NO 95
<211> LENGTH: 336
<212> TYPE: DNA
<213> ORGANISM: Artificial Sequence
<220> FEATURE:
<223> OTHER INFORMATION: Synthetic

<400> SEQUENCE: 95

```
cagtctgtgc tgacgcagcc gccctcagtg tctggggccc cagggcagag ggtcaccatc    60
tcctgcactg ggatgaactc caacatcggg gcaggttatg atgtatactg gtaccaacaa   120
cttccaggaa ctgcccccaa actcctcatc tatggtaaca gcaatcggcc ctcaggggtc   180
cctgaccgat tctctggctc caggtctggc acctcagcct ccctggccat cactgggctc   240
caggctgagg atgaggctga ttattactgc cagtcctatg acaccagcct gaatggttgg   300
gctttcggcg agggaccaa gttgaccgtc ctaggc                               336
```

<210> SEQ ID NO 96
<211> LENGTH: 381
<212> TYPE: DNA
<213> ORGANISM: Artificial Sequence
<220> FEATURE:
<223> OTHER INFORMATION: Synthetic

<400> SEQUENCE: 96

```
gaggtgcagc tggtggagtc tgggggaggc ttggtacagc cagggcggtc cctgagactc    60
agctgtgcgg cctctgggtt tagttttggt gatcatgcta tgagctgggt ccgccaggct   120
ccagggaagg ggctggagtg ggtaggtttc attagaaaga caacttatgg tgcgacaaca   180
cactacgccg cggctgtgag aggcagattc accatctcgc gagatgattc taaaagcatt   240
gtctatctgc aaatgaacag cctgaaaacc gaggacacag ccgtgtattt ctgtgctaga   300
gtgcagcttg actatggccc gggataccag tactacggta tggacgtctg gggccaaggg   360
accacggtca ccgtctcctc a                                              381
```

<210> SEQ ID NO 97
<211> LENGTH: 217
<212> TYPE: PRT
<213> ORGANISM: Artificial Sequence
<220> FEATURE:
<223> OTHER INFORMATION: Synthetic

<400> SEQUENCE: 97

```
Gln Ser Val Leu Thr Gln Pro Pro Ser Val Ser Gly Ala Pro Gly Gln
 1               5                  10                  15

Arg Val Thr Ile Ser Cys Thr Gly Met Asn Ser Asn Ile Gly Ala Gly
                 20                  25                  30

Tyr Asp Val Tyr Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
        50                  55                  60
```

Ser Gly Ser Arg Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Ser
            85                  90                  95

Leu Asn Gly Trp Ala Phe Gly Gly Gly Thr Lys Leu Thr Val Leu Gly
        100                 105                 110

Gln Pro Lys Ala Ala Pro Ser Val Thr Leu Phe Pro Pro Ser Ser Glu
    115                 120                 125

Glu Leu Gln Ala Asn Lys Ala Thr Leu Val Cys Leu Val Ser Asp Phe
130                 135                 140

Tyr Pro Gly Ala Val Thr Val Ala Trp Lys Ala Asp Gly Ser Pro Val
145                 150                 155                 160

Lys Val Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Arg Val Thr His Glu Gly Ser Thr Val Glu
        195                 200                 205

Lys Thr Val Ala Pro Ala Glu Cys Ser
    210                 215

<210> SEQ ID NO 98
<211> LENGTH: 457
<212> TYPE: PRT
<213> ORGANISM: Artificial Sequence
<220> FEATURE:
<223> OTHER INFORMATION: Synthetic

<400> SEQUENCE: 98

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr Thr His Tyr Ala Ala
    50                  55                  60

Ala Val Arg Gly Arg Phe Thr Ile Ser Arg Asp Asp Ser Lys Ser Ile
65                  70                  75                  80

Val Tyr Leu Gln Met Asn Ser Leu Lys Thr Glu Asp Thr Ala Val Tyr
            85                  90                  95

Phe Cys Ala Arg Val Gln Leu Asp Tyr Gly Pro Gly Tyr Gln Tyr Tyr
        100                 105                 110

Gly Met Asp Val Trp Gly Gln Gly Thr Thr Val Thr Val Ser Ser Ala
    115                 120                 125

Ser Thr Lys Gly Pro Ser Val Phe Pro Leu Ala Pro Ser Ser Lys Ser
130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

```
Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 99
<211> LENGTH: 457
<212> TYPE: PRT
<213> ORGANISM: Artificial Sequence
<220> FEATURE:
<223> OTHER INFORMATION: Synthetic

<400> SEQUENCE: 99

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr Thr His Tyr Ala Ala
    50                  55                  60

Ala Val Arg Gly Arg Phe Thr Ile Ser Arg Asp Asp Ser Lys Ser Ile
65                  70                  75                  80

Val Tyr Leu Gln Met Asn Ser Leu Lys Thr Glu Asp Thr Ala Val Tyr
                85                  90                  95

Phe Cys Ala Arg Val Gln Leu Asp Tyr Gly Pro Gly Tyr Gln Tyr Tyr
            100                 105                 110
```

```
Gly Met Asp Val Trp Gly Gln Gly Thr Thr Val Thr Val Ser Ser Ala
            115                 120                 125
Ser Thr Lys Gly Pro Ser Val Phe Pro Leu Ala Pro Ser Ser Lys Ser
    130                 135                 140
Thr Ser Gly Gly Thr Ala Ala Leu Gly Cys Leu Val Lys Asp Tyr Phe
145                 150                 155                 160
Pro Glu Pro Val Thr Val Ser Trp Asn Ser Gly Ala Leu Thr Ser Gly
                165                 170                 175
Val His Thr Phe Pro Ala Val Leu Gln Ser Ser Gly Leu Tyr Ser Leu
            180                 185                 190
Ser Ser Val Val Thr Val Pro Ser Ser Leu Gly Thr Gln Thr Tyr
        195                 200                 205
Ile Cys Asn Val Asn His Lys Pro Ser Asn Thr Lys Val Asp Lys Lys
    210                 215                 220
Val Glu Pro Lys Ser Cys Asp Lys Thr His Thr Cys Pro Pro Cys Pro
225                 230                 235                 240
Ala Pro Glu Leu Leu Gly Gly Pro Ser Val Phe Leu Phe Pro Pro Lys
                245                 250                 255
Pro Lys Asp Thr Leu Met Ile Ser Arg Thr Pro Glu Val Thr Cys Val
            260                 265                 270
Val Val Asp Val Ser His Glu Asp Pro Glu Val Lys Phe Asn Trp Tyr
        275                 280                 285
Val Asp Gly Val Glu Val His Asn Ala Lys Thr Lys Pro Arg Glu Glu
    290                 295                 300
Gln Tyr Asn Ser Thr Tyr Arg Val Val Ser Val Leu Thr Val Leu His
305                 310                 315                 320
Gln Asp Trp Leu Asn Gly Lys Glu Tyr Lys Cys Lys Val Ser Asn Lys
                325                 330                 335
Ala Leu Pro Ala Pro Ile Glu Lys Thr Ile Ser Lys Ala Lys Gly Gln
            340                 345                 350
Pro Arg Glu Pro Gln Val Tyr Thr Leu Pro Pro Ser Arg Asp Glu Leu
        355                 360                 365
Thr Lys Asn Gln Val Ser Leu Thr Cys Leu Val Lys Gly Phe Tyr Pro
    370                 375                 380
Ser Asp Ile Ala Val Glu Trp Glu Ser Asn Gly Gln Pro Glu Asn Asn
385                 390                 395                 400
Tyr Lys Thr Thr Pro Pro Val Leu Asp Ser Asp Gly Ser Phe Phe Leu
                405                 410                 415
Tyr Ser Lys Leu Thr Val Asp Lys Ser Arg Trp Gln Gln Gly Asn Val
            420                 425                 430
Phe Ser Cys Ser Val Leu His Glu Ala Leu His Ser His Tyr Thr Gln
        435                 440                 445
Lys Ser Leu Ser Leu Ser Pro Gly Lys
    450                 455

<210> SEQ ID NO 100
<211> LENGTH: 651
<212> TYPE: DNA
<213> ORGANISM: Artificial Sequence
<220> FEATURE:
<223> OTHER INFORMATION: Synthetic

<400> SEQUENCE: 100
cagtctgtgc tgacgcagcc gccctcagtg tctggggccc cagggcagag ggtcaccatc      60
```

```
tcctgcactg ggatgaactc caacatcggg gcaggttatg atgtatactg gtaccaacaa      120
cttccaggaa ctgccccaa actcctcatc tatggtaaca gcaatcggcc ctcagggtc        180 cctgaccgat tctctggctc caggtctggc acctcagcct ccctggccat cactgggctc      240
caggctgagg atgaggctga ttattactgc cagtcctatg acaccagcct gaatggttgg      300
gctttcggcg agggaccaa gttgaccgtc ctaggccagc ccaaggctgc cccctcggtc       360
actctgttcc caccctcctc tgaggagctt caagccaaca aggccacact ggtgtgtctc      420
gtaagtgact tctacccggg agccgtgaca gtggcctgga aggcagatgg cagccccgtc      480
aaggtgggag tggagaccac caaaccctcc aaacaaagca caacaagta tgcggccagc      540 agctacctga gcctgacgcc cgagcagtgg aagtcccaca aagctacag ctgccgggtc       600 acgcatgaag ggagcaccgt ggagaagaca gtggcccctg cagaatgctc t               651
```

<210> SEQ ID NO 101
<211> LENGTH: 1371
<212> TYPE: DNA
<213> ORGANISM: Artificial Sequence
<220> FEATURE:
<223> OTHER INFORMATION: Synthetic

<400> SEQUENCE: 101

```
gaggtgcagc tggtggagtc tggggaggc ttggtacagc cagggcggtc cctgagactc        60
agctgtgcgg cctctgggtt tagttttggt gatcatgcta tgagctgggt ccgccaggct      120
ccagggaagg ggctggagtg ggtaggtttc attagaaaga caacttatgg tgcgacaaca      180
cactacgccg cggctgtgag aggcagattc accatctcgc gagatgattc taaaagcatt      240
gtctatctgc aaatgaacag cctgaaaacc gaggacacag ccgtgtattt ctgtgctaga      300
gtgcagcttg actatggccc gggataccag tactacggta tggacgtctg gggccaaggg      360
accacggtca ccgtctcctc agcctccacc aagggcccat cggtcttccc cctggcaccc      420
tcctccaaga gcacctctgg gggcacagca gccctgggct gcctggtcaa ggactacttc      480
cccgaaccgg tgacggtgtc gtggaactca ggcgccctga ccagcggcgt gcacaccttc      540
ccggctgtcc tacagtcctc aggactctac tccctcagca gcgtggtgac cgtgccctcc      600
agcagcttgg gcacccagac ctacatctgc aacgtgaatc acaagcccag caacaccaag      660
gtggacaaga aagttgagcc caaatcttgt gacaaaactc acacatgccc accgtgccca      720
gcacctgaac tcctgggggg accgtcagtc ttcctcttcc cccaaaaacc caaggacacc      780
ctcatgatct cccggacccc tgaggtcaca tgcgtggtgg tggacgtgag ccacgaagac      840
cctgaggtca agttcaactg gtacgtggac ggcgtggagg tgcataatgc caagacaaag      900
ccgcgggagg agcagtacaa cagcacgtac cgtgtggtca gcgtcctcac cgtcctgcac      960
caggactggc tgaatggcaa ggagtacaag tgcaaggtct ccaacaaagc cctcccagcc     1020
cccatcgaga aaaccatctc caaagccaaa gggcagcccc gagaaccaca ggtgtacacc     1080
ctgcccccat cccgggatga gctgaccaag aaccaggtca gcctgacctg cctggtcaaa     1140
ggcttctatc ccagcgacat cgccgtggag tgggagagca atgggcagcc ggagaacaac     1200
tacaagacca cgcctcccgt gctggactcc gacggctcct tcttcctcta cagcaagctc     1260
accgtggaca agagcaggtg gcagcagggg aacgtcttct catgctccgt gatgcatgag     1320
gctctgcaca accactacac acagaagagc ctctccctgt ctccgggtaa a              1371
```

<210> SEQ ID NO 102
<211> LENGTH: 1371

<212> TYPE: DNA
<213> ORGANISM: Artificial Sequence
<220> FEATURE:
<223> OTHER INFORMATION: Synthetic

<400> SEQUENCE: 102

```
gaggtgcagc tggtggagtc tgggggaggc ttggtacagc cagggcggtc cctgagactc      60
agctgtgcgg cctctgggtt tagttttggt gatcatgcta tgagctgggt ccgccaggct     120
ccagggaagg ggctggagtg ggtaggtttc attagaaaga caacttatgg tgcgacaaca     180
cactacgccg cggctgtgag aggcagattc accatctcgc gagatgattc aaaagcatt      240
gtctatctgc aaatgaacag cctgaaaacc gaggacacag ccgtgtattt ctgtgctaga     300
gtgcagcttg actatggccc gggataccag tactacggta tggacgtctg gggccaaggg     360
accacggtca ccgtctcctc agcctccacc aagggcccat cggtcttccc cctggcaccc     420
tcctccaaga gcacctctgg gggcacagca gccctgggct gcctggtcaa ggactacttc     480
cccgaaccgg tgacggtgtc gtggaactca ggcgccctga ccagcggcgt gcacaccttc     540
ccggctgtcc tacagtcctc aggactctac tccctcagca gcgtggtgac cgtgccctcc     600
agcagcttgg gcacccagac ctacatctgc aacgtgaatc acaagcccag caacaccaag     660
gtggacaaga agttgagccc aaatcttgt gacaaaactc acacatgccc accgtgccca     720
gcacctgaac tcctgggggg accgtcagtc ttcctcttcc ccccaaaacc caaggacacc     780
ctcatgatct cccggacccc tgaggtcaca tgcgtggtgg tggacgtgag ccacgaagac     840
cctgaggtca gttcaactg gtacgtggac ggcgtggagg tgcataatgc caagacaaag     900
ccgcgggagg agcagtacaa cagcacgtac cgtgtggtca gcgtcctcac cgtcctgcac     960
caggactggc tgaatggcaa ggagtacaag tgcaaggtct ccaacaaagc cctcccagcc    1020
cccatcgaga aaaccatctc caaagccaaa gggcagcccc gagaaccaca ggtgtacacc    1080
ctgcccccat cccgggatga gctgaccaag aaccaggtca gcctgacctg cctggtcaaa    1140
ggcttctatc ccagcgacat cgccgtggag tgggagagca atgggcagcc ggagaacaac    1200
tacaagacca cgcctcccgt gctggactcc gacggctcct tcttcctcta cagcaagctc    1260
accgtggaca agagcaggtg gcagcagggg aacgtcttct catgctccgt gctgcatgag    1320
gctctgcact cccactacac acagaagagc ctctccctgt ctccgggtaa a              1371
```

<210> SEQ ID NO 103
<211> LENGTH: 112
<212> TYPE: PRT
<213> ORGANISM: Artificial Sequence
<220> FEATURE:
<223> OTHER INFORMATION: Synthetic

<400> SEQUENCE: 103

```
Gln Ser Val Leu Thr Gln Pro Pro Ser Val Ser Gly Ala Pro Gly Gln
1               5                   10                  15
Arg Val Thr Ile Ser Cys Thr Gly Met Asn Ser Asn Ile Gly Ala Gly
            20                  25                  30
Tyr Asp Val Tyr Trp Tyr Gln Gln Leu Pro Gly Thr Ala Pro Lys Leu
        35                  40                  45
Leu Ile Tyr Gly Asn Ser Asn Arg Pro Ser Gly Val Pro Asp Arg Phe
    50                  55                  60
Ser Gly Ser Arg Ser Gly Thr Ser Ala Ser Leu Ala Ile Thr Gly Leu
65                  70                  75                  80
Gln Ala Glu Asp Glu Ala Asp Tyr Tyr Cys Gln Ser Tyr Asp Thr Ser
```

```
                    85                  90                  95
Leu Asn Gly Trp Ala Phe Gly Gly Gly Thr Lys Leu Thr Val Leu Gly
                100                 105                 110
```

<210> SEQ ID NO 104
<211> LENGTH: 127
<212> TYPE: PRT
<213> ORGANISM: Artificial Sequence
<220> FEATURE:
<223> OTHER INFORMATION: Synthetic

<400> SEQUENCE: 104

```
Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Ser Phe Gly Asp His
                20                  25                  30

Ala Met Ser Trp Val Arg Gln Ala Pro Gly Lys Gly Leu Glu Trp Val
            35                  40                  45

Gly Phe Ile Arg Lys Thr Thr Tyr Gly Ala Thr Thr His Tyr Ala Ala
        50                  55                  60

Ala Val Arg Gly Arg Phe Thr Ile Ser Arg Asp Asp Ser Lys Ser Thr
65                  70                  75                  80

Val Tyr Leu Gln Met Asn Ser Leu Lys Ala Glu Asp Thr Ala Val Tyr
                85                  90                  95

Phe Cys Thr Arg Val Gln Leu Asp Tyr Gly Pro Gly Tyr Gln Tyr Tyr
                100                 105                 110

Gly Met Asp Val Trp Gly Gln Gly Thr Thr Val Thr Val Ser Ser
            115                 120                 125
```

<210> SEQ ID NO 105
<211> LENGTH: 336
<212> TYPE: DNA
<213> ORGANISM: Artificial Sequence
<220> FEATURE:
<223> OTHER INFORMATION: Synthetic

<400> SEQUENCE: 105

```
cagtctgtgc tgacgcagcc gccctcagtg tctggggccc cagggcagag ggtcaccatc      60
tcctgcactg ggatgaactc caacatcggg gcaggttatg atgtatactg gtaccaacaa     120
cttccaggaa ctgcccccaa actcctcatc tatggtaaca gcaatcggcc ctcaggggtc     180
cctgaccgat tctctggctc caggtctggc acctcagcct ccctggccat cactgggctc     240
caggctgagg atgaggctga ttattactgc cagtcctatg acaccagcct gaatggttgg     300
gctttcggcg agggaccaa gttgaccgtc ctaggc                                336
```

<210> SEQ ID NO 106
<211> LENGTH: 381
<212> TYPE: DNA
<213> ORGANISM: Artificial Sequence
<220> FEATURE:
<223> OTHER INFORMATION: Synthetic

<400> SEQUENCE: 106

```
gaggtgcagc tggtggagtc tgggggaggc ttggtacagc cagggcggtc cctgagactc      60
agctgtacag cctctgggtt tagttttggt gatcatgcta tgagctgggt ccgccaggct     120
ccagggaagg ggctggagtg ggtaggtttc attagaaaga caacttatgg tgcgacaaca     180
cactacgccg cggctgtgag aggcagattc accatctcgc gagatgattc taaaagcact     240
```

```
gtctatctgc aaatgaacag cctgaaagca gaggacacag ccgtgtattt ctgtactaga    300
gtgcagcttg actatggccc gggataccag tactacggta tggacgtctg gggccaaggg    360
accacggtca ccgtctcctc a                                              381
```

<210> SEQ ID NO 107
<211> LENGTH: 217
<212> TYPE: PRT
<213> ORGANISM: Artificial Sequence
<220> FEATURE:
<223> OTHER INFORMATION: Synthetic

<400> SEQUENCE: 107

```
Gln Ser Val Leu Thr Gln Pro Pro Ser Val Ser Gly Ala Pro Gly Gln
1               5                   10                  15

Arg Val Thr Ile Ser Cys Thr Gly Met Asn Ser Asn Ile Gly Ala Gly
            20                  25                  30

Tyr Asp Val Tyr Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Arg Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Ser
                85                  90                  95

Leu Asn Gly Trp Ala Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Val Ser Asp Phe
    130                 135                 140

Tyr Pro Gly Ala Val Thr Val Ala Trp Lys Ala Asp Gly Ser Pro Val
145                 150                 155                 160

Lys Val Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Arg Val Thr His Glu Gly Ser Thr Val Glu
        195                 200                 205

Lys Thr Val Ala Pro Ala Glu Cys Ser
    210                 215
```

<210> SEQ ID NO 108
<211> LENGTH: 457
<212> TYPE: PRT
<213> ORGANISM: Artificial Sequence
<220> FEATURE:
<223> OTHER INFORMATION: Synthetic

<400> SEQUENCE: 108

```
Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr Thr His Tyr Ala Ala
    50                  55                  60
```

Ala Val Arg Gly Arg Phe Thr Ile Ser Arg Asp Asp Ser Lys Ser Thr
65                  70                  75                  80

Val Tyr Leu Gln Met Asn Ser Leu Lys Ala Glu Asp Thr Ala Val Tyr
                85                  90                  95

Phe Cys Thr Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 109
<211> LENGTH: 457

```
<212> TYPE: PRT
<213> ORGANISM: Artificial Sequence
<220> FEATURE:
<223> OTHER INFORMATION: Synthetic

<400> SEQUENCE: 109
```

| Glu | Val | Gln | Leu | Val | Glu | Ser | Gly | Gly | Gly | Leu | Val | Gln | Pro | Gly | Arg |
|-----|-----|-----|-----|-----|-----|-----|-----|-----|-----|-----|-----|-----|-----|-----|-----|
| 1 | | | | 5 | | | | | 10 | | | | | 15 | |
| Ser | Leu | Arg | Leu | Ser | Cys | Thr | Ala | Ser | Gly | Phe | Ser | Phe | Gly | Asp | His |
| | | | 20 | | | | | 25 | | | | | 30 | | |
| Ala | Met | Ser | Trp | Val | Arg | Gln | Ala | Pro | Gly | Lys | Gly | Leu | Glu | Trp | Val |
| | | 35 | | | | | 40 | | | | | 45 | | | |
| Gly | Phe | Ile | Arg | Lys | Thr | Thr | Tyr | Gly | Ala | Thr | His | Tyr | Ala | Ala |
| | 50 | | | | | 55 | | | | | 60 | | | |
| Ala | Val | Arg | Gly | Arg | Phe | Thr | Ile | Ser | Arg | Asp | Asp | Ser | Lys | Ser | Thr |
| 65 | | | | | 70 | | | | | 75 | | | | | 80 |
| Val | Tyr | Leu | Gln | Met | Asn | Ser | Leu | Lys | Ala | Glu | Asp | Thr | Ala | Val | Tyr |
| | | | | 85 | | | | | 90 | | | | | 95 | |
| Phe | Cys | Thr | Arg | Val | Gln | Leu | Asp | Tyr | Gly | Pro | Gly | Tyr | Gln | Tyr | Tyr |
| | | | 100 | | | | | 105 | | | | | 110 | | |
| Gly | Met | Asp | Val | Trp | Gly | Gln | Gly | Thr | Thr | Val | Thr | Val | Ser | Ser | Ala |
| | | | 115 | | | | | 120 | | | | | 125 | | |
| Ser | Thr | Lys | Gly | Pro | Ser | Val | Phe | Pro | Leu | Ala | Pro | Ser | Ser | Lys | Ser |
| | 130 | | | | | 135 | | | | | 140 | | | | |
| Thr | Ser | Gly | Gly | Thr | Ala | Ala | Leu | Gly | Cys | Leu | Val | Lys | Asp | Tyr | Phe |
| 145 | | | | | 150 | | | | | 155 | | | | | 160 |
| Pro | Glu | Pro | Val | Thr | Val | Ser | Trp | Asn | Ser | Gly | Ala | Leu | Thr | Ser | Gly |
| | | | | 165 | | | | | 170 | | | | | 175 | |
| Val | His | Thr | Phe | Pro | Ala | Val | Leu | Gln | Ser | Ser | Gly | Leu | Tyr | Ser | Leu |
| | | | 180 | | | | | 185 | | | | | 190 | | |
| Ser | Ser | Val | Val | Thr | Val | Pro | Ser | Ser | Ser | Leu | Gly | Thr | Gln | Thr | Tyr |
| | | | 195 | | | | | 200 | | | | | 205 | | |
| Ile | Cys | Asn | Val | Asn | His | Lys | Pro | Ser | Asn | Thr | Lys | Val | Asp | Lys | Lys |
| | 210 | | | | | 215 | | | | | 220 | | | | |
| Val | Glu | Pro | Lys | Ser | Cys | Asp | Lys | Thr | His | Thr | Cys | Pro | Pro | Cys | Pro |
| 225 | | | | | 230 | | | | | 235 | | | | | 240 |
| Ala | Pro | Glu | Leu | Leu | Gly | Gly | Pro | Ser | Val | Phe | Leu | Phe | Pro | Pro | Lys |
| | | | | 245 | | | | | 250 | | | | | 255 | |
| Pro | Lys | Asp | Thr | Leu | Met | Ile | Ser | Arg | Thr | Pro | Glu | Val | Thr | Cys | Val |
| | | | 260 | | | | | 265 | | | | | 270 | | |
| Val | Val | Asp | Val | Ser | His | Glu | Asp | Pro | Glu | Val | Lys | Phe | Asn | Trp | Tyr |
| | | 275 | | | | | 280 | | | | | 285 | | | |
| Val | Asp | Gly | Val | Glu | Val | His | Asn | Ala | Lys | Thr | Lys | Pro | Arg | Glu | Glu |
| | 290 | | | | | 295 | | | | | 300 | | | | |
| Gln | Tyr | Asn | Ser | Thr | Tyr | Arg | Val | Val | Ser | Val | Leu | Thr | Val | Leu | His |
| 305 | | | | | 310 | | | | | 315 | | | | | 320 |
| Gln | Asp | Trp | Leu | Asn | Gly | Lys | Glu | Tyr | Lys | Cys | Lys | Val | Ser | Asn | Lys |
| | | | | 325 | | | | | 330 | | | | | 335 | |
| Ala | Leu | Pro | Ala | Pro | Ile | Glu | Lys | Thr | Ile | Ser | Lys | Ala | Lys | Gly | Gln |
| | | | 340 | | | | | 345 | | | | | 350 | | |
| Pro | Arg | Glu | Pro | Gln | Val | Tyr | Thr | Leu | Pro | Pro | Ser | Arg | Asp | Glu | Leu |
| | | | 355 | | | | | 360 | | | | | 365 | | |
| Thr | Lys | Asn | Gln | Val | Ser | Leu | Thr | Cys | Leu | Val | Lys | Gly | Phe | Tyr | Pro |
| | 370 | | | | | 375 | | | | | 380 | | | | |

```
Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Leu His Glu Ala Leu His Ser His Tyr Thr Gln
        435                 440                 445

Lys Ser Leu Ser Leu Ser Pro Gly Lys
    450                 455
```

```
<210> SEQ ID NO 110
<211> LENGTH: 651
<212> TYPE: DNA
<213> ORGANISM: Artificial Sequence
<220> FEATURE:
<223> OTHER INFORMATION: Synthetic

<400> SEQUENCE: 110
cagtctgtgc tgacgcagcc gccctcagtg tctggggccc cagggcagag ggtcaccatc      60
tcctgcactg ggatgaactc caacatcggg gcaggttatg atgtatactg gtaccaacaa     120
cttccaggaa ctgcccccaa actcctcatc tatggtaaca gcaatcggcc ctcaggggtc     180
cctgaccgat tctctggctc caggtctggc acctcagcct ccctggccat cactgggctc     240
caggctgagg atgaggctga ttattactgc agtcctatg acaccagcct gaatggttgg      300
gctttcggcg agggaccaa gttgaccgtc ctaggccagc ccaaggctgc ccctcggtc       360 actctgttcc caccctcctc tgaggagctt caagccaaca aggccacact ggtgtgtctc     420
gtaagtgact ctacccgggg agccgtgaca gtggcctgga aggcagatgg cagcccccgtc    480 aaggtgggag tggagaccac caaaccctcc aaacaaagca caacaagta tgcggccagc     540 agctacctga gcctgacgcc cgagcagtgg aagtcccaca gaagctacag ctgccgggtc    600
acgcatgaag ggagcaccgt ggagaagaca gtggcccctg cagaatgctc t             651
```

```
<210> SEQ ID NO 111
<211> LENGTH: 1371
<212> TYPE: DNA
<213> ORGANISM: Artificial Sequence
<220> FEATURE:
<223> OTHER INFORMATION: Synthetic

<400> SEQUENCE: 111
gaggtgcagc tggtggagtc tgggggaggc ttggtacagc cagggcggtc cctgagactc      60
agctgtacag cctctgggtt tagttttggt gatcatgcta tgagctgggt ccgccaggct     120
ccagggaagg ggctggagtg ggtaggtttc attagaaaga caacttatgg tgcgacaaca    180
cactacgccg cggctgtgag aggcagattc accatctcgc gagatgattc aaaagcact     240 gtctatctgc aaatgaacag cctgaaagca gaggacacag ccgtgtattt ctgtactaga    300
gtgcagcttg actatggccc gggataccag tactacggta tggacgtctg gggccaaggg    360
accacggtca ccgtctcctc agcctccacc aagggcccat cggtcttccc cctggcaccc    420
tcctccaaga gcacctctgg gggcacagca gccctgggct gcctggtcaa ggactacttc    480
cccgaaccgg tgacggtgtc gtggaactca ggcgccctga ccagcggcgt gcacaccttc    540
ccggctgtcc tacagtcctc aggactctac tccctcagca gcgtggtgac cgtgccctcc    600
agcagcttgg gcacccagac ctacatctgc aacgtgaatc acaagcccag caacaccaag    660
```

```
gtggacaaga aagttgagcc caaatcttgt gacaaaactc acacatgccc accgtgccca      720
gcacctgaac tcctgggggg accgtcagtc ttcctcttcc ccccaaaacc caaggacacc      780
ctcatgatct cccggacccc tgaggtcaca tgcgtggtgg tggacgtgag ccacgaagac      840
cctgaggtca agttcaactg gtacgtggac ggcgtggagg tgcataatgc caagacaaag      900
ccgcgggagg agcagtacaa cagcacgtac cgtgtggtca gcgtcctcac cgtcctgcac      960
caggactggc tgaatggcaa ggagtacaag tgcaaggtct ccaacaaagc cctcccagcc     1020
cccatcgaga aaccatctc caaagccaaa gggcagcccc gagaaccaca ggtgtacacc     1080
ctgcccccat cccgggatga gctgaccaag aaccaggtca gcctgacctg cctggtcaaa     1140
ggcttctatc ccagcgacat cgccgtggag tgggagagca atgggcagcc ggagaacaac     1200
tacaagacca cgcctcccgt gctggactcc gacggctcct tcttcctcta cagcaagctc     1260
accgtggaca agagcaggtg gcagcagggg aacgtcttct catgctccgt gatgcatgag     1320
gctctgcaca accactacac acagaagagc ctctccctgt ctccgggtaa a              1371

<210> SEQ ID NO 112
<211> LENGTH: 1371
<212> TYPE: DNA
<213> ORGANISM: Artificial Sequence
<220> FEATURE:
<223> OTHER INFORMATION: Synthetic

<400> SEQUENCE: 112
gaggtgcagc tggtggagtc tgggggaggc ttggtacagc cagggcggtc cctgagactc       60
agctgtacag cctctgggtt tagttttggt gatcatgcta tgagctgggt ccgccaggct      120
ccagggaagg ggctggagtg ggtaggtttc attagaaaga caacttatgg tgcgacaaca      180
cactacgccg cggctgtgag aggcagattc accatctcgc gagatgattc taaaagcact      240
gtctatctgc aaatgaacag cctgaaagca gaggacacag ccgtgtattt ctgtactaga      300
gtgcagcttg actatggccc gggataccag tactacggta tggacgtctg gggccaaggg      360
accacggtca ccgtctcctc agcctccacc aagggcccat cggtcttccc cctggcaccc      420
tcctccaaga gcacctctgg gggcacagca gccctgggct gcctggtcaa ggactacttc      480
cccgaaccgg tgacggtgtc gtggaactca ggcgccctga ccagcggcgt gcacaccttc      540
ccggctgtcc tacagtcctc aggactctac tccctcagca gcgtggtgac cgtgccctcc      600
agcagcttgg gcacccagac ctacatctgc aacgtgaatc acaagcccag caacaccaag      660
gtggacaaga agttgagcc caaatcttgt gacaaaactc acacatgccc accgtgccca      720
gcacctgaac tcctgggggg accgtcagtc ttcctcttcc ccccaaaacc caaggacacc      780
ctcatgatct cccggacccc tgaggtcaca tgcgtggtgg tggacgtgag ccacgaagac      840
cctgaggtca agttcaactg gtacgtggac ggcgtggagg tgcataatgc caagacaaag      900
ccgcgggagg agcagtacaa cagcacgtac cgtgtggtca gcgtcctcac cgtcctgcac      960
caggactggc tgaatggcaa ggagtacaag tgcaaggtct ccaacaaagc cctcccagcc     1020
cccatcgaga aaccatctc caaagccaaa gggcagcccc gagaaccaca ggtgtacacc     1080
ctgcccccat cccgggatga gctgaccaag aaccaggtca gcctgacctg cctggtcaaa     1140
ggcttctatc ccagcgacat cgccgtggag tgggagagca atgggcagcc ggagaacaac     1200
tacaagacca cgcctcccgt gctggactcc gacggctcct tcttcctcta cagcaagctc     1260
accgtggaca agagcaggtg gcagcagggg aacgtcttct catgctccgt gctgcatgag     1320
gctctgcact cccactacac acagaagagc ctctccctgt ctccgggtaa a              1371
```

<210> SEQ ID NO 113
<211> LENGTH: 112
<212> TYPE: PRT
<213> ORGANISM: Artificial Sequence
<220> FEATURE:
<223> OTHER INFORMATION: Synthetic

<400> SEQUENCE: 113

```
Gln Ser Val Leu Thr Gln Pro Pro Ser Val Ser Gly Ala Pro Gly Gln
1               5                   10                  15

Arg Val Thr Ile Ser Cys Thr Gly Met Asn Ser Asn Ile Gly Ala Gly
            20                  25                  30

Tyr Asp Val Tyr Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Arg Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Ser
                85                  90                  95

Leu Asn Gly Trp Ala Phe Gly Gly Gly Thr Lys Leu Thr Val Leu Gly
            100                 105                 110
```

<210> SEQ ID NO 114
<211> LENGTH: 127
<212> TYPE: PRT
<213> ORGANISM: Artificial Sequence
<220> FEATURE:
<223> OTHER INFORMATION: Synthetic

<400> SEQUENCE: 114

```
Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr Thr His Tyr Ala Ala
    50                  55                  60

Ala Val Arg Gly Arg Phe Thr Ile Ser Arg Asp Asp Ser Lys Ser Thr
65                  70                  75                  80

Val Tyr Leu Gln Met Asn Ser Leu Lys Thr Glu Asp Thr Ala Val Tyr
                85                  90                  95

Phe Cys Ala Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser
        115                 120                 125
```

<210> SEQ ID NO 115
<211> LENGTH: 336
<212> TYPE: DNA
<213> ORGANISM: Artificial Sequence
<220> FEATURE:
<223> OTHER INFORMATION: Synthetic

<400> SEQUENCE: 115

```
cagtctgtgc tgacgcagcc gccctcagtg tctggggccc cagggcagag ggtcaccatc    60
tcctgcactg ggatgaactc caacatcggg gcaggttatg atgtatactg gtaccaacaa   120
```

-continued

```
cttccaggaa ctgcccccaa actcctcatc tatggtaaca gcaatcggcc ctcagggtc       180 cctgaccgat tctctggctc caggtctggc acctcagcct ccctggccat cactgggctc     240
caggctgagg atgaggctga ttattactgc cagtcctatg acaccagcct gaatggttgg     300
gctttcggcg agggaccaa gttgaccgtc ctaggc                                336
```

<210> SEQ ID NO 116
<211> LENGTH: 381
<212> TYPE: DNA
<213> ORGANISM: Artificial Sequence
<220> FEATURE:
<223> OTHER INFORMATION: Synthetic

<400> SEQUENCE: 116

```
gaggtgcagc tggtggagtc tgggggaggc ttggtacagc cagggcggtc cctgagactc      60
agctgtacag cctctgggtt tagttttggt gatcatgcta tgagctgggt ccgccaggct     120
ccagggaagg ggctggagtg ggtaggtttc attagaaaga caacttatgg tgcgacaaca     180
cactacgccg cggctgtgag aggcagattc accatctcgc gagatgattc taaaagcact     240
gtctatctgc aaatgaacag cctgaaaacc gaggacacag ccgtgtattt ctgtgctaga     300
gtgcagcttg actatggccc gggataccag tactacggta tggacgtctg gggccaaggg     360
accacggtca ccgtctcctc a                                               381
```

<210> SEQ ID NO 117
<211> LENGTH: 217
<212> TYPE: PRT
<213> ORGANISM: Artificial Sequence
<220> FEATURE:
<223> OTHER INFORMATION: Synthetic

<400> SEQUENCE: 117

```
Gln Ser Val Leu Thr Gln Pro Pro Ser Val Ser Gly Ala Pro Gly Gln
1               5                   10                  15

Arg Val Thr Ile Ser Cys Thr Gly Met Asn Ser Asn Ile Gly Ala Gly
            20                  25                  30

Tyr Asp Val Tyr Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Arg Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Ser
                85                  90                  95

Leu Asn Gly Trp Ala Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Val Ser Asp Phe
    130                 135                 140

Tyr Pro Gly Ala Val Thr Val Ala Trp Lys Ala Asp Gly Ser Pro Val
145                 150                 155                 160

Lys Val Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190
```

```
His Arg Ser Tyr Ser Cys Arg Val Thr His Glu Gly Ser Thr Val Glu
        195                 200                 205

Lys Thr Val Ala Pro Ala Glu Cys Ser
    210                 215

<210> SEQ ID NO 118
<211> LENGTH: 457
<212> TYPE: PRT
<213> ORGANISM: Artificial Sequence
<220> FEATURE:
<223> OTHER INFORMATION: Synthetic

<400> SEQUENCE: 118

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr Thr His Tyr Ala Ala
    50                  55                  60

Ala Val Arg Gly Arg Phe Thr Ile Ser Arg Asp Asp Ser Lys Ser Thr
65                  70                  75                  80

Val Tyr Leu Gln Met Asn Ser Leu Lys Thr Glu Asp Thr Ala Val Tyr
                85                  90                  95

Phe Cys Ala Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335
```

```
Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 119
<211> LENGTH: 457
<212> TYPE: PRT
<213> ORGANISM: Artificial Sequence
<220> FEATURE:
<223> OTHER INFORMATION: Synthetic

<400> SEQUENCE: 119

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr Thr His Tyr Ala Ala
    50                  55                  60

Ala Val Arg Gly Arg Phe Thr Ile Ser Arg Asp Asp Ser Lys Ser Thr
65                  70                  75                  80

Val Tyr Leu Gln Met Asn Ser Leu Lys Thr Glu Asp Thr Ala Val Tyr
                85                  90                  95

Phe Cys Ala Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240
```

Ala Pro Glu Leu Leu Gly Gly Pro Ser Val Phe Leu Phe Pro Pro Lys
            245                 250                 255

Pro Lys Asp Thr Leu Met Ile Ser Arg Thr Pro Glu Val Thr Cys Val
        260                 265                 270

Val Val Asp Val Ser His Glu Asp Pro Glu Val Lys Phe Asn Trp Tyr
    275                 280                 285

Val Asp Gly Val Glu Val His Asn Ala Lys Thr Lys Pro Arg Glu Glu
290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Leu His Glu Ala Leu His Ser His Tyr Thr Gln
        435                 440                 445

Lys Ser Leu Ser Leu Ser Pro Gly Lys
    450                 455

<210> SEQ ID NO 120
<211> LENGTH: 651
<212> TYPE: DNA
<213> ORGANISM: Artificial Sequence
<220> FEATURE:
<223> OTHER INFORMATION: Synthetic

<400> SEQUENCE: 120
cagtctgtgc tgacgcagcc gccctcagtg tctggggccc cagggcagag ggtcaccatc     60
tcctgcactg ggatgaactc caacatcggg gcaggttatg atgtatactg gtaccaacaa    120
cttccaggaa ctgcccccaa actcctcatc tatggtaaca gcaatcggcc ctcaggggtc    180
cctgaccgat tctctggctc caggtctggc acctcagcct ccctggccat cactgggctc    240
caggctgagg atgaggctga ttattactgc cagtcctatg acaccagcct gaatggttgg    300
gctttcggcg agggaccaa gttgaccgtc ctaggccagc ccaaggctgc ccctcggtc     360 actctgttcc cacctcctc tgaggagctt caagccaaca ggccacact ggtgtgtctc     420 gtaagtgact tctacccggg agccgtgaca gtggcctgga aggcagatgg cagcccgtc     480 aaggtgggag tggagaccac caaaccctcc aaacaaagca acaacaagta tgcggccagc    540
agctacctga gcctgacgcc cgagcagtgg aagtcccaca gaagctacag ctgccgggtc    600
acgcatgaag ggagcaccgt ggagaagaca gtggccccctg cagaatgctc t            651

<210> SEQ ID NO 121
<211> LENGTH: 1371
<212> TYPE: DNA
<213> ORGANISM: Artificial Sequence

```
<220> FEATURE:
<223> OTHER INFORMATION: Synthetic

<400> SEQUENCE: 121
gaggtgcagc tggtggagtc tgggggaggc ttggtacagc cagggcggtc cctgagactc      60
agctgtacag cctctgggtt tagttttggt gatcatgcta tgagctgggt ccgccaggct     120
ccagggaagg ggctggagtg ggtaggtttc attagaaaga caacttatgg tgcgacaaca     180
cactacgccg cggctgtgag aggcagattc accatctcgc gagatgattc taaaagcact     240
gtctatctgc aaatgaacag cctgaaaacc gaggacacag ccgtgtattt ctgtgctaga     300
gtgcagcttg actatggccc gggataccag tactacggta tggacgtctg gggccaaggg     360
accacggtca ccgtctcctc agcctccacc aagggcccat cggtcttccc cctggcaccc     420
tcctccaaga gcacctctgg gggcacagca gccctgggct gcctggtcaa ggactacttc     480
cccgaaccgg tgacggtgtc gtggaactca ggcgccctga ccagcggcgt gcacaccttc     540
ccggctgtcc tacagtcctc aggactctac tccctcagca gcgtggtgac cgtgccctcc     600
agcagcttgg gcacccagac ctacatctgc aacgtgaatc acaagcccag caacaccaag     660
gtggacaaga agttgagccc aaatcttgt gacaaaactc acacatgccc accgtgccca     720
gcacctgaac tcctgggggg accgtcagtc ttcctcttcc ccccaaaacc caaggacacc     780
ctcatgatct cccggacccc tgaggtcaca tgcgtggtgg tggacgtgag ccacgaagac     840
cctgaggtca agttcaactg gtacgtggac ggcgtggagg tgcataatgc caagacaaag     900
ccgcgggagg agcagtacaa cagcacgtac cgtgtggtca gcgtcctcac cgtcctgcac     960
caggactggc tgaatggcaa ggagtacaag tgcaaggtct ccaacaaagc cctcccagcc    1020
cccatcgaga aaaccatctc caaagccaaa gggcagcccc gagaaccaca ggtgtacacc    1080
ctgcccccat cccgggatga gctgaccaag aaccaggtca gcctgacctg cctggtcaaa    1140
ggcttctatc ccagcgacat cgccgtggag tgggagagca atgggcagcc ggagaacaac    1200
tacaagacca cgcctcccgt gctggactcc gacggctcct tcttcctcta cagcaagctc    1260
accgtggaca gagcaggtg gcagcagggg aacgtcttct catgctccgt gatgcatgag    1320
gctctgcaca accactacac acagaagagc ctctccctgt ctccgggtaa a             1371

<210> SEQ ID NO 122
<211> LENGTH: 1371
<212> TYPE: DNA
<213> ORGANISM: Artificial Sequence
<220> FEATURE:
<223> OTHER INFORMATION: Synthetic

<400> SEQUENCE: 122
gaggtgcagc tggtggagtc tgggggaggc ttggtacagc cagggcggtc cctgagactc      60
agctgtacag cctctgggtt tagttttggt gatcatgcta tgagctgggt ccgccaggct     120
ccagggaagg ggctggagtg ggtaggtttc attagaaaga caacttatgg tgcgacaaca     180
cactacgccg cggctgtgag aggcagattc accatctcgc gagatgattc taaaagcact     240
gtctatctgc aaatgaacag cctgaaaacc gaggacacag ccgtgtattt ctgtgctaga     300
gtgcagcttg actatggccc gggataccag tactacggta tggacgtctg gggccaaggg     360
accacggtca ccgtctcctc agcctccacc aagggcccat cggtcttccc cctggcaccc     420
tcctccaaga gcacctctgg gggcacagca gccctgggct gcctggtcaa ggactacttc     480
cccgaaccgg tgacggtgtc gtggaactca ggcgccctga ccagcggcgt gcacaccttc     540
```

-continued

```
ccggctgtcc tacagtcctc aggactctac tccctcagca gcgtggtgac cgtgccctcc    600
agcagcttgg gcacccagac ctacatctgc aacgtgaatc acaagcccag caacaccaag    660
gtggacaaga aagttgagcc caaatcttgt gacaaaactc acacatgccc accgtgccca    720
gcacctgaac tcctgggggg accgtcagtc ttcctcttcc ccccaaaacc caaggacacc    780
ctcatgatct cccggacccc tgaggtcaca tgcgtggtgg tggacgtgag ccacgaagac    840
cctgaggtca agttcaactg gtacgtggac ggcgtggagg tgcataatgc caagacaaag    900
ccgcgggagg agcagtacaa cagcacgtac cgtgtggtca gcgtcctcac cgtcctgcac    960
caggactggc tgaatggcaa ggagtacaag tgcaaggtct ccaacaaagc cctcccagcc    1020
cccatcgaga aaaccatctc caaagccaaa gggcagcccc gagaaccaca ggtgtacacc    1080
ctgcccccat cccgggatga gctgaccaag aaccaggtca gcctgacctg cctggtcaaa    1140
ggcttctatc ccagcgacat cgccgtggag tgggagagca atgggcagcc ggagaacaac    1200
tacaagacca cgcctcccgt gctggactcc gacggctcct tcttcctcta cagcaagctc    1260
accgtggaca gagcaggtg gcagcagggg aacgtcttct catgctccgt gctgcatgag    1320
gctctgcact cccactacac acagaagagc ctctccctgt ctccgggtaa a             1371
```

```
<210> SEQ ID NO 123
<211> LENGTH: 112
<212> TYPE: PRT
<213> ORGANISM: Artificial Sequence
<220> FEATURE:
<223> OTHER INFORMATION: Synthetic

<400> SEQUENCE: 123

Gln Ser Val Leu Thr Gln Pro Pro Ser Val Ser Gly Ala Pro Gly Gln
1               5                   10                  15

Arg Val Thr Ile Ser Cys Thr Gly Met Asn Ser Asn Ile Gly Ala Gly
            20                  25                  30

Tyr Asp Val Tyr Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Arg Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Ser
                85                  90                  95

Leu Asn Gly Trp Ala Phe Gly Gly Gly Thr Lys Leu Thr Val Leu Gly
            100                 105                 110
```

```
<210> SEQ ID NO 124
<211> LENGTH: 127
<212> TYPE: PRT
<213> ORGANISM: Artificial Sequence
<220> FEATURE:
<223> OTHER INFORMATION: Synthetic

<400> SEQUENCE: 124

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr Thr His Tyr Ala Ala
```

```
            50                  55                  60
Ala Val Arg Gly Arg Phe Thr Ile Ser Arg Asp Asp Ser Lys Ser Ile
 65                  70                  75                  80

Val Tyr Leu Gln Met Asn Ser Leu Lys Ala Glu Asp Thr Ala Val Tyr
                 85                  90                  95

Phe Cys Ala Arg Val Gln Leu Asp Tyr Gly Pro Gly Tyr Gln Tyr Tyr
                100                 105                 110

Gly Met Asp Val Trp Gly Gln Gly Thr Thr Val Thr Val Ser Ser
            115                 120                 125

<210> SEQ ID NO 125
<211> LENGTH: 336
<212> TYPE: DNA
<213> ORGANISM: Artificial Sequence
<220> FEATURE:
<223> OTHER INFORMATION: Synthetic

<400> SEQUENCE: 125
cagtctgtgc tgacgcagcc gccctcagtg tctggggccc cagggcagag ggtcaccatc      60
tcctgcactg ggatgaactc caacatcggg gcaggttatg atgtatactg gtaccaacaa     120
cttccaggaa ctgccccaa actcctcatc tatggtaaca gcaatcggcc ctcaggggtc      180
cctgaccgat tctctggctc caggtctggc acctcagcct ccctggccat cactgggctc     240
caggctgagg atgaggctga ttattactgc agtcctatg acaccagcct gaatggttgg      300
gctttcggcg agggaccaa gttgaccgtc ctaggc                                 336

<210> SEQ ID NO 126
<211> LENGTH: 381
<212> TYPE: DNA
<213> ORGANISM: Artificial Sequence
<220> FEATURE:
<223> OTHER INFORMATION: Synthetic

<400> SEQUENCE: 126
gaggtgcagc tggtggagtc tggggaggc ttggtacagc cagggcggtc cctgagactc       60
agctgtacag cctctgggtt tagttttggt gatcatgcta tgagctgggt ccgccaggct     120
ccagggaagg ggctggagtg ggtaggttc attagaaaga caacttatgg tgcgacaaca      180
cactacgccg cggctgtgag aggcagattc accatctcgc gagatgattc taaaagcatt     240
gtctatctgc aaatgaacag cctgaaagca gaggacacag ccgtgtattt ctgtgctaga     300
gtgcagcttg actatggccc gggataccag tactacggta tggacgtctg gggccaaggg     360
accacggtca ccgtctcctc a                                               381

<210> SEQ ID NO 127
<211> LENGTH: 217
<212> TYPE: PRT
<213> ORGANISM: Artificial Sequence
<220> FEATURE:
<223> OTHER INFORMATION: Synthetic

<400> SEQUENCE: 127

Gln Ser Val Leu Thr Gln Pro Pro Ser Val Ser Gly Ala Pro Gly Gln
  1               5                  10                  15

Arg Val Thr Ile Ser Cys Thr Gly Met Asn Ser Asn Ile Gly Ala Gly
                 20                  25                  30

Tyr Asp Val Tyr Trp Tyr Gln Gln Leu Pro Gly Thr Ala Pro Lys Leu
             35                  40                  45
```

```
Leu Ile Tyr Gly Asn Ser Asn Arg Pro Ser Gly Val Pro Asp Arg Phe
 50                  55                  60

Ser Gly Ser Arg Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Thr Ser
                 85                  90                  95

Leu Asn Gly Trp Ala Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Val Ser Asp Phe
130                 135                 140

Tyr Pro Gly Ala Val Thr Val Ala Trp Lys Ala Asp Gly Ser Pro Val
145                 150                 155                 160

Lys Val Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Arg Val Thr His Glu Gly Ser Thr Val Glu
        195                 200                 205

Lys Thr Val Ala Pro Ala Glu Cys Ser
210                 215

<210> SEQ ID NO 128
<211> LENGTH: 457
<212> TYPE: PRT
<213> ORGANISM: Artificial Sequence
<220> FEATURE:
<223> OTHER INFORMATION: Synthetic

<400> SEQUENCE: 128

Glu Val Gln Leu Val Glu Ser Gly Gly Gly Leu Val Gln Pro Gly Arg
 1               5                  10                  15

Ser Leu Arg Leu Ser Cys Thr Ala Ser Gly Phe Ser Phe Gly Asp His
             20                  25                  30

Ala Met Ser Trp Val Arg Gln Ala Pro Gly Lys Gly Leu Glu Trp Val
         35                  40                  45

Gly Phe Ile Arg Lys Thr Thr Tyr Gly Ala Thr Thr His Tyr Ala Ala
 50                  55                  60

Ala Val Arg Gly Arg Phe Thr Ile Ser Arg Asp Asp Ser Lys Ser Ile
 65                  70                  75                  80

Val Tyr Leu Gln Met Asn Ser Leu Lys Ala Glu Asp Thr Ala Val Tyr
                 85                  90                  95

Phe Cys Ala Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190
```

Ser Ser Val Val Thr Val Pro Ser Ser Leu Gly Thr Gln Thr Tyr
            195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
            245                 250                 255

Pro Lys Asp Thr Leu Met Ile Ser Arg Thr Pro Glu Val Thr Cys Val
        260                 265                 270

Val Val Asp Val Ser His Glu Asp Pro Glu Val Lys Phe Asn Trp Tyr
    275                 280                 285

Val Asp Gly Val Glu Val His Asn Ala Lys Thr Lys Pro Arg Glu Glu
290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
            325                 330                 335

Ala Leu Pro Ala Pro Ile Glu Lys Thr Ile Ser Lys Ala Lys Gly Gln
        340                 345                 350

Pro Arg Glu Pro Gln Val Tyr Thr Leu Pro Pro Ser Arg Asp Glu Leu
    355                 360                 365

Thr Lys Asn Gln Val Ser Leu Thr Cys Leu Val Lys Gly Phe Tyr Pro
        370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
            405                 410                 415

Tyr Ser Lys Leu Thr Val Asp Lys Ser Arg Trp Gln Gln Gly Asn Val
        420                 425                 430

Phe Ser Cys Ser Val Met His Glu Ala Leu His Asn His Tyr Thr Gln
    435                 440                 445

Lys Ser Leu Ser Leu Ser Pro Gly Lys
    450                 455

<210> SEQ ID NO 129
<211> LENGTH: 457
<212> TYPE: PRT
<213> ORGANISM: Artificial Sequence
<220> FEATURE:
<223> OTHER INFORMATION: Synthetic

<400> SEQUENCE: 129

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr Thr His Tyr Ala Ala
    50                  55                  60

Ala Val Arg Gly Arg Phe Thr Ile Ser Arg Asp Asp Ser Lys Ser Ile
65                  70                  75                  80

Val Tyr Leu Gln Met Asn Ser Leu Lys Ala Glu Asp Thr Ala Val Tyr
            85                  90                  95

Phe Cys Ala Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Leu His Glu Ala Leu His Ser His Tyr Thr Gln
        435                 440                 445

Lys Ser Leu Ser Leu Ser Pro Gly Lys
    450                 455

<210> SEQ ID NO 130
<211> LENGTH: 651
<212> TYPE: DNA
<213> ORGANISM: Artificial Sequence
<220> FEATURE:
<223> OTHER INFORMATION: Synthetic

<400> SEQUENCE: 130

```
cagtctgtgc tgacgcagcc gccctcagtg tctggggccc cagggcagag ggtcaccatc      60
tcctgcactg ggatgaactc caacatcggg gcaggttatg atgtatactg gtaccaacaa     120
cttccaggaa ctgcccccaa actcctcatc tatggtaaca gcaatcggcc ctcagggctc     180
cctgaccgat tctctggctc caggtctggc acctcagcct ccctggccat cactgggctc     240
caggctgagg atgaggctga ttattactgc cagtcctatg acaccagcct gaatggttgg     300
gctttcggcg agggaccaag ttgaccgtc ctaggccagc ccaaggctgc ccctcggtc       360 actctgttcc caccctcctc tgaggagctt caagccaaca aggccacact ggtgtgtctc     420
gtaagtgact ctacccgggg agccgtgaca gtggcctgga aggcagatgg cagccccgtc     480
aaggtgggag tggagaccac caaaccctcc aaacaaagca caacaagta tgcggccagc      540 agctacctga gcctgacgcc cgagcagtgg aagtcccaca agctacag ctgccgggtc       600 acgcatgaag ggagcaccgt ggagaagaca gtggcccctg cagaatgctc t              651
```

<210> SEQ ID NO 131
<211> LENGTH: 1371
<212> TYPE: DNA
<213> ORGANISM: Artificial Sequence
<220> FEATURE:
<223> OTHER INFORMATION: Synthetic

<400> SEQUENCE: 131

```
gaggtgcagc tggtggagtc tgggggaggc ttggtacagc cagggcggtc cctgagactc      60
agctgtacag cctctgggtt tagttttggt gatcatgcta tgagctgggt ccgccaggct     120
ccagggaagg ggctggagtg ggtaggtttc attagaaaga caacttatgg tgcgacaaca     180
cactacgccg cggctgtgag aggcagattc accatctcgc gagatgattc aaaagcatt      240 gtctatctgc aaatgaacag cctgaaagca gaggacacag ccgtgtattt ctgtgctaga     300
gtgcagcttg actatggccc gggataccag tactacggta tggacgtctg gggccaaggg     360
accacggtca ccgtctcctc agcctccacc aagggcccat cggtcttccc cctggcaccc     420
tcctccaaga gcacctctgg gggcacagca gccctgggct gcctggtcaa ggactacttc     480
cccgaaccgg tgacggtgtc gtggaactca ggcgccctga ccagcggcgt gcacaccttc     540
ccggctgtcc tacagtcctc aggactctac tccctcagca gcgtggtgac cgtgccctcc     600
agcagcttgg gcacccagac ctacatctgc aacgtgaatc acaagcccag caacaccaag     660
gtggacaaga aagttgagcc caaatcttgt gacaaaactc acacatgccc accgtgccca     720
gcacctgaac tcctggggg accgtcagtc ttcctcttcc ccccaaaacc caaggacacc      780
ctcatgatct cccggacccc tgaggtcaca tgcgtggtgg tggacgtgag ccacgaagac     840
cctgaggtca agttcaactg gtacgtggac ggcgtggagg tgcataatgc caagacaaag     900
ccgcgggagg agcagtacaa cagcacgtac cgtgtggtca gcgtcctcac cgtcctgcac     960
caggactggc tgaatggcaa ggagtacaag tgcaaggtct ccaacaaagc cctcccagcc    1020
cccatcgaga aaaccatctc caaagccaaa gggcagcccc gagaaccaca ggtgtacacc    1080
ctgcccccat cccgggatga gctgaccaag aaccaggtca gcctgacctg cctggtcaaa    1140
ggcttctatc ccagcgacat cgccgtggag tgggagagca atgggcagcc ggagaacaac    1200
tacaagacca cgcctcccgt gctggactcc gacggctcct tcttcctcta cagcaagctc    1260
accgtggaca gagcaggtg gcagcagggg aacgtcttct catgctccgt gatgcatgag     1320
gctctgcaca accactacac acagaagagc ctctccctgt ctccgggtaa a              1371
```

<210> SEQ ID NO 132
<211> LENGTH: 1371
<212> TYPE: DNA
<213> ORGANISM: Artificial Sequence
<220> FEATURE:
<223> OTHER INFORMATION: Synthetic

<400> SEQUENCE: 132

```
gaggtgcagc tggtggagtc tgggggaggc ttggtacagc cagggcggtc cctgagactc      60
agctgtacag cctctgggtt tagttttggt gatcatgcta tgagctgggt ccgccaggct     120
ccagggaagg ggctggagtg ggtaggtttc attagaaaga caacttatgg tgcgacaaca     180
cactacgccg cggctgtgag aggcagattc accatctcgc gagatgattc taaaagcatt     240
gtctatctgc aaatgaacag cctgaaagca gaggacacag ccgtgtattt ctgtgctaga     300
gtgcagcttg actatggccc gggataccag tactacggta tggacgtctg gggccaaggg     360
accacggtca ccgtctcctc agcctccacc aagggcccat cggtcttccc cctggcaccc     420
tcctccaaga gcacctctgg gggcacagca gccctgggct gcctggtcaa ggactacttc     480
cccgaaccgg tgacggtgtc gtggaactca ggcgccctga ccagcggcgt gcacaccttc     540
ccggctgtcc tacagtcctc aggactctac tccctcagca gcgtggtgac cgtgccctcc     600
agcagcttgg gcacccagac ctacatctgc aacgtgaatc acaagcccag caacaccaag     660
gtggacaaga agttgagccc aaatcttgtg acaaaactca cacatgccca ccgtgccca      720
gcacctgaac tcctgggggg accgtcagtc ttcctcttcc cccccaaaacc caaggacacc     780
ctcatgatct cccggacccc tgaggtcaca tgcgtggtgg tggacgtgag ccacgaagac     840
cctgaggtca agttcaactg gtacgtggac ggcgtggagg tgcataatgc caagacaaag     900
ccgcgggagg agcagtacaa cagcacgtac cgtgtggtca gcgtcctcac cgtcctgcac     960
caggactggc tgaatggcaa ggagtacaag tgcaaggtct ccaacaaagc cctcccagcc    1020
cccatcgaga aaaccatctc caaagccaaa gggcagcccc gagaaccaca ggtgtacacc    1080
ctgcccccat cccgggatga gctgaccaag aaccaggtca gcctgacctg cctggtcaaa    1140
ggcttctatc ccagcgacat cgccgtggag tgggagagca atgggcagcc ggagaacaac    1200
tacaagacca cgcctcccgt gctggactcc gacggctcct tcttcctcta cagcaagctc    1260
accgtggaca agagcaggtg gcagcagggg aacgtcttct catgctccgt gctgcatgag    1320
gctctgcact cccactacac acagaagagc ctctccctgt ctccgggtaa a              1371
```

<210> SEQ ID NO 133
<211> LENGTH: 112
<212> TYPE: PRT
<213> ORGANISM: Artificial Sequence
<220> FEATURE:
<223> OTHER INFORMATION: Synthetic

<400> SEQUENCE: 133

```
Gln Ser Val Leu Thr Gln Pro Pro Ser Val Gly Ala Pro Gly Gln
1               5                   10                  15

Arg Val Thr Ile Ser Cys Thr Gly Met Asn Ser Asn Ile Gly Ala Gly
            20                  25                  30

Tyr Asp Val Tyr Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Arg Ser Gly Thr Ser Ala Ser Leu Ala Ile Thr Gly Leu
65                  70                  75                  80
```

Gln Ala Glu Asp Glu Ala Asp Tyr Tyr Cys Gln Ser Tyr Asp Thr Ser
            85                  90                  95

Leu Asn Gly Trp Ala Phe Gly Gly Gly Thr Lys Leu Thr Val Leu Gly
        100                 105                 110

<210> SEQ ID NO 134
<211> LENGTH: 127
<212> TYPE: PRT
<213> ORGANISM: Artificial Sequence
<220> FEATURE:
<223> OTHER INFORMATION: Synthetic

<400> SEQUENCE: 134

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr His Tyr Ala Ala
    50                  55                  60

Ala Val Arg Gly Arg Phe Thr Ile Ser Arg Asp Asp Ser Lys Ser Thr
65                  70                  75                  80

Val Tyr Leu Gln Met Asn Ser Leu Lys Ala Glu Asp Thr Ala Val Tyr
                85                  90                  95

Phe Cys Thr Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser
        115                 120                 125

<210> SEQ ID NO 135
<211> LENGTH: 336
<212> TYPE: DNA
<213> ORGANISM: Artificial Sequence
<220> FEATURE:
<223> OTHER INFORMATION: Synthetic

<400> SEQUENCE: 135
cagtctgtgc tgacgcagcc gccctcagtg tctggggccc cagggcagag ggtcaccatc     60
tcctgcactg ggatgaactc caacatcggg caggttatg atgtatactg gtaccaacaa    120
cttccaggaa ctgcccccaa actcctcatc tatggtaaca gcaatcggcc ctcaggggtc    180
cctgaccgat tctctggctc caggtctggc acctcagcct ccctggccat cactgggctc    240
caggctgagg atgaggctga ttattactgc cagtcctatg acaccagcct gaatggttgg    300
gctttcggcg agggaccaa gttgaccgtc ctaggc                               336

<210> SEQ ID NO 136
<211> LENGTH: 381
<212> TYPE: DNA
<213> ORGANISM: Artificial Sequence
<220> FEATURE:
<223> OTHER INFORMATION: Synthetic

<400> SEQUENCE: 136
gaggtgcagc tggtggagtc tgggggaggc ttggtacagc cagggcggtc cctgagactc     60
agctgtgcgg cctctgggtt tagttttggt gatcatgcta tgagctgggt ccgccaggct    120
ccagggaagg ggctggagtg ggtaggtttc attagaaaga caacttatgg tgcgacaaca    180

```
cactacgccg cggctgtgag aggcagattc accatctcgc gagatgattc taaaagcact    240
gtctatctgc aaatgaacag cctgaaagca gaggacacag ccgtgtattt ctgtactaga    300
gtgcagcttg actatggccc gggataccag tactacggta tggacgtctg gggccaaggg    360
accacggtca ccgtctcctc a                                              381
```

<210> SEQ ID NO 137
<211> LENGTH: 217
<212> TYPE: PRT
<213> ORGANISM: Artificial Sequence
<220> FEATURE:
<223> OTHER INFORMATION: Synthetic

<400> SEQUENCE: 137

```
Gln Ser Val Leu Thr Gln Pro Pro Ser Val Gly Ala Pro Gly Gln
1               5                   10                  15

Arg Val Thr Ile Ser Cys Thr Gly Met Asn Ser Asn Ile Gly Ala Gly
            20                  25                  30

Tyr Asp Val Tyr Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
50                  55                  60

Ser Gly Ser Arg Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Ser
                85                  90                  95

Leu Asn Gly Trp Ala Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Val Ser Asp Phe
130                 135                 140

Tyr Pro Gly Ala Val Thr Val Ala Trp Lys Ala Asp Gly Ser Pro Val
145                 150                 155                 160

Lys Val Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Arg Val Thr His Glu Gly Ser Thr Val Glu
        195                 200                 205

Lys Thr Val Ala Pro Ala Glu Cys Ser
    210                 215
```

<210> SEQ ID NO 138
<211> LENGTH: 457
<212> TYPE: PRT
<213> ORGANISM: Artificial Sequence
<220> FEATURE:
<223> OTHER INFORMATION: Synthetic

<400> SEQUENCE: 138

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ser Phe Gly Asp His
            20                  25                  30

Ala Met Ser Trp Val Arg Gln Ala Pro Gly Lys Gly Leu Glu Trp Val
        35                  40                  45
```

```
Gly Phe Ile Arg Lys Thr Thr Tyr Gly Ala Thr Thr His Tyr Ala Ala
 50                  55                  60

Ala Val Arg Gly Arg Phe Thr Ile Ser Arg Asp Asp Ser Lys Ser Thr
 65                  70                  75                  80

Val Tyr Leu Gln Met Asn Ser Leu Lys Ala Glu Asp Thr Ala Val Tyr
                 85                  90                  95

Phe Cys Thr Arg Val Gln Leu Asp Tyr Gly Pro Gly Tyr Gln Tyr Tyr
                100                 105                 110

Gly Met Asp Val Trp Gly Gln Gly Thr Thr Val Thr Val Ser Ser Ala
            115                 120                 125

Ser Thr Lys Gly Pro Ser Val Phe Pro Leu Ala Pro Ser Ser Lys Ser
        130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
450                 455
```

```
<210> SEQ ID NO 139
<211> LENGTH: 457
<212> TYPE: PRT
<213> ORGANISM: Artificial Sequence
<220> FEATURE:
<223> OTHER INFORMATION: Synthetic

<400> SEQUENCE: 139

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr Thr His Tyr Ala Ala
    50                  55                  60

Ala Val Arg Gly Arg Phe Thr Ile Ser Arg Asp Asp Ser Lys Ser Thr
65                  70                  75                  80

Val Tyr Leu Gln Met Asn Ser Leu Lys Ala Glu Asp Thr Ala Val Tyr
                85                  90                  95

Phe Cys Thr Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
```

```
            370                 375                 380
Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Leu His Glu Ala Leu His Ser His Tyr Thr Gln
            435                 440                 445

Lys Ser Leu Ser Leu Ser Pro Gly Lys
    450                 455
```

<210> SEQ ID NO 140
<211> LENGTH: 651
<212> TYPE: DNA
<213> ORGANISM: Artificial Sequence
<220> FEATURE:
<223> OTHER INFORMATION: Synthetic

<400> SEQUENCE: 140

```
cagtctgtgc tgacgcagcc gccctcagtg tctggggccc cagggcagag ggtcaccatc    60
tcctgcactg ggatgaactc caacatcggg gcaggttatg atgtatactg gtaccaacaa   120
cttccaggaa ctgcccccaa actcctcatc tatggtaaca gcaatcggcc ctcaggggtc   180
cctgaccgat tctctggctc caggtctggc acctcagcct ccctggccat cactgggctc   240
caggctgagg atgaggctga ttattactgc cagtcctatg acaccagcct gaatggttgg   300
gctttcggcg gagggaccaa gttgaccgtc ctaggccagc ccaaggctgc ccctcggtc    360
actctgttcc caccctcctc tgaggagctt caagccaaca ggccacact ggtgtgtctc    420
gtaagtgact tctacccggg agccgtgaca gtggcctgga aggcagatgg cagccccgtc   480
aaggtgggag tggagaccac caaaccctcc aaacaaagca acaacaagta tgcggccagc   540
agctacctga gcctgacgcc cgagcagtgg aagtcccaca gaagctacag ctgccgggtc   600
acgcatgaag ggagcaccgt ggagaagaca gtggcccctg cagaatgctc t             651
```

<210> SEQ ID NO 141
<211> LENGTH: 1371
<212> TYPE: DNA
<213> ORGANISM: Artificial Sequence
<220> FEATURE:
<223> OTHER INFORMATION: Synthetic

<400> SEQUENCE: 141

```
gaggtgcagc tggtggagtc tgggggaggc ttggtacagc cagggcggtc cctgagactc    60
agctgtgcgg cctctgggtt tagttttggt gatcatgcta tgagctgggt ccgccaggct   120
ccagggaagg gctggagtg gtaggtttca ttagaaagaa caacttatgg tgcgacaaca   180
cactacgccg cggctgtgag aggcagattc accatctcgc gagatgattc aaaagcact   240
gtctatctgc aaatgaacag cctgaaagca gaggacacag ccgtgtattt ctgtactaga   300
gtgcagcttg actatggccc gggataccag tactacggta tggacgtctg gggccaaggg   360
accacggtca ccgtctcctc agcctccacc aaggcccat cggtcttccc cctggcaccc   420
tcctccaaga gcacctctgg gggcacagca gccctgggct gcctggtcaa ggactacttc   480
cccgaaccgg tgacggtgtc gtggaactca ggcgccctga ccagcggcgt gcacaccttc   540
ccggctgtcc tacagtcctc aggactctac tccctcagca gcgtggtgac cgtgccctcc   600
```

| | |
|---|---|
| agcagcttgg gcacccagac ctacatctgc aacgtgaatc acaagcccag caacaccaag | 660 |
| gtggacaaga aagttgagcc caaatcttgt gacaaaactc acacatgccc accgtgccca | 720 |
| gcacctgaac tcctgggggg accgtcagtc ttcctcttcc ccccaaaacc caaggacacc | 780 |
| ctcatgatct cccggacccc tgaggtcaca tgcgtggtgg tggacgtgag ccacgaagac | 840 |
| cctgaggtca agttcaactg gtacgtggac ggcgtggagg tgcataatgc caagacaaag | 900 |
| ccgcgggagg agcagtacaa cagcacgtac cgtgtggtca gcgtcctcac cgtcctgcac | 960 |
| caggactggc tgaatggcaa ggagtacaag tgcaaggtct ccaacaaagc cctcccagcc | 1020 |
| cccatcgaga aaaccatctc caaagccaaa gggcagcccc gagaaccaca ggtgtacacc | 1080 |
| ctgcccccat cccgggatga gctgaccaag aaccaggtca gcctgacctg cctggtcaaa | 1140 |
| ggcttctatc ccagcgacat cgccgtggag tgggagagca atgggcagcc ggagaacaac | 1200 |
| tacaagacca cgcctcccgt gctggactcc gacggctcct tcttcctcta cagcaagctc | 1260 |
| accgtggaca agagcaggtg gcagcagggg aacgtcttct catgctccgt gatgcatgag | 1320 |
| gctctgcaca accactacac acagaagagc ctctccctgt ctccgggtaa a | 1371 |

<210> SEQ ID NO 142
<211> LENGTH: 1371
<212> TYPE: DNA
<213> ORGANISM: Artificial Sequence
<220> FEATURE:
<223> OTHER INFORMATION: Synthetic

<400> SEQUENCE: 142

| | |
|---|---|
| gaggtgcagc tggtggagtc tgggggaggc ttggtacagc cagggcggtc cctgagactc | 60 |
| agctgtgcgg cctctgggtt tagttttggt gatcatgcta tgagctgggt ccgccaggct | 120 |
| ccagggaagg ggctggagtg ggtaggtttc attagaaaga caacttatgg tgcgacaaca | 180 |
| cactacgccg cggctgtgag aggcagattc accatctcgc gagatgattc aaaaagcact | 240 |
| gtctatctgc aaatgaacag cctgaaagca gaggacacag ccgtgtattt ctgtactaga | 300 |
| gtgcagcttg actatggccc gggataccag tactacggta tggacgtctg gggccaaggg | 360 |
| accacggtca ccgtctcctc agcctccacc aagggcccat cggtcttccc cctggcaccc | 420 |
| tcctccaaga gcacctctgg gggcacagca gccctgggct gcctggtcaa ggactacttc | 480 |
| cccgaaccgg tgacggtgtc gtggaactca ggcgccctga ccagcggcgt gcacaccttc | 540 |
| ccggctgtcc tacagtcctc aggactctac tccctcagca gcgtggtgac cgtgccctcc | 600 |
| agcagcttgg gcacccagac ctacatctgc aacgtgaatc acaagcccag caacaccaag | 660 |
| gtggacaaga agttgagcc caaatcttgt gacaaaactc acacatgccc accgtgccca | 720 |
| gcacctgaac tcctgggggg accgtcagtc ttcctcttcc ccccaaaacc caaggacacc | 780 |
| ctcatgatct cccggacccc tgaggtcaca tgcgtggtgg tggacgtgag ccacgaagac | 840 |
| cctgaggtca agttcaactg gtacgtggac ggcgtggagg tgcataatgc caagacaaag | 900 |
| ccgcgggagg agcagtacaa cagcacgtac cgtgtggtca gcgtcctcac cgtcctgcac | 960 |
| caggactggc tgaatggcaa ggagtacaag tgcaaggtct ccaacaaagc cctcccagcc | 1020 |
| cccatcgaga aaaccatctc caaagccaaa gggcagcccc gagaaccaca ggtgtacacc | 1080 |
| ctgcccccat cccgggatga gctgaccaag aaccaggtca gcctgacctg cctggtcaaa | 1140 |
| ggcttctatc ccagcgacat cgccgtggag tgggagagca atgggcagcc ggagaacaac | 1200 |
| tacaagacca cgcctcccgt gctggactcc gacggctcct tcttcctcta cagcaagctc | 1260 |
| accgtggaca agagcaggtg gcagcagggg aacgtcttct catgctccgt gctgcatgag | 1320 | gctctgcact cccactacac acagaagagc ctctccctgt ctccgggtaa a          1371

<210> SEQ ID NO 143
<211> LENGTH: 112
<212> TYPE: PRT
<213> ORGANISM: Artificial Sequence
<220> FEATURE:
<223> OTHER INFORMATION: Synthetic

<400> SEQUENCE: 143

```
Gln Ser Val Leu Thr Gln Pro Pro Ser Val Ser Gly Ala Pro Gly Gln
1               5                   10                  15

Arg Val Thr Ile Ser Cys Thr Gly Met Asn Ser Asn Ile Gly Ala Gly
            20                  25                  30

Tyr Asp Val Tyr Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Arg Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Ser
                85                  90                  95

Leu Asn Gly Trp Ala Phe Gly Gly Gly Thr Lys Leu Thr Val Leu Gly
            100                 105                 110
```

<210> SEQ ID NO 144
<211> LENGTH: 127
<212> TYPE: PRT
<213> ORGANISM: Artificial Sequence
<220> FEATURE:
<223> OTHER INFORMATION: Synthetic

<400> SEQUENCE: 144

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr Thr His Tyr Ala Ala
    50                  55                  60

Ala Val Arg Gly Arg Phe Thr Ile Ser Arg Asp Asp Ser Lys Ser Thr
65                  70                  75                  80

Val Tyr Leu Gln Met Asn Ser Leu Lys Thr Glu Asp Thr Ala Val Tyr
                85                  90                  95

Phe Cys Ala Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser
        115                 120                 125
```

<210> SEQ ID NO 145
<211> LENGTH: 336
<212> TYPE: DNA
<213> ORGANISM: Artificial Sequence
<220> FEATURE:
<223> OTHER INFORMATION: Synthetic

<400> SEQUENCE: 145
cagtctgtgc tgacgcagcc gccctcagtg tctggggccc cagggcagag ggtcaccatc          60

```
tcctgcactg ggatgaactc caacatcggg gcaggttatg atgtatactg gtaccaacaa    120
cttccaggaa ctgcccccaa actcctcatc tatggtaaca gcaatcggcc ctcagggttc    180
cctgaccgat tctctggctc caggtctggc acctcagcct ccctggccat cactgggctc    240
caggctgagg atgaggctga ttattactgc cagtcctatg acaccagcct gaatggttgg    300
gctttcggcg gagggaccaa gttgaccgtc ctaggc                              336
```

<210> SEQ ID NO 146
<211> LENGTH: 381
<212> TYPE: DNA
<213> ORGANISM: Artificial Sequence
<220> FEATURE:
<223> OTHER INFORMATION: Synthetic

<400> SEQUENCE: 146

```
gaggtgcagc tggtggagtc tgggggaggc ttggtacagc cagggcggtc cctgagactc     60
agctgtgcgg cctctgggtt tagttttggt gatcatgcta tgagctgggt ccgccaggct    120
ccagggaagg ggctggagtg ggtaggtttc attagaaaga caacttatgg tgcgacaaca    180
cactacgccg cggctgtgag aggcagattc accatctcgc gagatgattc aaaaagcact    240
gtctatctgc aaatgaacag cctgaaaacc gaggacacag ccgtgtattt ctgtgctaga    300
gtgcagcttg actatggccc gggataccag tactacggta tggacgtctg ggggccaaggg    360 accacggtca ccgtctcctc a                                              381
```

<210> SEQ ID NO 147
<211> LENGTH: 217
<212> TYPE: PRT
<213> ORGANISM: Artificial Sequence
<220> FEATURE:
<223> OTHER INFORMATION: Synthetic

<400> SEQUENCE: 147

```
Gln Ser Val Leu Thr Gln Pro Pro Ser Val Ser Gly Ala Pro Gly Gln
1               5                   10                  15

Arg Val Thr Ile Ser Cys Thr Gly Met Asn Ser Asn Ile Gly Ala Gly
            20                  25                  30

Tyr Asp Val Tyr Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Arg Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Ser
                85                  90                  95

Leu Asn Gly Trp Ala Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Val Ser Asp Phe
    130                 135                 140

Tyr Pro Gly Ala Val Thr Val Ala Trp Lys Ala Asp Gly Ser Pro Val
145                 150                 155                 160

Lys Val Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
```

```
                    180                 185                 190
His Arg Ser Tyr Ser Cys Arg Val Thr His Glu Gly Ser Thr Val Glu
            195                 200                 205

Lys Thr Val Ala Pro Ala Glu Cys Ser
        210                 215

<210> SEQ ID NO 148
<211> LENGTH: 457
<212> TYPE: PRT
<213> ORGANISM: Artificial Sequence
<220> FEATURE:
<223> OTHER INFORMATION: Synthetic

<400> SEQUENCE: 148

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr Thr His Tyr Ala Ala
    50                  55                  60

Ala Val Arg Gly Arg Phe Thr Ile Ser Arg Asp Asp Ser Lys Ser Thr
65                  70                  75                  80

Val Tyr Leu Gln Met Asn Ser Leu Lys Thr Glu Asp Thr Ala Val Tyr
                85                  90                  95

Phe Cys Ala Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
```

```
                      325                 330                 335
Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
            355                 360                 365

Thr Lys Asn Gln Val Ser Leu Thr Cys Leu Val Lys Gly Phe Tyr Pro
        370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
            405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
            435                 440                 445

Lys Ser Leu Ser Leu Ser Pro Gly Lys
        450                 455

<210> SEQ ID NO 149
<211> LENGTH: 457
<212> TYPE: PRT
<213> ORGANISM: Artificial Sequence
<220> FEATURE:
<223> OTHER INFORMATION: Synthetic

<400> SEQUENCE: 149

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr His Tyr Ala Ala
    50                  55                  60

Ala Val Arg Gly Arg Phe Thr Ile Ser Arg Asp Asp Ser Lys Ser Thr
65                  70                  75                  80

Val Tyr Leu Gln Met Asn Ser Leu Lys Thr Glu Asp Thr Ala Val Tyr
                85                  90                  95

Phe Cys Ala Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
            165                 170                 175

Val His Thr Phe Pro Ala Val Leu Gln Ser Ser Gly Leu Tyr Ser Leu
        180                 185                 190

Ser Ser Val Val Thr Val Pro Ser Ser Ser Leu Gly Thr Gln Thr Tyr
            195                 200                 205

Ile Cys Asn Val Asn His Lys Pro Ser Asn Thr Lys Val Asp Lys Lys
        210                 215                 220

Val Glu Pro Lys Ser Cys Asp Lys Thr His Thr Cys Pro Pro Cys Pro
```

```
            225                 230                 235                 240
Ala Pro Glu Leu Leu Gly Gly Pro Ser Val Phe Leu Phe Pro Pro Lys
                    245                 250                 255

Pro Lys Asp Thr Leu Met Ile Ser Arg Thr Pro Glu Val Thr Cys Val
                260                 265                 270

Val Val Asp Val Ser His Glu Asp Pro Glu Val Lys Phe Asn Trp Tyr
            275                 280                 285

Val Asp Gly Val Glu Val His Asn Ala Lys Thr Lys Pro Arg Glu Glu
        290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Leu His Glu Ala Leu His Ser His Tyr Thr Gln
        435                 440                 445

Lys Ser Leu Ser Leu Ser Pro Gly Lys
    450                 455
```

<210> SEQ ID NO 150
<211> LENGTH: 651
<212> TYPE: DNA
<213> ORGANISM: Artificial Sequence
<220> FEATURE:
<223> OTHER INFORMATION: Synthetic

<400> SEQUENCE: 150

```
cagtctgtgc tgacgcagcc gccctcagtg tctggggccc cagggcagag ggtcaccatc      60
tcctgcactg ggatgaactc caacatcggg gcaggttatg atgtatactg gtaccaacaa     120
cttccaggaa ctgcccccaa actcctcatc tatggtaaca gcaatcggcc ctcaggggtc     180
cctgaccgat tctctggctc caggtctggc acctcagcct ccctggccat cactgggctc     240
caggctgagg atgaggctga ttattactgc cagtcctatg acaccagcct gaatggttgg     300
gctttcggcg gagggaccaa gttgaccgtc ctaggccagc ccaaggctgc cccctcggtc     360
actctgttcc caccctcctc tgaggagctt caagccaaca ggccacact ggtgtgtctc      420 gtaagtgact tctacccggg agccgtgaca gtggcctgga aggcagatgg cagccccgtc     480
aaggtgggag tggagaccac caaaccctcc aaacaaagca acaacaagta tgcggccagc     540
agctacctga gcctgacgcc cgagcagtgg aagtcccaca gaagctacag ctgccgggtc     600
acgcatgaag ggagcaccgt ggagaagaca gtggcccctg cagaatgctc t              651
```

<210> SEQ ID NO 151
<211> LENGTH: 1371

<212> TYPE: DNA
<213> ORGANISM: Artificial Sequence
<220> FEATURE:
<223> OTHER INFORMATION: Synthetic

<400> SEQUENCE: 151

| | | | | | |
|---|---|---|---|---|---|
| gaggtgcagc | tggtggagtc | tgggggaggc | ttggtacagc | cagggcggtc | cctgagactc | 60 |
| agctgtgcgg | cctctgggtt | tagttttggt | gatcatgcta | tgagctgggt | ccgccaggct | 120 |
| ccagggaagg | ggctggagtg | ggtaggtttc | attagaaaga | caacttatgg | tgcgacaaca | 180 |
| cactacgccg | cggctgtgag | aggcagattc | accatctcgc | gagatgattc | taaaagcact | 240 |
| gtctatctgc | aaatgaacag | cctgaaaacc | gaggacacag | ccgtgtattt | ctgtgctaga | 300 |
| gtgcagcttg | actatggccc | gggataccag | tactacggta | tggacgtctg | gggccaaggg | 360 |
| accacggtca | ccgtctcctc | agcctccacc | aagggcccat | cggtcttccc | cctggcaccc | 420 |
| tcctccaaga | gcacctctgg | gggcacagca | gccctgggct | gcctggtcaa | ggactacttc | 480 |
| cccgaaccgg | tgacggtgtc | gtggaactca | ggcgccctga | ccagcggcgt | gcacaccttc | 540 |
| ccggctgtcc | tacagtcctc | aggactctac | tccctcagca | gcgtggtgac | cgtgccctcc | 600 |
| agcagcttgg | gcacccagac | ctacatctgc | aacgtgaatc | acaagcccag | caacaccaag | 660 |
| gtggacaaga | aagttgagcc | caaatcttgt | gacaaaactc | acacatgccc | accgtgccca | 720 |
| gcacctgaac | tcctgggggg | accgtcagtc | ttcctcttcc | ccccaaaacc | caaggacacc | 780 |
| ctcatgatct | cccggacccc | tgaggtcaca | tgcgtggtgg | tggacgtgag | ccacgaagac | 840 |
| cctgaggtca | agttcaactg | gtacgtggac | ggcgtggagg | tgcataatgc | caagacaaag | 900 |
| ccgcgggagg | agcagtacaa | cagcacgtac | cgtgtggtca | gcgtcctcac | cgtcctgcac | 960 |
| caggactggc | tgaatggcaa | ggagtacaag | tgcaaggtct | ccaacaaagc | cctcccagcc | 1020 |
| cccatcgaga | aaaccatctc | caaagccaaa | gggcagcccc | gagaaccaca | ggtgtacacc | 1080 |
| ctgcccccat | cccgggatga | gctgaccaag | aaccaggtca | gcctgacctg | cctggtcaaa | 1140 |
| ggcttctatc | ccagcgacat | cgccgtggag | tgggagagca | atgggcagcc | ggagaacaac | 1200 |
| tacaagacca | cgcctcccgt | gctggactcc | gacggctcct | tcttcctcta | cagcaagctc | 1260 |
| accgtggaca | agagcaggtg | gcagcagggg | aacgtcttct | catgctccgt | gatgcatgag | 1320 |
| gctctgcaca | accactacac | acagaagagc | ctctccctgt | ctccgggtaa | a | 1371 |

<210> SEQ ID NO 152
<211> LENGTH: 1371
<212> TYPE: DNA
<213> ORGANISM: Artificial Sequence
<220> FEATURE:
<223> OTHER INFORMATION: Synthetic

<400> SEQUENCE: 152

| | | | | | |
|---|---|---|---|---|---|
| gaggtgcagc | tggtggagtc | tgggggaggc | ttggtacagc | cagggcggtc | cctgagactc | 60 |
| agctgtgcgg | cctctgggtt | tagttttggt | gatcatgcta | tgagctgggt | ccgccaggct | 120 |
| ccagggaagg | ggctggagtg | ggtaggtttc | attagaaaga | caacttatgg | tgcgacaaca | 180 |
| cactacgccg | cggctgtgag | aggcagattc | accatctcgc | gagatgattc | taaaagcact | 240 |
| gtctatctgc | aaatgaacag | cctgaaaacc | gaggacacag | ccgtgtattt | ctgtgctaga | 300 |
| gtgcagcttg | actatggccc | gggataccag | tactacggta | tggacgtctg | gggccaaggg | 360 |
| accacggtca | ccgtctcctc | agcctccacc | aagggcccat | cggtcttccc | cctggcaccc | 420 |
| tcctccaaga | gcacctctgg | gggcacagca | gccctgggct | gcctggtcaa | ggactacttc | 480 |

```
cccgaaccgg tgacggtgtc gtggaactca ggcgccctga ccagcggcgt gcacaccttc    540
ccggctgtcc tacagtcctc aggactctac tccctcagca gcgtggtgac cgtgccctcc    600
agcagcttgg gcacccagac ctacatctgc aacgtgaatc acaagcccag caacaccaag    660
gtggacaaga aagttgagcc caaatcttgt gacaaaactc acacatgccc accgtgccca    720
gcacctgaac tcctgggggg accgtcagtc ttcctcttcc ccccaaaacc caaggacacc    780
ctcatgatct cccggacccc tgaggtcaca tgcgtggtgg tggacgtgag ccacgaagac    840
cctgaggtca agttcaactg gtacgtggac ggcgtggagg tgcataatgc caagacaaag    900
ccgcgggagg agcagtacaa cagcacgtac cgtgtggtca gcgtcctcac cgtcctgcac    960
caggactggc tgaatggcaa ggagtacaag tgcaaggtct ccaacaaagc cctcccagcc   1020
cccatcgaga aaaccatctc caaagccaaa gggcagcccc gagaaccaca ggtgtacacc   1080
ctgcccccat cccgggatga gctgaccaag aaccaggtca gcctgacctg cctggtcaaa   1140
ggcttctatc ccagcgacat cgccgtggag tgggagagca atgggcagcc ggagaacaac   1200
tacaagacca cgcctcccgt gctggactcc gacggctcct tcttcctcta cagcaagctc   1260
accgtggaca agagcaggtg gcagcagggg aacgtcttct catgctccgt gctgcatgag   1320
gctctgcact cccactacac acagaagagc ctctccctgt ctccgggtaa a            1371
```

<210> SEQ ID NO 153
<211> LENGTH: 112
<212> TYPE: PRT
<213> ORGANISM: Artificial Sequence
<220> FEATURE:
<223> OTHER INFORMATION: Synthetic

<400> SEQUENCE: 153

Gln Ser Val Leu Thr Gln Pro Pro Ser Val Gly Ala Pro Gly Gln
1               5                   10                  15

Arg Val Thr Ile Ser Cys Thr Gly Met Asn Ser Asn Ile Gly Ala Gly
            20                  25                  30

Tyr Asp Val Tyr Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Arg Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Ser
                85                  90                  95

Leu Asn Gly Trp Ala Phe Gly Gly Gly Thr Lys Leu Thr Val Leu Gly
            100                 105                 110

<210> SEQ ID NO 154
<211> LENGTH: 127
<212> TYPE: PRT
<213> ORGANISM: Artificial Sequence
<220> FEATURE:
<223> OTHER INFORMATION: Synthetic

<400> SEQUENCE: 154

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr Thr His Tyr Ala Ala
    50                  55                  60

Ala Val Arg Gly Arg Phe Thr Ile Ser Arg Asp Asp Ser Lys Ser Ile
65                  70                  75                  80

Val Tyr Leu Gln Met Asn Ser Leu Lys Ala Glu Asp Thr Ala Val Tyr
                85                  90                  95

Phe Cys Ala Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser
        115                 120                 125

<210> SEQ ID NO 155
<211> LENGTH: 336
<212> TYPE: DNA
<213> ORGANISM: Artificial Sequence
<220> FEATURE:
<223> OTHER INFORMATION: Synthetic

<400> SEQUENCE: 155
cagtctgtgc tgacgcagcc gccctcagtg tctggggccc cagggcagag ggtcaccatc      60
tcctgcactg ggatgaactc caacatcggg gcaggttatg atgtatactg gtaccaacaa     120
cttccaggaa ctgcccccaa actcctcatc tatggtaaca gcaatcggcc ctcaggggtc     180
cctgaccgat tctctggctc caggtctggc acctcagcct ccctggccat cactgggctc     240
caggctgagg atgaggctga ttattactgc cagtcctatg acaccagcct gaatggttgg     300
gctttcggcg agggaccaa gttgaccgtc ctaggc                                336

<210> SEQ ID NO 156
<211> LENGTH: 381
<212> TYPE: DNA
<213> ORGANISM: Artificial Sequence
<220> FEATURE:
<223> OTHER INFORMATION: Synthetic

<400> SEQUENCE: 156
gaggtgcagc tggtggagtc tgggggaggc ttggtacagc cagggcggtc cctgagactc      60
agctgtgcgg cctctgggtt tagttttggt gatcatgcta tgagctgggt ccgccaggct     120
ccagggaagg ggctggagtg ggtaggtttc attagaaaga caacttatgg tgcgacaaca     180
cactacgccg cggctgtgag aggcagattc accatctcgc gagatgattc aaaagcatt      240 gtctatctgc aaatgaacag cctgaaagca gaggacacag ccgtgtattt ctgtgctaga     300
gtgcagcttg actatggccc gggataccag tactacggta tggacgtctg gggccaaggg     360
accacggtca ccgtctcctc a                                                381

<210> SEQ ID NO 157
<211> LENGTH: 217
<212> TYPE: PRT
<213> ORGANISM: Artificial Sequence
<220> FEATURE:
<223> OTHER INFORMATION: Synthetic

<400> SEQUENCE: 157

Gln Ser Val Leu Thr Gln Pro Pro Ser Val Ser Gly Ala Pro Gly Gln
1               5                   10                  15

Arg Val Thr Ile Ser Cys Thr Gly Met Asn Ser Asn Ile Gly Ala Gly
            20                  25                  30

Tyr Asp Val Tyr Trp Tyr Gln Gln Leu Pro Gly Thr Ala Pro Lys Leu

```
            35                  40                  45
Leu Ile Tyr Gly Asn Ser Asn Arg Pro Ser Gly Val Pro Asp Arg Phe
    50                  55                  60

Ser Gly Ser Arg Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Ser
                85                  90                  95

Leu Asn Gly Trp Ala Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Val Ser Asp Phe
    130                 135                 140

Tyr Pro Gly Ala Val Thr Val Ala Trp Lys Ala Asp Gly Ser Pro Val
145                 150                 155                 160

Lys Val Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Arg Val Thr His Glu Gly Ser Thr Val Glu
        195                 200                 205

Lys Thr Val Ala Pro Ala Glu Cys Ser
    210                 215

<210> SEQ ID NO 158
<211> LENGTH: 457
<212> TYPE: PRT
<213> ORGANISM: Artificial Sequence
<220> FEATURE:
<223> OTHER INFORMATION: Synthetic

<400> SEQUENCE: 158

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr Thr His Tyr Ala Ala
    50                  55                  60

Ala Val Arg Gly Arg Phe Thr Ile Ser Arg Asp Asp Ser Lys Ser Ile
65                  70                  75                  80

Val Tyr Leu Gln Met Asn Ser Leu Lys Ala Glu Asp Thr Ala Val Tyr
                85                  90                  95

Phe Cys Ala Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
```

```
                180                 185                 190
Ser Ser Val Val Thr Val Pro Ser Ser Leu Gly Thr Gln Thr Tyr
            195                 200                 205
Ile Cys Asn Val Asn His Lys Pro Ser Asn Thr Lys Val Asp Lys Lys
        210                 215                 220
Val Glu Pro Lys Ser Cys Asp Lys Thr His Thr Cys Pro Pro Cys Pro
225                 230                 235                 240
Ala Pro Glu Leu Leu Gly Gly Pro Ser Val Phe Leu Phe Pro Pro Lys
            245                 250                 255
Pro Lys Asp Thr Leu Met Ile Ser Arg Thr Pro Glu Val Thr Cys Val
            260                 265                 270
Val Val Asp Val Ser His Glu Asp Pro Glu Val Lys Phe Asn Trp Tyr
        275                 280                 285
Val Asp Gly Val Glu Val His Asn Ala Lys Thr Lys Pro Arg Glu Glu
        290                 295                 300
Gln Tyr Asn Ser Thr Tyr Arg Val Val Ser Val Leu Thr Val Leu His
305                 310                 315                 320
Gln Asp Trp Leu Asn Gly Lys Glu Tyr Lys Cys Lys Val Ser Asn Lys
            325                 330                 335
Ala Leu Pro Ala Pro Ile Glu Lys Thr Ile Ser Lys Ala Lys Gly Gln
            340                 345                 350
Pro Arg Glu Pro Gln Val Tyr Thr Leu Pro Pro Ser Arg Asp Glu Leu
            355                 360                 365
Thr Lys Asn Gln Val Ser Leu Thr Cys Leu Val Lys Gly Phe Tyr Pro
        370                 375                 380
Ser Asp Ile Ala Val Glu Trp Glu Ser Asn Gly Gln Pro Glu Asn Asn
385                 390                 395                 400
Tyr Lys Thr Thr Pro Pro Val Leu Asp Ser Asp Gly Ser Phe Phe Leu
            405                 410                 415
Tyr Ser Lys Leu Thr Val Asp Lys Ser Arg Trp Gln Gln Gly Asn Val
            420                 425                 430
Phe Ser Cys Ser Val Met His Glu Ala Leu His Asn His Tyr Thr Gln
        435                 440                 445
Lys Ser Leu Ser Leu Ser Pro Gly Lys
        450                 455

<210> SEQ ID NO 159
<211> LENGTH: 457
<212> TYPE: PRT
<213> ORGANISM: Artificial Sequence
<220> FEATURE:
<223> OTHER INFORMATION: Synthetic

<400> SEQUENCE: 159

Glu Val Gln Leu Val Glu Ser Gly Gly Gly Leu Val Gln Pro Gly Arg
1               5                   10                  15
Ser Leu Arg Leu Ser Cys Ala Ala Ser Gly Phe Ser Phe Gly Asp His
            20                  25                  30
Ala Met Ser Trp Val Arg Gln Ala Pro Gly Lys Gly Leu Glu Trp Val
        35                  40                  45
Gly Phe Ile Arg Lys Thr Thr Tyr Gly Ala Thr His Tyr Ala Ala
    50                  55                  60
Ala Val Arg Gly Arg Phe Thr Ile Ser Arg Asp Asp Ser Lys Ser Ile
65                  70                  75                  80
Val Tyr Leu Gln Met Asn Ser Leu Lys Ala Glu Asp Thr Ala Val Tyr
```

85                  90                  95
Phe Cys Ala Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser Ala
            115                 120                 125

Ser Thr Lys Gly Pro Ser Val Phe Pro Leu Ala Pro Ser Ser Lys Ser
            130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
            195                 200                 205

Ile Cys Asn Val Asn His Lys Pro Ser Asn Thr Lys Val Asp Lys Lys
            210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
            275                 280                 285

Val Asp Gly Val Glu Val His Asn Ala Lys Thr Lys Pro Arg Glu Glu
            290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
            355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
            405                 410                 415

Tyr Ser Lys Leu Thr Val Asp Lys Ser Arg Trp Gln Gln Gly Asn Val
            420                 425                 430

Phe Ser Cys Ser Val Leu His Glu Ala Leu His Ser His Tyr Thr Gln
            435                 440                 445

Lys Ser Leu Ser Leu Ser Pro Gly Lys
450                 455

<210> SEQ ID NO 160
<211> LENGTH: 651
<212> TYPE: DNA
<213> ORGANISM: Artificial Sequence
<220> FEATURE:
<223> OTHER INFORMATION: Synthetic

<400> SEQUENCE: 160

| | | | | | |
|---|---|---|---|---|---|
| cagtctgtgc | tgacgcagcc | gccctcagtg | tctggggccc | cagggcagag | ggtcaccatc | 60 |
| tcctgcactg | ggatgaactc | caacatcggg | gcaggttatg | atgtatactg | gtaccaacaa | 120 |
| cttccaggaa | ctgccccaa | actcctcatc | tatggtaaca | gcaatcggcc | ctcagggtc | 180 |
| cctgaccgat | tctctggctc | caggtctggc | acctcagcct | ccctggccat | cactgggctc | 240 |
| caggctgagg | atgaggctga | ttattactgc | cagtcctatg | acaccagcct | gaatggttgg | 300 |
| gctttcggcg | agggaccaa | gttgaccgtc | ctaggccagc | ccaaggctgc | ccctcggtc | 360 |
| actctgttcc | caccctcctc | tgaggagctt | caagccaaca | aggccacact | ggtgtgtctc | 420 |
| gtaagtgact | tctacccggg | agccgtgaca | gtggcctgga | aggcagatgg | cagcccgtc | 480 |
| aaggtgggag | tggagaccac | caaaccctcc | aaacaaagca | caacaagta | tgcggccagc | 540 |
| agctacctga | gcctgacgcc | cgagcagtgg | aagtcccaca | gaagctacag | ctgccgggtc | 600 |
| acgcatgaag | ggagcaccgt | ggagaagaca | gtggcccctg | cagaatgctc | t | 651 |

<210> SEQ ID NO 161
<211> LENGTH: 1371
<212> TYPE: DNA
<213> ORGANISM: Artificial Sequence
<220> FEATURE:
<223> OTHER INFORMATION: Synthetic

<400> SEQUENCE: 161

| | | | | | |
|---|---|---|---|---|---|
| gaggtgcagc | tggtggagtc | tgggggaggc | ttggtacagc | cagggcggtc | cctgagactc | 60 |
| agctgtgcgg | cctctgggtt | tagttttggt | gatcatgcta | tgagctgggt | ccgccaggct | 120 |
| ccagggaagg | ggctggagtg | ggtaggtttc | attagaaaga | caacttatgg | tgcgacaaca | 180 |
| cactacgccg | cggctgtgag | aggcagattc | accatctcgc | gagatgattc | taaaagcatt | 240 |
| gtctatctgc | aaatgaacag | cctgaaagca | gaggacacag | ccgtgtattt | ctgtgctaga | 300 |
| gtgcagcttg | actatggccc | gggataccag | tactacggta | tggacgtctg | ggggccaaggg | 360 |
| accacggtca | ccgtctcctc | agcctccacc | aagggcccat | cggtcttccc | cctggcaccc | 420 |
| tcctccaaga | gcacctctgg | gggcacagca | gccctgggct | gcctggtcaa | ggactacttc | 480 |
| cccgaaccgg | tgacggtgtc | gtggaactca | ggcgccctga | ccagcggcgt | gcacaccttc | 540 |
| ccggctgtcc | tacagtcctc | aggactctac | tccctcagca | gcgtggtgac | cgtgccctcc | 600 |
| agcagcttgg | gcacccagac | ctacatctgc | aacgtgaatc | acaagcccag | caacaccaag | 660 |
| gtggacaaga | aagttgagcc | caaatcttgt | gacaaaactc | acacatgccc | accgtgccca | 720 |
| gcacctgaac | tcctggggg | accgtcagtc | ttcctcttcc | ccccaaaacc | caaggacacc | 780 |
| ctcatgatct | cccggacccc | tgaggtcaca | tgcgtggtgg | tggacgtgag | ccacgaagac | 840 |
| cctgaggtca | agttcaactg | gtacgtggac | ggcgtggagg | tgcataatgc | caagacaaag | 900 |
| ccgcgggagg | agcagtacaa | cagcacgtac | cgtgtggtca | gcgtcctcac | cgtcctgcac | 960 |
| caggactggc | tgaatggcaa | ggagtacaag | tgcaaggtct | ccaacaaagc | cctcccagcc | 1020 |
| cccatcgaga | aaaccatctc | caaagccaaa | gggcagcccc | gagaaccaca | ggtgtacacc | 1080 |
| ctgcccccat | cccgggatga | gctgaccaag | aaccaggtca | gcctgacctg | cctggtcaaa | 1140 |
| ggcttctatc | ccagcgacat | cgccgtggag | tgggagagca | atgggcagcc | ggagaacaac | 1200 |
| tacaagacca | cgcctcccgt | gctggactcc | gacggctcct | tcttcctcta | cagcaagctc | 1260 |
| accgtggaca | agagcaggtg | gcagcagggg | aacgtcttct | catgctccgt | gatgcatgag | 1320 |
| gctctgcaca | accactacac | acagaagagc | ctctccctgt | ctccgggtaa | a | 1371 |

<210> SEQ ID NO 162
<211> LENGTH: 1371
<212> TYPE: DNA
<213> ORGANISM: Artificial Sequence
<220> FEATURE:
<223> OTHER INFORMATION: Synthetic

<400> SEQUENCE: 162

```
gaggtgcagc tggtggagtc tgggggaggc ttggtacagc cagggcggtc cctgagactc      60
agctgtgcgg cctctgggtt tagttttggt gatcatgcta tgagctgggt ccgccaggct     120
ccagggaagg ggctggagtg ggtaggtttc attagaaaga caacttatgg tgcgacaaca     180
cactacgccg cggctgtgag aggcagattc accatctcgc gagatgattc aaaagcatt      240
gtctatctgc aaatgaacag cctgaaagca gaggacacag ccgtgtattt ctgtgctaga     300
gtgcagcttg actatggccc gggataccag tactacggta tggacgtctg gggccaaggg     360
accacggtca ccgtctcctc agcctccacc aagggcccat cggtcttccc cctggcaccc     420
tcctccaaga gcacctctgg gggcacagca gccctgggct gcctggtcaa ggactacttc     480
cccgaaccgg tgacggtgtc gtggaactca ggcgccctga ccagcggcgt gcacaccttc     540
ccggctgtcc tacagtcctc aggactctac tccctcagca gcgtggtgac cgtgccctcc     600
agcagcttgg gcacccagac ctacatctgc aacgtgaatc acaagcccag caacaccaag     660
gtggacaaga agttgagccc aaatcttgt gacaaaactc acacatgccc accgtgccca     720
gcacctgaac tcctgggggg accgtcagtc ttcctcttcc ccccaaaacc caaggacacc     780
ctcatgatct cccggacccc tgaggtcaca tgcgtggtgg tggacgtgag ccacgaagac     840
cctgaggtca agttcaactg gtacgtggac ggcgtggagg tgcataatgc caagacaaag     900
ccgcgggagg agcagtacaa cagcacgtac cgtgtggtca gcgtcctcac cgtcctgcac     960
caggactggc tgaatggcaa ggagtacaag tgcaaggtct ccaacaaagc cctcccagcc    1020
cccatcgaga aaaccatctc caaagccaaa gggcagcccc gagaaccaca ggtgtacacc    1080
ctgcccccat cccgggatga gctgaccaag aaccaggtca gcctgacctg cctggtcaaa    1140
ggcttctatc ccagcgacat cgccgtggag tgggagagca atgggcagcc ggagaacaac    1200
tacaagacca cgcctcccgt gctggactcc gacggctcct tcttcctcta cagcaagctc    1260
accgtggaca gagcaggtg gcagcagggg aacgtcttct catgctccgt gctgcatgag    1320
gctctgcact cccactacac acagaagagc ctctccctgt ctccgggtaa a             1371
```

<210> SEQ ID NO 163
<211> LENGTH: 112
<212> TYPE: PRT
<213> ORGANISM: Artificial Sequence
<220> FEATURE:
<223> OTHER INFORMATION: Synthetic

<400> SEQUENCE: 163

```
Gln Ser Val Leu Thr Gln Pro Pro Ser Val Ser Gly Ala Pro Gly Gln
  1               5                  10                  15

Arg Val Thr Ile Ser Cys Thr Gly Met Asn Ser Asn Ile Gly Ala Gly
             20                  25                  30

Tyr Asp Val Tyr Trp Tyr Gln Gln Leu Pro Gly Thr Ala Pro Lys Leu
         35                  40                  45

Leu Ile Tyr Gly Asn Ser Asn Arg Pro Ser Gly Val Pro Asp Arg Phe
     50                  55                  60
```

```
Ser Gly Ser Arg Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Thr Ser
                 85                  90                  95

Leu Asn Gly Trp Ala Phe Gly Gly Gly Thr Lys Leu Thr Val Leu Gly
            100                 105                 110

<210> SEQ ID NO 164
<211> LENGTH: 127
<212> TYPE: PRT
<213> ORGANISM: Artificial Sequence
<220> FEATURE:
<223> OTHER INFORMATION: Synthetic

<400> SEQUENCE: 164

Glu Val Gln Leu Val Glu Ser Gly Gly Gly Leu Val Gln Pro Gly Arg
 1               5                  10                  15

Ser Leu Arg Leu Ser Cys Thr Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr Thr His Tyr Ala Ala
 50                  55                  60

Ala Val Arg Gly Arg Phe Thr Ile Ser Arg Asp Asp Ser Lys Ser Thr
 65                  70                  75                  80

Val Tyr Leu Gln Met Asn Ser Leu Lys Ala Glu Asp Thr Ala Val Tyr
                 85                  90                  95

Phe Cys Ala Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser
        115                 120                 125

<210> SEQ ID NO 165
<211> LENGTH: 336
<212> TYPE: DNA
<213> ORGANISM: Artificial Sequence
<220> FEATURE:
<223> OTHER INFORMATION: Synthetic

<400> SEQUENCE: 165
cagtctgtgc tgacgcagcc gccctcagtg tctggggccc cagggcagag ggtcaccatc      60
tcctgcactg ggatgaactc caacatcggg gcaggttatg atgtatactg gtaccaacaa     120
cttccaggaa ctgcccccaa actcctcatc tatggtaaca gcaatcggcc ctcaggggtc     180
cctgaccgat tctctggctc caggtctggc acctcagcct ccctggccat cactgggctc     240
caggctgagg atgaggctga ttattactgc cagtcctatg acaccagcct gaatggttgg     300
gctttcggcg gagggaccaa gttgaccgtc ctaggc                               336

<210> SEQ ID NO 166
<211> LENGTH: 381
<212> TYPE: DNA
<213> ORGANISM: Artificial Sequence
<220> FEATURE:
<223> OTHER INFORMATION: Synthetic

<400> SEQUENCE: 166
gaggtgcagc tggtggagtc tgggggaggc ttggtacagc cagggcggtc cctgagactc      60
agctgtacag cctctgggtt tagttttggt gatcatgcta tgagctgggt ccgccaggct     120
```

```
ccagggaagg ggctggagtg ggtaggtttc attagaaaga caacttatgg tgcgacaaca    180
cactacgccg cggctgtgag aggcagattc accatctcgc gagatgattc taaaagcact    240
gtctatctgc aaatgaacag cctgaaagca gaggacacag ccgtgtattt ctgtgctaga    300
gtgcagcttg actatggccc gggataccag tactacggta tggacgtctg gggccaaggg    360
accacggtca ccgtctcctc a                                              381
```

```
<210> SEQ ID NO 167
<211> LENGTH: 217
<212> TYPE: PRT
<213> ORGANISM: Artificial Sequence
<220> FEATURE:
<223> OTHER INFORMATION: Synthetic

<400> SEQUENCE: 167
```

Gln Ser Val Leu Thr Gln Pro Pro Ser Val Ser Gly Ala Pro Gly Gln
1               5                   10                  15

Arg Val Thr Ile Ser Cys Thr Gly Met Asn Ser Asn Ile Gly Ala Gly
            20                  25                  30

Tyr Asp Val Tyr Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Arg Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Ser
                85                  90                  95

Leu Asn Gly Trp Ala Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Val Ser Asp Phe
    130                 135                 140

Tyr Pro Gly Ala Val Thr Val Ala Trp Lys Ala Asp Gly Ser Pro Val
145                 150                 155                 160

Lys Val Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Arg Val Thr His Glu Gly Ser Thr Val Glu
        195                 200                 205

Lys Thr Val Ala Pro Ala Glu Cys Ser
    210                 215

```
<210> SEQ ID NO 168
<211> LENGTH: 457
<212> TYPE: PRT
<213> ORGANISM: Artificial Sequence
<220> FEATURE:
<223> OTHER INFORMATION: Synthetic

<400> SEQUENCE: 168
```

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Ser Phe Gly Asp His
            20                  25                  30

Ala Met Ser Trp Val Arg Gln Ala Pro Gly Lys Gly Leu Glu Trp Val

-continued

```
                35                  40                  45
Gly Phe Ile Arg Lys Thr Thr Tyr Gly Ala Thr Thr His Tyr Ala Ala
 50                  55                  60

Ala Val Arg Gly Arg Phe Thr Ile Ser Arg Asp Asp Ser Lys Ser Thr
 65                  70                  75                  80

Val Tyr Leu Gln Met Asn Ser Leu Lys Ala Glu Asp Thr Ala Val Tyr
                 85                  90                  95

Phe Cys Ala Arg Val Gln Leu Asp Tyr Gly Pro Gly Tyr Gln Tyr Tyr
                100                 105                 110

Gly Met Asp Val Trp Gly Gln Gly Thr Thr Val Thr Val Ser Ser Ala
                115                 120                 125

Ser Thr Lys Gly Pro Ser Val Phe Pro Leu Ala Pro Ser Ser Lys Ser
130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
                180                 185                 190

Ser Ser Val Val Thr Val Pro Ser Ser Ser Leu Gly Thr Gln Thr Tyr
                195                 200                 205

Ile Cys Asn Val Asn His Lys Pro Ser Asn Thr Lys Val Asp Lys Lys
210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
                260                 265                 270

Val Val Asp Val Ser His Glu Asp Pro Glu Val Lys Phe Asn Trp Tyr
                275                 280                 285

Val Asp Gly Val Glu Val His Asn Ala Lys Thr Lys Pro Arg Glu Glu
                290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
                340                 345                 350

Pro Arg Glu Pro Gln Val Tyr Thr Leu Pro Pro Ser Arg Asp Glu Leu
                355                 360                 365

Thr Lys Asn Gln Val Ser Leu Thr Cys Leu Val Lys Gly Phe Tyr Pro
                370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
                420                 425                 430

Phe Ser Cys Ser Val Met His Glu Ala Leu His Asn His Tyr Thr Gln
                435                 440                 445

Lys Ser Leu Ser Leu Ser Pro Gly Lys
                450                 455
```

```
<210> SEQ ID NO 169
<211> LENGTH: 457
<212> TYPE: PRT
<213> ORGANISM: Artificial Sequence
<220> FEATURE:
<223> OTHER INFORMATION: Synthetic

<400> SEQUENCE: 169
```

| | | | | | | | | | | | | | | | |
|---|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Arg |
| 1 | | | | 5 | | | | | 10 | | | | | 15 | |
| Ser | Leu | Arg | Leu | Ser | Cys | Thr | Ala | Ser | Gly | Phe | Ser | Phe | Gly | Asp | His |
| | | | 20 | | | | | 25 | | | | | 30 | | |
| Ala | Met | Ser | Trp | Val | Arg | Gln | Ala | Pro | Gly | Lys | Gly | Leu | Glu | Trp | Val |
| | | 35 | | | | | 40 | | | | | 45 | | | |
| Gly | Phe | Ile | Arg | Lys | Thr | Thr | Tyr | Gly | Ala | Thr | His | Tyr | Ala | Ala |
| | 50 | | | | | 55 | | | | | 60 | | | | |
| Ala | Val | Arg | Gly | Arg | Phe | Thr | Ile | Ser | Arg | Asp | Asp | Ser | Lys | Ser | Thr |
| 65 | | | | | 70 | | | | | 75 | | | | | 80 |
| Val | Tyr | Leu | Gln | Met | Asn | Ser | Leu | Lys | Ala | Glu | Asp | Thr | Ala | Val | Tyr |
| | | | | 85 | | | | | 90 | | | | | 95 | |
| Phe | Cys | Ala | Arg | Val | Gln | Leu | Asp | Tyr | Gly | Pro | Gly | Tyr | Gln | Tyr | Tyr |
| | | | 100 | | | | | 105 | | | | | 110 | | |
| Gly | Met | Asp | Val | Trp | Gly | Gln | Gly | Thr | Thr | Val | Thr | Val | Ser | Ser | Ala |
| | | 115 | | | | | 120 | | | | | 125 | | | |
| Ser | Thr | Lys | Gly | Pro | Ser | Val | Phe | Pro | Leu | Ala | Pro | Ser | Ser | Lys | Ser |
| | 130 | | | | | 135 | | | | | 140 | | | | |
| Thr | Ser | Gly | Gly | Thr | Ala | Ala | Leu | Gly | Cys | Leu | Val | Lys | Asp | Tyr | Phe |
| 145 | | | | | 150 | | | | | 155 | | | | | 160 |
| Pro | Glu | Pro | Val | Thr | Val | Ser | Trp | Asn | Ser | Gly | Ala | Leu | Thr | Ser | Gly |
| | | | | 165 | | | | | 170 | | | | | 175 | |
| Val | His | Thr | Phe | Pro | Ala | Val | Leu | Gln | Ser | Ser | Gly | Leu | Tyr | Ser | Leu |
| | | | 180 | | | | | 185 | | | | | 190 | | |
| Ser | Ser | Val | Val | Thr | Val | Pro | Ser | Ser | Ser | Leu | Gly | Thr | Gln | Thr | Tyr |
| | | 195 | | | | | 200 | | | | | 205 | | | |
| Ile | Cys | Asn | Val | Asn | His | Lys | Pro | Ser | Asn | Thr | Lys | Val | Asp | Lys | Lys |
| | 210 | | | | | 215 | | | | | 220 | | | | |
| Val | Glu | Pro | Lys | Ser | Cys | Asp | Lys | Thr | His | Thr | Cys | Pro | Pro | Cys | Pro |
| 225 | | | | | 230 | | | | | 235 | | | | | 240 |
| Ala | Pro | Glu | Leu | Leu | Gly | Gly | Pro | Ser | Val | Phe | Leu | Phe | Pro | Pro | Lys |
| | | | | 245 | | | | | 250 | | | | | 255 | |
| Pro | Lys | Asp | Thr | Leu | Met | Ile | Ser | Arg | Thr | Pro | Glu | Val | Thr | Cys | Val |
| | | | 260 | | | | | 265 | | | | | 270 | | |
| Val | Val | Asp | Val | Ser | His | Glu | Asp | Pro | Glu | Val | Lys | Phe | Asn | Trp | Tyr |
| | | 275 | | | | | 280 | | | | | 285 | | | |
| Val | Asp | Gly | Val | Glu | Val | His | Asn | Ala | Lys | Thr | Lys | Pro | Arg | Glu | Glu |
| | 290 | | | | | 295 | | | | | 300 | | | | |
| Gln | Tyr | Asn | Ser | Thr | Tyr | Arg | Val | Val | Ser | Val | Leu | Thr | Val | Leu | His |
| 305 | | | | | 310 | | | | | 315 | | | | | 320 |
| Gln | Asp | Trp | Leu | Asn | Gly | Lys | Glu | Tyr | Lys | Cys | Lys | Val | Ser | Asn | Lys |
| | | | | 325 | | | | | 330 | | | | | 335 | |
| Ala | Leu | Pro | Ala | Pro | Ile | Glu | Lys | Thr | Ile | Ser | Lys | Ala | Lys | Gly | Gln |
| | | | 340 | | | | | 345 | | | | | 350 | | |
| Pro | Arg | Glu | Pro | Gln | Val | Tyr | Thr | Leu | Pro | Pro | Ser | Arg | Asp | Glu | Leu |
| | | 355 | | | | | 360 | | | | | 365 | | | |

```
Thr Lys Asn Gln Val Ser Leu Thr Cys Leu Val Lys Gly Phe Tyr Pro
    370                 375                 380
Ser Asp Ile Ala Val Glu Trp Glu Ser Asn Gly Gln Pro Glu Asn Asn
385                 390                 395                 400
Tyr Lys Thr Thr Pro Pro Val Leu Asp Ser Asp Gly Ser Phe Phe Leu
                405                 410                 415
Tyr Ser Lys Leu Thr Val Asp Lys Ser Arg Trp Gln Gln Gly Asn Val
            420                 425                 430
Phe Ser Cys Ser Val Leu His Glu Ala Leu His Ser His Tyr Thr Gln
        435                 440                 445
Lys Ser Leu Ser Leu Ser Pro Gly Lys
    450                 455

<210> SEQ ID NO 170
<211> LENGTH: 651
<212> TYPE: DNA
<213> ORGANISM: Artificial Sequence
<220> FEATURE:
<223> OTHER INFORMATION: Synthetic

<400> SEQUENCE: 170
cagtctgtgc tgacgcagcc gccctcagtg tctggggccc cagggcagag ggtcaccatc      60
tcctgcactg ggatgaactc caacatcggg gcaggttatg atgtatactg gtaccaacaa     120
cttccaggaa ctgcccccaa actcctcatc tatggtaaca gcaatcggcc ctcaggggtc     180
cctgaccgat tctctggctc caggtctggc acctcagcct ccctggccat cactgggctc     240
caggctgagg atgaggctga ttattactgc cagtcctatg acaccagcct gaatggttgg     300
gctttcggcg agggaccaa gttgaccgtc ctaggccagc ccaaggctgc ccctcggtc      360 actctgttcc caccctcctc tgaggagctt caagccaaca aggccacact ggtgtgtctc     420
gtaagtgact tctacccggg agccgtgaca gtggcctgga aggcagatgg cagcccgtc     480 aaggtgggag tggagaccac caaaccctcc aaacaaagca caacaagta tgcggccagc      540 agctacctga gcctgacgcc cgagcagtgg aagtcccaca aagctacag ctgccgggtc     600 acgcatgaag ggagcaccgt ggagaagaca gtggcccctg cagaatgctc t              651

<210> SEQ ID NO 171
<211> LENGTH: 1371
<212> TYPE: DNA
<213> ORGANISM: Artificial Sequence
<220> FEATURE:
<223> OTHER INFORMATION: Synthetic

<400> SEQUENCE: 171
gaggtgcagc tggtggagtc tgggggaggc ttggtacagc cagggcggtc cctgagactc      60
agctgtacag cctctgggtt tagttttggt gatcatgcta tgagctgggt ccgccaggct     120
ccagggaagg ggctggagtg gtaggtttc attagaaaga caacttatgg tgcgacaaca     180
cactacgccg cggctgtgag aggcagattc accatctcgc gagatgattc aaaagcact      240 gtctatctgc aaatgaacag cctgaaagca gaggacacag ccgtgtattt ctgtgctaga     300
gtgcagcttg actatggccc gggataccag tactacggta tggacgtctg ggccaaggg      360 accacggtca ccgtctcctc agcctccacc aagggcccat cggtcttccc cctggcaccc     420
tcctccaaga gcacctctgg gggcacagca gccctgggct gcctggtcaa ggactacttc     480
cccgaaccgg tgacggtgtc gtggaactca ggcgccctga ccagcggcgt gcacaccttc     540
```

| | |
|---|---|
| ccggctgtcc tacagtcctc aggactctac tccctcagca gcgtggtgac cgtgccctcc | 600 |
| agcagcttgg gcacccagac ctacatctgc aacgtgaatc acaagcccag caacaccaag | 660 |
| gtggacaaga agttgagcc caaatcttgt gacaaaactc acacatgccc accgtgccca | 720 |
| gcacctgaac tcctgggggg accgtcagtc ttcctcttcc ccccaaaacc caaggacacc | 780 |
| ctcatgatct cccggacccc tgaggtcaca tgcgtggtgg tggacgtgag ccacgaagac | 840 |
| cctgaggtca agttcaactg gtacgtggac ggcgtggagg tgcataatgc caagacaaag | 900 |
| ccgcgggagg agcagtacaa cagcacgtac cgtgtggtca gcgtcctcac cgtcctgcac | 960 |
| caggactggc tgaatggcaa ggagtacaag tgcaaggtct ccaacaaagc cctcccagcc | 1020 |
| cccatcgaga aaaccatctc caaagccaaa gggcagcccc gagaaccaca ggtgtacacc | 1080 |
| ctgcccccat cccgggatga gctgaccaag aaccaggtca gcctgacctg cctggtcaaa | 1140 |
| ggcttctatc ccagcgacat cgccgtggag tgggagagca atgggcagcc ggagaacaac | 1200 |
| tacaagacca cgcctcccgt gctggactcc gacggctcct tcttcctcta cagcaagctc | 1260 |
| accgtggaca agagcaggtg gcagcagggg aacgtcttct catgctccgt gatgcatgag | 1320 |
| gctctgcaca accactacac acagaagagc ctctccctgt ctccgggtaa a | 1371 |

<210> SEQ ID NO 172
<211> LENGTH: 1371
<212> TYPE: DNA
<213> ORGANISM: Artificial Sequence
<220> FEATURE:
<223> OTHER INFORMATION: Synthetic

<400> SEQUENCE: 172

| | |
|---|---|
| gaggtgcagc tggtggagtc tgggggaggc ttggtacagc cagggcggtc cctgagactc | 60 |
| agctgtacag cctctgggtt tagttttggt gatcatgcta tgagctgggt ccgccaggct | 120 |
| ccagggaagg gctggagtg gtaggtttc attagaaaga caacttatgg tgcgacaaca | 180 |
| cactacgccg cggctgtgag aggcagattc accatctcgc gagatgattc aaaagcact | 240 |
| gtctatctgc aaatgaacag cctgaaagca gaggacacag ccgtgtattt ctgtgctaga | 300 |
| gtgcagcttg actatggccc gggataccag tactacggta tggacgtctg gggccaaggg | 360 |
| accacggtca ccgtctcctc agcctccacc aagggcccat cggtcttccc cctggcaccc | 420 |
| tcctccaaga gcacctctgg gggcacagca gccctgggct gcctggtcaa ggactacttc | 480 |
| cccgaaccgg tgacggtgtc gtggaactca ggcgccctga ccagcggcgt gcacaccttc | 540 |
| ccggctgtcc tacagtcctc aggactctac tccctcagca gcgtggtgac cgtgccctcc | 600 |
| agcagcttgg gcacccagac ctacatctgc aacgtgaatc acaagcccag caacaccaag | 660 |
| gtggacaaga agttgagcc caaatcttgt gacaaaactc acacatgccc accgtgccca | 720 |
| gcacctgaac tcctgggggg accgtcagtc ttcctcttcc ccccaaaacc caaggacacc | 780 |
| ctcatgatct cccggacccc tgaggtcaca tgcgtggtgg tggacgtgag ccacgaagac | 840 |
| cctgaggtca agttcaactg gtacgtggac ggcgtggagg tgcataatgc caagacaaag | 900 |
| ccgcgggagg agcagtacaa cagcacgtac cgtgtggtca gcgtcctcac cgtcctgcac | 960 |
| caggactggc tgaatggcaa ggagtacaag tgcaaggtct ccaacaaagc cctcccagcc | 1020 |
| cccatcgaga aaaccatctc caaagccaaa gggcagcccc gagaaccaca ggtgtacacc | 1080 |
| ctgcccccat cccgggatga gctgaccaag aaccaggtca gcctgacctg cctggtcaaa | 1140 |
| ggcttctatc ccagcgacat cgccgtggag tgggagagca atgggcagcc ggagaacaac | 1200 |
| tacaagacca cgcctcccgt gctggactcc gacggctcct tcttcctcta cagcaagctc | 1260 |

```
accgtggaca agagcaggtg gcagcagggg aacgtcttct catgctccgt gctgcatgag    1320
gctctgcact cccactacac acagaagagc ctctcccctgt ctccgggtaa a            1371
```

<210> SEQ ID NO 173
<211> LENGTH: 112
<212> TYPE: PRT
<213> ORGANISM: Artificial Sequence
<220> FEATURE:
<223> OTHER INFORMATION: Synthetic

<400> SEQUENCE: 173

```
Gln Ser Val Leu Thr Gln Pro Pro Ser Val Gly Ala Pro Gly Gln
1               5                   10                  15

Arg Val Thr Ile Ser Cys Thr Gly Met Asn Ser Asn Ile Gly Ala Gly
            20                  25                  30

Tyr Asp Val Tyr Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Arg Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Ser
                85                  90                  95

Leu Asn Gly Trp Ala Phe Gly Gly Gly Thr Lys Leu Thr Val Leu Gly
            100                 105                 110
```

<210> SEQ ID NO 174
<211> LENGTH: 127
<212> TYPE: PRT
<213> ORGANISM: Artificial Sequence
<220> FEATURE:
<223> OTHER INFORMATION: Synthetic

<400> SEQUENCE: 174

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr Thr His Tyr Ala Ala
    50                  55                  60

Ala Val Arg Gly Arg Phe Thr Ile Ser Arg Asp Asp Ser Lys Ser Thr
65                  70                  75                  80

Val Tyr Leu Gln Met Asn Ser Leu Lys Ala Glu Asp Thr Ala Val Tyr
                85                  90                  95

Phe Cys Ala Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser
        115                 120                 125
```

<210> SEQ ID NO 175
<211> LENGTH: 336
<212> TYPE: DNA
<213> ORGANISM: Artificial Sequence
<220> FEATURE:
<223> OTHER INFORMATION: Synthetic

<400> SEQUENCE: 175

```
cagtctgtgc tgacgcagcc gccctcagtg tctggggccc cagggcagag ggtcaccatc    60
tcctgcactg ggatgaactc caacatcggg gcaggttatg atgtatactg gtaccaacaa   120
cttccaggaa ctgcccccaa actcctcatc tatggtaaca gcaatcggcc ctcaggggtc   180
cctgaccgat tctctggctc caggtctggc acctcagcct ccctggccat cactgggctc   240
caggctgagg atgaggctga ttattactgc cagtcctatg acaccagcct gaatggttgg   300
gctttcggcg agggaccaa gttgaccgtc ctaggc                              336
```

<210> SEQ ID NO 176
<211> LENGTH: 381
<212> TYPE: DNA
<213> ORGANISM: Artificial Sequence
<220> FEATURE:
<223> OTHER INFORMATION: Synthetic

<400> SEQUENCE: 176

```
gaggtgcagc tggtggagtc tgggggaggc ttggtacagc cagggcggtc cctgagactc    60
agctgtgcgg cctctgggtt tagttttggt gatcatgcta tgagctgggt ccgccaggct   120
ccagggaagg ggctggagtg ggtaggtttc attagaaaga caacttatgg tgcgacaaca   180
cactacgccg cggctgtgag aggcagattc accatctcgc gagatgattc aaaagcact   240 gtctatctgc aaatgaacag cctgaaagca gaggacacag ccgtgtattt ctgtgctaga   300
gtgcagcttg actatggccc gggataccag tactacggta tggacgtctg gggccaaggg   360
accacggtca ccgtctcctc a                                             381
```

<210> SEQ ID NO 177
<211> LENGTH: 217
<212> TYPE: PRT
<213> ORGANISM: Artificial Sequence
<220> FEATURE:
<223> OTHER INFORMATION: Synthetic

<400> SEQUENCE: 177

Gln Ser Val Leu Thr Gln Pro Pro Ser Val Gly Ala Pro Gly Gln
1               5                  10                  15

Arg Val Thr Ile Ser Cys Thr Gly Met Asn Ser Asn Ile Gly Ala Gly
            20                  25                  30

Tyr Asp Val Tyr Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Arg Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Ser
                85                  90                  95

Leu Asn Gly Trp Ala Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Val Ser Asp Phe
    130                 135                 140

Tyr Pro Gly Ala Val Thr Val Ala Trp Lys Ala Asp Gly Ser Pro Val
145                 150                 155                 160

Lys Val Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Arg Val Thr His Glu Gly Ser Thr Val Glu
        195                 200                 205

Lys Thr Val Ala Pro Ala Glu Cys Ser
    210                 215

<210> SEQ ID NO 178
<211> LENGTH: 457
<212> TYPE: PRT
<213> ORGANISM: Artificial Sequence
<220> FEATURE:
<223> OTHER INFORMATION: Synthetic

<400> SEQUENCE: 178

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr Thr His Tyr Ala Ala
    50                  55                  60

Ala Val Arg Gly Arg Phe Thr Ile Ser Arg Asp Asp Ser Lys Ser Thr
65                  70                  75                  80

Val Tyr Leu Gln Met Asn Ser Leu Lys Ala Glu Asp Thr Ala Val Tyr
                85                  90                  95

Phe Cys Ala Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

```
Gln Asp Trp Leu Asn Gly Lys Glu Tyr Lys Cys Lys Val Ser Asn Lys
            325                 330                 335

Ala Leu Pro Ala Pro Ile Glu Lys Thr Ile Ser Lys Ala Lys Gly Gln
        340                 345                 350

Pro Arg Glu Pro Gln Val Tyr Thr Leu Pro Pro Ser Arg Asp Glu Leu
    355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 179
<211> LENGTH: 457
<212> TYPE: PRT
<213> ORGANISM: Artificial Sequence
<220> FEATURE:
<223> OTHER INFORMATION: Synthetic

<400> SEQUENCE: 179

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ser Phe Gly Asp His
            20                  25                  30

Ala Met Ser Trp Val Arg Gln Ala Pro Gly Lys Gly Leu Glu Trp Val
        35                  40                  45

Gly Phe Ile Arg Lys Thr Thr Tyr Gly Ala Thr Thr His Tyr Ala Ala
    50                  55                  60

Ala Val Arg Gly Arg Phe Thr Ile Ser Arg Asp Asp Ser Lys Ser Thr
65                  70                  75                  80

Val Tyr Leu Gln Met Asn Ser Leu Lys Ala Glu Asp Thr Ala Val Tyr
                85                  90                  95

Phe Cys Ala Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220
```

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
            245                 250                 255

Pro Lys Asp Thr Leu Met Ile Ser Arg Thr Pro Glu Val Thr Cys Val
        260                 265                 270

Val Val Asp Val Ser His Glu Asp Pro Glu Val Lys Phe Asn Trp Tyr
    275                 280                 285

Val Asp Gly Val Glu Val His Asn Ala Lys Thr Lys Pro Arg Glu Glu
290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
            325                 330                 335

Ala Leu Pro Ala Pro Ile Glu Lys Thr Ile Ser Lys Ala Lys Gly Gln
        340                 345                 350

Pro Arg Glu Pro Gln Val Tyr Thr Leu Pro Pro Ser Arg Asp Glu Leu
    355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
            405                 410                 415

Tyr Ser Lys Leu Thr Val Asp Lys Ser Arg Trp Gln Gln Gly Asn Val
        420                 425                 430

Phe Ser Cys Ser Val Leu His Glu Ala Leu His Ser His Tyr Thr Gln
    435                 440                 445

Lys Ser Leu Ser Leu Ser Pro Gly Lys
    450                 455

<210> SEQ ID NO 180
<211> LENGTH: 651
<212> TYPE: DNA
<213> ORGANISM: Artificial Sequence
<220> FEATURE:
<223> OTHER INFORMATION: Synthetic

<400> SEQUENCE: 180
cagtctgtgc tgacgcagcc gccctcagtg tctggggccc cagggcagag ggtcaccatc      60
tcctgcactg ggatgaactc caacatcggg gcaggttatg atgtatactg gtaccaacaa     120
cttccaggaa ctgcccccaa actcctcatc tatggtaaca gcaatcggcc ctcaggggtc     180
cctgaccgat tctctggctc caggtctggc acctcagcct ccctggccat cactgggctc     240
caggctgagg atgaggctga ttattactgc cagtcctatg acaccagcct gaatggttgg     300
gctttcggcg gagggaccaa gttgaccgtc ctaggccagc ccaaggctgc ccctcggtc      360 actctgttcc accctcctc tgaggagctt caagccaaca ggccacact ggtgtgtctc       420 gtaagtgact tctacccggg agccgtgaca gtggcctgga aggcagatgg cagcccgtc     480 aaggtgggag tggagaccac caaaccctcc aaacaaagca acaacaagta tgcggccagc     540
agctacctga gcctgacgcc cgagcagtgg aagtcccaca gaagctacag ctgccgggtc     600
acgcatgaag ggagcaccgt ggagaagaca gtggcccctg cagaatgctc t              651

<210> SEQ ID NO 181
<211> LENGTH: 1371
<212> TYPE: DNA
<213> ORGANISM: Artificial Sequence
<220> FEATURE:
<223> OTHER INFORMATION: Synthetic

<400> SEQUENCE: 181

```
gaggtgcagc tggtggagtc tgggggaggc ttggtacagc cagggcggtc cctgagactc      60
agctgtgcgg cctctgggtt tagttttggt gatcatgcta tgagctgggt ccgccaggct     120
ccagggaagg ggctggagtg ggtaggtttc attagaaaga caacttatgg tgcgacaaca     180
cactacgccg cggctgtgag aggcagattc accatctcgc gagatgattc aaaaagcact     240
gtctatctgc aaatgaacag cctgaaagca gaggacacag ccgtgtattt ctgtgctaga     300
gtgcagcttg actatggccc gggataccag tactacggta tggacgtctg ggggccaaggg     360
accacggtca ccgtctcctc agcctccacc aagggcccat cggtcttccc cctggcaccc     420
tcctccaaga gcacctctgg gggcacagca gccctgggct gcctggtcaa ggactacttc     480
cccgaaccgg tgacggtgtc gtggaactca ggcgccctga ccagcggcgt gcacaccttc     540
ccggctgtcc tacagtcctc aggactctac tccctcagca gcgtggtgac cgtgccctcc     600
agcagcttgg gcacccagac ctacatctgc aacgtgaatc acaagcccag caacaccaag     660
gtggacaaga agttgagccc aaatcttgt gacaaaactc acacatgccc accgtgccca     720
gcacctgaac tcctgggggg accgtcagtc ttcctcttcc ccccaaaacc caaggacacc     780
ctcatgatct cccggacccc tgaggtcaca tgcgtggtgg tggacgtgag ccacgaagac     840
cctgaggtca agttcaactg gtacgtggac ggcgtggagg tgcataatgc caagacaaag     900
ccgcgggagg agcagtacaa cagcacgtac cgtgtggtca gcgtcctcac cgtcctgcac     960
caggactggc tgaatggcaa ggagtacaag tgcaaggtct ccaacaaagc cctcccagcc    1020
cccatcgaga aaaccatctc caaagccaaa gggcagcccc gagaaccaca ggtgtacacc    1080
ctgcccccat cccgggatga gctgaccaag aaccaggtca gcctgacctg cctggtcaaa    1140
ggcttctatc ccagcgacat cgccgtggag tgggagagca atgggcagcc ggagaacaac    1200
tacaagacca cgcctcccgt gctggactcc gacggctcct tcttcctcta cagcaagctc    1260
accgtggaca agagcaggtg gcagcagggg aacgtcttct catgctccgt gatgcatgag    1320
gctctgcaca accactacac acagaagagc ctctccctgt ctccgggtaa a             1371
```

<210> SEQ ID NO 182
<211> LENGTH: 1371
<212> TYPE: DNA
<213> ORGANISM: Artificial Sequence
<220> FEATURE:
<223> OTHER INFORMATION: Synthetic

<400> SEQUENCE: 182

```
gaggtgcagc tggtggagtc tgggggaggc ttggtacagc cagggcggtc cctgagactc      60
agctgtgcgg cctctgggtt tagttttggt gatcatgcta tgagctgggt ccgccaggct     120
ccagggaagg ggctggagtg ggtaggtttc attagaaaga caacttatgg tgcgacaaca     180
cactacgccg cggctgtgag aggcagattc accatctcgc gagatgattc aaaaagcact     240
gtctatctgc aaatgaacag cctgaaagca gaggacacag ccgtgtattt ctgtgctaga     300
gtgcagcttg actatggccc gggataccag tactacggta tggacgtctg ggggccaaggg     360
accacggtca ccgtctcctc agcctccacc aagggcccat cggtcttccc cctggcaccc     420
```

-continued

```
tcctccaaga gcacctctgg gggcacagca gccctgggct gcctggtcaa ggactacttc       480
cccgaaccgg tgacggtgtc gtggaactca ggcgccctga ccagcggcgt gcacaccttc       540
ccggctgtcc tacagtcctc aggactctac tccctcagca gcgtggtgac cgtgccctcc       600
agcagcttgg gcacccagac ctacatctgc aacgtgaatc acaagcccag caacaccaag       660
gtggacaaga agttgagcc caaatcttgt gacaaaactc acacatgccc accgtgccca        720
gcacctgaac tcctgggggg accgtcagtc ttcctcttcc ccccaaaacc caaggacacc       780
ctcatgatct cccggacccc tgaggtcaca tgcgtggtgg tggacgtgag ccacgaagac       840
cctgaggtca agttcaactg gtacgtggac ggcgtggagg tgcataatgc caagacaaag       900
ccgcgggagg agcagtacaa cagcacgtac cgtgtggtca gcgtcctcac cgtcctgcac       960
caggactggc tgaatggcaa ggagtacaag tgcaaggtct ccaacaaagc cctcccagcc      1020
cccatcgaga aaaccatctc caaagccaaa gggcagcccc gagaaccaca ggtgtacacc      1080
ctgcccccat cccgggatga gctgaccaag aaccaggtca gcctgacctg cctggtcaaa      1140
ggcttctatc ccagcgacat cgccgtggag tgggagagca tgggcagcc ggagaacaac       1200 tacaagacca cgcctcccgt gctggactcc gacggctcct tcttcctcta cagcaagctc      1260
accgtggaca gagcaggtg gcagcagggg aacgtcttct catgctccgt gctgcatgag       1320
gctctgcact cccactacac acagaagagc ctctccctgt ctccgggtaa a               1371
```

<210> SEQ ID NO 183
<211> LENGTH: 14
<212> TYPE: PRT
<213> ORGANISM: Artificial Sequence
<220> FEATURE:
<223> OTHER INFORMATION: Synthetic

<400> SEQUENCE: 183

Thr Gly Met Asn Ser Asn Ile Gly Ala Gly Tyr Asp Val Tyr
1               5                   10

<210> SEQ ID NO 184
<211> LENGTH: 7
<212> TYPE: PRT
<213> ORGANISM: Artificial Sequence
<220> FEATURE:
<223> OTHER INFORMATION: Synthetic

<400> SEQUENCE: 184

Gly Asn Ser Asn Arg Pro Ser
1               5

<210> SEQ ID NO 185
<211> LENGTH: 11
<212> TYPE: PRT
<213> ORGANISM: Artificial Sequence
<220> FEATURE:
<223> OTHER INFORMATION: Synthetic

<400> SEQUENCE: 185

Gln Ser Tyr Asp Thr Ser Leu Asp Gly Trp Ala
1               5                   10

<210> SEQ ID NO 186
<211> LENGTH: 5
<212> TYPE: PRT
<213> ORGANISM: Artificial Sequence
<220> FEATURE:
<223> OTHER INFORMATION: Synthetic

```
<400> SEQUENCE: 186

Asp His Ala Met Ser
1               5

<210> SEQ ID NO 187
<211> LENGTH: 19
<212> TYPE: PRT
<213> ORGANISM: Artificial Sequence
<220> FEATURE:
<223> OTHER INFORMATION: Synthetic

<400> SEQUENCE: 187

Phe Ile Arg Lys Thr Thr Tyr Gly Ala Thr Thr Lys Tyr Ala Ala Ala
1               5                   10                  15

Val Lys Gly

<210> SEQ ID NO 188
<211> LENGTH: 16
<212> TYPE: PRT
<213> ORGANISM: Artificial Sequence
<220> FEATURE:
<223> OTHER INFORMATION: Synthetic

<400> SEQUENCE: 188

Val Gln Leu Asp Tyr Gly Pro Gly Tyr Gln Tyr Tyr Gly Met Asp Val
1               5                   10                  15

<210> SEQ ID NO 189
<211> LENGTH: 14
<212> TYPE: PRT
<213> ORGANISM: Artificial Sequence
<220> FEATURE:
<223> OTHER INFORMATION: Synthetic

<400> SEQUENCE: 189

Thr Gly Met Asn Ser Asn Ile Gly Ala Gly Tyr Asp Val Tyr
1               5                   10

<210> SEQ ID NO 190
<211> LENGTH: 7
<212> TYPE: PRT
<213> ORGANISM: Artificial Sequence
<220> FEATURE:
<223> OTHER INFORMATION: Synthetic

<400> SEQUENCE: 190

Gly Asn Ser Asn Arg Pro Ser
1               5

<210> SEQ ID NO 191
<211> LENGTH: 11
<212> TYPE: PRT
<213> ORGANISM: Artificial Sequence
<220> FEATURE:
<223> OTHER INFORMATION: Synthetic

<400> SEQUENCE: 191

Gln Ser Tyr Asp Thr Ser Leu Asp Gly Trp Ala
1               5                   10

<210> SEQ ID NO 192
<211> LENGTH: 5
<212> TYPE: PRT
<213> ORGANISM: Artificial Sequence
<220> FEATURE:
<223> OTHER INFORMATION: Synthetic
```

<400> SEQUENCE: 192

Asp His Ala Met Ser
1               5

<210> SEQ ID NO 193
<211> LENGTH: 19
<212> TYPE: PRT
<213> ORGANISM: Artificial Sequence
<220> FEATURE:
<223> OTHER INFORMATION: Synthetic

<400> SEQUENCE: 193

Phe Ile Arg Lys Thr Thr Tyr Gly Ala Thr Thr Lys Tyr Ala Ala Ala
1               5                   10                  15

Val Lys Gly

<210> SEQ ID NO 194
<211> LENGTH: 16
<212> TYPE: PRT
<213> ORGANISM: Artificial Sequence
<220> FEATURE:
<223> OTHER INFORMATION: Synthetic

<400> SEQUENCE: 194

Val Gln Leu Asp Tyr Gly Pro Gly Tyr Gln Tyr Tyr Gly Met Asp Val
1               5                   10                  15

<210> SEQ ID NO 195
<211> LENGTH: 112
<212> TYPE: PRT
<213> ORGANISM: Artificial Sequence
<220> FEATURE:
<223> OTHER INFORMATION: Synthetic

<400> SEQUENCE: 195

Glu Ser Val Leu Thr Gln Pro Pro Ser Val Ser Gly Ala Pro Gly Gln
1               5                   10                  15

Arg Val Thr Ile Ser Cys Thr Gly Met Asn Ser Asn Ile Gly Ala Gly
                20                  25                  30

Tyr Asp Val Tyr Trp Tyr Gln Gln Leu Pro Gly Arg Ala Pro Lys Leu
            35                  40                  45

Leu Ile Tyr Gly Asn Ser Asn Arg Pro Ser Gly Val Pro Asp Arg Phe
        50                  55                  60

Ser Gly Ser Arg Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Ser
                85                  90                  95

Leu Asp Gly Trp Ala Phe Gly Gly Gly Thr Lys Leu Thr Val Leu Gly
            100                 105                 110

<210> SEQ ID NO 196
<211> LENGTH: 127
<212> TYPE: PRT
<213> ORGANISM: Artificial Sequence
<220> FEATURE:
<223> OTHER INFORMATION: Synthetic

<400> SEQUENCE: 196

Glu Val Gln Leu Val Glu Ser Gly Gly Gly Leu Val Gln Pro Gly Arg
1               5                   10                  15

Ser Leu Arg Leu Pro Cys Thr Ala Ser Gly Phe Ser Phe Gly Asp His

```
                20                  25                  30
Ala Met Ser Trp Val Arg Gln Ala Pro Gly Lys Gly Leu Glu Trp Val
            35                  40                  45

Gly Phe Ile Arg Lys Thr Thr Tyr Gly Ala Thr Lys Tyr Ala Ala
        50                  55                  60

Ala Val Lys Gly Arg Phe Thr Ile Ser Arg Asp Asp Ser Lys Ser Ile
65                  70                  75                  80

Val Tyr Leu Gln Met Asn Ser Leu Lys Thr Glu Asp Thr Ala Val Tyr
                85                  90                  95

Phe Cys Thr Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser
            115                 120                 125

<210> SEQ ID NO 197
<211> LENGTH: 336
<212> TYPE: DNA
<213> ORGANISM: Artificial Sequence
<220> FEATURE:
<223> OTHER INFORMATION: Synthetic

<400> SEQUENCE: 197
gagtctgtgc tgacgcagcc gccctcagtg tctggggccc cagggcagag ggtcaccatc      60
tcctgcactg ggatgaactc caacatcggg gcaggttatg atgtatactg gtaccaacaa     120
cttccaggaa gagcccccaa actcctcatc tatggtaaca gcaatcggcc ctcaggggtc     180
cctgaccgat tctctggctc caggtctggc acctcagcct ccctggccat cactgggctc     240
caggctgagg atgaggctga ttattactgc cagtcctatg acaccagcct ggacggttgg     300
gctttcggcg agggaccaa gttgaccgtc ctaggc                                336

<210> SEQ ID NO 198
<211> LENGTH: 381
<212> TYPE: DNA
<213> ORGANISM: Artificial Sequence
<220> FEATURE:
<223> OTHER INFORMATION: Synthetic

<400> SEQUENCE: 198
gaggtgcagc tggtggagtc tgggggaggc ttggtacagc cagggcggtc cctgagactc      60
ccctgtacag cctctgggtt tagttttggt gatcatgcta tgagctgggt ccgccaggct     120
ccagggaagg ggctggagtg ggtaggtttc attagaaaga caacttatgg tgcgacaaca     180
aagtacgccg cggctgtgaa ggcagattc accatctcgc gagatgattc taaaagcatt     240
gtctatctgc aaatgaacag cctgaaaacc gaggacacag ccgtgtattt ctgtactaga     300
gtgcagcttg actatggccc gggataccag tactacggta tggacgtctg gggccaaggg     360
accacggtca ccgtctcctc a                                               381

<210> SEQ ID NO 199
<211> LENGTH: 217
<212> TYPE: PRT
<213> ORGANISM: Artificial Sequence
<220> FEATURE:
<223> OTHER INFORMATION: Synthetic

<400> SEQUENCE: 199

Glu Ser Val Leu Thr Gln Pro Pro Ser Val Ser Gly Ala Pro Gly Gln
1               5                   10                  15
```

```
Arg Val Thr Ile Ser Cys Thr Gly Met Asn Ser Asn Ile Gly Ala Gly
                 20                  25                  30

Tyr Asp Val Tyr Trp Tyr Gln Gln Leu Pro Gly Arg Ala Pro Lys Leu
             35                  40                  45

Leu Ile Tyr Gly Asn Ser Asn Arg Pro Ser Gly Val Pro Asp Arg Phe
         50                  55                  60

Ser Gly Ser Arg Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Thr Ser
                 85                  90                  95

Leu Asp Gly Trp Ala Phe Gly Gly Gly Thr Lys Leu Thr Val Leu Gly
             100                 105                 110

Gln Pro Lys Ala Ala Pro Ser Val Thr Leu Phe Pro Pro Ser Ser Glu
         115                 120                 125

Glu Leu Gln Ala Asn Lys Ala Thr Leu Val Cys Leu Val Ser Asp Phe
130                 135                 140

Tyr Pro Gly Ala Val Thr Val Ala Trp Lys Ala Asp Gly Ser Pro Val
145                 150                 155                 160

Lys Val Gly Val Glu Thr Thr Lys Pro Ser Lys Gln Ser Asn Asn Lys
                 165                 170                 175

Tyr Ala Ala Ser Ser Tyr Leu Ser Leu Thr Pro Glu Gln Trp Lys Ser
             180                 185                 190

His Arg Ser Tyr Ser Cys Arg Val Thr His Glu Gly Ser Thr Val Glu
         195                 200                 205

Lys Thr Val Ala Pro Ala Glu Cys Ser
         210                 215

<210> SEQ ID NO 200
<211> LENGTH: 457
<212> TYPE: PRT
<213> ORGANISM: Artificial Sequence
<220> FEATURE:
<223> OTHER INFORMATION: Synthetic

<400> SEQUENCE: 200

Glu Val Gln Leu Val Glu Ser Gly Gly Gly Leu Val Gln Pro Gly Arg
 1               5                  10                  15

Ser Leu Arg Leu Pro Cys Thr Ala Ser Gly Phe Ser Phe Gly Asp His
                 20                  25                  30

Ala Met Ser Trp Val Arg Gln Ala Pro Gly Lys Gly Leu Glu Trp Val
             35                  40                  45

Gly Phe Ile Arg Lys Thr Thr Tyr Gly Ala Thr Thr Lys Tyr Ala Ala
         50                  55                  60

Ala Val Lys Gly Arg Phe Thr Ile Ser Arg Asp Asp Ser Lys Ser Ile
 65                  70                  75                  80

Val Tyr Leu Gln Met Asn Ser Leu Lys Thr Glu Asp Thr Ala Val Tyr
                 85                  90                  95

Phe Cys Thr Arg Val Gln Leu Asp Tyr Gly Pro Gly Tyr Gln Tyr Tyr
             100                 105                 110

Gly Met Asp Val Trp Gly Gln Gly Thr Thr Val Thr Val Ser Ser Ala
         115                 120                 125

Ser Thr Lys Gly Pro Ser Val Phe Pro Leu Ala Pro Ser Ser Lys Ser
130                 135                 140

Thr Ser Gly Gly Thr Ala Ala Leu Gly Cys Leu Val Lys Asp Tyr Phe
145                 150                 155                 160
```

```
Pro Glu Pro Val Thr Val Ser Trp Asn Ser Gly Ala Leu Thr Ser Gly
            165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
            195                 200                 205

Ile Cys Asn Val Asn His Lys Pro Ser Asn Thr Lys Val Asp Lys Lys
            210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
            245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
            275                 280                 285

Val Asp Gly Val Glu Val His Asn Ala Lys Thr Lys Pro Arg Glu Glu
            290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
            325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
            355                 360                 365

Thr Lys Asn Gln Val Ser Leu Thr Cys Leu Val Lys Gly Phe Tyr Pro
            370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
            405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
            435                 440                 445

Lys Ser Leu Ser Leu Ser Pro Gly Lys
            450                 455

<210> SEQ ID NO 201
<211> LENGTH: 457
<212> TYPE: PRT
<213> ORGANISM: Artificial Sequence
<220> FEATURE:
<223> OTHER INFORMATION: Synthetic

<400> SEQUENCE: 201

Glu Val Gln Leu Val Glu Ser Gly Gly Gly Leu Val Gln Pro Gly Arg
1               5                   10                  15

Ser Leu Arg Leu Pro Cys Thr Ala Ser Gly Phe Ser Phe Gly Asp His
            20                  25                  30

Ala Met Ser Trp Val Arg Gln Ala Pro Gly Lys Gly Leu Glu Trp Val
            35                  40                  45

Gly Phe Ile Arg Lys Thr Thr Tyr Gly Ala Thr Thr Lys Tyr Ala Ala
    50                  55                  60
```

```
Ala Val Lys Gly Arg Phe Thr Ile Ser Arg Asp Asp Ser Lys Ser Ile
 65                  70                  75                  80

Val Tyr Leu Gln Met Asn Ser Leu Lys Thr Glu Asp Thr Ala Val Tyr
                 85                  90                  95

Phe Cys Thr Arg Val Gln Leu Asp Tyr Gly Pro Gly Tyr Gln Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
        195                 200                 205

Ile Cys Asn Val Asn His Lys Pro Ser Asn Thr Lys Val Asp Lys Lys
210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Leu His Glu Ala Leu His Ser His Tyr Thr Gln
        435                 440                 445

Lys Ser Leu Ser Leu Ser Pro Gly Lys
    450                 455

<210> SEQ ID NO 202
<211> LENGTH: 651
<212> TYPE: DNA
```

<213> ORGANISM: Artificial Sequence
<220> FEATURE:
<223> OTHER INFORMATION: Synthetic

<400> SEQUENCE: 202

```
gagtctgtgc tgacgcagcc gccctcagtg tctggggccc cagggcagag ggtcaccatc    60
tcctgcactg ggatgaactc caacatcggg gcaggttatg atgtatactg gtaccaacaa   120
cttccaggaa gagcccccaa actcctcatc tatggtaaca gcaatcggcc ctcaggggtc   180
cctgaccgat tctctggctc caggtctggc acctcagcct ccctggccat cactgggctc   240
caggctgagg atgaggctga ttattactgc cagtcctatg acaccagcct ggacggttgg   300
gctttcggcg agggaccaa gttgaccgtc ctaggccagc ccaaggctgc ccctcggtc    360
actctgttcc cacctcctc tgaggagctt caagccaaca ggccacact ggtgtgtctc    420
gtaagtgact tctacccggg agccgtgaca gtggcctgga aggcagatgg cagcccgtc    480
aaggtgggag tggagaccac caaaccctcc aaacaaagca caacaagta tgcggccagc    540
agctacctga gcctgacgcc cgagcagtgg aagtcccaca aagctacag ctgccgggtc    600
acgcatgaag ggagcaccgt ggagaagaca gtggcccctg cagaatgctc t            651
```

<210> SEQ ID NO 203
<211> LENGTH: 1371
<212> TYPE: DNA
<213> ORGANISM: Artificial Sequence
<220> FEATURE:
<223> OTHER INFORMATION: Synthetic

<400> SEQUENCE: 203

```
gaggtgcagc tggtggagtc tgggggaggc ttggtacagc cagggcggtc cctgagactc    60
ccctgtacag cctctgggtt tagttttggt gatcatgcta tgagctgggt ccgccaggct   120
ccagggaagg ggctggagtg ggtaggtttc attagaaaga caacttatgg tgcgacaaca   180
aagtacgccg cggctgtgaa gggcagattc accatctcgc gagatgattc taaaagcatt   240
gtctatctgc aaatgaacag cctgaaaacc gaggacacag ccgtgtattt ctgtactaga   300
gtgcagcttg actatggccc gggataccag tactacggta tggacgtctg gggccaaggg   360
accacggtca ccgtctcctc agcctccacc aagggcccat cggtcttccc cctggcaccc   420
tcctccaaga gcacctctgg gggcacagca gccctgggct gcctggtcaa ggactacttc   480
cccgaaccgg tgacggtgtc gtggaactca ggcgccctga ccagcggcgt gcacaccttc   540
ccggctgtcc tacagtcctc aggactctac tccctcagca gcgtggtgac cgtgccctcc   600
agcagcttgg gcacccagac ctacatctgc aacgtgaatc acaagcccag caacaccaag   660
gtggacaaga aagttgagcc caaatcttgt gacaaaactc acacatgccc accgtgccca   720
gcacctgaac tcctgggggg accgtcagtc ttcctcttcc ccccaaaacc caaggacacc   780
ctcatgatct cccggacccc tgaggtcaca tgcgtggtgg tggacgtgag ccacgaagac   840
cctgaggtca agttcaactg gtacgtggac ggcgtggagg tgcataatgc caagacaaag   900
ccgcgggagg agcagtacaa cagcacgtac cgtgtggtca gcgtcctcac cgtcctgcac   960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgccccat cccgggatga gctgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
```

```
accgtggaca agagcaggtg gcagcagggg aacgtcttct catgctccgt gatgcatgag      1320
gctctgcaca accactacac acagaagagc ctctccctgt ctccgggtaa a               1371
```

<210> SEQ ID NO 204
<211> LENGTH: 1371
<212> TYPE: DNA
<213> ORGANISM: Artificial Sequence
<220> FEATURE:
<223> OTHER INFORMATION: Synthetic

<400> SEQUENCE: 204

```
gaggtgcagc tggtggagtc tgggggaggc ttggtacagc cagggcggtc cctgagactc       60
ccctgtacag cctctgggtt tagttttggt gatcatgcta tgagctgggt ccgccaggct      120
ccagggaagg ggctggagtg ggtaggtttc attagaaaga caacttatgg tgcgacaaca      180
aagtacgccg cggctgtgaa gggcagattc accatctcgc gagatgattc aaaaagcatt      240
gtctatctgc aaatgaacag cctgaaaacc gaggacacag ccgtgtattt ctgtactaga      300
gtgcagcttg actatggccc gggataccag tactacggta tggacgtctg gggccaaggg      360
accacggtca ccgtctcctc agcctccacc aagggcccat cggtcttccc cctggcaccc      420
tcctccaaga gcacctctgg gggcacagca gccctgggct gcctggtcaa ggactacttc      480
cccgaaccgg tgacggtgtc gtggaactca ggcgccctga ccagcggcgt gcacaccttc      540
ccggctgtcc tacagtcctc aggactctac tccctcagca gcgtggtgac cgtgccctcc      600
agcagcttgg gcacccagac ctacatctgc aacgtgaatc acaagcccag caacaccaag      660
gtggacaaga agttgagccc aaatcttgt gacaaaactc acacatgccc accgtgccca      720
gcacctgaac tcctgggggg accgtcagtc ttcctcttcc ccccaaaacc caaggacacc      780
ctcatgatct cccggacccc tgaggtcaca tgcgtggtgg tggacgtgag ccacgaagac      840
cctgaggtca agttcaactg gtacgtggac ggcgtggagg tgcataatgc caagacaaag      900
ccgcgggagg agcagtacaa cagcacgtac cgtgtggtca gcgtcctcac cgtcctgcac      960
caggactggc tgaatggcaa ggagtacaag tgcaaggtct ccaacaaagc cctcccagcc     1020
cccatcgaga aaaccatctc caaagccaaa gggcagcccc gagaaccaca ggtgtacacc     1080
ctgcccccat cccgggatga gctgaccaag aaccaggtca gcctgacctg cctggtcaaa     1140
ggcttctatc ccagcgacat cgccgtggag tgggagagca atgggcagcc ggagaacaac     1200
tacaagacca cgcctcccgt gctggactcc gacggctcct tcttcctcta cagcaagctc     1260
accgtggaca gagcaggtg gcagcagggg aacgtcttct catgctccgt gctgcatgag     1320
gctctgcact cccactacac acagaagagc ctctccctgt ctccgggtaa a              1371
```

<210> SEQ ID NO 205
<211> LENGTH: 11
<212> TYPE: PRT
<213> ORGANISM: Artificial Sequence
<220> FEATURE:
<223> OTHER INFORMATION: Synthetic

<400> SEQUENCE: 205

```
Arg Ala Ser Gln Ser Ile Ser Ser Trp Leu Ala
1               5                   10
```

<210> SEQ ID NO 206
<211> LENGTH: 7
<212> TYPE: PRT
<213> ORGANISM: Artificial Sequence

```
<220> FEATURE:
<223> OTHER INFORMATION: Synthetic

<400> SEQUENCE: 206

Asp Ala Ser Ser Leu Glu Ser
1               5

<210> SEQ ID NO 207
<211> LENGTH: 10
<212> TYPE: PRT
<213> ORGANISM: Artificial Sequence
<220> FEATURE:
<223> OTHER INFORMATION: Synthetic

<400> SEQUENCE: 207

Gln Gln Tyr Asn Ser Tyr Ser Phe Trp Thr
1               5                   10

<210> SEQ ID NO 208
<211> LENGTH: 5
<212> TYPE: PRT
<213> ORGANISM: Artificial Sequence
<220> FEATURE:
<223> OTHER INFORMATION: Synthetic

<400> SEQUENCE: 208

Thr Tyr Gly Met His
1               5

<210> SEQ ID NO 209
<211> LENGTH: 17
<212> TYPE: PRT
<213> ORGANISM: Artificial Sequence
<220> FEATURE:
<223> OTHER INFORMATION: Synthetic

<400> SEQUENCE: 209

Ile Ile Trp Tyr Asp Gly Ser Gln Lys Tyr Tyr Ala Asp Ser Val Gln
1               5                   10                  15

Gly

<210> SEQ ID NO 210
<211> LENGTH: 14
<212> TYPE: PRT
<213> ORGANISM: Artificial Sequence
<220> FEATURE:
<223> OTHER INFORMATION: Synthetic

<400> SEQUENCE: 210

Val Arg Phe Ser Val Gly Pro His Gly Ser Ala Phe Asp Leu
1               5                   10

<210> SEQ ID NO 211
<211> LENGTH: 11
<212> TYPE: PRT
<213> ORGANISM: Artificial Sequence
<220> FEATURE:
<223> OTHER INFORMATION: Synthetic

<400> SEQUENCE: 211

Arg Ala Ser Gln Ser Ile Ser Ser Trp Leu Ala
1               5                   10

<210> SEQ ID NO 212
<211> LENGTH: 7
<212> TYPE: PRT
```

```
<213> ORGANISM: Artificial Sequence
<220> FEATURE:
<223> OTHER INFORMATION: Synthetic

<400> SEQUENCE: 212

Asp Ala Ser Ser Leu Glu Ser
1               5

<210> SEQ ID NO 213
<211> LENGTH: 11
<212> TYPE: PRT
<213> ORGANISM: Artificial Sequence
<220> FEATURE:
<223> OTHER INFORMATION: Synthetic

<400> SEQUENCE: 213

Gln Gln Tyr Asn Ser Tyr Ser Phe Trp Thr Phe
1               5                   10

<210> SEQ ID NO 214
<211> LENGTH: 5
<212> TYPE: PRT
<213> ORGANISM: Artificial Sequence
<220> FEATURE:
<223> OTHER INFORMATION: Synthetic

<400> SEQUENCE: 214

Thr Tyr Gly Met His
1               5

<210> SEQ ID NO 215
<211> LENGTH: 17
<212> TYPE: PRT
<213> ORGANISM: Artificial Sequence
<220> FEATURE:
<223> OTHER INFORMATION: Synthetic

<400> SEQUENCE: 215

Ile Ile Trp Tyr Asp Gly Ser Gln Lys Tyr Tyr Ala Asp Ser Val Gln
1               5                   10                  15

Gly

<210> SEQ ID NO 216
<211> LENGTH: 5
<212> TYPE: PRT
<213> ORGANISM: Artificial Sequence
<220> FEATURE:
<223> OTHER INFORMATION: Synthetic

<400> SEQUENCE: 216

Ser Ala Phe Asp Leu
1               5

<210> SEQ ID NO 217
<211> LENGTH: 109
<212> TYPE: PRT
<213> ORGANISM: Artificial Sequence
<220> FEATURE:
<223> OTHER INFORMATION: Synthetic

<400> SEQUENCE: 217

Gly Val Gln Met Thr Gln Ser Pro Ser Thr Leu Ser Ala Ser Val Gly
1               5                   10                  15

Asp Arg Val Thr Leu Thr Cys Arg Ala Ser Gln Ser Ile Ser Ser Trp
            20                  25                  30
```

Leu Ala Trp Tyr Gln Gln Lys Pro Gly Lys Ala Pro Lys Leu Leu Ile
         35                  40                  45

Tyr Asp Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Ser Phe
                 85                  90                  95

Trp Thr Phe Gly Gln Gly Thr Lys Val Glu Ile Lys Arg
            100                 105

<210> SEQ ID NO 218
<211> LENGTH: 123
<212> TYPE: PRT
<213> ORGANISM: Artificial Sequence
<220> FEATURE:
<223> OTHER INFORMATION: Synthetic

<400> SEQUENCE: 218

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Ala Phe Asn Thr Tyr
             20                  25                  30

Gly Met His Trp Val Arg Gln Thr Pro Gly Lys Gly Leu Glu Trp Val
         35                  40                  45

Ala Ile Ile Trp Tyr Asp Gly Ser Gln Lys Tyr Tyr Ala Asp Ser Val
 50                  55                  60

Gln Gly Arg Phe Ile Ile Ser Arg Asp Asn Lys Asn Thr Leu Ser
 65                  70                  75                  80

Leu Gln Met Asn Gly Leu Arg Ala Glu Asp Thr Ala Val Tyr Phe Cys
                 85                  90                  95

Val Arg Val Arg Phe Ser Val Gly Pro His Gly Ser Ala Phe Asp Leu
            100                 105                 110

Trp Gly Gln Gly Thr Met Val Ile Val Ser Ser
        115                 120

<210> SEQ ID NO 219
<211> LENGTH: 327
<212> TYPE: DNA
<213> ORGANISM: Artificial Sequence
<220> FEATURE:
<223> OTHER INFORMATION: Synthetic

<400> SEQUENCE: 219
ggcgtccaga tgacccagtc tccttccacc ctgtctgcat ctgtgggaga cagagtcacc    60
ctcacttgcc gggccagtca gagtattagt agttggttgg cctggtatca gcagaaacca   120
gggaaagccc ctaaactcct gatctatgat gcctccagtt tggaaagtgg ggtcccatca   180
aggttcagcg gcagtggatc tgggacagaa ttcactctca ccatcagcag cctgcaacct   240
gatgattttg caacttatta ctgccaacag tataatagtt attcttttg gacgttcggc    300 caagggacca aggtggaaat caaacgc                                        327

<210> SEQ ID NO 220
<211> LENGTH: 369
<212> TYPE: DNA
<213> ORGANISM: Artificial Sequence
<220> FEATURE:
<223> OTHER INFORMATION: Synthetic -continued

<400> SEQUENCE: 220

```
caggtgcaac tggtggagtc tgggggaggc gtggtccagc ctgggaggtc cctgagactc    60
tcctgtgcag cgtctgggtt cgctttcaat acctatggca tgcactgggt ccgccagact   120
ccaggcaagg ggctggagtg ggtggcaatt atctggtatg atgggagcca gaaatactat   180
gcagactccg tgcagggccg attcatcatc tccagagaca atcacaagaa cacgttgtct   240
ctgcaaatga acggcctgag agccgaggac acggctgtgt atttctgtgt gagagtccgc   300
tttagcgttg gcccccacgg gagtgctttt gatctctggg gccaggggac aatggtcatc   360
gtctcttca                                                           369
```

<210> SEQ ID NO 221
<211> LENGTH: 215
<212> TYPE: PRT
<213> ORGANISM: Artificial Sequence
<220> FEATURE:
<223> OTHER INFORMATION: Synthetic

<400> SEQUENCE: 221

Gly Val Gln Met Thr Gln Ser Pro Ser Thr Leu Ser Ala Ser Val Gly
1               5                   10                  15

Asp Arg Val Thr Leu Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Phe
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 222
<211> LENGTH: 453
<212> TYPE: PRT
<213> ORGANISM: Artificial Sequence
<220> FEATURE:
<223> OTHER INFORMATION: Synthetic

<400> SEQUENCE: 222

Gln Val Gln Leu Val Glu Ser Gly Gly Gly Val Val Gln Pro Gly Arg

-continued

```
1               5                   10                  15
Ser Leu Arg Leu Ser Cys Ala Ala Ser Gly Phe Ala Phe Asn Thr Tyr
            20                  25                  30
Gly Met His Trp Val Arg Gln Thr Pro Gly Lys Gly Leu Glu Trp Val
            35                  40                  45
Ala Ile Ile Trp Tyr Asp Gly Ser Gln Lys Tyr Tyr Ala Asp Ser Val
            50                  55                  60
Gln Gly Arg Phe Ile Ile Ser Arg Asp Asn His Lys Asn Thr Leu Ser
65                  70                  75                  80
Leu Gln Met Asn Gly Leu Arg Ala Glu Asp Thr Ala Val Tyr Phe Cys
                85                  90                  95
Val Arg Val Arg Phe Ser Val Gly Pro His Gly Ser Ala Phe Asp Leu
                100                 105                 110
Trp Gly Gln Gly Thr Met Val Ile Val Ser Ser Ala Ser Thr Lys Gly
                115                 120                 125
Pro Ser Val Phe Pro Leu Ala Pro Ser Ser Lys Ser Thr Ser Gly Gly
                130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
                180                 185                 190
Thr Val Pro Ser Ser Ser Leu Gly Thr Gln Thr Tyr Ile Cys Asn Val
                195                 200                 205
Asn His Lys Pro Ser Asn Thr Lys Val Asp Lys Lys Val Glu Pro Lys
                210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
                260                 265                 270
Ser His Glu Asp Pro Glu Val Lys Phe Asn Trp Tyr Val Asp Gly Val
                275                 280                 285
Glu Val His Asn Ala Lys Thr Lys Pro Arg Glu Glu Gln Tyr Asn Ser
                290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
                340                 345                 350
Gln Val Tyr Thr Leu Pro Pro Ser Arg Asp Glu Leu Thr Lys Asn Gln
                355                 360                 365
Val Ser Leu Thr Cys Leu Val Lys Gly Phe Tyr Pro Ser Asp Ile Ala
                370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
                420                 425                 430
```

```
Val Met His Glu Ala Leu His Asn His Tyr Thr Gln Lys Ser Leu Ser
        435                 440                 445

Leu Ser Pro Gly Lys
    450
```

<210> SEQ ID NO 223
<211> LENGTH: 453
<212> TYPE: PRT
<213> ORGANISM: Artificial Sequence
<220> FEATURE:
<223> OTHER INFORMATION: Synthetic

<400> SEQUENCE: 223

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Asn Thr Tyr
                20                  25                  30

Gly Met His Trp Val Arg Gln Thr Pro Gly Lys Gly Leu Glu Trp Val
            35                  40                  45

Ala Ile Ile Trp Tyr Asp Gly Ser Gln Lys Tyr Tyr Ala Asp Ser Val
        50                  55                  60

Gln Gly Arg Phe Ile Ile Ser Arg Asp Asn His Lys Asn Thr Leu Ser
65                  70                  75                  80

Leu Gln Met Asn Gly Leu Arg Ala Glu Asp Thr Ala Val Tyr Phe Cys
                85                  90                  95

Val Arg Val Arg Phe Ser Val Gly Pro His Gly Ser Ala Phe Asp Leu
            100                 105                 110

Trp Gly Gln Gly Thr Met Val Ile Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335
```

```
Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Leu His Glu Ala Leu His Ser His Tyr Thr Gln Lys Ser Leu Ser
        435                 440                 445

Leu Ser Pro Gly Lys
    450
```

```
<210> SEQ ID NO 224
<211> LENGTH: 645
<212> TYPE: DNA
<213> ORGANISM: Artificial Sequence
<220> FEATURE:
<223> OTHER INFORMATION: Synthetic

<400> SEQUENCE: 224
ggcgtccaga tgacccagtc tccttccacc ctgtctgcat ctgtgggaga cagagtcacc      60
ctcacttgcc gggccagtca gagtattagt agttggttgg cctggtatca gcagaaacca    120
gggaaagccc ctaaactcct gatctatgat gcctccagtt tggaaagtgg ggtcccatca    180
aggttcagcg gcagtggatc tgggacagaa ttcactctca ccatcagcag cctgcaacct    240
gatgattttg caacttatta ctgccaacag tataatagtt attcttttg gacgttcggc    300 caagggacca aggtggaaat caaacgcact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgt                     645
```

```
<210> SEQ ID NO 225
<211> LENGTH: 1359
<212> TYPE: DNA
<213> ORGANISM: Artificial Sequence
<220> FEATURE:
<223> OTHER INFORMATION: Synthetic

<400> SEQUENCE: 225
caggtgcaac tggtggagtc tgggggaggc gtggtccagc ctggaggtc cctgagactc      60 tcctgtgcag cgtctgggtt cgctttcaat acctatggca tgcactgggt ccgccagact    120
ccaggcaagg gctggagtg gtggcaatt atctggtatg atgggagcca gaaatactat    180
gcagactccg tgcagggccg attcatcatc tccagagaca atcacaagaa cacgttgtct    240
ctgcaaatga acggcctgag agccgaggac acggctgtgt attctgtgt gagagtccgc    300 tttagcgttg gcccccacgg gagtgctttt gatctctggg gccaggggac aatggtcatc    360
```

```
gtctcttcag cctccaccaa gggcccatcg gtcttccccc tggcaccctc ctccaagagc      420
acctctgggg gcacagcagc cctgggctgc ctggtcaagg actacttccc cgaaccggtg      480
acggtgtcgt ggaactcagg cgccctgacc agcggcgtgc acaccttccc ggctgtccta      540
cagtcctcag gactctactc cctcagcagc gtggtgaccg tgccctccag cagcttgggc      600
acccagacct acatctgcaa cgtgaatcac aagcccagca acaccaaggt ggacaagaaa      660
gttgagccca atcttgtgac aaaactcaca catgcccacc gtgcccagca cctgaactc       720 ctgggggac cgtcagtctt cctcttcccc ccaaaaccca aggacaccct catgatctcc       780 cggaccctg aggtcacatg cgtggtggtg gacgtgagcc acgaagaccc tgaggtcaag       840
ttcaactggt acgtggacgg cgtggaggtg cataatgcca agacaaagcc gcgggaggag      900
cagtacaaca gcacgtaccg tgtggtcagc gtcctcaccg tcctgcacca ggactggctg      960
aatggcaagg agtacaagtg caaggtctcc aacaaagccc tcccagcccc catcgagaaa      1020
accatctcca agccaaaagg gcagccccga gaaccacagg tgtacaccct gcccccatcc      1080
cgggatgagc tgaccaagaa ccaggtcagc ctgacctgcc tggtcaaagg cttctatccc      1140
agcgacatcg ccgtggagtg ggagagcaat gggcagccgg agaacaacta caagaccacg      1200
cctcccgtgc tggactccga cggctccttc ttcctctaca gcaagctcac cgtggacaag      1260
agcaggtggc agcaggggaa cgtcttctca tgctccgtga tgcatgaggc tctgcacaac      1320
cactacacac agaagagcct ctccctgtct ccgggtaaa                             1359

<210> SEQ ID NO 226
<211> LENGTH: 1359
<212> TYPE: DNA
<213> ORGANISM: Artificial Sequence
<220> FEATURE:
<223> OTHER INFORMATION: Synthetic

<400> SEQUENCE: 226
caggtgcaac tggtggagtc tgggggaggc gtggtccagc ctgggaggtc cctgagactc       60
tcctgtgcag cgtctgggtt cgctttcaat acctatggca tgcactgggt ccgccagact      120
ccaggcaagg ggctggagtg ggtggcaatt atctggtatg atgggagcca gaaatactat      180
gcagactccg tgcagggccg attcatcatc tccagagaca atcacaagaa cacgttgtct      240
ctgcaaatga acggcctgag agccgaggac acggctgtgt atttctgtgt gagagtccgc      300
tttagcgttg gccccacgg gagtgctttt gatctctggg gccaggggac aatggtcatc       360
gtctcttcag cctccaccaa gggcccatcg gtcttccccc tggcaccctc ctccaagagc      420
acctctgggg gcacagcagc cctgggctgc ctggtcaagg actacttccc cgaaccggtg      480
acggtgtcgt ggaactcagg cgccctgacc agcggcgtgc acaccttccc ggctgtccta      540
cagtcctcag gactctactc cctcagcagc gtggtgaccg tgccctccag cagcttgggc      600
acccagacct acatctgcaa cgtgaatcac aagcccagca acaccaaggt ggacaagaaa      660
gttgagccca atcttgtgac aaaactcaca catgcccacc gtgcccagca cctgaactc       720 ctgggggac cgtcagtctt cctcttcccc ccaaaaccca aggacaccct catgatctcc       780 cggaccctg aggtcacatg cgtggtggtg gacgtgagcc acgaagaccc tgaggtcaag       840
ttcaactggt acgtggacgg cgtggaggtg cataatgcca agacaaagcc gcgggaggag      900
cagtacaaca gcacgtaccg tgtggtcagc gtcctcaccg tcctgcacca ggactggctg      960
aatggcaagg agtacaagtg caaggtctcc aacaaagccc tcccagcccc catcgagaaa      1020
accatctcca agccaaaagg gcagccccga gaaccacagg tgtacaccct gcccccatcc      1080
```

```
cgggatgagc tgaccaagaa ccaggtcagc ctgacctgcc tggtcaaagg cttctatccc    1140
agcgacatcg ccgtggagtg ggagagcaat gggcagccgg agaacaacta caagaccacg    1200
cctcccgtgc tggactccga cggctccttc ttcctctaca gcaagctcac cgtggacaag    1260
agcaggtggc agcaggggaa cgtcttctca tgctccgtgc tgcatgaggc tctgcactcc    1320
cactacacac agaagagcct ctccctgtct ccgggtaaa                           1359
```

<210> SEQ ID NO 227
<211> LENGTH: 109
<212> TYPE: PRT
<213> ORGANISM: Artificial Sequence
<220> FEATURE:
<223> OTHER INFORMATION: Synthetic

<400> SEQUENCE: 227

Gly Val Gln Met Thr Gln Ser Pro Ser Thr Leu Ser Ala Ser Val Gly
1               5                   10                  15

Asp Arg Val Thr Leu Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Phe
                85                  90                  95

Trp Thr Phe Gly Gln Gly Thr Lys Val Glu Ile Lys Arg
            100                 105

<210> SEQ ID NO 228
<211> LENGTH: 123
<212> TYPE: PRT
<213> ORGANISM: Artificial Sequence
<220> FEATURE:
<223> OTHER INFORMATION: Synthetic

<400> SEQUENCE: 228

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Asn Thr Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Ser Gln Lys Tyr Tyr Ala Asp Ser Val
    50                  55                  60

Gln Gly Arg Phe Ile Ile Ser Arg Asp Asn His Lys Asn Thr Leu Ser
65                  70                  75                  80

Leu Gln Met Asn Ser Leu Arg Ala Glu Asp Thr Ala Val Tyr Phe Cys
                85                  90                  95

Val Arg Val Arg Phe Ser Val Gly Pro His Gly Ser Ala Phe Asp Leu
            100                 105                 110

Trp Gly Gln Gly Thr Met Val Thr Val Ser Ser
        115                 120

<210> SEQ ID NO 229
<211> LENGTH: 327

```
<212> TYPE: DNA
<213> ORGANISM: Artificial Sequence
<220> FEATURE:
<223> OTHER INFORMATION: Synthetic

<400> SEQUENCE: 229
ggcgtccaga tgacccagtc tccttccacc ctgtctgcat ctgtgggaga cagagtcacc      60
ctcacttgcc gggccagtca gagtattagt agttggttgg cctggtatca gcagaaacca     120
gggaaagccc ctaaactcct gatctatgat gcctccagtt tggaaagtgg ggtcccatca     180
aggttcagcg gcagtggatc tgggacagaa ttcactctca ccatcagcag cctgcaacct     240
gatgattttg caacttatta ctgccaacag tataatagtt attcttttg dacgttcggc      300 caagggacca aggtggaaat caaacgc                                         327

<210> SEQ ID NO 230
<211> LENGTH: 369
<212> TYPE: DNA
<213> ORGANISM: Artificial Sequence
<220> FEATURE:
<223> OTHER INFORMATION: Synthetic

<400> SEQUENCE: 230
caggtgcaac tggtggagtc tgggggaggc gtggtccagc ctgggaggtc cctgagactc      60
tcctgtgcag cgtctgggtt cgctttcaat acctatggca tgcactgggt ccgccaggca    120
ccaggcaagg ggctggagtg ggtggcaatt atctggtatg atgggagcca gaaatactat    180
gcagactccg tgcagggccg attcatcatc tccagagaca atcacaagaa cacgttgtct    240
ctgcaaatga actccctgag agccgaggac acggctgtgt atttctgtgt gagagtccgc    300
tttagcgttg gccccacgg gagtgctttt gatctctggg gccaggggac aatggtcaca    360
gtctcttca                                                           369

<210> SEQ ID NO 231
<211> LENGTH: 215
<212> TYPE: PRT
<213> ORGANISM: Artificial Sequence
<220> FEATURE:
<223> OTHER INFORMATION: Synthetic

<400> SEQUENCE: 231

Gly Val Gln Met Thr Gln Ser Pro Ser Thr Leu Ser Ala Ser Val Gly
1               5                  10                  15

Asp Arg Val Thr Leu Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Phe
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140
```

```
Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
        180                 185                 190

Tyr Ala Cys Glu Val Thr His Gln Gly Leu Ser Ser Pro Val Thr Lys
    195                 200                 205

Ser Phe Asn Arg Gly Glu Cys
    210                 215

<210> SEQ ID NO 232
<211> LENGTH: 453
<212> TYPE: PRT
<213> ORGANISM: Artificial Sequence
<220> FEATURE:
<223> OTHER INFORMATION: Synthetic

<400> SEQUENCE: 232

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Asn Thr Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Ser Gln Lys Tyr Tyr Ala Asp Ser Val
    50                  55                  60

Gln Gly Arg Phe Ile Ile Ser Arg Asp Asn His Lys Asn Thr Leu Ser
65                  70                  75                  80

Leu Gln Met Asn Ser Leu Arg Ala Glu Asp Thr Ala Val Tyr Phe Cys
                85                  90                  95

Val Arg Val Arg Phe Ser Val Gly Pro His Gly Ser Ala Phe Asp Leu
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
        180                 185                 190

Thr Val Pro Ser Ser Ser Leu Gly Thr Gln Thr Tyr Ile Cys Asn Val
    195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
        260                 265                 270

Ser His Glu Asp Pro Glu Val Lys Phe Asn Trp Tyr Val Asp Gly Val
    275                 280                 285
```

Glu Val His Asn Ala Lys Thr Lys Pro Arg Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 233
<211> LENGTH: 453
<212> TYPE: PRT
<213> ORGANISM: Artificial Sequence
<220> FEATURE:
<223> OTHER INFORMATION: Synthetic

<400> SEQUENCE: 233

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Asn Thr Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Ser Gln Lys Tyr Tyr Ala Asp Ser Val
    50                  55                  60

Gln Gly Arg Phe Ile Ile Ser Arg Asp Asn His Lys Asn Thr Leu Ser
65                  70                  75                  80

Leu Gln Met Asn Ser Leu Arg Ala Glu Asp Thr Ala Val Tyr Phe Cys
                85                  90                  95

Val Arg Val Arg Phe Ser Val Gly Pro His Gly Ser Ala Phe Asp Leu
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Leu Gly Thr Gln Thr Tyr Ile Cys Asn Val
        195                 200                 205

Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Leu His Glu Ala Leu His Ser His Tyr Thr Gln Lys Ser Leu Ser
        435                 440                 445

Leu Ser Pro Gly Lys
    450

<210> SEQ ID NO 234
<211> LENGTH: 645
<212> TYPE: DNA
<213> ORGANISM: Artificial Sequence
<220> FEATURE:
<223> OTHER INFORMATION: Synthetic

<400> SEQUENCE: 234
ggcgtccaga tgacccagtc tccttccacc ctgtctgcat ctgtgggaga cagagtcacc    60
ctcacttgcc gggccagtca gagtattagt agttggttgg cctggtatca gcagaaacca   120
gggaaagccc ctaaactcct gatctatgat gcctccagtt tggaaagtgg ggtcccatca   180
aggttcagcg gcagtggatc tgggacagaa ttcactctca ccatcagcag cctgcaacct   240
gatgattttg caacttatta ctgccaacag tataatagtt attcttttg gacgttcggc   300 caagggacca aggtggaaat caaacgcact gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540

| | |
|---|---|
| acgctgagca aagcagacta cgagaaacac aaagtctacg cctgcgaagt cacccatcag | 600 |
| ggcctgagct cgcccgtcac aaagagcttc aacaggggag agtgt | 645 |

<210> SEQ ID NO 235
<211> LENGTH: 1359
<212> TYPE: DNA
<213> ORGANISM: Artificial Sequence
<220> FEATURE:
<223> OTHER INFORMATION: Synthetic

<400> SEQUENCE: 235

| | |
|---|---|
| caggtgcaac tggtggagtc tgggggaggc gtggtccagc ctgggaggtc cctgagactc | 60 |
| tcctgtgcag cgtctgggtt cgctttcaat acctatggca tgcactgggt ccgccaggca | 120 |
| ccaggcaagg ggctggagtg ggtggcaatt atctggtatg atgggagcca gaaatactat | 180 |
| gcagactccg tgcagggccg attcatcatc tccagagaca atcacaagaa cacgttgtct | 240 |
| ctgcaaatga actccctgag agccgaggac acggctgtgt atttctgtgt gagagtccgc | 300 |
| tttagcgttg gcccccacgg gagtgctttt gatctctggg gccaggggac aatggtcaca | 360 |
| gtctcttcag cctccaccaa gggcccatcg gtcttccccc tggcaccctc ctccaagagc | 420 |
| acctctgggg gcacagcagc cctgggctgc ctggtcaagg actacttccc cgaaccggtg | 480 |
| acggtgtcgt ggaactcagg cgccctgacc agcggcgtgc acaccttccc ggctgtccta | 540 |
| cagtcctcag gactctactc cctcagcagc gtggtgaccg tgccctccag cagcttgggc | 600 |
| acccagacct acatctgcaa cgtgaatcac aagcccagca caccaaggt ggacaagaaa | 660 |
| gttgagccca aatcttgtga caaaactcac acatgcccac cgtgcccagc acctgaactc | 720 |
| ctggggggac cgtcagtctt cctcttcccc ccaaaaccca aggacaccct catgatctcc | 780 |
| cggacccctg aggtcacatg cgtggtggtg gacgtgagcc acgaagaccc tgaggtcaag | 840 |
| ttcaactggt acgtggacgg cgtggaggtg cataatgcca agacaaagcc gcgggaggag | 900 |
| cagtacaaca gcacgtaccg tgtggtcagc gtcctcaccg tcctgcacca ggactggctg | 960 |
| aatggcaagg agtacaagtg caaggtctcc aacaaagccc tcccagcccc catcgagaaa | 1020 |
| accatctcca aagccaaagg gcagccccga gaaccacagg tgtacaccct gcccccatcc | 1080 |
| cgggatgagc tgaccaagaa ccaggtcagc ctgacctgcc tggtcaaagg cttctatccc | 1140 |
| agcgacatcg ccgtggagtg ggagagcaat gggcagccgg agaacaacta caagaccacg | 1200 |
| cctcccgtgc tggactccga cggctccttc ttcctctaca gcaagctcac cgtggacaag | 1260 |
| agcaggtgg agcaggggaa cgtcttctca tgctccgtga tgcatgaggc tctgcacaac | 1320 |
| cactacacac agaagagcct ctccctgtct ccgggtaaa | 1359 |

<210> SEQ ID NO 236
<211> LENGTH: 1359
<212> TYPE: DNA
<213> ORGANISM: Artificial Sequence
<220> FEATURE:
<223> OTHER INFORMATION: Synthetic

<400> SEQUENCE: 236

| | |
|---|---|
| caggtgcaac tggtggagtc tgggggaggc gtggtccagc ctgggaggtc cctgagactc | 60 |
| tcctgtgcag cgtctgggtt cgctttcaat acctatggca tgcactgggt ccgccaggca | 120 |
| ccaggcaagg ggctggagtg ggtggcaatt atctggtatg atgggagcca gaaatactat | 180 |
| gcagactccg tgcagggccg attcatcatc tccagagaca atcacaagaa cacgttgtct | 240 |

```
ctgcaaatga actccctgag agccgaggac acggctgtgt atttctgtgt gagagtccgc    300
tttagcgttg gcccccacgg gagtgctttt gatctctggg gccaggggac aatggtcaca    360
gtctcttcag cctccaccaa gggcccatcg gtcttccccc tggcaccctc ctccaagagc    420
acctctgggg gcacagcagc cctgggctgc ctggtcaagg actacttccc cgaaccggtg    480
acggtgtcgt ggaactcagg cgccctgacc agcggcgtgc acaccttccc ggctgtccta    540
cagtcctcag gactctactc cctcagcagc gtggtgaccg tgccctccag cagcttgggc    600
acccagacct acatctgcaa cgtgaatcac aagcccagca caccaaggt ggacaagaaa    660 gttgagccca atcttgtga caaaactcac acatgcccac cgtgcccagc acctgaactc    720
ctggggggac cgtcagtctt cctcttcccc ccaaaaccca aggacaccct catgatctcc    780
cggacccctg aggtcacatg cgtggtggtg gacgtgagcc acgaagaccc tgaggtcaag    840
ttcaactggt acgtggacgg cgtggaggtg cataatgcca agacaaagcc gcgggaggag    900
cagtacaaca gcacgtaccg tgtggtcagc gtcctcaccg tcctgcacca ggactggctg    960
aatggcaagg agtacaagtg caaggtctcc aacaaagccc tcccagcccc catcgagaaa   1020
accatctcca aagccaaagg gcagccccga gaaccacagg tgtacaccct gcccccatcc   1080
cgggatgagc tgaccaagaa ccaggtcagc ctgacctgcc tggtcaaagg cttctatccc   1140
agcgacatcg ccgtggagtg ggagagcaat gggcagccgg agaacaacta caagaccacg   1200
cctcccgtgc tggactccga cggctccttc ttcctctaca gcaagctcac cgtggacaag   1260
agcaggtggc agcaggggaa cgtcttctca tgctccgtgc tgcatgaggc tctgcactcc   1320
cactacacac agaagagcct ctccctgtct ccgggtaaa                         1359

<210> SEQ ID NO 237
<211> LENGTH: 109
<212> TYPE: PRT
<213> ORGANISM: Artificial Sequence
<220> FEATURE:
<223> OTHER INFORMATION: Synthetic

<400> SEQUENCE: 237

Gly Val Gln Met Thr Gln Ser Pro Ser Thr Leu Ser Ala Ser Val Gly
1               5                   10                  15

Asp Arg Val Thr Leu Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Phe
                85                  90                  95

Trp Thr Phe Gly Gln Gly Thr Lys Val Glu Ile Lys Arg
            100                 105

<210> SEQ ID NO 238
<211> LENGTH: 123
<212> TYPE: PRT
<213> ORGANISM: Artificial Sequence
<220> FEATURE:
<223> OTHER INFORMATION: Synthetic

<400> SEQUENCE: 238
```

-continued

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Asn Thr Tyr
            20                  25                  30

Gly Met His Trp Val Arg Gln Ala Pro Gly Lys Gly Leu Glu Trp Val
            35                  40                  45

Ala Ile Ile Trp Tyr Asp Gly Ser Gln Lys Tyr Tyr Ala Asp Ser Val
50                  55                  60

Gln Gly Arg Phe Ile Ile Ser Arg Asp Asn His Lys Asn Thr Leu Ser
65                  70                  75                  80

Leu Gln Met Asn Ser Leu Arg Ala Glu Asp Thr Ala Val Tyr Phe Cys
            85                  90                  95

Val Arg Val Arg Phe Ser Val Gly Pro His Gly Ser Ala Phe Asp Leu
            100                 105                 110

Trp Gly Gln Gly Thr Met Val Thr Val Ser Ser
            115                 120
```

<210> SEQ ID NO 239
<211> LENGTH: 327
<212> TYPE: DNA
<213> ORGANISM: Artificial Sequence
<220> FEATURE:
<223> OTHER INFORMATION: Synthetic

<400> SEQUENCE: 239

```
ggcgtccaga tgacccagtc tccttccacc ctgtctgcat ctgtgggaga cagagtcacc    60
ctcacttgcc gggccagtca gagtattagt agttggttgg cctggtatca gcagaaacca   120
gggaaagccc ctaaactcct gatctatgat gcctccagtt tggaaagtgg ggtcccatca   180
aggttcagcg gcagtggatc tgggacagaa ttcactctca ccatcagcag cctgcaacct   240
gatgattttg caacttatta ctgccaacag tataatagtt attcttttg gacgttcggc    300
caagggacca aggtggaaat caaacgc                                        327
```

<210> SEQ ID NO 240
<211> LENGTH: 369
<212> TYPE: DNA
<213> ORGANISM: Artificial Sequence
<220> FEATURE:
<223> OTHER INFORMATION: Synthetic

<400> SEQUENCE: 240

```
caggtgcaac tggtggagtc tgggggaggc gtggtccagc ctgggaggtc cctgagactc    60
tcctgtgcag cgtctgggtt cactttcaat acctatggca tgcactgggt ccgccaggca   120
ccaggcaagg ggctggagtg ggtggcaatt atctggtatg atgggagcca gaaatactat   180
gcagactccg tgcagggccg attcatcatc tccagagaca atcacaagaa cacgttgtct   240
ctgcaaatga actccctgag agccgaggac acggctgtgt atttctgtgt gagagtccgc   300
tttagcgttg gccccacgg gagtgctttt gatctctggg gccagggac aatggtcaca    360
gtctcttca                                                           369
```

<210> SEQ ID NO 241
<211> LENGTH: 215
<212> TYPE: PRT
<213> ORGANISM: Artificial Sequence
<220> FEATURE:
<223> OTHER INFORMATION: Synthetic

<400> SEQUENCE: 241

Gly Val Gln Met Thr Gln Ser Pro Ser Thr Leu Ser Ala Ser Val Gly
1               5                   10                  15

Asp Arg Val Thr Leu Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65              70                  75                  80

Asp Asp Phe Ala Thr Tyr Tyr Cys Gln Gln Tyr Asn Ser Tyr Ser Phe
            85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 242
<211> LENGTH: 453
<212> TYPE: PRT
<213> ORGANISM: Artificial Sequence
<220> FEATURE:
<223> OTHER INFORMATION: Synthetic

<400> SEQUENCE: 242

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Thr Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Ser Gln Lys Tyr Tyr Ala Asp Ser Val
    50                  55                  60

Gln Gly Arg Phe Ile Ile Ser Arg Asp Asn His Lys Asn Thr Leu Ser
65              70                  75                  80

Leu Gln Met Asn Ser Leu Arg Ala Glu Asp Thr Ala Val Tyr Phe Cys
            85                  90                  95

Val Arg Val Arg Phe Ser Val Gly Pro His Gly Ser Ala Phe Asp Leu
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys
    450

<210> SEQ ID NO 243
<211> LENGTH: 453
<212> TYPE: PRT
<213> ORGANISM: Artificial Sequence
<220> FEATURE:
<223> OTHER INFORMATION: Synthetic

<400> SEQUENCE: 243

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Thr Tyr
            20                  25                  30

Gly Met His Trp Val Arg Gln Ala Pro Gly Lys Gly Leu Glu Trp Val
        35                  40                  45

```
Ala Ile Ile Trp Tyr Asp Gly Ser Gln Lys Tyr Tyr Ala Asp Ser Val
         50                  55                  60

Gln Gly Arg Phe Ile Ile Ser Arg Asp Asn His Lys Asn Thr Leu Ser
 65                  70                  75                  80

Leu Gln Met Asn Ser Leu Arg Ala Glu Asp Thr Ala Val Tyr Phe Cys
                 85                  90                  95

Val Arg Val Arg Phe Ser Val Gly Pro His Gly Ser Ala Phe Asp Leu
            100                 105                 110

Trp Gly Gln Gly Thr Met Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Leu His Glu Ala Leu His Ser His Tyr Thr Gln Lys Ser Leu Ser
        435                 440                 445

Leu Ser Pro Gly Lys
    450
```

<210> SEQ ID NO 244
<211> LENGTH: 645
<212> TYPE: DNA
<213> ORGANISM: Artificial Sequence
<220> FEATURE:
<223> OTHER INFORMATION: Synthetic

<400> SEQUENCE: 244

```
ggcgtccaga tgacccagtc tccttccacc ctgtctgcat ctgtgggaga cagagtcacc    60
ctcacttgcc gggccagtca gagtattagt agttggttgg cctggtatca gcagaaacca   120
gggaaagccc ctaaactcct gatctatgat gcctccagtt tggaaagtgg ggtcccatca   180
aggttcagcg gcagtggatc tgggacagaa ttcactctca ccatcagcag cctgcaacct   240
gatgattttg caacttatta ctgccaacag tataatagtt attcttttg gacgttcggc   300
caagggacca aggtggaaat caaacgcact gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag acagcacct acagcctcag cagcaccctg   540
acgctgagca aagcagacta cgagaaacac aaagtctacg cctgcgaagt cacccatcag   600
ggcctgagct cgcccgtcac aaagagcttc aacaggggag agtgt                  645
```

<210> SEQ ID NO 245
<211> LENGTH: 1359
<212> TYPE: DNA
<213> ORGANISM: Artificial Sequence
<220> FEATURE:
<223> OTHER INFORMATION: Synthetic

<400> SEQUENCE: 245

```
caggtgcaac tggtggagtc tgggggaggc gtggtccagc ctgggaggtc cctgagactc    60
tcctgtgcag cgtctgggtt cactttcaat acctatggca tgcactgggt ccgccaggca   120
ccaggcaagg ggctggagtg ggtggcaatt atctggtatg atgggagcca gaaatactat   180
gcagactccg tgcagggccg attcatcatc tccagagaca tcacaagaa cacgttgtct   240
ctgcaaatga actccctgag agccgaggac acggctgtgt atttctgtgt gagagtccgc   300
tttagcgttg gccccacgg gagtgctttt gatctctggg gccaggggac aatggtcaca   360
gtctcttcag cctccaccaa gggcccatcg gtcttccccc tggcaccctc ctccaagagc   420
acctctgggg gcacagcagc cctgggctgc ctggtcaagg actacttccc cgaaccggtg   480
acggtgtcgt ggaactcagg cgccctgacc agcggcgtgc acaccttccc ggctgtccta   540
cagtcctcag gactctactc cctcagcagc gtggtgaccg tgccctccag cagcttgggc   600
acccagacct acatctgcaa cgtgaatcac aagcccagca caccaaggt ggacaagaaa   660
gttgagccca atcttgtga caaaactcac acatgcccac cgtgcccagc acctgaactc   720
ctggggggac cgtcagtctt cctcttcccc ccaaaaccca aggacaccct catgatctcc   780
cggacccctg aggtcacatg cgtggtggtg gacgtgagcc acgaagaccc tgaggtcaag   840
ttcaactggt acgtggacgg cgtggaggtg cataatgcca agacaaagcc gcggaggag   900
cagtacaaca gcacgtaccg tgtggtcagc gtcctcaccg tcctgcacca ggactggctg   960
aatggcaagg agtacaagtg caaggtctcc aacaaagccc tcccagcccc catcgagaaa  1020
accatctcca aagccaaagg gcagccccga gaaccacagg tgtacaccct gcccccatcc  1080
cgggatgagc tgaccaagaa ccaggtcagc ctgacctgcc tggtcaaagg cttctatccc  1140
```

```
agcgacatcg ccgtggagtg ggagagcaat gggcagccgg agaacaacta caagaccacg   1200
cctcccgtgc tggactccga cggctccttc ttcctctaca gcaagctcac cgtggacaag   1260
agcaggtggc agcaggggaa cgtcttctca tgctccgtga tgcatgaggc tctgcacaac   1320
cactacacac agaagagcct ctccctgtct ccgggtaaa                          1359

<210> SEQ ID NO 246
<211> LENGTH: 1359
<212> TYPE: DNA
<213> ORGANISM: Artificial Sequence
<220> FEATURE:
<223> OTHER INFORMATION: Synthetic

<400> SEQUENCE: 246
caggtgcaac tggtggagtc tgggggaggc gtggtccagc ctgggaggtc cctgagactc     60
tcctgtgcag cgtctgggtt cactttcaat acctatggca tgcactgggt ccgccaggca    120
ccaggcaagg gctggagtg gtggcaatt atctggtatg atgggagcca gaaatactat      180
gcagactccg tgcagggccg attcatcatc tccagagaca atcacaagaa cacgttgtct    240
ctgcaaatga actccctgag agccgaggac acggctgtgt atttctgtgt gagagtccgc    300
tttagcgttg gccccacgg gagtgctttt gatctctggg gccaggggac aatggtcaca    360
gtctcttcag cctccaccaa gggcccatcg gtcttccccc tggcaccctc ctccaagagc    420
acctctgggg gcacagcagc cctgggctgc ctggtcaagg actacttccc cgaaccggtg    480
acggtgtcgt ggaactcagg cgccctgacc agcggcgtgc acaccttccc ggctgtccta    540
cagtcctcag gactctactc cctcagcagc gtggtgaccg tgccctccag cagcttgggc    600
acccagacct acatctgcaa cgtgaatcac aagcccagca acaccaaggt ggacaagaaa    660
gttgagccca atcttgtga caaaactcac acatgcccac cgtgcccagc acctgaactc    720
ctggggggac cgtcagtctt cctcttcccc ccaaaaccca aggacaccct catgatctcc    780
cggacccctg aggtcacatg cgtggtggtg gacgtgagcc acgaagaccc tgaggtcaag    840
ttcaactggt acgtggacgg cgtggaggtg cataatgcca agacaaagcc gcggaggag     900 cagtacaaca gcacgtaccg tgtggtcagc gtcctcaccg tcctgcacca ggactggctg    960
aatggcaagg agtacaagtg caaggtctcc aacaaagccc tcccagcccc catcgagaaa   1020
accatctcca aagccaaagg gcagcccga gaaccacagg tgtacaccct gcccccatcc    1080
cgggatgagc tgaccaagaa ccaggtcagc ctgacctgcc tggtcaaagg cttctatccc   1140
agcgacatcg ccgtggagtg ggagagcaat gggcagccgg agaacaacta caagaccacg   1200
cctcccgtgc tggactccga cggctccttc ttcctctaca gcaagctcac cgtggacaag   1260
agcaggtggc agcaggggaa cgtcttctca tgctccgtgc tgcatgaggc tctgcactcc   1320
cactacacac agaagagcct ctccctgtct ccgggtaaa                          1359

<210> SEQ ID NO 247
<211> LENGTH: 109
<212> TYPE: PRT
<213> ORGANISM: Artificial Sequence
<220> FEATURE:
<223> OTHER INFORMATION: Synthetic

<400> SEQUENCE: 247

Gly Val Gln Met Thr Gln Ser Pro Ser Thr Leu Ser Ala Ser Val Gly
1               5                   10                  15

Asp Arg Val Thr Leu Thr Cys Arg Ala Ser Gln Ser Ile Ser Ser Trp
```

20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Phe
                85                  90                  95

Trp Thr Phe Gly Gln Gly Thr Lys Val Glu Ile Lys Arg
            100                 105

<210> SEQ ID NO 248
<211> LENGTH: 123
<212> TYPE: PRT
<213> ORGANISM: Artificial Sequence
<220> FEATURE:
<223> OTHER INFORMATION: Synthetic

<400> SEQUENCE: 248

Gln Val Gln Leu Val Glu Ser Gly Gly Val Val Gln Pro Gly Arg
1               5                   10                  15

Ser Leu Arg Leu Ser Cys Ala Ala Ser Gly Phe Ala Phe Asn Thr Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Ser Gln Lys Tyr Tyr Ala Asp Ser Val
    50                  55                  60

Gln Gly Arg Phe Thr Ile Ser Arg Asp Asn His Lys Asn Thr Leu Ser
65                  70                  75                  80

Leu Gln Met Asn Ser Leu Arg Ala Glu Asp Thr Ala Val Tyr Phe Cys
                85                  90                  95

Val Arg Val Arg Phe Ser Val Gly Pro His Gly Ser Ala Phe Asp Leu
            100                 105                 110

Trp Gly Gln Gly Thr Met Val Thr Val Ser Ser
        115                 120

<210> SEQ ID NO 249
<211> LENGTH: 327
<212> TYPE: DNA
<213> ORGANISM: Artificial Sequence
<220> FEATURE:
<223> OTHER INFORMATION: Synthetic

<400> SEQUENCE: 249
ggcgtccaga tgacccagtc tccttccacc ctgtctgcat ctgtgggaga cagagtcacc      60
ctcacttgcc gggccagtca gagtattagt agttggttgg cctggtatca gcagaaacca    120
gggaaagccc ctaaactcct gatctatgat gcctccagtt tggaaagtgg ggtcccatca    180
aggttcagcg gcagtggatc tgggacagaa ttcactctca ccatcagcag cctgcaacct    240
gatgattttg caacttatta ctgccaacag tataatagtt attcttttg gacgttcggc    300 caagggacca aggtggaaat caaacgc                                        327

<210> SEQ ID NO 250
<211> LENGTH: 369
<212> TYPE: DNA
<213> ORGANISM: Artificial Sequence
<220> FEATURE:

-continued

<223> OTHER INFORMATION: Synthetic

<400> SEQUENCE: 250

```
caggtgcaac tggtggagtc tgggggaggc gtggtccagc ctgggaggtc cctgagactc      60
tcctgtgcag cgtctgggtt cgctttcaat acctatggca tgcactgggt ccgccaggca     120
ccaggcaagg ggctggagtg ggtggcaatt atctggtatg atggagccga aaatactat      180
gcagactccg tgcagggccg attcactatc tccagagaca atcacaagaa cacgttgtct     240
ctgcaaatga actccctgag agccgaggac acggctgtgt atttctgtgt gagagtccgc     300
tttagcgttg ccccccacgg gagtgctttt gatctctggg gccaggggac aatggtcaca     360
gtctcttca                                                             369
```

<210> SEQ ID NO 251
<211> LENGTH: 215
<212> TYPE: PRT
<213> ORGANISM: Artificial Sequence
<220> FEATURE:
<223> OTHER INFORMATION: Synthetic

<400> SEQUENCE: 251

```
Gly Val Gln Met Thr Gln Ser Pro Ser Thr Leu Ser Ala Ser Val Gly
1               5                   10                  15

Asp Arg Val Thr Leu Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Phe
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 252
<211> LENGTH: 453
<212> TYPE: PRT
<213> ORGANISM: Artificial Sequence
<220> FEATURE:
<223> OTHER INFORMATION: Synthetic

<400> SEQUENCE: 252

-continued

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Asn Thr Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Ser Gln Lys Tyr Tyr Ala Asp Ser Val
50                  55                  60

Gln Gly Arg Phe Thr Ile Ser Arg Asp Asn His Lys Asn Thr Leu Ser
65                  70                  75                  80

Leu Gln Met Asn Ser Leu Arg Ala Glu Asp Thr Ala Val Tyr Phe Cys
                85                  90                  95

Val Arg Val Arg Phe Ser Val Gly Pro His Gly Ser Ala Phe Asp Leu
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415
```

<210> SEQ ID NO 253
<211> LENGTH: 453
<212> TYPE: PRT
<213> ORGANISM: Artificial Sequence
<220> FEATURE:
<223> OTHER INFORMATION: Synthetic

<400> SEQUENCE: 253

```
Thr Val Asp Lys Ser Arg Trp Gln Gln Gly Asn Val Phe Ser Cys Ser
                420                 425                 430
Val Met His Glu Ala Leu His Asn His Tyr Thr Gln Lys Ser Leu Ser
            435                 440                 445
Leu Ser Pro Gly Lys
        450

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Ala Phe Asn Thr Tyr
            20                  25                  30
Gly Met His Trp Val Arg Gln Ala Pro Gly Lys Gly Leu Glu Trp Val
        35                  40                  45
Ala Ile Ile Trp Tyr Asp Gly Ser Gln Lys Tyr Tyr Ala Asp Ser Val
    50                  55                  60
Gln Gly Arg Phe Thr Ile Ser Arg Asp Asn His Lys Asn Thr Leu Ser
65                  70                  75                  80
Leu Gln Met Asn Ser Leu Arg Ala Glu Asp Thr Ala Val Tyr Phe Cys
                85                  90                  95
Val Arg Val Arg Phe Ser Val Gly Pro His Gly Ser Ala Phe Asp Leu
            100                 105                 110
Trp Gly Gln Gly Thr Met Val Thr Val Ser Ser Ala Ser Thr Lys Gly
        115                 120                 125
Pro Ser Val Phe Pro Leu Ala Pro Ser Ser Lys Ser Thr Ser Gly Gly
    130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Lys Val Glu Pro Lys
    210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
    290                 295                 300
Thr Tyr Arg Val Val Ser Val Leu Thr Val Leu His Gln Asp Trp Leu
305                 310                 315                 320
```

Asn Gly Lys Glu Tyr Lys Cys Lys Val Ser Asn Lys Ala Leu Pro Ala
              325                 330                 335

Pro Ile Glu Lys Thr Ile Ser Lys Ala Lys Gly Gln Pro Arg Glu Pro
          340                 345                 350

Gln Val Tyr Thr Leu Pro Pro Ser Arg Asp Glu Leu Thr Lys Asn Gln
              355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
              405                 410                 415

Thr Val Asp Lys Ser Arg Trp Gln Gln Gly Asn Val Phe Ser Cys Ser
              420                 425                 430

Val Leu His Glu Ala Leu His Ser His Tyr Thr Gln Lys Ser Leu Ser
              435                 440                 445

Leu Ser Pro Gly Lys
            450

<210> SEQ ID NO 254
<211> LENGTH: 645
<212> TYPE: DNA
<213> ORGANISM: Artificial Sequence
<220> FEATURE:
<223> OTHER INFORMATION: Synthetic

<400> SEQUENCE: 254
ggcgtccaga tgacccagtc tccttccacc ctgtctgcat ctgtgggaga cagagtcacc      60
ctcacttgcc gggccagtca gagtattagt agttggttgg cctggtatca gcagaaacca     120
gggaaagccc ctaaactcct gatctatgat gcctccagtt tggaaagtgg ggtcccatca     180
aggttcagcg gcagtggatc tgggacagaa ttcactctca ccatcagcag cctgcaacct     240
gatgattttg caacttatta ctgccaacag tataatagtt attcttttg gacgttcggc      300 caagggacca aggtggaaat caaacgcact gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacac aaagtctacg cctgcgaagt cacccatcag     600
ggcctgagct cgcccgtcac aaagagcttc aacaggggag agtgt                    645

<210> SEQ ID NO 255
<211> LENGTH: 1359
<212> TYPE: DNA
<213> ORGANISM: Artificial Sequence
<220> FEATURE:
<223> OTHER INFORMATION: Synthetic

<400> SEQUENCE: 255
caggtgcaac tggtggagtc tggggaggc gtggtccagc ctgggaggtc cctgagactc       60
tcctgtgcag cgtctgggtt cgctttcaat acctatggca tgcactgggt ccgccaggca     120
ccaggcaagg gctggagtg gtggcaatt atctggtatg atgggagcca gaaatactat       180
gcagactccg tgcagggccg attcactatc tccagagaca atcacaagaa cacgttgtct     240
ctgcaaatga actccctgag agccgaggac acggctgtgt atttctgtgt gagagtccgc     300

```
tttagcgttg gccccacgg gagtgctttt gatctctggg gccaggggac aatggtcaca      360
gtctcttcag cctccaccaa gggcccatcg gtcttccccc tggcaccctc ctccaagagc      420
acctctgggg gcacagcagc cctgggctgc ctggtcaagg actacttccc cgaaccggtg      480
acggtgtcgt ggaactcagg cgccctgacc agcggcgtgc acaccttccc ggctgtccta      540
cagtcctcag gactctactc cctcagcagc gtggtgaccg tgccctccag cagcttgggc      600
acccagacct acatctgcaa cgtgaatcac aagcccagca acaccaaggt ggacaagaaa      660
gttgagccca atcttgtgac aaaactcac acatgcccac cgtgcccagc acctgaactc      720
ctggggggac cgtcagtctt cctcttcccc ccaaaaccca aggacaccct catgatctcc      780
cggacccctg aggtcacatg cgtggtggtg gacgtgagcc acgaagaccc tgaggtcaag      840
ttcaactggt acgtggacgg cgtggaggtg cataatgcca agacaaagcc gcgggaggag      900
cagtacaaca gcacgtaccg tgtggtcagc gtcctcaccg tcctgcacca ggactggctg      960
aatggcaagg agtacaagtg caaggtctcc aacaaagccc tcccagcccc catcgagaaa     1020
accatctcca aagccaaagg gcagccccga gaaccacagg tgtacaccct gcccccatcc     1080
cgggatgagc tgaccaagaa ccaggtcagc ctgacctgcc tggtcaaagg cttctatccc     1140
agcgacatcg ccgtggagtg ggagagcaat gggcagccgg agaacaacta caagaccacg     1200
cctcccgtgc tggactccga cggctccttc ttcctctaca gcaagctcac cgtggacaag     1260
agcaggtggc agcaggggaa cgtcttctca tgctccgtga tgcatgaggc tctgcacaac     1320
cactacacac agaagagcct ctccctgtct ccgggtaaa                            1359
```

<210> SEQ ID NO 256
<211> LENGTH: 1359
<212> TYPE: DNA
<213> ORGANISM: Artificial Sequence
<220> FEATURE:
<223> OTHER INFORMATION: Synthetic

<400> SEQUENCE: 256

```
caggtgcaac tggtggagtc tgggggaggc gtggtccagc ctgggaggtc cctgagactc       60
tcctgtgcag cgtctgggtt cgctttcaat acctatggca tgcactgggt ccgccaggca      120
ccaggcaagg ggctggagtg ggtggcaatt atctggtatg atgggagcca gaaatactat      180
gcagactccg tgcagggccg attcactatc tccagagaca atcacaagaa cacgttgtct      240
ctgcaaatga actccctgag agccgaggac acggctgtgt atttctgtgt gagagtccgc      300
tttagcgttg gccccacgg gagtgctttt gatctctggg gccaggggac aatggtcaca      360
gtctcttcag cctccaccaa gggcccatcg gtcttccccc tggcaccctc ctccaagagc      420
acctctgggg gcacagcagc cctgggctgc ctggtcaagg actacttccc cgaaccggtg      480
acggtgtcgt ggaactcagg cgccctgacc agcggcgtgc acaccttccc ggctgtccta      540
cagtcctcag gactctactc cctcagcagc gtggtgaccg tgccctccag cagcttgggc      600
acccagacct acatctgcaa cgtgaatcac aagcccagca acaccaaggt ggacaagaaa      660
gttgagccca atcttgtgac aaaactcac acatgcccac cgtgcccagc acctgaactc      720
ctggggggac cgtcagtctt cctcttcccc ccaaaaccca aggacaccct catgatctcc      780
cggacccctg aggtcacatg cgtggtggtg gacgtgagcc acgaagaccc tgaggtcaag      840
ttcaactggt acgtggacgg cgtggaggtg cataatgcca agacaaagcc gcgggaggag      900
cagtacaaca gcacgtaccg tgtggtcagc gtcctcaccg tcctgcacca ggactggctg      960
aatggcaagg agtacaagtg caaggtctcc aacaaagccc tcccagcccc catcgagaaa     1020
```

```
accatctcca aagccaaagg gcagccccga gaaccacagg tgtacaccct gcccccatcc   1080
cgggatgagc tgaccaagaa ccaggtcagc ctgacctgcc tggtcaaagg cttctatccc   1140
agcgacatcg ccgtggagtg ggagagcaat gggcagccgg agaacaacta caagaccacg   1200
cctcccgtgc tggactccga cggctccttc ttcctctaca gcaagctcac cgtggacaag   1260
agcaggtggc agcaggggaa cgtcttctca tgctccgtgc tgcatgaggc tctgcactcc   1320
cactacacac agaagagcct ctccctgtct ccgggtaaa                          1359
```

<210> SEQ ID NO 257
<211> LENGTH: 109
<212> TYPE: PRT
<213> ORGANISM: Artificial Sequence
<220> FEATURE:
<223> OTHER INFORMATION: Synthetic

<400> SEQUENCE: 257

```
Gly Val Gln Met Thr Gln Ser Pro Ser Thr Leu Ser Ala Ser Val Gly
1               5                   10                  15

Asp Arg Val Thr Leu Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Phe
                85                  90                  95

Trp Thr Phe Gly Gln Gly Thr Lys Val Glu Ile Lys Arg
            100                 105
```

<210> SEQ ID NO 258
<211> LENGTH: 123
<212> TYPE: PRT
<213> ORGANISM: Artificial Sequence
<220> FEATURE:
<223> OTHER INFORMATION: Synthetic

<400> SEQUENCE: 258

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Asn Thr Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Ser Gln Lys Tyr Tyr Ala Asp Ser Val
    50                  55                  60

Gln Gly Arg Phe Thr Ile Ser Arg Asp Asn His Lys Asn Thr Leu Ser
65                  70                  75                  80

Leu Gln Met Asn Ser Leu Arg Ala Glu Asp Thr Ala Val Tyr Phe Cys
                85                  90                  95

Val Arg Val Arg Phe Ser Val Gly Pro His Gly Ser Ala Phe Asp Leu
            100                 105                 110

Trp Gly Gln Gly Thr Met Val Thr Val Ser Ser
        115                 120
```

<210> SEQ ID NO 259
<211> LENGTH: 327
<212> TYPE: DNA
<213> ORGANISM: Artificial Sequence
<220> FEATURE:
<223> OTHER INFORMATION: Synthetic

<400> SEQUENCE: 259

```
ggcgtccaga tgacccagtc tccttccacc ctgtctgcat ctgtgggaga cagagtcacc      60
ctcacttgcc gggccagtca gagtattagt agttggttgg cctggtatca gcagaaacca     120
gggaaagccc ctaaactcct gatctatgat gcctccagtt tggaaagtgg ggtcccatca     180
aggttcagcg gcagtggatc tgggacagaa ttcactctca ccatcagcag cctgcaacct     240
gatgattttg caacttatta ctgccaacag tataatagtt attcttttg dacgttcggc      300
caagggacca aggtggaaat caaacgc                                        327
```

<210> SEQ ID NO 260
<211> LENGTH: 369
<212> TYPE: DNA
<213> ORGANISM: Artificial Sequence
<220> FEATURE:
<223> OTHER INFORMATION: Synthetic

<400> SEQUENCE: 260

```
caggtgcaac tggtggagtc tggggggaggc gtggtccagc ctgggaggtc cctgagactc      60
tcctgtgcag cgtctgggtt cactttcaat acctatggca tgcactgggt ccgccaggca     120
ccaggcaagg ggctggagtg ggtggcaatt atctggtatg atgggagcca gaaatactat     180
gcagactccg tgcagggccg attcactatc tccagagaca atcacaagaa cacgttgtct     240
ctgcaaatga actccctgag agccgaggac acggctgtgt atttctgtgt gagagtccgc     300
tttagcgttg gccccacgg gagtgctttt gatctctggg gccaggggac aatggtcaca     360
gtctcttca                                                          369
```

<210> SEQ ID NO 261
<211> LENGTH: 215
<212> TYPE: PRT
<213> ORGANISM: Artificial Sequence
<220> FEATURE:
<223> OTHER INFORMATION: Synthetic

<400> SEQUENCE: 261

```
Gly Val Gln Met Thr Gln Ser Pro Ser Thr Leu Ser Ala Ser Val Gly
1               5                   10                  15

Asp Arg Val Thr Leu Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Phe
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125
```

```
Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
210                 215

<210> SEQ ID NO 262
<211> LENGTH: 453
<212> TYPE: PRT
<213> ORGANISM: Artificial Sequence
<220> FEATURE:
<223> OTHER INFORMATION: Synthetic

<400> SEQUENCE: 262

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Thr Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Ser Gln Lys Tyr Tyr Ala Asp Ser Val
50                  55                  60

Gln Gly Arg Phe Thr Ile Ser Arg Asp Asn His Lys Asn Thr Leu Ser
65                  70                  75                  80

Leu Gln Met Asn Ser Leu Arg Ala Glu Asp Thr Ala Val Tyr Phe Cys
            85                  90                  95

Val Arg Val Arg Phe Ser Val Gly Pro His Gly Ser Ala Phe Asp Leu
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270
```

```
Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 263
<211> LENGTH: 453
<212> TYPE: PRT
<213> ORGANISM: Artificial Sequence
<220> FEATURE:
<223> OTHER INFORMATION: Synthetic

<400> SEQUENCE: 263

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Thr Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Ser Gln Lys Tyr Tyr Ala Asp Ser Val
    50                  55                  60

Gln Gly Arg Phe Thr Ile Ser Arg Asp Asn His Lys Asn Thr Leu Ser
65                  70                  75                  80

Leu Gln Met Asn Ser Leu Arg Ala Glu Asp Thr Ala Val Tyr Phe Cys
                85                  90                  95

Val Arg Val Arg Phe Ser Val Gly Pro His Gly Ser Ala Phe Asp Leu
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175
```

```
Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Leu His Glu Ala Leu His Ser His Tyr Thr Gln Lys Ser Leu Ser
        435                 440                 445

Leu Ser Pro Gly Lys
    450

<210> SEQ ID NO 264
<211> LENGTH: 645
<212> TYPE: DNA
<213> ORGANISM: Artificial Sequence
<220> FEATURE:
<223> OTHER INFORMATION: Synthetic

<400> SEQUENCE: 264
ggcgtccaga tgacccagtc tccttccacc ctgtctgcat ctgtgggaga cagagtcacc      60
ctcacttgcc gggccagtca gagtattagt agttggttgg cctggtatca gcagaaacca     120
gggaaagccc ctaaactcct gatctatgat gcctccagtt tggaaagtgg ggtcccatca     180
aggttcagcg gcagtggatc tgggacagaa ttcactctca ccatcagcag cctgcaacct     240
gatgattttg caacttatta ctgccaacag tataatagtt attcttttg gacgttcggc      300 caagggacca aggtggaaat caaacgcact gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
```

```
caggagagtg tcacagagca ggacagcaag acagcacct acagcctcag cagcaccctg        540
acgctgagca aagcagacta cgagaaacac aaagtctacg cctgcgaagt cacccatcag        600
ggcctgagct cgcccgtcac aaagagcttc aacaggggag agtgt                        645
```

<210> SEQ ID NO 265
<211> LENGTH: 1359
<212> TYPE: DNA
<213> ORGANISM: Artificial Sequence
<220> FEATURE:
<223> OTHER INFORMATION: Synthetic

<400> SEQUENCE: 265

```
caggtgcaac tggtggagtc tgggggaggc gtggtccagc ctgggaggtc cctgagactc         60
tcctgtgcag cgtctgggtt cactttcaat acctatggca tgcactgggt ccgccaggca        120
ccaggcaagg ggctggagtg ggtggcaatt atctggtatg atgggagcca gaaatactat        180
gcagactccg tgcagggccg attcactatc tccagagaca tcacaagaa cacgttgtct         240 ctgcaaatga actccctgag agccgaggac acggctgtgt atttctgtgt gagagtccgc        300
tttagcgttg gcccccacgg gagtgctttt gatctctggg gccaggggac aatggtcaca        360
gtctcttcag cctccaccaa gggcccatcg gtcttccccc tggcaccctc ctccaagagc        420
acctctgggg gcacagcagc cctgggctgc ctggtcaagg actacttccc cgaaccggtg        480
acggtgtcgt ggaactcagg cgccctgacc agcggcgtgc acaccttccc ggctgtccta        540
cagtcctcag gactctactc cctcagcagc gtggtgaccg tgccctccag cagcttgggc        600
acccagacct acatctgcaa cgtgaatcac aagcccagca caccaaggt ggacaagaaa        660 gttgagccca atcttgtga caaaactcac acatgcccac cgtgcccagc acctgaactc        720
ctggggggac cgtcagtctt cctcttcccc ccaaaaccca aggacaccct catgatctcc        780
cggacccctg aggtcacatg cgtggtggtg gacgtgagcc acgaagaccc tgaggtcaag        840
ttcaactggt acgtggacgg cgtggaggtg cataatgcca agacaaagcc gcgggaggag        900
cagtacaaca gcacgtaccg tgtggtcagc gtcctcaccg tcctgcacca ggactggctg        960
aatggcaagg agtacaagtg caaggtctcc aacaaagccc tcccagcccc catcgagaaa       1020
accatctcca aagccaaagg gcagccccga gaaccacagg tgtacaccct gcccccatcc       1080
cgggatgagc tgaccaagaa ccaggtcagc ctgacctgcc tggtcaaagg cttctatccc       1140
agcgacatcg ccgtggagtg ggagagcaat gggcagccgg agaacaacta caagaccacg       1200
cctcccgtgc tggactccga cggctccttc ttcctctaca gcaagctcac cgtggacaag       1260
agcaggtggc agcaggggaa cgtcttctca tgctccgtga tgcatgaggc tctgcacaac       1320
cactacacac agaagagcct ctccctgtct ccgggtaaa                             1359
```

<210> SEQ ID NO 266
<211> LENGTH: 1359
<212> TYPE: DNA
<213> ORGANISM: Artificial Sequence
<220> FEATURE:
<223> OTHER INFORMATION: Synthetic

<400> SEQUENCE: 266

```
caggtgcaac tggtggagtc tgggggaggc gtggtccagc ctgggaggtc cctgagactc         60
tcctgtgcag cgtctgggtt cactttcaat acctatggca tgcactgggt ccgccaggca        120
ccaggcaagg ggctggagtg ggtggcaatt atctggtatg atgggagcca gaaatactat        180
```

```
gcagactccg tgcagggccg attcactatc tccagagaca atcacaagaa cacgttgtct     240
ctgcaaatga actccctgag agccgaggac acggctgtgt atttctgtgt gagagtccgc     300
tttagcgttg gcccccacgg gagtgctttt gatctctggg gccaggggac aatggtcaca     360
gtctcttcag cctccaccaa gggcccatcg gtcttccccc tggcaccctc ctccaagagc     420
acctctgggg gcacagcagc cctgggctgc ctggtcaagg actacttccc cgaaccggtg     480
acggtgtcgt ggaactcagg cgccctgacc agcggcgtgc acaccttccc ggctgtccta     540
cagtcctcag gactctactc cctcagcagc gtggtgaccg tgccctccag cagcttgggc     600
acccagacct acatctgcaa cgtgaatcac aagcccagca caccaaggt ggacaagaaa      660 gttgagccca atcttgtga caaaactcac acatgcccac cgtgcccagc acctgaactc      720
ctggggggac cgtcagtctt cctcttcccc ccaaaaccca aggacaccct catgatctcc     780
cggacccctg aggtcacatg cgtggtggtg gacgtgagcc acgaagaccc tgaggtcaag     840
ttcaactggt acgtggacgg cgtggaggtg cataatgcca agacaaagcc gcgggaggag     900
cagtacaaca gcacgtaccg tgtggtcagc gtcctcaccg tcctgcacca ggactggctg     960
aatggcaagg agtacaagtg caaggtctcc aacaaagccc tcccagcccc catcgagaaa    1020
accatctcca aagccaaagg gcagccccga gaaccacagg tgtacaccct gcccccatcc    1080
cgggatgagc tgaccaagaa ccaggtcagc ctgacctgcc tggtcaaagg cttctatccc    1140
agcgacatcg ccgtggagtg ggagagcaat gggcagccgg agaacaacta caagaccacg    1200
cctcccgtgc tggactccga cggctccttc ttcctctaca gcaagctcac cgtggacaag    1260
agcaggtggc agcaggggaa cgtcttctca tgctccgtgc tgcatgaggc tctgcactcc    1320
cactacacac agaagagcct ctccctgtct ccgggtaaa                           1359

<210> SEQ ID NO 267
<211> LENGTH: 109
<212> TYPE: PRT
<213> ORGANISM: Artificial Sequence
<220> FEATURE:
<223> OTHER INFORMATION: Synthetic

<400> SEQUENCE: 267

Gly Val Gln Met Thr Gln Ser Pro Ser Thr Leu Ser Ala Ser Val Gly
1               5                   10                  15

Asp Arg Val Thr Leu Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Phe
                85                  90                  95

Trp Thr Phe Gly Gln Gly Thr Lys Val Glu Ile Lys Arg
            100                 105

<210> SEQ ID NO 268
<211> LENGTH: 123
<212> TYPE: PRT
<213> ORGANISM: Artificial Sequence
<220> FEATURE:
<223> OTHER INFORMATION: Synthetic
```

<400> SEQUENCE: 268

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Asn Thr Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Ser Gln Lys Tyr Tyr Ala Asp Ser Val
    50                  55                  60

Gln Gly Arg Phe Thr Ile Ser Arg Asp Asn His Lys Asn Thr Leu Tyr
65                  70                  75                  80

Leu Gln Met Asn Ser Leu Arg Ala Glu Asp Thr Ala Val Tyr Phe Cys
                85                  90                  95

Val Arg Val Arg Phe Ser Val Gly Pro His Gly Ser Ala Phe Asp Leu
            100                 105                 110

Trp Gly Gln Gly Thr Met Val Thr Val Ser Ser
        115                 120

<210> SEQ ID NO 269
<211> LENGTH: 327
<212> TYPE: DNA
<213> ORGANISM: Artificial Sequence
<220> FEATURE:
<223> OTHER INFORMATION: Synthetic

<400> SEQUENCE: 269
ggcgtccaga tgacccagtc tccttccacc ctgtctgcat ctgtgggaga cagagtcacc      60
ctcacttgcc gggccagtca gagtattagt agttggttgg cctggtatca gcagaaacca     120
gggaaagccc ctaaactcct gatctatgat gcctccagtt tggaaagtgg ggtcccatca     180
aggttcagcg gcagtggatc tgggacagaa ttcactctca ccatcagcag cctgcaacct     240
gatgattttg caacttatta ctgccaacag tataatagtt attcttttg dacgttcggc      300 caagggacca aggtggaaat caaacgc                                         327

<210> SEQ ID NO 270
<211> LENGTH: 369
<212> TYPE: DNA
<213> ORGANISM: Artificial Sequence
<220> FEATURE:
<223> OTHER INFORMATION: Synthetic

<400> SEQUENCE: 270
caggtgcaac tggtggagtc tgggggaggc gtggtccagc ctgggaggtc cctgagactc      60
tcctgtgcag cgtctgggtt cactttcaat acctatggca tgcactgggt ccgccaggca     120
ccaggcaagg ggctggagtg ggtggcaatt atctggtatg atgggagcca gaaatactat     180
gcagactccg tgcagggccg attcactatc tccagagaca atcacaagaa cacgttgtac     240
ctgcaaatga actccctgag agccgaggac acggctgtgt atttctgtgt gagagtccgc     300
tttagcgttg gcccccacgg gagtgctttt gatctctggg gccagggaca atggtcaca     360 gtctcttca                                                            369

<210> SEQ ID NO 271
<211> LENGTH: 215
<212> TYPE: PRT
<213> ORGANISM: Artificial Sequence
<220> FEATURE:
<223> OTHER INFORMATION: Synthetic

```
<400> SEQUENCE: 271

Gly Val Gln Met Thr Gln Ser Pro Ser Thr Leu Ser Ala Ser Val Gly
1               5                   10                  15

Asp Arg Val Thr Leu Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Phe
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
210                 215

<210> SEQ ID NO 272
<211> LENGTH: 453
<212> TYPE: PRT
<213> ORGANISM: Artificial Sequence
<220> FEATURE:
<223> OTHER INFORMATION: Synthetic

<400> SEQUENCE: 272

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Asn Thr Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Ser Gln Lys Tyr Tyr Ala Asp Ser Val
50                  55                  60

Gln Gly Arg Phe Thr Ile Ser Arg Asp Asn His Lys Asn Thr Leu Tyr
65                  70                  75                  80

Leu Gln Met Asn Ser Leu Arg Ala Glu Asp Thr Ala Val Tyr Phe Cys
                85                  90                  95

Val Arg Val Arg Phe Ser Val Gly Pro His Gly Ser Ala Phe Asp Leu
            100                 105                 110

Trp Gly Gln Gly Thr Met Val Thr Val Ser Ser Ala Ser Thr Lys Gly
        115                 120                 125
```

```
Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 273
<211> LENGTH: 453
<212> TYPE: PRT
<213> ORGANISM: Artificial Sequence
<220> FEATURE:
<223> OTHER INFORMATION: Synthetic

<400> SEQUENCE: 273

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Thr Tyr
            20                  25                  30
```

```
Gly Met His Trp Val Arg Gln Ala Pro Gly Lys Gly Leu Glu Trp Val
        35                  40                  45

Ala Ile Ile Trp Tyr Asp Gly Ser Gln Lys Tyr Tyr Ala Asp Ser Val
 50                  55                  60

Gln Gly Arg Phe Thr Ile Ser Arg Asp Asn His Lys Asn Thr Leu Tyr
 65                  70                  75                  80

Leu Gln Met Asn Ser Leu Arg Ala Glu Asp Thr Ala Val Tyr Phe Cys
                85                  90                  95

Val Arg Val Arg Phe Ser Val Gly Pro His Gly Ser Ala Phe Asp Leu
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Leu His Glu Ala Leu His Ser His Tyr Thr Gln Lys Ser Leu Ser
        435                 440                 445

Leu Ser Pro Gly Lys
```

<210> SEQ ID NO 274
<211> LENGTH: 645
<212> TYPE: DNA
<213> ORGANISM: Artificial Sequence
<220> FEATURE:
<223> OTHER INFORMATION: Synthetic

<400> SEQUENCE: 274

```
ggcgtccaga tgacccagtc tccttccacc ctgtctgcat ctgtgggaga cagagtcacc      60
ctcacttgcc gggccagtca gagtattagt agttggttgg cctggtatca gcagaaacca     120
gggaaagccc ctaaactcct gatctatgat gcctccagtt tggaaagtgg ggtcccatca     180
aggttcagcg gcagtggatc tgggacagaa ttcactctca ccatcagcag cctgcaacct     240
gatgattttg caacttatta ctgccaacag tataatagtt attcttttttg gacgttcggc    300
caagggacca aggtggaaat caaacgcact gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagacta cgagaaacac aaagtctacg cctgcgaagt cacccatcag     600
ggcctgagct cgcccgtcac aaagagcttc aacaggggag agtgt                     645
```

<210> SEQ ID NO 275
<211> LENGTH: 1359
<212> TYPE: DNA
<213> ORGANISM: Artificial Sequence
<220> FEATURE:
<223> OTHER INFORMATION: Synthetic

<400> SEQUENCE: 275

```
caggtgcaac tggtggagtc tgggggaggc gtggtccagc ctgggaggtc cctgagactc      60
tcctgtgcag cgtctgggtt cactttcaat acctatggca tgcactgggt ccgccaggca    120
ccaggcaagg ggctggagtg ggtggcaatt atctggtatg atgggagcca gaaatactat    180
gcagactccg tgcagggccg attcactatc tccagagaca atcacaagaa cacgttgtac    240
ctgcaaatga actccctgag agccgaggac acggctgtgt atttctgtgt gagagtccgc    300
tttagcgttg gcccccacgg gagtgctttt gatctctggg gccaggggac aatggtcaca    360
gtctcttcag cctccaccaa gggcccatcg gtcttccccc tggcaccctc ctccaagagc    420
acctctgggg gcacagcagc cctgggctgc ctggtcaagg actacttccc cgaaccggtg    480
acggtgtcgt ggaactcagg cgccctgacc agcggcgtgc acaccttccc ggctgtccta    540
cagtcctcag gactctactc cctcagcagc gtggtgaccg tgccctccag cagcttgggc    600
acccagacct acatctgcaa cgtgaatcac aagcccagca caccaaggt ggacaagaaa     660
gttgagccca atcttgtga caaaactcac acatgcccac cgtgcccagc acctgaactc    720
ctggggggac cgtcagtctt cctcttcccc ccaaaaccca aggacaccct catgatctcc    780
cggacccctg aggtcacatg cgtggtggtg gacgtgagcc acgaagaccc tgaggtcaag    840
ttcaactggt acgtggacgg cgtggaggtg cataatgcca agacaaagcc gcgggaggag    900
cagtacaaca gcacgtaccg tgtggtcagc gtcctcaccg tcctgcacca ggactggctg    960
aatggcaagg agtacaagtg caaggtctcc aacaaagccc tcccagcccc catcgagaaa   1020
accatctcca aagccaaagg gcagccccga gaaccacagg tgtacaccct gcccccatcc   1080
```

```
cgggatgagc tgaccaagaa ccaggtcagc ctgacctgcc tggtcaaagg cttctatccc      1140
agcgacatcg ccgtggagtg ggagagcaat gggcagccgg agaacaacta caagaccacg      1200
cctcccgtgc tggactccga cggctccttc ttcctctaca gcaagctcac cgtggacaag      1260
agcaggtggc agcaggggaa cgtcttctca tgctccgtga tgcatgaggc tctgcacaac      1320
cactacacac agaagagcct ctccctgtct ccgggtaaa                             1359
```

<210> SEQ ID NO 276
<211> LENGTH: 1359
<212> TYPE: DNA
<213> ORGANISM: Artificial Sequence
<220> FEATURE:
<223> OTHER INFORMATION: Synthetic

<400> SEQUENCE: 276

```
caggtgcaac tggtggagtc tgggggaggc gtggtccagc ctggagggtc cctgagactc       60
tcctgtgcag cgtctgggtt cactttcaat acctatggca tgcactgggt ccgccaggca      120
ccaggcaagg gctggagtg gtggcaatt atctggtatg atgggagcca gaaatactat        180
gcagactccg tgcagggccg attcactatc tccagagaca atcacaagaa cacgttgtac      240
ctgcaaatga actccctgag agccgaggac acggctgtgt atttctgtgt gagagtccgc      300
tttagcgttg gccccacgg gagtgctttt gatctctggg gccaggggac aatggtcaca       360
gtctcttcag cctccaccaa gggcccatcg gtcttccccc tggcaccctc ctccaagagc      420
acctctgggg gcacagcagc cctgggctgc ctggtcaagg actacttccc cgaaccggtg      480
acggtgtcgt ggaactcagg cgccctgacc agcggcgtgc acaccttccc ggctgtccta      540
cagtcctcag gactctactc cctcagcagc gtggtgaccg tgccctccag cagcttgggc      600
acccagacct acatctgcaa cgtgaatcac aagcccagca caccaaggt ggacaagaaa       660 gttgagccca atcttgtga caaaactcac acatgcccac cgtgcccagc acctgaactc       720 ctgggggac cgtcagtctt cctcttcccc ccaaaaccca aggacaccct catgatctcc       780 cggaccccctg aggtcacatg cgtggtggtg gacgtgagcc acgaagaccc tgaggtcaag      840
ttcaactggt acgtggacgg cgtggaggtg cataatgcca agacaaagcc gcgggaggag      900
cagtacaaca gcacgtaccg tgtggtcagc gtcctcaccg tcctgcacca ggactggctg      960
aatggcaagg agtacaagtg caaggtctcc aacaaagccc tcccagcccc catcgagaaa     1020
accatctcca aagccaaagg gcagccccga gaaccacagg tgtacaccct gcccccatcc     1080
cgggatgagc tgaccaagaa ccaggtcagc ctgacctgcc tggtcaaagg cttctatccc     1140
agcgacatcg ccgtggagtg ggagagcaat gggcagccgg agaacaacta caagaccacg     1200
cctcccgtgc tggactccga cggctccttc ttcctctaca gcaagctcac cgtggacaag     1260
agcaggtggc agcaggggaa cgtcttctca tgctccgtgc tgcatgaggc tctgcactcc     1320
cactacacac agaagagcct ctccctgtct ccgggtaaa                            1359
```

<210> SEQ ID NO 277
<211> LENGTH: 19
<212> TYPE: PRT
<213> ORGANISM: Artificial Sequence
<220> FEATURE:
<223> OTHER INFORMATION: Synthetic

<400> SEQUENCE: 277

```
Met Ala Trp Ala Leu Leu Leu Leu Thr Leu Leu Thr Gln Gly Thr Gly
1               5                   10                  15
```

Ser Trp Ala

<210> SEQ ID NO 278
<211> LENGTH: 22
<212> TYPE: PRT
<213> ORGANISM: Artificial Sequence
<220> FEATURE:
<223> OTHER INFORMATION: Synthetic

<400> SEQUENCE: 278

Met Asp Met Arg Val Pro Ala Gln Leu Leu Gly Leu Leu Leu Leu Trp
1               5                   10                  15

Leu Arg Gly Ala Arg Cys
            20

<210> SEQ ID NO 279
<211> LENGTH: 24
<212> TYPE: PRT
<213> ORGANISM: Artificial Sequence
<220> FEATURE:
<223> OTHER INFORMATION: Synthetic

<400> SEQUENCE: 279

Asn Ala Asn Pro Asn Ala Asn Pro Asn Ala Asn Pro Asn Ala Asn Pro
1               5                   10                  15

Asn Ala Asn Pro Asn Ala Asn Pro
            20

<210> SEQ ID NO 280
<211> LENGTH: 12
<212> TYPE: PRT
<213> ORGANISM: Artificial Sequence
<220> FEATURE:
<223> OTHER INFORMATION: Synthetic

<400> SEQUENCE: 280

Asn Pro Asn Ala Asn Pro Asn Ala Asn Pro Asn Ala
1               5                   10

<210> SEQ ID NO 281
<211> LENGTH: 20
<212> TYPE: PRT
<213> ORGANISM: Artificial Sequence
<220> FEATURE:
<223> OTHER INFORMATION: Synthetic

<400> SEQUENCE: 281

Asn Val Asp Pro Asn Ala Asn Pro Asn Val Asp Pro Asn Ala Asn Pro
1               5                   10                  15

Asn Val Asp Pro
            20

<210> SEQ ID NO 282
<211> LENGTH: 16
<212> TYPE: PRT
<213> ORGANISM: Artificial Sequence
<220> FEATURE:
<223> OTHER INFORMATION: Synthetic

<400> SEQUENCE: 282

Asn Pro Asp Pro Asn Ala Asn Pro Asn Val Asp Pro Asn Ala Asn Pro
1               5                   10                  15

<210> SEQ ID NO 283

```
<211> LENGTH: 12
<212> TYPE: PRT
<213> ORGANISM: Artificial Sequence
<220> FEATURE:
<223> OTHER INFORMATION: Synthetic

<400> SEQUENCE: 283

Asp Pro Asn Ala Asn Pro Asn Val Asp Pro Asn Ala
1               5                   10

<210> SEQ ID NO 284
<211> LENGTH: 15
<212> TYPE: PRT
<213> ORGANISM: Artificial Sequence
<220> FEATURE:
<223> OTHER INFORMATION: Synthetic

<400> SEQUENCE: 284

Lys Gln Pro Ala Asp Gly Asn Pro Asp Pro Asn Ala Asn Pro Asn
1               5                   10                  15

<210> SEQ ID NO 285
<211> LENGTH: 424
<212> TYPE: PRT
<213> ORGANISM: Artificial Sequence
<220> FEATURE:
<223> OTHER INFORMATION: Synthetic

<400> SEQUENCE: 285

Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
                20                  25                  30

Arg Val Leu Asn Glu Leu Asn Tyr Asp Asn Ala Gly Ile Asn Leu Tyr
            35                  40                  45

Asn Glu Leu Glu Met Asn Tyr Tyr Gly Lys Gln Glu Asn Trp Tyr Ser
        50                  55                  60

Leu Lys Lys Asn Ser Arg Ser Leu Gly Glu Asn Asp Asp Gly Asn Asn
65                  70                  75                  80

Asn Asn Gly Asp Asn Gly Arg Glu Gly Lys Asp Glu Asp Lys Arg Asp
                85                  90                  95

Gly Asn Asn Glu Asp Asn Glu Lys Leu Arg Lys Pro Lys His Lys Lys
            100                 105                 110

Leu Lys Gln Pro Gly Asp Gly Asn Pro Asp Pro Asn Ala Asn Pro Asn
        115                 120                 125

Val Asp Pro Asn Ala Asn Pro Asn Val Asp Pro Asn Ala Asn Pro Asn
    130                 135                 140

Val Asp Pro Asn Ala Asn Pro Asn Ala Asn Pro Asn Ala Asn Pro Asn
145                 150                 155                 160

Ala Asn Pro Asn Ala Asn Pro Asn Ala Asn Pro Asn Ala Asn Pro Asn
                165                 170                 175

Ala Asn Pro Asn Ala Asn Pro Asn Ala Asn Pro Asn Ala Asn Pro Asn
            180                 185                 190

Ala Asn Pro Asn Ala Asn Pro Asn Ala Asn Pro Asn Ala Asn Pro Asn
        195                 200                 205

Ala Asn Pro Asn Ala Asn Pro Asn Ala Asn Pro Asn Ala Asn Pro Asn
    210                 215                 220

Ala Asn Pro Asn Ala Asn Pro Asn Ala Asn Pro Asn Ala Asn Pro Asn
225                 230                 235                 240
```

Ala Asn Pro Asn Ala Asn Pro Asn Ala Asn Pro Asn
            245                 250                 255

Ala Asn Pro Asn Ala Asn Pro Asn Ala Asn Pro Asn
        260                 265                 270

Ala Asn Pro Asn Ala Asn Pro Asn Ala Asn Pro Asn
        275                 280                 285

Ala Asn Pro Asn Ala Asn Pro Asn Lys Asn Asn Gln
        290                 295                 300

Gly Asn Gly Gln Gly His Asn Met Pro Asn Asp Pro Asn Arg Asn Val
305                 310                 315                 320

Asp Glu Asn Ala Asn Ala Asn Asn Ala Val Lys Asn Asn Asn Asn Glu
                325                 330                 335

Glu Pro Ser Asp Lys His Ile Glu Gln Tyr Leu Lys Lys Ile Gln Asn
                340                 345                 350

Ser Leu Ser Thr Glu Trp Ser Pro Cys Ser Val Thr Cys Gly Asn Gly
            355                 360                 365

Ile Gln Val Arg Ile Lys Pro Gly Ser Ala Asn Lys Pro Lys Asp Glu
            370                 375                 380

Leu Asp Tyr Glu Asn Asp Ile Glu Lys Lys Ile Cys Lys Met Glu Lys
385                 390                 395                 400

Cys Ser Ser Val Phe Asn Val Val Asn Ser Ser Ile Gly Leu Ile Met
                405                 410                 415

Val Leu Ser Phe Leu Phe Leu Asn
            420

<210> SEQ ID NO 286
<211> LENGTH: 236
<212> TYPE: PRT
<213> ORGANISM: Artificial Sequence
<220> FEATURE:
<223> OTHER INFORMATION: Synthetic

<400> SEQUENCE: 286

Met Ala Trp Ala Leu Leu Leu Thr Leu Leu Thr Gln Gly Thr Gly
1               5                   10                  15

Ser Trp Ala Glu Ser Val Leu Thr Gln Pro Pro Ser Val Ser Gly Ala
            20                  25                  30

Pro Gly Gln Arg Val Thr Ile Ser Cys Thr Gly Met Asn Ser Asn Ile
        35                  40                  45

Gly Ala Gly Tyr Asp Val Tyr Trp Tyr Gln Gln Leu Pro Gly Arg Ala
    50                  55                  60

Pro Lys Leu Leu Ile Tyr Gly Asn Ser Asn Arg Pro Ser Gly Val Pro
65                  70                  75                  80

Asp Arg Phe Ser Gly Ser Arg Ser Gly Thr Ser Ala Ser Leu Ala Ile
                85                  90                  95

Thr Gly Leu Gln Ala Glu Asp Glu Ala Asp Tyr Tyr Cys Gln Ser Tyr
            100                 105                 110

Asp Thr Ser Leu Asn Gly Trp Ala Phe Gly Gly Gly Thr Lys Leu Thr
        115                 120                 125

Val Leu Gly Gln Pro Lys Ala Ala Pro Ser Val Thr Leu Phe Pro Pro
    130                 135                 140

Ser Ser Glu Glu Leu Gln Ala Asn Lys Ala Thr Leu Val Cys Leu Val
145                 150                 155                 160

Ser Asp Phe Tyr Pro Gly Ala Val Thr Val Ala Trp Lys Ala Asp Gly
                165                 170                 175

```
Ser Pro Val Lys Val Gly Val Glu Thr Thr Lys Pro Ser Lys Gln Ser
            180                 185                 190

Asn Asn Lys Tyr Ala Ala Ser Ser Tyr Leu Ser Leu Thr Pro Glu Gln
            195                 200                 205

Trp Lys Ser His Arg Ser Tyr Ser Cys Arg Val Thr His Glu Gly Ser
            210                 215                 220

Thr Val Glu Lys Thr Val Ala Pro Ala Glu Cys Ser
225                 230                 235

<210> SEQ ID NO 287
<211> LENGTH: 479
<212> TYPE: PRT
<213> ORGANISM: Artificial Sequence
<220> FEATURE:
<223> OTHER INFORMATION: Synthetic

<400> SEQUENCE: 287

Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
            20                  25                  30

Leu Val Gln Pro Gly Arg Ser Leu Arg Leu Pro Cys Thr Ala Ser Gly
        35                  40                  45

Phe Ser Phe Gly Asp His Ala Met Ser Trp Val Arg Gln Ala Pro Gly
    50                  55                  60

Lys Gly Leu Glu Trp Val Gly Phe Ile Arg Lys Thr Thr Tyr Gly Ala
65                  70                  75                  80

Thr Thr His Tyr Ala Ala Ala Val Arg Gly Arg Phe Thr Ile Ser Arg
                85                  90                  95

Asp Asp Ser Lys Ser Ile Val Tyr Leu Gln Met Asn Ser Leu Lys Thr
            100                 105                 110

Glu Asp Thr Ala Val Tyr Phe Cys Thr Arg Val Gln Leu Asp Tyr Gly
        115                 120                 125

Pro Gly Tyr Gln Tyr Tyr Gly Met Asp Val Trp Gly Gln Gly Thr Thr
    130                 135                 140

Val Thr Val Ser Ser Ala Ser Thr Lys Gly Pro Ser Val Phe Pro Leu
145                 150                 155                 160

Ala Pro Ser Ser Lys Ser Thr Ser Gly Gly Thr Ala Ala Leu Gly Cys
                165                 170                 175

Leu Val Lys Asp Tyr Phe Pro Glu Pro Val Thr Val Ser Trp Asn Ser
            180                 185                 190

Gly Ala Leu Thr Ser Gly Val His Thr Phe Pro Ala Val Leu Gln Ser
        195                 200                 205

Ser Gly Leu Tyr Ser Leu Ser Ser Val Val Thr Val Pro Ser Ser Ser
    210                 215                 220

Leu Gly Thr Gln Thr Tyr Ile Cys Asn Val Asn His Lys Pro Ser Asn
225                 230                 235                 240

Thr Lys Val Asp Lys Lys Val Glu Pro Lys Ser Cys Asp Lys Thr His
                245                 250                 255

Thr Cys Pro Pro Cys Pro Ala Pro Glu Leu Leu Gly Gly Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300
```

```
Val Lys Phe Asn Trp Tyr Val Asp Gly Val Glu His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Leu His Glu Ala Leu
    450                 455                 460

His Ser His Tyr Thr Gln Lys Ser Leu Ser Leu Ser Pro Gly Lys
465                 470                 475

<210> SEQ ID NO 288
<211> LENGTH: 237
<212> TYPE: PRT
<213> ORGANISM: Artificial Sequence
<220> FEATURE:
<223> OTHER INFORMATION: Synthetic

<400> SEQUENCE: 288

Met Asp Met Arg Val Pro Ala Gln Leu Leu Gly Leu Leu Leu Leu Trp
1               5                   10                  15

Leu Arg Gly Ala Arg Cys Gly Val Gln Met Thr Gln Ser Pro Ser Thr
            20                  25                  30

Leu Ser Ala Ser Val Gly Asp Arg Val Thr Leu Thr Cys Arg Ala Ser
        35                  40                  45

Gln Ser Ile Ser Ser Trp Leu Ala Trp Tyr Gln Gln Lys Pro Gly Lys
    50                  55                  60

Ala Pro Lys Leu Leu Ile Tyr Asp Ala Ser Ser Leu Glu Ser Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Asp Asp Phe Ala Thr Tyr Tyr Cys Gln Gln
            100                 105                 110

Tyr Asn Ser Tyr Ser Phe Trp Thr Phe Gly Gln Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190
```

```
Asp Ser Thr Tyr Ser Leu Ser Thr Leu Thr Leu Ser Lys Ala Asp
            195                 200                 205

Tyr Glu Lys His Lys Val Tyr Ala Cys Glu Val Thr His Gln Gly Leu
210                 215                 220

Ser Ser Pro Val Thr Lys Ser Phe Asn Arg Gly Glu Cys
225                 230                 235
```

<210> SEQ ID NO 289
<211> LENGTH: 475
<212> TYPE: PRT
<213> ORGANISM: Artificial Sequence
<220> FEATURE:
<223> OTHER INFORMATION: Synthetic

<400> SEQUENCE: 289

```
Met Asp Met Arg Val Pro Ala Gln Leu Leu Gly Leu Leu Leu Leu Trp
1               5                   10                  15

Leu Arg Gly Ala Arg Cys Gln Val Gln Leu Val Glu Ser Gly Gly Gly
                20                  25                  30

Val Val Gln Pro Gly Arg Ser Leu Arg Leu Ser Cys Ala Ala Ser Gly
            35                  40                  45

Phe Ala Phe Asn Thr Tyr Gly Met His Trp Val Arg Gln Thr Pro Gly
50                  55                  60

Lys Gly Leu Glu Trp Val Ala Ile Ile Trp Tyr Asp Gly Ser Gln Lys
65                  70                  75                  80

Tyr Tyr Ala Asp Ser Val Gln Gly Arg Phe Ile Ile Ser Arg Asp Asn
                85                  90                  95

His Lys Asn Thr Leu Ser Leu Gln Met Asn Gly Leu Arg Ala Glu Asp
            100                 105                 110

Thr Ala Val Tyr Phe Cys Val Arg Val Arg Phe Ser Val Gly Pro His
        115                 120                 125

Gly Ser Ala Phe Asp Leu Trp Gly Gln Gly Thr Met Val Ile Val Ser
130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
290                 295                 300

Trp Tyr Val Asp Gly Val Glu Val His Asn Ala Lys Thr Lys Pro Arg
305                 310                 315                 320
```

-continued

```
Glu Glu Gln Tyr Asn Ser Thr Tyr Arg Val Val Ser Val Leu Thr Val
            325             330             335

Leu His Gln Asp Trp Leu Asn Gly Lys Glu Tyr Lys Cys Lys Val Ser
            340             345             350

Asn Lys Ala Leu Pro Ala Pro Ile Glu Lys Thr Ile Ser Lys Ala Lys
            355             360             365

Gly Gln Pro Arg Glu Pro Gln Val Tyr Thr Leu Pro Pro Ser Arg Asp
    370             375             380

Glu Leu Thr Lys Asn Gln Val Ser Leu Thr Cys Leu Val Lys Gly Phe
385             390             395             400

Tyr Pro Ser Asp Ile Ala Val Glu Trp Glu Ser Asn Gly Gln Pro Glu
            405             410             415

Asn Asn Tyr Lys Thr Thr Pro Pro Val Leu Asp Ser Asp Gly Ser Phe
            420             425             430

Phe Leu Tyr Ser Lys Leu Thr Val Asp Lys Ser Arg Trp Gln Gln Gly
        435             440             445

Asn Val Phe Ser Cys Ser Val Leu His Glu Ala Leu His Ser His Tyr
    450             455             460

Thr Gln Lys Ser Leu Ser Leu Ser Pro Gly Lys
465             470             475
```